(12) United States Patent
Losert et al.

(10) Patent No.: US 11,781,192 B2
(45) Date of Patent: *Oct. 10, 2023

(54) DOUBLE-FLOWERING DWARF CALIBRACHOA

(71) Applicant: Klemm+Sohn GmbH & Co. KG, Stuttgart (DE)

(72) Inventors: Dominik Losert, Aspach (DE); Nils Klemm, Stuttgart (DE); Andrea Dohm, Pforzheim (DE); Ulrich Sander, Stuttgart (DE); Anita Stover, Ostfildern (DE)

(73) Assignee: Klemm+Sohn GMBH & CO. KG, Stuttgart (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/503,926

(22) Filed: Oct. 18, 2021

(65) Prior Publication Data

US 2022/0119895 A1  Apr. 21, 2022

Related U.S. Application Data

(62) Division of application No. 17/072,837, filed on Oct. 16, 2020, now Pat. No. 11,155,884.

(51) Int. Cl.
*A01H 1/04* (2006.01)
*C12Q 1/6895* (2018.01)
*A01H 5/02* (2018.01)
*A01H 6/82* (2018.01)
*A01H 1/00* (2006.01)

(52) U.S. Cl.
CPC ............ *C12Q 1/6895* (2013.01); *A01H 1/121* (2021.01); *A01H 1/1215* (2021.01); *A01H 5/02* (2013.01); *A01H 6/821* (2018.05); *C12Q 2600/13* (2013.01); *C12Q 2600/156* (2013.01)

(58) Field of Classification Search
CPC .................................. C12Q 1/6895; A01H 1/04
See application file for complete search history.

(56) References Cited

U.S. PATENT DOCUMENTS

| | | | |
|---|---|---|---|
| 5,034,323 A | 7/1991 | Jorgensen et al. | |
| 5,107,065 A | 4/1992 | Shewmaker et al. | |
| 5,453,566 A | 9/1995 | Shewmaker et al. | |
| 5,463,175 A | 10/1995 | Barry et al. | |
| 5,500,365 A | 3/1996 | Fischhoff et al. | |
| 5,633,435 A | 5/1997 | Barry et al. | |
| 5,689,052 A | 11/1997 | Brown et al. | |
| 5,759,829 A | 6/1998 | Shewmaker et al. | |
| 5,880,275 A | 3/1999 | Fischhoff et al. | |
| 5,959,185 A | 9/1999 | Streit et al. | |
| 5,973,234 A | 10/1999 | Mueller et al. | |
| 5,977,445 A | 11/1999 | Soper et al. | |
| 6,423,885 B1 | 7/2002 | Waterhouse et al. | |
| 6,453,242 B1 | 9/2002 | Eisenberg et al. | |
| 6,528,700 B1 | 3/2003 | Baszczynski et al. | |
| 6,753,139 B1 | 6/2004 | Baulcombe et al. | |
| 6,785,613 B2 | 8/2004 | Eisenberg et al. | |
| 6,911,575 B1 | 6/2005 | Baszczynski et al. | |
| 7,138,565 B2 | 11/2006 | Waterhouse et al. | |
| 7,151,201 B2 | 12/2006 | Barbas, III et al. | |
| 7,177,766 B2 | 2/2007 | Eisenberg et al. | |
| PP20,201 P2 | 8/2009 | Klemm | |
| PP21,018 P2 | 5/2010 | Klemm et al. | |
| 7,713,715 B2 | 5/2010 | Speer et al. | |
| 7,786,342 B2 | 8/2010 | Stover et al. | |
| 7,788,044 B2 | 8/2010 | Eisenberg et al. | |
| PP21,465 P3 | 11/2010 | Westhoff | |
| PP21,525 P3 | 11/2010 | Westhoff | |
| PP22,600 P3 | 3/2012 | Klemm et al. | |
| PP23,191 P3 | 11/2012 | Klemm et al. | |
| PP24,381 P2 | 4/2014 | Ui | |
| PP29,491 P2 | 7/2018 | Nguyen | |
| PP30,114 P3 | 1/2019 | Nguyen | |
| PP30,803 P2 | 8/2019 | Sakazaki | |
| PP30,804 P2 | 8/2019 | Sakazaki | |
| PP30,835 P2 | 8/2019 | Klemm et al. | |
| 11,155,884 B1* | 10/2021 | Losert et al. | A01H 5/02 |
| 2014/0179006 A1 | 6/2014 | Zhang | |
| 2014/0294773 A1 | 10/2014 | Brouns et al. | |

FOREIGN PATENT DOCUMENTS

| | | |
|---|---|---|
| CA | 4591 | 10/2013 |
| NL | 238195 | 9/1965 |
| NL | 238194 | 2/2013 |
| NL | 238053 | 5/2013 |
| NL | 242570 | 5/2013 |
| NL | 242568 | 2/2015 |
| NL | 242569 | 2/2015 |

(Continued)

OTHER PUBLICATIONS

Aukerman & Sakai, "Regulation of Flowering Time and Floral Organ Idenity by a MicroRNA and Its APETALA2-Like Target Genes," The Plant Cell, 15:2730-2741 (2003).
Baulcombe, "Fast forward genetics based on virus-induced gene silencing," Curr. Op. Plant Bio., 2(2):109-113 (1999).
Burton et al., "Virus-Induced Silencing of a Plant Cellulose Synthase Gene," Plant Cell, 12:691-705 (2000).
Creissen et al., "Molecular characterization of glutathione reductase cDNAs from pea (*Pisum sativum* L.)," The Plant Journal, 2(1):129-131 (1991).
Daboussi et al., "Engineering Meganuclease for Precise Plant Genome Modification" in Advances in New Technology for Targeted Modification of Plant Genomes. Springer Science+Business, pp. 21-38 (2015).
DeBloc et al., "Expression of foreign genes in regenerated plants and in their progeny," The EMBO J., 3:1681-1689 (1984).

(Continued)

*Primary Examiner* — Keith O. Robinson
(74) *Attorney, Agent, or Firm* — COOLEY LLP

(57) ABSTRACT

The disclosure relates to *Calibrachoa* plants comprising a double-flowering characteristic and a dwarf growth characteristic, methods for generating said plants, and molecular markers corresponding to the double-flowering and dwarf growth traits.

5 Claims, 23 Drawing Sheets
(22 of 23 Drawing Sheet(s) Filed in Color)

Specification includes a Sequence Listing.

(56) References Cited

FOREIGN PATENT DOCUMENTS

| | | |
|---|---|---|
| NL | 242571 | 2/2015 |
| NL | 242572 | 2/2015 |
| NL | 242573 | 2/2015 |
| NL | 243713 | 6/2015 |
| NL | 246123 | 4/2016 |
| NL | 246124 | 4/2016 |
| NL | 246125 | 4/2016 |
| NL | 246326 | 5/2016 |
| QZ | 51562 | 2/2018 |
| QZ | 51563 | 2/2018 |
| QZ | 51564 | 2/2018 |
| QZ | 51565 | 2/2018 |
| QZ | 51566 | 2/2018 |
| QZ | 51567 | 2/2018 |
| QZ | 51568 | 2/2018 |
| WO | WO9931248 A1 | 6/1999 |

OTHER PUBLICATIONS

Dubin et al., "Transposons: a blessing curse," Current Opinion in Plant Biology, 42:23-29 (2018); ff10.1016/j.pbi.2018.01.003ff. ffhal-01713131f.

European Application No. EP20202350.3, filed Oct. 16, 2020 by [Inventor].

Ferrie et al., "Review of Doubled Haploidy Methodologies in Ornamental Species," Propagation of Ornamental Plants, 11(2):63-77 (2011).

Flavell, "Inactivation of Gene Expression in Plants as a Consequence of Specific Sequence Duplication," PNAS USA, 91(9):3490-3496 (1994).

Fletcher et al., "QTL analysis of root morphology, flowering time, and yield reveals trade-offs in response to drought in Brassica napus," Journal of Experimental Biology, 66(1):245-256 (2015).

Frontes et al., "Characterization of an Immunoglobulin Binding Protein Homolog in the Maize floury-2 Endosperm Mutant," The Plant Cell, 3:483-496 (1991).

Gould et al., "A conserved tripeptide sorts proteins to peroxisomes," J. Cell. Biol., 108:1657-1654 (1989).

Ishino et al., "Nucleotide sequence of the iap gene, responsible for alkaline phosphatase isozyme conversion in Escherichia coli, and identification of the gene product," J. Bacteriol., 169:5429-5433 (1987).

Johnson et al., "Vast potential for using the piggyBac transposon to engineer transgenic plants at specific genomic locations," Bioengineered, 7(1):3-6 (2016).

Kalderon et al., "A Short Amino Acid Sequence Able to Specify Nuclear Location," Cell, 39:499-509 (1984).

Koncz et al., "Expression and assembly of functional bacterial luciferase in plants," Proc. Natl. Acad. Sci. USA, 84:131-135 (1987).

Lerner et al., "Cloning and Characterization of Root-Specific Barley Lectin," Plant Physiol., 91:124-129 (1989).

Luciana et al., "Tissue culture in ornamental plant breeding: A review," Crop Breeding and Applied Technology, 1(3):283-300 (2001).

Malzhan et al. "Plant genome editing with TALEN and CRISPR," Cell & Bioscience, vol. 7:21 (Apr. 2017), 18 pages.

Matsuoka et al., "Propeptide of a precursor to a plant vacuolar protein required for vacuolar targeting," Proc. Natl. Acad. Sci., 88(3):834 (1991).

Montgomery et al., "RNA as a target of double-stranded RNA-mediated genetic interference in Caenorhabditis elegans," PNAS USA, 95(26):15502-15507 (1998).

Napoli et al., "Introduction of a Chimeric Chalcone Synthase Gene into Petunia Results in Reversible Co-Suppression of Homologous Genes in trans," The Plant Cell, 2:279-289 (1990).

Needleman & Wunsch, "A general method applicable to the search for similarities in the amino acid sequence of two proteins," Journal of Molecular Biology, 48(3):443-53 (1970).

Non-Final Office Action dated Apr. 14, 2021 for U.S. Appl. No. 17/072,837, 12 pages.

Pandey et al., "Plant regeneration from leaves and hypocotyl explants," Japan J. Breed., 42:1-5 (1992).

Pearson, W.R., et al., Improved tools for biological sequence comparison. Proceedings of the National Academy of Sciences (Apr. 1, 1988); 85(8): 2444-2448.

Petolino, "Genome editing in plants via designed zinc finger nucleases," In Vitro Cell Dev Biol Plant, 51(1):1-8 (2015).

Sander and Joung, " CRISPR-Cas systems for editing, regulating and targeting genomes," Nature Biotechnology, 32:347-355 (2014).

Shah et al.,"Engineering herbicide tolerance in transgenic plants," Science, 233:478-481 (1986).

Sharp, "RNAi and double-strand RNA," 1999, Genes & Dev., 13, 139-141, Downloaded from genesdev.cshlp.org on May 10, 2018—Published by Cold Spring Harbor Laboratory Press.

Sheehy et al., "Reduction of polygalacturonase activity in tomato fruit by antisense RNA," PNAS USA, 85:8805-8809 (1988).

Smith et al., "Total silencing by intron-spliced hairpin RNAs," Nature, 407:319-320 (2000).

Smith, TF et al., 'Identification of Common Molecular Subsequences,' Journal of Molecular Biology, 147:195-197, PMID 7265238. doi:10.1016/0022-2836(81)90087-5, (1981).

Sorek et al., "CRISPR-mediated adaptive immune systems in bacteria and archaea," Annu. Rev. Biochem., Jun. 2013.

Steifel et al., "Expression of a Maize Cell Wall Hydroxyproline-Rich Glycoprotein Gene in Early Leaf and Root Vascular Differentiation," Plant Cell, 2:785-793 (1990).

Steinecke et al., "Expression of a chimeric ribozyme gene results in endonucleolytic cleavage of target mRNA and a concomitant reduction of gene expression in vivo," EMBO J., 11(4):1525-1530 (1992).

Stephens et al., "Agronomic evaluation of tissue-culture-derived soybean plants," Theor. Appl. Genet., 82:633-635 (1991).

Taylor, "Comprehending Cosuppression," Plant Cell 9:1245-1249 (1997).

Teeri et al., "Gene fusions to lacZ reveal new expression patterns of chimeric genes in transgenic plants," EMBO J., 8:343-350 (1989).

Wang et al., "Efficient targeted mutagenesis in potato by the CRISPR/Cas9 system," Plant Cell Reports, 34:1473-1476 (2015).

Zamore et al., "RNAi: double-stranded RNA directs the ATP-dependent cleavage of mRNA at 21 to 23 nucleotide intervals," 2000, Cell, 101, 25-33.

Zhang et al., "Exploiting the CRISPR/Cas9 System for Targeted Genome Mutagenesis in Petunia," Science Reports, vol. 6, No. 20315, pp. 1-8 (2016).

* cited by examiner

Figure 2A

CCCTCATCTTTCTCTTTCAGAAGAGCCTACTTTCGCCCATGGTTCGCGTCGCTAT
CGTGCTTGGTCCGTTCGCTACTCTCTTTTCAGCCATTATTGTATGCGTGTAGCCT
AAGTCTACCCTTCGATTGGACTTTCTCCAGATCCTTTGACACCCGCTCATCTTAC
TTCCCATTCTGGTAGGTTGGTGCGTGATGATTCGTGGAGTACAAGGCTCTCTCTG
GTTGGGTACGTAGGCTGGTCCTGCAG[A/C]TTGTGGAGGTGACCAGCGCTGCAT
GCCCGAATGGAATATTGACTATCCCGTAGAACTGACCTAGTCGCTCGT[G/C]AA
GGAGCTGGTCATTATGGAATATACTATATGTAGGCGCAGGTCTTCCTAGAGCGAA
CCTCCATGTGTTTTATATTAAACATATAAAAATCAACAGTGGAAGAGGCACTGGT
TGTGCGAGATCATTATGACTGGAGGAAGCCCATTCGACAACCATAATAGGCTCTA
TAACCGGATCACGCACGCTAAGAACACAGCGGATTAGAGGGACAAGAGGTTCCA
CT

Figure 2B

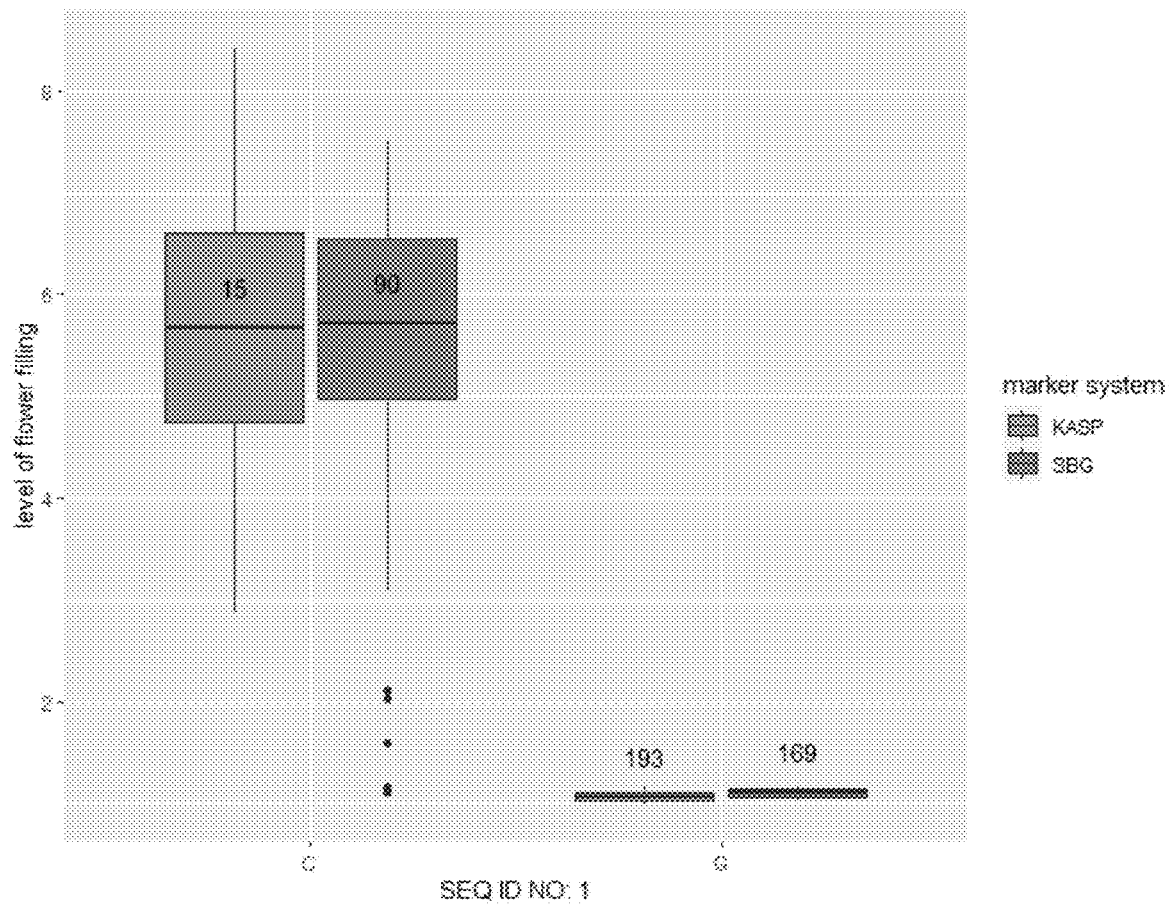

ATRCCACCACTGAACCACCRGCTGCAATGGCGGAGAAGGTGT[G/C]TGATGAAC
CATTTTTGGTGGTGGGACACGGTGGATTCTTGGGCTGAAAAAACAAGAATGGAAA
ACGCAGTG

Figure 5
Female mtC320/GG x Male mtG320/CC
F₁ Female mtC320/GC x Male mtG320/CC
F₂ (50%) mtC320/CC and (50%) mtC320/GC
Figure 6
Female mtC320/GC x Male mtG320/GG      Female mtG320/GG x Male mtG320/CC
   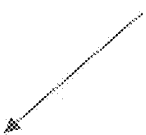
F₁ Female mtC320/GC x F₁ Male mtG320/GC
F₂ (25%) mtC320/CC; (50%) mtC320/GC; (25%) mtC320/GG

DOUBLE-FLOWERING DWARF *CALIBRACHOA*

CROSS REFERENCE TO RELATED APPLICATIONS

This application is a divisional of U.S. patent application Ser. No. 17/072,837, filed Oct. 16, 2020, which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (file name: SELE_003_01US_SeqList_ST25; date recorded Sep. 21, 2021; file size: 596 kb).

BACKGROUND

Double-flowering *Calibrachoa* varieties have been around since at least 2006, when the first Plant Patent Application was filed (PP18,694). Since then a number of double-flowering varieties have been developed, encompassing a wide range of colors and patterns. However as with all *Calibrachoa* varieties, these plants show high vigor and therefore plant growth regulators (PGR) need to be applied in order to achieve a more compact plant shape, which is commercially and economically desired. However, growth regulators are increasingly being banned by regulators. For instance, the growth regulator TILT® is banned in the USA, Canada, Germany and Sweden.

Additionally, the timing of PGR application is very important for the shape of end products, but the correct moment of application is influenced by temperature and development stages of the plants. This means that it is difficult for a grower to apply PGR at the correct moment. Incorrect PGR application regularly leads to economic loss during cultivation. It is therefore also commercially interesting to breed *Calibrachoa* plants in which plants can be grown without PGRs.

Breeding of new plant varieties requires the continuous development of genetic diversity to obtain new, improved characteristics and traits. New genetic diversity can be established by crossing, random mutagenesis, or with the help of modern biotechnology.

The foregoing examples of the related art and limitations related therewith are intended to be illustrative and not exclusive. Other limitations of the related art will become apparent to those of skill in the art upon a reading of the specification.

SUMMARY

The present disclosure relates to a *Calibrachoa* plant comprising a double-flowering characteristic and a dwarf growth characteristic, wherein said double-flowering characteristic is caused by a mitochondrial allele associated with at least one single nucleotide polymorphism (SNP) mutation selected from the group consisting of a G to C nucleotide substitution at position number 320 of SEQ ID NO: 1 and an A to C nucleotide substitution at position number 247 in SEQ ID NO: 1, and wherein said dwarf growth characteristic is caused by a homozygous recessive nuclear allele associated with a SNP mutation consisting of a G to C nucleotide substitution at position 43 of SEQ ID NO: 2.

In some embodiments, the present disclosure relates to plants comprising double-flowering and dwarf growth characteristics, wherein the plant has a petaloid stamina rating of at least 2. In some embodiments, the plant at maturity has a vigor rating of less than 5 compared to plants having a G/C or G/G genotype at position 43 of SEQ ID NO: 2 when grown under the same environmental conditions. In some embodiments, the plant exhibits male sterility.

In some embodiments, the present disclosure relates to plants comprising double-flowering and dwarf growth characteristics, wherein the plant is grown without the addition of synthetic plant growth regulators. In some embodiments, the plant comprises no detectable residue of a synthetic plant growth regulator or a related breakdown of a synthetic plant growth regulator product.

In some embodiments, the present disclosure relates to plants comprising double-flowering and dwarf growth characteristics, wherein the plant further comprises a mutation affecting flower color and/or flower color pattern, wherein said mutation is the result of induced random or targeted mutagenesis. In another embodiment, the targeted mutagenesis is a gene editing tool or technology.

In further embodiments, the present disclosure teaches a method of producing a *Calibrachoa* plant comprising a double-flowering characteristic and a dwarf growth characteristic comprising the steps of crossing a first female *Calibrachoa* plant with a first male *Calibrachoa* plant to produce $F_1$ plants, wherein said first female *Calibrachoa* plant comprises a mitochondrial allele associated with at least one SNP mutation selected from the group consisting of a G to C nucleotide substitution at position number 320 of SEQ ID NO: 1 and an A to C nucleotide substitution at position number 247 in SEQ ID NO: 1 and exhibiting a double-flowering characteristic, and wherein said first male *Calibrachoa* plant has at least one copy of nuclear, recessive allele associated with a SNP mutation consisting of a G to C nucleotide substitution at position 43 of SEQ ID NO: 2, wherein when said nuclear allele is in the homozygous form, plants exhibit a dwarf growth characteristic; screening said $F_1$ plants for the presence of said nuclear SNP mutation; selecting an $F_1$ female plant exhibiting said double-flowering characteristic and further comprising at least one copy of said nuclear SNP mutation; crossing said $F_1$ female plant with said first male or a second male *Calibrachoa* plant having at least one copy of said nuclear SNP mutation to produce $F_2$ plants; screening said $F_2$ plants for the presence of said nuclear SNP mutation; and selecting an $F_2$ plant exhibiting said double-flowering characteristic and being homozygous for said nuclear SNP mutation.

In some embodiments, the first or second male *Calibrachoa* plant is homozygous for said nuclear SNP mutation and exhibits a dwarf growth characteristic. In some embodiments, the method further comprises asexual propagation or sexual reproduction of the selected $F_2$ plant.

In some embodiments, the present disclosure relates to plants produced by the methods disclosed herein, wherein the plant produced is further asexually propagated and grown without synthetic growth regulators. In some embodiments, the plant produced by the methods disclosed herein has a petaloid stamina rating of at least 2 and a vigor rating of less than 5 at maturity when compared to plants having a non-dwarf growth characteristic when grown under the same environmental conditions, wherein said non-dwarf plant has at least one copy of the allele associated with a SNP mutation consisting of a G at position 43 of SEQ ID NO: 2 (i.e., having a G/C or G/G genotype at position 43 of SEQ ID NO: 2).

In some embodiments, the plant produced by the methods disclosed herein further comprises a mitochondrial allele associated with an A to C nucleotide substitution at position number 247 in SEQ ID NO: 1.

In some embodiments, the plant produced by the methods disclosed herein exhibits male sterility.

In some embodiments, the plant produced by the methods disclosed herein further comprises a mutation affecting flower color and/or flower color pattern.

In some embodiments, the present disclosure teaches a method for producing a double-flowering dwarf *Calibrachoa* plant having a desired trait comprising applying a plant breeding technique to the *Calibrachoa* plant produced by the methods disclosed herein. In some embodiments, the plant breeding techniques are selected from the group consisting of recurrent selection, mass selection, hybridization, open-pollination, backcrossing, pedigree breeding, mutation breeding, haploid/double haploid production, and marker enhanced selection. In some embodiments, the plant breeding technique is mutation breeding and the mutation selected is spontaneous or artificially induced.

In some embodiments, the present disclosure relates to a plant produced by the methods disclosed herein, wherein said plant exhibits dwarf growth, double-flowering, and a desired trait. In some embodiments, the desired trait is flower color and/or flower color pattern.

In further embodiments, the present disclosure relates to a molecular marker for distinguishing a plant having at least one allele for a double-flowering characteristic comprising at least one sequence selected from the group consisting of SEQ ID NO: 1, cDNA sequences thereof, fragments of at least 20 consecutive nucleotides thereof, and complementary sequences thereof.

In further embodiments, the present disclosure relates to a molecular marker for distinguishing a plant having at least one allele for a dwarf growth characteristic comprising at least one sequence selected from the group consisting of SEQ ID NO: 2, cDNA sequences thereof, fragments of at least 20 consecutive nucleotides thereof, and complementary sequences thereof.

In some embodiments, the present disclosure relates to a molecular marker for distinguishing a plant having an allele for a double-flowering characteristic, comprising a sequence of at least 20 consecutive nucleotides of SEQ ID NO: 7, or the complementary sequence.

In some embodiments, the present disclosure teaches a method for distinguishing a plant having at least one allele for a double-flowering characteristic comprising using SEQ ID NO: 1, cDNA sequences thereof, fragments of at least 20 consecutive nucleotides thereof, or complementary sequences thereof, and detecting at least one of a C nucleotide at position number 320 of SEQ ID NO: 1 and a C nucleotide at position number 247 in SEQ ID NO: 1. In another embodiment, detecting at least one of a C nucleotide at position number 320 of SEQ ID NO: 1 and a C nucleotide at position number 247 in SEQ ID NO: 1 comprises obtaining genetic material; obtaining a nucleic acid, wherein said nucleic acid has at least a portion of sequence complementary to the molecular markers disclosed herein; and base-pairing said nucleic acid with said genetic material and examining the result of said base-pairing. In some embodiments, the genetic material is deoxyribonucleic acid, ribonucleic acid, or a combination thereof. In some embodiments, the nucleic acid is a primer set, a probe, or combination thereof.

In some embodiments, the present disclosure teaches a method for distinguishing a plant having at least one allele for a dwarf growth characteristic comprising using SEQ ID NO: 2, cDNA sequences thereof, fragments of at least 20 consecutive nucleotides thereof, or complementary sequences thereof, and detecting a C nucleotide at position 43 of SEQ ID NO: 2. In another embodiment, detecting a C nucleotide at position 43 of SEQ ID NO: 2 comprises obtaining genetic material; obtaining a nucleic acid, wherein said nucleic acid has at least a portion of sequence complementary to the molecular markers disclosed herein; and base-pairing said nucleic acid with said genetic material and examining the result of said base-pairing. In some embodiments, the genetic material is deoxyribonucleic acid, ribonucleic acid, or a combination thereof. In some embodiments, the nucleic acid is a primer set, a probe, or combination thereof.

In some embodiments, the present disclosure relates to a plant distinguished by the markers and methods of using the markers disclosed herein, wherein the plant is homozygous for the allele for a dwarf growth characteristic, and wherein the plant is subsequently grown without synthetic growth regulators.

The following embodiments and aspects thereof are described and illustrated in conjunction with products and methods, which are meant to be exemplary and illustrative, not limiting in scope.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1A shows a flower having five single petals and a rating of 1. FIG. 1B shows a flower having a double-flowering rating of 3. FIG. 1C shows a flower having a double-flowering rating of 5. FIG. 1D shows a flower having a double-flowering rating of 7. FIG. 1E shows a flower having a double-flowering rating of 9.

FIG. 2A corresponds to SEQ ID NO: 1 and shows the results of the Kompetitive Allele Specific PCR (KASP) assay of a single-flowering trait and the related sequence with the corresponding double-flowering trait. Two polymorphisms were identified in the double-flowering trait; an A to C nucleotide substitution at position number 247 and a G to C nucleotide substitution at position number 320, both indicated by bold, underlined font within brackets.

FIG. 2B is a boxplot of the level of flower filling (y-axis) of genotypes having a C at position number 320 of SEQ ID NO: 1 compared to those having a G at position 320 of SEQ ID NO: 1 (x-axis). The validation of the findings within the SBG approach (turquoise box plots) is displayed in FIG. 2B with additional box plots for the KASP assay (red box plots). The number within the boxplot indicates the number of genotypes in each group.

FIG. 5 represents an example breeding scheme to produce plants having a double-flowering dwarf phenotype.

FIG. 6 represents another example breeding scheme to produce plants having a double-flowering dwarf phenotype.

DEFINITIONS

Figures 1A, 1B, 1C, 1D, 1E:
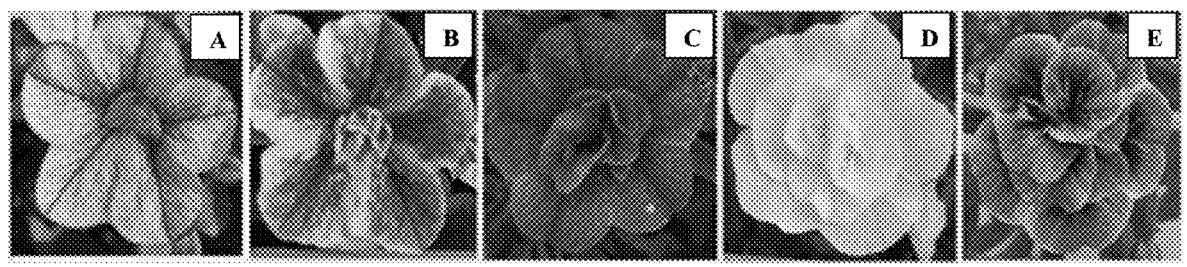
FIGS. 1A-1E shows photographs of flowers having different ratings (1-9) of flower filling (double-flowering), wherein 1 corresponds to single flowers and 9 corresponds to the highest level of flower filling.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art.

Following long-standing patent law convention, the terms "a," "an," and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about." The term "about," as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one or more of the elements to which the "and/or" refers can also individually be present in single or multiple occurrences in the combinations(s) and/or subcombination(s).

As used herein, the phrase "an allele associated with [a particular SNP mutation or mutation]" can mean the actual causative mutation of the phenotype, or a linkage—either physical or functional, for example as a regulatory element or some sort of epistatic relationship. It is a recognizable and/or assayable relationship between two entities. Additionally, the SNP mutation or mutation "associated with" the allele serves as an indicator of whether the allele is present in a plant/germplasm and can be used to predict whether a plant is homozygous or heterozygous for the allele.

As used herein, the phrase "dwarf" as it relates to *Calibrachoa* refers to a plant phenotype (or trait or characteristic) caused by a homozygous recessive nuclear allele associated with a C nucleotide at position 43 of SEQ ID NO: 2. A "non-dwarf" plant would have at least one copy of an allele associated with a G nucleotide at position 43 of SEQ ID NO: 2.

As used herein, the phrase "flower filling" or "filled" refers to the degree of the double-flowering characteristic and is measured herein according to UPOV's scale of 1-9 for quantitative traits.

"Genotype" as used herein refers to the genetic constitution of an individual organism.

As used herein, the term "human-induced mutation" or "induced mutagenesis" refers to any mutation that occurs as a result of either direct or indirect human action. This term includes, but is not limited to, mutations obtained by any method of targeted or human-induced random mutagenesis including for example, irradiation and treatment with mutation-inducing chemicals.

"mtC320" as used herein refers to the G to C nucleotide substitution (SNP mutation) at position number 320 of SEQ ID NO: 1 in the mitochondrial genome of a *Calibrachoa* plant.

"mtC247" as used herein refers to the A to C nucleotide substitution (SNP mutation) at position number 247 of SEQ ID NO: 1 in the mitochondrial genome of a *Calibrachoa* plant.

As used herein, the term "nucleotide sequence identity" refers to the presence of identical nucleotides at corresponding positions of two polynucleotides. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, Calif., United States of America. See also Smith & Waterman, 1981; Needleman & Wunsch, 1970; Pearson & Lipman, 1988; Ausubel et al., 1988; and Sambrook & Russell, 2001. One example of an algorithm that is suitable for determining percent sequence identity and sequence similarity is the BLAST algorithm, which is described in Altschul et al., 1990. Unless otherwise noted, alignments disclosed herein utilized ClustalW.

As used herein, the term "plant" can refer to a whole plant, any part thereof, or a cell or tissue culture derived from a plant. Thus, the term "plant" can refer to any of whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

"Phenotype" as used herein refers to the observable characteristics or traits of an organism that are produced by the interaction of the genotype and the environment.

As used herein, "vigor" relates to overall plant size as measured by their potential to produce biomass and is rated herein according to UPOV's scale of 1-9 for quantitative traits.

DETAILED DESCRIPTION

All publications, patents and patent applications, including any drawings and appendices, are herein incorporated by reference to the same extent as if each individual publication or patent application was specifically and individually indicated to be incorporated by reference.

The following description includes information that may be useful in understanding the present disclosure. It is not an admission that any of the information provided herein is prior art or relevant to the presently claimed disclosures, or that any publication specifically or implicitly referenced is prior art.

Overview

Embodiments described herein relate to *Calibrachoa* plants comprising a double-flowering characteristic and a dwarf growth characteristic, wherein said double-flowering characteristic is caused by a mitochondrial allele associated with at least one single nucleotide polymorphism (SNP) mutation of a G to C nucleotide substitution at position number 320 of SEQ ID NO: 1 and an A to C nucleotide substitution at position number 247 in SEQ ID NO: 1, and wherein said dwarf growth characteristic is caused by a homozygous recessive nuclear allele associated with a SNP mutation consisting of a G to C nucleotide substitution at position 43 of SEQ ID NO: 2, methods for generating said plants, and molecular markers corresponding to SEQ ID NO: 1 and SEQ ID NO: 2, cDNA sequences thereof, fragments of at least 20 consecutive nucleotides thereof, and complementary sequences thereof.

History of the Double-Flowering Trait, U.S. Pat. No. 7,786,342

Double-flowering *Calibrachoa* varieties were generated by Applicant through an intensive breeding program which began with screening 17,500 first generation plants. A handful of sections from these $F_1$ plants exhibited some flowers having more than 5 petals, and were then the subject of extensive breeding which included, for example, intercrossing siblings or half-siblings, back-crossing, out-crossing (to increase diversity and circumvent inbreeding depression), and open pollinations through the third and higher generations. Since then a number of double-flowering varieties have been developed, encompassing a wide range of colors and patterns (see Table 1 below).

TABLE 1

Double-flowering *Calibrachoa* varieties

| Denomination | Trade name | Patent No./ PVP No. |
|---|---|---|
| KLECA20428 | Superbells ® Double Amber | |
| KLECA20459 | Superbells ® Double Orange | |
| KLECA14275 | Superbells ® Double Orchid | |
| KLECA19067 | MiniFamous ® Neo Double OrangeTastic | |
| KLECA18085 | MiniFamous ® Uno Double PinkTastic ® | |
| KLECA07162 | MiniFamous ® Double Blue | PP20,201 |
| KLECA08164 | MiniFamous ® Double Pink Blush | |
| KLECA08182 | Compact MiniFamous ® Double Yellow | PP21,018 |
| KLECA09204 | Compact MiniFamous ® Double Lemon | PP23,191 |
| KLECA09207 | MiniFamous ® Double Hot Pink | |
| KLECA09208 | MiniFamous ® Neo Double Amethyst | PP22,600 |
| KLECA10220 | MiniFamous ® Double Pink | |
| KLECA11225 | MiniFamous ® Neo Double Yellow | |
| KLECA11226 | MiniFamous ® Double Nostalgia | |
| KLECA12231 | MiniFamous ® Double Blue | |
| KLECA12233 | MiniFamous ® Double Purple Red | |
| KLECA12234 | MiniFamous ® Neo Double Pink Vein | |
| KLECA13242 | MiniFamous ® Uno Double White | |
| KLECA13255 | MiniFamous ® Neo Double Dark Red | |
| KLECA13257 | Compact MiniFamous ® Double Red | |
| KLECA14261 | MiniFamous ® Double Orchid | |
| KLECA14264 | MiniFamous ® Uno Double Pink | |
| KLECA15269 | MiniFamous ® Neo Double Blue '15 | |
| KLECA14272 | Can-Can Rosies Blue | |
| KLECA14273 | Can-Can Rosies Dark Yellow | |
| KLECA14274 | Can-Can Rosies White | |
| KLECA14275 | Can-Can Rosies Pink Vein | |
| KLECA14276 | MiniFamous ® Double Purple | |
| KLECA14277 | Can-Can Rosies Magenta | |
| KLECA14283 | MiniFamous ® Double Apricot | |
| KLECA15290 | MiniFamous ® Neo Double Lemon '15 | |
| KLECA15332 | Compact MiniFamous ® Double Rose | |
| KLECA16356 | MiniFamous ® Uno Double PinkMania! | |
| KLECA16364 | MiniFamous ® Neo Double Light Blue | |
| KLECA19508 | MiniFamous ® Uno Double Blue | |
| KLECA20509 | MiniFamous ® Neo Double light violet 098 | |
| KLECA18510 | MiniFamous ® Uno Double LavTastic | |
| KLECA18511 | MiniFamous ® Uno Double White Pink Vein | |

TABLE 1-continued

Double-flowering *Calibrachoa* varieties

| Denomination | Trade name | Patent No./ PVP No. |
|---|---|---|
| KLECA18514 | MiniFamous ® Uno Double Red | |
| USCAL81302 | Superbells ® Doublette Love Swept ™ | PP30,804 |
| USCAL83901 | Superbells ® Double Ruby | Can4591 |
| US08CJ0202 | Superbells ® Double Rose | |
| USCAL51505 | Superbells ® Double Chiffon | PP30,803 |
| Duealdubcit | Aloha Double Citric | NL238194 |
| Duealdublav | Aloha Double Lavender | NL238053 |
| Dueldubstra | Aloha Double Strawberry | NL238195 |
| | Aloha Double Orange | |
| | Aloha Double Pink | |
| | Aloha Double Purple | |
| | Aloha Double Cherry Red | |
| DCALNOADBZ | Noa ™ Double Bronze | |
| | Noa ™ Double Pineapple | |
| WESCADOBL(U) | Celebration Double Blue | PP21,525 |
| WESCADODARE | Celebration Double Dark Red | |
| WESCADOFU | Celebration Double Fuchsia | |
| WESCADOLEM | Celebration Double Lemon | |
| WESCADOORE | Celebration Double Orange Pink | |
| WESCADOPI | Celebration Double Pink | PP21,465 |
| WESCADOSOPI | Celebration Double Soft Pink | |
| WESCADOWEIM | Celebration Double White Improved | |
| WESCADOYEL | Celebration Double Yellow | |
| WESCACHADOPIYE | CHAMELEON ® Double Pink Yellow | |
| WESCACHAMTIPI | CHAMELEON ® Double Ticld Pink | |
| | COLIBRI ™ Double Copper | |

As with all *Calibrachoa* varieties, these plants show high vigor and therefore growth regulators need to be applied in order to achieve a more compact plant shape, which is commercially desired.

History of the Dwarf Growth Trait

*Calibrachoa* varieties naturally show high vigor and therefore plant growth regulators (PGR) need to be applied in order to achieve a more compact plant shape, which is commercially and economically desired. However, growth regulators are increasingly being banned. For instance, the growth regulator TILT® is banned in the USA, Canada, Germany and Sweden. Additionally, the timing of PGR application is very important for the shape of end products, but the correct moment of application is influenced by temperature and development stages of the plants. This means that it is difficult for a grower to apply PGR at the correct moment. Incorrect PGR application regularly leads to economic loss during cultivation. It is therefore also commercially interesting to breed *Calibrachoa* plants which can be grown without PGRs.

*Calibrachoa* plants with dwarf phenotypes have been described and are known in the art (see Table 2a below, for example). These example varieties, while sometimes labeled "compact" are in fact distinct from other compact varieties and are herein referred to as dwarf varieties. The dwarf trait is recessive and breeding with the dwarf trait has been difficult, thus there are a limited number of commercially available lines. Examples of compact varieties are shown in Table 2b.

TABLE 2a

Dwarf Varieties

| Denomination | Trade name | Patent No./PVP No. |
|---|---|---|
| SAKCAL106 | MiniFamous ® Piu Pink Calipetite ® Blue | NL242570 |
| SAKCAL105 | Calipetite ® Red | PP24,381; NL242571 |
| SAKCAL104 | Calipetite ® Rose | NL242572 |
| SAKCAL108 | Calipetite ® White | NL242568 |
| SAKCAL107 | Calipetite ® Yellow | NL242569 |
| Balcongraniss | Conga ™ Orange Kiss | PBR51567 |
| Balcongcink | Conga ™ Pink | PBR51563 |
| Balcongite | Conga ™ White | PBR51565 |
|  | Conga ™ Peach Kiss |  |
| Wescaebreim | Early Bird ™ Red |  |
| Wescaebsu | Early Bird ™ Sun |  |
|  | Pocket ™ Lilac |  |
|  | Pocket ™ Yellow |  |

TABLE 2b

Compact varieties

| Denomination | Trade name | Patent No./PVP No. |
|---|---|---|
| KLECA17002 | MiniFamous ® Piu White |  |
| KLECA17038 | MiniFamous ® Piu Red | PP30,835 |
| KLECA17288 | MiniFamous ® Piu Light Blue |  |
| KLECA17338 | MiniFamous ® Piu Yellow |  |
| KLECA17340 | MiniFamous ® Piu Yellow + Red Veins |  |
| KLECA17343 | Calita ® Scarlet Red Eye |  |
|  | MiniFamous ® Piu Orange |  |
|  | Calita ® Compact Lemon |  |
| SAKCAL114 | Calipetite ® Pink Vein | NL243713 |
| SAKCAL110 | Calipetite ® Plum | NL242573 |
| Balcongetiss | Conga ™ Sunset Kiss |  |
| Balcongarlu | Conga ™ Dark Blue | PP29,491; PBR51562 |
| Balcongcriss | Conga ™ Coral Kiss | NL246124 |
| Balconglow | Conga ™ Lemon | NL246125 |
| Balcongor | Conga ™ Orange | NL246126 |
| Balconginkiss | Conga ™ Pink Kiss | NL246123 |
| Balcongosiss | Conga ™ Rose Kiss | NL246326 |
| Balcabscarim | Conga ™ Red |  |
| Balconglipar | Conga ™ Light Pink Star |  |
| Balconginar | Conga ™ Pink Star |  |
| Balconglav | Conga ™ Lavender | PP30,114 |
| Balcongrissm | Conga ™ Rose Kiss | PBR51568 |
| Balcongdel | Conga ™ Deep Yellow | PBR51564 |
| Balcongosiss | Conga ™ Rose | PBR51566 |
| Wescaebblim | Early Bird ™ Blue |  |
| Wescaebli | Early Bird ™ Lilac |  |
| Wescaebpi | Early Bird ™ Pink |  |
| Wescaebwe | Early Bird ™ White |  |
|  | Pocket ™ Apricot Eye |  |
|  | Pocket ™ Dark Pink |  |
|  | Pocket ™ Light Red |  |
|  | Pocket ™ Rose |  |
|  | Pocket ™ White |  |
|  | Aloha Nani Yellow |  |
|  | Aloha Nani Cherry Red |  |
|  | Aloha Nani Blue |  |
|  | Aloha Nani Dark Red |  |
|  | Aloha Nani Tropicana |  |
|  | Aloha Nani Red Cart Wheel |  |
|  | Aloha Nani White |  |
|  | Aloha Nani Golden Girl |  |
|  | Colibri ™ Malibu Pink |  |
|  | Colibri ™ Mellow Yellow |  |
|  | Colibri ™ Pink Flamingo |  |
|  | Colibri ™ Yellow Canary |  |
| DCALCOLBL | Colibri ™ Blizzard |  |
|  | Colibri ™ Lemon |  |
| DCALCOPILA | Colibri ™ Pink Lace |  |
| DCALCOCHLA | Colibri ™ Cherry Lace |  |
| DCALCORANG | Colibri ™ Orange |  |
|  | Colibri ™ Pink |  |
| DCALCOPULA | Colibri ™ Purple Lace |  |
| DCALCOFUCH | Colibri ™ Fuchsia |  |
|  | Colibri ™ Plum |  |

Thus, in order for the double-flowering and dwarf traits to be combined, one would require the underlying molecular mechanisms and/or markers for any successful breeding program.

Detection of Single Nucleotide Polymorphisms (SNP) Associated with the Mitochondrial Allele that Causes a Double-Flowering Phenotype A diverse collection of *Calibrachoa* plants, were phenotypically and genetically analyzed. The experimental trials for this analysis were grown in multi-location sites worldwide over several years. The plant cultivation tests were conducted in an experimental design containing several sub-experiments to capture the crop growth performance affected by different or no inhibiting substances (Paclobutrazol, Daminozide, no plant growth regulator). In total, 464 plants were analyzed (343 single flowering and 121 double-flowering).

For the phenotypic analysis, the level of flower filling, or the petaloid stamina rating, was scored visually on a 1-9 scale, based on the UPOV scale for quantitative traits, where 1 means single flowers having five petals per flower and a score of 2 or higher means flowers containing converted anthers. See for example FIGS. 1A-1E and Table 3 below.

TABLE 3

States of Double Flower Expression

| Approximate percentage of flower dimeter covered by additional petals or petaloids | Scale |
|---|---|
| >1 | 1 |
| 1-10 | 2 |
| 10.1-30 | 3 |
| 30.1-40 | 4 |
| 40.1-50 | 5 |
| 50.1-60 | 6 |
| 60.1-70 | 7 |
| 70.1-80 | 8 |
| >80 | 9 |

As shown in FIGS. 1A-1E and described above in Table 3, a plant having a petaloid stamina rating of 1 exhibits single flowers with five petals (FIG. 1A). Plants having a petaloid stamina rating of 2 have rudimentary converted anthers, while plants scoring 3 (FIG. 1B) or higher covering a bigger size of the total flower diameter by additional petals or petaloids.

For the genotypic analysis, an applied Sequence Based Genotyping (SBG) approach for the simultaneous Single-Nucleotide Polymorphism (SNP) discovery was conducted to genotype 288 plants (186 double-flowering, 102 single flowering). SBG libraries were prepared on the basis of genomic Deoxyribonucleic Acid (DNA) including both nuclear and mitochondrial DNA of 288 *Calibrachoa* samples and subsequently sequenced using the Illumina HiSeq. The resulting alignments were subsequently mined for SNP mutations (Truong et al. 2012). Quality checks were performed, leading to 11,641 SNP mutation markers. A Genome-Wide Association Study (GWAS) implemented with the high-quality data revealed a major Quantitative Trait Locus (QTL) in which one of the alleles is responsible for double-flowering phenotypes. The nucleotides between brackets in FIG. 2A indicate the position of the SNP mutations: an A to C nucleotide substitution at position number 247 in SEQ ID NO: 1 and a G to C nucleotide substitution at position number 320 of SEQ ID NO: 1. Genotypes having the "G" allele at position 320 displayed in all cases the single flower phenotypic trait. Genotypes having the "C" allele at position 320 displayed in all cases the double-flowering phenotype.

Other than for the SNP mutations described above, the sequence shown by SEQ ID NO: 1 is identical in the single and the double-flowering lines. The findings were confirmed with a Kompetitive Allele Specific PCR (KASP) assay (Chunlin et al. 2014). For the validation with the KASP, 234 plants were genotyped (210 single flowering, 24 double-flowering). 58 genotypes were analyzed with both SBG and KASP parallel.

Scoring and Genotyping the Double-Flowering Trait

The data from the SBG and KASP assay was further evaluated using linear mixed model analysis adjusted for influencing factors like genotype-environment-interactions (Best linear unbiased Predictors).

The results of the analysis are shown in FIG. 2B, which depicts a boxplot of the level of flower filling (y-axis) of genotypes having a C at position number 320 of SEQ ID NO: 1 compared to those having a G at position 320 of SEQ ID NO: 1 (x-axis). The validation of the findings within the SBG approach (turquoise box plots, 259 of the 288 plants analyzed) is displayed with additional box plots for the KASP assay (red box plots, 208 of the 234 plants analyzed). The number within the boxplot indicates the number of genotypes in each group, while the outward lines indicate the minimum and maximum values. As shown in FIG. 2B, plants having a C at position number 320 of SEQ ID NO: 1 have transformed anthers to additional petals or petaloids a flower filling rating of at least 2, while plants having a G at position 320 of SEQ ID NO: 1 exhibited a flowering filing rating of 1.

Thus, an embodiment of the present disclosure provides a molecular marker for distinguishing a plant having an allele for a double-flowering characteristic comprising at least one sequence selected from the group consisting of SEQ ID NO: 1, cDNA sequences thereof, fragments of at least 20 consecutive nucleotides thereof, and complementary sequences thereof. As will be understood by one skilled in the art, fragments may comprise lengths of at least 30, at least 40, at least 50, at least 60, least 70, at least 80, at least 90, at least 100, at least 125, at least 150, at least 175, at least 200, etc., nucleotides and upwards to the entire length of the sequence.

As will be understood by those skilled in the art, the SNP mutations shown in SEQ ID NO: 1 may be detected by any number of mechanisms, including but not limited to, Restriction Fragment Length Polymorphisms (RFLPs), Dynamic Allele-Specific Hybridization (DASH), molecular beacon, SNP microarray, PCR-based method, Flap endonuclease (FEN), Single-strand conformation polymorphism, temperature gradient gel electrophoresis, Denaturing High Performance Liquid Chromatography (DHPLC), DNA mismatch binding proteins, or sequencing.

Another embodiment of the present disclosure teaches a method for distinguishing a plant having at least one allele for a double-flowering characteristic comprising using SEQ ID NO: 1, and detecting at least one of a C nucleotide at position number 320 of SEQ ID NO: 1 and a C nucleotide at position number 247 in SEQ ID NO: 1. In another embodiment, detecting at least one of a C nucleotide at position number 320 of SEQ ID NO: 1 and a C nucleotide at position number 247 in SEQ ID NO: 1 comprises obtaining genetic material, obtaining a nucleic acid, wherein said nucleic acid has at least a portion of sequence complementary to the molecular marker for the double-flowering trait disclosed herein, and base-pairing said nucleic acid with said genetic material and examining the result of said base-pairing. The genetic material may be deoxyribonucleic acid, ribonucleic acid, or a combination thereof. The nucleic acid may be a primer set, a probe, or combination thereof.

Another embodiment of the present disclosure relates to double-flowering dwarf *Calibrachoa* plants having a petaloid stamina rating of at least 2. Another embodiment of the present disclosure relates to double-flowering dwarf *Calibrachoa* plants exhibiting male sterility.

Detection of Single Nucleotide Polymorphisms (SNP) Associated with the Dwarf Phenotype The diverse collection of *Calibrachoa* plants described above (464 plants total), including a wide range of growth vigor from very dwarf to very vigorous varieties were phenotypically and genetically analyzed. The experimental trials were grown in multi-location sites worldwide over several years. The plant cultivation tests were conducted in an experimental design containing several sub-experiments to capture the crop growth performance affected by different or no inhibiting substances (Paclobutrazol, Daminozide, no plant growth regulator).

Figure 3:
FIG. 3 is a photograph of nine plants corresponding to the 1-9 rating scale for vigor (level of compactness), wherein a rating of 1 corresponds to very dwarf and 9 to extremely vigorous plants. In the foreground, from left to right, are plants exhibiting ratings of 7, 8, and 9, respectively. The middle row, from left to right, shows plants exhibiting ratings of 4, 5, and 6, respectively. In the background, from left to right, are plants exhibiting ratings of 1, 2, and 3, respectively. All plants shown are the same age.

For the phenotypic analysis, growth vigor, or the determination of biomass, was rated on a 1-9 scale, where 1 refers to very dwarf and 9 to extreme vigorous plants. Plants representing each rating are shown in FIG. 3, specifically, in the foreground, from left to right, are plants exhibiting ratings of 7, 8, and 9, respectively. The middle row, from left to right, shows plants exhibiting ratings of 4, 5, and 6, respectively. In the background, from left to right, are plants exhibiting ratings of 1, 2, and 3, respectively.

The genotypic analysis described above further revealed a major Quantitative Trait Locus (QTL) in which one of the alleles is responsible for a dwarf phenotype. The nucleotides between brackets in FIG. 4A indicate the position of the SNP mutation comprising a G to C nucleotide substitution at position number 43 of SEQ ID NO: 2. Genotypes heterozygous or homozygous for the "G" allele at position 43 displayed in all cases the normal, vigorous plant growth. Genotypes homozygous for the "C" allele at position 43 displayed in all cases the dwarf phenotype. The confirmation of these findings was conducted with a Kompetitive Allele Specific PCR (KASP) assay.

Scoring and Genotyping the Dwarf Trait

The data from the SBG and KASP assay was further evaluated using linear mixed model analysis adjusted for influencing factors like genotype-environment-interactions (Best linear unbiased Predictors).

Figures 4A, 4B:
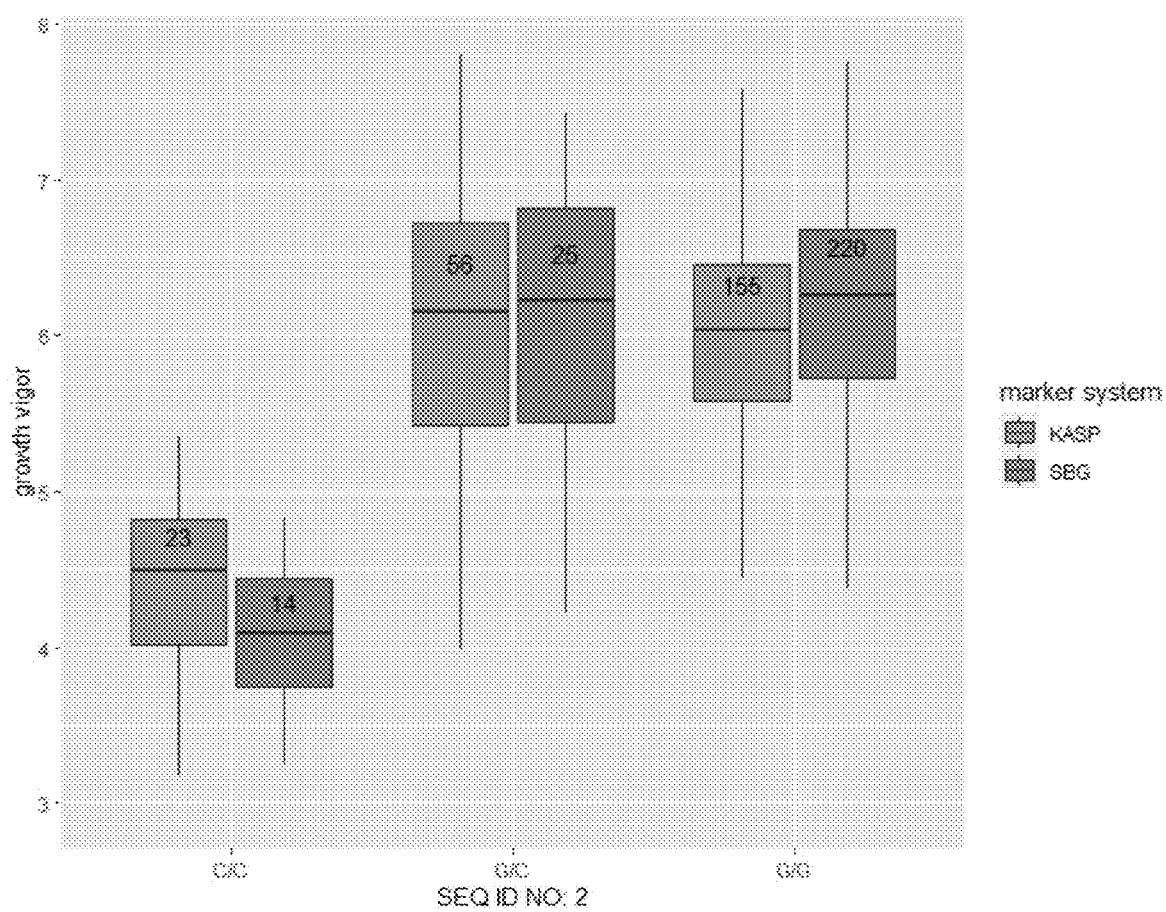
FIG. 4A corresponds to SEQ ID NO: 2 and shows the results of the Kompetitive Allele Specific PCR (KASP) assay of wild-type and the related sequence with the corresponding dwarf trait. A G to C polymorphism was identified at position 43 of SEQ ID NO: 2 indicated by bold, underlined font within brackets.
FIG. 4B is a boxplot of the level of growth vigor (y-axis) of genotypes carrying different allele composition for the detected nuclear "dwarf" polymorphism (x-axis) represented by SEQ ID NO: 2 (see also FIG. 4A). The validation of the findings within the SBG approach (turquoise box plots) is displayed in FIG. 4B with additional box plots for the KASP assay (red box plots). The number within the boxplot indicates the number of genotypes in each group.

The results of the analysis are shown in FIG. 4B, which depicts a boxplot of the level of growth vigor (y-axis) of genotypes homozygous for C at position number 43 of SEQ ID NO: 2 compared to those heterozygous or homozygous for G at position 43 of SEQ ID NO: 2 (x-axis). The validation of the findings within the SBG approach (turquoise box plots, 259 of the 288 plants analyzed) is displayed with additional box plots for the KASP assay (red box plots, 234 plants analyzed). The number within the boxplot indicates the number of genotypes in each group; while the outward lines indicate the minimum and maximum values. As shown in FIG. 4B, plants homozygous for C at position number 43 of SEQ ID NO: 2 exhibited much less growth vigor, while plants having at least one G allele at position 43 of SEQ ID NO: 2 exhibited a significantly stronger growth vigor.

Thus, an embodiment of the present disclosure provides a molecular marker for distinguishing a plant having at least one allele for a dwarf characteristic comprising at least one sequence selected from the group consisting of SEQ ID NO: 2, cDNA sequences thereof, fragments of at least 20 consecutive nucleotides thereof, and complementary sequences thereof. As will be understood by one skilled in the art, fragments may comprise lengths of at least 30, at least 40, at least 50, at least 60, least 70, at least 80, at least 90, at least 100, at least 125, at least 150, at least 175, at least 200, etc., nucleotides and upwards to the entire length of the sequence.

As will be understood by those skilled in the art, the SNP mutation shown in SEQ ID NO: 2 may be detected by any number of mechanisms, including but not limited to, Restriction Fragment Length Polymorphisms (RFLPs), Dynamic Allele-Specific Hybridization (DASH), molecular beacon, SNP microarray, PCR-based method, Flap endonuclease (FEN), Single-strand conformation polymorphism, temperature gradient gel electrophoresis, Denaturing High Performance Liquid Chromatography (DHPLC), DNA mismatch binding proteins, or sequencing.

Another embodiment of the present disclosure teaches a method for distinguishing a plant having at least one allele for a dwarf characteristic comprising using SEQ ID NO: 2, and detecting a C nucleotide at position 43 of SEQ ID NO: 2. In another embodiment, detecting a C nucleotide at position 43 of SEQ ID NO: 2 comprises obtaining genetic material, obtaining a nucleic acid, wherein said nucleic acid has at least a portion of sequence complementary to the molecular marker for the dwarf trait disclosed herein, and base-pairing said nucleic acid with said genetic material and examining the result of said base-pairing. The genetic material may be deoxyribonucleic acid, ribonucleic acid, or a combination thereof. The nucleic acid may be a primer set, a probe, or combination thereof.

In another embodiment, the present disclosure provides for a plant distinguished by the markers and methods disclosed herein, wherein said plant is homozygous for said allele for a dwarf growth characteristic, and wherein said plant is subsequently grown without growth regulators. In another embodiment, the plant comprises no detectable residue of a synthetic plant growth regulator or a related breakdown of a plant growth regulator product.

Another embodiment of the present disclosure relates to double-flowering dwarf *Calibrachoa* plants having a significantly smaller growth vigor rating of less than 5 at maturity, when compared to plants having a G/C or G/G genotypes at position 43 of SEQ ID NO: 2 when grown under the same environmental conditions.

Plant Growth Regulators (PGRs)

Plant growth regulators (PGRs) (herein also called synthetic plant growth regulators) are widely used in the ornamental plant business. PGRs consist of a large group of synthetically produced organic chemicals and considered as helping tool in the actual production system of ornamentals. The application of them is exercised by the commercial growers as a part of cultural practice. There are many methods of application of PGRs, most common used is drenching, foliar spraying and pre-plant soaking. According to professional experience and literature research, one or more PGRs have been used in *Calibrachoa* cultivation (Table 4 below).

TABLE 4

Widely used Plant Growth Regulators (PGRs) for *Calibrachoa* (modified according Wipker 2013 and 2019)

| PGR | Active Ingredient | Application rate | Method |
| --- | --- | --- | --- |
| Dazide (B-Nine) | Daminozide | 2,500-5,000 ppm | Spray |
| Citadel (Cycocel) + Dazide (B-Nine) | Chlormequat + Daminozide | 1,500 ppm (Citadel) + 2,500 ppm (Dazide) | Tank-mix spray |
| Concise (Sumagic) | Uniconazole-p | 10-25 ppm | Spray |
| Piccolo (Bonzi, Paczol, Downsize)) | Paclobutrazol | 3-8 ppm | Drench |
| Piccolo (Bonzi, Paczol) | Paclobutrazol | 3-50 ppm | Spray |
| Florel | Ethephon | 300-500 ppm | Spray |
| Toplor | Flurprimidol | 150-300 ppm | Spray |

The dangerous effects on both grower and end consumer health have increasingly become the focus of awareness worldwide. Various countries and international organizations have issued regulations by setting up the maximum authorized residue levels of PGRs in various plants and this will likely intensify in the future.

A large number of analytical methods for the determination of PGRs or residues of them have been developed. The methods of detection are enzyme-linked immunosorbent assay (ELISA) (Qian et al. 2009; Jiang et al. 2011), gas chromatography (GC) (Brinkmann et al. 1996; Xu et al. 2011), liquid chromatography-diode array detection (LC-DAD) (Das and Prasad 2015), gas chromatography-mass spectrometry (GC-MS) (Müller et al. 2002; Du et al. 2015), liquid chromatography-tandem mass spectrometry (LC-MS/MS) (Riediker et al. 2002; Ma et al. 2013; Kim et al. 2016), and high-performance liquid chromatography coupled with tandem mass spectrometry (HPLC-MS/MS) (Luo et al. 2019). Accredited laboratories (e.g. Analytisches Insitut Bostel, https://bostel.de/) analyze plant material for residue level conform to legal requirements (e.g. German Federal Office of Consumer Protection and Food Safety, § 64 LFGB).

Figure 4C:
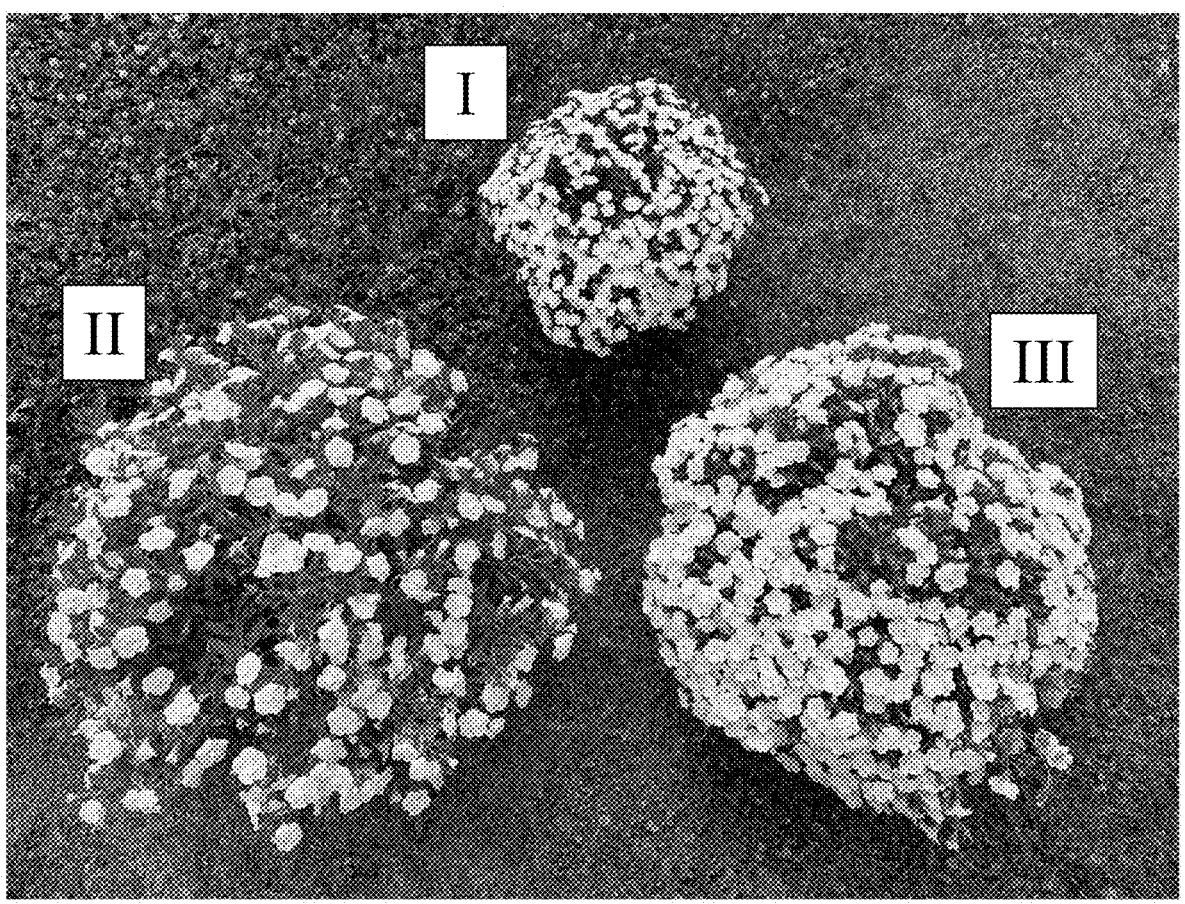
FIG. 4C shows three Calibrachoa plants of two different genotypes. Calibrachoa plant I is a genotype with a combination of the double-flowering trait (SEQ ID NO: 1; "C") and a dwarf growth trait (SEQ ID NO: 2; "C/C"), not treated with any plant growth regulators and has a vigor rating of 3. Calibrachoa plants II and III demonstrate the same genotype with the double-flowering trait (SEQ ID NO: 1; "C") but do not comprise the dwarf growth trait (SEQ ID NO: 2; "G/G"). Plant II is untreated with any plant growth regulators and has a vigor rating of 7. Plant III was growth inhibited according to good horticultural practice (5 treatments of Dazide/B-Nine) and has a vigor rating of 6.

The double-flowering dwarf *Calibrachoa* plants of the present disclosure inherently exhibit a significantly smaller growth vigor, therefore another embodiment of the present disclosure provides for double-flowering dwarf *Calibrachoa* plants grown without the addition of synthetic plant growth regulators. FIG. 4C shows three *Calibrachoa* plants of two different genotypes. *Calibrachoa* plant I is a genotype with a combination of the double-flowering trait (SEQ ID NO: 1; "C") and a dwarf growth trait (SEQ ID NO: 2; "C/C"), not treated with any plant growth regulators and has a vigor rating of 3. *Calibrachoa* plants II and III demonstrate the same genotype with the double-flowering trait (SEQ ID NO: 1; "C") but do not comprise the dwarf growth trait (SEQ ID NO: 2; "G/G"). Plant II is untreated with any plant growth regulators, and has a vigor rating of 7. Plant III was growth inhibited according to good horticultural practice (5 treatments of Dazide/B-Nine) and has a vigor rating of 6.

Another embodiment provides for double-flowering dwarf *Calibrachoa* plants which comprise no detectable residue of a synthetic plant growth regulator or a related breakdown of a plant growth regulator product.

Methods of a Producing Double-Flowering Dwarf *Calibrachoa*

An embodiment of the present disclosure provides a method of producing a *Calibrachoa* plant comprising a double-flowering characteristic and a dwarf growth characteristic comprising the steps of: crossing a first female *Calibrachoa* plant with a first male *Calibrachoa* plant to produce $F_1$ plants, wherein said first female *Calibrachoa* plant comprises a mitochondrial allele associated with at least one SNP mutation selected from the group consisting of (i) a G to C nucleotide substitution at position number 320 of SEQ ID NO: 1 and (ii) an A to C nucleotide substitution at position number 247 in SEQ ID NO: 1 and exhibiting a double-flowering characteristic, and wherein said first male *Calibrachoa* plant has at least one copy of a nuclear, recessive allele associated with a SNP mutation consisting of a G to C nucleotide substitution at position 43 of SEQ ID NO: 2, wherein when said nuclear allele is in the homozygous form plants exhibit a dwarf growth characteristic; screening said $F_1$ plants for the presence of said nuclear SNP mutation; selecting an $F_1$ female plant exhibiting said double-flowering characteristic and further comprising at least one copy of said nuclear SNP mutation; crossing said $F_1$ female plant with said first male or a second male *Calibrachoa* plant having at least one copy said nuclear SNP mutation to produce $F_2$ plants; screening said $F_2$ plants for the presence of said nuclear SNP mutation; and selecting an $F_2$ plant exhibiting said double-flowering characteristic and being homozygous for said nuclear SNP mutation. In another embodiment, the first or second male *Calibrachoa* plant is homozygous for said nuclear SNP mutation and exhibits a dwarf growth characteristic.

As will be understood by those skilled in the art, the first and/or second male *Calibrachoa* plant may be homozygous for the nuclear dwarf growth characteristic. As shown in FIG. 5, a first female *Calibrachoa* plant comprising a mitochondrial allele associated with a G to C nucleotide substitution at position number 320 of SEQ ID NO: 1 and (ii) an A to C nucleotide substitution at position number 247 in SEQ ID NO: 1 and exhibiting a double-flowering characteristic (mtC320) with vigorous growth G/G) is crossed with a male exhibiting single flowers (mtG320) and a dwarf growth trait (C/C). An $F_1$ female progeny from this cross having a double-flowering characteristic (mtC320) and vigorous growth (G/C) is then bred to a second male exhibiting single flowers (mtG320) and a dwarf growth trait (C/C). While FIG. 5 depicts this as an outcrossing, those skilled in the art will understand that this may also be accomplished via backcrossing to the first male *Calibrachoa*. 50% of the $F_2$ progeny from this cross will exhibit double-flowering and dwarf growth, and the other 50% will exhibit double-flowering and normal, vigorous growth as they will be heterozygous for the dwarf allele (G/C).

As will be understood by those skilled in the art, additional crosses may be conducted to produce the parental lines described above. Shown in FIG. 6 is an example wherein a double-flowering female (mtC320) carrying the dwarf allele (G/C) is crossed with a male having single flowers (mtG320) and no dwarf allele (G/G) but may comprise some other desirable trait (not depicted). An $F_1$ progeny is selected for having double-flowers (mtC320) and carrying the dwarf allele (G/C) and additional desired trait (not depicted) to be used as the female parent in a cross with a male having single flowers (mtG320) and carrying the dwarf allele (G/C). This male parental line may have been produced to carry, for example, the same desirable trait as the $F_1$ female parental line, or may carry a second desirable trait, and may have been produced as depicted in FIG. 6, from a cross between a single-flowering (mtG320) vigorous female (G/G) with a single flowering (mtCG20) dwarf male (C/C). As will be understood by those skilled the art, the $F_1$ male parental line carrying the dwarf allele shown in FIG. 6 may have been produced by any number of crosses, for example, by one or both parental lines being heterozygous for the dwarf allele.

As shown in FIG. 6, all $F_2$ progeny will exhibit double-flowering (mtC320) as this is inherited from the mitochondria of the $F_1$ female parent. Additionally, approximately 25% of $F_2$ progeny will also be homozygous for the dwarf allele and exhibit the dwarf growth trait (C/C).

Additional Breeding Methods

Any plants produced using the double-flowering dwarf plants and/or markers of the double-flowering and dwarf traits disclosed herein are also an embodiment. These methods are well-known in the art and some of the more commonly used breeding methods are described herein. Descriptions of breeding methods can be found in one of several reference books (e.g., Allard, "Principles of Plant Breeding" (1999); and Vainstein, "Breeding for Ornamentals: Classical and Molecular Approaches," Kluwer Academic Publishers (2002); Callaway, "Breeding Ornamental Plants," Timber Press (2000).

Breeding steps that may be used in a plant breeding program can include for example, pedigree breeding, backcrossing, mutation breeding, and recurrent selection. In conjunction with these steps, techniques such as RFLP-enhanced selection, genetic marker enhanced selection (for example, SSR markers), gene editing and the making of double haploids may be utilized.

In another embodiment, the present disclosure teaches a method of producing a double-flowering dwarf *Calibrachoa* plant having a desired trait comprising applying a plant breeding technique to the double-flowering dwarf *Calibrachoa* plant produced from the breeding methods disclosed herein. The desirable trait may be for example, a mutation affecting flower color and/or pattern. Thus, in another embodiment, the present disclosure provides for plants produced by the breeding methods disclosed herein and further comprising a mutation affecting flower color and/or pattern.

In another embodiment the present disclosure provides for plants produced by the breeding methods disclosed herein, wherein said plant has a petaloid stamina rating of at least three and wherein said plant at maturity has a vigor rating of less than five compared to plants having a G/C or G/G genotype at position 43 of SEQ ID NO: 2 when grown under the same environmental conditions.

In another embodiment, plants produced from the breeding methods disclosed herein may be asexually propagated or sexually reproduced. In another embodiment, the plants produced are grown without plant growth regulators.

Recurrent Selection and Mass Selection

In some embodiments, the plant breeding technique is recurrent selection. In some embodiments, the plant breeding technique is mass selection. Mass and recurrent selections can be used to improve populations of either self- or cross-pollinating crops. A genetically variable population of heterozygous individuals is either identified, or created, by intercrossing several different parents. The plants are selected based on individual superiority, outstanding progeny, or excellent combining ability. The selected plants are intercrossed to produce a new population in which further cycles of selection are continued.

Recurrent selection is a method used in a plant breeding program to improve a population of plants. Double-flowering dwarf *Calibrachoa* plants disclosed herein are suitable for use in a modified recurrent selection program. The method entails individual plants cross pollinating with each other to form progeny. The progeny are grown and the superior progeny selected. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties. Once a desired plant is obtained with improved traits, it can be used as a breeding line in crosses to generate double-flowering dwarf *Calibrachoa* plants.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. In addition to self-pollination, directed pollination could be used as part of the breeding program.

Open-Pollination and Hybridization

In some embodiments, the plant breeding technique is open-pollination. Open-pollination is when pollination occurs by insect, bird, wind, humans, or other natural mechanisms. This can yield greater variation and more genetically diverse plants. In some embodiments, the plant breeding technique is hybridization, Hybridization is a controlled method of pollination in which the pollen of two different varieties or species is crossed by human intervention. For example, *Calibrachoa* can hybridize with *petunia* to produce *petunia-Calibrachoa* hybrids. Thus, an embodiment of the present disclosure are *petunia-Calibrachoa* hybrids exhibiting the double-flowering and/or dwarf traits disclosed herein.

Backcross Breeding

In some embodiments, the plant breeding technique is backcrossing. Backcross breeding has been used to transfer genes for a simply inherited, highly heritable trait into a desirable homozygous variety or inbred variety which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent. This is also known as single gene conversion and/or backcross conversion.

In addition to being used to create a backcross conversion, backcrossing can also be used in combination with pedigree breeding. Backcrossing can be used to transfer one or more specifically desirable traits from one variety, the donor parent, to a developed variety called the recurrent parent, which has overall good commercial characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selection. This approach leverages the value and strengths of the recurrent parent for use in new *Calibrachoa* varieties.

Pedigree Breeding

In some embodiments, the plant breeding technique is pedigree breeding. Pedigree breeding starts with the crossing of two genotypes, such as the double-flowering and dwarf alleles disclosed herein, and another variety having one or more desirable characteristics that is lacking or which complements double-flowering dwarf *Calibrachoa* plants. If the two original parents do not provide all the desired characteristics, other sources can be included in the breeding population. In the pedigree method, superior plants are selected in successive filial generations.

Mutation Breeding

In some embodiments, the plant breeding technique is mutation breeding, wherein said mutation breeding selects for a mutation that is spontaneous or artificially induced. Mutation breeding is another method of introducing new traits into the double-flowering dwarf *Calibrachoa* plants of the present disclosure. Mutations that occur spontaneously or are artificially induced can be useful sources of variability for a plant breeder. The goal of artificial mutagenesis is to increase the rate of mutation for a desired characteristic. Mutation rates can be increased by many different means. Examples of mutagens that may be used with the method disclosed herein include: radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (for example from 250 to 290 nm), temperature, long-term seed storage, tissue culture conditions, or chemical mutagens (such as base analogues (5-bromo-uracil)), related compounds (8-ethoxy caffeine), antibiotics (streptonigrin), alkylating agents (sulfur mustards, nitrogen mustards, epoxides, ethyleneamines, sulfates, sulfonates, sulfones, lactones), azide, hydroxylamine, nitrous acid, or acridines, proflavine, ICR191 and ethidium bromide. Other techniques such as gene editing are also possible and lie well within the scope of the skilled person.

Once a desired trait is observed through mutagenesis the trait may then be incorporated into existing germplasm by traditional breeding techniques. Details of mutation breeding can be found in Allard, *Principles of Plant Breeding*, John Wiley & Sons, Inc. (1960) but may include, for example, crossing, recurrent selection, backcrossing, pedigree breeding, marker enhanced selection, haploid/double haploid production, or transformation.

In another embodiment, the double-flowering dwarf *Calibrachoa* plants of the present disclosure further comprises a mutation affecting flower color and/or flower color pattern, wherein said mutation is the result of a gene editing tool or technology.

Breeding with Molecular Markers

In some embodiments, the plant breeding technique is marker enhanced selection. In addition to the sequences disclosed herein which may be used as molecular markers for the double-flowering and dwarf traits, molecular markers can be used during the breeding process for the selection of other traits. For example, markers closely linked to alleles or markers containing sequences within the actual alleles of interest can be used to select plants that contain the alleles of interest during a breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms, may be used in plant breeding methods. See Vainstein, "Breeding for Ornamentals: Classical and Molecular Approaches," Kluwer Academic Publishers (2002).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See for example, Fletcher, Richard S., et al., "QTL analysis of root morphology, flowering time, and yield reveals trade-offs in response to drought in *Brassica napus*" *Journal of Experimental Biology*. 66 (1): 245-256 (2014). QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Molecular Techniques Using Double-Flowering Dwarf *Calibrachoa* Plants

The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See Vainstein, "Breeding for Ornamentals: Classical and Molecular Approaches," Kluwer Academic Publishers (2002). Expression vectors can be introduced into plant tissues using a direct gene transfer method, such as microprojectile-mediated delivery, DNA injection, electroporation, and the like, or by using either microprojectile-mediated delivery with a biolistic device or by using *Agrobacterium*-mediated transformation. Transformant plants obtained with the protoplasm of the present disclosure are intended to be within the scope of the embodiments.

Expression Vectors for *Calibrachoa* Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. Positive selection methods are also known in the art.

One commonly used selectable marker gene for plant transformation is neomycin phosphotransferase II (nptII) which, when under the control of plant regulatory signals, confers resistance to kanamycin. Another commonly used selectable marker gene is the hygromycin phosphotransferase gene which confers resistance to the antibiotic hygromycin.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.*, 13:67 (1987); Shah, et al., *Science*, 233:478 (1986); Charest, et al., *Plant Cell Rep.*, 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., *Plant Mol. Biol. Rep.*, 5:387 (1987); Teen, et al., *EMBO J.*, 8:343 (1989); Koncz, et al., *Proc. Natl. Acad. Sci. USA*, 84:131 (1987); DeBlock, et al., *EMBO J.*, 3:1681 (1984)).

Expression Vectors for *Calibrachoa* Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.
Signal Sequences for Targeting Proteins to Subcellular Compartments Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., *Plant Mol. Biol.,* 20:49 (1992); Knox, C., et al., *Plant Mol. Biol.,* 9:3-17 (1987); Lerner, et al., *Plant Physiol.,* 91:124-129 (1989); Frontes, et al., *Plant Cell,* 3:483-496 (1991); Matsuoka, et al., *Proc. Natl. Acad. Sci.,* 88:834 (1991); Gould, et al., *J. Cell. Biol.,* 108:1657 (1989); Creissen, et al., *Plant J.,* 2:129 (1991); Kalderon, et al., *Cell,* 39:499-509 (1984); Steifel, et al., *Plant Cell,* 2:785-793 (1990).
Foreign Genes: Transformation Various promoters, targeting sequences, enhancing sequences, and other DNA sequences can be inserted into the genome for the purpose of altering the expression of genes.

Many techniques for altering gene expression are well-known to one of skill in the art, including, but not limited to, knock-outs (such as by insertion of a transposable element such as Mu (Vicki Chandler, The Maize Handbook, Ch. 118 (Springer-Verlag 1994)) or other genetic elements such as a FRT, Lox, or other site specific integration sites; antisense technology (see, e.g., Sheehy, et al., PNAS USA, 85:8805-8809 (1988) and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, PNAS USA, 91:3490-3496 (1994); Finnegan, et al., *Bio/Technology,* 12:883-888 (1994); Neuhuber, et al., *Mol. Gen. Genet.,* 244:230-241 (1994)); RNA interference (Napoli, et al., *Plant Cell,* 2:279-289 (1990); U.S. Pat. No. 5,034,323; Sharp, *Genes Dev.,* 13:139-141 (1999); Zamore, et al., *Cell,* 101:25-33 (2000); Montgomery, et al., *PNAS USA,* 95:15502-15507 (1998)), virus-induced gene silencing (Burton, et al., *Plant Cell,* 12:691-705 (2000); Baulcombe, *Curr. Op. Plant Bio.,* 2:109-113 (1999)); target-RNA-specific ribozymes (Haseloff, et al., *Nature,* 334:585-591 (1988)); hairpin structures (Smith, et al., *Nature,* 407:319-320 (2000); U.S. Pat. Nos. 6,423,885, 7,138,565, 6,753,139, and 7,713,715); MicroRNA (Aukerman & Sakai, *Plant Cell,* 15:2730-2741 (2003)); ribozymes (Steinecke, et al., *EMBO J.,* 11:1525 (1992); Perriman, et al., *Antisense Res. Dev.,* 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); transposable elements (e.g. Dubin, M. J., et al., Transposons: a blessing curse, *Current opinion in plant biology*, Vol: 42, Page: 23-29, 2018 and Eric T. Johnson, Jesse B. Owens & Stefan Moisyadi (2016) Vast potential for using the piggyBac transposon to engineer transgenic plants at specific genomic locations, *Bioengineered*, 7:1, 3-6) and other methods or combinations of the above methods known to those of skill in the art.

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular *Calibrachoa* variety using the foregoing transformation techniques could be moved into another variety using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene.

Likewise, by means of one embodiment, plants can be genetically engineered to express various phenotypes of interest, including, but not limited to, genes that confer resistance to pests or disease, genes that confer resistance to an herbicide, genes that confer or contribute to a value-added or desired trait, genes that control male sterility, genes that create a site for site specific DNA integration, and genes that affect abiotic stress resistance. Non-limiting examples of particular genes and corresponding phenotypes one may choose to introduce into a plant include one or more genes for insect tolerance, such as a *Bacillus thuringiensis* (Bt.), pest tolerance such as genes for fungal disease control, herbicide tolerance such as genes conferring glyphosate tolerance, and genes for quality improvements such as, environmental or stress tolerances, or any desirable changes in plant physiology, growth, development, morphology or plant product(s). For example, *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety. Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.,* 9:207, 1991). The RNA could also be a catalytic RNA molecule (i.e., a ribozyme) engineered to cleave a desired endogenous mRNA product (see for example, Gibson and Shillito, *Mol. Biotech.,* 7:125, 1997). Thus, any sequence which produces a phenotype or morphology change of interest may be used with the double-flowering dwarf *Calibrachoa* plants disclosed herein.

Tissue Culture

Further reproduction can occur by tissue culture and regeneration. Tissue culture of various tissues of ornamental plants and regeneration of plants therefrom is well-known and widely published. For example, reference may be had to Valla Rego, Luciana et al., *Crop Breeding and Applied Technology.* 1(3): 283-300 (2001); Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992). Thus, another embodiment is to provide cells which upon growth and differentiation produce *Calibrachoa* plants exhibiting, or carrying the alleles for, double-flowering and dwarf traits described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Production of Double Haploids

The production of double haploids can also be used for the development of plants with a homozygous phenotype in the breeding program. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. For example, see, Ferrie, Alison M. R., et al., "Review of Doubled Haploidy Methodologies in Ornamental Species" *Propagation of Ornamental Plants.* 11(2): pp. 63-77 (2011).

Protoplast Fusion

Also known as somatic fusion, this process can be used with the double-flowering dwarf *Calibrachoa* plants of the present disclosure to create hybrids. The resulting hybrid plants have the chromosomes of each parent and thus the process is useful for incorporating new traits. The protoplast fusion technique is well known in the art; see for example Hamill J. D., Cocking E. C. (1988) Somatic Hybridization of Plants and its Use in Agriculture. In: Pais M. S. S., Mavituna F., Novais J. M. (eds) *Plant Cell Biotechnology.* NATO ASI Series (Series H: *Cell Biology*), vol 18.

Gene Editing Using CRISPR

Targeted gene editing can be done using CRISPR/Cas9 technology (Saunders & Joung, *Nature Biotechnology*, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system, for example *petunia*, a close relative of *Calibrachoa*. See for example, Zhang, B. et al., "Exploiting the CRISPR/Cas9 System for Targeted Genome Mutagenesis in *Petunia*" *Science Reports*, Vol. 6, February 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:237-266, 2013; and Wang, S. et al., *Plant Cell Rep* (2015) 34: 1473-1476.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing in double-flowering dwarf *Calibrachoa* plants. The technique is well known in the art; see for example Malzahn, Aimee et al. "Plant genome editing with TALEN and CRISPR" *Cell & Bioscience* vol. 7 21. 24 Apr. 2017.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in *Advances in New Technology for Targeted Modification of Plant Genomes.* Springer Science+Business. pp 21-38 (2015).

EXAMPLES

The following examples are provided to illustrate further the various applications and are not intended to limit the disclosure beyond the limitations set forth in the appended claims.

Example 1: Breeding with Purple Double-Flowering and Dwarf Traits

Figure 7:
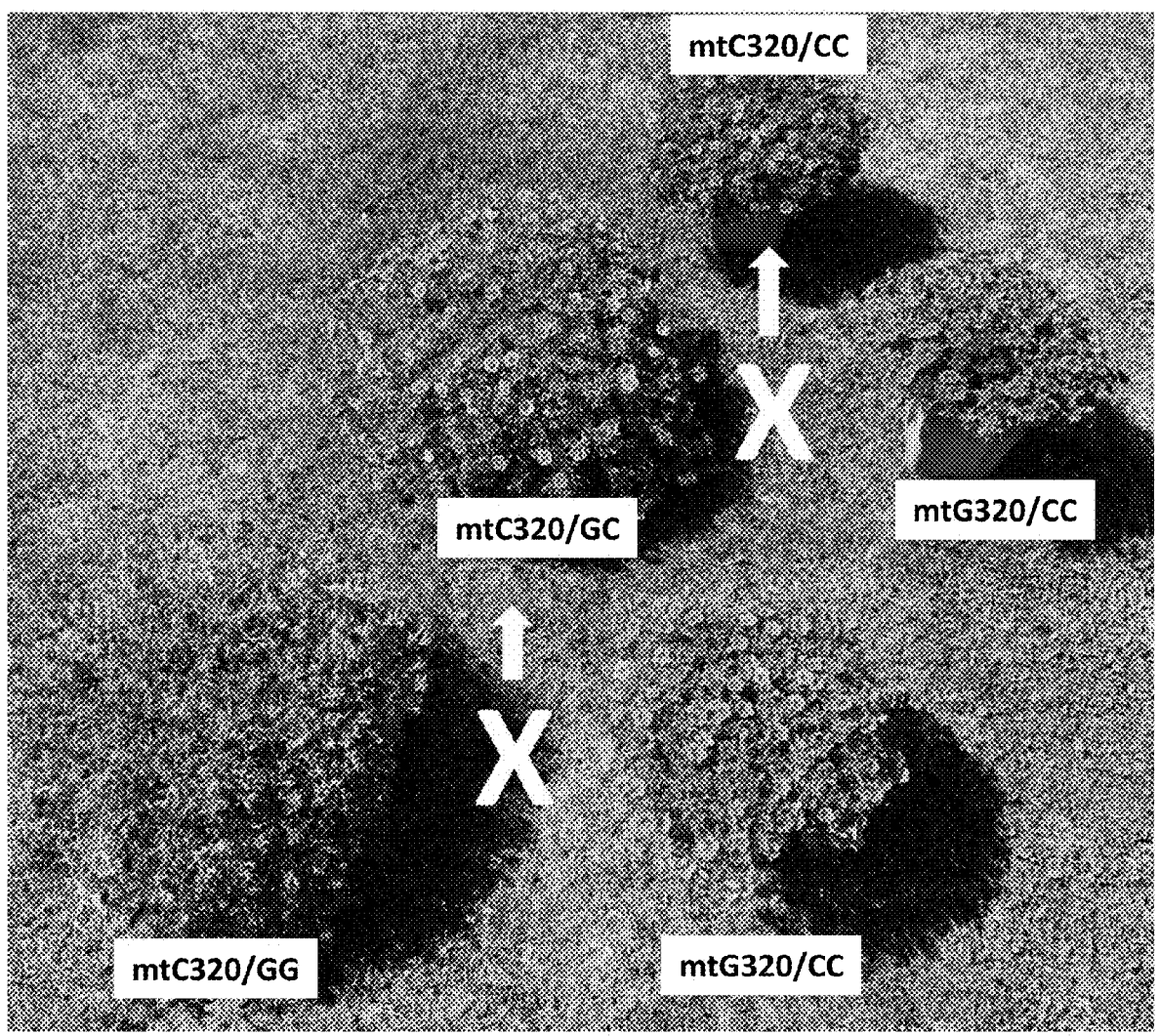
FIG. 7 is a photograph of parental lines and progeny plants from a breeding scheme to produce a purple double-flowering dwarf Calibrachoa plant.

*Calibrachoa* plants having both the double-flowering and dwarf traits were bred using the molecular markers disclosed herein. As shown in FIG. 7, a purple plant having double-flowers (mtC320) and normal vigorous growth (G/G) was used as the female parent and crossed with a purple dwarf plant (C/C) having single flowers (mtG320) as the male parent. The $F_1$ progeny exhibited purple double-flowers (mtC320) and normal vigorous growth as it was heterozygous for the recessive dwarf allele (G/C). This $F_1$ progeny was used a female parent in a cross with a male purple dwarf plant (C/C) having single flowers (mtG320). While an outcrossing is shown in FIG. 7, those skilled in the art will understand that this progeny could also be backcrossed to the first male parent. $F_2$ progeny were genotyped for the molecular markers disclosed herein using methods well known in the art. A selected $F_2$ progeny from this cross is shown at the top of FIG. 7, a purple double-flowering (mtC320) dwarf (C/C) *Calibrachoa*.

Example 2: Breeding with White Double-Flowering and Dwarf Traits

Figure 8:
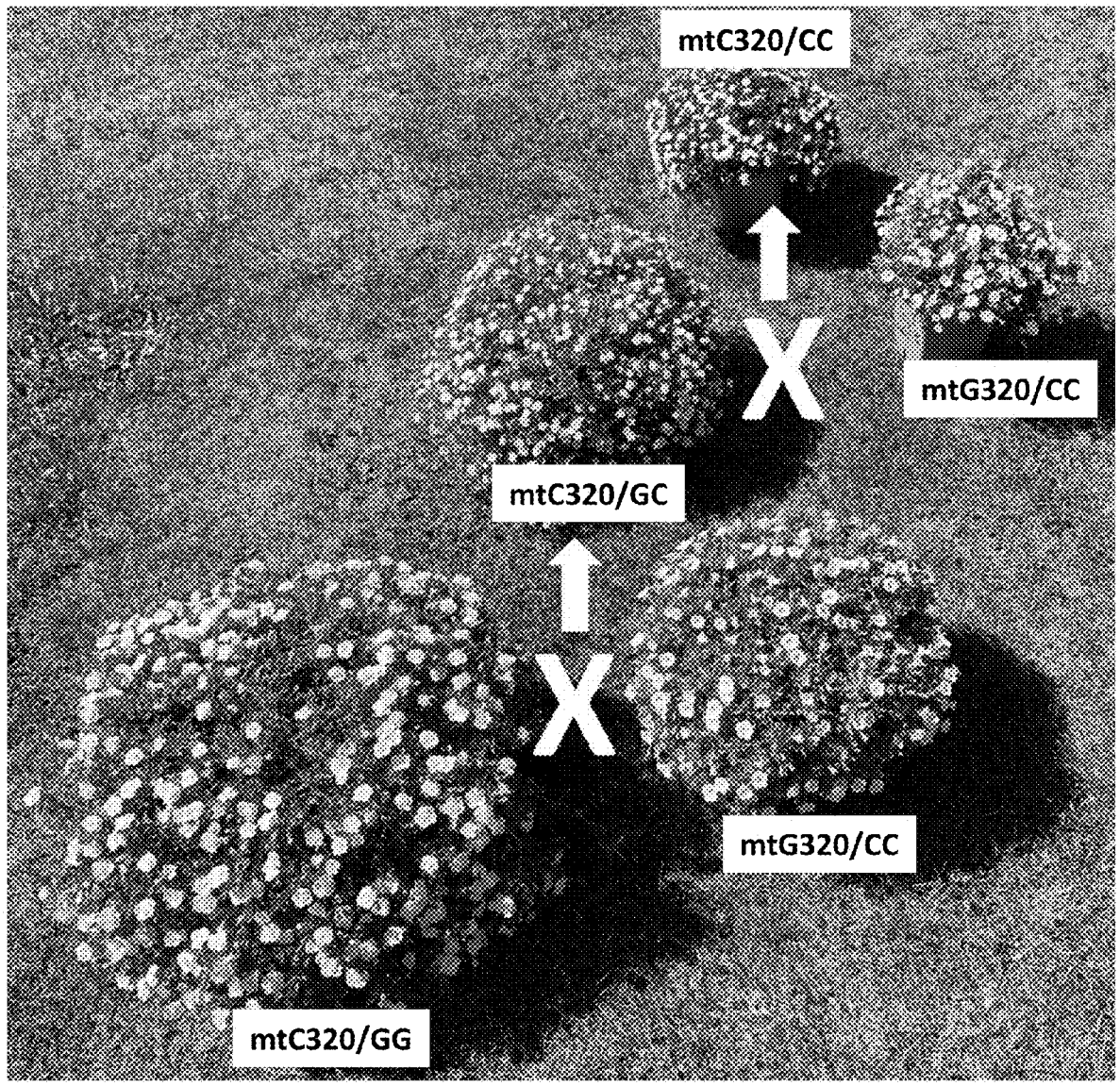
FIG. 8 is a photograph of parental lines and progeny plants from a breeding scheme to produce a white double-flowering dwarf Calibrachoa plant.

As shown in FIG. 8, a white plant having double-flowers (mtC320) and normal vigorous growth (G/G) was used as the female parent and crossed with a white dwarf (C/C) plant having single flowers (mtG320) as the male parent. The $F_1$ progeny exhibited white double-flowers (mtC320) and normal vigorous growth as it was heterozygous for the recessive dwarf allele (G/C). This $F_1$ progeny was used a female parent in a cross with a male white dwarf (C/C) plant having single flowers (mtG320). While an outcrossing is shown in FIG. 8, those skilled in the art will understand that this progeny could also be backcrossed to the first male parent. $F_2$ progeny were genotyped for the molecular markers disclosed herein using methods well known in the art. A selected $F_2$ progeny from this cross is shown at the top of FIG. 8, a white double-flowering (mtC320) dwarf (C/C) *Calibrachoa*.

Example 3: Double-Flowering Varieties with and without the Dwarf Trait

Figure 9A:
FIGS. 9A-9E show plants of different colors all having the double-flowering trait combined with either a wild-type allele for growth, (plant pictured left, "G/G" or "G/C"), or homozygous for the recessive dwarf allele associated with the nucleotide polymorphism shown in FIG. 4A (plant pictured right, "C/C"). Shown in FIG. 9A are yellow varieties. Shown in FIG. 9B are red varieties. Shown in FIG. 9C are pink varieties. Shown in FIG. 9D are pink-purple varieties. Shown in FIG. 9E are purple-red varieties.
Figure 9B:
Figure 9C:
Figure 9D:
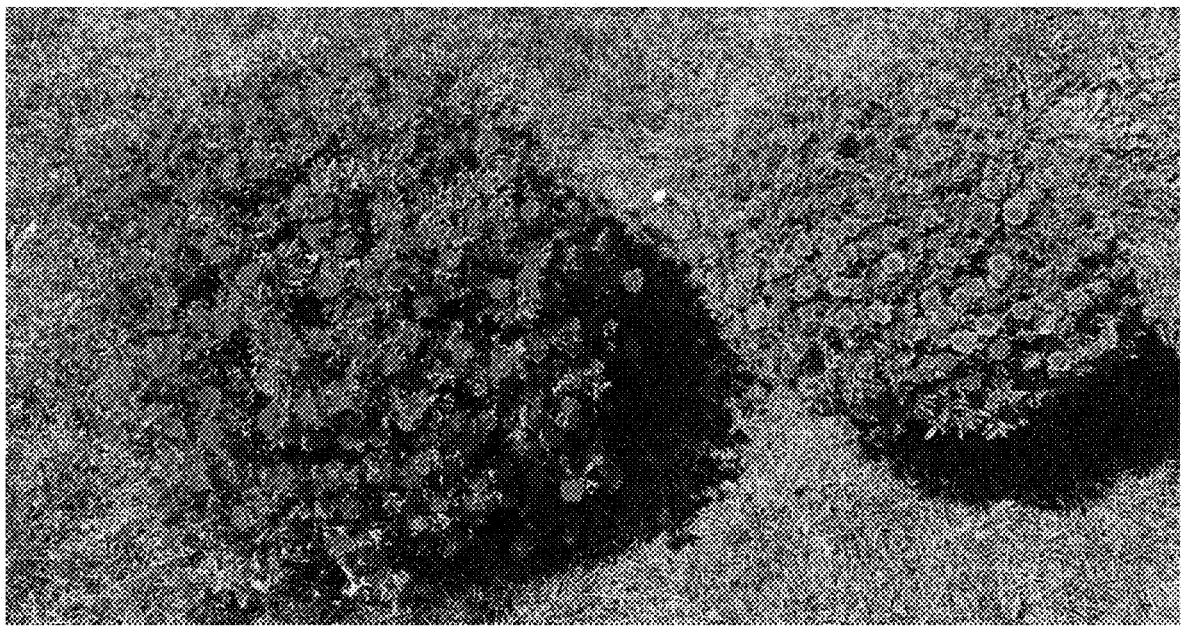
Figure 9E:
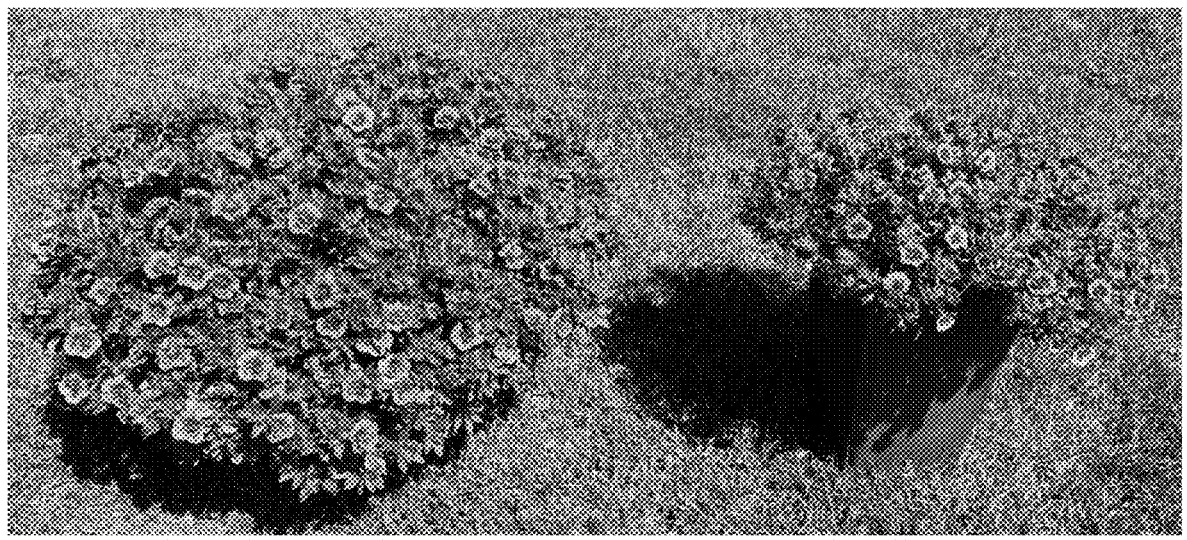

FIGS. 9A-9G show plants of different colored varieties all having the double-flowering trait combined with either a wild-type allele for the dwarf trait (plant pictured left, G/G or G/C), or homozygous for the recessive dwarf allele (plant pictured right) associated with the nucleotide polymorphism shown in FIG. 4A (C/C). Plants were bred using the breeding methods and schemes disclosed herein. Shown in FIG. 9A are plants of yellow varieties. Shown in FIG. 9B are plants of red varieties. Shown in FIG. 9C are plants of pink varieties. Shown in FIG. 9D are plants of pink-purple varieties, and shown in FIG. 9E are plants of purple-red varieties.

Figures 10A, 10B, 10C, 10D, 10E, 10F:
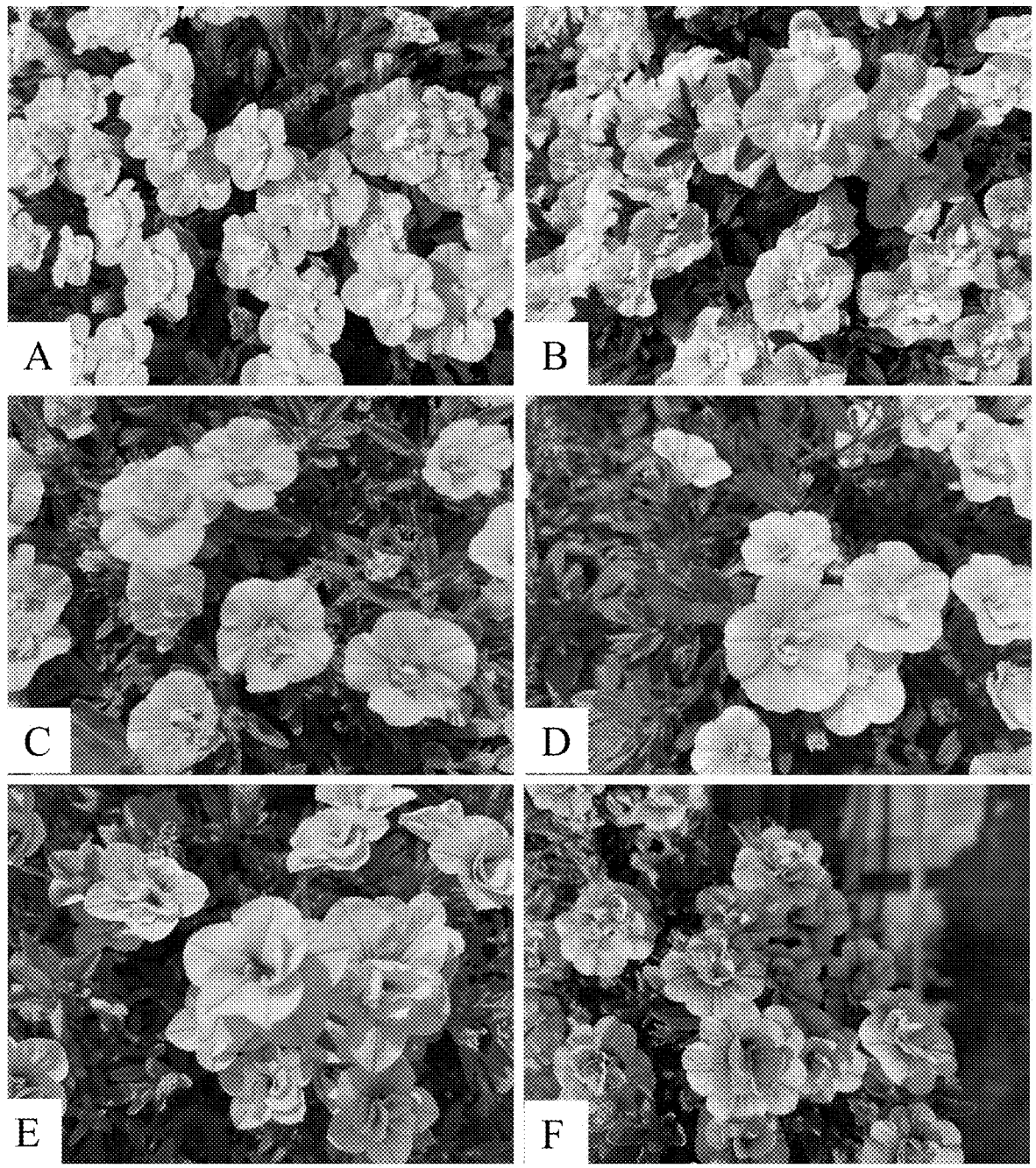
FIGS. 10A-10F are photographs of double-flowering dwarf Calibrachoa plants of the present disclosure having varying shades of white colored flowers (FIGS. 10A and 10B), yellow colored flowers (FIGS. 10C and 10D) and yellow-orange colored flowers (FIGS. 10E and 10F).

Example 4: White, Yellow, and Orange Double-Flowering Dwarf *Calibrachoa* Varieties Generated Using the Methods Disclosed Herein FIGS. 10A-10F are close up photographs of double-flowering dwarf *Calibrachoa* plants of the present disclosure having varying shades of white colored flowers (FIGS. 10A and 10B), yellow colored flowers (FIGS. 10C and 10D) and yellow-orange colored flowers (FIGS. 10E and 10F). Shown in FIGS. 10A and 10B are plants of white varieties designated CA-2020-0723 and CA-2020-0710 respectively. Shown in FIG. 10C is a plant of a yellow variety designated CA-2020-0743. Shown in FIG. 10D is a plant of a light yellow variety having a large area of yellow at the transition to the corolla tube designated CA-2020-0735. Shown in FIG. 10E is a plant of a light orange variety having strong red veins, designated CA-2020-0611, and shown in FIG. 10F is a plant of a yellow-orange variety having strong red veins designated CA-2020-0931.

Figures 11A, 11B, 11C, 11D, 11E, 11F:
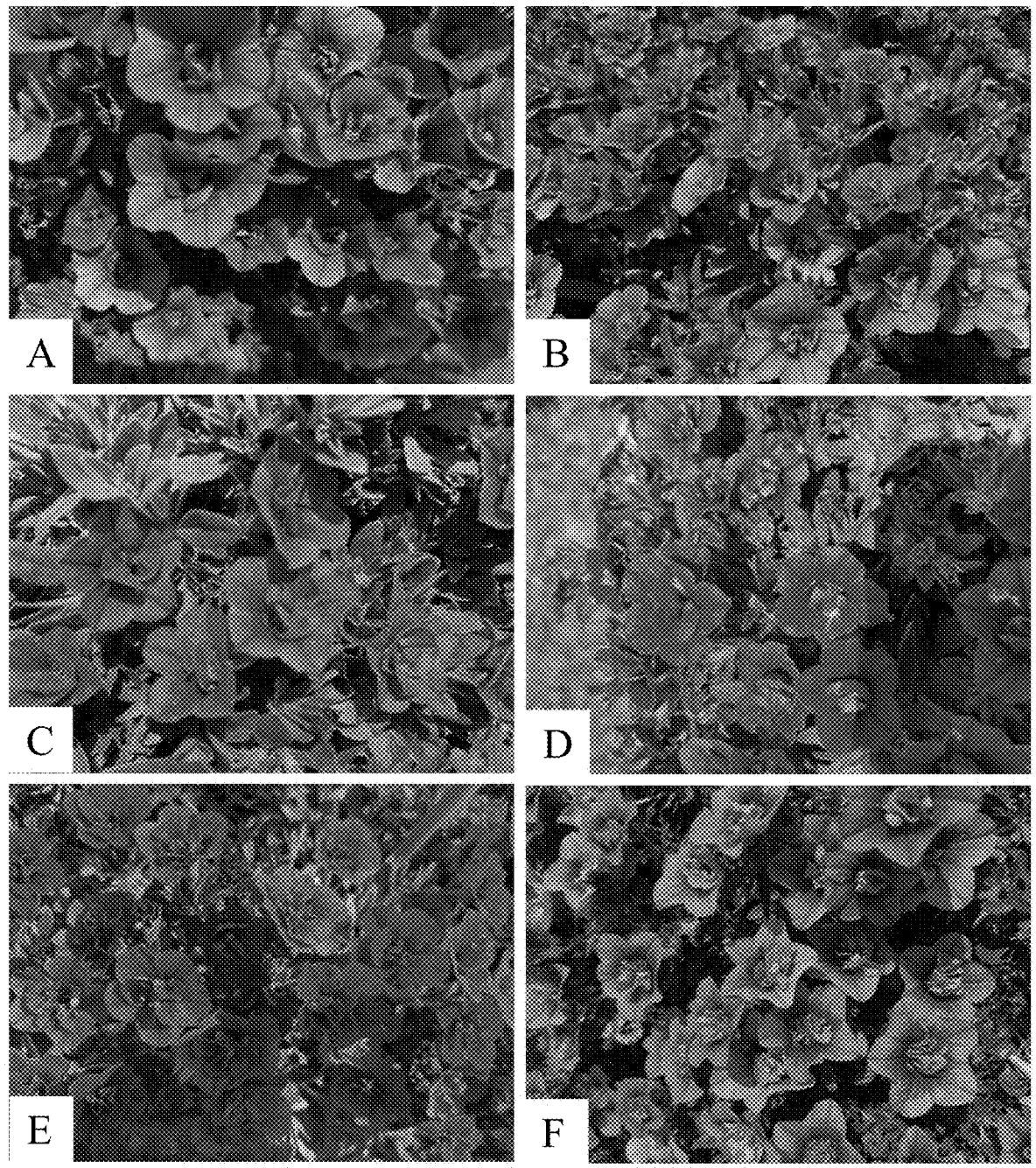
FIGS. 11A-11F are photographs of double-flowering dwarf Calibrachoa plants of the present disclosure having varying shades of orange colored flowers (FIGS. 11A and 11B) and red colored flowers (FIGS. 11C-11F).

Example 5: Double-Flowering Dwarf *Calibrachoa* Varieties in Varying Shades of Red and Orange Generated Using the Methods Disclosed Herein FIGS. 11A-11F are close up photographs of double-flowering dwarf *Calibrachoa* plants of the present disclosure having varying shades of red and orange colored flowers. Shown in FIGS. 11A and 11B are two plants of orange varieties, designated CA-2020-0825 and CA-2020-0833 respectively. Shown in FIG. 11C (CA-2020-0810), FIG. 11D (CA-2020-0805) and FIG. 11E (CA-2020-0697) are three plants of red varieties, and FIG. 11F shows a plant of a light red variety designated CA-2020-0809.

Figures 12A, 12B, 12C, 12D, 12E, 12F:
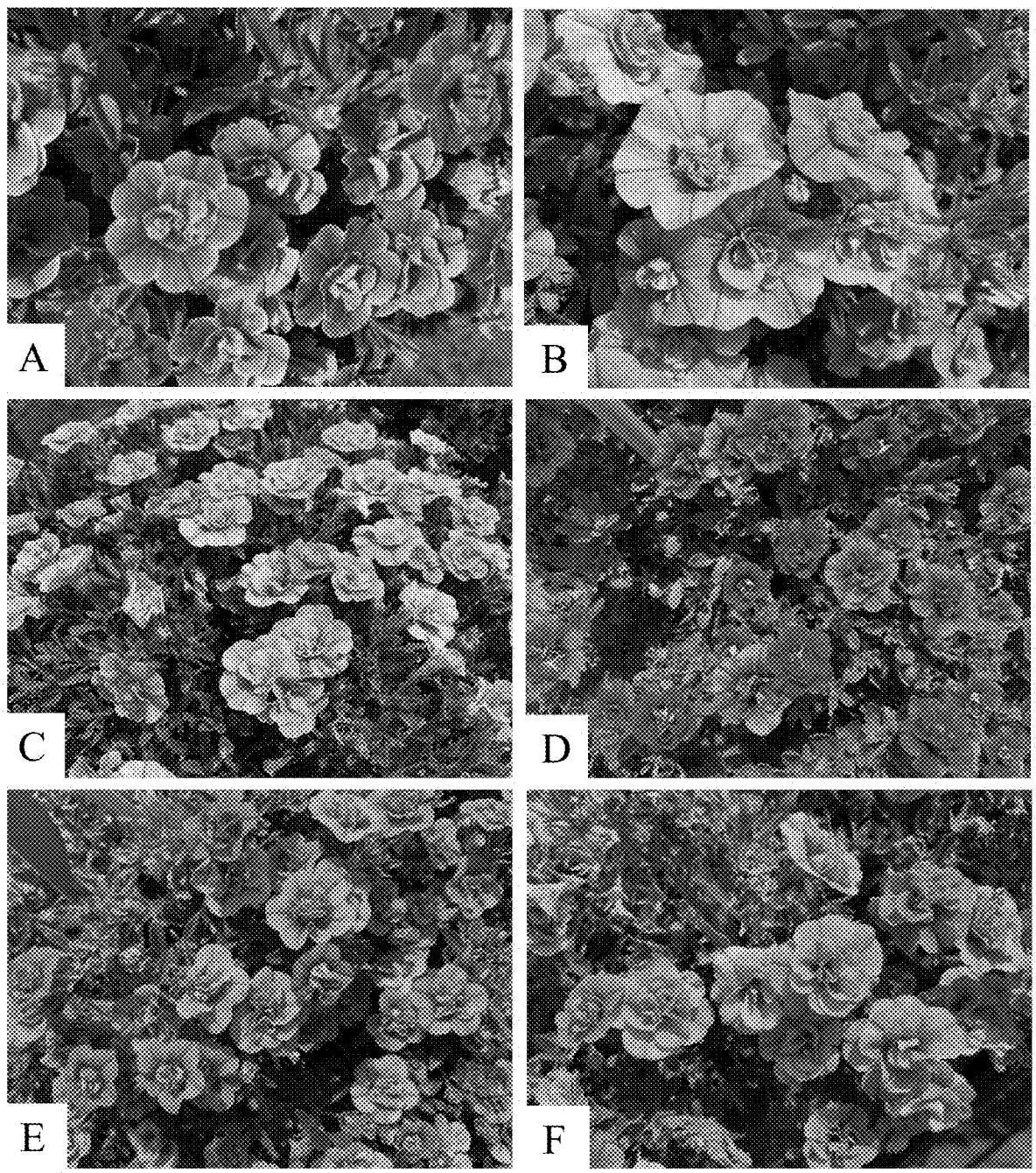
FIGS. 12A-12F are photographs of double-flowering dwarf Calibrachoa plants of the present disclosure having varying shades of pink colored flowers.

Example 6: Double-Flowering Dwarf *Calibrachoa* Varieties in Varying Shades of Pink Generated Using the Methods Disclosed Herein FIGS. 12A-12F, FIGS. 13A-13F, and FIGS. 14A-14D are close up photographs of double-flowering dwarf *Calibrachoa* plants of the present disclosure having varying shades of pink colored flowers. In FIG. 12A, a plant of a pink-purple variety is shown having a white color at the margin of the corolla lobes and designated CA-2020-0766. FIGS. 12B and 12C show plants of two purple-pink varieties designated CA-2020-0604 and CA-2020-0748 respectively. In FIG. 12D a plant of a dark pink-red variety having irregular magenta and yellow colored petaloids, designated CA-2020-0775, is shown. FIGS. 12E and 12F show plants of two dark pink varieties having strong veins, designated CA-2020-0772 and CA-2020-0762 respectively.

Figures 13A, 13B, 13C, 13D, 13E, 13F:
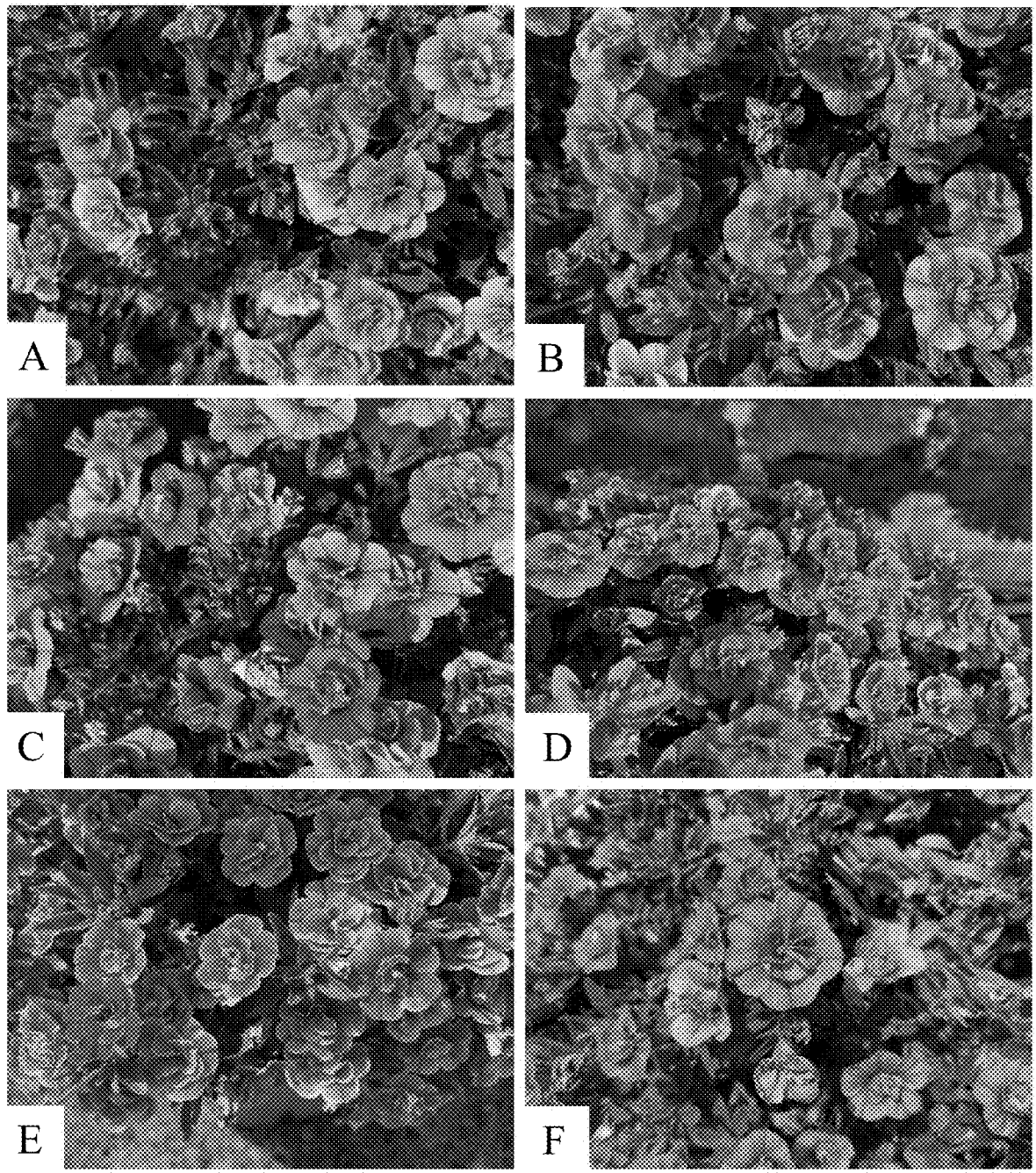
FIGS. 13A-13F are photographs of double-flowering dwarf Calibrachoa plants of the present disclosure having varying shades of pink colored flowers.

FIG. 13A (CA-2020-0784), FIG. 13B (CA-2020-0782) and FIG. 13C (CA-2020-0780) show plants of three purple-pink varieties. FIG. 13D shows a plant of a dark pink-red variety designated CA-2020-0778. In FIG. 13E, a plant of variety CA-2019-5055 is shown having pink flowers with a white color at the margin of the corolla lobes, and FIG. 13F shows a plant of a pink variety designated CA-2019-4954.

Figures 14A, 14B, 14C, 14D:
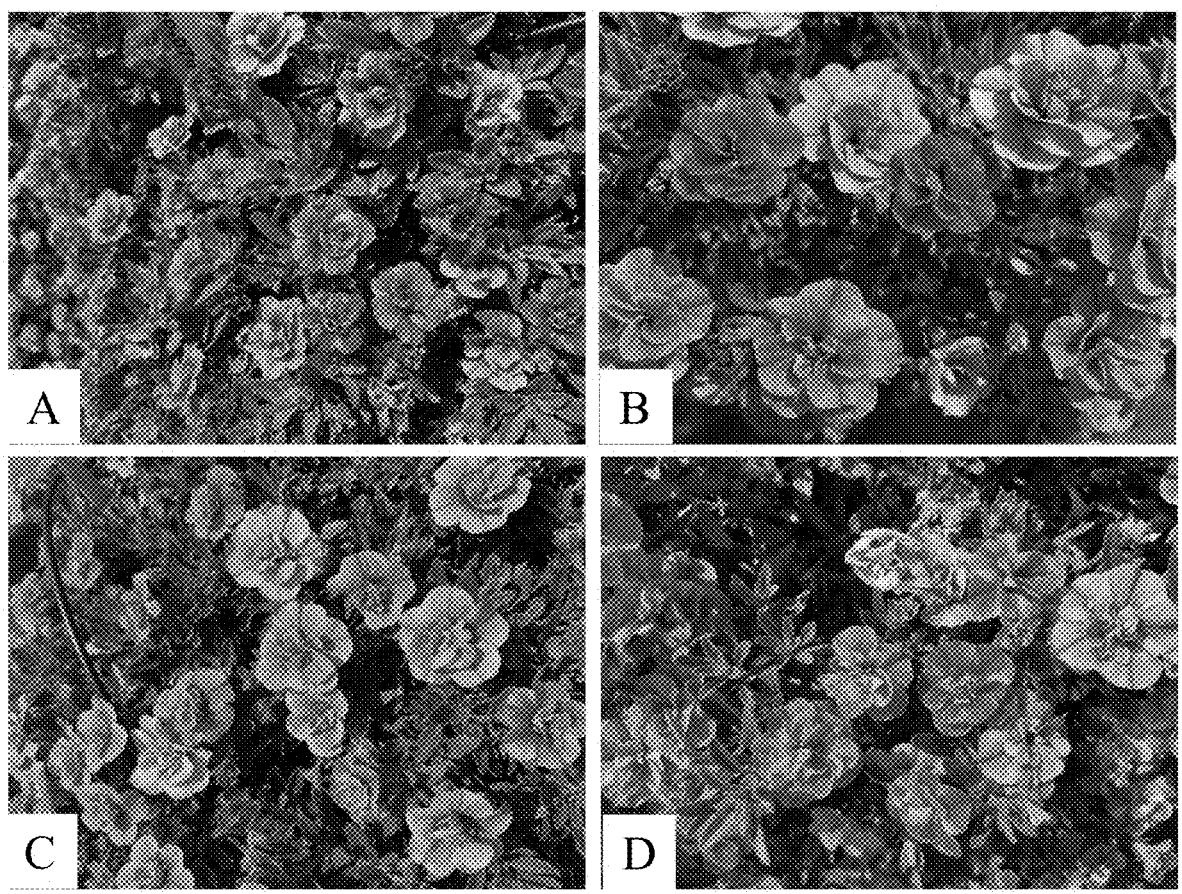
FIGS. 14A-14D are photographs of double-flowering dwarf Calibrachoa plants of the present disclosure having varying shades of pink colored flowers.

FIGS. 14A and 14B show plants of two purple-red varieties designated CA-2020-0763 and CA-2020-0755 respectively. FIG. 14C shows plants of a dark pink-red variety designated CA-2020-0788 and FIG. 14D shows a plant of a purple-pink variety designated CA-2020-0797.

Figures 15A, 15B, 15C, 15D, 15E, 15F:
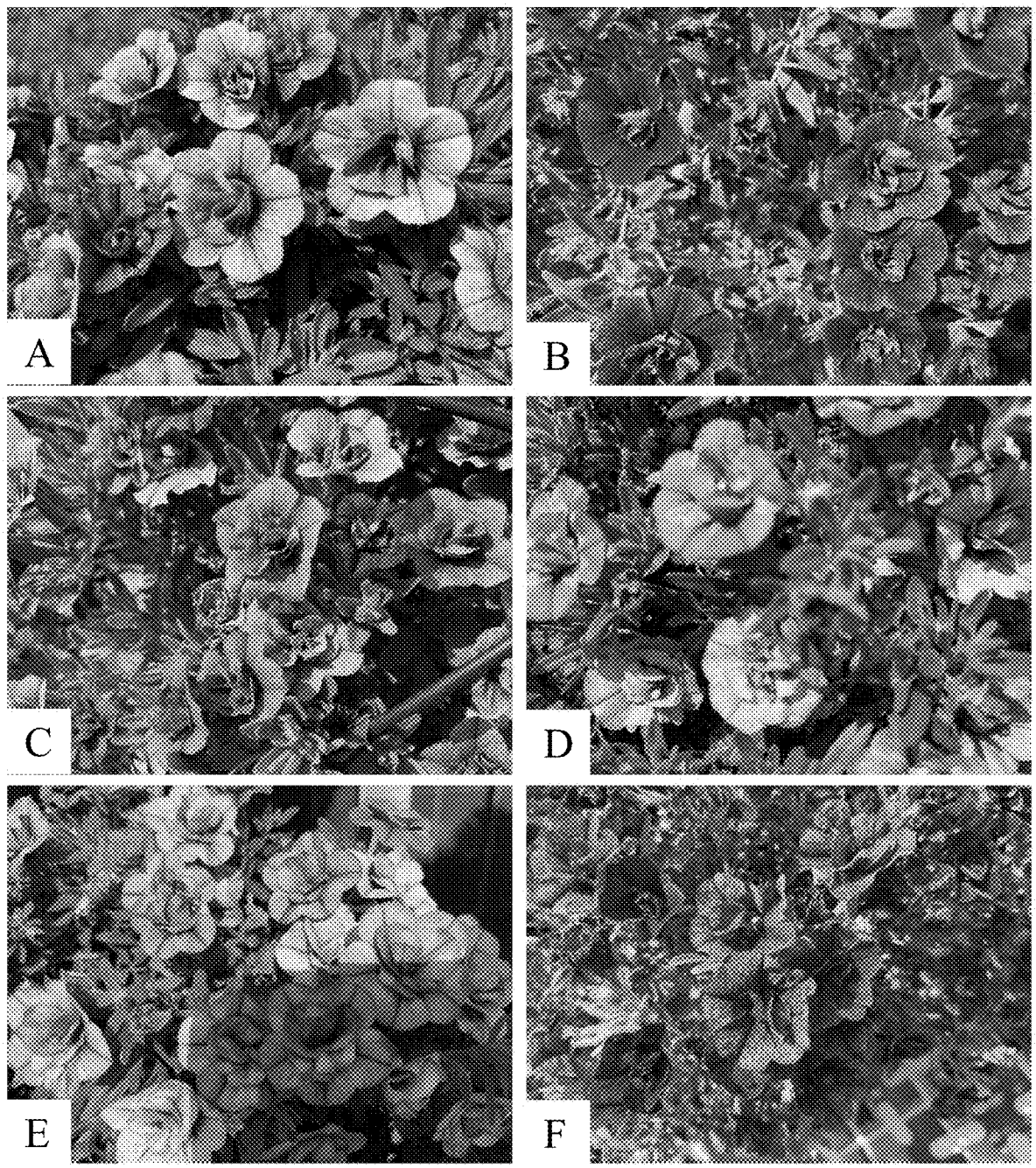
FIGS. 15A-15F are photographs of double-flowering dwarf Calibrachoa plants of the present disclosure having varying shades of purple colored flowers.

Example 7: Double-Flowering Dwarf *Calibrachoa* Varieties in Varying Shades of Purple Generated Using the Methods Disclosed Herein FIGS. 15A-15F are close up photographs of double-flowering dwarf *Calibrachoa* plants of the present disclosure having varying shades of purple colored flowers. FIGS. 15A and 15B show plants of two dark pink-violet varieties having strong veins, designated CA-2020-0842 and CA-2020-0708 respectively. FIG. 15C shows a plant of a brown-orange variety with strong purple veins designated CA-2020-0837. FIG. 15D shows a plant of a light violet variety having medium violet veins, designated CA-2020-0843. FIG. 15E shows a plant of a violet variety designated CA-2020-0846, and FIG. 15F shows a plant of a purple variety with strong veins, designated CA-2019-5258.

Figures 16A, 16B, 16C, 16D, 16E, 16F:
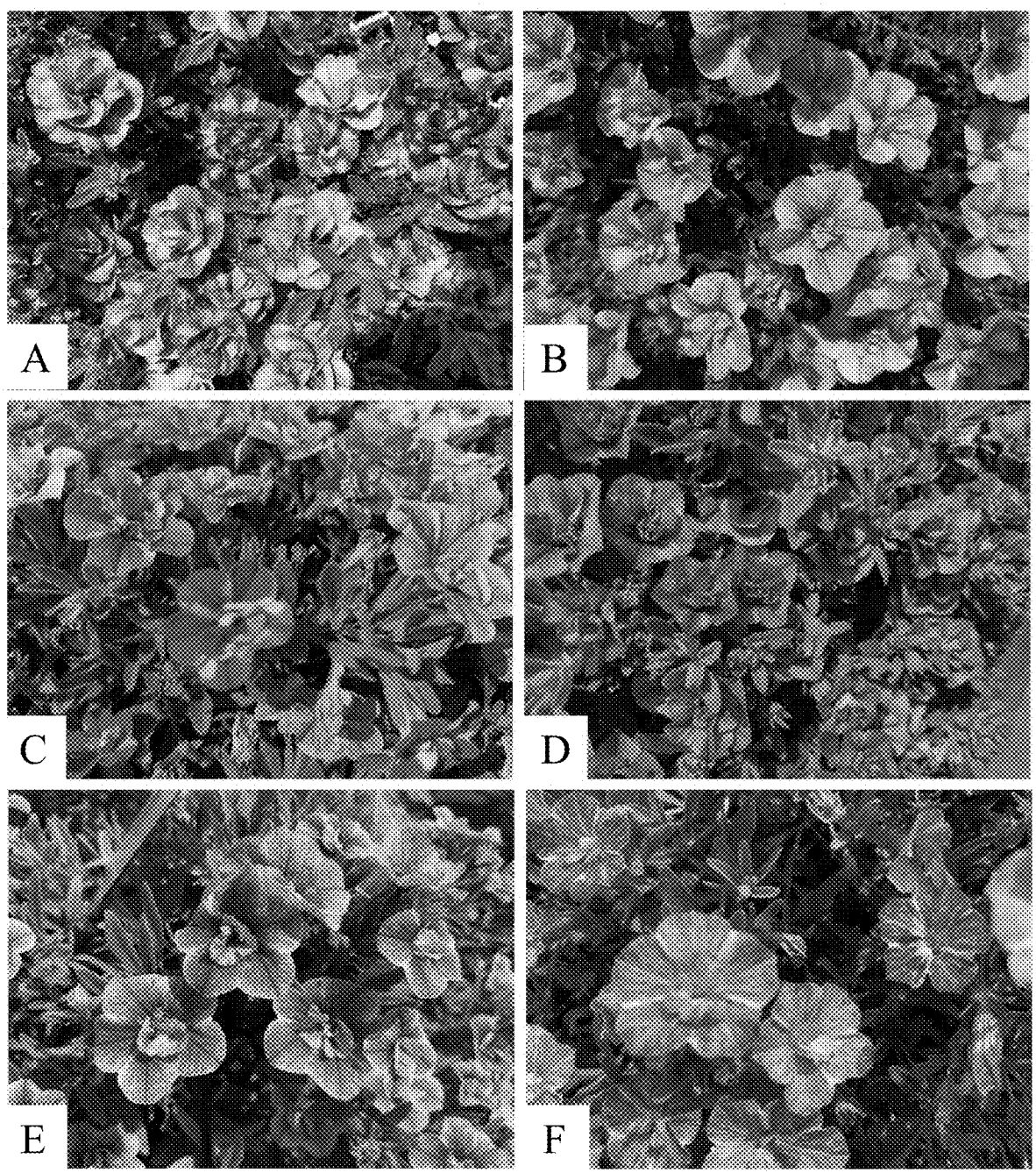
FIGS. 16A-16F are photographs of double-flowering dwarf Calibrachoa plants of the present disclosure having patterns in different main and secondary colored flowers.

Example 8: Double-Flowering Dwarf *Calibrachoa* Varieties in Varying Colors and Patterns Generated Using the Methods Disclosed Herein FIGS. 16A-16F are close up photographs of double-flowering dwarf *Calibrachoa* plants of the present disclosure having varying colors and patterns. FIG. 16A shows a plant of a variety designated CA-2019-5264 having light purple flowers with a darker purple color at the distal part of the corolla lobes. FIG. 16B shows a plant of a variety designated CA-2020-0900 having red-pink flowers with a broad yellow color along the fused parts of the corolla lobes. FIG. 16C shows a plant of a variety designated CA-2020-0765 having pink-purple flowers with irregular light-pink color distribution. FIG. 16D shows a plant of a variety designated CA-2020-0812 having orange-red flowers with irregular yellow color distribution. FIG. 16E shows a plant of a variety designated CA-2020-0680 having pink-purple flowers with a small area of black at the transition to the corolla tube and a white margin on the corolla lobes. FIG. 16F shows a plant of a variety designated CA-2020-0589 having pink-purple flowers with irregular white color distribution.

Figures 17A, 17B, 17C, 17D, 17E, 17F:
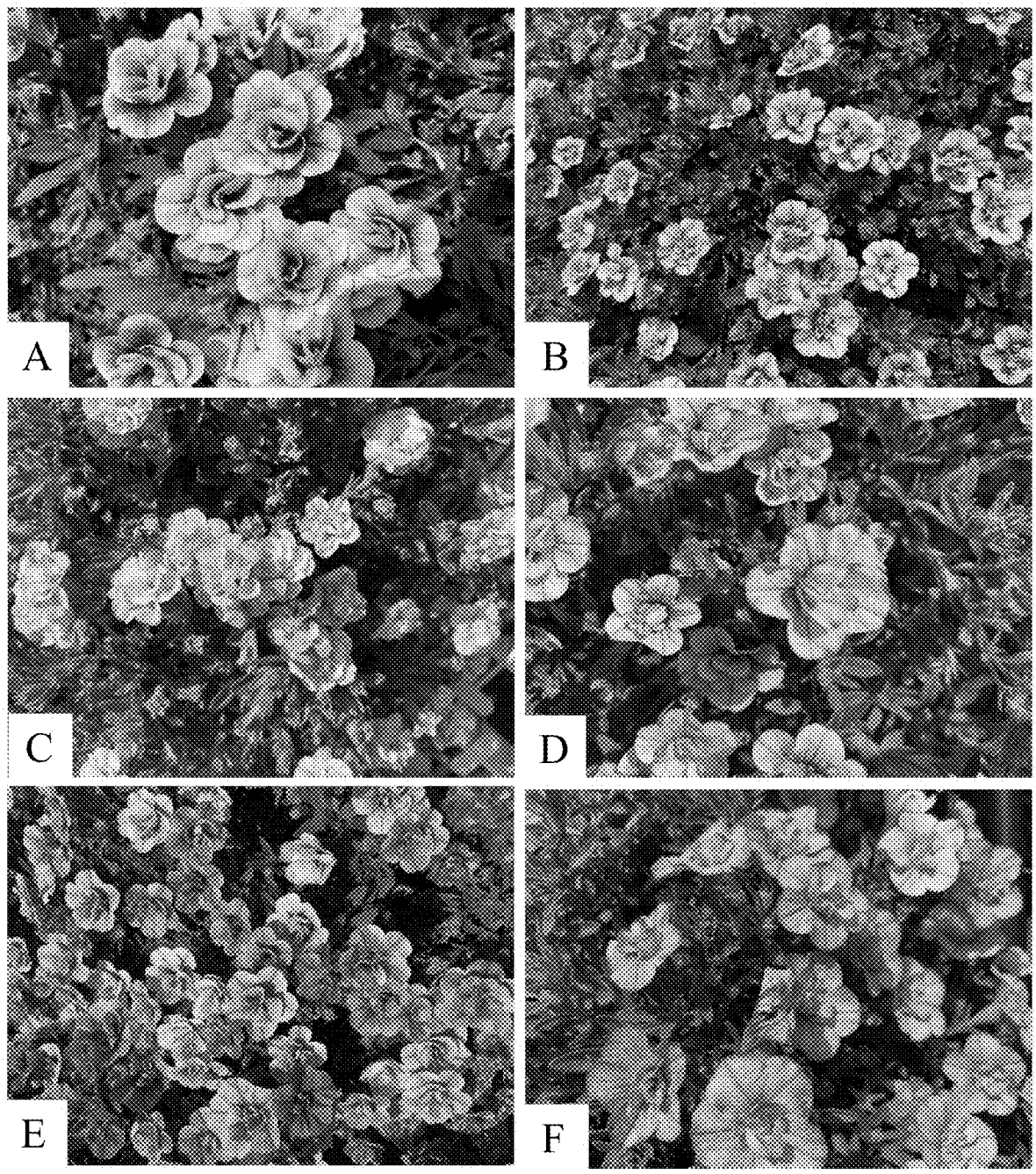
FIGS. 17A-17F are photographs of double-flowering dwarf Calibrachoa plants of the present disclosure having different colored flowers with contrasting veins and flowers with color change during growing season.

Example 9: Double-Flowering Dwarf *Calibrachoa* Varieties in Varying Colors with Contrasting Veins Generated Using the Methods Disclosed Herein FIGS. 17A-17F are close up photographs of double-flowering dwarf *Calibrachoa* plants of the present disclosure having different colored flowers with contrasting veins. Shown in FIG. 17A is a plant of a purple variety with white margins on the corolla lobes and dark purple veins, designated CA-2020-5194. Shown in FIG. 17B is a plant of a light yellow-orange variety with strong red veins, designated CA-2020-0773. Shown in FIG. 17C is a plant of a light yellow variety with very strong purple veins, designated CA-2016-8659. Shown in FIG. 17D is a plant of a light yellow variety with very strong red veins, designated CA-2020-0612. In FIG. 17E, a plant of a purple-red variety with strong pink veins designated CA-2020-0790 is shown, and in FIG. 17F, a plant of variety designated CA-2020-0923 having light yellow flowers with strong red veins and a red color at the margin of corolla tubes is shown.

Figures 18A, 18B, 18C, 18D, 18E, 18F:
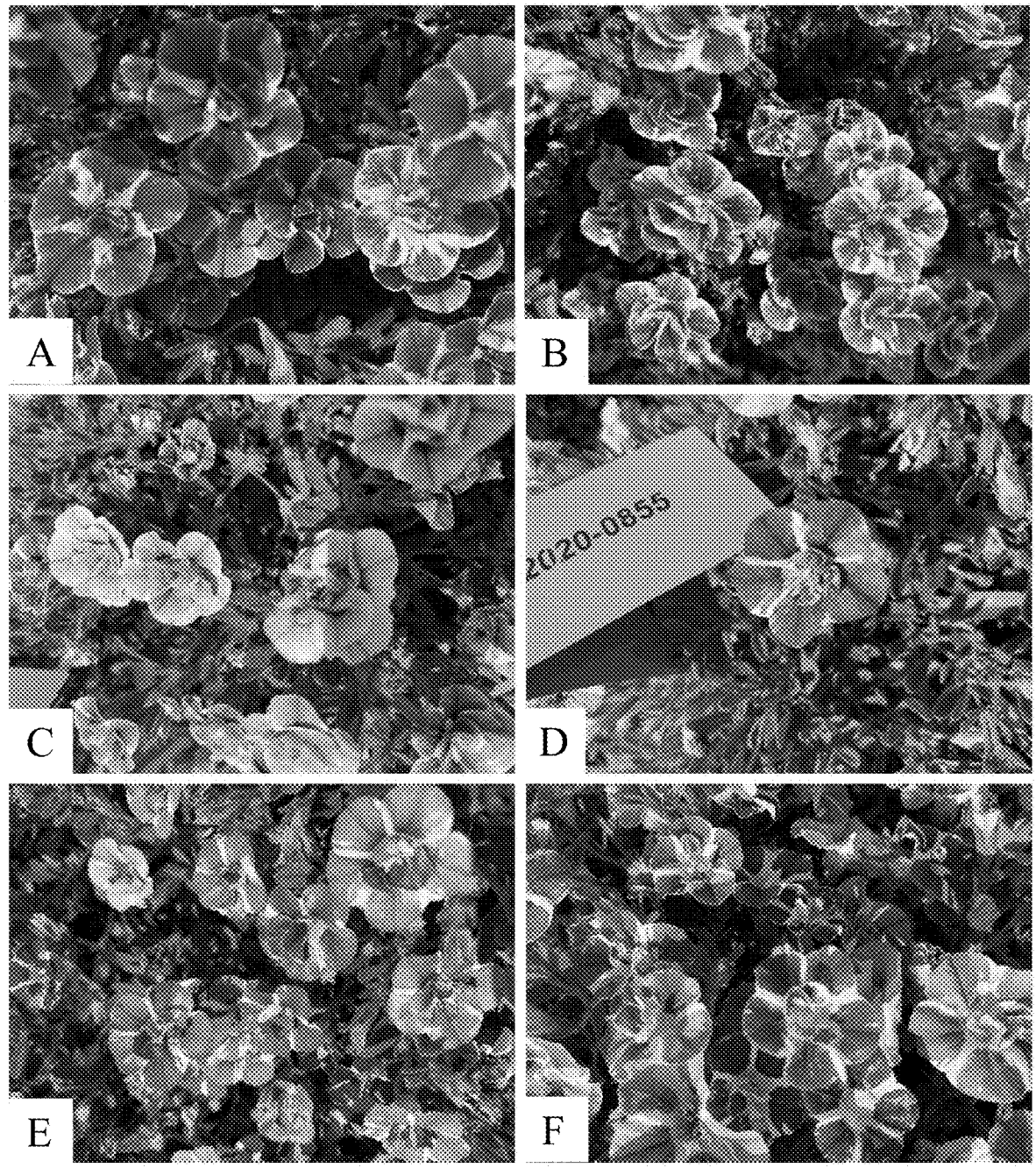
FIGS. 18A-18F are photographs of double-flowering dwarf Calibrachoa plants of the present disclosure having different main colored flowers and variations of secondary flower color distribution.

Example 10: Double-Flowering Dwarf *Calibrachoa* Varieties in Varying Colors with Variations of the Star Pattern Generated Using the Methods Disclosed Herein FIGS. 18A-18F are close up photographs of double-flowering dwarf *Calibrachoa* plants of the present disclosure having different colored flowers and variations of the star pattern. Shown in FIGS. 18A and 18B are plants of two varieties, designated CA-2020-0579 and CA-2020-0581 respectively, having pink-purple flowers with very large yellow markings at the transition to the corolla tube and a white color along the fused parts of the corolla lobes. In FIGS. 18C and 18D, plants of violet and dark violet varieties designated CA-2020-0854 and CA-2020-0855 respectively are shown having a white color along the fused parts of the corolla lobes. FIGS. 18E and 18F show plants of two varieties, designated CA-2020-0856 and CA-2020-0857 respectively, having dark pink-violet flowers with a white color along the fused parts of the corolla lobes.

Figures 19A, 19B, 19C, 19D, 19E, 19F:
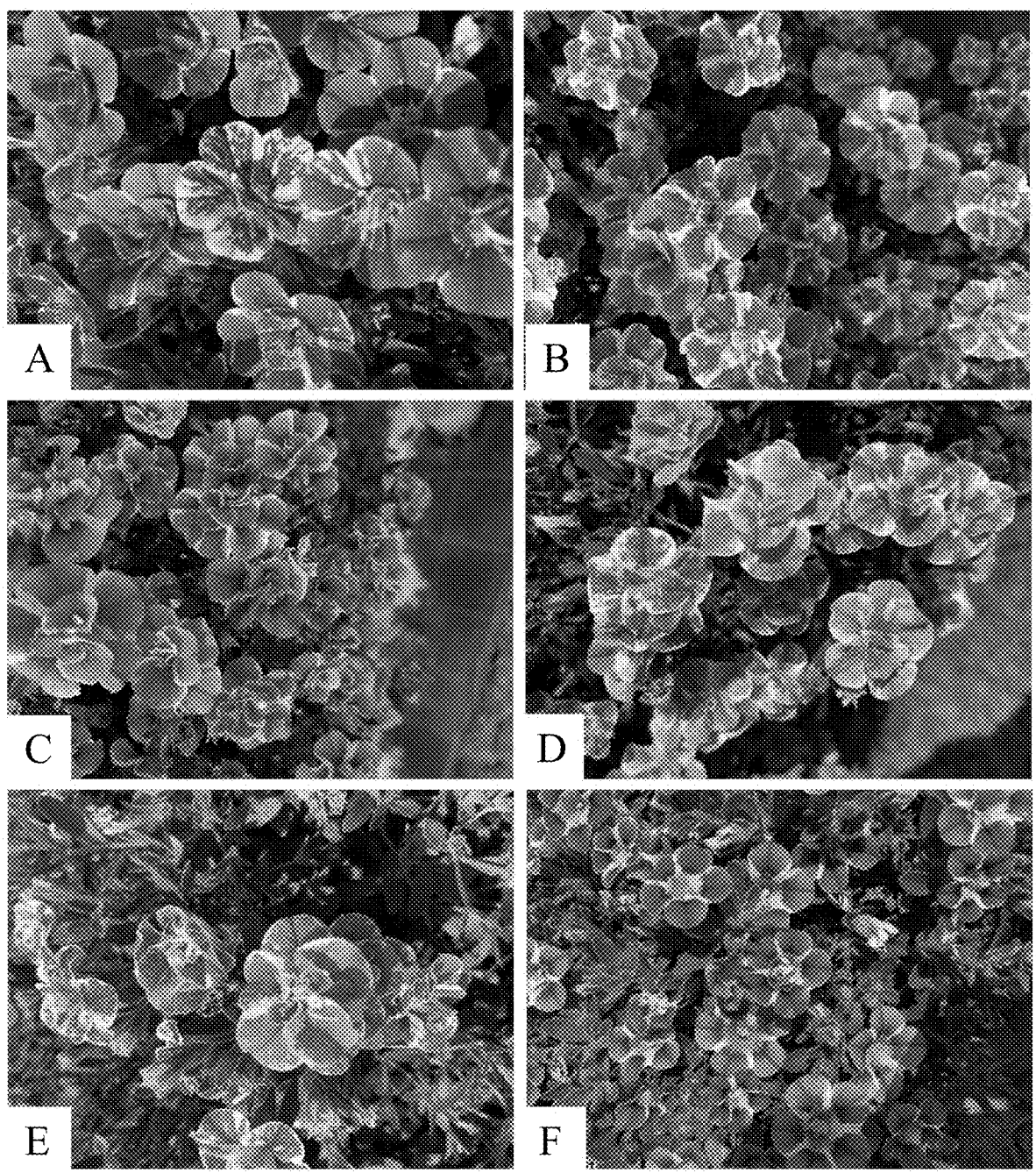
FIGS. 19A-19F are photographs of double-flowering dwarf Calibrachoa plants of the present disclosure having different main colored flowers and variations of secondary flower color distribution.

Example 11: Double-Flowering Dwarf *Calibrachoa* Varieties in Varying Shades of Pink-Purple with the Star Pattern Generated Using the Methods Disclosed Herein FIGS. 19A-19F are close up photographs of double-flowering dwarf *Calibrachoa* plants of the present disclosure in varying shades of pink-purple with the star pattern, all having some degree of white coloration along the fused parts of the corolla lobes. FIG. 19A shows a plant of variety designated CA-2020-0862, which also exhibits some irregular white color distribution in addition to the star pattern. FIG. 19B shows a plant of variety designated CA-2020-0864. FIGS. 19C and 19D show plants of varieties designated CA-2020-0870 and CA-2020-0883, respectively, and FIG. 19E shows a plant of a variety designated CA-2020-0875. FIG. 19F shows a plant of a variety designated CA-2020-0889 having a milder double-flowering phenotype, with an additional darker color at the transition to the corolla tube.

Figures 20A, 20B, 20C, 20D:
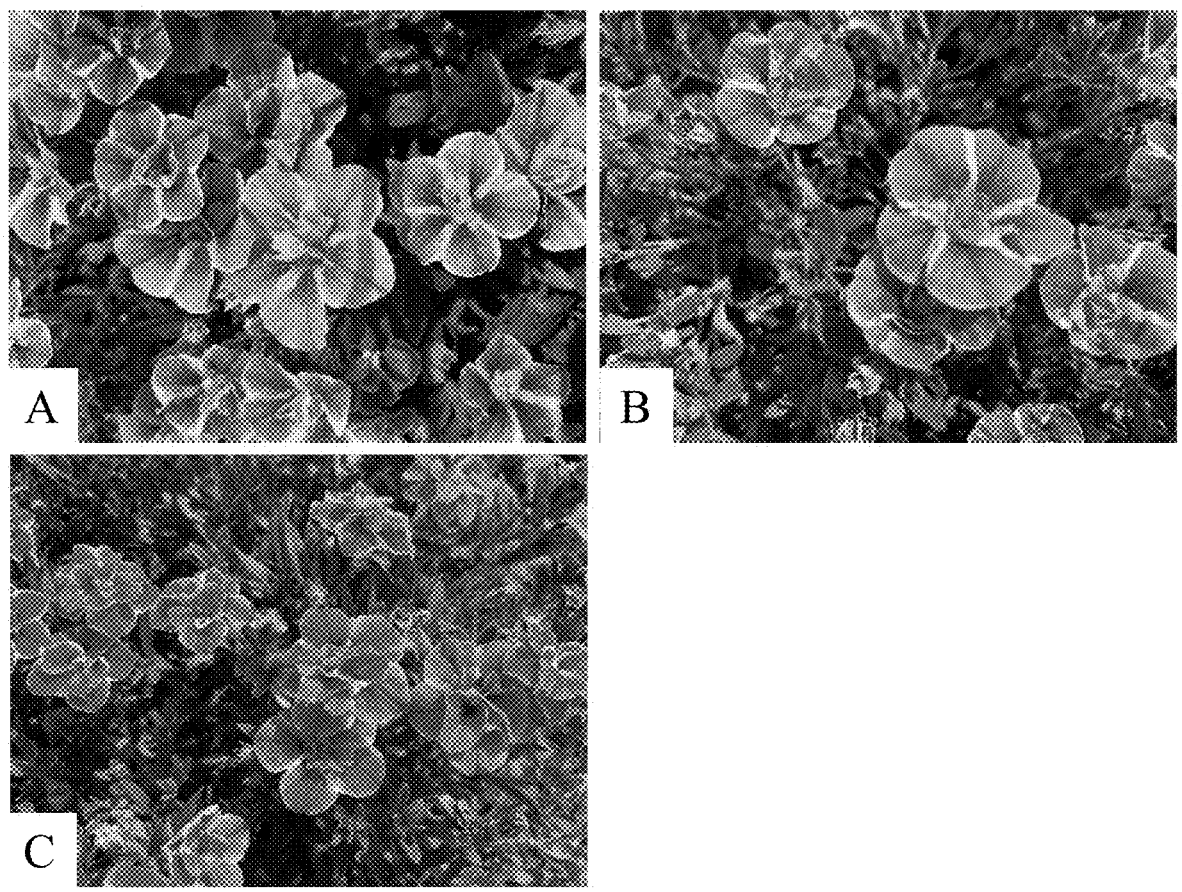
FIGS. 20A-20C are photographs of double-flowering dwarf Calibrachoa plants of the present disclosure having different main colored flowers and variations of secondary flower color distribution.

Example 12: Double-Flowering Dwarf *Calibrachoa* Varieties in Different Colors with Variations of the Star Pattern Generated Using the Methods Disclosed Herein FIGS. 20A-20D are close up photographs of double-flowering dwarf *Calibrachoa* plants of the present disclosure having different colored flowers and variations of the star pattern. A plant of a red variety having yellow along the fused parts of the corolla lobes, designated CA-2019-5092 is shown in FIG. 20A. A plant of a purple-pink variety designated CA-2020-0678 with medium white color along the fused parts of the corolla lobes is shown in FIG. 20B. FIG. 20C shows a plant of a variety designated CA-2020-0750 having purple-pink flowers with white margins of the corolla lobes.

Figures 21A, 21B, 21C, 21D, 21E, 21F:
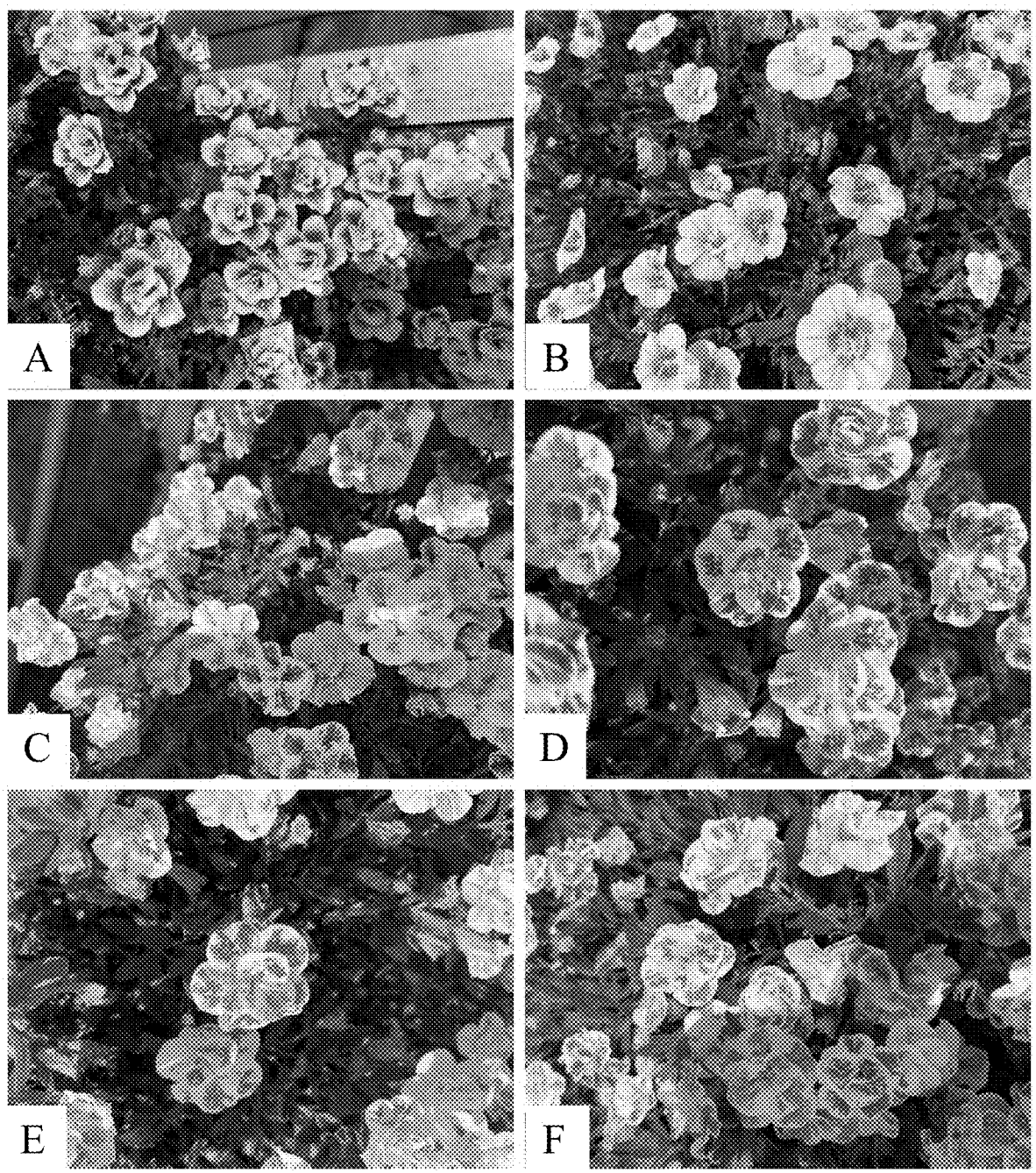
FIGS. 21A-21F are photographs of double-flowering dwarf Calibrachoa plants of the present disclosure having different main colored flowers showing variations of secondary flower color distribution and flowers with color change during growing season.

Example 13: Double-Flowering Dwarf *Calibrachoa* Varieties in Different Colors with Variations of White Margins Generated Using the Methods Disclosed Herein FIGS. 21A-21F are close up photographs of double-flowering dwarf *Calibrachoa* plants of the present disclosure having different colored flowers and varying amounts of white coloration at the distal portions of the corolla lobes. Shown in FIG. 21A is a plant of a purple variety designated CA-2017-1140 having a white margin of the corolla lobes. FIG. 21B shows a plant of a variety designated CA-2020-0907 having purple-pink flowers with white at the distal part of the corolla tubes. FIG. 21C shows a plant of a violet variety designated CA-2020-0899 having a white color at the margin of the corolla lobes. FIGS. 21D-21F show plants of purple-pink varieties having a white color at the margin of the corolla lobes designated CA-2020-0868, CA-2020-0869, and CA-2020-0894, respectively.

Example 14: Generating a Double-Flowering and/or Dwarf *Calibrachoa* Via a Gene Editing Tool or Technology In the event that the SNP mutations disclosed herein are the causative SNP mutations for the double-flowering and/or dwarf trait, single flowering vigorous *Calibrachoa* plants may be converted to a double-flowering and/or dwarf phenotype by targeted genetic engineering. Such methods may include, for example, the CRISPR system. Many plants have already been modified using the CRISPR system, for example *Petunia*, a close relative of *Calibrachoa*. See for example, Zhang, B. et al., "Exploiting the CRISPR/Cas9 System for Targeted Genome Mutagenesis in *Petunia*" *Science Reports*, Vol. 6, February 2016.

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing in *Calibrachoa*. The technique is well known in the art; see for example Malzahn, Aimee et al. "Plant genome editing with TALEN and CRISPR" *Cell & Bioscience* vol. 7 21. 24 Apr. 2017.

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in *Advances in New Technology for Targeted Modification of Plant Genomes.* Springer Science+Business. pp 21-38 (2015).

Example 15: Double-Flowering Dwarf *Petunia-Calibrachoa* (Petchoa) Hybrids

*Petunia* and *Calibrachoa* are closely related. In the 1990's, several species of *Petunia* were crossed with *Calibrachoa*. The resulting hybrid offspring was named Petchoa. The double-flowering dwarf *Calibrachoa* plants disclosed herein can be used in a plant breeding program to produce double-flowering dwarf Petchoas. For example, a female double-flowering dwarf *Calibrachoa* may be crossed with a male *Petunia* carrying at least one allele for a dwarf trait. Embryos may be rescued and cultured by techniques well known in the art, and the plant(s) can be grown and further propagated by tissue culture and cuttings.

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Further, European Application No. EP20202350.3, filed Oct. 16, 2020, and entitled: Double-Flowering Dwarf *Calibrachoa* is hereby incorporated by reference.

Numbered Embodiments

Further embodiments contemplated by the disclosure are listed below.
1. A *Calibrachoa* plant comprising a double-flowering characteristic and a dwarf growth characteristic, wherein said double-flowering characteristic is caused by a mitochondrial allele associated with at least one single nucleotide polymorphism (SNP) mutation selected from the group consisting of (i) a G to C nucleotide substitution at position number 320 of SEQ ID NO: 1 and (i) an A to C nucleotide substitution at position number 247 in SEQ ID NO: 1, and wherein said dwarf growth characteristic is caused by a homozygous recessive nuclear allele associated with a SNP mutation consisting of a G to C nucleotide substitution at position 43 of SEQ ID NO: 2.
2. The *Calibrachoa* plant of embodiment 1, wherein said plant has a petaloid stamina rating of at least 2.
3. The *Calibrachoa* plant of embodiment 1, wherein said plant has a petaloid stamina rating of at least 3.
4. The *Calibrachoa* plant of embodiment 1, wherein said plant has a petaloid stamina rating of at least 4.
5. The *Calibrachoa* plant of embodiment 1, wherein said plant has a petaloid stamina rating of at least 5.
6. The *Calibrachoa* plant of embodiment 1, wherein said plant has a petaloid stamina rating of at least 6.
7. The *Calibrachoa* plant of any one of embodiments 1-6, where said plant comprises both the G to C nucleotide substitution at position number 320 of SEQ ID NO: 1 and (i) the A to C nucleotide substitution at position number 247 in SEQ ID NO: 1.
8. The *Calibrachoa* plant of any one of embodiments 1-7, wherein said plant at maturity has a vigor rating of less than 5 compared to plants having a non-dwarf growth characteristic when grown under the same environmental conditions, wherein said non-dwarf plant has at least one copy of the allele associated with a SNP mutation consisting of a G at position 43 of SEQ ID NO: 2.
9. The *Calibrachoa* plant of any one of embodiments 1-6, wherein said plant at maturity has a vigor rating of less than 4 compared to plants having a non-dwarf growth characteristic when grown under the same environmental conditions, wherein said non-dwarf plant has at least one copy of the allele associated with a SNP mutation consisting of a G at position 43 of SEQ ID NO: 2.
10. The *Calibrachoa* plant of any one of embodiments 1-6, wherein said plant at maturity has a vigor rating of less than 3 compared to plants having a non-dwarf growth characteristic when grown under the same environmental conditions, wherein said non-dwarf plant has at least one copy of the allele associated with a SNP mutation consisting of a G at position 43 of SEQ ID NO: 2.
11. The *Calibrachoa* plant of any one of embodiments 1-10, wherein said plant exhibits male sterility.
12. The *Calibrachoa* plant of any one of embodiments 1-11, wherein said plant is grown without the addition of synthetic plant growth regulators.
13. The *Calibrachoa* plant of any one of embodiments 1-12, wherein said plant comprises no detectable residue of a synthetic plant growth regulator or a related breakdown of a plant growth regulator product.
14. The *Calibrachoa* plant of any one of embodiments 1-13, wherein said plant further comprises a mutation affecting flower color and/or flower color pattern, wherein said mutation is the result of an induced random or targeted mutagenesis.
15. The *Calibrachoa* plant of embodiment 14, wherein said targeted mutagenesis is a gene editing tool or technology.
16. The *Calibrachoa* plant of embodiment 15, wherein the gene editing tool or technology is selected from the group consisting of homing endonucleases/meganucleases (EMNs), zinc finger nucleases (ZFNs), transcription activator-like effector nucleases (TALENs), and CRISPR/Cas enzymes.
17. A method of producing a *Calibrachoa* plant comprising a double-flowering characteristic and a dwarf growth characteristic comprising the steps of:
(i) crossing a first female *Calibrachoa* plant with a first male *Calibrachoa* plant to produce $F_1$ plants, wherein said first female *Calibrachoa* plant comprises a mitochondrial allele associated with at least one SNP mutation selected from the group consisting of (i) a G to C nucleotide substitution at position number 320 of SEQ ID NO: 1 and (ii) an A to C nucleotide substitution at position number 247 in SEQ ID NO: 1 and exhibiting a double-flowering characteristic, and wherein said first male *Calibrachoa* plant has at least one copy of a nuclear, recessive allele associated with a SNP mutation consisting of a G to C nucleotide substitution at position 43 of SEQ ID NO: 2, wherein when said nuclear allele is in the homozygous form, plants exhibit a dwarf growth characteristic;
(ii) screening said $F_1$ plants for the presence of said nuclear SNP mutation;
(iii) selecting an $F_1$ female plant exhibiting said double-flowering characteristic and further comprising at least one copy of said nuclear SNP mutation;
(iv) crossing said $F_1$ female plant with said first male or a second male *Calibrachoa* plant having at least one copy said nuclear SNP mutation to produce $F_2$ plants;
(v) screening said $F_2$ plants for the presence of said nuclear SNP mutation; and
(vi) selecting an $F_2$ plant exhibiting said double-flowering characteristic and being homozygous for said nuclear SNP mutation.

18. The method of embodiment 17, wherein said first female *Calibrachoa* plant comprises both the G to C nucleotide substitution at position number 320 of SEQ ID NO: 1 and (i) the A to C nucleotide substitution at position number 247 in SEQ ID NO: 1.

19. The method of embodiment 17 or 18, wherein the first or second male *Calibrachoa* plant is homozygous for said nuclear SNP mutation and exhibits a dwarf growth characteristic.

20. The method of any one of embodiment 17-19, further comprising asexual propagation or sexual reproduction of said selected $F_2$ plant.

21. A plant produced by the method of any one of embodiments 17-20, wherein said plant is asexually propagated and grown without synthetic growth regulators.

22. A *Calibrachoa* plant produced by the method of any one of embodiments 17-20, wherein said plant has a petaloid stamina rating of at least three and wherein said plant at maturity has a vigor rating of less than 5 compared to plants having a non-dwarf growth characteristic when grown under the same environmental conditions, wherein said non-dwarf plant has at least one copy of the allele associated with a SNP mutation consisting of a G at position 43 of SEQ ID NO: 2.

23. A *Calibrachoa* plant produced by the method of any one of embodiments 17-21, wherein said plant has a petaloid stamina rating of at least 4.

24. A *Calibrachoa* plant produced by the method of any one of embodiments 17-21, wherein said plant has a petaloid stamina rating of at least 5.

25. A *Calibrachoa* plant produced by the method of any one of embodiments 17-21, wherein said plant has a petaloid stamina rating of at least 6.

26. A *Calibrachoa* plant produced by the method of any one of embodiments 17-21, wherein said plant has a petaloid stamina rating of at least 7.

27. A *Calibrachoa* plant produced by the method of any one of embodiments 17-21, wherein said plant at maturity has a vigor rating of less than 4 compared to plants having a non-dwarf growth characteristic when grown under the same environmental conditions, wherein said non-dwarf plant has at least one copy of the allele associated with a SNP mutation consisting of a G at position 43 of SEQ ID NO: 2.

28. A *Calibrachoa* plant produced by the method of any one of embodiments 17-21, wherein said plant at maturity has a vigor rating of less than 3 compared to plants having a non-dwarf growth characteristic when grown under the same environmental conditions, wherein said non-dwarf plant has at least one copy of the allele associated with a SNP mutation consisting of a G at position 43 of SEQ ID NO: 2.

29. The *Calibrachoa* plant of any one of embodiments 17-28 further comprising a mitochondrial allele associated with an A to C nucleotide substitution at position number 247 in SEQ ID NO: 1.

30. The *Calibrachoa* plant of any one of embodiments 17-29, wherein said plant exhibits male sterility.

31. The *Calibrachoa* plant of any one of embodiments 17-30, wherein said plant further comprises a mutation affecting flower color and/or flower color pattern, wherein said mutation is the result of an induced random or targeted mutagenesis.

32. The *Calibrachoa* plant of embodiment 30, wherein said targeted mutagenesis is a gene editing tool or technology.

33. The *Calibrachoa* plant of embodiment 32, wherein the gene editing tool or technology is selected from the group consisting of homing endonucleases/meganucleases (EMNs), zinc finger nucleases (ZFNs), transcription activator-like effector nucleases (TALENs), and CRISPR/Cas enzymes.

34. A method for producing a double-flowering dwarf *Calibrachoa* plant having a desired trait comprising applying a plant breeding technique to the *Calibrachoa* plant of any one of embodiments 21-29.

35. The method of embodiment 34, wherein said plant breeding technique is selected from the group consisting of recurrent selection, mass selection, hybridization, open-pollination, backcrossing, pedigree breeding, mutation breeding, and marker enhanced selection.

36. The method of embodiment 35, wherein said plant breeding technique is mutation breeding and the mutation selected is spontaneous or artificially induced.

37. A plant produced by the method of any one of embodiments 34-36, wherein said plant exhibits dwarf growth, double-flowering, and the desired trait.

38. The plant of any one of embodiments 34-37, wherein the desired trait is flower color and/or flower color pattern.

39. The plant of any one of embodiments 34-37, wherein the desired trait is tolerance or resistance to a disease or pest.

40. The plant of any one of embodiments 34-37, wherein the desired trait is tolerance or resistance to abiotic or biotic stress.

41. A molecular marker for distinguishing a plant having an allele for a double-flowering characteristic comprising at least one sequence selected from the group consisting of SEQ ID NO: 1, fragments of at least 20 consecutive nucleotides thereof, and complementary sequences thereof 42. A method for distinguishing a plant having a mitochondrial allele for a double-flowering characteristic, comprising: using the molecular marker of embodiment 41 and detecting at least one SNP mutation selected from the group consisting of (i) a C nucleotide at position number 320 of SEQ ID NO: 1 and (ii) a C nucleotide at position number 247 in SEQ ID NO: 1.

43. A method for distinguishing a plant having a mitochondrial allele for a double-flowering characteristic, comprising: using the molecular marker of embodiment 41 and detecting at least one of a G nucleotide at position number 320 of SEQ ID NO: 1 and an A nucleotide at position number 247 in SEQ ID NO: 1.

44. The method of embodiment 42 or 43, wherein said molecular marker is detected by Restriction Fragment Length Polymorphisms (RFLPs), Dynamic Allele-Specific Hybridization (DASH), molecular beacon, SNP microarray, PCR-based method, Flap endonuclease (FEN), Single-strand conformation polymorphism, temperature gradient gel electrophoresis, Denaturing High Performance Liquid Chromatography (DHPLC), DNA mismatch binding proteins, or sequencing.

45. A molecular marker for distinguishing a plant having at least one allele for a dwarf growth characteristic comprising at least one sequence selected from the group consisting of SEQ ID NO: 2, fragments of at least 20 consecutive nucleotides thereof, and complementary sequences thereof.

46. A method for distinguishing a plant having at least one allele for a dwarf growth characteristic, comprising: using the molecular marker of embodiment 45 and detecting a C nucleotide at position 43 of SEQ ID NO: 2.

47. A method for distinguishing a plant having at least one allele for a dwarf growth characteristic, comprising: using the molecular marker of embodiment 45 and detecting a G nucleotide at position 43 of SEQ ID NO: 2.

48. The method of embodiment 46 or 47, wherein said molecular marker is detected by Restriction Fragment Length Polymorphisms (RFLPs), Dynamic Allele-Specific Hybridization (DASH), molecular beacon, SNP microarray, PCR-based method, Flap endonuclease (FEN), Single-strand conformation polymorphism, temperature gradient gel electrophoresis, Denaturing High Performance Liquid Chromatography (DHPLC), DNA mismatch binding proteins, or sequencing.

49. A method for distinguishing a plant having a mitochondrial allele for a double-flowering characteristic comprising
obtaining genetic material;
obtaining a nucleic acid, wherein said nucleic acid has at least a portion of sequence complementary to the molecular marker of embodiment 41; and base-pairing said nucleic acid with said genetic material and examining the result of said base-pairing.

50. The method of embodiment 49, wherein said genetic material is deoxyribonucleic acid, ribonucleic acid, or a combination thereof 51. The method of embodiment 49, wherein said nucleic acid is a primer set, a probe, or combination thereof 52. A method for distinguishing a plant having at least one allele for a dwarf growth characteristic comprising
obtaining genetic material;
obtaining a nucleic acid, wherein said nucleic acid has at least a portion of sequence complementary to the molecular marker of embodiment 45; and base-pairing said nucleic acid with said genetic material and examining the result of said base-pairing.

53. The method of embodiment 52, wherein said genetic material is deoxyribonucleic acid, ribonucleic acid, or a combination thereof 54. The method of embodiment 52, wherein said nucleic acid is a primer set, a probe, or combination thereof 55. A plant distinguished by the marker of embodiment 45 or the method of any one of embodiments 46-47 or 52-54, wherein said plant is homozygous for said allele for a dwarf growth characteristic, and wherein said plant is subsequently grown without growth regulators.

56. The plant of embodiment 55, wherein said plant comprises no detectable residue of a synthetic plant growth regulator or a related breakdown of a plant growth regulator product.

57. A method for producing a double-flowering dwarf *Calibrachoa* comprising providing a double-flowering *Calibrachoa* plant and crossing it with a dwarf *Calibrachoa* plant.

58. A method for producing a double-flowering dwarf *Calibrachoa* comprising providing a double-flowering *Calibrachoa* plant, wherein said plant is heterozygous for a dwarf allele, and producing a double haploid.

59. A method for producing a double-flowering dwarf *Calibrachoa* having a desired trait comprising providing a double-flowering dwarf *Calibrachoa* and applying a plant breeding technique to introduce a desired trait.

60. The method of embodiment 59, wherein said plant breeding technique is selected from the group consisting of recurrent selection, mass selection, hybridization, open-pollination, backcrossing, pedigree breeding, mutation breeding, and marker enhanced selection.

61. The method of embodiment 60, wherein said plant breeding technique is mutation breeding and the mutation selected is spontaneous or artificially induced.

62. A method for producing a double-flowering dwarf *Calibrachoa* plant having a desired trait comprising providing a double-flowering dwarf *Calibrachoa* plant and applying a gene editing tool or technology to introduce a desired trait.

63. The method of embodiment 62, wherein said gene editing tool or technology is random mutagenesis, targeted mutagenesis, transformation, an engineered nuclease, or a natural nuclease.

64. The method of embodiment 63, wherein the engineered or natural nuclease is selected from the group consisting of homing endonucleases/meganucleases (EMNs), zinc finger nucleases (ZFNs), and transcription activator-like effector nucleases (TALENs).

65. The method of embodiment 62, wherein said gene editing tool or technology is utilizing a clustered regularly interspaced short palindromic repeats (CRISPR)-Cas nuclease.

66. The method of embodiment 65, wherein the nuclease is selected from the group consisting of Cas9, Cas12a, CasX, CasY, and Cas12J (Casϕ).

67. A plant produced by the method of any one of embodiments 59-66, wherein said plant exhibits dwarf growth, double-flowering, and the desired trait.

68. The plant of embodiment 67, wherein the desired trait is flower color and/or flower color pattern.

69. The plant of embodiment 67, wherein the desired trait is tolerance or resistance to a disease or pest.

70. The plant of embodiment 67, wherein the desired trait is tolerance or resistance to abiotic or biotic stress.

71. A mitochondrial genome of a plant having a double-flowering characteristic, wherein said genome comprises SEQ ID NO: 7, or a sequence at least 90% identical thereto, and complementary sequences thereof 72. The mitochondrial genome of embodiment 71, wherein said genome is isolated.

73. A fragment of at least 20 consecutive nucleotides of the mitochondrial genome described by SEQ ID NO: 7 or its complementary sequence.
74. The fragment of embodiment 73, wherein said fragment is isolated.
75. A method of using an isolated sequence of embodiment 72 or an isolated sequence of the fragment of embodiment 74 in a *Calibrachoa* breeding program.
76. A method for identifying a plant comprising an allele for a double-flowering trait comprising using a fragment of at least 20 consecutive nucleotides of SEQ ID NO: 7 or the complementary sequence thereof, as a marker for said double-flowering trait.
77. A method for generating a plant having a double-flowering characteristic, wherein said method comprising using a fragment of at least 20 consecutive nucleotides of SEQ ID NO: 7, or the complementary sequence thereof, in a gene editing technology.
78. The *Calibrachoa* plant of embodiment 1, wherein at least one of the SNPs selected from the group consisting of
    i. the G to C nucleotide substitution at position number 320 of SEQ ID NO: 1 and
    ii. the A to C nucleotide substitution at position number 247 in SEQ ID NO: 1, and
    iii. the G to C nucleotide substitution at position 43 of SEQ ID NO: 2 is not exclusively the result of the sexual crossing of plants.
79. The *Calibrachoa* plant of embodiment 1, wherein said plant further comprises an additional trait in its genome, which has been introduced or modified by a step of a technical nature so that the introduction or modification of that trait is not exclusively the result of the mixing of the genes of the plants by sexual crossing, said step of a technical nature preferably being selected from the group consisting of spontaneous mutagenesis, induced random mutagenesis, and targeted mutagenesis and/or
    said additional trait being an additional mutation affecting flower color or flower color pattern and wherein preferably said mutation is the result of an induced random or targeted mutagenesis.
80. The *Calibrachoa* plant of embodiment 79, wherein at least one at least one of the SNPs of embodiment 78 or the additional trait of embodiment 79 is not exclusively obtained by essentially biological processes.
81. A method of producing a *Calibrachoa* plant comprising a double-flowering characteristic and a dwarf growth characteristic, comprising the steps of:
    (i) crossing a first female *Calibrachoa* plant with a first male *Calibrachoa* plant to produce F1 plants, wherein said first female *Calibrachoa* plant comprises a mitochondrial allele associated with at least one SNP mutation selected from the group consisting of (i) a G to C nucleotide substitution at position number 320 of SEQ ID NO: 1 and (ii) an A to C nucleotide substitution at position number 247 in SEQ ID NO: 1 and exhibiting a double-flowering characteristic, and wherein said first male *Calibrachoa* plant has at least one copy of a nuclear, recessive allele associated with a SNP mutation consisting of a G to C nucleotide substitution at position 43 of SEQ ID NO: 2, wherein, when said nuclear allele is in the homozygous form plants exhibit a dwarf growth characteristic;
    (ii) screening said F1 plants for the presence of said nuclear SNP mutation;
    (iii) selecting an F1 female plant exhibiting said double-flowering characteristic and further comprising at least one copy of said nuclear SNP mutation;
    (iv) crossing said F1 female plant with said first male or a second male *Calibrachoa* plant having at least one copy of said nuclear SNP mutation to produce F2 plants;
    (v) screening said F2 plants for the presence of said nuclear SNP mutation; and
    (vi) selecting an F2 plant exhibiting said double-flowering characteristic and being homozygous for said nuclear SNP mutation,
    said crossing with said first male *Calibrachoa* plant preferably introducing at least one copy of a nuclear, recessive allele associated with a SNP mutation consisting of a G to C nucleotide substitution at position 43 of SEQ ID NO: 2 into the genome of the resulting *Calibrachoa* plant.
82. A method of selecting a *Calibrachoa* plant comprising a double-flowering characteristic and a dwarf growth characteristic, comprising the steps of:
    (i) crossing a first female *Calibrachoa* plant with a first male *Calibrachoa* plant to produce F1 plants, wherein said first female *Calibrachoa* plant comprises a mitochondrial allele associated with at least one SNP mutation selected from the group consisting of (i) a G to C nucleotide substitution at position number 320 of SEQ ID NO: 1 and (ii) an A to C nucleotide substitution at position number 247 in SEQ ID NO: 1 and exhibiting a double-flowering characteristic, and wherein said first male *Calibrachoa* plant has at least one copy of a nuclear, recessive allele associated with a SNP mutation consisting of a G to C nucleotide substitution at position 43 of SEQ ID NO: 2, wherein, when said nuclear allele is in the homozygous form plants exhibit a dwarf growth characteristic;
    (ii) screening said F1 plants for the presence of said nuclear SNP mutation;
    (iii) selecting an F1 female plant exhibiting said double-flowering characteristic and further comprising at least one copy of said nuclear SNP mutation;
    (iv) crossing said F1 female plant with said first male or a second male *Calibrachoa* plant having at least one copy of said nuclear SNP mutation to produce F2 plants;
    (v) screening said F2 plants for the presence of said nuclear SNP mutation; and
    (vi) selecting an F2 plant exhibiting said double-flowering characteristic and being homozygous for said nuclear SNP mutation.

BRIEF DESCRIPTION OF THE SEQUENCE LISTINGS

SEQ ID NO: 1 is a sequence from the mitochondrial genome of *Calibrachoa* (SEQ ID NO: 7) identifying the location of two single nucleotide polymorphisms at positions 247 and 320.

SEQ ID NO: 2 is a sequence from the nuclear genome of *Calibrachoa* identifying the location a single nucleotide polymorphisms at position 43.

SEQ ID NO: 3 is a sequence from the mitochondrial genome of *Calibrachoa* comprising two single nucleotide polymorphisms at positions 247 and 320 associated with an allele for double-flowering.

SEQ ID NO: 4 is a wild-type (single flower) sequence from the mitochondrial genome of *Calibrachoa*.

SEQ ID NO: 5 is a sequence from the nuclear genome of *Calibrachoa* comprising a single nucleotide polymorphism at position 43.

SEQ ID NO: 6 is a wild-type (non-dwarf) sequence from the nuclear genome of *Calibrachoa*.

SEQ ID NO: 7 is a whole mitochondrial genome sequence from *Calibrachoa*, and shows the single nucleotide polymorphisms of SEQ ID NO: 1, here at positions 224,919 and 224,992.

While a number of exemplary aspects and embodiments have been discussed above, those of skill in the art will recognize certain modifications, permutations, additions, and sub-combinations thereof. It is therefore intended that the following appended claims and claims hereafter are interpreted to include all such modifications, permutations, additions, and sub-combinations as are within their true spirit and scope.

What is claimed is:

1. A method for producing a *Calibrachoa* plant, or hybrid thereof, comprising a dwarf trait, wherein the method comprises at least one of:
    marker assisted breeding, wherein said marker detects a recessive nuclear allele associated with a C nucleotide at position 43 of SEQ ID NO: 2; and
    targeted mutagenesis, wherein said targeted mutagenesis targets a nuclear allele associated with a G nucleotide at position 43 of SEQ ID NO: 2, wherein said marker assisted breeding and/or targeted mutagenesis produces a plant homozygous for said nuclear recessive allele and having a dwarf growth trait.

2. The method of claim 1, wherein the targeted mutagenesis is an engineered nuclease selected from the group consisting of CRISPR-associated proteins, transcription activator-like effector nucleases, engineered homing endonucleases/meganucleases, and zinc finger nucleases.

3. The method of claim 1, wherein the marker comprises at least one sequence selected from the group consisting of SEQ ID NO: 2, cDNA sequences thereof, fragments of at least 20 consecutive nucleotides thereof, and complementary sequences thereof.

4. The method of claim 1, wherein the method is targeted mutagenesis and at least a portion of SEQ ID NO: 2 is used to produce a guide RNA or donor template.

5. The method of claim 1, further comprising applying a plant breeding technique, wherein said plant breeding technique is selected from the group consisting of recurrent selection, mass selection, hybridization, open-pollination, backcrossing, pedigree breeding, and mutation breeding.

* * * * *

SEQUENCE LISTING

```
<160> NUMBER OF SEQ ID NOS: 7

<210> SEQ ID NO 1
<211> LENGTH: 544
<212> TYPE: DNA
<213> ORGANISM: Calibrachoa x hybrida

<400> SEQUENCE: 1
ccctcatctt tctctttcag aagagcctac tttcgcccat ggttcgcgtc gctatcgtgc      60
ttggtccgtt cgctactctc ttttcagcca ttattgtatg cgtgtagcct aagtctaccc     120
ttcgattgga ctttctccag atcctttgac acccgctcat cttacttccc attctggtag     180
gttggtgcgt gatgattcgt ggagtacaag gctctctctg gttgggtacg taggctggtc     240
ctgcagmttg tggaggtgac cagcgctgca tgcccgaatg gaatattgac tatcccgtag     300
aactgaccta gtcgctcgts aaggagctgg tcattatgga atatactata tgtaggcgca     360
ggtcttccta gagcgaacct ccatgtgttt tatattaaac atataaaaat caacagtgga     420
agaggcactg gttgtgcgag atcattatga ctggaggaag cccattcgac aaccataata     480
ggctctataa ccggatcacg cacgctaaga acacagcgga ttagagggga caagaggttc     540
cact                                                                  544

<210> SEQ ID NO 2
<211> LENGTH: 114
<212> TYPE: DNA
<213> ORGANISM: Calibrachoa x hybrida

<400> SEQUENCE: 2
atrccaccac tgaaccaccr gctgcaatgg cggagaaggt gtstgatgaa ccattttggg      60
tggtgggaca cggtggattc ttgggctgaa aaaacaagaa tggaaaacgc agtg           114

<210> SEQ ID NO 3
<211> LENGTH: 544
<212> TYPE: DNA
<213> ORGANISM: Calibrachoa x hybrida

<400> SEQUENCE: 3
ccctcatctt tctctttcag aagagcctac tttcgcccat ggttcgcgtc gctatcgtgc      60
ttggtccgtt cgctactctc ttttcagcca ttattgtatg cgtgtagcct aagtctaccc     120
ttcgattgga ctttctccag atcctttgac acccgctcat cttacttccc attctggtag     180
gttggtgcgt gatgattcgt ggagtacaag gctctctctg gttgggtacg taggctggtc     240
ctgcagcttg tggaggtgac cagcgctgca tgcccgaatg gaatattgac tatcccgtag     300
aactgaccta gtcgctcgtc aaggagctgg tcattatgga atatactata tgtaggcgca     360
ggtcttccta gagcgaacct ccatgtgttt tatattaaac atataaaaat caacagtgga     420
agaggcactg gttgtgcgag atcattatga ctggaggaag cccattcgac aaccataata     480
```

```
ggctctataa ccggatcacg cacgctaaga acacagcgga ttagagggga caagaggttc    540
cact                                                                 544

<210> SEQ ID NO 4
<211> LENGTH: 544
<212> TYPE: DNA
<213> ORGANISM: Calibrachoa x hybrida

<400> SEQUENCE: 4
ccctcatctt tctctttcag aagagcctac tttcgcccat ggttcgcgtc gctatcgtgc     60
ttggtccgtt cgctactctc ttttcagcca ttattgtatg cgtgtagcct aagtctaccc    120
ttcgattgga ctttctccag atcctttgac acccgctcat cttacttccc attctggtag    180
gttggtgcgt gatgattcgt ggagtacaag gctctctctg gttgggtacg taggctggtc    240
ctgcagattg tggaggtgac cagcgctgca tgcccgaatg gaatattgac tatcccgtag    300
aactgaccta gtcgctcgtg aaggagctgg tcattatgga atatactata tgtaggcgca    360
ggtcttccta gagcgaacct ccatgtgttt tatattaaac atataaaaat caacagtgga    420
agaggcactg gttgtgcgag atcattatga ctggaggaag cccattcgac aaccataata    480
ggctctataa ccggatcacg cacgctaaga acacagcgga ttagagggga caagaggttc    540
cact                                                                 544

<210> SEQ ID NO 5
<211> LENGTH: 114
<212> TYPE: DNA
<213> ORGANISM: Calibrachoa x hybrida

<400> SEQUENCE: 5
atrccaccac tgaaccaccr gctgcaatgg cggagaaggt gtctgatgaa ccattttttgg    60 tggtgggaca cggtggattc ttgggctgaa aaaacaagaa tggaaaacgc agtg          114

<210> SEQ ID NO 6
<211> LENGTH: 114
<212> TYPE: DNA
<213> ORGANISM: Calibrachoa x hybrida

<400> SEQUENCE: 6
atrccaccac tgaaccaccr gctgcaatgg cggagaaggt gtgtgatgaa ccattttttgg    60 tggtgggaca cggtggattc ttgggctgaa aaaacaagaa tggaaaacgc agtg          114

<210> SEQ ID NO 7
<211> LENGTH: 465789
<212> TYPE: DNA
<213> ORGANISM: Calibrachoa x hybrida
<220> FEATURE:
<221> NAME/KEY: misc_feature
<222> LOCATION: (24511)..(24511)
<223> OTHER INFORMATION: n is a, c, g, or t
<220> FEATURE:
<221> NAME/KEY: misc_feature
<222> LOCATION: (24513)..(24515)
<223> OTHER INFORMATION: n is a, c, g, or t
<220> FEATURE:
<221> NAME/KEY: misc_feature
<222> LOCATION: (24518)..(24519)
<223> OTHER INFORMATION: n is a, c, g, or t
<220> FEATURE:
<221> NAME/KEY: misc_feature
<222> LOCATION: (24521)..(24521)
<223> OTHER INFORMATION: n is a, c, g, or t
<220> FEATURE:
```

```
<221> NAME/KEY: misc_feature
<222> LOCATION: (42971)..(42977)
<223> OTHER INFORMATION: n is a, c, g, or t
<220> FEATURE:
<221> NAME/KEY: misc_feature
<222> LOCATION: (148862)..(148863)
<223> OTHER INFORMATION: n is a, c, g, or t
<220> FEATURE:
<221> NAME/KEY: misc_feature
<222> LOCATION: (157905)..(157905)
<223> OTHER INFORMATION: n is a, c, g, or t
<220> FEATURE:
<221> NAME/KEY: misc_feature
<222> LOCATION: (293054)..(293054)
<223> OTHER INFORMATION: n is a, c, g, or t
<220> FEATURE:
<221> NAME/KEY: misc_feature
<222> LOCATION: (293985)..(293985)
<223> OTHER INFORMATION: n is a, c, g, or t
<220> FEATURE:
<221> NAME/KEY: misc_feature
<222> LOCATION: (294064)..(294064)
<223> OTHER INFORMATION: n is a, c, g, or t
<220> FEATURE:
<221> NAME/KEY: misc_feature
<222> LOCATION: (294372)..(294372)
<223> OTHER INFORMATION: n is a, c, g, or t
<220> FEATURE:
<221> NAME/KEY: misc_feature
<222> LOCATION: (294386)..(294386)
<223> OTHER INFORMATION: n is a, c, g, or t
<220> FEATURE:
<221> NAME/KEY: misc_feature
<222> LOCATION: (294412)..(294412)
<223> OTHER INFORMATION: n is a, c, g, or t
<220> FEATURE:
<221> NAME/KEY: misc_feature
<222> LOCATION: (298184)..(298186)
<223> OTHER INFORMATION: n is a, c, g, or t
<220> FEATURE:
<221> NAME/KEY: misc_feature
<222> LOCATION: (417943)..(417944)
<223> OTHER INFORMATION: n is a, c, g, or t
<220> FEATURE:
<221> NAME/KEY: misc_feature
<222> LOCATION: (465621)..(465621)
<223> OTHER INFORMATION: n is a, c, g, or t
<220> FEATURE:
<221> NAME/KEY: misc_feature
<222> LOCATION: (465754)..(465754)
<223> OTHER INFORMATION: n is a, c, g, or t
<220> FEATURE:
<221> NAME/KEY: misc_feature
<222> LOCATION: (465764)..(465764)
<223> OTHER INFORMATION: n is a, c, g, or t
<220> FEATURE:
<221> NAME/KEY: misc_feature
<222> LOCATION: (465770)..(465770)
<223> OTHER INFORMATION: n is a, c, g, or t
<220> FEATURE:
<221> NAME/KEY: misc_feature
<222> LOCATION: (465776)..(465776)
<223> OTHER INFORMATION: n is a, c, g, or t

<400> SEQUENCE: 7
wymytrtyst ykhhgtvggt aghswhavat stdhawtgta tatagkwdah cymaawratc        60
cgahvcctcv ratkcawyay catatcatgg ccgtbyctaw sadttgctyt ttgtgatgca       120
gcggaaccat ggcaattagg atctmaagmc gcagmammry cwmtmaykyw wgrmakwwmw       180
rmswtacmws amgatgttty wghattcgtt attctgattt tgggtttcgt atcatggatc       240
ttgggtcgcg ctttatggca tttccactat aaaaaaaatc caatcccgca aaggattgtt       300
catggaacta ctatcgagat tcttcggacc atatttccta gtatcatccc tatgttcatt       360
gctataccat catttgctct gttatactca atggacgagg tagtagtaga tccagccatt       420
```

```
actataaaag ctattggaca tcaatggtat cggagtgcgc ctcttcacga gggtgattaa    480
agtgcaacga aatgccttaa agttgaatat ggttcgcgaa gcatctggct taccggtaat    540
ctcccattcc cgccgtcgag agactttaat aactatagca tgccagaaac ggggagttga    600
ggtggttaga cctataccec gaaatgctcc cagcatagga gcctatggtt ccattcttgt    660
tgttgctgga ggtacacatc cctcttctcg gtgtggaacg atatacgaga aatagatgct    720
cagcctgcaa tgtccgataa cggcgctgaa gtagtgaatc tatcggcacc atagcagtgg    780
tatacaactt tggacctaac ggccggccta gtaaccttc ggaatggggg atccccgttg    840
gcaacaacca cggtagtagt tgcggaacta ctgggccggg agaggacaac ctcttgttcc    900
tgctcctctt tcttcgcttc ggggacggag gtcctacggt aggtaacagc aggcacaagc    960
aagttgaccg aagggacca cgcgcttctac tcctccaccg aggagccgtt cttgcgagaa   1020
gcaagggatg tcgtgaacgg tgggaggtca cagagaattg acctattcat agagtgatcc   1080
tatgatcgat acaggatata gactatctca ttctttattc tattctattt ctgaaaaaaa   1140
aaagaagggt gactcaactt ctcagctaga gttggtggtg ggacctcttg gcataatgca   1200
cgctggaacg tgggaattcg aggtctcatg aactactact aaaaaccgac tttgttttg    1260 ttttgtttgt ggacaaacga tatccggtca ggcctatggc tggatccttt tagatctacg   1320
ggccggccgg ccccggccgt ttacatgagc atagggaatc tatactcgag cgttccactg   1380
ggcccctgac aggataggtg aggaatcact ctggatcttc ttttttttggg ctacaacttc   1440 gccgagccga ctagcatccc tttccactgt gcattttcg aacaaagaag acgactatag   1500
gatcgaattc gctcttcaag aaactgctcg tcccatacct tctgcctgtc tcatatgtgt   1560
ggaacctggt ctttttcggt tccagcctct ccctcgaata catagggtag gtagggctgg   1620
gtgataaagg gttccctctt gccaataaac tttccccggc cttcgattaa ccttactcat   1680
aaagggtctt acgtcggga gaactaccta actaaagaaa aatagtgttc tttctaagag   1740
taggcgtgga gagcttttg cggggaaact tgcaagtaca gtttgggggg aggcgggcgt   1800
cgaccctacc ttatgagtat tcggactata acagttccga tgaacagtca ctcacttttg   1860
acagttatac gattccagaa gatgatccag aattgggtca atcacgttta ttagaagtcg   1920
acaatagagt ggttgtacca gcaaaaagtt atatacgttt tattgtaaca tctgctgatg   1980
tacctcatag ttgggctgta ccttccttag gtgtcaaatg tgatgctgta cctggtcgtt   2040
taaatcagac ctctatttcg gtacaacgag aaggagttta ctatggtcag tgcagtgaga   2100
tttgtggaac taatcatgcc tttatgccta tcgtcgtaga agctgttcct aggaaagatt   2160
atgggtctcg ggtatccaat caattaatcc cacaaaccgc agaagcttct ccagtcttcg   2220
tcggttcccc aaaagaagac actattcttt tgggagacc cgtcgtcgac gaagatgagc   2280
tctacgaagc ggcttaccac cccttctacg cggccaacgt agtccacatc cctggggaaa   2340
ttgaagaccc ctttactctg gctaaattaa gtaaattaaa tgggactctc ctagccatag   2400
cggatctctt tttcaacggc cagataaggg gatcgtacac taaagagctg caacttgaat   2460
tgaatgcgac cgaagaaggc gagctggcgg ctaagctgga agagctgcgg attagggaaa   2520
agcggcgcta aatttacgc tagggtgagc aagcgctagc tctttctctt gcggtgaaat   2580
aaccgccgta tagaggcgaa cagcccttat agcaatagca aacggcctac ttatagcctt   2640
tcaacaggtc agtcaatatc agtaagtagg ggtcctcttg cctaacggag tcagcccaac   2700
atggacaatg ataggcagac caaagattta cgcagtcgtt gcgtgcttgc tttgcgcacc   2760
```

```
ggcatagcag aattagaatc cgctggctca gatgagtggc tcttggcttc gtaaacatat    2820
ctatgttgtt gcttttcac taccaatgag taggcagctt tggatgctta tggagatatg    2880
gcttggccca ggactattgg ctttccgtca agtgtcagtt cagccataga cattcaattc    2940
aatctcggag atagtcaaaa tgccattgtc cgttctaaat gaaaggaatg agataggccg    3000
cttacacacg cttcaagtct tcttttgctg attcaataac agtctggaaa ttcgactgaa    3060
taagtcttag tgtggttaag ccggggccag ggtcagaagt tcttccatct cctgagataa    3120
gatcagacag agcctatacg ccttcttgct ttgctgcagc taccgggtat tcattcaaaa    3180
agaatgcatt taccttttct cccccttcct tcggcatccc tgactcgggc atccctttca    3240
ggtgcagttg acgtacaatt taggtaattt ataaggacta aacgtactga tgaaagggaa    3300
aacttaggaa agaatagcta aggagaatcc ttcgtttgag gaaagagatg ataaaataag    3360
tcatgaaaaa aacccagttt gttttaaggc tctcatgaag ccttagggcg aattcctctc    3420
acattggaaa cttcgctcac ttcctatatt attcgcgcac ctacctacca caatccggtt    3480
ccaagtcctt tattttaaaa tcgaggagta gttcaacttt tctctcttcg ggactaagag    3540
aacttactta ctaattgaaa aaaaaagaca actagaacga ggttttttttt tacgtgatcg    3600 gaaatcaccc gtcggtgatg aaccagtacg cacttaggat agcacttcgg gagagtgaga    3660
tccaggtggc atatcaaaaa gacttatcaa aatcgccacc atacgagact tgcagggcat    3720
gcccgccaga aagtgaagag aggtttataa gcaccccgac ttaggaatca tgacccaccg    3780
aagaaaagaa gactcgagga aaactattga tcccttgat gactctcctc ttcatcttcg    3840
cgggttgcag agaagaatcc gaactgagga aatgaaaaaa aaaagaaaa gtatctcttt    3900 ctctttctac gatcacctgt agcgtcctta aaaagtctta gaggagaat ctaactattc    3960 tcgaagagat tcttgccaac accattagga agatgaggga aaggggaaaa gaagtcaaat    4020
tcgctatttc cgacagctac ggtagtagag aaggagaggg actacttatg agaaagagga    4080
gttctctctt ctactcccgg gtattgaacc gggatgcttt ggtactagac tgggcgggcg    4140
agccataatc acaggggag aaaggcgcag atcttttcat cctccgccaa caagcagagc    4200
cgacaccgag ctacttcgta cctttttcat tcaaacggga atgactccac tctcagtccc    4260
agtgtggctt agactagtag aaggcgtaag gatgctagac cgctgctcaa tactggataa    4320
tccacgttca tcggtctgca gcaagcactg actttaggg ggcggcaact aaagaggtag    4380
cgagactaag cgcaatttca ggaagagttg gacccttgcc tctaagcttc cttctaccct    4440
tgtgctaaag gacaggaaaa acaacttctt tctttctttt ttttaatat attgaataat    4500 ggataactc gaaccctact aaagagtggc tttcagctcc tccccttct ttcattcagc    4560 gactgggtac gcacttcgcc atgaaagatc ttggtgatct tcatttcttt cttaggaatc    4620
gaagtcaaag gtacatcgac ttctctagtc ttgactcaga ctaaatacac cttggaatta    4680
ctcgaactca tttgcaagac tccaagccat gtcccacacc ccttgcgtct ggcttaaagc    4740
tctctgcata cgatggtcct cctctctctg atgcaacgga atatcgtagc attgttggcg    4800
cccttcaata cctcactctc accaccgtat atctccaggc tgtaaaaggc atcttacggt    4860
atatgaaggg ttttcttggg cttggcctaa ccatcactca gggactttaa accaccttct    4920
ttgcattctc cgatgccgac tgggctggct gtcccgatag cagacggtcc actacttgct    4980
tctgcgtatt tctcggaaac aacctactga cttgggtttc aaaaaaaaaa aagaaaccga    5040
ttctttccag gtctagtgcc gaagcagagt acaaggcact cgctcttact acctctgaac    5100
tcttatgact ttcttactta ctacgcgatc tagcggtgcc gtttcgctat caattttttcg    5160
```

```
tgcactgtga taatgctagc gctacacact tggtggccaa tcctgtgttc catgtccgct    5220
ctaagtacat agaagttgac taccacttcg ttcgtgacct cgtcgtcgca ggcaaattgc    5280
tcattcgact tgttcgtagc aacaatcaag tggcggacct tttcactaaa ggattacctg    5340 aaccccccctt ccatcatttt ctgctgtctc ccgcctgccc ttctcgaaag aatgggctcc   5400
tggccgtcct atctcattga aaggacaaa aaccatttac ttttccaatc aaagaaagtg     5460
aagccaccaa aaaaaagaa aagggtata gtaatatata tataaagtca aagttcaatg      5520
gtaacgactt cttccattga cttcaggatt gcttggtttc agggaaagtc tctcgctcct    5580
ctccttatag cgctggcctc tgtctttgat cttggctcga gctctgtcct ctcctctccc    5640
tatgtgagag tggctgcttg aagcttttcg tatgaatagt caaagctcgg acttaggagc    5700
tgctggcctt tgttgatccg cttgaagaga gttctcacga ccctgctaca tcgcgatcgt    5760
ttattcccaa ggaatagaga atacaaagca cacaaggcgc atgatgaaca agagtaactt    5820
cccgtccctt actccatttc ttgtcttaaa tagacaaaat agtgggcttc ctgccccctt    5880
ctcaaagaga ggaggacggg ttattcattc atatttcatt tgatggtcag aggcgaattg    5940
aaagctaagc agtgggaatt ctaaagattc cccgggggaa aaatagagat gtctcctacg    6000
ttacccataa tatgtggaag tatcgacgta atttcataga gtcattcggt ctgaatgcta    6060
catgaagaac ataagccaga tgacggaacg ggaagaccca ggatgtagaa gatcataaca    6120
tgagtgattc ggcagatttg gattcatata tatatccacc catgtggtac ttcattctac    6180
gatatatata agatccatct gtatagatat catcatctac atccagaaag ccgtatgctt    6240
tggaagaagc ttgtacagtt tgggaagggg ttttgattga tcaaaagaag aatctacttc    6300
aaccgatatg cccttaggca cggccataca taacatagaa atcacacttg gaaagggtgg    6360
acaattagct agagcagcgg gtgctgtagc gaaactgatt gcaaagagg ggaaatcggc     6420 cacattaaaa ttaccttctg gagaggtccg tttgatatcc aaaaactgct cagcaacagt    6480
cggacaagtg gggaatgttg gggtgaacca gaaaagtttg ggtagagccg gatctaagcg    6540
ttggctaggt aagcgtcctg tagtaagagg agtagttatg aaccctgtag accatcccym    6600
kmcmtgtggg tcgagcctcc ttttcagtcg ccctctacaa ctaagtcagt tgagctctct    6660
cggctcctag accagctgtg atctttcctc ctgttggttt gcttagttaa atatatgcat    6720
ccttagagtc agtccctttt tttggagaaa aattccgagc cggtaagcaa gacaaagcaa    6780
gtcaacgtgg gaaaaagctc tcgatggcca tagacctgaa tggttggagt gtggaggatc    6840
actcctgaaa ctttcttcct ttatataagg aatcctcttg gttggtcgaa gctagaagac    6900
ggctggacga actgctattt tgcataggggg gagtaagata ggctaggtgc ttttactcaa   6960
ctcgtgaagg ttcatttcta gttagcaagg ataaggaagc aaaggtagag tcctttaata    7020
atatgtctgt cattacgtgc gactatctcc actatagaaa gaaaaaaagg aaagaacaac    7080
attttcagca catttatacg aaaaagtctt tattattata ttagcataag taggaaacat    7140
tttccactag ggttttttccc atacatgcaa acataaaaaa gaaaagcaaa caaagataat   7200
tagcatagat aggagtctat ctccagtaag catcggagta gatctccact aaaaaagaca    7260
aagaacaccc taaattaaaa cacattactt tgcgtctaca gacacttatt taaaccttct    7320
aaaactaaaa agagtcgacg gactcttcta ttctagtctc cctggcgacc acgggtgaca    7380
gcacccacaa ttaggtcttc ctgttttttgg aggagggccc gtttcctgtc ttccaggacg    7440
ctaatgcggt cccggatccg ctgcatggct gcagccacaa gtgcaggatc gatgggaggc    7500
```

```
aggtgctccc aaaaggcagc cagggtttgc tccgattgga gcttctcctc ttccacttga    7560
gagatttctt gcgaaatttc ttgaagtctt ataaaagaat ccatggctac actcaaagct    7620 ttttttttgcc gacttctaag ttcctctccg tctcccttttg ccaaatagag actgaaagaa   7680 gcttctatttt ataggcgttg gaggccctta acccttctt attattagta agataggttg    7740
tcttggttcc gtaacatgga tcatttcaaa cctggctttt catgaatatg gaacccccctc   7800 cactagattt tagtgtgctg aataattatc ttcgtactcc aatccgtacg aagggcccct    7860
ttcttttggc gggtatcgcc acgtggctta atcccggatc actccttaag gaataggaca    7920
caataatata gcgcacatca gagaagagag tacccccttt attataagac aggccccacg    7980
cgtcctttct taagagatgg agcaatcgtc actcgacagc tcaaagctga ccggtacaac    8040
ccgcgtgctt gcctactcgt cttttcaccgg cctatttgta cccagctaca atctcttccc    8100
ttagaaaaga aaagggcccc ctcggccaat cgtcactcga cagctcgaaa gcggatcagt    8160
acaaaaccat gtgatctgta cttgtttacg tactgcccct taggcctagg gcttcgtcgt    8220
accctgctta ctcctctttc actttcactg gcttctactt gtctttttt ttttttattgg    8280 cttatttaga aaatggtatc agcatttgag acgactctcc ccggccaatc ctcagtcgtc    8340
cgtccttgct taggagaaaa ccgaaccact atctcttgat agatctgttt ttttctacct    8400
ttacagctcg ctctgtaagt tcactagcaa tacagcacta gcactagcta tagcagtaac    8460
tagtacaatg agttagggt cgggtcgggt gaattcaata atagacgcct gttggcattc     8520
cagccttcct atccgaaaga gaatccatta tttcttggtc gtgaatatct gaactggttg    8580
ttcactgttc aagaattctt gtttagacaa ttcagaccat ccatacatag tcttttaatc    8640
taagattgaa attcttccat attttattgc taaaatattg ttccatggag ctaaggtcca    8700
aaatatggaa gaaagaagtg tttccacgac tctccagtca attctgttcc acttaatccc    8760
tctttcatgg caacatctct ttccggctaa ggaatgggaa atctttctcc tgttacatga    8820 atcaagttttt cattttatcc ggaaaagccc ctttccagct gacgctgtca gtccactaac    8880
agcggtatac agtaagtcag tataagtcag tacaggaagg gcacgcgaaa tagacaacta    8940
cttactaggc tagggtagta gttttttcat cttcccttta ttttacttta ccctagtgga    9000
aattcatttt taaaagtgac taggtaatta gtgaagaggt ttataaaagt gacaagcttg    9060
gtggaaagct cttatcttag gaggaaaagc taagtatgcc cgagtagtct tgatattggt    9120
tggtttgagg tttcgttagt tttatactaa caagcaagct tcggttcggc gaccgctcga    9180
cctagcgcct tagccccagt actataggga aggcctatgc gaagaaaagg cctgcccatc    9240
atcaaagcaa gcccaagtcc atgcaagaag gccctccaga tctgtccaaa ttcaaagccc    9300
gtcaaaggca tatgaaatca tgcaaaggat ccgagcccat ccaaatgatg ttcagcgggc    9360
taaacccaag tagctctggc ccatgatcca agagacccga aactagttaa tcactccgtg    9420
ccttaccttc taaccaatcg gccaatcacg ctatccttac cttttcaacca acccccttcga   9480 ttcagtttct gcagcagtat agaatctcgg acccgatgga tgcctacaga aaaatgagtt    9540
ttccagcagt gatggcaaga atccgcgaaa taatgttctt tctcctttttt gtgttctttc    9600 tgaatggagc tacgcgaggg aaagctcagc tttctactct gccgcaaaag ggggccgctt    9660
tcttcccccc caaaatgcca gttccgccat cagggcctag caagaagcat aattctgttc    9720
caaagcttcg tttcattcca gcaacagtag tctatggttc gaagcgccgt gttccatccg    9780
gcgcgaatcc tctccataac tagtatagtg gaggtcttac ttgtattgca ataatgaaaa    9840
aatgtacgaa cacaaataat gagcagacca gcccactttt atatgtgggt tcatttcaga    9900
```

```
atgttttttt gttttgaata aagaagcgcg tgaactttta gtgtaaggca ggtgttttc      9960
tcggtggatg gatgggataa atgcctatat tgctttataa tgttattgtt atgttgatgt    10020
tatattaaag aatgaaatct aaaaaagttg cttagtccca ttctttataa ttgtctttct    10080
catactgtgt aaacaaactt caagtctgaa ttgtgtactg tactcaacag gaagcgtcac    10140
agccacccc  gatgtcgatc tgcagtatta gtttgagaaa gtcgtttggt ttttaaccta    10200
gagcgattgg tttacctgta tcatgcaaat gtccaacact taggtgcttt ctaagatcat    10260
cctatatgaa agatgtatga catgtgtgga taatgaatga cttgcagggt atgcaatatc    10320
ttaagtacaa aaggtaagac ctaaaaagag aaatgagctt agcacaacac gggatagaaa    10380
gctaatccta gaaggagaaa acccatcaca gaacaatcat aggaaaagaa gaaatgggtt    10440
cagaccaagt gacagaactc tctatgagtt gggctacata aaagatcctt ttctactaaa    10500
atggatgtag gcttaactaa agcccaatgc aggttgaact ctatggaatc taagcctcac    10560
taccttacc  ctcttagagg gttacaagga atttaggcc  ggccccatat agattcagct    10620
taggggttta tgagagattg attgatggac ctaagctaaa caactaagat tgaacctaaa    10680
ccaaaaccta tagactgaat taggagagca gaggttaat  tcaagaccag gaaagcaagt    10740
tatatcgaag cccaatgcca agcaaagccc tagactacaa gtgaagaaat tgggttcaac    10800
taagccctta acccaagatg aggtggagcc ttaacccgac acaagagggg ccctgtagga    10860
tagtgggctt agtcagccca acataggttg ttaaccaaaa aggagaagtt cccgtgaaaa    10920
cagaaaaaga cctcccccctt aaccccccc  ttacttggca gattcacatt cgtaggaaag    10980
gtctgttctt ttgtctcttt ccctcaagcg aaggaaccta ttaataagat aataatatct    11040
ctctgcttcc tagatcgata acgaatcctt cggttgctta tcctgtcatc cgagcccggc    11100
gttccgaaca acaatgattc ggaaagataa ggtctacgaa agaaaagaaa atttacaatt    11160
tgccctactc ctcaagaaat actgcgagcg gtattgtaaa ggtatgggct ttttcggtcg    11220
attttgctca agagggtggg gggacttcga ctttatcgaa gcagcacatg agattgccca    11280
gaaggattac tttttattta acctagtgcg gatgtggact ccctaaaaaaa cctgctccac   11340
tttgtacgaa aaacatagta atgcagctaa gtgggagtct tacatgaacg cgcacttgat    11400
ctttgacttg gtccgccgcg atccataagg aaggggtttt cgttcgcaac aaggtagccg    11460
tagggaaacc cctatgggct ggattgaatc ttttccttttcc ttctccctct cacctgatcc   11520
attaaaggaa aacagactca aggattgggc catttttccat atgtctctag aaagatagga   11580
gctaatcaaa attcttatta cttatgtaaa tgtaactctc aaatttgata ttactccatg    11640
tgtaacgcca aaggggcctt gtattcaatt gaaacagagg atctcccaca ttgatataca    11700
catccttcac ccaatctgct caaagtattt tcaactcttt catggtatca gagcactagc    11760
tcttgggaaa ggttcagttg gttcgtgtga agtgtggtct gaataccttc ttcttaggtg    11820
tttttctcttt ggcgctgtcc accgtctgt ctctatcctt ctcctcagca cttagttagt    11880
atcccgtcca tcgaaattga gttttccata gcgtctgttt caatttttatg gaaaactaag   11940
aaaattgctt tttttgaagc acaagatctt ctcagtttcg ttgatggaac tggaaaagaa    12000
ccaaagaaag gactttcttg agactgatca caaaggtaag ataatgaatc ctgagtacgt    12060
cccctggaga agaacagacc gactactcaa aagtttaatg atgcacacca tgccctttcc    12120
caggcgtcga ggttgcctag ccgtaatcca caggctggct tcgacagatg tcagagtgaa    12180
tccgattctt cgattcaatt acttttccaa ttccaacccc gcgcgtggat gtagaaaagt    12240
```

```
gtgtgaatgg catacgtaag attggggatg acaacatca attcatttag tatagtcagc    12300
taggaagcac tagctaggca agtcatactg ggaatgctgt tccacacatt ggctcaattc    12360
taccttccac atccaattct tccttcatta caaggcccag cttcgctaaa ctcgcaccga    12420
cccttagtta aatatgcggg tagcttttca cgaaagattg ttggcatgcc tcccataaga    12480
agtaggataa aaaaacctat gagaccccct tgttctaatc ttttttcctaa agagcaatcg    12540 attactatac tagtgcatgc aaactgaaat cttagagaac cttgatccta ttgatcagaa    12600
agagctcggg cgagaaggtc tgcggggtca gaagagttca gagaaagctg gatccgggaa    12660
ggcttacgcc gataacgaag gattttgaaa ccgatcgata tgcagacgct gcaaaagcaa    12720
atgacttcgc ttcctcaatc aaggtaaggt aatttgagaa gctatcgaaa ctattccgaa    12780
gttgatgatt tcgttctagc tagggcaatt taaaagagag aagtttacgc tctccaacaa    12840
agaagcactc acctcctaat agaagagata acgtaagaaa gactagcaga tgcggacgat    12900
gtaagcggtc aatcaattga gactacttag agtccgctaa ctaggggaaa gagaagcact    12960
aagatgaaaa gatataacta gattcccctt acataatgct cctgttgaaa ctaaaaaaag    13020
ataagaaggg acttgaagct tacagtcctt actcaactac aagtacatag agaaatgctt    13080
ccacctatta gactatgcat tgacgttgca gatgttaaat tgcagttggc attaggagat    13140
agagagcaaa aggaatgaat ctagtatact taaggcaatc caaaaaaaga aagcgcttag    13200
tccttatgca actaaagcac aggcaggaaa taaagctaca tccacaaaga aagagatggt    13260
tgcatctaag ggcttcttat cttattgggt ctagcttctt agaaagccat agggagagac    13320
cgaacaatct gatgatatat acttgtgatg tcagaaaaaa gttccgaaga gtggaggcag    13380
ctttttcctc tccaattttc tgttggattc taataggatt caggaaaaaa ataggaattc    13440
gacagagcgc aaaaagatag tcgagcaatc agcgggcagg cataggtagt cgacagcagc    13500
aatcgaccat cttgagcaac aagagaaaga aggaccaacg acgatcaagg aaagaaagac    13560
taagtaaagg cagacaacga gacgaagata gcagacttgc ctcgaaacag gaacatagca    13620
taggggcatt tctccggact agttaagtag ttgagcccgg ctcccccgct tggctcctct    13680
ttgctcctag tagactacta gacatcttgt ctactctgct tttatggaag agctcagtcc    13740
aagaagggct ctcaaaaaaa gaaaattgtc aagctttcga actcgccttg aagttgatga    13800
atgattgcaa ggctagcaac aagcaggctc gcttatgatc tgctgaaaga gtacatcagg    13860
tttttttatt aatccctcac attcatgaag cagattgtcg aaaagggctt tctgcaagca    13920
ggaaaacgac ctttttttacg atccacaggg tctagcttga tcccggtctc gggacttccc    13980
aagtcacgga gtctttgatc aagttgtaaa ctaaggagt ataacctatc caatatatat    14040
atattttcgc ttattgttag taagaaaggt gtcactaaca aataaatcct taatcagtag    14100
tggactacta gttaacgcac tactaaagca gagtagccag catgcgcaca taatttttg    14160 ccagaggatt tttcagcgaa tggaagaagc aggcagggat agatataatt ttttagggaa    14220
aaagtgcttt gtttgatttg ttcccaggtg agatccaaga tctttcaacg cgttgatttc    14280
ctactaaaga aactgggctt ctatcaggag tttgatcatt ggaaagggtc gaaaactctt    14340
gctttatgct tgagaaagag ccttcccggc gatctgcttc atttatggag ggtttgcaag    14400
gaagacaact gaatagcggg aattaaaaga gaaggatttc cagaggtcaa tatctggcat    14460
tgagcctgcc tatcctaagt atgagttggg agagcgagat agagacaaag acccaatgga    14520
cgttcccctg ctctctctct cgatgtggta cctttcagtc tgctctgtca aaactttctc    14580
gcaatgccga aaggtagagc agcttcaagg tcttcggcaa cgagatcaac tgctgaccca    14640
```

```
agaaggtagg gaagagagga ggaagggcca atccccgagt cagggcatc tatctttatt    14700
tacgcaaagc tattttcgat ttagatatgt tcattggcct gcgactgatc tcatcgtccg    14760
ttttccccct ctttcctatt caagagttct cctccctaac ggcacactgt atataatctc    14820
tctagatggc caatgtgaac agttcaatca aacttgtatg tgtgaagcat attgaaagtg    14880
acattgacaa agcaaagcac agattcccta gaatgttaga actcagacat gacagagaag    14940
gtagtcaaaa acgtacgct aagctccttg cttcgtcgct tctgttttca gttattcaaa    15000
gaatgatgtt ttaagcatct ctatatgcca gtcatctatc tgacctgaca aggaggtcga    15060
ctttgatatc tcacccctga tctctacggt tggttgaagg tgtcttggaa gacgggtcga    15120
aatcagatct ggatagaaga ttcatctacg ctggcaaaag ggctatcaga aagagtccaa    15180
tcccgaggag agttcatgtg tgaaatttct ttgttgaatg gaggtgagtt caagggcttc    15240
tttgatcggg aaatgcacgc acttcttttg ttgtcattaa ggtcccttcc ccctgagttc    15300
aagatgtccc ttccgcttct ctttcactac tttcctcatt gggattggtc aagctccttc    15360
acttattgct cgatccgatc cggaacctat tgggatagca ccctttcctc ctatttatta    15420
gtaggtcttc ttgcccgttc agttcctcta ctggtagtct agttgtagtt ttgagcgggt    15480
gaacccatgt tctatctcgt agtcacctaa gcggcagagt ctgtaaactc aaatggtctg    15540
agagttgcct ttggcttctg aacctctgaa actggactgg agcaagctac caagctcctc    15600
ttccccctcc atcactctct atctccggcc cttgccatta gttagcttgc acttcccttg    15660
cttgccctt gagttttcaa agtcaaggtg cctttccctt ttctgcctta cctcttactg    15720
aagtgaaaga actgactgtt gtctacctt gattctgtct tccgggtgaa ggtcctgcgg    15780
aggtctttt tagtgatcaa aattgattag ggacagtgac ccatgatgaa aggagctatt    15840
gacctaagtg gttttctatt tgtatttgaa aagcaaggta ggtttgttaa cgaaaggata    15900
aggttaggct ggaatgggat atagtaagtg tgccacgagt gctcccttct aaggcttctg    15960
cttctctcta ataacgagaa aatgactctt tcagaaagca aagctacaac tcttcagtct    16020
aagctatcta agctagaact taaggccgac ctcttttcca gggataccc acttcccggt    16080
ctagcttcac taactgtatt cacagctttc cagatctcgg aaccagatct actttctcat    16140
cggcattctc taaatgaatt acgttatggt cttgaactct cgatatatca tatgtaatga    16200
atgatcgagg ttgtcttttc ggaagaggtg ggtgggagtg gggcagggca agaaagtaac    16260
aatcataccc gatattcaga gcgccggaga tagaagcggc ggcagccata agtggagaa    16320
tttccatcca tttgctgtct ccttcgctac cgctccgtgg ggtcaacatt acgaaattag    16380
ccaggttcag ttctgactat agctgcaacc tatctcatat ttggccgccc tcgatcacaa    16440
actcgaaatt ttgaagata aagtaaagaa agaatttcgg gctaggttca aggtatgccc    16500
aaaggtatgc cagttgattg aaaaagaaac tcaactttca agattcaaga ttaggtaagt    16560
gttcagtgta ctaaggtaca agatcgaaaa aaaagcgcgg atagcaaatt ccttaggcta    16620
gatagagtgg tggttgtaaa ttactaggta gccatacaac actcggccca agcaacgccc    16680
aaaagcccat gcctttcttg gtcggaccaa cccaaccggc gatttccgac aagtctttct    16740
gaattggaag agcaagaagc ggaacttgaa gaaaactttc tttctcttta tggatagaca    16800
gtcttttca aattctcctt ctaattcatc ttccccggtg gatttaggtt tatctctgag    16860
gtcccacgaa ggttcgacta gtagcactct gtcggacgcc aattcgggtg atattactag    16920
cactcaagtt ttgagtgata tcaccgctct ttttgagcaa cgaatggaag tgggaaagaa    16980
```

```
ttcacaccag aatggagccc aatagagttc tgccaagcgg tttttgggga agaagcggtg    17040
aatgacctat ctttattgaa agacatctat tgtgatctag cggaccatgg aatgctaagt    17100
tggtattggg aaccagcttg gggctttcta aatctcatta gcaatagtcc aggaatgaca    17160
tagccttcct gtgcaatggg tgtcttaacg tactaagtaa ggtggttttt tctaaagcgg    17220
cattctccct tctatctatc aacaatagaa ttatggaact ttctcccga gctgcggaac     17280 taacgagtct gatcaataga gtccgtcatt ttttctattc cttcctactt cttcttcctc    17340
tattatgtgc ttttattcta tttgcctgaa actcgagaaa atagagttgt tgagaccaa     17400 atgttataga gttgggggct ctctggggag gcacaccttc acttccttct taatgaaggg    17460
gttccccggg agtctgacct tgtcctttct tttaattgtc ggggccgtca tgagtgccga    17520
aacctatttc ggtaagatga tgatggctcc ttcgggcgca tcaagctctg aagatccaaa    17580
ctggacggaa gccctgagat cttctaaagg gcagggagag acttcagaaa gggaaagcac    17640
aggcacatcg tcgtccatca acctacaaaa agaaagagca cgtccggcgc ctgccccaaa    17700
tgaagtagct tccctgccc ctgtcgtccc ctttccatat caagaagatg agatcatagg     17760
gggcgacagt gtagaaagca tccaagagcg tttaatttga ggagaaaaac ccctccttct    17820
gccgaggtca tacatcatac aacaggcccg aattgaagcc gaagacctat tcgaggtcaa    17880
ggtcgatatt ttcaggggca tgtctggcct tgatccagaa ggagattggc tgggacgggg    17940
agctcgggcc ctcgagaatc cgcgtaccgc cacggggag cattccttgg agaaactcca     18000
tacccttctt tcggatctcg aatcgagggg agtcaattcc gagtccttct ctcaattaaa    18060
agggaaggta ccctgcgaa ggggtgggga cgaacactct accacatagt ggagtggata     18120
gctaggacta ctaaaatgga gatcgtgtac aacaacaatc ctatatttga tgtcgattca    18180
tccacacttc cattccttgt agaggaaggc taactgcttg ctggctggga gctgtatgag    18240
cggtaacgtc cacgtacagc tccgtgagaa gggcggtgga cagaaatggc cttgttgtac    18300
ctcactctcg tcttcaatgg ggtctgctct ttctttttg ggagagtatg ccaatatgat     18360
cttaatgagg tgcggggctt tgcatctgac attcgttggg cttctctctt cgggagcctg    18420
cgccccggcg ttttttgtgca ataaaccct ccggccgaag actagtggta ggtggtcctg    18480
cggagctttc ggaaaagggt agccttgtgt gtaagcacag caatgaaccg cggcgaaccc    18540
tcagacgacc tatctaagat tagggggga tcctcagtag tggtgaccct ttcactcttc    18600
cacggactga tacatgtacc gaatgctcat acgggaaagt tgactcctgg gtctggaacc    18660 tgggggttg ctccgagaaa acctttcttt ctcgtccact caggggggtg cggacacacc    18720
tgcgcggatt acaggtgaca gttacaagaa tggcggggaa gttaacagta cccgacgaca    18780
ttcagggatg gatgtagacc catcgggcag ggataatcat tccggtcctg ggagaagtgg    18840
cgaccattct caagaaccaa aaagactgag ctgagggaag ccctatgagt cactgaaacg    18900
acggcaggag tgccctttt ctatcaatag agggagcaaa aaaggggcct tgctcccctt     18960
tacaatatga agaaagaaat aagggtcgaa gtttagaccg ctcacagtag ttctacctat    19020
agaaaggatc atgaaagagg cgatcagaat ggtactcgaa tccatttacg atctcgagtt    19080
tccagacaca tcgcacttcc gctcgggtcg aggcttccac tccgtcctaa dacgatcaa    19140 agaagagtgg ggaacctctc gctggttttt ggaattcgac atcaggaagt gttttcacac    19200
catcgaccga catcgactca tcccaatctt taaggaagag atcgacgatc caagttctt     19260 ttaccccatt cagaaagtct tttccgccgg acgactcgta ggaggtgaga agggccctta    19320
ctccgtccca cacagtgtat tactatcggc cctaccaggc aacatctacc tacacaagct    19380
```

```
cgatcaggag ataggaggga tccgacagaa gtacgaaatt ccgattgttc agagaataag    19440
atcggttcta ttaagaacag gtcgtattga tgaccaagaa aactctggag aagaagcaag    19500
cttcaacgct ccccaagaca acagagccat cattgtgggg aggttaaaga gcatccaacg    19560
caaagcggcc tttcattccc ttgtttcgtc gtggcacacc ccccccacaa gcaccccccg    19620
gctcaggggg gaccagaaaa cgcctttcgt tttccaccct tcgtcggccc ttgccgcctt    19680
ccttaacaag ccctcgagcc tcctttgcgc cgccttcttc atagaagccg ccgggtttac    19740
ccggaagtcc gaattctatg gtagagaacg ctgtaataat aattgggtca tgagagactc    19800
ttttaagtat tgcaaaagaa agggcccgct gatagagctg ggcggggagg cgatacttgt    19860
tatcaggtca gagagaggcc tggcccgtaa gctggccccc ttaaaaacct attacttaat    19920
aaggatttgt tacgcgcgat atgccgacga cttactactg ggaatcgtgg gttccgtcga    19980
gcttctcata gaaatacaaa aacgtatcgc ccacttccta caatctggct tgaacctttg    20040
ggtagactct gcaggatcaa caaccatagc tgcacggagt acgtagaat tcctcggtac    20100 ggtcattcgg gaagtccctc cgagggcgac tcccatacaa ttcttgcgag agctggagaa    20160
gcgtctacgg gtaaagcacc gtatccaaat aactggttgc cacctacgct ccgccatcca    20220
ttccaagttt aggaacctag gtaatagtat cccgatcaaa gagctgacga aggggatgag    20280
cggaagaggg agtctactgg acgcggttca actagcggag actcttggaa cagctggagt    20340
aagaagtccc caagtgagcg tcttatgggg ggccgtcaag cacatacggc aaggatcaag    20400
ggagatctcg ttgttgcata gctcaggtcg gagcaaggtg ccatcggacg ttcaacaggt    20460
agtctcacga tcgggcactc atgccccgac attgtcattg tatactcccg cgggtcggaa    20520
ggcggcgggg gaaggagggg gacactgggc gagatctatc agcagcgaat tccccataca    20580
aatagaggca cctatcaaaa agatacttcg aaggcttcgg gatcgaggtc tcattagccg    20640
aagaagaccc tggccaatcc acgtggcctg cttgacgaac gtcagcgacg gagacatcgt    20700
aaattggtcc gcgggcatcg cgataagtcc tctgtcctac tacaggtgct gcgacaacct    20760
ttaccaagtc cgaacgattg tcgaccacca gatccgctgg tctgcaatat tcaccccggc    20820
ccacaagcac aaatcctcgg cgcggaatat aatcctaaag tactccaaag actcaaatat    20880
agtcaatcaa gaaggtggta agacccttgc agagttcccc aacagcatag agcttgggaa    20940
gctcggatcc ggtcaagatc cgaacaagaa tgagcactca actactagta aaaagggaga    21000
aagttgactt tgagaaagaa ggtgcttctt gccgctttat tagtaagtaa gcttgtttta    21060
tatctcctca ataaaggcga aagatcactc ctaaaagcaa gctttctctt atatacgata    21120
ccataccaca gaatttcatt tgccttcctg cttaaggcac tagttcggat ggaaaccctg    21180
atcaggcagg tggcctagct aacatagcta tccgtcagaa atagcagcat tccattgcag    21240
gctactatag aggcatataa ttttccgggt gttaagaaag atattgaatc gaaagcggac    21300
atgcttgctc actggctaga tcgggctgtc tgtaccttttg ctaactcttc tgcctgtaag    21360
gaagcttgaa agagggaatt ctctgatcta tgaccccgaa agaaagatag tcttttttcg    21420
attccgcgca ttggaactga aaagggctat tcataaacag tcttccttgc ttcttacctc    21480
ttatcttatt gtaggagata tcggagaga gaaaagtctt cctatcaatt ccttttgaat    21540
aaggctacgc tcctccaagc ctttgaaact attgaaaatc gaatctttgt tttcaggcgg    21600
gttttcttct ccaccaacaa ccaagacgca tgaaagcggt ttccagcgct gctgggcaga    21660
aagacatgat ggcatgaaac tcgattacgt acgctgattg ttcgtccact tcaaaggctc    21720
```

```
aaaacagacc attttccgtg tgaaatgaca gggattggtt tggttactta gggaatccca   21780
agcaaagcaa tctacgcaat ttccgggttc agtagtagga aagaaaggga cctctcactc   21840
aattcaataa catgttctag ggcatccttt tctaataata atgttcgcat ttgaccaggc   21900
tttttggacg ttccatgatt aaaccgacta gcggcacttt cgagatgcca ccttgtttct   21960 aaaagagtc ttttcaattc catttgactc ggggcgtcag ggaccctcca acagaaacct   22020
cgtctttttt gtcgtcgata agttctccct cagtgcccta ctattcataa gaaagactga   22080
tttaaaagag actgatttat taaagcccgg tgaggcctca accgacagct aagcttcgtt   22140
ctgcggcggt tttcaagcta gcaccccttt cagcatatca tctcgctcga ttccaaaaaa   22200
aaaaagagac gcagtttttg attatccagt tctatatcga aaacgagcag ttgatcccac   22260
gaaagcaagg ctggctttgt tgcgggttca actggaattg taagaagtga ggtaaattgc   22320 cttctcccc accgcatatg cctcctctgc ttatgccact ggtgatgaac tcactatggc   22380
tattcaacgt caaactcaga gttttctac tacataggcg gctaaacgaa gccccagtct   22440
tttttagtaa aaccccaacc cccttattag tagccgaagt aaaggccagc atgagatcaa   22500
agtcacttgc cgtccgttcg ctctctgttc aacaaaggcg atcgatattc ccttacttct   22560
caagttttga atttatgag cccttcgatt gtatcccata agaaaatctc tctgataaac   22620
atcttgtcga tgattcgatt atattattta gaatcttcgt gtgcgctttt cgcctgaggc   22680
tttcggacaa gactacttac tccagtaggt tagtaagcta cctcttccgc tttcaggcaa   22740
gggtagctct gaagggagag ttgagcggaa ccaggcataa ggagcaagaa tcgctattga   22800
gagttccccc gctaggggaa cgtcaggagg gggacatgct ctatgtccac tgattctgtt   22860
tagtacagta taggaagccc ttgtttgagt gagagcttct agaatgccat tcatttcgca   22920
ataagaaact tttccacata gaggtttcag ctacttaaag cgagagtgca tccaaaaatt   22980
cgagaagagt gctcggcctt ggttgaaaca attataggtg tcaatggacc gatttcacta   23040
gcagagcact ttctccaatg tgcgcaaaca gagatgccac tttcaatgat ggacaccggc   23100
ccttgtgtta aagtagcatc gagtttcgct tggaaaccgg caagtttcta gtttccaaat   23160
aagtggtacc ctttctttag agtccggtag gtcaattaag ttgcctaaat ctcttcctta   23220
tctgctgctc tgtagctgcc ttcctcgctt cgtcttcggc tttcagagtt gtgaactaac   23280
ctcttccttt tacagccaga caactggcag ataagctggg catctaaaga acataagatc   23340
cgagttgccg ccaggcataa aagtcatatt gtcaactagg gaaattggca caaccaggca   23400
tctcaaacat tgataaggga agaatcaggc tttcattagg atgatattcc tttcatccga   23460
atggcaaggc ttgctagttt cctgaagtac actcgcatct gtctatctat gtcatagttg   23520
cttggaagga aggtctcaga tgtaccttcg gcatgtatga gatttttcttt cctctatcta   23580 tgtcatactt gggattcact gacagccaat tccaagtaga tcctccctcc ccctcgctcc   23640
acttcgtttc gctcgttttc tctttccttc tgcctgcaaa aaaagtgatg agattggttt   23700
tgtgtgcgtt agcgatcatc aaacctgtga catagataag attggagttc atgcagttgg   23760
aatgcctgag accactttt gccttgctgc tcttgcttct ctggctactg ctccggctaa   23820
ggctttcttt ccgctttgac ttgccttcct tatctttcaa tctggacttg catgtgttcc   23880
gcatatgact atttcgagtg attgctgcta tctggcttga gttagacaag cagagaagga   23940
tcttatgcca ccggtgaccg gcctgcctat ctagtatcta gtactaggac tagtagagta   24000
gaggcactac tgggcggggc ttcctcgatc acagcttctc gcttagctaa ctgccagaca   24060
aggatgcaaa tcaactcctt atatagaatg cagatcgaca cattcaatga agcagccagt   24120
```

```
acggcagaca agctactttc ttattctagg actggaagat cctctatcta ttagcatacc   24180
cgtaccggca gttagactag cactctctcc ccaatcaatc gcagtaactg gctgtaagag   24240
agctgactgt ctactatcta tgtcatgcct tggcaggtga atatgagaga gaggctgtaa   24300
gtgcattctc tccttctcca tcttctggaa agcactcttt gagcatgctg acagaatgat   24360
tgacactcac atctctctca tttccagtga tttcgctaca gtttactagc gcattcctag   24420
actaagacta cggcattgaa gaagcaagct cactctcatt ccaggaatca gaggaaggca   24480
ttctgtccgg taatgaagtt agaagtttcc ngnnngcnnt ntctcttctc ttgcagttgg   24540
tccggccagt caaccttgtt ccgggccttc tcttctactc tatctgctta ttggattggt   24600
aggtacagtc tttcttctag gcttctgatt gaactttaag gtaatgggag agaaggcaat   24660
cgacagataa ctggtaagta aagctatgga ctgggttctc actctaagcc agtaccagta   24720
atttgaaaaa acgatagaca tctagcgcat tcactcgttt tttctttctg atcggccaac   24780
tcaaagaggg aaatgcaagg ggcgttagcg gtctttttg cctcgcctgc tactgggaag   24840
agagagccgc tgtcattctt cgcttcgttc gagaatcaac tgcacatgaa taggctcctc   24900
cttaggcctt caaggaggaa gcggcttttt tccaaaattc ccgggaaaat gaaacttttg   24960
aaattctttt cgtaaggcaa gaaagttgcc taaggaaagt agaagtctat gcacactaac   25020
cgaatctttg gggaaggatg gtggtgctgg ccttttccct tctcctttct aaagcaaaaa   25080
agaatgtcat cattctgatc gtgacttgaa aaagaaaga agagaaggaa cttggagttg   25140
gcgcccacat aacggattgc ttgcttacca agccatcctg gcttttcgct cctctcctta   25200
cagtcaagtg gctttcactc ctccagttct attattattg acttgactta ttattaaaaa   25260
aactactcac tatccaaatg aaagacgatc gattatctac ccaagaagat agagagtccc   25320
acatacgaga aaaggtcaca aatagagttg aaccaagtaa cattgcaaag gcataatgat   25380
agtagggtcg ggatatcccc gccctccgaa ccggacgtga gggtctcccc tcatccggct   25440
ctctgcaggg gaatctccac tcactgcttc ccctaatatc ctccccttac cacatcatgg   25500
gggtttacag gagatcccag aggctcgctc ggaaaggctg ctataccata ccttttgact   25560
taactctact ctagtagtca ctagactcac tatagtagtc cgtctggctg ctcttgctga   25620
aatcattact cttaattctc ccgtgctcta gcaattgcgc tccctagacc actaccatgt   25680
agttaggtag ggacaatcag tccgtagtga cgggaatcta ggaatgaatg gggatcccta   25740
tcaatataaa aagaatatct aattrgakwt tthttttttty bmrmvsagda vgvgatatvh   25800
gagdtbcght abdgtcbhgt gcdctvvgag atgtdtaaaa gctatgggat agatggtaga   25860
gggctgcctg cgcccaaaag cgatgattca cttgtcccct tgtccatagg gacctcgtgg   25920
catacaaccg aaacgactcc cgctagatag ccgccccttt ctctcttttt acagcctcgt   25980
ggacggacga agaagggaa gttacagaac ggggcagtga aggctcgcga agtagacagc   26040
aagcagcaag caacagcttc tcagccccct aacctttctc ttttttaata atactttttt   26100
tatcaggtaa gctttgaagc tggctgctct gctatactat actagttgta gggcgctagc   26160
gcttgactaa tataatagaa agtaaaggga ctctattatg atcttacgaa tctaaagatc   26220
tcaaaatgga agaacgagct cttttgctcg cccctatctc taaggggcg taagcacttc   26280 actcgctagg ggatgggatt cattcacttg cattcctgct agcactacaa aaagctccgg   26340
tcttaacgcc cctactactg ctgtgcagcc tttcctcggg ttcgtagagt cgggtttccc   26400
gtttacccac aacggaggag ccgcccccac caggcaggcg gccacgggtc ataacgcact   26460
```

```
cttcgcacaa caaatccact ttgaagttga cttattcgct cggccaatcg tcggaatgtg    26520
tacgagatac cataagggcc caatatctca atagcacctt tgtctaaagc ttcgaaggag    26580
acttcatatc cgaaacgcag gaacgatctg actagaaagt cattcaaaac ttgatcgaaa    26640
aaccagcgtt tattgaagaa gctatagagt cgattactaa tagtactagt ttgaaaggct    26700
cgttggaatt gatccgctac gggattaaca ttatacgcaa cataagcacc tgaagtacta    26760
aacagaatag gtattagttt ggtaatggtt ggagcagcaa actcggattc ggcaagaatc    26820
tcattttttg gtagtacgaa gggggaattg gcccaaaaat tggatggggg tcaagacgct    26880
gtcgggcgcc ggcggctgac tcaagtgccc ccgaaccgc gcgaaatggt cgcctattac     26940
acggctcact aactctgcct ggggtgtggg tacctattat tcgtcggcgg tccggcgcac    27000
ccctactata caaagccgcc cccccaactc acttaaagga tgctggttaa ttacgaagga    27060
aattctttct taatcgaggg acttcctttt cgttaagcgc atcgaaccag gagtggacat    27120
tatcatcatc tgcagaaaaa tccagattct ctttcatcat tagcgaaagt ggaatagtat    27180
gactggcttt ccggaaaata agacgaaacc cgctttatcg atatgataaa catgcgctca    27240
aaaagacctc ctaaacccccc ctgccaagcg atcgagttta gtctgaattt gctctagaag   27300
tagctcccgc tccagactga cttcaaggaa agaaagggtt gggcaattcc gccggttctg    27360
gagcttacct tattattaag gggaaaggga tttttatag atgttgaggt gagtaagggg     27420
gggcgtagct tgaggcttct cagccgcagg aacaggaac gaatcctcca aaaatggaat     27480
gagttcgcaa ttaataccac aagaaagccg ccaccctcgc cctttagaga taggggcgca   27540 acaaaagta ttcaaaaagg gcgccggagg cctcaaactc atccggagtt ggagaatgaa     27600
ataaaaaaaa aaagattctc aagaggaatg tatcaacaaa actgcccttc catatagatc    27660
gtcgtggcat gaactttgtc aatagattcc tagcttccta ttgatcttga ttagttctag   27720
cttcgttttt tttgttgaga gttatctttc tggaccggac ccactttat accgtctcct     27780 gaaacacctg cttatcctgc atgtgctttc ggggccccca ctcaaaaaat cacttgcttg    27840
tgattgcagc cattccccga aaaggggag ggtggatgta attcagctcg aacgaagtga    27900 gagggtaat agactattac cgttcagttc atgtgacgaa ccgaacatcg ttaggtcccg     27960
aattctgcga agcaccggat ctagatcaag atctccatta cgtcgtacga tatatcgatc    28020
cggagaactt actttcagtt taagtcatcc attctgctcc tatctaaagt gatgctaggc    28080
tgcttcacag aggtgcgctt cgctcgacca catgatgaac atgttttaag ctaactgcat    28140
gtcgagcgct taagcggagc ttgtggtcac tcgttcctcg cttgttcgaa agagcttcag    28200
attggattct acactacata cgatattcca ttccggccct cactagctct ttgcttgctt    28260
gtacaaagag catgcccgag ggggctacta cgctcaccgc gcacttgcat taccacctga    28320
gcttcgctac cgttccgccc agctcctacg cctaccacga acttgaatca tcacatggct    28380
gctaaagcaa gctaagcttc acacggccct gaggaagcca aaagaccctc tcacggccga    28440
aggctccgca acacgttgga gagcttttag atcccgcct aaaacgccca ttcccctaga    28500
gttccgaagt gattctcatt ctcaccgcag ccttcttaag ccgaaagaaa gccgggcaag   28560
aatctcatgg tagtacgaag ggggagcgga atcgtatctg ggagtggttc ttcggatcga    28620
tcacagattc tcggccccgt cctttggctt ccactccagt tgacctctct tctttccatc    28680
ccaccgtgag aaggtagaga gcaaaaccaa cccagcaaac aactatgact atgcccctat    28740
tagtaaagca tgtacttctt gcaaggcttg ctgagcttct tcatgtgaca gacatcgcaa    28800
aagtagtccg ttgaacgatc gccgatcgag ggcatcgtaa tagtatacta tttttgaacc    28860
```

```
ctgatgggtt tcgcagtcga ccatttgata gccctgttcc tgaatataca cagaataggg    28920
cttcgatgag ccctagatgt aaaggggttc ttgaacccett ctaagcaatt agaagagcgc    28980
ggaattggac ctccctcaaa tagatggatc tgggattgat tgtggaaccg agcatagaga    29040 accggggggcg ggcaggaaga taggctaggc ggagtagtcg ctctggagca ggttcttcga   29100
ctggatcaat gcatgtatga acccctaaaaa aatcccgaag gtctagtcta gaaaaaaccc   29160
ggattttgtt gggttagctt tttggtagga aaggcggtca caggaagaaa tgccctacca    29220
atgaatagat tagtctacta acgtcaacaa tctctttctt catatacgag accgtctgct    29280
tttatatcct aaactataga tatgaaacaa aaagaaaga aaggaaaaca ggcagggagg     29340
taagagcgag taagactagg ttatagcaag acaacagagg ttagatagct cttaccggag    29400
gaagagggtt caggtcaccc gtccccttga cccagacacg aactaatcct tctctctctc    29460
gaatgtatgc ccggttttcg tcgaatcttt ttgatcacct tcaaaaacaa accggaattc    29520
cgtcttgaca tgataaatag tgatgccacc ctgcagagcg tagccctccc tgcagccttg    29580
aagtagacta ttttcgagt ctgatcttat ccccaaagcc tttttgcaaa aggagtaggt     29640
agcgagatag atgactaaaa gctgatgatc tttgcctctt actagtaaag ggaaaagccc    29700
tatatatctg attagtcaag cctaaaggcc ctttactaat ataatagaag gtaagaccgg    29760 cttttcgcgca gctgctgcgc ccttgcttct tgcccataga gagttaggat attttgtgag   29820
ctccttcgcc tagcggaaac ctccgctttt cggccgtaat cccgtgcttt accaacgcat    29880
tcaatggatt ccaccatgaa ccgggagcgg gcgaagacat gcagcttcca ttttcggggt    29940
acacagtcac gtgctgagca aagaggtata tatcacactc attcacaagc gcaaggtgcg    30000
gcatccgcct gaacggggag aggatttccc taaaacaaag ataggcgtgt caggaaagaa    30060
tgtgaagtca ccccctatttc gctgtccagg gagctgttga ctaatgacct aaaaatgcg    30120 tgacgtttgg gaagcatgag caaccccttcg cgcacgagat agcaatgaca ggagattgac   30180 cggtcgggt cgagtgatct caggggtta ggggtgcttc tcctgctgcg actacctctc      30240
tattttcaaa agtatataga aatggtaggc actgggagtg agtgaactac ccggggagaa    30300
aggggcaacc tctctataga agggaaggga aagggttctc cgctcataat gattgtgag     30360 tctctcgggg ttggaggtct aatagtagtc acatcaagtc ctccccctct tactcagaat    30420
agctagcgag aggaagacta ctgattatct atgaaagaag gctttttaaga atgaaaaaaa   30480 tcttatctta aggatagaga gcccccccgcc tgcgttttca gatacgagtg agtgagcgct   30540
ttttctgcta tgaatgaatg acctctccat ttattttcaa gcttgctctt caaaccggcc    30600
tatcgctctc ctctatgaaa aggttcttcc gtaatcactc tcaataagac atccattccc    30660
ctttcaaatg aaaagagaac tagacttttc tcttcatcat tgaaatccgc cattcaatcg    30720
cagtgcggtg ctctcaaaag gctcaatcct ctaaggctga aacgaatagg tcaggaattc    30780
gacctgggat ccgcccgttc cgatccttgc ctactaaaca gttgcacccc cggatatgta    30840
tgttgggaga accccatgat ccttccgtgt ggaagggaag gaagaaagaa ggcgaacacg    30900
aatactaaaa agcggttcat ggggaccccc caaaaagggg atagagagcg cggaacgggc    30960
tttccaagca taaaacaatc cctacctata cattccatgg caacagacag aaggcagttt    31020
tgtcgttgtt cttaaccccca ggcacatttc cgttcccaat aatctccatg aaaagactac    31080
catgatttcc gaacgaaccg agggagagtc gaggcatgaa aaaacttatc tatgatctgc    31140
ttatttccaa gtacgtatca tccgctgcct tatccgccgt ctctgcggcc gccaaaagcc    31200
```

```
taccctctct cggatattga gtgggttgac cggggaagag atccggacga accttccaac    31260
aagcagaata gaagttgacc acaaggccat ctctgtggga ggctgctacc cataaggcca    31320
tctcgggcat gggaaagaaa ggcggcggac aaccgactta actggagagc ctaaacggca    31380
tagaggatga gtccaccggt cgacaaacgg cttctatcta caggtgcttt cattatggat    31440
cggtcgactt gtcacgattg attgctcaca cacaattagg ttaggcaggc ttggggaggt    31500
gatctgaatc gctatcgata cgatgcgggg ctgatttgct gaccgtaacg aacttgactc    31560
tgcccctgaa aaaaagggc gggaagacct ttgacctggg ctggggaggg attggggtcg    31620
cttttcttta ggactttagt ccgtaacaag gctcgaagac ctccggctgg atttgaaatg    31680
gatcaggtag ggcatccgtt tacgacgtgg gtgggattag cagttttctc tattttcttc    31740
aatggtagga aatacgcatc agcggggggta tatgggagga aaccagtctg cagtaattca    31800
aattgctcct tcggatcact aagtaaaatc ttgactcaca cataccgcgg tgtattgttg    31860
tcaactcaca tagtcgcacc taccagcaac aagacgacta ctccctgcac gccactaaac    31920
ggcgctattt aacgcttggg ttcgcccaat acaagaacta cagcccaacc tagcttaagg    31980
ctaaagccgt ggactacacc cccgtgagag ccctctattt tactaacata ctcccttttg    32040
atctccccca taccttcata tcaaagctgg gaatgattga ctttcggatt aaaataatag    32100
cgcataatgg cagtactcct tcccatttct tcttttatga tcttatctac ttgaaatgct    32160
tacctgtaag tgcggagaag gtacccaggg gaccaaacga aagggcactg aaaggtcttc    32220
aattaaagct tcgccagtac ttgaaagact cgaaagacct acttgatgag tttccttatg    32280
agtgagttcg taggtgcctt taagtcgagt gtagcgaagg gattctccta agagaagctt    32340
tagcccttga acctgaaacg acttttatga gctgtctcag tagtgaccga ctttatttta    32400
ttagctgtat gattagtggc ttagctctta gctgtctaaa agctacggta aaaaaaatcc    32460
cttttgaaaa taaaccacta atccgcctta ggtactcttt taagtccgtg taaggcggag    32520
ggaatgaagg gacctgcagg aggctgaaaa gccgtagtgc gctagcgcta gcagttagc    32580
gcaacaactt agtgtcttgt tttcttcgct gcttttttg tccgcaggaa agcggttgct    32640
aaggcttgta gcttgcttct gtccttagtc aattttggac tgaagctgtt ctgactgccg    32700
tatctttttt gaaccgaata ccttcctctg tcatctctgg tctgtctctt tttgagagaa    32760
gattttctac cccgcctgcc tatgaagaac ttcaagtcta tcgggaaagg atgtggtggt    32820
aaccccgca gctttgtcta gaaccgggcg tccagccgtg taggaagact cacctagcc    32880
actatagcga ccccaccccc aaccctagct gagaagcacc ctyvdgccac tcccdthttt    32940
ccgtgtgccc aaaagcccgc ccgcccggtt tttgagaccc tttctgattc cctcacccaa    33000
tctcatgaga agcaagccca gcaggccctg ccttaacctg tcctcagaca gccagccctc    33060
accaggctgc tggcattgct aaatgctccg ccacgaagca agctttcccg aatacgacag    33120
atgcggaagt ggctaaagaa gtcggaggaa gaaagttgtt ggacaactgt atacacgagg    33180
gtacattagt attctgggaa ttggcaacat tgacagaaag ggtaaggggt aggaagaaac    33240
ttttttaggt cttgctctac taaagtagtc ggcctaacct tcggttcccg taaccaagtt    33300
tttctttctc actccttatg tacttttttt tacttcatcc atactttttt acttttttctg    33360
aagtgtgggg caaacggcgc cctctacttc tacttctaac taaaggcgaa cagccggcat    33420
tgcaagcaaa tagaaagccc ccgcccgttt gagccggaaa gcgtaccggc tgtttgagtc    33480
gcgaaagggc cgcttgctta atattatta tataataata atagatagat aatattatat    33540
tatataacta tctataaaga taaataaaaa actacagaaa atactttttt ttttataaaa    33600
```

```
ttcttcattc ctgggaagag gaagaagcag ataqggcaaa ggccttctct ttccgtccgc   33660
tcttcccgaa gtgagcgaat tgcatgtaga gatccgtagg ggcttatagt ttaattggtt   33720
gaaacgtacc gctcataacg gtgatattgt aggttcgagc cctactaagc ctaccacccc   33780
cttctcttca cctgatacaa ggcagtcgaa gtacccgcca ccctgcagat ctcaatctag   33840
cgacggcatc tggaaccaca ctgctgccgc tgcccttcgg gcacgcctcc tatgcttatc   33900
actcacctac gctcttgcag catgcccct tcgggcaata cggtgtaata cgcgaagcag   33960
ctgagccata gctcttcgat cgctatattc ttgcggcgtg gttcatcctc taagagagag   34020
tagatgcgaa ggttcggatc gaagatcttc gcgagacagc cccggggcac catagcatgt   34080
cgggaataag ggggacatag tgaacactcc cttggttggg ggctgtgact cccctatcct   34140
ttcaattttt tgattcccag gtctttttta ttatcactgt tggaatcttt tttaagacga   34200
cttggtcagg gcggttcaca atttctttgc tgaaggcgct gttaagccct aagtttgaat   34260
tcaaatttca ttgcccttct tccgaaagtc taaagtcctt caaattttca ccaattccga   34320
cctaccttta tttatgggat atttgaagga gagctttgta actgtttcta gaaaattctc   34380
tctagctcga agaatttgtt tgattctccc tataaaaata gttaaggaaa aagggggcgct   34440 tttgttaaag gactaactat tgtagagaag atctccttgg ctcacgaggt ggctttaagt   34500 gatagggat tttaacctaa agacaacata ggagggaggg gggtcaaaag aaagtcagga   34560
tatggcaaaa gcatcttttt ggatcgaatg ggcttttgtg ataaatggcg gaatttgata   34620
catggatgtt tatgtaatga agactttgga gtgcttgtgg atggtgtgcc acatgggtac   34680
tttccagctt ctcgagggct gcgacaaggg ttccaaacct agcctgttga ttttagctga   34740
agaagtgcta agccgggact tggtatcatt gaaaatgata acatcttacc atgcttcgag   34800
atcgtgccca gcactctcct actttctctt tgataacgat gttctaatat tatataatag   34860
ccataaacgg aatcttaaga agcagaaaat ctttctggaa agaagtaaga agctgattgt   34920
aatgttgtaa tggccaaaag gtcaatttcg ataagagcca gtgcttcctc tcgaacagag   34980
ctcctcgcag aaattccaga tcattgaaga ggaatcaaaa aaggtagttt tcctatcaag   35040
tacctggaag ttttcttgtc cctcaagaga ataagagag aaccttcctc tactggagaa   35100
aatgaaaaag agaatctcag attggaaaag taaattgttg tcctccggag gtcgactaag   35160
gcttattaaa catgttatag tcttcctatg cacatgtgca agttttttcc ttaattagcc   35220
ggcccacact tcggctacta ataatgggat aagaccttac tactatatag gatatgttac   35280
cctctctcca gtgagtgcag tgaaggactc tcgcctcacc cgcccgtttg acttatggca   35340
tcatcgactt gcttttcaat caaagcgatt tcataaccat aaagaaagac ctctccttcg   35400
ggatcagtcc cgtccctaga tgtagtagtc aatcagcggg acattcaaag aagctatgca   35460
ccttcactga atgttaatga agaaaagccc tttcatccta atctcatcta ctgaaaaggg   35520
ggccgggcgt agcacgttct tttttgggac acataggcta ttacagacgc atcaaaaaag   35580
acttttcgaa gcgcggaatc cctgaatgga atcattgcag aagaaaggta taacggttgg   35640
gaaccggaac aggattaagc ctttaagcat gcagatgagt gtttgctgtc agccccaatc   35700
cttcggtttc cggattggaa taaggagttc catgttcata ctgacgcatc actctatgcc   35760
attggatgta tgttggcgca agaagggccg cttgatcact ccatctactt ttaaagtata   35820
cgactttccg ctttggaatt atagaaccac cgaaccttct ttatcatgat tcgacccata   35880
cctcagaccc aagatcgagc accagagctg ctcataacaa ggtaccaaaa agaagaatgc   35940
```

```
gagaagttca tattctccag attcgactat aaaccaggta gtgaggatga aaaaaagcat    36000
aagctacctc gttcgtgctc ccgtctttct cgctgccatc ttcggtggat gcgcccttc    36060 acttaaaggc ggccaaacca acccactgag ccaaccttt agattgaaaa aagttactaa    36120
gctagtcacc tcacctctct ttcttacccg cccttattag tagtaggcaa cctttctttc    36180
tcgcctttct tccagctttt tccagataaa gatctaatag agttgcgctt tcttagtaca    36240
ttgcctttca ttaccaatct gtcgttttac agcacgaagt tacctgatgt tcgctactac    36300
taataagggc ggagagatgt taacctttcg ctattagtaa gcactcccct agttttgacc    36360
taatgagctt tctttacgtt gagttaatta acccggcggg ttcgcctaga tgcctagtaa    36420
agaacgagct ggtgggaaag agctggagat catgaaaaag atttccacac aaggaggcag    36480
gcgaccggga agctttgctt ctcgaatgcc gactacatgg gaacagatgt tatataggtt    36540
gattctcatt cttgctgccc gctcgattcc gaggaataaa gggagggctt taccacaatt    36600
tcccaagtaa gagatagaat ctcactaatt ggaaggaaaa ggagggcttc gatccattgt    36660
gattcgcttt cttggtatgg agagatctct gccataaaag agagagctcc taagccttat    36720
tctgcagatc aaagagcgag gtaattcccc attcatccga aatagtcttt tagtaaagaa    36780
gagaggcatt ctgggccgac tactacgact acatgcccat ctagtgcagt ggcttggaag    36840
caagctacct tgaccatctt ccgaagttct aaataattta ctgatcaaag ctgtaagggg    36900
cggactgctc tacattcagc cacaccacag tgacccgaa gcgatcttct tctagttgcg    36960
ggacgaaatc cgacagccaa ttgctggctc tgaataacca gcccagcaat aagctcaatt    37020
cttccataac ataaggggc gggcttgcgc gcgagccgaa tgacgtaggt gcacaagagt    37080
acttcgcgcc acaaccatct cctttttata ggttctacgg accgatgcct gctgcttcat    37140
ctgggagaaa agaatcatag atatgccggt cattagaagg aagaaccgcc ataaaaagat    37200
tcctcgtgta tcatctgtag caaaactatg aacgggagct agcaatccgg accgtattga    37260
aaaggttcct gagacacagc atggaaaagt aacaatatta agaaacgagg tccaagaatg    37320
aagaaggggt tgaattactg aatgaatacg agctgtggct aatacccgag gcataaaaga    37380
agcattttct acgggatccc gaaaccacca gccaccccga cctaattcat gataagccca    37440
ccaacttcct ggcaaaatgc ctacggttaa aaaccaccga catgtcaaga tccaaattcg    37500
aattggttcc tggtcctggt cagagaccac tgtgttcgcg ccggcggtcc aacaaagagg    37560
cgaagtagtg gtatctttct ttccattacg aacgacacgc ttcgcctgct ccctccccgt    37620
gtccactagc gctcctgtcc agagcgaaga gaaggcgaaa aagcgccgcc gaagcagcat    37680
aagcaggctt ctattgctac gtaacaataa agcaggatag cattttgcgc ccacatgttt    37740
gaatttgagg gtaaagagct cgcttgttat acgggatccg acgcatccaa cagagcgaaa    37800
cagtgttcca ttcttttcgg cggcatcctt ccgcattggc ggcgagtgga gtgccacaat    37860
cccattcatc attttgatc tacataagcc aaagcccata gcactggcga cgtcccggc    37920 ataaatgcaa ggaggatgta tagctgatat aggatcttgt ggaacaggat ttgattctgc    37980
aagcggttca gtacaaacga agaaatttcg aacaaagggg tcggaactcg ctgataggaa    38040
aggagagaaa aacaaagcaa tgccaagagc tccgtcaatc cgctgttcat cgatagacga    38100
agctctctct ttatcatctc gtgccagatg caacatcctt tttccttctc gcgaaccacg    38160
ggagcgccta gcgcccagag gagcaaagct cattttcctt tcagggtaaa gcggcgcata    38220
aaaaagggct ggcccgtcaa aagtccggtt ccttcgcgaa cgaagttcag aatcaacaag    38280
ggttcgtaga acgaagggag tgtataactg gggcgcagcc ccacttttt gttcgtaacg    38340
```

```
agggagagat agaatggagt tcttcacgaa gttcgaaaca aaggaataaa aaaaagtttc    38400
tctatggcct cctcgttttg agacattatg gcttaggggt cgaccccggt aacaaagaag    38460
gaatccataa aaacttagga tccaacacca tgataaaata ctaccctcat gattagacca    38520
tgtccctgag atttgataaa agaaaggtgc attagcggtt aatacgttgt aattggataa    38580
gttattagga atatgacgga acgaagacc  aaggaaagaa agaagaatac accaaaatgc    38640
aagtgctgca ccaaagactg gtggttgttt cttgttgtaa gtgaatgcaa cgaaaagacc    38700
cggaaataac gaataatgaa acaattcata tattgacatt tcgtgctcat ttccaaattt    38760
atgctttgtt attcccatca tccggtaacc acaggatgat ccacaagaaa ggtggcagga    38820
ttcgaaccta tggccggcct gcccctgacc tgctgggttg ggtggccggg ttagcacccc    38880
tcgtcgcctc tgtacccgaa acagatgcgc tgcgctaccc agcgcctaac cttgtctccc    38940
ctactcctct tctggttgtg ccattaccaa tcgcgggtaa ccccgggtcc ggccgcccct    39000
gacctaagaa gaactattat ccttatgacc aaacaaggac cagcttactt acttctcgag    39060
cgatagttcc acgatcccga ccagcaactt cttgggagta ggggcatcaa agcttgccca    39120
acctagtaaa ggggcttggg gatagagggt ttctggggg  agagaaagtt tccaggttgg    39180 atttttgag  atcaaatagt actagttggg tagatagagg tggtgaaatc taacctttgc    39240
atcgatcttc tttagcaggg cgggtcgctt gagtgtcaaa accaagcggt ggttgttttt    39300
ccttggctta tcgaaccagc gtatgcccat tcctcctttg atgactccca gtagagaaag    39360
cctaaatttt ccgatgtgga ttgaaaggaa gttggggatg gacatagatc cttccgccta    39420
tccggagtgt tggaaatata gcaatgtttt ttgtattttt gatttcccga tcattggaag    39480
caatcttcac tggcacaagg atctcctcac agcaacctcc actacgatag aaaccgacaa    39540
tgagtttacg aaggcttcga gtagtgcggg ataggctaat caccagactg ctctggaata    39600
ggttaatcgc tggagacaag aacgagtgaa tctagtttcg agagcatgcc ttactctaat    39660 aggggcgta  gagtttctaa gtgaaggcaa gcgctactat atatgtaata tcctagctgt    39720
cagcaaggca ggtccgctat aaagcctacc ggccagaaag tccttaagaa cgagaaagcc    39780
gactaaaagg ctattccata accgactctt gttgccgagt cgaggggct  tggctggtac    39840 caggctctaa aagagttttc ttcgagcgag cggtcttttct atctttttgg gttgcatgcc    39900
caaggcaatg cttttgtag  attgagatgg attgatcttc gctatcgtgc ctcctccttg    39960
taccagttga tgctggggca gtgcttaatt aatatgagtt ttctcctgcc ccagacagct    40020
tcgaggttcc catcgatcga ttacagaggt ttctaccact gaacttgctt atgctcccct    40080
ttgatcgagt gctatttcta taaataagat tgagtaggaa aatgttgaat tggcttcaat    40140
cgagattgcc tcggcttctt aggcacatga ggaaccggcc taacatcttt tcaatcgaaa    40200
tcccaatcaa agacaagttc taccaaggcc aggatctgaa agagaggatt cactttccga    40260
aattccaagt gacatgattc ctccttcaga agctaaagtt gaatgatcga agtctccttt    40320
aggttcagtc gaagagatcg aagcgaagtc atcaattcaa ccattcgaat ggtctcccca    40380
aagattgacc tcttttccaa ataaaccgaa cctcgatacc agattcatca aaagatatg    40440 gccatctctc taggttgcac aaccccttta gatcgttcta ttcgtgcttg aaaaacgacc    40500
ccatcggtcc gctccttta  atggacattc ttagccgtcc tccgagggtt aacaccccat    40560
agatcagatc gtgaactctt tcagaccctt agtttcactt ggttggggca gagtttcagc    40620
ctgccttcca ccgaatataa aaaaccttag agctgcctaa cctgctgaca tcccggcgaa    40680
```

```
gagagtcatt atttgtgtta catcttcgaa ttcgagagaa ggcttttcctc ttatctctca   40740 aattataggc attgaagcga tcgagagaaa gtaagaaaac tattgcacac gccccccatt   40800 cgcccttac taatataata gaaggtaagg caaaagcaag agtgaaacta cgagctaaaa    40860
gcaggcgtgc ctctcttata agagaatatg ataccatccc ccacttttgg cgcacttctt   40920
tgatgagcta agcctaagcg ccatagaagt caaaagctag cctgagacct aaaaaagcaa   40980
ggtcgaaatc catccctctt tttcctgtat ttgactagta gggctaatga acgacccttt   41040
gatctatgtc gttccaagtt cagccaggtc tgattagaag ttcaaaaatg agtggagcga   41100
ggggctttag agggaaaaaa ggggggggcga gctttaattg aagtaggggc ggagctcctc   41160
atagagagtt agaaagcgtc agttctcata gcgaggctta ggccgacggg gtagggcgcg   41220
gccccccaat tctcaacccc gacctagaca agtggttttt taacccacat tttgaaaagt   41280
tctgttaggt tcttagtagc aatcggcgac cttttcctct tttacttcac atagcttttc   41340
gtctccttga tagctggaag ttctccaaaa gtatgaaaag ctggaggact ttgtaccatc   41400
cattccggtg tggttggatt ctgttcaaca gcccaaggac ttggagcaca tcttttgttc   41460
tttccactgc ttgaagtgat tgttacgacc acgaagaaac gacaaatccc aactacggat   41520
atataagagc caaaactgct aagggcattc catccagcgt aagcatctgg ataatctgga   41580
atgcgacgtg cataccgca aagccctaag aaatgcatag gaagaaggt catattaacc     41640 ccgaaaaaag tgatccaaaa atggatttga cctaaagttt cagggtatgt ccgaccaaag   41700
attttaccta cccaatagtg aaatcctgca ataaagcaa aaacggctcc catagaaagt    41760
acataatgga aatgtgcaac cacataataa gtatcatgta gagcaatgtc tagcccagaa   41820
ttagccagaa ctattccagt gagtcctcct atggtgaaca aaaagatgaa ccctacagca   41880
aataacatgg gtgttttgta ttgtatcgaa ccccccaca tggtagcgat ccaactaaag    41940
attttgattc cagtggggac agctatgatc atggtagctg cggtgaagta ggcacgggta   42000
tcaacgtcta agcccacagt aaacatatga tgagcccaaa caagaaatcc aagaacacct   42060
atactgatca tggcataaac catgcctaga tacccgaaaa ccggtttcc cgaaaaagta    42120 gaaacgatat gacttatgat accggatcca ggcagaatgg gaatatacac ctctggatga   42180
ccgaagaacc aaaagagatg ctggtataat atagggtccc cccctccagc gggatcagaa   42240
aaggttgtat taaagtttcg atcggttaat aacatggtaa ttgccctgc cagtaccgga    42300 agtgataata aaagtgggaa tgctgtcact agaacggacc acacaaatag aggtgatcta   42360
tgcatagtca ttccaggtcc acgcatgttg aagatagttg ttataaaatt aatagaacct   42420
aaaatggatg aaacaccaga tagatgaaga ctagaaattg ctaaatcaac agctcctcca   42480
gaatggctgg taataccact taagggcgga tagaccgtcc acccagtgcc gctacccact   42540
tctactaagg ctgggcttaa taggagcaag agacttggag gcaacaacca gaatgaaata   42600
ttatttaatc gtggaaatgc catgtcaggc gcacctatca gaatcggaac agaccaatta   42660
ccagatccac ctatcatcgc cggcataacc ataaaaaaga tcattaaaaa agcgtgagcc   42720
gttattaaaa cattataaag ttgatgattc ccaccaagaa tttgatcgcc gggtcgtgct   42780
aattccatac gaatcagtac tgagaagcat gtgcccatca ctccagcaat ggcaccgaag   42840
atgaaataaa gagtccctat atccttgtgg ttagtggaga acagccatcg gaccggattt   42900
gtcgtaaaat tgagattatt tcgtttcctt ccttatcaga gaggggcccg cggggcttat   42960
ttattgaaaa nnnnnnnrgg ggrgkgrggg gggaaggaag aatggaaagc cctcacttta   43020
ttgatgggac attttgatcc ccttttcctc tcatcctccc ccggttctgg ttcaggaaag   43080
```

```
ggtcaacgca aggatcttat ttcgaagcaa tctctggagt tttcccttat ccgaacgggt    43140
cttgcaagaa aataggattt catattgagc tccaaatata cgctattggg atgggatggc    43200
tcctactagc tctccccccc taagaaccgc acgtgcgagt tccccgcat acggctcaag     43260 tggcgaaggc cctttccttc gcgcttggta agcgcttcgc tgtagccaag cttactgcta    43320
gcctatcggc tagagccaag cttcgaccgc gactgctcgt cgcttctggc cgccttattc    43380
cgtcacccga gatccaagtc agcaccggca aagatctctt gattcctcgc ggtcgggccg    43440
gcttggaagc aagctacctc ttgcctatct cacctccttc cttcagctgg gtgagccttc    43500 gcttttttgga tcgtcttctg cccaatgcgg taccccccgt tttttggttc ccattgggtt    43560
taccttgttc acaggtcgac cccatggcag caagaaaagg cgatcttgtg ctatactccg    43620
gtgatctctt tcctaccgag acacgcaaac tcccatcgtg tcccagatca cattccgtga    43680
atcgaaaggg gaagcctact catctatcag ctcctctcgt agatcggtgt ggttttacga    43740
agcgtctaag cacagttcac tcgcgttgat caatcaagag ggttgccgcc actccttaag    43800
gttatctgtt gtatcataca cttcttgcat tctgtcccac gcttcatacc tcctctttct    43860
tcttaaggta agataaaggg ccaggcatgg tggggtagga gcatccagtc ggcaatcttt    43920
ttggcttgac caagaagtct tatgtcctcc gagtcgcacg gcgttttaac cgaaagaact    43980
tcttgcgcaa ttcatgcctt tctgttttta tgaccagaaa ttctttcttt attttcatat    44040
aaaattgttc tctggacttt ttatcaatat gaggtgatcg taacacagta tataagactc    44100
gtgattcagg caatccaatc ttccgtgtgt aaggcggaag cccccaaaaa tggttttcaa    44160
aaaatgggtg atcaaaagat cgaattacta tgcctatctt ggtggtcgtt acttttggtg    44220
gtctttcttt ttggctgact cctatagacg aagtgcttcg tttcagatca attcttcgct    44280
gcaatcgctt cgatccaccc cctcggtgaa aaaccgtaat acgccctgag gaattcctac    44340
cagcagactt ccctgtactc aaagtgaatt gtctaagtgc tctcctttgt ctcattgttt    44400
atctcgtaat cattcgattc cgcccctaaa gctagcgcct actcctcctc cttctcctcc    44460
tgaatcctcc ttggtccttt ttacataaca ctctcggccg cccaagagga ctggctatct    44520
ttctctttat acgcacaata tcttgaaagg caaagaaaaa gatctacctt ggcaacgaag    44580
acgtcattga ctgatagttt atcttccgaa ccggttaaat acctataaca aaaaaaggcc    44640
aaagcccgct gaagcactgg aaaaatgttg accacgattt ctaacgcttt tcaaaaacca    44700
tttgcttgca acgccttgag tggacagata attacggcca ctagatcctt catactctta    44760
ctaaagtaca cttaagactc aaccaatctt gaaagtggag tggacaactg gcataccttg    44820
aatctagcct gcaatccttt cgcacttctc ttatcaaatt tctagttaga gagagagcta    44880
accgctgcca aaatgcagca gttttttctta tatacgatag cacccctgc cctccttgtt    44940 caagtagttc aagagtgaaa gggcgtagtg aaagaaggga aagatctctt tcaaagatat    45000
tctacccata aaggcagttc tcttatatgg caatactaga ttggcgagac aagagagaaa    45060
gcttataaag tagtaaggtg tctatggggc ttgccttaca ggtagtgact ataccactta    45120
catatcgaac agatcttact ctcaatggag tcatttcgat atgacctagg aacttacaga    45180
ataccgaact tggataatcg gtagaagaat gattggctag atcatttgct tcactgcgga    45240
agaaccccct tctacgctac gttcccaata aaaagccgtc atccttctgt cgcctgttag    45300
ccacaccaga ccaagaaaag gcaaactaat caaccaagac tcagtcacga cctttgtaac    45360
ctcacggcca ctttctttcc tagagcttgc agccattatc ttcgcttttc agatatggtg    45420
```

```
acattacttg tatgggggga agtgccagat ctttacggat cataagagct tgaggtactt    45480
gatgacacag aaggagttga accttcgcca ggatggcaca cttctattcc ggggacgagt    45540
atgtgttcct caggacagtg acctgtgcca tgatatcttg gaggaggcgc atagctcacc    45600
ttttttcctg cacccaggga gcacgaagat gtacaggacg atccgcccac actattggtg    45660
gaaaggtatg aagagggatg tcgctgagta tgtggctaaa tgcttagtgt gccagctggt    45720
taaggctgag caccagagac cagcaggacc cttacagcca gttcagatac cacagtggaa    45780
gtgggacgag atagccatgg actttgtctc tggattgccg aagactgcga ggcaacatga    45840
cgccatttgg gtgattattg atcggctgac caagtcagct cacttcctgc cgatcagtat    45900
gacttactct acgggcaagc tagcccagat atatattgat gagatagtgc gcctacacgg    45960
gataccatca tccatagtat cagacagaga tccacggttc acttcagcct tgtggcagag    46020
cctacagaag gctttgggta gcagagtgag tcttagcaca gccttccatc ctcagaccga    46080
tggccagtct aagaggacca tccagacatt ggaggctatg cggaggtaat cccttgattt    46140
tcgaggttgt tgggacagac atctacccct tggtggagttc gcctataaca agagttatca    46200
ggcgagtata ggcatgccac ctttgaggc actctatgga cgcaagtgca ggactcccct    46260
atgctgggat gaagtagggg agagacagat tcttgggcca gagattgtac aggagacctc    46320
ttccttcggt ccggttagta caaggttctg tcgtttacct tgcgcctatc tattcctta    46380 agcttatatc ttataccatt gcaatcagac tcattggata tcttcctttt ctcttctact    46440
atcgagagtc gtacgggtga ggaggtgagc tctaagcgta tacacataga taggtctggg    46500
taagcgacca tcagcggtat gggtagcagc tactatcagt acgccagtct aaggctgttc    46560
gtagaggtag gtcgtagaga tctatgaagg gctatattta gcataaatag catggttaat    46620
tatagaatag cgtgatggcc gtaagaagat cataaataag gtaaatagtc tggagtggat    46680
gtctagatca gggtgtcggc atcacacata tagcatgtgt gccgtgagtg agagggtggt    46740
cgtagatcag ccctcagctc ttcttttcgaa attctcgaac atgatgactt atcggcttga    46800
ggcttctttt cttttcaagc tgagtagaaa tttcataaga gaagaaaagt tcacagaagg    46860
ttcttcaata gtatgcctgg ttcacgaggt tctaccactg cagggcccag ttgccattcc    46920
cccattactc aagtcgtcca agggacagga cccccgcact gtaaaaagtt tccttttat    46980 acaactcatg atatctttct tctgtgcata tctcggtttt aataacttct gggtttatac    47040
caaatcgacc gtagagagag ttcattagta tcttgtagat atataccata gctgcatcat    47100
cctttatctt tgcttcttgt cttctagcga agatgtctga tacaaagcct tcgaaaggac    47160
tcttcttttt ctcatacaag tagcccctta gcgggaaaat tctataaccc aagtttcggg    47220
cataaaaaaa ttcttcgcta aaatagacgc ctacgaattt acctgttggg aaggttaaag    47280
cattatgtct atccttatag ggtaagaagg cttctctat tgtagagagg acacactaca    47340
aaagcctcaa taaagccaaa gaagttatcc aattccgcct tttctaaatt attatgccag    47400
acgggtacac cccctggcat cggataagtt ttcattataa atggatataa ggagttcaca    47460
tcgtaatagt ctaaattttc accataggc ttatagacat cggcatgtcc tccataataa    47520
ccacgccgaa tgaagcgttc ttggtttcga gttggtatat ggatgggcca actctttggg    47580
tcgtaatagt gcatacgaaa gattgataga gctagcgatg acaacgttat tgtatcaacg    47640
atgtctattt tgtacagatt ccaataaatc tcttgtgcct tcagcataac gccacctaag    47700
agacgaatat cttgtttcag ataagccaac aattgttgac ctatctccgg aagatactca    47760
agtcgtaatt tctcataggg aatggtgcct ttagaaccca atttcgggca taaatcctgg    47820
```

```
gccaagttat ttagcgcagc ggcaaggaga aggtaggaat ccctatacg gaacaataat    47880 ttctttttt catttccacg atagactttt aactcgtaca ttttatgctt cctcatcacc    47940
gtttggaagg agtacttgcc gatctgagaa ggaaaagctc tcgttactat aatgccatcg    48000
tatcgtgaaa agttatggaa atagaccgtt cgaatttctt tttcatctga taccacagcc    48060
gctaaacgtt ctataaagtc gagcatcata cgttcacttc gttttttgaa atcagatatt    48120
gagaaatcct tatcttcact gaaatatgtt tcaatataat attcagactt ggaagcaaga    48180
tcttcacccg gcttaaccac taagaacccc actgcgcaag gaacatgaac atcgtcgtgg    48240
agagcagcct ctatatcggc aacaatgaat gggctccttt ttattttatt aattgctttc    48300
agtgcgggta tatgatcggg acgacgactc ttcttaccca tagctaccac ttctacaggt    48360
tcatcactca ttgtcccgcc atccgttaat tcatcacaaa gttgcttaaa aatttcctct    48420
aggctaaaag ggtggacttc acggtgttca accctatcga agagatagat tcgaacccct    48480
actcggtcta gctgccccctc ttcgtatttc tcagccttt cacagacttg tttcaaaatt    48540
tcattatata cacgaagcgg gggtacttct gcgttatcgg cctttactaa aattgcattt    48600
cctgctgtaa agtcggctcg ttcgttattt gtatgtatca gaccataatg gatagtgaat    48660
ttaatagaac gaaatccgct attgtatgca tattttatta acagtatcat taccgctaat    48720
gagataactt caatttcgac acatttaagg taaggttttt taaagcggaa ttctgctatt    48780
cttattgact caagggggct atgatatttt tcctcagcga tcaacttgta gagaaatcca    48840
gactggaact attgatgatt ctacgttagc tctaaagtaa ggagaccact taaaaaccct    48900
catcggataa gaaaagatat accagataga gcttccctt gaggcatgcc tgagagcaaa    48960
gatagatgca ctctcttccg aagcggattc cgcgcttata ccttctccgg agacagctga    49020
ctcggactcc gttcctgcct tctgactttc aataaccatg cgcgtacttt aattaggaat    49080
gaaccaaaga gttaccttag tatagagaaa tggaagccag ggtcttctat aaataataag    49140
tatttcacct aggtgactcg ttcacctatc acgaataaat aggtgggtgg ctgcgtaata    49200
gaatagaacc tgctgaaact acctcatcca gggaagctgc ccggatttcc ttaagttaag    49260 tcttttttctg agctgtctta cttaaggtgt taccagtctt taccctcttt gtatggcgct    49320
aaagcgacta gtctatgacc caattccgga tggcgtctca gggtccctgc tcacctatcc    49380
tatttattgg aggtagcagc cacaactgaa cgctttcaag cacagtttca ttacgtgata    49440
ttgagttctt tcagctctaa cagagctaag acttcggttt catcaatcct gtttcgggat    49500
cgaattcgaa ctggtccaat ccacgtactc catcgcaact ggttaaactc tcatgatcga    49560
tgtaattgag agaaatgcca ccagagctca tatccggcaa tggaggattg aactttcaaa    49620
gaactcctaa ttcgaatagg aaatgcctgg caaaggaaga atagttcatt ggacaaggtc    49680
gcgtaagctg aaaggtcagc agagtcaaca actacatcgg aagcttttc ccgaagaggt    49740 ctttaagtgc tcgaacgaat gtgagaggag tgaatgtggg aagtgaaaat aaatcctcta    49800
agaattccct ctccttgctc gcagcaagta ttacgctcgc tggatagacc tatttctctc    49860
tttataatca gcaagggcct cagcgtattg aatggccgtc ctgaggtcag ggatatcatc    49920
gccaccattt cgttgcgagc ccaatctttc aaccctctta tgaaatagaa cacttttcc    49980 ttctcagtta catcatccac atgagcaaga ttatcaaggt actccttgat atattctttt    50040
atggtgccag tatgctttgt atcaacaaag cgcatttag cctcaaagta agccgttttc    50100
ggatagaact gcttcttaag ctcacgcttt cactcgcccc aatccacgat agggtcggct    50160
```

```
atgccttcat cagcatccat tttcaatcta cgccaccatg acgctgcgcc atcttgcagc   50220
caatatgtgg cttgtttgat tttcaagagg tcatcctcta tgttttgccc ctcaaagaat   50280
tgctcgcatc cccaacgcat caatctctcg ggcatccctt gcgcctttat atggcttggg   50340
cttgggtgcc tccagcttgt tttgagccac agaaatggtg gtagagcctt tggttaggcc   50400
tagcaccgtg gtcttcaaaa gaccaagctc attctcagct gccgtcaacc gattcaaggc   50460
ttcagtcaaa tcagccctca gagagttatt ctcagccact aacgagttaa tcctcccagt   50520
gagagattca tttccctcgg tcacagtttt gccaagctct tcaacagtct ttcccaaggt   50580
cttcaagtca tcctccacgt cggagactcg gtcttcaacc ttttcctctt ctttcttctc   50640
gttcttggga ctctatttag gattgattga ttcccgttag gtggattggt tgctgcgcag   50700
ctaactacca accccgaaat tacgtacaga gaaagggctt gtggaactac ctttcttcat   50760
ggtcaggatt cactgctacg gcgggtagcc tggatctcat ggattagcca gaacagtgga   50820
gaagcaagga cctgctagct acatcttcag tctgtagtga ctcattcatc gggagcggag   50880
ggaattgctt ccccgtgggt cgtaaattga atatgcagaa accctgactt cctgtcttct   50940
cacagctctt tatccatcat gctagcgaaa aaagtgaaag tgcgacgggc tcctccatga   51000 gaaagggat tccttagtat ataggatatg tcctttaagt tggaagattg gaacccttg    51060 ggcgtccttc ggactttagt tagcatcgag ccctcttttt aggaagaata ggaaaagagt   51120
ttcaatattg aaacagcatt ggataaagga agtcttcgtt cattcaacgg cattaccgac   51180
cggcctaggc tcttcgggag cagagaatag gataggctgc tggtaggact ggcttgttgg   51240
gataggtcag gcaaattcct ctagtggaag gaatatgccc atagagaaaa agcctattag   51300
taagtaagat cgaaagagca gggacagcta gccctactcc ttctccttct cttactaatg   51360
ttaaatcatt cccttccttc tttgctcttc gaatggcgct tgccttgcat tctatgcatc   51420
ttatttacta ctagatgtaa tttccttgtc cgattcaagg ccatcaccag attcaatagc   51480
cggggattcc ttctttcgat ccatgtcatc tggcatacta gctctgacga cgagtcttct   51540
gttaattatt aattaaatct ctcctgcgaa tccttatcct tcaaaaagct tcttctcgac   51600
gcaggagatt cgtgaacaag cccatctaag agcctagcaa gcagcccttta gtgcgacaga   51660 gagagcttcc aacaatacaa taaaagatct atcccatctc gtgccctgta agaaggaact   51720
tcatcagtcc cagagcctat tcgacgtcat cttccctgtc ctcttccgat tcaacctcat   51780
attactcgta caacaactat ggcaaccaag agctcggagt cgacaatagg aattaaagca   51840
tcatcaaaat gaagagtgag cacttttgt gacggaattc cttcgttccc tttctcaaat   51900
gcaataggaa gatagccttt ttttcgtaat agaagaaagc tctcgtcttc ttctagggct   51960
gtcaggaagt ctcgttcttt gttctttaca attagaagct cttcctttaa ttacaggacc   52020
agaacaatct aagaagaaga ggaaaagggg ctaaggttga taggtagata ggttacgtag   52080
ctcaacgaaa gcatatacat aatatctttt cttttctctt gcctacaaag tttttggcgg   52140
tatatcgtat ataagaaga tcacggtttt aggagtgatc ttttctttc ctctcactcg    52200 aaatatcata agagaacaga aaggttttga ttcgaggttt ctagccgtct tcactgactg   52260
gaacccaaac caaataaagc aatggcgtct gtttacgtca gggtccgaag gaacgaagtg   52320
ctcgaccgga agggaagtag tatgtccggt tcactaggtt ctaccactgc agggctcaat   52380
catgctagtt gggctatatg cttaacacat gcaagtcgaa tgacgttttc ttggaaacgg   52440
gagtgaacga aggaccaacg acgatgaagg aggagttggg gaagacgcgg ggtagaggaa   52500
ttggtcaact catcaggctc atgacctgaa gattgcaggt tcgaatcctg tccccgccta   52560
```

```
atcagtggaa cactgttcac cgggatagaa ggccggtccc aacccgtcta caaaatgggg   52620
ctagtgttca gtcttggttg gttccacctc tttgcagggt gatgacacca gtagctgtgg   52680
agcacagatg accatttctt agactattga attccaactt agagctcctt ctactctaaa   52740
ctactgtgtg cctatttgga cttttcaca gtcaaagtca aaggtttctt ggtggcaaga    52800
tcggcatgcc ttctagttgt agttgacttt aagcgcacct gaactaccca tagtcgtcta   52860
tttacgggct tgcactcaat agtcaatcaa ttcgttttc cgctttctat cgcacgcttc    52920
aactatttgt ttatatagtc taactaatgg aaagtgccta tgaattagtt ccaagaaagc   52980
gtccgttcac gtcaggaata gaggccgtta aggatgtact tgcttttcct tttttgcgtc   53040
gagattgggt tggtgttcag tgtaccgctt gtctagccta tgctttgcaa gcctacatag   53100
ggtacaagat cgaaaagaat gcattggatg gatgcccggg cattgagaag gaaggacgct   53160
ttcagaggcg aaaggccatg gggagatacc gtctgtgatc catggatctc cgatcgggaa   53220
accgtatcca agctccgtgg ctagtctgcg ctctttggac ttttcaaact tagcgaactg   53280
aaacatctta gtagctaaag gaagggaaat caaccgagac cccgttagta gcggcgagcg   53340
agagcggatt gggggtttga agaaaaacaa agacgaagct tcgttcctca gcaaagtgtt   53400
cacttctttt tcgccaggtt tcattcgatt tgttgtggat tggatgatgg aaaaaccagc   53460
aagctacggc ttcaaagctt accttattta gaaaggggga aagggctttt ttatagatgt   53520
tgaggttgag taagggggc ggagcttgaa gagcgaagcg agccgcgcta gcctagcaac    53580 gttttcagc agcaagctac ggtctaacga cccctaacc taggttgggg cgaaaactcc     53640
aaaatccaaa acgttggtta gggttccaaa ccttctctc agaataaggt aagctttcaa    53700
gccgccgccc tttaaaggag cgggcgcagt gaactgtaat tgtgaaaaga ttggaagatc   53760
tggccaaaga aggtgatagc cctgtagatt cgttcccatg gttcgatcct tcccagtaaa   53820
acgcggcgtg ttcgaattct gatcgctttt acgcgagaaa gggggaccac cctctaagcc   53880
taagtattcc tcaatgaccg atagcgtaca agtaccgtga gggaaaggtg aaaagaaccc   53940
tatttaggga gtgcaataga gaacctgaga tccgatgcga acaatcagtc gaaggagcgg   54000
agcttagagc ctttactta tgtaaagcgc actcactcta acggcgtacc ttttgcatga    54060
tgggtcagcg aggaaatggg aacagcggct taagccatta ggtgtaggcg cttccagag    54120 gtggaatctt ctagttcttc ctatttgacc cgaaaccgat cgatctagcc atgagcaggt   54180
tgaagagagc tctaacaggc cttggaggac cgaacccacg tatgtggcaa atacgggga    54240 tgacttgtgg ctaggggtga aaggccaacc aagatcggat atagctggtt ttccgcgaaa   54300
tctatttcag tagagcgtat gatgtcgatg gcccgaggta gagcactcaa tgggctaggg   54360
tggccccatt tcgccttacc aaccccaggg aaactccgaa tacaggccta gatcgtttgt   54420
acagacagac ttttgggtg ctaagatcca aagtcgagag ggaaacagcc cagatcgtac    54480
gctaaggtcc ctaagcaatc acttagtgga aaggaagtg atcgagcgat gacaaccagg    54540
aggtgggctt ggaagcagcc atcctttgaa gaaagcgtaa tagctcactg gtctagctcc   54600
atggcaccga aaatgtatca gggctcaagt gattcaccga agcgacgaga ccttgaaagc   54660
tgctttttca agtgtcagta gcggaacgtt ctgtcaatcg gggaaggttt ttggtgacaa   54720
gacctggaga tatcagaagt gagaatgctg acatgagtaa cgaaaaatcc tgtgaaaaac   54780
acgatcgcct gccagtggaa ggttttctgc gttcagtcaa tctacgcaga gtgaatcggt   54840
ccctaaggaa ccccgaaag ggctgccgtc cgatgggtac acgaaagtga cgaagttgct    54900
```

```
ttgactacag aaccatgcct gtctgttgga gcgaattgga tgatcgggcc gagggctgcc     54960
ccctcttccc ctcactctcc tttccctaat atgaaccttg agtcatcaaa gcctttctga     55020
ctcggcctgg cccggtcgcc ctacgcgact ggcgcttcaa aaggcgaaac tctcggtcgt     55080
agtttggcga cctatcttca gtaggggcct ttagtctttt gattagagta ggggtcgcga     55140
gagagcagag cgtaccgccc tgccatagtc acgagtctgt ttatagtcgc gactgttgtc     55200
atagtcaaca aggttgaaac ttccaggaaa aaacttcgaa ttgggagggc gatcctcccg     55260
gtgaactgac cgtaccccaa accgacacag gtgaacaagt agagtatact agggcgcttg     55320
agagaaccat gtcgaaggaa ctcggcaaaa tgaccccgta acttcgggag aaggggtgct     55380
ctcctatctt ttgattagga aagcggcaca taccagggggg tagcgactgt ttattaaaaa    55440
cacaggactc tgctaagtgg taacacgatg tatagagtct gacacctgcc cggtgctgga     55500
aggtcggaag gagaagtgtt ataagctttg aatggaagcc ccggtaaacg gcggcagtaa     55560
ctctaactgt cctaaggtag cgaaattcct tgtcgcataa gtagcgacct gcacgaatgg     55620
tgtaacgact gccccgctgt ctccgacatg gacccggtga aattgaattc ccgtgaaga     55680
tgcggagtac caacggctag acggtaagac cccgtgcacc ttaactatag cttcgcagtg     55740
acaaccttaa tcgaatgtgt aggataggtg ggaggtggtg acacacaacg accaatcctg     55800
aaagaccact ctttcgtcta aggatgccta accgccgcac cgatcattcg gggggaggcg     55860
ggacactgcg agtggggtag tttatctggg gcggatgcct cctaaagagt aacgaggtg     55920
tgcgaaggta ggctcaagct aagattctgc tcgtgagcgt aatggtataa gcctgcctga     55980
ctgtgagacc gactggtcga acagagacga aagtcggcca tagtgatccg ggagtcccgt     56040
gtggaagggc tctcgctcaa cggatcaaag gtacgccggg gataacaggc tgatgactcc     56100
caagagctct tatcgacgga gtcgtttggc acctcgatgt cgactcatca catcctgggg     56160
ttgaagaagg tcccaagggt tcggttgttc gccgattcaa gtggtacgtg agttgggttt     56220
agaacgtcgt gagacagttc ggttcctatc taccgttggt gttaaaggga gaactgcgag     56280
gagccaaccc tagtacgaga ggactgggtt gggctaacct atggtgtacc ggttgttatg     56340
ccaatagcag cgccgggcag ctaagttggt atggaagaac tgctgcgccg cgggaaatcc     56400
ttctctatac aagttctcgg acgaggtttt tgaacagaac ttcgataggc gagaggtgta     56460
agcaccgcga ggtgtgaagc gatctcgtac taaacgaaac gactttcact ttccataaca     56520
aaaatgaaag aaagtcaacc tattcctgaa attgcggtca gtctcgctac ctctttagtt     56580
gccgcccct acttgctcct ttctctaata ataaggtagc cccaacctat acaagggggt      56640
cgttagaccg ccgcttacta agcgctggtt ctatcccggc caagcaacca aagccgggga     56700
cctggcaaaa taggaagcag aaaaccgctt ataccgagtt ccccaacagc agcttagctt     56760
agtaacaaca ctctttctac cggcggcgtg gccctgctgg atgcatttga tcaatagaac     56820
acgaagagga ggaagaagaa aagaagcttt gttatgaaaa agtttccatt tctttcccaa     56880
ataataagaa cttttggtgc tgtagtcact tttgcctttg gacgttttct ttttttcggg     56940
gcagaaagaa cgatcgcgcc tagctggatc cttctctttc tcttttgtct tatacttatg     57000
attcgggcaa aagaaagaac aagaagaaaa aggagtgtgg ttcatttttt cgttgagttc     57060
ttcctccttt ttcttttttct ttcccttctg cgcctactca tcatggacgg gatttcttcc    57120
tttctaggcc tgaccctggg cctgaccact tcttttgttt cttatgtttc gtctggatcc     57180
aatgaaagtg ggaattcggc tcctgaatca gggggtcctc cccctttaga atccgagtcg     57240
agttcggcgt cacttaacac ctttcgaaac cagatcgctg cggataatga agccgatata     57300
```

```
tatcggcgca tacaaatttt agaaaaccag gaatactaca accttcctcc ccagaacagt   57360
cctggtgact acgaaaggct ggttcgcgag aacttcgatt cagccataaa tgtcaatcat   57420
tttcggacga ttttttgatag ggaatacttt gaccttcgag tcttagagag aagggcgtc   57480 gtacaagacc aactccaaga tctaatgctt cgggaggaga atatttcaca gattctagag   57540
aaatctcctt attcgaacat taggaaagaa gcctattact atcttgagca caagctcaac   57600
cccgttagcg atccacgcca tgcctttcag cgagacattc ttgacaccag tctcgacttc   57660
tttcaacgag atttgaatct gagaggcaaa gattcaacca tttacaagga gtttaagacg   57720 tatttatgg acgaatgatt gggaggagta gtcttcttga cataaaaagt caagagggcg   57780
aggcccctag caatgggggg aaaggggagt gggtaagggg gccccttttca cttgactgct   57840 tagttaggag tgatctttt tcatctccac tcttttttcct attcaataag agagcaacta   57900
cgattgcgac aaccatcgca tagctattca gagttgcact cggagactta cgattcctcg   57960
aactcgctga acactttcta tatctatctg tcttcatcga atttccgcta tctgtcttga   58020
gttagacaag cacaggccta tcttagctcc cggtgaccgg cttcgcgaga ccttttcgct   58080
ccacactgga gaagtcctct ctcgggctag gctctattgg gcggaggatc accttctctt   58140
actagaggag caggaaagaa gagacttaca tacgtaattc tagaggtgaa ccagcttggt   58200
cggtagaatt ttttcgaatc tagcaaaagg aaggaaatga tgcttttctt aaggcaatcc   58260
ataagtcaga aatagaatga ggaagagaga ggaccccacg gaatggtatg tgggccctcc   58320
tcaagcaatc ccctatgact caacctttgt tcttgtgcaa aagcgtcctc ccccttcctctc   58380 ctgtttttcg agctcactaa ggcaagcggc gccccatttg tgtctgtctg cgatcgtgcc   58440
tagctgggca gttcatcagg agctgctatc tgggaccaag cactaagcac tcttgatttt   58500 cttttcttaat tggtttctaa caggattggc aaatgtcact gtgcgtaaca catctaattg   58560
gaagtggaat gaagataatg cgcttgactc tttcatttgt agctggatta cccccttgttg   58620 ggttgggcta acttaacttg aatctgttct gtttagtttt tcactaagcc tcatctgagt   58680
gctatataca tagctccttg attacttatc aaataaaatg aacattcttt aagaactttt   58740
tctcccgatc ttattagctt agtagcatgg aagtcacaat agttgtagca gagtaagcta   58800
gaagatgacc aatcccgccc catcatgatt ggtgtcgagt ccattgtgag aggcgcttaa   58860
aaggccgtta aggcattaga ctcagggtgt aacccacagg ggaggggaga ggttgcttcc   58920
tatcctaaaa acaactggct ttggctcgtt gcctttgatt ccttacccat agcataagat   58980
aaagggtgcg tgcttcaaca tctaagtttc acacaaggaa cctcctgctc ttaaggataa   59040
actacgatat ttgatggact gacaggtcag ccacgtaatt tatccctcaa gctgaacgaa   59100
cttgacctgc tcctttattt agtttagggc tatagagtttt acttgcttct cactaagggc   59160
agaatcatga gcttcatcac tcgactctaa accaaattaa aaagactcgg ctataggatg   59220
acaatccttc actccggaag ggtaggttcc ataccgacaa gacctcctat cccagaatcc   59280
gctcatttca caccaactaa agcggaactt aatcaccaag gtagagttgt ataaaaccct   59340
aatgtaactg aacgaagtgg aaaacccgca atacgagagc aaaaaccttc tgtgtgtaag   59400
aagaaaagca acatcgagtt aggtaggatg tagatcgagc gcaataagct acaggagtta   59460
ttatttcgct ttggaaggaa aaaagcatct caaacaattt cattgcctca ctcagctctc   59520
aggctgtctg ggaatagctc caccagacat agaagaaagg agtataggat tggtaagctt   59580
tgccggaaag aagctactcg actaattcag gaggctacta ccggcgaagc ccgcttgctt   59640
```

```
cggagcgtgc tattgcgtga agcggaaagg gacagcggaa tctaagacca caccagacag   59700
ggaaaaggag gattagatat ttcgtcaacc accacttgag cgcgattcgc ttatctgttg   59760
aaaagtacca tccagacagt aaacctttag ggcatatgac tagtaaggta aatcaaccta   59820
tcgtatcgac gagatgcaac agaatcaatt accagacgga ctggctttcc aatttctctg   59880
tcctaacagc gttcgaagcc taacatcctt gcaagctttg gattctttcc tatctctgac   59940
cgggaaagag gttaccaagc aagtgaaact gaagtgaaac tgtactcgcc tcttctcctt   60000
cttgtcctct tgtacttccg ttcttcttat tctcgtatcc ggaaccggaa caagctcttc   60060
tttagcagcc tcgctttgtt agcagtacta gtttgtactc tttattgacc tggaacacaa   60120
gctttaccag ccaacccgat ctgaccttcg aaactctctt ctcatactcc tcgttcgtcg   60180
ttccaggcgt actccagtta gctcttctct tacagagcct tgtctgttcg attgcttttcc  60240 tagtcttctt cctgcttcat tagataaagc gtcttcacta atagatagat aggattgttt   60300
gcttcaaagt gtctttatat caaataaagg cccttgaaag gggatgaaac tcttatttta   60360
acgcccaaag ataggcctct gcagcccttt ctaatgaaga tgatgcatag gaaaggtcct   60420
atcgaaaagg ctgttgtcgt cattttttgct ctttgcatct tccctgaccc ctcgtcactg   60480
ctttctgatc atgtctcttt tcgaatacgc gaaaggaaag gacaaagtga gggctgcttc   60540
ttcgcgtcag tagttgaata tgaatgaaaa cacagaaaat ccaagtatgg ccctagcaac   60600
agttctaaag gcagttgaaa gaccgtaagc caggcaaggg ttaggggcaa gctcccataa   60660
aaaacttcta aaggagagag ctccggaggc aaggcgaaag gcatgcactg ggtaccgccg   60720
aaacgaatag ctaacatagt tatcccggtg atttttgcccg aagagtttag ggcagagtct   60780
gattatgctc ctccaacagt tcacgccaaa cgttgtactt cacaaaaggt agaaaacaaa   60840
gaaccaaatc ctgagactag ggtgatatgc ccactctcca gaaaaagaa gaggtggctc    60900 atgccggtga aagaagcaaa aaaagaaaag tctgattcct gatccaaaac cggttttttg   60960
aatgaagtta gaaagaagtt ctattgctcc ggaaggaagg cggtaggtgg gcttagataa   61020
gaaatctagg aattttttct atatatcaat ccttcgataa agcaagagac gactataaaa   61080
aaaactgact tttccatttta ccggaagaaa cgtcgtcaaa ctgagcgtct gaataaaagg   61140
actcagtccc cgtgaacggc ctaatgtccg ccgcctctag ccgatgcgca ctataatgag   61200
caaaaatgct ttcctttctc catacctcct accctctgaa cttcctggat tgagctggtc   61260
caaagtgttt ccggcaaagc taggaacgtg cgtcaaacct ttcggccccg tgttaaccac   61320
ataaaagaga cgattcattc tattccctcg gttatatttg actaagaccc agaggatatc   61380
ctaaagtggg cattcgggct catccctccc ttcacggtcg cagtcctctt agccatagggg  61440 ttttcttgct cgcccgtaac tcctctgttg gcattggttc atttttcggta tggctactga   61500 ggatttgatt caattcataa acgaagctcg caggatctaa agtggagtct ggctacaagt   61560
cgagttgaaa tggaaagaaa aatggactca acctctcaac gaaagagaga cgcaggtctt   61620
ttcacggctt cgttcgataa agcactcaaa ccaacgagta aggaaaggag gccttgagtt   61680
gatatttaaa agaaggagtt cgtcctggtg tgctgcttcc tttcctgcca ctactttttg   61740
agtcaaaaag tcctctattg gtttaattca tattcaagtt tctctagcgg aattagactt   61800
tcatttctat ttcttcaaat ccagcatgac atgtgtcaag aagcgaccca tcaaagaaaa   61860
gttagaaaat cctgtttttgg cgaattcaat gtttccatat agatgacctt ccctccggac   61920
aggaaatcat atattgaata gagggtactc cacctctgta gaggatacaa cacattgaaa   61980
taaaggaatt ggtggatctc tcccatcaga cagatcaacg gcaccgggca tgggatacac   62040
```

```
aggcaggaga gccgatttga ccgcgcagac caaatgagcg aaattttttt aaagcgaaag    62100
cgctgtgcca acttgcgtac aagatttata tgtggatttg atacaatagt caaatcctct    62160
tcataagtcc tttcttacag gctattcaag gtctattggc tttcttgctt atgcggtact    62220
tcgaaggcta agcctcgttt atgcaccgag aaagatcgtc ggtaggaaag ctctgttatg    62280
caccaacgac ggccccttct ctttaccttt cccgtgccct acttcattcc tttgctggct    62340
tgaattccat ctcttttctt ctttgtttga aaatggcttc aattgatttc tttcaggccc    62400
tacttgaaaa ggttgggttc tctgtggggg gtcgagccct ctcctttgca ttatgtaagt    62460
tgggctgctc cagctggatt gcattagaaa tcgcttttgc tgtgcgtggg attgccgggg    62520
aaccccccga tttggctcat tctatgttgc ctgggtcctc tcaccaaccg cacgaacctc    62580
aagatgacga agactcgccc tcttcgagaa aaagaagaat ggatgaggat cgagacgggg    62640
atgtcggccc ctcctcagta cgaagaaggg tgggttccag agaggattgc gccaaccaaa    62700
gctttgactc tgagagtgag agttggcgtc aatctcacgc cttgtcatca gataacaaag    62760
tagatttcgc cccagaaccc tccgcagccc ggggcccccc cttaggggag gccgaccaag    62820
agcaaggaac ccccggcgcc ggcggcttag gcacttctga cgcgcggacg gggaaagatc    62880
ccttagaaag tcaacaatct ttttctgcga gtgaaaaccc taaaaaaaaa tgcgaaggga    62940
tccttatgct caattagttg aggacgcaca acaaaaaact atcaaaatcc agggtgtaat    63000
agacgaattg gaagaagaaa cgtcttccat ggacaatgtg gatgagatca taaggaagtt    63060
ctcaaataag ctaagaatcc aaagttcctc ttcctcctat aaggaaggcg attcgccgac    63120
agaaccagaa tgaaccgccg ccgtgaaaga ggtaagaaaa gagtttgcaa tgtcgagaat    63180 gaaactatg atcttttagt tgagggcccc ttcacttgag ctaattccgg ctttccagcg    63240
gaggctgcaa agcaaaggtt aagatactaa cccacggagc ggtaggctaa gcgggaaagg    63300
gagagagtgg agttagatcc gatgccattg attctgttgg aggaaggtca gcaggaaaga    63360
gaattgcttt tgttgaagaa gcaacaataa aataagctct tgctcaccga atcccttca    63420 ggtgcagatg aatatgctgt ttagcttggg actagggctt atgatccttc tcttaacggt    63480
agaacaaaaa taacaaagga gctctcctaa cctaagcaag ccgcggagtc gtagaccatt    63540
gctttaaaga cgggatggaa tcttcttc tgatcctaag ctgtgaactc atggtcaaat    63600
ggcttccgag gtgggctttc ccttctctat ggtagtactg tgaaaacgga gattgcttgt    63660
cctgctcgag ccattaagga gggagctgag ggagaggagt ggctccttac gctgggaccc    63720
cttggctcta gttattggtc ggcagagggt gcttgggatg accgggatta gtggattcct    63780 ttttttatg cttttctttc gtttcggctt tcctgcagct cttttcccga tctcttttc    63840 ttcattaaat ttacaagccg cagacatata gccagggagt gccatcccta aaaagaaaa    63900 aaatcactct tttagagcta tgacttactt agtttaatcc tactagaaga gcagtgagtg    63960
acctacattg agtaggaata aggcaatatc ccctctaagc ctaggagctc ttggaggcat    64020 taccccatc acattggagt tgacggtccc agtctttct gtttgcgtag gagttcttcc    64080
tcttgctcca tcgaatgcac tgagaaaagt agctgtgagg aataaagagc gtattctgtg    64140
gcatttgatt ccattcttgc taacagctga ttctatagat tctcgaacag cgggtacgca    64200
aacaagggca ccaacggata ctgtcacacc ggttacgaga acagctataa gagtaggagg    64260
gaattcaata ccaattgaag ttttctaaga catttgggat ttgtcttgca aacaagcctt    64320
ccctccctca catctgattc aatagcactg gtaattcctc caacaccatc caccgcggat    64380
```

```
acgatagatg attctatgcc atcctcttcc cttcttgtct atctccttcg atcagatagt   64440
tctgcttccg gtgccggagg aagggtagtt tcagagttcg agatgtctga gcttgggggt   64500
tccgcttctc taatgttata ataaagctgc ccagatcttg cgtcttcttt tgctggctag   64560
atgcgtaagt caaggttcac gcttgggccc ttgacgagta cttttgatttt agttagacca   64620 taggtgctaa agggtatagg aagatattac ggaggagtgt catacacatc catcggcaaa   64680
tgcggataga gtagcagatc aaaatccgga agcaggggtg ggaggatcat ctgaccctag   64740
catgatcctc taccggacca agctgataga gaaggttgga ccaatcgagg gagggagtga   64800 ggcttttcaac cggaccgggg ggggtcggg tagagctgta tttgccgagg caaggttgga   64860
ccggaatcaa cagagattgg tgctgcgagg gcgaagcgaa aataactccg tgccgcttgc   64920
tgcgcgaagt caaacttcgc gacggaagca agaaaagaaa gaaattacga cttcaccaac   64980
cacttcggcc taatcatccc acttctttcc tcaatcccaa taaggatat cgatttacga   65040 taaccacttt cgcccgatcc aattcacctc catcgaggca gcgaactagt agatcatctt   65100
tcctgaggaa tggaaggatg gagtggtatt cgaattctcc ggctacacga tgagaaaaaa   65160
acatccgtga actccttatt aagacttttct tctatctgct acttaattaa gatgaaagcc   65220
actaagaagt gcatcttgct tggacgttgc cgaagaaagg gctattagat gggcgattcc   65280
cccctttcca ttgaaatagg gaaagcggga tgaaagctct aagcccgcat cttcagcttc   65340
tattagaggg gctgtggatc caatccattc gaagggggag cagagcagca ggcaggcaaa   65400
gcaggggaag agatatggat tgcaccgaaa gcaatgccct tcggagcgca ttgcttgggc   65460
taagtcaaag ttgctgatct cttttttattg tattctcttc cttgggaaac aaacctccca   65520
catcatctgc tgtctcgcat ccatcgggat gagtcttgcg tctgtcttat cttcccctaa   65580
ggtctattgt attgaaaggc catctctcga atccgagcaa tgaaaggagg aagaaccata   65640
tagatattca gtaatgaata cgatgtggat ccgttccaaa gcccctaatt caaaatatag   65700
tgtgaggggg gcagagcttc catttccagg gacaatcctc cgcctcaggg cgttcttttt   65760
tccaggaatc tgtcaatcgg aggagcgcaa ccaagtttca aacctcaaag cccttcaagg   65820
gatgtgaagc ccttctcaat gtcttccact cgccaggagg caaggggaat ccgttgattg   65880
aatccattcc tgatgatgtg ccgctaacaa ggcctaccta ttctcccaat gcaacccggc   65940 ttttagggg catggcattc aatcctatct caatatatgc tcctccaagg cctgagggtg   66000
gattgaatcc aatcccatcc agcataggcg ggtagagttc actcatccgg tagttagagg   66060
atgatgaaca atgatgctat atctgctcac cttttcctaat ctgccttgtt gtgatagggg   66120
gcttaacggc ccaccaacca atctttcttt ctatctcgaa ttcttgatct ttggtgccag   66180
tggagcaaag gaagcggggg acgaactcct ctatttaccc tagaaatggg ttggatctat   66240
tgaatgaaat cctggagaca gggctgggag gtatgagtcg atcggatgca gggaagccca   66300
ggcaatcttt tcctatcaat cattcgtcag gaagcagtgg agaaagaatc gtcttttgaa   66360
atctcattgt tgaaggcgta gagagggctg aaaaaaaat aggatcattt ttgatagcca   66420
tctcgttaat caaaaattgt gtaattaatt ggaccccttct gcccggcagg caatttctgt   66480
gcaactagac tttctctagt ccctgctatg ccagcaatag ggaatcctta gaaaagcgga   66540
atgcaagttg cgtgatagtt ttattcccca caaatgagaa gtccccaagc ttgaccccctc   66600 ccacacaggg gcgactggct ggggcccctgg tggatttctt tctcagttaa taaatgtctg   66660
gaatcttggg ttactaattg gtggaatact gggcaatccg aaattttttt gaataatatt   66720
caagaaaaga gtcttctaga aaaattcata gaattagagg aactcctctt cttggacgaa   66780
```

```
atgatcaagg aatactcgga aacacatcta gaagagtttg ggataggaat ccataaagaa    66840
acgatccaat taatcaagat acaaaatgag aatcgtatac atacgatttt gcacttctcg    66900
acaaatatca tctgttttat tattctaagc gggtattcaa ttttgggtaa tgaaaaactt    66960
gttattctta actcttgggc tcaggaattc ctatataact taagtgacac agtaaaagct    67020
ttttctattc ttttattaac tgatttatgt atcggattcc attcacccca cggttgggaa    67080
ttaatgattg gctctatcta taaagatttt ggatttgttc ataatgatca aattatatcg    67140
ggtcttgttt ccacctttcc agtcattctc gatacaattt taaatattg gattttccgt     67200 tatttaaatc gtctgtctcc gtcacttgta gttatttatc attcaatgaa tgactgataa    67260
aggatccgtt gatattaatc taatccaatt agaatgcttg gtactttgta gttgtacata    67320
agcaaagtat tgaaaatcgt atttactctt tctatttcta accatcgggg agattcatcc    67380
tatattattc ctagattatt ccagcaaata gcagaatcgt ggctagggaa ctatattagc    67440
gacctaccca atttattgta gaatttttcg cgatcaatga ttggaccatg caaactagaa    67500 atgcttttc ttggctaaag aaacagatta ctcgatctat ttccgtatcg ctcatgatat     67560
atatcttaac tcggacatcc atttcaagtg catatcctat ttttgcacag cagggttatg    67620
aaaatccacg agaagcgact gggcgtattg tatgtgccaa ttgccattta gctaataagc    67680
ccgtggagat tgaggttcca caagcggtac ttcccgatac tgtatttgaa gcagttgttc    67740
gaattcctta tgataggcaa gtgaaacagg ttcttgctaa tggtaaaaag ggggggttga    67800 acgtggggggc tgttcttatt ttgccggagg ggtttgaatt agctcctccc gatcgtattt   67860
ctcccgagat gaaagaaaag attggcaatt tgtcttttca gagctatcgc cccaataaaa    67920
aaaatattct tgtggtaggc cctgtccctg gtcaaaaata tagtgaaata accttcccta    67980
ttcttccccc ggaccctgct actaagaagg atgtttactt cttaaaatat cctatatacg    68040
taggcgggaa caggggaagg ggccagattt atcccgacgg cagcaagagt aacaatacag    68100
tttataatgc tacagcggct ggtatagtaa gcaaaatcat acgaaaagaa aaaggggat    68160 atgagataac cataacggat gcgtcggatg gacgtcaagt ggttgatatt gtccctcccg    68220
gaccagagct tcttgtttcc gagggcgaat ctatcaaatt tgatcaacca ttaacgagta    68280
atcctaatgt aggcggattt ggtcaggagag atgcagaaat agtacttcaa gatccattac    68340
gtgtccaagg acttttgttc ttcttagcat ctgttatttt ggcacaaatc ttttttggttc   68400 ttaaaagaa acagttcgag aaggttcaat tggccgaaat gaatttctag attcgcagat     68460
ttatcgacat caagttcgta aaaagaacca aattcttctt ggcgattatt tatgatcaaa    68520
aaaataaaat tatgaaaacc cctttgtctt atttatactc ttcgccaaaa tctacatact    68580
atgtggtaca aaggattccc agcgggaatc ccgttgagtt cttacgatttt catgttgaca   68640 actcaattca ttcgattact acagggatga acccaatccg gaatatgaac cataaaagaa    68700
aatacctact aaaccgatta caagaatacc agctacagta cctattatcc aaagaggaat    68760
ccttccagta gtatcggcca tttaccccac ttccctccag atttcatcaa gtggtcatgc    68820
tagagacata aacagtcatg gataatttaa ttatgagatc cttccgaatg agctaagaga    68880 atcttatta ttctctttca ttttcttaat tgaagaaata attggaaaat aaaacagcaa    68940
gtacaaaaat gagtaataac ccccagtaga gactggtacg attcaattca acattttgtt    69000
cgttcgggtt tgattgtgtc gtagctctat aattcggatt aagtttatcg ttggatgaac    69060
tgcattgctg atattgatcc caaaaaaaag acggtaggta cagctaggcc gtgaacagcc    69120
```

```
aaccatcgta ctgtaaaaat tggataggtt cgatctatag tcattagggc ctcctaaaac    69180
gatctactaa attcatcgag ttgttccaaa ggatcaaaac ggccagttat taatggaatt    69240
ccttgtcggc tctctgtaaa atactcgttt ggccgagggc ttccaaacac atcgtaagct    69300
aaaccggtgc tgacaaataa ccaacccgca atgaataggg aaggtatagt aatgctatga    69360
atgacccagt atcgaatact ggtaataata tcagcaaacg aacgttctcc tgtgcttcca    69420
gacatgctga gctccacata ttcttgtaca gtcaaagagg atcgattccg taaaagatga    69480
gatcagtaaa tgacaattca ctgaaattta atctttgtga gatcgtcaat attgtaccga    69540
gggcgtcttt agagtatacc gaatcagtat agctatcctt cttctgacac agcaacgcaa    69600
tttgaattag tatcaaaagt aagtactaaa taatttcttt tttcctttac ttgttgatgt    69660
aaaataatct tccattcaat agaaaattct ttcaattcaa cgaaagagat tctaaaattc    69720
ccacaattta agtagatccg agatatagaa attttctttt cgtagttgtg gaagcggttt    69780
tgttgttgga atccttttt taaagaagag gttaatggtc gagtaagaaa taagagtagt    69840
agatcatatt cgatgaaagg aaaaatagaa taattggaat ccatagttgt gatgcattgt    69900
tgtggatctc gacccaaagg ttctttcttg atctagctac aagggtgggg cggtatggaa    69960
agataaaatg tggaacctaa tagaaattac tagttttaga atctagttgg acaaaaaaag    70020 atttttcaa gcaattgtgt gatacccttt tcttcttctc catcattcaa atatattgt     70080 gaatttatat attactgaat ctaatgagtt aaacttaaat taaagtaaaa agaaaaggtt    70140
ttataaggta actgttcgct ttaaaatcga aaatggattc gatacaattc aacagaatct    70200
aagaaatgat caaattcgaa agtcatttct attttgattc tataaaaatt aaagtttcat    70260
ttttgaatga agttagacga tacagctctt attagtttaa tagtttaccc aagagttact    70320
caatgaatcg gttgattgga attgcgagat agatagatgt tacagatgat gaatcaattt    70380
attttatatg tctgtcactt tatctttgtt agtgctgtct gcctataatg atagatgaat    70440
caaaaacttt tcattcaact tattctttca attgaaattg agattttgc ctatcctcct    70500 attttatttt gcaaaaattg aaacttaggt aagtgctttt taaacatatg tataaaaga    70560 acatatttca tttaatttag ccccctcatg cttactataa ctagttattt cggttttcta    70620
ttagcggctt taactataac ctcagctcta tttattggtc taagcaagat acgacttatt    70680
taaactgaat atttaaaatg aagaattcat aaaaataaat cttctgtgg gattacgtgt    70740 attctatatt tacttacgtt acctattctc aattttgtt cattgtcatt gagattcatg     70800
gcaattcgga ttaatattta ggtatcaata ttacttcttt ttttttctcct ttcaaacaaa   70860 taaaaatgat tgaagttttt ctatttggaa tcgtgttagg tctaattcct attactttgg    70920
ctggattatt cgtaactgca tatttacaat acaggcgtgg tgatcagttg gaccttttgat   70980 taattaacat atcttttga ttgacctcct cctttcttta attcacaggc acaggaggtc     71040
aaattccgat tgttgtgaaa gttacggaat gcatttattt ggttctaatt cgatctaaga    71100 agaaaaaat cacgctctgt aggatttgaa cctacgacat cgggttttgg agacccacgt     71160
tctaccgaac tgaactaaga gcgctttctt atcagaatag ataagactgt aaacaaaagg    71220
attcttttca gaacccccaat acattttgta tgcatatact agaatagcgt gataaaaata    71280
aaagattatg tccagtttga ggcgatctca attgatccct cgttactgct caaaggagca    71340
gtaataggta gggatgacag gatttgaacc cgtgacattt tgtacccaaa acaaacgcgc    71400
taccaagctg cgctacatcc cttcaattgt tccacagtgt aattgtagag aattcctgtc    71460
ttgttttcca catggttatt ttctccattg atatatacaa attttctgct catttcgtct    71520
```

```
ttttggtctc atttaacata taatagtaaa aggaaaagac ttctcttata gacttactta    71580
cttataagca aaaaaaaggg ttctaaataa gaagcccttt gaataagcga ggctttcccg    71640
atagaaagat ttgcatgcaa cagagatccc aattccgtgt atccggttaa gcaagccctg    71700
cccgccagct tccacccaga caaaaaaggt gagcgcctag cgcgaaaggt tgctttacta    71760
agtaagataa ggcaagaagc aagggcgtag cagctgcgcg aaagccgttg cgccttagcg    71820
catccgtttt cttgctcgtt agcgctcttt tttgaaagaa ggggcggagc ttgaagaagc    71880
gaagcgagcc tagagtagca gcctattacg ttttttcagg ccccttttgat atgttattag    71940 tcaagcgcta gcgccccttt agagtaagtc ttttctgtta tcaatgaaac cgaaagaaag    72000
aaaaaagacc agtgcctttc gtatagatcg agacttgtag cttgattctt tactcattcc    72060
atactgggaa gaattgcagg aaatcgttcg ataacacttc ttcctatttc tttctcaatg    72120
atatccgacg atcaagacaa ttcccgtgaa actctttcat ttcatagaag tgaattctta    72180
ttcttacgaa gcaaatagca tttcctattg atttgtcccc tggactggac ctattctgat    72240
tctgaattat ccgtcgctac gctgttccca aggactagca aaatcgaaat agcgaaattc    72300
ttgggtcatc tcaatgggtt cagaaaccac acgtttctct ggatcatcat agcgtacttc    72360
cacatatcca ctcagaggaa ggtcttttcg taatggatga ccctcgaaac cataatctgt    72420
tgatatacgg cgtagatccg gatgattgat ggaagaaaca ccaaacatat cccaaacttc    72480
tcgctcccac cggccggctg atggaaatag actgactacc ggagatattc gtgttacttc    72540
gtctgcactg gtttgtacac gaatgcgtga gttataccga atactcagta aattatagac    72600
cacttcaaat ctttgttttc gagagggata atcaactccg caaatatcga tcgaaacttg    72660 aaccccttgta taggtatgca atttcagaaa gcacaacaat tgaaataggt agtccgtatt    72720
ggtatcagat ctattcccat gttccgatct ttccattttt ttgacccatt tcttgggtaa    72780
agtctcccaa ctatatttga aaatgaattg gttatccata aagagaaaga aagttttctt    72840
caagttccgc ttcttgctct tccaattcag aaagacttgt cggaaatcgc cggttgggtt    72900
ggtccgacca agaaaggcat gggacttttg ggcattgctt gggccgagtg ttgtatggct    72960
acctagtgat ttacaagcac cctcactgca cactttctat atatctgtct ccatccaatc    73020
aaagacgtcc atgccataga gaatcaggct cggcaaaaac gagactaggg accatgctcc    73080
ccgctttctt cctgtggtta ctattagaac acaagccaag gaactcaaaa ccacaacaca    73140
agcacccttt atttactagt tttggagttt tcgccctttg cttccggctt taatgaaggt    73200
aaatagtcaa aaaagttccc cgtagaacgc gagcgttgag ctttcatcg aaacaaagag    73260 agaggcccgg ctggtgcttt tttctgtgtt agccaggtga aaggcttgct tgactctaaa    73320
tagattagtg tattaagtaa ggaactacta aaacctctat tcccgttttt gggctataag    73380
actcttagct tccagcgagc taggtgcata agcttttttt actacaaaaa cgattcctcc    73440
cccggcaaaa agtggtccgc caactgaact tgccttgttg tgatagggggt accgcctttt    73500 cattcccacc aaggagccgt agctttactt agatagggct tgactgcctt accttctatt    73560
atattagtaa agggcccttta ggcttgactt tactaatata atatcaagta aaggggcatg    73620
tatccttttt ttgtaaagaa agagggctac ttcacgagcc gctactaata atcgaaaagg    73680
ttcacagcga gttcagtcta tagtgacaaa gggaacgttt ccgccggagg ggtttgtctc    73740
catggaaaaa gtattcacta ctgcttacag caccttcatt cactcgtctt gctacttcgg    73800
aactgttcag cggacacgtg gagtcgaacg tctctctaca atgttgcgta ggtagactga    73860
```

```
ttattgtagg tgactgtctc tagtggttta gaaagagttc tgttgctacc aacttctttc    73920
tttgtagtct agtagatcta catgctctag tggatctaaa gtaggtttat gttcagcaac    73980
agaaagaggt gaggttctgc tttcttacct gagaatattt acaaggggga agcctcgaaa    74040
ggcatacgag tgcgcctctc gtagacgaat accgactcag tccgctccta ctgcgcggga    74100
gtatcagccg gtcggtgtcg ggtcggcccc tagggcacta ttcgccttgg gagtggttcg    74160
gccatcaagc tactttgtgg ggtaggggac cagactggtg actgctgcgg ttgttgtctg    74220
cagggtatgt gacaccccac aagttgacta gtgctgagcc aggagatttt cctttggatc    74280
gttacaacgc tcgttgaacg gttcaagtag aagtgaatag gtaagaagta gaaaccccca    74340
tatcaatcca tctccatagg agacaatatg agcaaaagac aggaatccct aaatcccgca    74400
gaaaagaact cactccgggg gagtggagtg aggggggtat tcaaaaaggg gagccgcggg    74460
ttctttcttt ccttgtagga aaggtcttgg tttggtatgg cattagagaa aacttgttat    74520
ggttatgcgg ctatatagaa aaggcgggtg gggcttcagg cggcttttt tatgaatata    74580 atcaatcaaa attccatcga ttgtagctag tgattgcccg ggtcggtgtg tgatcaccaa    74640
aggtgaagta acccttcaga tgctctctcc gcccatgccg aataccccg gccggttccg    74700 ccgggtaagg ccaggagctg gtttggggaa tcacggggcc ttacttattc agggggggact    74760 tgattctgaa atggaatgat tgatagaatc gagatttcat agaagaatga ccgagaccat    74820
aaaatccttt cacacccgca catgtggctg aatatataag gaagttcaca caccctggaa    74880
aaatccatcc tgtatccctg acttgccagc ttgatcgctt gtcttattta ccctttctt    74940 agcgggtggt ttatgtctgg tcctttcggg tcgcctgacc tgggctgatg gcgcttcgta    75000
acggcttgtc tggagtccag cggctctcta aggcttcgat gtactagtac ctgccaccaa    75060
aacatcgtga aggattcagt gaacgtcttg aaacttagta acacaagaca attcactgaa    75120
tggttgttgg ctctaccgga ggagtctgaa atcaacaacg tgtaactgct tgggcattga    75180
gtgttccgct gcttgaggaa gtatgtgaga ggatcgatgt tgagcagaag tggggttaaa    75240
gcagccaaca acgcatcccc ctttacttag tagggcttga aaggctggac agtttgtttt    75300
cctttcctgt ccagtatttt caatccaagc cgaaatagga aaagccgcaa gcaccactag    75360
gcccggtcgt cggttgaacg tcagtagggt ccgatattca ttccttactc aaataggaag    75420
gtggcagtct caatctagcg gcgtggtcca gaacaagcct ttgctgatcc atggggtttt    75480
cgttttggtt acaagaagtg cttctttgct cgcttgcagc gcctcgactc gagtttccgc    75540
tgtaggattg agtgaggtga cgagagctga agccaaggtt ccttgctatg ctccatagat    75600
gttcgtacga ttcttgtgga ttttgggtgt gtttgaattc agcctctcgt taggtcttca    75660
ctgaaggatt gtccaccttc tcaagcctct ctaccatacc cttagaaagt gacaacggat    75720
gacttccatt actaaatgga agaacttttc aaactagttg atagttgttc cctggttgca    75780
ccccacaatg ggttctaatt tactaaatca catgttctg ttttcggaac atcacatgta    75840
gagttttttg ggggagaatc actcggcgcg gggcctcccg tgtgaggtca ggtgatggtc    75900
aacaactcag gcaggaaatg ctgaaaagcg gctaacgatg caagagctct tttcccctta    75960
tacgctctaa aaaagggta tgtcgggttt ttggacccta tgttgagtaa gggttccaaa    76020
ccttccaaaa gtgataggta tgtgttcttt cttggcactc tctttctata ttatgccaac    76080
ctaaaaagag cgatggaaag tggatttcag gttcgatagt ctcgagaagg tattagccac    76140
cggtgaccat actttcgtaa aagcaccatt gggcggtggt tcctctcctt cctcttgaac    76200
ctcgaacaaa aaatcgatct cgccatcagc tcgactaaga gttccgaatc gaaaaagtaa    76260
```

```
acttcacttt acttaagacg aaggaagcga gtgccgaaaa aaaccgcttt cttaaggctt    76320
caaactacta gtcattaaga ctactatgaa tgaaaaggca aggaagtcct tttcttgact    76380
tggcctgcgt gcattatacc taacctttta acttgatttc aatctcaaca aagaaatgaa    76440
agcataactc tttgctcgct tgcagcgcct cttagtcttt tattttagcc tgccttgtga    76500
agatctctcg agtgtctacg gcagatccga tcagtctcgt gatgaagaga agtctttccc    76560
gatgttgaaa ggtatcgtca cgacaactca atttgtccgg taaactactc ggggctcccc    76620
atggtttagt aaaagggagg ggagattttt gcttcatccg ggggttcatt cattatgaac    76680
taaaaagtgg ttggctgatt agtgaggtct taaaaacgtc atagaattca tgatcggcca    76740
ttccattttt gctttcagca agtaggcgac gcgaatctat gctttctatc tttcaatcgg    76800
ataccaattg cttggatgcg tttgaaagcc tcgagatgac ttgcagaaaa aattcttttct    76860 aggtttgtct tgtgtctccg aaacaaaggg tccatttatt gatgggcgaa cgacggggat    76920 tgaaccccgcg cgtggtggat tcacaatcca ctgccttgat ccacttggct acatccgccc    76980 ctaccccccgc acaggttgaa gtctctatct acgatcagat cctttctgaa ctcccctatg    77040
accgcttatc aaagagaagc ttttttcctat actatagtgg caagtctatt gttgtgtttc    77100
ggaattaggg gaaacaaagc ttcaacaagt agaagcttcc tggcaaagct tcaaacaaag    77160
aggttgggct gttcacttca ttgatttgac ttcactttac ttaagattaa agataggggc    77220
cgggcgggca gtgaaggctc atttagtaga cagcgagcga gctgcaagca cctactccta    77280
tcaaaatgaa aagctgcaag cggaacttga acttgaagaa gcgagcctct atcagagaaa    77340
gccattgcgc gctagcccct tgtatagggt tccaaacctg cgcaccccta aactacaagc    77400 tttcttttgaa gccctacaa catgggatat ttgaagaatc ccctttctat tagtaaggtt    77460
gtcaaaaggc tttcctttag ttcctttata actagaatct aaataatagg ggtaggggggg   77520 cgctaacgag caaaaaaacg gatgcgctaa ggcgcaaggg cttttcgcgca gctgctacgc    77580 ccttgcttct tgccttatct ttgactaaga aactaatcta aatagaagcc cttctttctc    77640
aaagtcaact ttctccctttc ttgctttagt gaaataaggg gcgctaacgc gaccttcctt    77700
cagctggctt cgccctatct attcatctat tttctcaaat ggatatttag ggatctctct    77760
tgttcataga tcttgaaacc agatcaatat ccatttctca atagatctat ttatcgatag    77820
aaagatctag atctctatat ggatctatct ccatatctaa atatgaagaa accgacactt    77880
aaagggcgta accaacggaa ggttctcacc ctgtccccga cattgttctc cgacgatgtc    77940
ccctgggcga aaggagccac cattctcttt cttttcttcaa tcgttccgat caggacaagt    78000
gggttggttc gtttcgtcct cctatctacg caattctctg tcttcgttcg tgatcatgtt    78060
gggcgaaagg tagttgtaga ggagcggctg tgaaagggcg attccccccct ttccattgaa    78120 gtagggaggg cctccttccc caccattccg gcctattatt gatagggatt ttaccgatgc    78180
tgaagatagc ttgcttacca agccgcccac ttgagaagct agtcgccagg aaagaagcga    78240
ggaggaagcg aagctgtcta cgaagctttg cttctccccc tgtagtcgta atactcggct    78300
tgtcgctact ttgattcaaa aggtaaccga cggttcccga ctttctccgc tttccgcaac    78360
cgtaaccact tgtcattccg attacttcat ccataaacct tttttttatt tcaaaatagc    78420
gatacgctct aaaaaagtaa aggagaagct tccattctag aagcggtagc ttcccgcctc    78480
cctcggggtg agaagttccc ttcccttttc taaaatgcct gagtggtctg ctcagcaaac    78540
gtacaaagtg gaccgcagtt tggctgaccc tcttcttccc attcggggttg ggttgaccca    78600
```

```
gaagtacagt aagaaggaat ggaaccactg gagagtcgtc tgcagttcac acttgggcaa    78660
agacgactga ctttggaagc ggaacacgaa cctatttccg ctattccggg ttcttattga    78720
gcgtagcgaa atcaaggttg atgataaagt cagcgaagtt tccatggtct tctacctttg    78780
cgtagtctcg gtccacagtg gaaggctccg cacctgagcc tcgttagact cagctgaagt    78840
gtaaggtgta agtgaagaaa atagaagaga tgaagtccgt cccttagcct agtctatatc    78900
cacagctgac gcaactccgt accgacgcct cactactact ttcattttc ttttattttg     78960 aaattcatta acggctaagc gatttcataa cctgagcttt ccttaaccag ctgaccttac    79020
ttcgtaacct tagcctccct ttctttatag ttttctagtt cgactaagtg acttcgtaac    79080
ctcaacgtac tttttttctt actgtagcat aggccttcgc cacttcaaac ggcttcaaag    79140
aagcccctct ttttttgaa ttagaaagag cggggtctga cttattcagg ggggatgaaa     79200
gacaaataaa gggatcaggg ggctttatga tcggagaaag agaggggggcg tggttggtgt   79260 gtcactgggt cggtgggga acccgtagga aggggggacg acccgccgaa ttcacatcag     79320
aaatcgccaa catgaacaca aacgaaatct tgaattgcgt atagaaacaa aacgaaccac    79380
ttctattctc ggagctgagg tatatgaaga atggctttt ggtccctttc gtccagtggt     79440
taggacatcg tcttttcatg tcgaagacac gggttcgatt cccgtaaggg ataggtactc    79500
attcccggcc gctttcagtt agtgttcatt gctgagtgat cgctcgctat ctggctggaa    79560
aagatggtcc ggaagcttcc tctctcccag caagcaagac gagatcacca cttctctcag    79620
taatggactt cctttacttc gtaaccttag ccttagatgt cctttcatag attctcgaac    79680
ctccgacaga cagaatctcc atgcatgcgt tcttctctc ctcccctccg ccatacatcc      79740 cttttttct tttggccgtt tttgttaggc attgaacccc accttaggtg ctgagtggtg     79800
tcctcccctc cctaataacct aaacagagtt ccgtctatgg agcctaaagc ttaaaccatg   79860
gcatggcagt aagcagtaag ttggcctagt ctctcgccca gccttcgcct tcttcagtgg    79920
ccaagttgaa gcgttcaacg tcggcctacc acccttttt tttcaaggtt gagcttgttc      79980
aattgaagct aatgctatgc tgcccttccc ttgttcaaga gaaagcgagg actttctttt    80040
agctaccggc ccaaacaaaa gagattagcc tcttgatcga tcgattgatt ggatcgaagt    80100
acgaaggggt tgattgaagt ctgagatcag cccaagacta aggccgagca actagctgct    80160
gcaggattgg acgtctatct atctcaccac gctcccctac tcctataaag gccggcggaa    80220
ggaatgctct gctcatcttt cttacggctc gttaccgcag cgctcgttca ccccttcggc    80280
ttcttccatt caaaaaaaaa ggtagtgttt ccttggtaaa tagcgtcttg aagtgaagcg    80340
aaggcattat tgaaggaaag aaatggcggg tcggtcaatt gcattaggta ggagatgcag    80400
gacctgtctt aaccgcaagt gcattcgcta ttcgattcca tcctaaatcc caccgaattt    80460
ggattccaaa gtgtgtatct cttctttact tttaagtgac aaggggggtg acaaagggta    80520
tactttcttc tctatgtcgc cgtctcatta atgagcgtag attaatagcc aagcctaccc    80580
ttttgtgctt gtcaatctgt atcccattct tcaggtatag ttttctttta tcacagatcg    80640
acaggtgatc cgtcctttct cccccttttcg tcataaggcg tggtctgact ctgagaaaga   80700
aaattcctgt gtttaggtcc ctactaagca gaattcgtaa actatgcaaa ggctctttga    80760
atactttttc aaaagttttt agcaaaaaca attctcaacg cccttacgag gtagtgatga    80820
gttaaactac tcgtgttggc atggaagtca gcccggtaaa ctgattccat tctgctacta    80880
gggttccaaa ccttcccctg agctctagaa tctagaaata cctttcaac tcaagaaatg      80940 ctaaagctat ttagagttgg tatttctaac taagtcggaa ggagggcttt gggcaaagag    81000
```

```
caactcgaaa gtactttact tcagtcccag tactgaaaga cgtgacttca ggagtggatt    81060
tcggaaggaa agacttcgtt tacttcctgc aaattgctta tgtaagaact agtagaaaga    81120
aaggcatttt gaaaaaaaaa agaaggcagc attgacattg aatgagaatg cttgaatggg    81180
aatcatctta gcaactgact atagacatga gtctaagccg ccgggagagg agagaccatt    81240
ttcatgagag agggacgagc aagtgacaga ttgggaaaaa aagaggtag gccttatgag     81300 cggtcattta ggggtcttgt tagcgaccca tcattcttcc ctaagctgtc agagtccgat    81360
cgaagcgagc aagagataga ggaatcctcg ctcatagatg tgaattgaaa aagcaagccc    81420
gaattctttt gaattaggct ctatagtctg gtccctgtcc ctggtaaggt ctgattgtta    81480
tccgtaagtc ttgttttgac cgcgggaagg tgaactttgc aaaagtgctt atttggttgg    81540
gaagaatagg acttctgact ccaagcctac cctacccgaa aaaagtttc cgctattgat     81600 gtagcctctt gtcgatacta ctagtcttct cgctacctac tagaaaaatc ccatcaagat    81660
agattgaatc gacgacctat acttcaacta aaggcacaag ggcgtagcga gcacagaaca    81720
gaggaaatgc acatgggtct ccttgaagaa cgaagtctag ggtaaagaaa gaaaggtaga    81780
gtgggcgcac tttgactgtg cttggattgg catggctgtc ccctttgct ggttgaggct     81840 cggcctttga ctccgcttgc ctctactttt catgtcaagc gtacaagtct agtttagtgg    81900
gatttacttc taaagacagg aattcttttt catctcccct gtcaaagtcg acgtcttaac    81960
ctgacttcct gagctcagtt gattcttgaa gcagtagctc tggatcgaga gctggatgct    82020
taccttatta ttatgaaatg aaaaggagaa agagctttt ttatagatgt tgaggtgagt     82080
aagggggggt ttgctggctt gctggctagc tcgtgcaatc aaggaaaaaa gccttcgcct    82140
tcttttttaa aaatgaaaaa gtaaactacc ttagtaagct agctttgtaa gctaagcaag    82200
ccgggcacta ggctaggacg tggatcgatc atgacgagaa tggacttctc cgtaatgtaa    82260
tgtaaatgta atagaagagg cagagtccag ttcccctccc ttctcgacca gacgaaggag    82320
atatgaattc catttaggcg ggtcagggct tggcttgacc ctgtgttctc ccgggtcgga    82380
ggcgagaact tgaaagtgaa tcattcagtg gtggggtgtt catagaacag aaggcctcgc    82440
ccaaggagtg atttggatgg agtctcgctt tgatgctggg gagatgagat ccatagatct    82500
ggatagagtc tcgctcatag aggaagagta cgcgcgctag cgcgctacgg cttacgtagt    82560
tgatcggatc agatagccct tccttcgggc aagcaaccaa acccggcaca tccaattcca    82620
ttccgatcaa gaacttggag gtatggctga gtggcttaag gcattggttt gctaaatcga    82680
catacaagaa gattgtatca tgggttcgaa tcccatttcc tccggtacgg aaatgaaacg    82740
ggcgggcgaa attacgtgag agaaagaacc tcttggtgga gtccagtccc ccggaggaca    82800
gaatagcact tcttagtgac taggagcgga gagcccgttg caccttgttt ttctttgacc    82860
ggcctatctt ctttctataa gcaagctccc tccggctgtc cagtccctgg gcggctttcg    82920
gttcttgagc atgttgggag attaggcggc agttgaaaga gctgctcgaa agcttgacga    82980
agaagcgaaa aaagcctatc tattcgattt tcttagttta gtaaagggct tttcccttac    83040
tagtcaagtg gtaaggtagg gcgctattcg atgaagaaaa cagactttag gaaagtggtt    83100
caggtagctc agctggttag agcaaaggac tgaaaatcct tgtgtcagtg gttcgaatcc    83160
acttctaagc aggcgaaagg tccaaaccgt agccgggagc gagccggatt tggaaatgaa    83220
agtgaaagag taagcaaaaa aatgtgagcg ctcctgcact atacgacgg cttttttggcg     83280 gtagggttgg ggtggcttgc ttgaggcaga ttcaaaaaaa agcggttgat tactcggatt    83340
```

```
ggttctcgca tccctgtgcc caaaaggatg ggcgagttcg gttcgagtct tcatagatcg   83400
ggtagatcta tatgcttcgg agggtgagac gaggtgtagc gcagtctggt cagcgcatct   83460
gttttgggta cagagggcca taggttcgaa tcctgtcacc ttgatgtggt agccttctcc   83520
gtggtcggac agtaaggcaa acagcgcaaa gcataaagta aagacatgat gcctcgacta   83580
agtaaagtct ttttgcccct tatcggtagt tccgtagcag gttgtttcgt acgttttcta   83640
ggatcagata gaagcaccac cccagaatgg atccttcttt tcttcttact tttactaagt   83700
ttgactcttg tttctcgttc aacaaaaaga aaaggagtg tgattctttt attcctaata    83760
ttttgcatct ctttctttt  ctattttctc ctgatctact tactttctcg cttagatgtt   83820 ctttttttg  gctgatcttt tctcttttgt tttgcttttg agtgtggggg gagggcaagg   83880
acttcctctt ccgggccctt caaactcctc atcggaagat ttattcgggc tccaggtcct   83940
gtcggagcct tggcccccga ctcacaatat agccttggag tcatcgatga taaataggat   84000
attggcaatg gaaaatacca atagcatttt tttgatggat aaggatagg  gggtctattg   84060 ggcagaagta aaacattcac tctaaaattc ttcctcccaa aaggaatata accaattgat   84120
cgagttcgag aatagggatc ttcggatccg tgagaaaaag cattcatgct attctctttt   84180
tcaacaaata cttacttcac atcctgcctt ggccgaaaat gccgcctaca cccccccaaga  84240 agccttttgt gacttttgg  atgagaaacg aagtgaactt gaccaacaag gcgggaatgt   84300
attagtaaag gaccagagag aactcgaatt ttggaatcta ctgtctcgcg atatacgaac   84360
acatggccaa aactcagcct atataaatag aatactcggt ggatgataat gaattggatt   84420
tgcactgaga agtccctatg gcgcggttga gggcagctga acgaaaggaa agcgggtagg   84480
ccgcctgggt gagacaaagc agaataatct aactggagga gtgaaagcca ggatggcttg   84540
gtaagcaagc aatccgttat gtgggcgcca actccaagtt ccctctcttc tttcttttt    84600 ttgtcacgat caaaatgaaa ggttgttctc tgggcctgtc ttttgctccc agagatgctg   84660
gttcgagtcc agctcgtgaa agagtttgtg agtatacctc gggatgactt tttatccact   84720
actcatcctc gaaatctagt ctagttcagc catagaggac ttgatactta tcttcgacaa   84780
acctcaagcg ggacgagtca atagcagatg cggattttat ttaatagctg cgcttacgcc   84840
ttcaaccccg aaaaggtcgg attcgtgcaa aaaagtaaca tccgagattt gtgaacagac   84900
cggcttggga cagagaaatc cggatgaata ccgcaagggg ggggcatagg gctgtgtgaa   84960
cgcggctttc actaagagaa agatgtgcct acaatgaaac tgttagacct tgttgatgc    85020 acatgaatta tctttccagc cggtgaagct aagaaaagaa gcccttagaa agcagagcta   85080
gacccacaca aatgcttaat cgaaagctct gtcctccttc ccctcctacc agatcgaaaa   85140
gaagaagctt gctcttccga cccaaaaggc ttttgccgtg atattacttc ccctattcg    85200 acgattcact cttcctggac ttgcttgact cgtccgaaaa aagagggaaa gtgctaagac   85260
cgctaatgca gctaggggag tttaaggact catttccaag gctagaagcc tagactagac   85320
tagaaaggag attgctttgg tcttcagtca gctctactag atgcagttgc ccaggaatcc   85380
aatgcactaa ctcctggaag ctccattcat gcccacctac cgaccgagga agacgctacc   85440
gatccctgaa tcgagggact acgcgctttc aatcccttac agctgccttc caagcccga    85500 actaccaatc gccccactat ctgctagtct ggttcgactc gaacttctgt catgtcaagc   85560
ttcctgacct gctttgtacc agccggtatt ttgtgtactt cggggcgctg actagccctg   85620
ctcaacgccc tacacccttc tcttgagcgc ttcattgagc atttctcttt cctatcccgt   85680
ccttaggcta cgctatccat aaggttgacc tagccctctc ttctctctct ttgtccacgc   85740
```

```
gaagattcca ttcctttcct agcctattca atgtggtcat gtatgtaata gaattcaatg   85800
ggaagacctc ctagttggac ccagactgcg atggtagtga atgtggcctc agctcccaca   85860
aatgcaggct cccaaagcct tagactgaga tagtaccaca aagcaggggt taacataaat   85920
gactctatgg aagtcctctc ccacttgaaa gctaaataag gagaagaagt gccccaaatc   85980
aatgcattcc attctttgca gaggttcctt ccatagaatc cctcgaagta cttcgctcac   86040
cttcgaagag tgaaaggatc attcaaagca gactaaaggc ataggcaaa ggagcttaga    86100 agggtgacgg aggggagtag taaggtatga aatcacttag atagaagcat gttggatgac   86160
ggaacgatga cttcatgctt caattcgaaa ttttagattt ctgaccttga gaaatgacgt   86220
aagtgataga tggaatcgtt cagtaggcta gtttccattt tcgattgaga aagcggcggg   86280
cccagtgagc tctccaatag tgcaccgaaa cggggccgga gagacggtaa accttagatc   86340
ggctaagatc gaattgaact gtctttgatt gagcgaatcc tgcccgattt tgatttccgt   86400
ccccgcggga gacatcgtaa atagtgaaat gtttgattcc cctattgaat tgaattagga   86460
atcgattgaa tgggacttgc ctatccctta ttcatatccg atttttctct ctttcttttt   86520
gatacttggt tggcagggtc agggcctttc tcactgggcg agcgaatccg tatttttcta   86580
tgtaaatgtg accttaacgg ccttttatttt aagcaattat tcgctccaag acgcacgaca  86640
agaccttcga tctctctctc tccataattg atatggaagt tggaaaaaat caaccactca   86700
aagctgacct caaaatgttc caaacacgca taagtgtgaa gattgaagac cttctattct   86760
atatttcata gagttgatta gtgcaaaaga aaagggcact ggttcacgca ttacgggtag   86820
attcctcttg cctaagaaat ggaaggggc acttcaccga atgataggta aagtatggga    86880
cgttcagtaa acaatccctt agctcaagtc ctcggagata cccaaggcag ctccccgtgt   86940
cctttatacc caacaggaca agagtctaca ggtctgccag gggcgaataa gagctcgtcg   87000
aaccgtcatt ctttacttcc ggggtcaatc aataggtagt cctcaaattt cttctcgaaa   87060
gcctgtttat aagaaatagc ttatgccact cgtattgccc cggattgaca aaataggctt   87120
ggattggaga ttcttgtgta aacattcaag ttgacaatcg ggtttctaga cagccagtgg   87180
actctgaaac caataccaat gatttcgctg gatctaagaa taacgtagca cagaaaagcg   87240
gactcaccaa ggatggcgaa tgggcaatac gtagagcttg ctccgcttcc tatggattgt   87300
tttatagcgg tacgattacg atgcttgctc cgaatggaag agagacggct ttcctttcgg   87360
atgttgcaaa cgcacaaacg aaagacctta gtcagcggaa gaagtcactc tcaatccgat   87420
ctagcaagaa atgctttacc ggtaaagtaa agcgagagac agtcgattct ttcttagggt   87480
tccaagtaat tcaactagtg ccaagaaaag tatccggttg tagagcgagg cagcaaaggg   87540
gagttggcac aatatgtaat ccctagggta tcggtgtcgg agaagggat cactcaatgc    87600 tgctacaggc actcattagt tcggattggg tagcgtgaag gagataatag aaggacccgc   87660
cgaaagtagt tccgtctttc caggtcttcc ggagtcaaaa tttcctcatc caatagcatt   87720
cttagttagt accattcaac taagcctgtt tttgacgagt gaagcggcta ggctacatgc   87780
ttagcctagt attcccggat tggtattgga taagaaagat tttgctttct tcccactcat   87840
gaagaacaat aaagtgaggg gagggcttcc gtggaaaaag ggtaagtttg ggatgagagg   87900
gtgaacacta aaatagtagt caccaaaccc aaagaaattt gactctttttt ttttatgaag  87960 gcgaattgat aagaaaaggt acttccatgt gtataaaagc acaagggaag ggggcccccta  88020 gtccaagtat aatagcatag gggggtgcaa gggtgaagat actagagtgg tttggcactc   88080
```

```
ctggtcagct ttctttcgtt cgggctttct ttcttctgcc tttacgcgag ccaattatgc    88140
gtggcgctga agaggaaggc gtcacttact gtactactat cggccataca atgatggcat    88200
tgtggatctc attcgtattc cagttttttt ggacaaagtt agagtagtca tttagggaat    88260 aagtctttt  taattattct attagcatag cattaagtgg taaacatttg acactagagg    88320
ttttaccata ctatacatgc aaacataaca aataaaacca acaaagata  gttagcatag    88380 ataggagtct atctccagta ggcaccggag tagatctcca ctagaacacc agacatgaaa    88440
acaaatgtct caagacactt atggaattta aaccttctaa aactaaaaag agtcgacgga    88500
ctcttttagt tttctcgggc accaaggaag attgcctcca cgatcagtgc ctgctgctcc    88560
tggcgtagtc cctggagtct ttcttctagt tcccgaattc tttgacggct tgcttccatt    88620
cgggcttcaa tagcagccgg gttcacgagg cgaagatgcc tcaagaaacc atttaacatt    88680
attcgagtat ttcgaagata attttctact ttttgtattt caacgttaat ttcagcaagt    88740
cgctggggaa tgtcgagaat ttgagcaggg agggccatgg cttctcgata tacactggta    88800
gaaaactctt ttctctttt  tgtttttttt tgtagaacac gaaggcttat cgagcctctt    88860
tttttagagt gtatagcaat tcttccaatg cagtacgaat tgcatggctg gcacaatatg    88920
agtactataa ccacgctgcc tgtatgaaaa acaaactttg cagaaccct  ttcacctaat    88980 cgatcgtggt gaagtcagca atggattcgg cggatcatac accttacgct aggatttggg    89040
aaggacattt acgagactga ggtgagtttt aagaaaaga  cggggggtgga ttttttgct   89100 ctaactggct gtgagcatgg gaattgcgtt gccgagcaga gggcggagag gaatttggtg    89160
ttgcaggttt tgatgactgtg agaggggttg aaaattgatt ggtttttttt agcaggtata    89220
ttggtatttt tgaacatatt aaagattata gaatgtagaa gaatctcgcc atacggcacg    89280
agcagttgag tacagtacta tcatgccttt gttttgtttt tgaagaaac  taaaaaactt    89340 gcgaagcacg cacctcaatc accctgcctg tgtgaattga acgaacttaa aagtacaacc    89400
agcttaagct ggttttccac ctattttttta gtgttcggcc attctagca  aagtataaag    89460 gacatattcg ttgccgattt ggggttctga tggaagatac tgctgaggtt atacaccaag    89520
tacacacgtg attctgctct ggcagaagtg cacgcgcaat tcagctctgg aaaaactccc    89580
tgaggtccag agagagatga agtttatagt aaacctctgc ctctcagata gctttctttt    89640
ccaacacttc tatgtggaga tggatgtaat attaatatga ttgatagttt cagtttacta    89700
tttgcagttt tccaaagtct caaatttagg acttggttcc ggccttgttt cgtagtgaat    89760
ttatggattt gaatacttct aagactgaat tcttttttgt aaattcaact tgacttgtac    89820
ctggaacaga gaaaagggt  atccaattga aatccaggca ctttttttcta tttttcgctt    89880 agatgtgctc ggcagatgct aaagccgag  cgtgatggca agaattgatc ggggagatgc    89940
ccttgaagat cacttaccca gctctggaag gacatgagtg gagaattgtc accggatttg    90000
atccaaaaaa cacagggcgg agttacctta ttggtgagtc ttggccgggt tagtgtttaa    90060
ggaagaaaac cttattgtag gttatttttt atttaaagag tgccaaattc aaaaagaaaa    90120
ggaaaaagat gcttgtacgc acattagatt tgctaactca attgatccta ctgtgtctag    90180
atcagggttc ccgttaaga  aagcttgtta gctttgtatt ggctcccatc ttacttaacg    90240
gggcccttag ttgaataccg atcaaaattg tttgaaattt tgaaactttt ccaataaaga    90300
attattcgtt atgttaaata ccccgaaaag ccgaaacctc ttattctggt ccttagaaaa    90360
actacgacta gtcaggaatt gcgtaagaga agagacgtcg caagtaacaa tagcgcaaaa    90420
gcaggcggcg gagatccgca aaggtaaccg gatgcctggg gcttaggaca aggggcgtcc    90480
```

```
ggagtctctt aagaaaggac aaagactaat taatatcatg tttacaccga tcggatttaa      90540
aaaagtgctt cgccccttat cttctcgtct atcttctatt ttgcatcgat ggtccattcc      90600
tttcctaatc ctcacctcta cctttttttg tgtctatctt ctttatcttc tgatcggatc      90660
gcctggcttc tttcaagccc tacttgaaag gcttgctttc ttaaaaaatg ctttctttat      90720
taagagtcct ttaagaagct aagctccttc agatagtaag attcgcttaa cttcatacct      90780
ctaagcgctc gtgactatcc gatgatagtc acttcgcttt cctttttagac tgaaaaagga    90840 aaactgaaag attgagcata aaaaaaatat agagaatgag ctattacgtg caaacaatgg      90900
aaattcaata ataagagtct gatcttctcc cttaagaata tgcgattcct ccggagtgaa      90960
gttgttgggg ggaagagaag atgaggaagc tagtttaatt gaggaagcca ctttctttaa      91020
tgtatactag ctggtctaca aaagcatgac gcatgacgct tctccttttt ttagtccact      91080
ctcccttaga aaacggagct ccttgaaagc agatttctaa attacatagg tgaatgtaga      91140
gatcaccggt gtcctactcg agacgaagta cttgtcgtcc ccaaaccaaa agggatgagg      91200
gaaaaaggct cgagaaagcg tccttggaag ggggaataag atcttaaaaa gtgttagcgg      91260
ggagcccatc cctctcgttc ttacagaaga cataaggggg aatacacgac ggacgaaaag      91320
cggggaaaca tccttttcct gtcttctctc cacagaggaa ggaaagcacc gccaagccaa      91380
caagaaagca gaaactgcat gaggtaagac taagggcctt gtgcgccctg caagagatta      91440 ccggggggtct cggtaccagg ggggcgcggg aacaagaaac tccagtaaat aaaagaaaga    91500
caataggagt cctctcaata gccgagggcc cacttcccta tatgcgctta cggaagggga      91560
aaagcttgat tctcatagat tagacaatac acatgtgcaa acaagaaaat caaactatct      91620
tcttattgat actatatatt tatcctttcc cctatagatc cacgtttctt caaaataaag      91680
atatagcaac taaagaaag ctaaatcgag tcggaatagg ataagaacg cacgaaggat       91740 cagagagaaa gaggattcta aaagctaaaa gcctagaaga ctagattgtc agactcggag      91800
gtagcagtaa gatctctgtc tccagagaag gcatgagggg tttctaaaag tctcctctca      91860
ttacttatgg ataaagctct taagcttaag ctttttacgaa cagaaagatc ttcccattct    91920
aaataagaat gagagtcttt caactagatg tgctcctttg gctgggtttg agagagagag      91980
cctgagatag ttggtctcct tactagtcca acttccttgt atctgaaagc gatgacagga      92040
tgttaggtct agtaaggaga cttttggag aattgacttc cacgaataga ctgttaggct      92100
aagaagaata ggttgggatt gatcccacct ttgaaagagt ggttttgttc tgtcaataca     92160
gcttatcgag ttatcaagct gaactgcctt ctgtaaggag cttgaatcgt tcgtttactc      92220
taagtcttat taccgacgcg atggattgct atttgaaaac actttcaata caaaaagagc      92280
tccttccggc tatactctag ttggacagtc tttgttcagt ttgagaagtc aaggaggcac      92340
gaagagctaa caaagagtct ttctatttga ctgtccgaaa tcaagtggga gattgaattg      92400
aaaaggcccc ttactataga tagggtgtta gcgctgtttt ttgaaataag gacgtttaga     92460
tttgactaat aagaaagaaa ggggcaagcc aaaacccact ctgctgagtt cggctttcgg      92520
ggctacctac tttagggctt atgtaatata taaagaagaa ccctcttagg gccttttttgt    92580 ttaagggctg ctcgccttt gaatagaagg aagtggggga gcagaggtta tttcggtaaa     92640
ccgatgcatg agctgaggct cccatgtccc gccgaccctc cgaaaaagta agggctcata     92700
gggagtcaga agcaagcaga gtaaaaggcg ggtaaaactc acataagcag aggggggagac   92760 acattcatga aaagcgagaa gccctgccgt gggggactga ccaactatga atagatctta     92820
```

-continued

| | | | | |
|---|---|---|---|---|
| cttatgctta | cgggtaagaa | catatattag | tccgtatcgt | gggtctattt | gttacaaaag | 92880 |
| gcgaacatcc | cctttccaaa | acattaacat | aggtcctcag | gcagacatcg | aaaagggggc | 92940 |
| gaaaagagtc | tatttacctt | tacaatattt | cggaatgtat | catggctcta | tctattcatt | 93000 |
| aaaaaaaaaa | agagttctgc | atctctccgg | ggctgggtga | acaaataggc | gtggggaaga | 93060 |
| gtgagagggg | gggctacgag | ccctctctcg | ttgttgttcc | cggaccaccc | atctcttcct | 93120 |
| tccccttcgc | ctggcccggt | gagatctgat | ttatagaacg | aagtgaagtg | ataggaagag | 93180 |
| aagactgctg | gcgggaaatc | cctattcatg | aaagcccctt | gttaaggtta | agggggaaaac | 93240 |
| gaaagtgcgc | tcctgcgcac | cagctgaaga | aaggagcttt | ggaagcttac | cttattatta | 93300 |
| tattaaaagg | ggaaagggtt | ccaaacctat | ctgactaata | agaagaaagg | ggcaagccaa | 93360 |
| aacctactcc | taacaagttg | ctggatcgaa | gtagtacatt | atacatctgc | ccgccagcag | 93420 |
| cagaggggt | tcgattcccg | ttatacgcga | tgtggcgaaa | aagactgatt | caacgagata | 93480 |
| tgccttgcct | gcattaagat | ttaaaacttg | tcgtctactt | tcaggaaatg | tttggaacag | 93540 |
| agaacttaca | ataatacaac | gccgtattct | ccgaagattg | aggaacaaga | agagatctat | 93600 |
| taagagaaag | atttattcta | gagaaaatct | taacagttac | atccaatcac | aaactacacg | 93660 |
| aaagttgtcc | cttttttatg | gagatttacc | catcacagat | atgcacagag | gaagagaacg | 93720 |
| aacttcatat | atccctttc | tactcaatcc | agaaacaaga | tcggacgtta | tcccggttcg | 93780 |
| tctccatttt | tgtgaaacta | ttcctcaagc | aaggcagccg | ataagtcatc | gaagggtttg | 93840 |
| tgtgaataat | ggaatggtta | acattactca | ttttaaactc | tcccacggtg | atataatatc | 93900 |
| ttttcaagaa | aatgatgcga | gaacccgcgg | tgaagaaata | aagagatcct | tctatatcga | 93960 |
| aatctcagtt | gaaaaaataa | taggaaaatt | cctggatcac | ccgtggagaa | gaaccaaaac | 94020 |
| agaatgcttc | cgcctactca | aaactaagag | gggatgccgc | ctactactaa | aatcccggtt | 94080 |
| tttgcaacag | ttgcgttctt | ctatgcaaaa | agaagactta | gaaagaacaa | agaagtttgg | 94140 |
| atccgaaaaa | gtatgcttag | gcagttcttt | cactgagcac | aacagaatga | agaggaattt | 94200 |
| gtatcatttc | aaatccctat | tcttatcgaa | gagaaggaac | gagaaaaacc | gaaatattcc | 94260 |
| tactcgaaca | agaagtccta | tagtttacaa | ctcttcttta | tatagtaatt | cgacctattg | 94320 |
| ctccgcatcc | ccccatcggt | ttactaaaaa | gatcaaaatc | aaaaggatcg | aactacctac | 94380 |
| tcattattcg | gaggtgaatc | atagaacacc | aaaagctgtg | gtatcttatg | gacctaacat | 94440 |
| aggtcacata | cctcacgaca | taagattgaa | agatccaaac | cttcttcttc | ggagcggaaa | 94500 |
| gggacgtggc | caaacatat | aaagatcggg | gtagtcgctc | atagggacat | atctatccgg | 94560 |
| atagaggata | gtctaggccg | attcatagat | agatctctct | ccatatagat | aggtatctcc | 94620 |
| gtgaatagag | ataaagatag | ggatccatct | agatcttgat | tcactatttc | catattttt | 94680 |
| cttgattctg | attgattgcc | ttttttttga | cgacaagttt | taaatcttaa | tgcaggcaag | 94740 |
| gaaagatcgt | ttttcaatta | ttacttgctg | ggtcggagcg | tagacgagcg | agcagagcca | 94800 |
| aggaaagagg | gaagcccgtc | atagagtagt | cgactagaag | tagaagactg | ctggcctgag | 94860 |
| agaaggcggc | ctctctcggg | aaagatggcc | caatttctct | tctttctttt | tgatttcagc | 94920 |
| tttcttttt | tttttcagg | ggtccagaag | gctaaaaggt | gggggagaag | gaagccgaac | 94980 |
| ctctaatcga | cctggacaca | taaaaaattc | tcggcgtcga | gagagatttg | agattccgta | 95040 |
| agtaactcag | tgactgcttt | ctaagaaggg | cttggaagaa | gaaaatgaaa | taggaacaac | 95100 |
| cgcgctggtc | gtaatagatc | gactttcatg | ctagttcttg | ctccagcatg | aaagttccat | 95160 |
| ttcagggaag | gacgacgtac | tatgatactt | tctgttttgt | cgagccctgc | tttggtctct | 95220 |

```
ggtttgatgg ttgtacgtgc taaaaatccg gtacattccg ttttgtttct catcccagtc   95280
tttcgcaaca cttcaggttt acttcttttg ttaggtctcg acttcttcgc tatgatcttc   95340
ccagtagttt atataggagc tatagccgtt tcattcctat tcgttgttat gatgttccat   95400
attcaaatag cggagattca cgaagaagta ttgcgctatt taccagtgag tggtattatt   95460
ggacttatct tttggtggga gatgttcttt attttagata tgaaagcat tccattacta    95520 ccaacccaaa gaaatacgac ctctctgaga tatacggttt atgccggaaa ggtacgaagt   95580
tggactaatt tggaaacatt gggcaattta ctttatacct actatttcgt ctggttttg    95640 gtttctagtc ttattttatt agtagccatg attggggcta tagtacttac tatgcatagg   95700
acgacgaagg tgaaaagaca ggatgtattt cgacgaaatg ctctggattc taggaggact   95760
ataatgagga ggacgacaga cccactcacg acaataagga gaagcagtgg ttcgaatcca   95820
catcgtgaga ccaggacagt gtggagaagc atcgataaat gctattaaca ttgatgatac   95880
ggcttagagg aattcctctc ttgctgccgg actgattcct ttccttttga tgtggacaaa   95940
tgggcatccc tagaatcagc tgctctcctt cctgttggag gaagacaatg cgaaaaaatt   96000
cataaataag taaggcaagg tgattgttcg ttgacaacat tggggcgtag cggattgact   96060
attgggatct ctttagcttt agtatgacta ttactatagg cgctggagga agcttgtcat   96120
agtatgtaaa ctttgtggtg gatacgacaa caaaaaagcc tttctcccca accgaggtga   96180
tagaccacct tatggccgat gtgattacca gccaagggc aaaaagacgg ggttgaatgc    96240
gactctacca ataccaatct cctctggagc aaggaaaggc aactctgcct ggtatcggta   96300
acgattaaca tattctttt ttttagagag gggaacccctt acttaagaac agagagtggc   96360
cgagcaaaaa agcaaggcaa gggataaagg agaagtaccc ggcccggcaa agaagggtct  96420
cccattaaca ggtttttcct tagtaagcta gctttgtaag ctaagcaagc caggttctct   96480
ttcactcctg gaatgagcct tttggcgact ctctctcaac acaaagaaag aagagatgaa   96540
aggatcttca agtagccctg actaaggttt gaaaagattc ccgggggtac tacagcttgc   96600
gtggaaggct agggtggttt ttagaaagcg cgaagacaga agacgtcgta gggaaccaat   96660
ttctatcgct ttcccctct agtggtcatt cattctttg atgactcgca gtcgaaagag    96720
ttggttggca gttcaaacct cagagggagt tgaagagagg cctttcagtt cgttcaaagg   96780
cactagggac gagccattac agacggtctg atgcttctgg agttcgctca tatcgaattg   96840
tccaaaagct catcaacctg tccgagggat gatgaaggcg atgccacaat tgagggaacc   96900 gccctttac tcttttttag ataagaatgc gaaagaccct gaccctgcca accaagccca    96960
ctcagataga ctaagtagac taaaaaagt gcacaagaaa gactaaggaa acaaaacctt    97020
ttctcgataa ggctgggcca agtagcgaca cttcacccag attcgatcat cacgtcaact   97080
tgctttattc aacaaagtga tcaagcttct tagccaccgg ggaccggcct cgtgaacgca   97140
ttcgctaaag gcactactgg ccggctttct caatcttcaa tctaacttca gaaatagaag   97200
aagcccactt gacgagattt gatctaattc tctttctaac attttttggat tgacaggaag  97260 ctttcttgct gtgtgattct gccccccact ctgccagcag cctatgtgtc gatctatacc   97320
cagttgatct accactattt tactttgcac gttctggata ggcgcgcatc ctcatagagc   97380
gaggggtaga aaagatcaat gaaagactag agcgcgagct agctgatcta ccgacaagtc   97440
cttgatttct tatccgcgaa ggcagacttg gactcattga agaaagcact tgaggtgaag   97500
actaatgagc gattgcgaca actacggacc ccttaactag gttttttact aaaaaaaacg   97560
```

```
aataggcttt cagaagcttt tccacacaaa gaggagagga agtgcttgct gccaacttgc  97620
cagacgagcg gacatctgag ctcagcagcg catttactat ttgatcgaag ggatggctaa  97680
aaggccaaat ccggctaaaa acaaaaagaa gagatcaagg agagggagct agacgagcac  97740
ttgcaagaga gcgaccggca gatctaaaac tgctatagta aagtagaacg aaagtacctc  97800
ccaaaggttc tacctttttct tgtgcgttcg ggaataaata gaaagttttt aaatgtatag  97860
aagactctcg attgattggt tgtaatgttc acgaggttgt atataatcca atgttcagtg  97920
atatgacttt cctactgact gaattgcttg aattagttga aggtgcggag tcttcttctt  97980
ttgatttgag acgaattcat ttttctactg aaagtgcttt tgatagggaa tagggaaaag  98040
ccttgcctta ttcaagagta ccaggaagga gaagaataag cattacctct gttgaaggga  98100
gaagcccctc cctttgctta tttattcttc ctggtcttcg ggtctcatct gaacggctcg  98160
ctgcctattt agttacattt tttgttttga ttccagaaca gaactagaga tcctggcccc  98220
ctcccttgaa agctcctggt gctgcgacta tcaccggtaa gttgcgtcgg atcaacatcg  98280
ggattaaaat aaactgcaaa agcaactaag tcaacgccta tttgctgtgg atctactggc  98340
ccggacgctt gaatctattc caccgcaaac aaccgaatat actactgcag gatcttctgc  98400
tgcttttgtt gttattgctc tcacctgtca ctacgccacc tcagcagctg ggactcccta  98460 acctttttcta tctatcttta gaagtagggc gagtgagtcc gttcctttcc cgtgaaggtt  98520
ttgggatatg tgaccagatg cttcctccag atctaacgtc tctatcaaca aaattctctt  98580
ttcttcaccg gatcgatact aacttaccta ctcctgctcc taccggatcc aagagggccg  98640
atgcccgatt ccccgaccca ttactcattc cttcccgact cgatagggat tgcaatctcg  98700
agagagggag caacaattga cctccgacaa taggtagatg gggtgggctc cgatggatac  98760
agtgaaatct atcctatttc cgcactccct ctcaccggcc tgaaacatat ataaatcatg  98820
aattcttcag agcgggccgg caggccgggc gtacgggac cgtcgaagaa gtgcctcaac  98880
gcgccgcagc cactactttg actccttta tgcaattatg aactccacgg aactttatca  98940
attccaacgc aacttatcct tttggagctg acgtaacaaa ctacgcgagc ctcccaacga  99000
agccaacata aatccgatcc gaataaaaaa agaaaagga agtttgatta ttgtggtata  99060
ccagccacca gttctggaac ttccagttcc aatcgaagca tatagatccg taaatagatt  99120
tgtatgtata gccacttcag tcgtgctcgt ccttttctcta aagtatcttt tttctgggaa  99180
catggtcaac cagaaattat tatgttcgcg attcttcatc caccgatgga aaaaatgctc  99240
cagttttcca ttctcatatg aggccggaaa gtggattggc aacaggtcgg cacgaagtga  99300
ttcatcatgc tcaaacatga gccgatcgct cgttagggac ggtttataga tcatcaaatt  99360
cccacaaatg gaatgaaaag tgggtccatg taaatgatca agacctcgca aacaacaacg  99420
ctccttcccc atatggagtt cggaacccaa aggcaatcgt tgagtgaact gtatcttttt  99480
tgtgttagtt gacctaagcc gcacccttac tgctggggtg gggctcggcc tccgaaccgt  99540
acgtgggacg agtttttgcc tcatacagct cgggccgaag accgggggaa gtttagaaga  99600 gatgggggaaa cctagcagct gccggtcggg gcggggataa gcttgcttct tcacaagcct  99660 atcccccaa aaaaccgac cctgtagcgc tagcgcttcg ccttctttct attccatccc  99720
attccattcc gggataggcg gctaatacta aaataataag tgaagtagtc gtcgtctgac  99780
caatcggctc ggacaccaga ccgcccgtgc ccgcccattt tgtctcgccc taaatggaat  99840
ggctctctta gttacgctgc gccccgaccc gagtccccac gtccgctttt ctcgcccgc  99900 aacccaataa gttggcaaag ccaacacaag attagggccg tccccttcat tctatgctga  99960
```

```
ccccggcccg ggctggcttc ttgggaagcc cgttcccacc gcgctcacgg cccggctggc 100020
ctgccagcgg tagtgggaat tctcccgttc cctggtcaaa gacttggttg gatgcggat  100080 ctactccacg aggagcggta cggacgtaga tgatatcatc acgacccctc ttttcgtacc 100140
gctagggatg cttaacgcca cttcgccaac tggcgttacc tgcgctttcg tgtctctcag 100200
tgtggtcagc actgggtgtt tccgagcagc gaggcttaca cccattcgca ttagttcatc 100260
caaagttcct taccottatg cacgaattat tgaataagcc atcttcctat caaggttaag 100320
gagtcaactg agcatctcag cggcgggatt gaatacccgg atcgaatcag agttcacgcc 100380
gcccgccctg aacaaatagg aggcgtgggc cacaggtcgc acataagccg ccgggtcgca 100440
cgacagaaga acacccaaca taaagatgca cactcctcca tgtgaaatat tcatcttcat 100500
agaagctttt tgatagtagt cgtgaccaac agccatcagc tctcggcttg ttggtaaggt 100560
gagagcttca agcccgattt caggtggcgc accctccaca caagcaccgc ccgacgaagg 100620
ggggacgggg aaagctacag gcccaaaacc ttcgacccct tcttctaaat gggggtgccc 100680
gaggcacctc atcttctcat ttcgtcgttg ctcattcccc ttaggccgaa gtctttggcc 100740
tttccttctc cgcgcccgct caggcttcgc tgacctatcg cgtggtaaaa agaagaaagt 100800
acgaaagaat agtaaacgga gcacaccgca gaaagattct aaatatgaga agtcccccttg 100860 ggattcgaga agaaggaaat gaagaacggg aacgaaacga aataaagcgt ttctagctct 100920
agtttcggat gagcttctcc taattatgtc tggtaataga atagggggc ttgctctgac 100980 caagactcca cttttttgctc cgtccgcgga gcgtatgaat ttcctggaat gtagatagac 101040
caaaagaggg aatgaagaga taggaatagg aattatagta ccattggaaa aaagggcacc 101100
tgtgggaaca tctctactga cgaaccattt caatagtacg ggtgctgccg tgccacgagg 101160
cacgaccatg gaagtaatga aaaagaaaaa gttatgtagt tggaccatct gttctatccg 101220
ttcgagtttt gcttctctag agaagatgag aggctaaaaa tgaaagtgtt cgcaacacat 101280
accgaaaggg tactaattaa gccgaccatt aatgactagt taaaacacca ggagtggtct 101340
gatcccctat ttgatcagac cgctctgaga aagagaaaaa gcaaactctc ataattcgga 101400
gcccagctcc aacaacttct tcgtaagtga ggtgaggtac ttcctttggt ttgaataggg 101460
ggtcgccctt ttttttggttg aagtagccac gactttggtc gtagtcagtt taacccata  101520 aacccagtcc acttgcagcc atgttgatca aaatgactaa gtttaatgac ttgaccagtc 101580
acaagccctc gtattataag attctctcac cctgtggtcg acattccatt cccettagtc 101640 gtaggtgctc gttctatttt gatttgaatg ggccggggct cccgaggtac atatggccgt 101700
cccttcgggt gtctcggtga tacaaagaaa gaaagacga tggtttttaa catacccttg 101760
aacaaaaggc caatccttac caaaggagga aatagaatag aataatctac cttctttttt 101820
ccttcccgtt gattcccccc gacaataaag ctgcacttcc ttctaacaag tggctgagag 101880
ttagcaagca accttggcct cttggcagga ggttcgctgt cccctccctt tccggtccgg 101940
ccgcagtacg gcacctgaac tcgaagctac gatcagatcc gattggatct ggtcctatcc 102000
gacccaaccc cggaacttag aacgccggc ctgtttggac ggtagaacgg ggagaggggg 102060
agtcgtgccc attctctatc cgggcacgag caggaacata aaaaaaaaat ggaaaaccga 102120
atacatgtac atgatctaac gacatattca aaaatacgtg atccgatttg ataggctgcc 102180
cgcagaaagg aaagagttta ccgaccgcat aacaattcat tcttgtgtgt agcgcgtggg 102240
cccatgtctc tcgaacgatc atagtacggc cgctcatcta atataaaatc aatgagtaga 102300
```

```
tctcacctcc ccttccccat accatagccg aagggatag cgtatccaca gaagagagag   102360
tacgggccct tgcccaacat ttagtttaga cgcggctcga atgcctttat gctataggct   102420
gtgttaagca tgcttctttg acagaaaaca aactcttttt ccatgacaac agtcgcgact   102480
ataaagggcg gggcggtaag ctctctatca acaataggg gctattcata gtaaaaaact    102540
actagactat atggattcca actgaacttc aacttctact tggttgatta attcaggggc   102600
agtgctccaa cataatgttg gacgatctcc atttccatat ggtaattgaa gtcaaacagg   102660
agcaaagcag gtgcaattca atccttattc ctagcacaaa aaagcaaaac ctcactagac   102720
cgaggcccat tgctatgggg actacactat ataagagaat gactaaggta attgccaata   102780
gtttctattg aaagacaggc tggctcttta aaaagggcgc cctcctaatc tcattttgat   102840
aggaagagat attgaaaatt tcccaagga ggcttactac tcagctgata gatcaggtga    102900
gccagccatg atcactaaac tcaccaaacc tgcagcatat tcaaattgga atcataggtt   102960
tctatatgct taaggaaaat gggatttgca gagtaggata cgaaagttta tttatataca   103020
atggaaagcc cctataatcc atggacgacc agtggagttc ataaaagaaa ccaaagaaag   103080
gtccgcgaca aagctgtccc ctctctccat atctctactt actggctggg tgcagataac   103140
actgtaataa taacaaagcc agatagagat actgttcgtt cagaattgat tcagatggcg   103200
aggacccacg gaaaaatcca ccttattcat gctccgcaca gcaacttgcc cggtcaatat   103260
tatatgtcta tgctaaactt ggtgatctat tttcgttgcc cccttaagc gtatgtgata    103320
taatcattct tatctcagaa gagaagtatg cattgtcccc acttaagtta ttaagtattc   103380
ccaaagacga ggcgatttct ttttatgttg aaacttatg tcagccaggg gaccctgatc    103440
ataaatgggt tgtttgtccc ggtgaaaggg acgctctcgt tttaatcgct ctggcgcata   103500
tgtttaatag ttgttttatg cgttcatcta tctttcagga gctgtcgtgt ggttttccca   103560
gagatcgccg tcagttcttt gccaaattag gtggagtggg gaagattaga actattttca   103620
tcttgaatct agcaccctca caaggtacta ttcctcataa aagaatttta cgaaagctgg   103680
caccccttggt gcgtgatagc tacgtaatat ccttagtttc atccttttta aagatagcag   103740
tttatgacca aaatgaatt aattgttcta ttacggaagt tgggatccca cacgctgggt     103800
taatcaaaaa ggtcttatac aatttatgt tggatgattt cgaccgggga tttaaacagc     103860
tataccctag tcttctttat tatcgttact tggctgactg ttacgtatta tttccattgt   103920
ttagtctcta aagcgagcag cagtgtgaag aagaaatgaa tagtatcctc ttagagttag   103980
atcttgatgg ggatatcaca actattctac ctggtggggg tgcccatgtg actcgtgatg   104040
ggcctttgat tattctaagt cgagattgca gtcttcacgt tgtcgaacag tcaacattct   104100
ttctttagtt caatttgtag tcaatatgtt ttatacaaaa aggaacccat gcttagatag   104160
gaaatccttt ttttagagag ccaatgcctt aagacagacc ctaatagcag ttgtcgccta   104220
cttcactgag ttgtggttct aaaaagagga ttttcttgg tatattccat caagagaaag    104280
ccatatctat atatataaag aaaaatcgaa attgtataca ggtgcttaca ctctcctgag   104340
gattctaaga cccgatcacc cgtcaaagaa atatccttag gtcttaagtc tacagctccg   104400
tagcttgtgt cgcctacata gggtagaaaa gaatgctttg cataaacatc tcaatgtcca   104460
agataaaagg aacgagggga agaatcgacg aggccagtgt tctcgaagag aaaatcgtga   104520
tggaaaaagc gtgaggagaa ttcgaaagtc gagatatgca aaataaaaag actccctggg   104580
agatggtatt ctttgtttta ggtcttgata gattttttcta ttgattgaag ttattacgct   104640
ggctgattaa atctcttcct aacgccttta ggggctgtga agagagccca gttccaggcc   104700
```

```
ctcttttaga aagaaaaaaa tggtacaaaa agagggcttg ggggtatata tactataaaa  104760
attgatgatg gtttatcatc atcagaacta agatcagtct aggtcgagat gaatggaaga  104820
tgcttctgga actagttttt gatagggtct atcttagctc gaaggaaaga acaaccaaag  104880
ttacaccccc aaagaatatg gattcaaatc agttagtatt tgacaaagaa cctaacgaaa  104940
tttaacaagc agtaaccgga atcaaagttt tcaaaaatgg tgtcaaccgg taatagaatg  105000
tagctagata actgatgcca cagcatccaa aatatgtggg atggagttca tggtacacta  105060
acttaacctt caaggtcaga tagtgctaca gtgaacatca atccactatc tagctcaaaa  105120
ttagcctcac gaactactaa cactattatt cgcgtagccc ttttgtgtgc tatttcatca  105180
taggctgtcg gaacttgctt cttagcgcta cgtgggaaga gaatttctct attcagcccc  105240
cccctattac aaactttaac ttctcggtct aacttggact aatcccttag caggcaagaa  105300
attcctacta accagacaga aagtaagttt ccactcacta ccaaagcgct gtcgcacctc  105360
tactattttc ggcgtaacga ggttttagtc tttacgaggg cacccctag ccagattcaa  105420 tcccaagggt caatcaagcc tttgaaacta gtgaaaatag tcgtcacagt ctgagttcct  105480
gctttcaacg agactttctt agcttgtcaa actttctctc cttcaccagg aaagttatcc  105540
ggtaagcaag atctttgatt gatgtgcctg aataaggttg atcaatggta gctgcttgga  105600
gctttctcta taccttaatt gaactaccct gctctttctt agctcgggtt cttgcttaat  105660
gaggcgtcct tgtttgctct tggattggac taagcggcaa tccttactgt ggaagcagac  105720
cttgtcattc ttctccttca atgccagtgg ataagtacac tagggctgga atgctctttt  105780
atcatgtatg tggattactt ggtcgattac ctgattgcac tagtctcata gccatctctt  105840
tagcgtcccg ccattccttc ttgttaacac aggaaatcta actcattcta aggtagagct  105900
cttagagtcc tacttaaagt taaaggtagt tctttagtta aagcaaggag agcagaaagc  105960
agctaccggc catcaggaga tccacgactt taagatccgc atgcatgcaa gggaagattc  106020
tttatagaag attctctta ttcccaccctc aagctcggtc attggctgtc ctcctcaatc  106080
gattagacta tggcgaatca cttgtgtatt ggtctttggg aaagtgtaag acgctattgc  106140
tcgcaactgg gtcttgagtg tcgatctaac aaaaaagtaa actctagttg cttctcttgt  106200
ccgatcggaa actggtcttc ttttatggt gtaagggtcg gcaacagctc cctttggaag  106260
gaatcgatcg tcaacgtctt tggttccctc cacccgccgc cttcggtcaa ctcaaacaag  106320
aggccaggaa ggacattgtt gaaggctcac tgagtgctta taggttaaag ggttgcacta  106380
gactcactcc acgggaacta gcttttcggt ttgcttaaga tttggcattc attccccctc  106440
cccttcctga atttcgcctt attgcttatt gtctgctatg ctagcctatg atgaagacct  106500 ttcatttttgg ctctgtaggg ctaccctatg gtatgggctg ttatctcaag ggccaggtta  106560
ggctcttctt gttggagtat cctcgctcag aggctaaaat gaatttcatt ctctcttttc  106620
ttttgggagt gcctgaagag acctgcttac tggaaggtac cattctaaaa gaatggtgaa  106680
aaggttacct accctatgat cctccttatc ttacagaggt ttactacgag ccatacccag  106740
cgggatacat attgcccaaa tggaacctaa aagatgggat gggtgatcca taagatcatt  106800
tggcgaggtt catccctcag cgtggggatc cttctggaaa taaaaacttg ttttgttgag  106860
gcaatttccc tcgtcgctta cccgcatttc tcttggtata cccacctgtg tgcctcctaa  106920
ttccgtgaag tccttgggagc atgtgcgatt tattcaggat ccttgtcaag aaagaagtca  106980
gtcccttatt cttgattta tgttaaaagg tctggactcg aagagggagt cgattcacgt  107040
```

```
acttcaccat tccctgggtc gttatcgcct ttccccggtt cagggtatgg gttctttctc    107100
tattaagaaa gtcccggtgt gaactcccct actgatctga ctccagcgga ttctcgagaa    107160
gccaattctc tctctcgatc tactttaccg acaagagctc ttaatgaatg agcaatgagt    107220
ttgattctaa ctattcaaag cagaggaaat agaatattat atagcctata gctatagggc    107280
taggctccgc tcctcgctcg agctaccagc tttcttagat ttcattcctg ttgactaatc    107340
cgagtccttg agagcttaga cgtcagcggg gaagaactcc gaaagaattt catcggctcc    107400
tcctctcttg ccctcttgat ggtatccagt tgaaatggtt gctggattgc ccctagttca    107460
agctctaagt caggcattca cgcaccaaag acctctgact acgctcctca gcctaggaaa    107520
gaaaattccc atttgcctaa tacgtactac tgtgcagcag atgatttagc tgccgttatt    107580
cctccaccag cttcttcttg gcatcaagcc agcccttatt ccttgcatca acaggcaatc    107640
ccgcataaaa gaaaggctac tgacttggct gattcaacaa gggaaaaagg catccattca    107700
aactgctccc attcctatgt tgacaccaaa ccaagagaaa gaaaccctgg agccttcctc    107760
tctatccatt cctttttcat aatcataaag gatggaaatg cttagcttac taaaccagca    107820
acagcggagt aagctcccat atccgtgaag gactgctttc cagcagagga aaacttctcg    107880
ttgctgagct tgccgttaaa gagtaagatg ctgattctat agcagctccg attccttcac    107940
cgagaacgag aaggaagtct tatagaacga acaagcgcta agaaggggg tgggatctct    108000
cctaaaagaa agaattgacc tcgagcctgt cctactcatt ctccttttcc cgttcctgac    108060
cctgagtgtc gagggttag ccttgagcca ggtcttgatt gtttattcca ttttgtcagt    108120
ttaagtactg gaatgggagt tacggatatt cattcctaaa ctatgtcacc gattggtgac    108180
ctgatcccgc taagcaagaa cagctaccga caccgactct atcttaacga ccggtaaagc    108240
cctctctcta ggatatggca cttcactgct cggagaggaa agaattcttc tccaaatcat    108300
ctcttccttt atttaagtta agaaagaagt caattacgtt cgagcttttt gtcaactgat    108360
tcaactcaag caatagaaag aaaagctatc tcctctaatc tctaagtatg cagagttcaa    108420
tcaagctaag aactagtcga cctccttact tttttaccgc tagaaccttc ctttcacgag    108480
tgaacccggg cacgagccta ccttgtaaga accaaaaaag gggtaccggc gtacctacca    108540
ttaccatata gggaatgaac tgagttagag gcatatgctt cctttaccga tagccggtac    108600
cgaactatcc gaaagccctc taaaaggctc aagaagaagg attggatgat ctgcggaacg    108660
gaatgagaaa gagcaacaat tgtctgacca aagtcttacc ctttctttcc ctttcgactg    108720
gcattatcac accgccatca ccagattcaa tagctgctcc tagcccgatt ccaagacctg    108780
accaggtttg aaagttcaag cagccttgat caactatagg aaagtaccag ttttccacag    108840
tgacaaggac ttcttagaaa gcattgattg gaggtctcat ggtggcaaag aaaaagaaag    108900
aggaagcgct cttgttcttg ttgcgcggac cccacaataa agaaagatgg aagacaagaa    108960
gctcagtagc aaggccgtct catagtcacc acttgtctgt cgtttcaagc ttccaaaaca    109020
agcagaaaaa cacgttgtcg gttcagcagc tcgaagttca tctcaataaa atgttaggtc    109080
aatcacatga ctcatcctgt tagtcgagca tagctaacgc taccaggacg ctacgctgcg    109140
cctgcactga cgtgacttgc aaacaaggct gacgccttat agccatatac gcaacgctcg    109200
ggaccacctc ccttcgcttc agagtcttag gcgcagctct tctagtcaga aagagtcca    109260
gttgcgaacc tgtgcgctcc tatcctattg ttgcttctat cacgatagg aatcgtgtga    109320
ttctttctat ccccgtactt tctcgctctt atggagttgt attccctagg ttatgcagtt    109380
atcttccctg gcctgacagt agtcaaggga aaatcacttg agcttttcg cctttgctcc    109440
```

```
ttctttccgg agcgcactaa cggaaaacct gagataaggt atggaagcag tctgattatt   109500
tccacttgag tcgacttaag tctttctctc ctcgtacagt cttggctcta gtaaagagaa   109560
agaatctctc cttaccctac tgcgggaaaa agcactttct atcccccgt gctacaaaac    109620 aaacttatct aagcactaaa agcaaagcaa caataaggaa tggaatggga gaagctatag   109680
tgcagatcac ttttcacttt ctctagagtc cagaccttgt ccttggttct atcagctatg   109740
gagtcttcct ctggttcttc ccgtctctag tacagatcaa atcacaggat ctctgtatgt   109800
atgcgctgag gagctatatc tcccggacga aagactttta aaccctgatt ccggaatgg    109860 cagcaatcga cttcttctg tcttacagct ttcttgtagt actgctctct tttcaagcga    109920
atctctattt caactgcatt cccttattgca aagaaatcaa cctcggttct ttctgttgat   109980
aggttagttt gattccaggt gtgagcctct tcagttgcag tgaaagttcc cgactctcta   110040
gtgctatccc ccctttttca gcctgacatt acaaaggtag acttcatcca ccggacgccc   110100
tggctttctt tttcgttttc aatcttctg tcctttcctt cattcttgca gatgcaaatc     110160
atagatgacc tagtggcatt tatgccagac cagagcattc ttctcaagaa agaaaagaa    110220 aggggagagg gtgactgaat ttcactcttt atcattcctt actactcctc aattcccatc   110280
aagtgttgtc ttatttccca agccactgct caatcctcct tttctgattg attgaaagta   110340
gcaaggaaag acaagcaaaa actttgttgg ctcaagaagc aactgaggag agacaaagag   110400
tagtaaagga aatacaagta gcagtctcag gtcaaaggaa tcaaggaaga atttcttctg   110460
atattgcggt tactcttcca gaatctcatc ctgagaccta agtatgccat tctcttcgtc   110520
aagaaagatc gagcagcata aagccttga cttcaagctt aggtcttttt tttgaaaaag     110580
ggaactaagg caacttttag gtgcagggaa agaggttcgc tagccttttc cctagctttt   110640
tttgtcaact atctatcttt ccgaactaga ttagacggac ttacttaaaa tgaaaaaagg   110700
gctaaaaaag aaggacgaag taatttcgta tataaagata tggcttttccg ggtttagatc   110760 gaaatggaat ccccgaaaac cagggctgga gtcttagact tcttctgctt cgatagaggg   110820
actgacagcc taagtggaat aagaatcatt cggccgattg ctctgactct tatccttcct   110880
tcgctgacag agaagagaga gagcactccc caagccaagg atgagtgcca aagagaagat   110940
gggcaagcta gtctatcaga aggagaaagc gagggagtga gattttcgct ttcattaggg   111000
tagactgaag accaagccaa tctcgattca aaaaagaaaa cttattgcaa ctacgaaggt   111060
gaagagatgc tttctcatta gactatttta accgaaaaag tctttatgtc gaccctaggc   111120
tacgattctt cttctcttat gaaatttata gttagatgaa gactgctctg ctgcatgacg   111180
gagtgatctt tccctcttat gaaaggcgct atctcacttt cgaaagagag tctcgacgtg   111240
gcggtctaga cctagctcca tagctgggct agtcactggc tagaggtcga gggacctagc   111300
ggaccggagg gagccgagaa tgttatgtaa aaaggaccaa ggaggattca ggaggagaag   111360
gaggaggagt aggagctagc tttaggggcg gaatcgaagc gaagaaatta gttcatgcca   111420
cgacgatcca tatggaaggg cagttttgtt gatgcattcc tcttgagaat gaagaagaag   111480
agagatcttc ttttaacag gaaaatttgg tcacgtagat cttctatttc gccggaattc     111540
gttgattgct ccgtacgaat ttacaatgga aaaactcctg ttcgttgtaa gattactgaa   111600
ggaaaggttg gtcataaatt tggagagttt gcttctacac ggaaacgaag accttcgaga   111660
acaaatattg gaccgggaag aaaaagggg aaaagtaaaa gtctaagcgc atatggcacg    111720
aaaaggaaat cctatttcgg taagacttga tctgaatcgt agttcagatt caagttggtt   111780
```

-continued

```
tagtgagggc gaccgcgaaa gtcaccgaat gggtcagtct tttagttctc ccagattcga   111840
atctcaaagg aggacgttgc agatgcccgg ggcggacacg acttcttctt aggctagaag   111900
accactggaa gacacccagg actatagcat gtcgtgaaag aagcacactg gacgggcgtg   111960
cttcgaccgt gtctccgggg cacagttgaa tgtagatatc atgaacgcga ggtgcaggat   112020
accaggccga gaaacccggg caaccattcc cctatgtgcc aatcgctagc gcatccaggg   112080
ccccggcgcc cagctcagct ggagaggcct agcctgatct gagaagtgct aattcggttc   112140
ggatagactt cattcaagaa tgccaccgcc ccgggaatca ataagaaaac aagtgctaag   112200
tttcagatca gtgaataaac cgaaggaaa gaagagacgt ttctcgctca gcgcctaaag    112260
cgcactatgc tccgcttcaa caaatgagag ttttcggtgg aaccggtgaa ccacgcgagc   112320
tggttagatg cgtgggacag agggctcgta gtacctgcta gcgcggctac gcagtggaag   112380
ggaaggagcc taaatcgacc cccttctttt tttctttgaa aaaagcagta aggagtaagg   112440
agattaaact ctcggatgag actaagcagc taccgaccgt tccgacgcgc ccttgaccta   112500
ttttgattaa gaccaaaaac ctatctctaa agtggagcct agtttaagct gtcaaacaag   112560
tgatgattga atgaaagaaa aaccactagt agggatatgg atggagtctc gctcagtaaa   112620
gagagttgta ggattcgtaa aacaggagaa gagcctttac tttcaaatga caactgcttc   112680
ttcctgctgc gagggccttg cacgaaacca aaccgccccc cgcccgatca agtaccagtt   112740
gcttcgctgg taggcctact taggttaggt ttggaaccct cagttcttac caacctccgg   112800
tgtgtaatct acatctttct agctagaact aggtcgaata agaatcattg actccctctg   112860
ctgtcaattt cttattcatt cattgcgttc ggccggtgct cctttctcat ctcaaaccat   112920
aactactctg aaccttaggg aagataaggg aagaccgcct gagcgaagcg accgaaggaa   112980
cttgacttat ccgaaccgaa cgatagcggc ttaaagcgtt gcctatcacg agcagcctcg   113040
ctccttgatc ggcggggagg agcatctcaa agtatggggc aaaggatgtt gcgttttgac   113100
tttgtctccc gggatccacc acaggttggg tttgagagcc gtgtgatagg tgactatcca   113160
gcacggttcg gagagcactt ttagtctgcg ctggtgaatg gaagcccccc ctatcaagca   113220
agaaggaagc ggctcttccc acggcggagt caccattgac tctatttatt attatgtaa    113280
atcagtgtat caagatgtca atctgagatc ttatttcggt tcgatacgtc cacctacgag   113340
actcaccttt ggctttcgtc tcggtaggtg tattattata cattttccca aaagaacatt   113400
cattcatttc tttcttcccc gtcgaccacg acgactgaaa cgacgcgaaa aatccagacc   113460
cgtaaaggag aagggccggt ggggggcatt tgggaaagtc gggccgatcg ggtgtcttca   113520
ttcaagcgac ggtacagaag aagaacgaaa cgaagtgaga ggccgggggg cagggaaaag   113580
agtcgagtcg atcaggctcg acgatcggga gaagcaaaac gaaatcagga tttgccgaa    113640
aaagaagcaa ggctatggat accatgaccg atcaccatcg ataaagaaaa atctgtctaa   113700
atcacttcgt gtcagcgggg ccttcaagca tccgaaatac gccgggattg aaaatgacat   113760
agccttcctg atagaaaatg acgactcctt cagaaaaaca aacttattca agttctttt    113820
cccaaagaag tcccgctccg accgcccgac gagtcatcta cttaaaagga ccctccccgc   113880
agtccgccct tccttgaatt attcggtcat gcaatactta ttgaatacaa agaacaaaat   113940
acatttcgac cccgtcgtag ttctcaatca tttcgtggca ccgggcgtgg ctgaaccatc   114000
tacgatgggg ggagctaatg cacagggaag aagcttagat aaaagaatac gttcttgcat   114060
cgcttttttt gtagaaagct cgaccagcga gaaaagtgtt ttggccgaag ccaaaaagag   114120
ggtgacccac tttattcgcc aagcgaatga tcttcgcttc gcgggaacaa caaaaaccac   114180
```

```
catctcgctc tttcctttct tcggtgctac cttttttttt ccaagggatg gggttggggt   114240
gtataataac cttttttttg aggatgcccg ggaacaactc ctaggtcaat taaggagaaa   114300
atgttggaac ctcatgggta aggataaggt aatggaattg atagagaaat tcatagacct   114360
aaataggata ggagaattga taaggggaat agagatgatg atagagatca tactgagaaa   114420
cagaagaatt ccgtacgggt acaactatta tttgaacgaa gtgaaaaaaa tgcgatcttt   114480
gttgtataat agaacaaaca ctaataccct aattgaatcg gtcaagatca aatctgttta   114540
tcaaagtgct tctccgattg ctcaagacat ctcttttcaa ccgaggaaca aaacaagatc   114600
atttcgttcc atttttagta aaatagtgaa ggatattcca ttagtaatga aaaaggggt    114660 ggagggatc cgtatatgtt gttcaggtcg attagaaggt gcagaaatag ctagaactga    114720
atgcggaaag tatggaaaaa catctcgtaa tgtatttaac cagaaaatag attatgctcc   114780
tgcggaagta tctactcgtt acggaatctc aggtgtcaaa gtgtggattt cttatagtaa   114840
aaaaaaaaag ggacgtgcta tatccgaaac gtacgaaata tagtaaatat cgtaaaggca   114900
gatgtagtag gggttgcaaa ccggacggta cacaacttgg ttttggaaga tatggcacta   114960
aaagttgtag agctggtcgt ctttcatatc gagccattga agcagcgcgt cgtgctataa   115020
tcgggcactt ccatcgtgct atgagcggac aattccgaag aaatggtaag atatgggtaa   115080
gagttctcgc agatatccct attaccggga aacctacaga agtaagaatg ggaagaggaa   115140
aaggaaatcc tacggggttgg attgctcgtg tgtccagggg acaaatccta tttgaaatgg   115200
atggtgtgag tttgtcaaat gctcgacaag ccgctacatt agcggcgcat aaactatgtt   115260
cgtcaaccaa gtttgttcag tggtcgtaag cttattaatc tgacccaaat tccccatttt   115320
ggtacacgcc aaagccttcc atttcggcgg attgaaagag ccatcaatga ctagaatctc   115380
cttttagatt cgaaattctt cgtttttttc tcccatgctt tccgttggtc aacaaccaac   115440
taaagtgctc tatacttctt cactactcgt acagggaagg tggaagaaat tcagtctctc   115500 tttttttgg ggggagcaga gcagtgaaag aatgaaccaa accaaatgat tgttctagaa   115560
tggctattcc tcacaattgc tccttgtgat gcagcggaac catggcaatt aggatctcaa   115620
gacgcagcaa cacctataat gcaaggaata acagacttac atcacgatgt ctttttcttc   115680
gttattctga ttttggtttt cgtatcatgg atcttgggtc gcgctttatg gcatttccac   115740
tataaaaaaa atccaatccc gcaaggatt gttcatggaa ctactatcga gattcttcgg    115800
accatatttc ctagtatcat ccctatgttc attgctatac catcatttgc tctgttatac   115860
tcaatggacg aggtagtagt agatccagcc attactataa aagctattgg acatcaatgg   115920
tatcggagtg cgcctcttca cgagggtgat taaagtgcaa cgaaatgcct taaagttgaa   115980
tatggttcgc gaagcatctg gcttaccggt aatctcccat tccgccgtc gagagacttt    116040 aataactata gcatgccaga acggggagt tgaggtggtt agacctatac cccgaaatgc    116100
tcccagcata ggagcctatg gttccattct tgttgttgct ggaggtacac atccctcttc   116160
tcggtgtgga acgatatacg agaaatagat gctcagcctg caatgtccga taacggcgct   116220
gaagtagtga atctatcggc accatagcag tggtatacaa cttttggacct aacggccggc   116280 cthgtaacct ttcggaatgg ggatcccgt tggcaacaac cacggtagta gttgcggaac    116340
tactgggccg ggagagkaca acctcttgtt cctgctcctc tttcttcgct tcggggacgg   116400
aggtcctacg gtaggtaaca gcaggcacaa gcaagttgac cgaaggggac cagcgcttct   116460
actcctccac cgaggagccg ttcttgcgag aagcaaggga tgtcgtgaac ggtgggaggt   116520
```

-continued

```
cacagagaat tgacctattc atagagtgat cctatgatcg atacaggata tagactatct   116580
cattctttvt tctatgcbat ttctgramaa aagarrahvb cgkactcaac ttctmascwa   116640
gagttkgkgg tkggacckct tggcataatg cacgctggaa cgtgggaatt cgaggtctca   116700
tgaactacta ctaaaaccga cttttgttttg ttttgtttgt ggacaaacga tatccggtca   116760
ggcctatggc tggatccttt tagatctaca ggccggccgg ccccggccgt ttacatgagc   116820
atagggaatc tatactcgag cgttccactg ggcccctgac aggataggtg aggaatcact   116880
ctggatcttc tttttttgggc tacaacttcg ccgagccgac tagcatccct ttccactgtg   116940
cattttcga acaaagaaga cgactatagg atcgaattcg ctcttcaaga aactgctcgt   117000
cccatacctt ctgcctgtct catatgtgtg aacctggtc ttttcggttc cagcctctcc   117060
ctcgaataca tagggtaggt agggctgggt gataaagggt tccctcttgc caataaactt   117120
tccccggcct tcgattaacc ttactcataa agggtcttac ggtcgggaga actacctaac   117180
taaagaaaaa tagtgttctt tctaagagta ggcgtggaga gcttttgcgg ggaaacttgc   117240
aagtacagtt tggggaggcg ggcgtcgacc ctaccttatg agtattcgga ctataacagt   117300
tccgatgaac agtcactcac ttttgacagt tatacgattc cagaagatga tccagaattg   117360
ggtcaatcac gtttattaga agtcgacaat agagtggttg taccagcaaa agttatatac   117420
gttttattgt aacatctgct gatgtacctc atagttgggc tgtaccttcc ttaggtgtca   117480
aatgtgatgc tgtacctggt cgtttaaatc agacctctat ttcggtacaa cgagaaggag   117540
tttactatgg tcagtgcagt gagatttgtg gaactaatca tgcctttatg cctatcgtcg   117600
tagaagctgt tcctaggaaa gattatgggt ctcgggtatc caatcaatta atcccacaaa   117660
ccgcagaagc ttctccagtc ttcgtcggtt ccccaaagaa gacactattc ttttgggaga   117720
cccgtcgtcg acgaagatga gctctacgaa gcggcttacc accccttcta cgcggccaac   117780
gtagtccaca tccctgggga aattgaagac cccttttactc tggctaaatt aagtaaatta   117840
aatgggactc tcctagccat agcggatctc ttttcaacgg ccagataagg ggatcgtaca   117900
ctaaagagct gcaacttgaa ttgaatgcga ccgaagaagg cgagctggcg gctaagctgg   117960
aagagctgcg gattagggaa aagcggcgct ataatttacg ctagggtgag caagcgctag   118020
ctctttctct tgcggtgaaa taaccgccgt atagaggcga acagcccta tagcaatagc   118080
aaacggccta cttatagcct ttcaacaggt cagtcaatat cagtaagtag ggtcctcttg   118140
cctaacggag tcagcccaac atggacaatg ataggcagac caaagattta cgcagtcgtt   118200
gcgtgcttgc tttgcgcacc ggcatagcag aattagaatc cgctggctca gatgagtggc   118260
tcttggcttc gtaaacatat ctatgttgtt gchbtccaca hccacbcagb tggcagcght   118320
ggatgcttat ggagatatgg cttggcccag gactattggc tttccgtcaa gtgtcagttc   118380
agccatagac attcaattca atctcggaga tagtcaaaat gccattgtcc gttctaaatg   118440
aaaggaatga gataggccgc ttacacacgc ttcaagtctt cttttgctga ttcaataaca   118500
gtctggaaat tcgactgaat aagtcttagt gtggttaagc cggggccagg gtcagaagtt   118560
cttccatctc ctgagataag atcagacaga gcctatacgc cttcttgctt tgctgcagct   118620
accgggtatt cattcaaaag aatgcattta cctttctcc ccttccttcg gcatccctga   118680
ctcgggcatc cctttcaggt gcagttgacg tacaattttag gtaatttata aggactaaac   118740
gtactgatga aagggaaaac ttaggaaaga atagctaagg agaatccttc gtttgaggaa   118800
agagatgata aaataagtca tgaaaaaaac ccagtttgtt ttaaggctct catgaagcct   118860
tagggcgaat tcctctcaca ttggaaactt cgctcacttc ctatattatt cgcgcaccta   118920
```

```
cctaccacaa tccggttcca agtcctttat tttaaaatcg aggagtagtt caacttttct  118980
ctcttcggga ctaagagaac ttacttacta attgaaaaaa aagacaacta gaacgaggtt  119040
tttttacgtg atcggaaatc acccgtcggt gatgaaccag tacgcactta ggatagcact  119100
tcgggagagt gagatccagg tggcatatca aaagacttat caaaatcgcc accatacgag  119160
acttgcaggg catgcccgcc agaaagtgaa gagaggttta taagcacccc gacttaggaa  119220
tcatgaccca ccgaagaaaa gaagactcga ggaaaactat tgatcccttt gatgactctc  119280
ctcttcatct tcgcgggttg cagagaagaa tccgaactga ggaaatgaaa aaaaagaaa   119340 agtatctctt tctcttttcta cgatcacctg tagcgtcctt aaaagtctta gaggagaat   119400 ctaactattc tcgaagagat tcttgccaac accattagga agatgaggga aaggggaaaa  119460
gaagtcaaat tcgctatttc cgacagctac ggtagtagag aaggagaggg actacttatg  119520
agaaagagga gtctctcttc tactcccggg tattgaaccg ggatgctttg gtactagact  119580
gggcgggcga gccataatca caggggagaa aggcgcagat cttttcatcc tccgccaaca  119640
agcagagccg acaccgagct acttcgtacc ttttcattca aacgggaatg actccactct  119700
cagtcccagt gtggcttaga ctagtagaag gcgtaaggat gctagaccgc tgctcaatac  119760
tggataatcc acgttcatcg gtctgcagca agcactgact tttaggggcg gcaactaaag  119820
aggtagcgag actaagcgca atttcaggaa gagttggacc cttgcctcta agcttccttc  119880 taccttgtg ctaaaggaca ggaaaaacaa cttctttctt tcttttttt taatatattg    119940 aataatggaa taactcgaac cctactaaag agtggctttc agctcctccc cttctttcat  120000
tcagcgactg ggtacgcact tcgccatgaa agatcttggt gatcttcatt tctttcttag  120060
gaatcgaagt caaaggtaca tcgacttctc tagtcttgac tcagactaaa tacaccttgg  120120
aattactcga actcatttgc aagactccaa gccatgtccc acacccttg cgtctggctt   120180 aaagctctct gcatacgatg gtcctcctct ctctgatgca acggaatatc gtagcattgt  120240
tggcgccctt caatacctca ctctcaccac cgtatatctc caggctgtaa aaggcatctt  120300
acggtatatg aagggttttc ttgggcttgg cctaaccatc actcagggac tttaaaccac  120360
cttctttgca ttctccgatg ccgactgggc tggctgtccc gatagcagac ggtccactac  120420
ttgcttctgc gtatttctcg gaaacaacct actgacttgg gtttcaaaaa aaaaagaaa   120480 ccgattcttt ccaggtctag tgccgaagca gagtacaagg cactcgctct tactacctct  120540
gaactcttat gactttctta cttactacgc gatctagcgg tgccgtttcg ctatcaattt  120600
tcgtgcactg tgataatgct agcgctacac acttggtggc caatcctgtg ttccatgtcc  120660
gctctaagta catagaagtt gactaccact tcgttcgtga cctcgtcgtc gcaggcaaat  120720
tgctcattcg acttgttcgt agcaacaatc aagtggcgga cctttcact aaaggattac   120780 ctgaaccccc ttccatcatt ttctgctgtc tcccgcctgc ccttctcgaa agaatgggct  120840
cctggccgtc ctatctcatt gaaaaggaca aaaccattta cttttccaat caagaaagt   120900 gaagccacca aaaaaaagaa aaagggtata gtaatatata tataaagtca agttcaatg   120960 gtaacgactt cttccattga cttcaggatt gcttggtttc agggaaagtc tctcgctcct  121020
ctccttatag cgctggcctc tgtctttgat cttggctcga gctctgtcct ctcctctccc  121080
tatgctattg atttacgtaa ttggaaataa ccaattaggt ttacgacgaa acctagaaat  121140
cgatcatgat ccaatttgag tacctctgca ggatagacct caacagaaaa ctgaagagta  121200
acggcagcaa gtgattgagt tcagtagttc ctcatataaa attattgact ctagagatat  121260
```

```
agtaatatgg agaagacaaa attgtttcaa gcaccgacag aaccggaagc gccccttctt   121320
tcaaagagag gaggacgggt tattcacatt tcatttgatg gtcagaggcg aattgaaagc   121380
taagcagtgg gaattctaaa gattccccgg gggaaaaata gagatgtctc ctacgttacc   121440
cataatatgt ggaagtatcg acgtaatttc atagagtcat tcggtctgaa tgctacatga   121500
agaacataag ccagatgacg gaacgggaag acccaggatg tagaagatca taacatgagt   121560
gattcggcag atttggattc atatatatat ccacccatgt ggtacttcat tctacgatat   121620
atataagatc catctgtata gatatcatca tctacatcca gaaagccgta tgctttggaa   121680
gaagcttgta cagtttggga aggggttttg attgatcaaa agaagaatct acttcaaccg   121740
atatgcccct taggcacggcc atacataaca tagaaatcac acttggaaag ggtggacaat   121800
tagctagagc agcggatgag ataggagcag agtcgtgaaa agagctaaaa gcattctata   121860
catacgaaag caccaagcac atttgcttat gaaagaagag cagcttattc tgtaacagat   121920
tttcaacctc ccttcgggaa gtaagagcaa ttttcccttg ccttgagcca gttccagtca   121980
tgagatgact tttcccttac tcttttcatt cacaatctct ctctgcccat cgctctccct   122040
gtgggtcgag cctccttttc agtcgccctc tacaactaag tcagttgagc tctctcggct   122100
cctagaccag ctgtgatctt tcctcctgtt ggtttgctta gttaaatata tgcatcctta   122160
gagtcagtcc cttttttttgg agaaaaattc cgagccggta agcaagacaa agcaagtcaa   122220
cgtgggaaaa agctctcgat ggccatagac ctgaatggtt ggagtgtgga ggatcactcc   122280
tgaaactttc ttcctttata taaggaatcc tcttggttgg tcgaagctag aagacggctg   122340
gacgaactgc tattttgcat aggggagta agataggcta ggtgcttta ctcaactcgt    122400 gaaggttcat ttctagttag caaggataag gaagcaaagg tagagtcctt taataatatg   122460
tctgtcatta cgtgcgacta tctccactat agaaagaaaa aaaggaaaga acaacatttt   122520
cagcacattt atacgaaaaa gtctttatta ttatattagc ataagtagga aacatttttcc   122580 actagggttt ttcccataca tgcaaacata aaaaagaaaa gcaaacaaag ataattagca   122640
tagataggag tctatctcca gtaagcatcg gagtagatct ccactaaaaa gacaaagaac   122700
accctaaatt aaaacacatt actttgcgtc tacagacact tatttaaacc ttctaaaact   122760
aaaagagtcg acggactctt ctattctagt ctccctggcg accacgggtg acagcaccca   122820
caattaggtc ttcctgtttt ggaggagggc ctgtttcctg tcttccagga cgctaatgcg   122880
gtcccggatc cgctgcatgg ctgcagccac aagtgcagga tcgatgggag gcaggtgctc   122940
ccaaaggcag ccagggtttg ctccgattgg agcttctcct cttccacttg agagatttct   123000
tgcgaaattt cttgaagtct tataaaagaa tccatggcta cactcaaagc ttttttttgc   123060
cgacttctaa gttcctctcc gtctcccttt gccaaataga gactgaaaga agcttctatt   123120
tataggcgtt ggaggcccctt aaccctttct tattattagt aagataggtt gtcttggttc   123180
cgtaacatgg atcatttcaa acctggcttt tcatgaatat ggaaccctcc actagattt    123240 agtgtgctga ataattatct tcgtactcca atccgtacga agggcccctt tctttggcgg   123300
gtatcgccac gtggcttaat cccggatcac tccttaagga ataggacaca ataatatagc   123360
gcacatcaga gaagagagta cccctttatt ataagacagg ccccacgcgt cctttcttaa   123420
gagatggagc aatcgtcact cgacagctca aagctgaccg gtacaacccg cgtgcttgcc   123480
tactcgtctt tcaccggcct atttgtaccc agctacaatc tcttcccttta gaaagaaaaa   123540 aggcccctcg gccaatcgtc actcgacagc tcgaagcgg atcagtacaa aaccatgtga    123600
tctgtacttg tttacgtact gcccccttagg cctagggctt cgtcgtaccc tgcttactcc   123660
```

```
tctttcactt tcactggctt ctacttgtct tttttttttt tattggctta tttagaaaat  123720
ggtatcagca tttgagacga ctctccccgg ccaatcctca gtcgtccgtc cttgcttagg  123780
agaaaaccga accactctgg taaaatgccc gcccgtaacc cagcagataa agtacattac  123840
atagtccagg gattggcgac ttacccattc agtgactttg gcactggacg ttcccaaaat  123900
ggggactatc gggtaaattc aatataatag acgcctgttg gcattccagc cttccttctc  123960
ctttcagggc ctatccgaaa gagaatccag tacttcttgg tcgtgaatat ctgaactggt  124020
tgtttgctgt tcaagaattc ttgtttaggc agttcatacc atccatacat agtgttttga  124080
tctaagattt caattcttcc gtgtttcagc agtaacatat tcttccatgg agctaaggtc  124140
caaaatatgg aagaaacaag cgtttccacg actctaccac ccagtcaatt ctgttccact  124200
taatccctct ttccggctaa ggaatgggaa atctttctcc tgttacatga atccaatttt  124260
catttcatcc gggaaaagcc acctttttct caacaatgtc tttgtcattt gatccaatag  124320
cgttccgtta gataggaaca gatttgataa atactgaata actctcggat agagtattag  124380
aacggaaaga tccattagat aatgaactat tggttctaag ccatctctga cgattcattt  124440
taaaagtgac taggtaatta gtgaagaggt ttataaaagt gacaagcttg gtggaaagct  124500
cttatcttag gaggaaaagc taagtatgcc cgagtagtct tgatattggt tggtttgagg  124560
tttcgttagt tttatactaa caagcaagct tcggttcggc gaccgctcga cctagcgcct  124620
tagccccagt actataggga aggcctatgc gaagaaaagg cctgcccatc atcaaagcaa  124680
gcccaagtcc atgcaagaag gccctccaga tctgtccaaa ttcaaagccc gtcaaaggca  124740
tatgaaatca tgcaaaggat ccgagcccat ccaaatgatg ttcagcgggc taaacccaag  124800
tagctctggc ccatgatcca agagacccga aactagttaa tcactccgtg ccttaccttc  124860
taaccaatcg gccaatcacg ctatccttac ctttcaacca accccttcga ttcagtttct  124920
gcagcagtat agaatctcgg acccgatgga tgcctacaga aaaatgagtt ttccagcagt  124980
gatggcaaga atccgcgaaa taatgttctt tctccttttg tgttctttct gaatggagct  125040
acgcgaggga aagctcagct ttctactctg ccgcaaaggg gccgctttct tccccaaaat  125100
gccagttccg ccatcagggc ctagcaagaa gcataattct gttccaaagc ttcgtttcat  125160
tccagcaaca gtagtctatg gttcgaagcg ccgtgttcca tccggcgcga atcctctcca  125220
taactagtat agtggaggtc ttacttgtat tgcaataatg aaaaatgtac gaacacaaat  125280
aatgagcaga ccagcccact tttatatgtg ggttcatttc agaatgtttt tttgtttga  125340 ataaagaagc gcgtgaactt ttagtgtaag gcaggtgttt tctcggtgga tggatgggat  125400
aaatgcctat attgctttat aatgttattg ttatgttgat gttatattaa agaatgaaat  125460
ctaaaaaagt tgcttagtcc cattctttat aattgtcttt ctcatactgt gtaaacaaac  125520
ttcaagtctg aattgtgtac tgtactcaac aggaagcgtc acagccaccc cgatgtcgat  125580
ctgcagtatt agtttgagaa agtcgtttgg ttttaaccta gagcgattgg tttacctgta  125640
tcatgcaaat gtccaacact taggtgcttt ctaagatcat cctatatgaa agatgtatga  125700
catgtgtgga taatgaatga cttgcagggt atgcaatatc ttaagtacaa aaggtaagac  125760
ctaaagagaa atgagctta gcacaacacg ggatagaaag ctaatcctag aaggagaaaa  125820
cccatcacag aacaatcata ggaaaagaag aaatgggttc agaccaagtg acagaactct  125880
ctatgagttg ggctacataa aagatccttt tctactaaaa tggatgtagg cttaactaaa  125940
gcccaatgca ggttgaactc tatggaatct aagcctcact acccttaccc tcttagaggg  126000
```

```
ttacaaggaa ttttaggccg gccccatata gattcagctt aggggtttat gagagattga    126060
ttgatggacc taagctaaac aactaagatt gaacctaaac caaaacctat agactgaatt    126120
aggagagcag aggtttaatt caagaccagg aaagcaagtt atatcgaagc ccaatgccaa    126180
gcaaagccct agactacaag tgaagaaatt gggttcaact aagcccttaa cccaagatga    126240
ggtggagcct taacccgaca caagaggggc ccwgtagrat agtgbghata gtcagcccaa    126300
cataggttgt taaccaaaag gagaagttcc cgtgaaaaca gaaaagacct ccccttaacc    126360
cccccttact tggcagattc acattcgtag gaaaggtctg ttcttttgtc tctttccctc    126420
aagcgaagga acctattaat aagataataa tatctctctg cttcctagat cgataacgaa    126480
tccttcggtt gcttatcctg tcatccgagc ccggcgttcc gaacaacaat gattcggaaa    126540
gataaggtct acgaaagaaa agaaaattta caatttgccc tactcctcaa gaaatactgc    126600
gagcggtatt gtaaaggtat gggcttttcg gtcgattttg ctcaagaggg tgggggactt    126660
cgactttatc gaagcagcac atgagattgc ccagaaggat tactttttat taacctagtg    126720
cggatgtgga ctcctaaaaa cctgctccac tttgtacgaa aacatagtaa tgcagctaag    126780
tgggagtctt acatgaacgc gcacttgatc tttgacttgg tccgccgcga tccataagga    126840
agggttttcg ttcgcaacaa ggtagccgta gggaaacccc tatgggctgg attgaatctt    126900
tcctttcctt ctccctctca cctgatccat taaaggaaaa cagactcaag gattgggcca    126960
ttttccatat gtctctagaa agataggagc taatcaaaat tcttattact tatgtaaatg    127020
taactctcaa atttgatatt actccatgtg taacgccaaa ggggccttgt attcaattga    127080
aacagaggat ctcccacatt gatatacaca tccttcaccc aatctgctca agtattttc    127140
aactctttca tggtatcaga gcactagctc ttgggaaagg ttcagttggt tcgtgtgaag    127200
tgtggtctga ataccttctt cttaggtgtt ttctctttgg cgctgtccac cgctctgtct    127260
ctatccttct cctcagcact tagttagtat cccgtccatc gaaattgagt tttccatagc    127320
gtctgtttca attttatgga aaactaagaa aattgskwky kwgrrgsrsv agawskwchc    127380
vgttdcgbtg abggaactgg aaaagaacca agaaaggac tttcttgaga ctgatcacaa    127440
aggtaagata atgaatcctg agtacgtccc ctggagaaga acagaccgac tactcaaaag    127500
tttaatgatg cacaccatgc cctttcccag gcgtcgaggt tgcctagccg taatccacag    127560
gctggcttcg acagatgtca gagtgaatcc gattcttcga ttcaattact tttccaattc    127620
caaccccgcg cgtggatgta gaaaagtgtg tgaatggcat acgkaagatt ggggatggac    127680
aacatcaatt catttagtat agtcagctag gaagcactag ctaggcaagt catactggga    127740
atgctgttcc acacattggc tcaattctac cttccacatc caattcttcc ttcattacaa    127800
ggcccagctt cgctaaactc gcaccgaccc ttagttaaat atgcgggtag cttttcacga    127860
aagattgttg gcatgcctcc cataagaagt aggataaaaa acctatgaga cccccttgtt    127920
ctaatctttt cctaaagagc aatcgattac tatactagtg catgcaaact gaaatcttag    127980
agaaccttga tcctattgat cagaaagagc tcgggcgaga aggtctgcgg ggtcagaaga    128040
gttcagagaa agctggatcc gggaaggctt acgccgataa cgaaggattt tgaaaccgat    128100
cgatatgcag acgctgcaaa agcaaatgac ttcgcttcct caatcaaggt aaggtaattt    128160
gagaagctat cgaaactatt ccgaagttga tgatttcgtt ctagctaggg caatttaaag    128220
agagaagttt acgctctcca acaaagaagc actcacctcc taatagaaga gataacgtaa    128280
gaaagactag cagatgcgga cgatgtaagc ggtcaatcaa ttgagactac ttagagtccg    128340
ctaactaggg aaagagaagc actaagatga aaagatataa ctagattccc cttacataat    128400
```

```
gctcctgttg aaactaaaaa aagataagaa gggacttgaa gcttacagtc cttactcaac 128460
tacaagtaca tagagaaatg cttccaccta ttagactatg cattgacgtt gcagatgtta 128520
aattgcagtt ggcattagga gatagagagc aaaaggaatg aatctagtat acttaaggca 128580
atccaaaaga aagcgcttag tccttatgca actaaagcac aggcaggaaa taaagctaca 128640
tccacaaaga aagagatggt tgcatctaag ggcttcttat cttattgggt ctagcttctt 128700
agaaagccat agggagagac cgaacaatct gatgatatat acttgtgatg tcagaaaaaa 128760
gttccgaaga gtggaggcag cttttcctc caattttctg ttggattcta ataggattca 128820
ggaaaaaata ggaattcgac agagcgcaaa agatagtcga gcaatcagcg ggcaggcata 128880
ggtagtcgac agcagcaatc gaccatcttg agcaacaaga gaaagaagga ccaacgacga 128940
tcaaggaaag aaagactaag taaaggcaga caacgagacg aagatagcag acttgcctcg 129000
aaacaggaac atagcatagg ggcatttctc cggactagtt aagtagttga gcccggctcc 129060
ccgcttggct cctctttgct cctagtagac tactagacat cttgtctact ctgcttttat 129120
ggaagagctc agtccaagaa gggctctcaa aaaagaaaa ttgtcaagct ttcgaactcg 129180
ccttgaagtt gatgaatgat tgcaaggcta gcaacaagca ggctcgctta tgatctgctg 129240
aaagagtaca tcaggttttt tattaatccc tcacattcat gaagcagatt gtcgaaaagg 129300
gctttctgca agcaggaaaa cgacctttta cgatccacag ggtctagctt gatcccggtc 129360
tcaggacttc ccaagtcacg gagtctttga tcaagttgta aactaaagga gtataaccta 129420
tccaatatat atatattttc gcttattgtt agtaagaaag gtgtcactaa caaataaatc 129480
cttaatcagt agtggactac tagttaacgc actactaaag cagagtagcc agcatgcgca 129540
cataattttt gccagaggat ttttcagcga atggaagaag caggcaggga tagatataat 129600
ttttaggaaa aagtgctttg tttgatttgt tcccaggtga gatccaagat cttcaacgc 129660
gttgatttcc tactaaagaa actgggcttc tatcaggagt ttgatcattg gaaagggtcg 129720
aaaactcttg ctttatgctt gagaaagagc cttcccggcg atctgcttca tttatggagg 129780
gtttgcaagg aagacaactg aatagcggga attaaagaga aggatttcca gaggtcaata 129840
tctggcattg agcctgccta tcctaagtat gagttgggag agcgagatag agacaaagac 129900
ccaatggacg ttccctgct ctctctcgat gtggtacctt tcagtctgct ctgtcaaaac 129960
tttctcgcaa tgccgaaagg tagagcagct tcaaggtctt cggcaacgag atcaactgct 130020
gacccaagaa ggtagggaag agaggaggaa gggccaatcc cgagtcaggg gcatctatct 130080
ttatttacgc aaagctattt tcgatttaga tatgttcatt ggcctgcgac tgatctcatc 130140
gtccgttttc ccctctttcc tattcaagag ttctcctccc taacggcaca ctgtatataa 130200
tctctagatg gccaatgtga acagttcaat caaacttgta tgtgtgaagc atattgaaag 130260
tgacattgac aaagcaaagc acagattccc tagaatgtta gaactcagac atgacagaga 130320
aggtagtcaa aacggtacgc taagctcctt gcttcgtcgc ttctgttttc agttattcaa 130380
agaatgatgt tttaagcatc tctatatgcc agtcatctat ctgacctgac aaggaggtcg 130440
actttgatat ctcaccctg atctctacgg ttggttgaag gtgtcttgga agacgggtcg 130500
aaatcagatc tggatagaag attcatctac gctggcaaaa gggctatcag aaagagtcca 130560
atcccgagga gagttcatgt gtgaaatttc tttgttgaat ggaggtgagt tcaagggctt 130620
ctttgatcgg gaaatgcacg cacttctttg ttgtcattaa ggtcccttcc cctgagttca 130680
agatgtccct tccgcttctc tttcactact ttcctcattg ggattggtca agctccttca 130740
```

```
cttattgctc gatccgatcc ggaacctatt gggatagcac cctttcctcc tatttattag    130800
taggtcttct tgcccgttca gttcctctac tggtagtcta gttgtagttt tgagcgggtg    130860
aacccatgtt ctatctcgta gtcacctaag cggcagagtc tgtaaactca aatggtctga    130920
gagttgcctt tggcttctga acctctgaaa ctggactgga gcaagctacc aagctcctct    130980
tccccttcat cactctctat ctccggccct tgccattagt tagcttgcac ttcccttgct    131040 tgcccttga gttttcaaag tcaaggtgcc tttcccttt ctgccttacc tcttactgaa      131100
gtgaaagaac tgactgttgt ctacctttga ttctgtcttc cgggtgaagg tcctgcggag    131160
gtctttttta gtgatcaaaa ttgattaggg acagtgaccc atgatgaaag gagctattga    131220
cctaagtggt ttctatttgt atttgaaaag caaggtaggt ttgttaacga aaggataagg    131280
ttaggctgga atgggatata gtaagtgtgc cacgagtgct ccttctaagg cttctgcttc    131340
tctctaataa cgagaaaatg actctttcag aaagcaaagc tacaactctt cagtctaagc    131400
tatctaagct agaacttaag gccgacctct tttcagggat accccacttc ccggtctagc    131460
ttcactaact gtattcacag ctttccagat ctcggaacca gatctacttt ctcatcggca    131520
ttctctaaat gaattacgtt atggtcttga actctcgata tatcatatgt aatgaatgat    131580
cgaggttgtc ttttcggaag aggtgggtgg gagtggggca gggcaagaaa gtaacaatca    131640
tacccgatat tcagagcgcc ggagatagaa gcggcggcag ccataaagtg gagaatttcc    131700
atccatttgc tgtctctttc gctaccgctc cgtggggtca acattacgaa attagccagg    131760
ttcagttctg actatagctg caacctatct catatttggc cgcccdcgat cacaaactcg    131820
aaatttggga agataaagta aagaaagaat ttcgggctag gttcaaggta tgcccaaagg    131880
tatgccagtt gattgaaaag aaactcaact ttcaagattc aagattaggt aagtgttcag    131940
tgtactaagg tacaagatcg aaaaaaagcg cggatagcaa attccttagg ctagatagag    132000
tggtggttgt aaattactag gtagccatac aacactcggc ccaagcaacg cccaaaagcc    132060
catgcctttc ttggtcggac caacccaacc ggcgatttcc gacaagtctt tctgaattgg    132120
aagagcaaga agcggaactt gaagaaaact ttctttctct ttatggatag acagtctttt    132180
caaattctcc ttctaattca tcttccccgg tggatttagg tttatctctg aggtcccacg    132240
aaggttcgac tagtagcact ctgtcggacg ccaattcggg tgatattact agcactcaag    132300
ttttgagtga tatcaccgct cttttgagca acgaatggaa gtgggaaaga attcaccaca    132360
gaatggagcc caatagagtt ctgccaagcg gttttgggga agaagcggtg aatgacctat    132420
ctttattgaa agacatctat tgtgatctag cggaccatgg aatgctaagt tggtattggg    132480
aaccagcttg gggctttcta aatctcatta gcaatagtcc aggaatgaca tagccttcct    132540
gtgcaatggg tgtcttaacg tactaagtaa ggtggttttt tctaaagcgg cattctcctt    132600
ctatctatca acaatagaat tatggaactt tctccccgag ctgcggaact aacgagtctg    132660
atcaatagag tccgtcattt ttctattcct tcctacttct tcttcctcta ttatgtgctt    132720
ttattctatt tgcctgaaac tcgagaaaat agagttgttt gagaccaaat gttatagagt    132780
tgggggctct ctgggaggca caccttcact tccttcttaa tgaagggggtt cccgggagtc    132840 tgaccttgtc ctttctttta attgtcgggg ccgtcatgag tgccgaaacc tatttcgta     132900 agatgatgat ggctccttcg ggcgcatcaa gctctgaaga tccaaactgg acggaagccc    132960
tgagatcttc taaagggcag ggagagactt cagaaaggga aagcacaggc acatcgtcgt    133020
ccatcaacct acaaaagaaa gagcacgtcc ggcgcctgcc ccaaatgaag tagcttccct    133080
gcccctgtcg tccccttcc atatcaagaa gatgagatca taggggcgac agtgtagaaa     133140
```

```
gcatccaaga gcgtttaatt tgaggagaaa accctccttc tgccgaggtc atacatcata  133200
caacaggccc gaattgaagc cgaagaccta ttcgaggtca aggtcgatat tttcaggggc  133260
atgtctggcc ttgatccaga aggagattgg ctgggacggg gagctcgggc cctcgagaat  133320
ccgcgtaccg ccacggggag cattccttgg agaaactcca tacccttctt tcggatctcg  133380
aatcgagggg agtcaattcc gagtccttct ctcaattaaa gggaaggtac ccctgcgaag  133440
gggtggggac gaacactcta ccacatagtg gagtggatag ctaggactac taaaatggag  133500
atcgtgtaca acaacaatcc tatatttgat gtcgattcat ccacacttcc attccttgta  133560
gaggaaggct aactgcttgc tggctgggag ctgtatgagc ggtaacgtcc acgtacagct  133620
ccgtgagaag ggcggtggac agaaatggcc ttgttgtacc tcactctcgt cttcaatggg  133680
gtctgctctt tcttttttgg gagagtatgc caatatgatc ttaatgaggt gcggggcttt  133740
gcatctgaca ttcgttgggc ttctctcttc gggagcctgc gccccggcgt tttgtgcaat  133800
aaacccctcc ggccgaagac tagtggtagg tggtcctgcg gagctttcgg aaagggtag   133860 ccttgtgtgt aagcacagca atgaaccgcg gcgaaccctc agacgaccta tctaagatta  133920
ggggatcctc agtagtggtg acccttcac tcttccacgg actgatacat gtaccgaatg   133980
ctcatacggg aaagttgact cctgggtctg gaacctgggg ggttgctccg agaaaacctt  134040
tctttctcgt ccactcaggg tgcggacaca cctgcgcgga ttacaggtga cagttacaag  134100
aatggcggga agttaacagt acccgacgac attcagggat ggatgtagac ccatcgggca  134160
gggataatca ttccggtcct gggagaagtg gcgaccattc tcaagaacca aaagactgag  134220
ctgagggaag ccctatgagt cactgaaacg acggcaggag tgcccttttc tatcaataga  134280
gggagcaaaa gggccttgct cccttttacaa tatgaagaaa gaaataaggg tcgaagttta  134340
gaccgctcac agtagttcta cctatagaaa ggatcatgaa agaggcgatc agaatggtac  134400
tcgaatccat ttacgatctc gagttttccag acacatcgca cttccgctcg ggtcgaggct  134460
tccactccgt cctaagacgg atcaaagaag agtggggaac ctctcgctgg ttttggaatt  134520
cgacatcagg aagtgttttc acaccatcga ccgacatcga ctcatcccaa tctttaagga  134580
agagatcgac gatcccaagt tcttttaccc cattcagaaa gtcttttccg ccggacgact  134640
cgtaggaggt gagaagggcc cttactccgt cccacacagt gtattactat cggccctacc  134700
aggcaacatc tacctacaca agctcgatca ggagatagga ggatccgaca gaagtacgaa  134760
attccgattg ttcagagaat aagatcggtt ctattaagaa caggtcgtat tgatgaccaa  134820
gaaaactctg gagaagaagc aagcttcaac gctccccaag acaacagagc catcattgtg  134880
gggaggttaa agagcatcca acgcaaagcg gcctttcatt cccttgtttc gtcgtggcac  134940
accccacaag cacccccccgg ctcagggac cagaaaacgc ctttcgtttt ccaccttcg   135000 tcggcccttg ccgccttcct taacaagccc tcgagcctcc tttgcgccgc cttcttcata  135060
gaagccgccg gtttaccccg gaagtccgaa ttctatggta gagaacgctg taataataat  135120
tgggtcatga gagactcttt taagtattgc aaagaaaggg cccgctgata gagctgggcg  135180
gggaggcgat acttgttatc aggtcagaga ggcctggccc gtaagctggc cccttaaaac  135240
ctattactta ataaggattt gttacgcgcg atatgccgac gacttactac tgggaatcgt  135300
gggttccgtc gagcttctca tagaaataca aaacgtatcg cccacttcct acaatctggc  135360
ttgaaccttt gggtagactc tgcaggatca acaaccatag ctgcacggag tacggtagaa  135420
ttcctcggta cggtcattcg ggaagtcctc cgagggcgac tcccatacaa ttcttgcgag  135480
```

```
agctggagaa gcgtctacgg gtaaagcacc gtatccaaat aactggttgc cacctacgct    135540
ccgccatcca ttccaagttt aggaacctag gtaatagtat cccgatcaaa gagctgacga    135600
aggggatgag cggaagaggg agtctactgg acgcggttca actagcggag actcttggaa    135660
cagctggagt aagaagtccc caagtgagcg tcttatgggg ccgtcaagca catacggcaa    135720
ggatcaaggg agatctcgtt gttgcatagc tcaggtcgga gcaaggtgcc atcggacgtt    135780
caacaggtag tctcacgatc gggcactcat gccccgacat tgtcattgta tactcccgcg    135840
ggtcggaagg cggcgggaa ggaggggaca ctgggcgaga tctatcagca gcgaattccc    135900
catacaaata gaggcaccta tcaaaagata cttcgaaggc ttcgggatcg aggtctcatt    135960
agccgaagaa gaccctggcc aatccacgtg gcctgcttga cgaacgtcag cgacggagac    136020
atcgtaaatt ggtccgcggg catcgcgata agtcctctgt cctactacag gtgctgcgac    136080
aacctttacc aagtccgaac gattgtcgac caccagatcc gctggtctgc aatattcacc    136140
ccggcccaca agcacaaatc ctcggcgcgg aatataatcc taaagtactc caaagactca    136200
aatatagtca atcaagaagg tggtaagacc cttgcagagt tccccaacag catagagctt    136260
gggaagctcg gatccggtca agatccgaac aagaatgagc actcaactac tagtaaaagg    136320
gagaaagttg actttgagaa agaaggtgct tcttgccgct ttattagtaa gtaagcttgt    136380
tttatatctc ctcaataaag gcgaaagatc actcctaaaa gcaagctttc tcttatatac    136440
gataccatac cacagaattt catttgcctt cctgcttaag gcactagttc ggatggaaac    136500
cctgatcagg caggtggcct agctaacata gctatccgtc agaaatagca gcattccatt    136560
gcaggctact atagaggcat ataattttcc gggtgttaag aaagatattg aatcgaaagc    136620
ggacatgctt gctcactggc tagatcgggc tgtctgtacc tttgctaact cttctgcctg    136680
taaggaagct tgaaagaggg aattctctga tctatgaccc cgaaagaaag atagtctttt    136740
tcgattccgc gcattggaac tgaaagggc tattcataaa cagtcttcct tgcttcttac    136800
ctcttatctt attgtaggag ataatcgaga gagaaaagtc ttcctatcaa ttccttttga    136860
ataaggctac gctcctccaa gcctttgaaa ctattgaaaa tcgaatcttt gttttcaggc    136920
gggttttctt ctccaccaac aaccaagacg catgaaagcg gttccagcg ctgctgggca    136980 gaaagacatg atggcatgaa actcgattac gtacgctgat tgttcgtcca cttcaaaggc    137040
tcaaaacaga ccatttttccg tgtgaaatga cagggattgg tttggttact tagggaatcc    137100
caagcaaagc aatctacgca atttccgggt tcagtagtag gaaagaaagg gacctctcac    137160
tcaattcaat aacatgttct agggcatcct tttctaataa taatgttcgc atttgaccag    137220
gcttttggac gttccatgat taaaccgact agcggcactt tcgagatgcc accttgtttc    137280
taaaagagtc ttttcaattc catttgactc ggggcgtcag ggaccctcca acagaaacct    137340
cgtcttttgt cgtcgataag ttctccctca gtgccctact attcataaga aagactgatt    137400
taaaagagac tgatttatta aagcccggtg aggcctcaac cgacagctaa gcttcgttct    137460
gcggcggttt tcaagctagc acccttttcag catatcatct cgctcgattc caaaaaaaaa    137520
aagagacgca gttttgatta tccagttcta tatcgaaaac gagcagttga tcccacgaaa    137580
gcaaggctgg ctttgttgcg ggttcaactg gaattgtaag aagtgaggta aattgccttt    137640
ctccccaccg catatgcctc ctctgcttat gccactggtg atgaactcac tatggctatt    137700
caacgtcaaa ctcagagttt tctactacat aggcggctaa acgaagcccc agtctttttt    137760
agtaaaaccc caaccctta ttagtagccg aagtaaaggc cagcatgaga tcaaagtcac    137820
ttgccgtccg ttcgctctct gttcaacaaa ggcgatcgat attcccttac ttctcaagtt    137880
```

```
ttgaatttta tgagcccttc gattgtatcc cataagaaaa tctctctgat aaacatcttg   137940
tcgatgattc gattatatta tttagaatct tcgtgtgcgc ttttcgcctg aggctttcgg   138000
acaagactac ttactccagt aggttagtaa gctacctctt ccgctttcag gcaagggtag   138060
ctctgaaggg agagttgagc ggaaccaggc ataaggagca agaatcgcta ttgagagttc   138120
cccgctaggg gaacgtcagg aggggacatg ctctatgtcc actgattctg tttagtacag   138180
tataggaagc ccttgtttga gtgagagctt ctagaatgcc attcatttcg caataagaaa   138240
cttttccaca tagaggtttc agctacttaa agcgagagtg catccaaaat tcgagaagag   138300
tgctcggcct tggttgaaac aattataggt gtcaatggac cgatttcact agcagagcac   138360
tttctccaat gtgcgcaaac agagatgcca ctttcaatga tggacaccgg cccttgtgtt   138420
aaagtagcat cgagtttcgc ttggaaaccg gcaagtttct agtttccaaa taagtggtac   138480
cctttcttta gagtccggta ggtcaattaa gttgcctaaa tctcttcctt atctgctgct   138540
ctgtagctgc cttcctcgct tcgtcttcgg ctttcagagt tgtgaactaa cctcttcctt   138600
ttacagccag acaactggca gataagctgg gcatctaaag aacataagat ccgagttgcc   138660
gccaggcata aaagtcatat tgtcaactag ggaaattggc acaaccaggc atctcaaaca   138720
ttgataaggg aagaatcagg cttttcattag gatgatattc ctttcatccg aatggcaagg   138780
cttgctagtt tcctgaagta cactcgcatc tgtctatcta tgtcatagtt gcttggaagg   138840
aaggtctcag atgtaccttc ggcatgtatg agattttctt tcctctatct atgtcatact   138900
tgggattcac tgacagccaa ttccaagtag atcctccctc cccctcgctc cacttcgttt   138960
cgctcgtttt ctctttcctt ctgcctgcaa aaaagtgat gagattggtt ttgtgtgcgt   139020
tagcgatcat caaacctgtg acatagataa gattggagtt catgcagttg gaatgcctga   139080
gaccactttt tgccttgctg ctcttgcttc tctggctact gctccggcta aggctttctt   139140
tccgctttga cttgccttcc ttatctttca atctggactt gcatgtgttc cgcatatgac   139200
tatttcgagt gattgctgct atctggcttg agttagacaa gcagagaagg atcttatgcc   139260
accggtgacc ggcctgccta tctagtatct agtactagga ctagtagagt agaggcacta   139320
ctgggcgggg cttcctcgat cacagcttct cgcttagcta actgccagac aaggatgcaa   139380
atcaactcct tatatagaat gcagatcgac acattcaatg aagcagccag tacggcagac   139440
aagctacttt cttattctag gactggaaga tcctctatct attagcatac ccgtaccggc   139500
agttagacta gcactctctc cccaatcaat cgcagtaact ggctgtaaga gagctgactg   139560
tctactatct atgtcatgcc ttggcaggtg aaatatgagag agaggctgta agtgcattct   139620
ctccttctcc atcttctgga aagcactctt tgagcatgct gacagaatga ttgacactca   139680
catctctctc atttccagtg atttcgctac agtttactag cgcattccta gactaagact   139740
acggcattga agaagcaagc tcactctcat tccaggaatc agaggaaggc attctgtccg   139800
gtaatgaagt tagaagtttc cggcttgctt tctctcttct cttgcagttg gcagtctcag   139860
tcaaccttgt tccgggcctt ctcttctact ctatctgctt attggattgg taggtacagt   139920 cttttcttcta ggcttctgat tgaactttaa ggtaatggga gagaaggcaa tcgacagata   139980
actggtaagt aaagctatgg actgggttct cactctaagc cagtaccagt aatttgaaaa   140040
aacgatagac atctagcgca ttcactcgtt ttttctttct gatcggccaa ctcaaagagg   140100
gaaatgcaag gggcgttagc ggtctttttt gcctcgcctg ctactgggaa gagagagccg   140160
ctgtcattct tcgcttcgtt cgagaatcaa ctgcacatga ataggctcct ccttaggcct   140220
```

```
tcaaggagga agcggctttt ttccaaaatt cccgggaaaa tgaaacttt  gaaattcttt   140280 tcgtaaggca agaaagttgc ctaaggaaag tagaagtctm tgyacdbthb thbatghgba   140340
tgabggcada vtggttbhgv cttabtcccb tctcctytca aawgaawaag aawgwcatca   140400
ttctgatcgt gacttgaaaa aagaaagaag agaaggaact tggagttggc gcccacataa   140460
cggattgctt gcttaccaag ccatcctggc ttttcgctcc tctccttaca gtcaagtggc   140520
tttcactcct ccagttctat tattattgac ttgacttatt attaaaaaaa ctactcacta   140580
tccaaatgaa agacgatcga ttatctaccc aagaagatag agagtcccac atacgagaaa   140640
aggtcacaaa tagagttgaa ccaagtaaca ttgcaaaggc ataatgatag tagggtcggg   140700
atatccccgc cctccgaacc ggacgtgagg gtctcccctc atccggctct ctgcagggga   140760
atctccactc actgcttccc ctaatatcct ccccttacca catcatgggg gtttacagga   140820
gatcccagag gctcgctcgg aaaggctgct ataccatacc ttttgactta actctactct   140880
agtagtcact agactcacta tagtagtccg tctggctgct cttgctgaaa tcattactct   140940
taattctccc gtgctctagc aattgcgctc cctagaccac taccatgtag ttaggtaggg   141000
acaatcagtc cgtagtgacg ggaatctagg aatgaatggg gatccctatc aatataaaaa   141060
gaatatctaa ttagagtttt ctcccttct ctcactcaat agatctatct ggtctgatac    141120
ggcacagtac aatacgagac gatggaatgc tatgggatag atggtagagg gctgcctgcg   141180
cccaaaagcg atgattcact tgtccccttg tccatagga cctcgtggca tacaaccgaa    141240
acgactcccg ctagatagcc gccccttct ctcttttac agcctcgtgg acggacgaaa     141300
gaagggaagt tacagaacgg ggcagtgaag gctcgcgaag tagacagcaa gcagcaagca   141360
acagcttctc agcccccctaa cctttctctt ttttaataat actttttta tcaggtaagc    141420 tttgaagctg gctgctctgc tatactatac tagttgtagg gcgctagcgc ttgactaata   141480
taatagaaag taaagggact ctattatgat cttacgaatc taaagatctc aaaatggaag   141540
aacgagctct tttgctcgcc cctatctcta aaggggcgta agcacttcac tcgctagggg   141600
atgggattca ttcacttgca ttcctgctag cactacaaaa gctccggtct taacgcccta   141660
ctactgctgt gcagccttc ctcgggttcg tagagtcggg tttcccgttt acccacaacg    141720
gaggagccgc ccccaccagg caggcggcca cgggtcataa cgcactcttc gcacaacaaa   141780
tccactttga agttgactta ttcgctcggc caatcgtcgg aatgtgtacg agataccata   141840
agggcccaat atctcaatag caccttttgtc taaagcttcg aaggagactt catatccgaa   141900
acgcaggaac gatctgacta gaaagtcatt caaaacttga tcgaaaacca gcgtttattg   141960
aagaagctat agagtcgatt actaatagta ctagtttgaa aggctcgttg gaattgatcc   142020
gctacgggat taacattata cgcaacataa gcacctgaag tactaaacag aataggtatt   142080
agtttggtaa tggttggagc agcaaactcg gattcggcaa gaatctcatt ttttggtagt   142140
acgaagggga attggcccaa aattggatgg ggtcaagacg ctgtcgggcg ccggcggctg   142200
actcaagtgc ccccgaaccg cgcgaaatgg tcgcctatta cacggctcac taactctgcc   142260
tggggtgtgg gtacctatta ttcgtcggcg gtccggcgca ccctactata caaagccgcc   142320
cccccaactc acttaaagga tgctggttaa ttacgaagga aattcttct taatcgaggg    142380 acttcctttt cgttaagcgc atcgaaccag gagtggacat tatcatcatc tgcagaaaaa   142440
tccagattct ctttcatcat tagcgaaagt ggaatagtat gactggcttt ccggaaaata   142500
agacgaaacc cgctttatcg atatgataaa catgcgctca aaaagacctc ctaaaccccc   142560
ctgccaagcg atcgagttta gtctgaattt gctctagaag tagctcccgc tccagactga   142620
```

```
cttcaaggaa agaaagggtt gggcaattcc gccggttctg gagcttacct tattattaag    142680
gggaaaggga tttttttatag atgttgaggt gagtaagggg gggcgtagct tgaggcttct    142740
cagccgcagg aacagggaac gaatcctcca aaaatggaat gagttcgcaa ttaataccac    142800
aagaaagccg ccaccctcgc cctttagaga tagggggcgca acaaaaagta ttcaaaaagg    142860
gcgccggagg cctcaaactc atccggagtt ggagaatgaa ataaaaaaaa aagattctca    142920
agaggaatgt atcaacaaaa ctgcccttcc atatagatcg tcgttgcatg aactttgtca    142980
atagattcct agcttcctat tgatcttgat tagttctagc ttcgtttttt ttgttgagag    143040
ttatctttct ggaccggacc cacttttata ccgtctcytg awacacmtgc tymkmsysca    143100
tgtgctttcg gggccccact caaaaaatca cttgcttgtg attgcagcca ttccccgaaa    143160 ggggaggggtg gatgtaaktc agctcgaacg aagtgagagg ggtaatagac tattaccgtt    143220
cagttcatgt gacgaaccga acatcgttag gtcccgaatt ctgcgaagca ccggatctag    143280
atcaagatct ccattacgtc gtacgatata tcgatccgga gaacttactt tcagtttaag    143340
tcatccattc tgctcctatc taaagtgatg ctaggctgct tcacagaggt gcgcttcgct    143400
cgaccacatg atgaacatgt tttaagctaa ctgcatgtcg agcgcttaag cggagcttgt    143460
ggtcactcgt tcctcgcttg ttcgaaagag cttcagattg gattctacac tacatacgat    143520
attccattcc ggccctcact agctctttgc ttgcttgtac aaagagcatg cccgaggggc    143580
tactacgctc accgcgcact tgcattacca cctgagcttc gctaccgttc cgcccagctc    143640
ctacgcctac cacgaacttg aatcatcaca tggctgctaa agcaagctaa gcttcacacg    143700
gccctgmgga agccaaaaga ccctckcacg gccgaaggct ccgcaacacg ttggagagct    143760
tttagatccc gccctaaaac gcccattccc tagagttccg aagtgattct cattctcacc    143820
gcagccttct taagccgaaa gaaagccggg caagaatctc atggtagtac gaagggggag    143880
cggaatcgta tctgggagtg gttcttcgga tcgatcacag attctcggcc ccgtcctttg    143940
gcttccactc cagttgacct ctcttctttc catcccaccg tgagaaggta gagagcaaaa    144000
ccaacccagc aaacaactat gactatgccc ctattagtaa agcatgtact tcttgcaagg    144060
cttgctgagc ttcttcatgt gacagacatc gcaaaagtag tccgttgaac gatcgccgat    144120
cgagggcatc gtaatagtat actatttttg aaccctgatg ggtctcgcdv ttaavcabat    144180
ghtcghvcbc hbbctdctda tdcaaatctc vdadvccabv hgagccctag atrtaaaggg    144240
ttcttgaacc cttctaagca attagaagag cgcggaattg gacctccctc aaatagatgg    144300
atctgggatt gattgtggaa ccgagcatag agaaccgggg gcgggcagga agataggcta    144360
ggcggagtag tcgctctgga gcaggttctt cgactggatc aatgcatgta tgaaccctaa    144420
aaaaatcccg aaggtctagt ctagaaaaac ccggattttg ttgggttagc ttttggtagg    144480
aaaggcggtc acaggaagaa atgccctacc aatgaataga ttagtctact aacgtcaaca    144540 atctcttttct tcatatacga gaccgtctgc ttttatatcc taaactatag atatgaaaca    144600
aaaaagaaag aaagaaaggc aggaggtaag agcgagtaag actaggttat agcaagacaa    144660
cagaggttag atagctctta ccggaggaag agggttcagg tcacccgtcc ccttgaccca    144720
gacacgaact aatccttctc tctctcgaat gtatgcccgg ttttcgtcga atcttttgat    144780
caccttcaaa acaaaccgga attccgtctt gacatgataa atagtgatgc ccacctgcag    144840
agcgtagccc tccctgcagc cttgaagtag actattttc gagtctgatc ttatcccaa    144900 agccttttgc aaaaggagta ggtagcgaga tagatgacta aaagctgatg atctttgcct    144960
```

```
cttactagta aagggaaaag ccctatatat ctgattagtc aagcctaaag gcccttact  145020 aatataatag aaggtaagac cggctttcgc gcagctgctg cgccttgctt cttgcccata  145080
gagagttagg atattttgtg agctccttcg cctagcggaa acctccgctt ttcggccgta  145140
atcccgtgct ttaccaacgc attcaatgga ttccaccatg aaccgggagc gggcgaagac  145200
atgcagcttc cattttcggg gtacacagtc acgtgctgag caaagaggta tatatcacac  145260
tcattcacaa gcgcaaggtg cggcatccgc ctgaacgggg agaggatttc cctaaaacaa  145320
agataggcgt gtcaggaaat awwrkrrast ccccctattt cgctgtccag ggagctgttg  145380
actaatgacc taaaaaatgc gtgacgtttg ggaagcatga gcaacccttc gcgcacgaga  145440
tagcaatgac aggagattga ccggtcgggg tcgagtgatc tcaggggttt aggggtgctt  145500
ctcctgctgc gactacctct ctattttcaa aagtatatag aaatggtagg cactgggagt  145560
gagtgaacta cccggggaga aaggggcaac ctctctatag aagggaaggg aaagggttct  145620
ccgctcataa tgattgtaga gtctctcggg gttggaggtc taatagtagt cacatcaagt  145680 cctcccccte ttactcagaa tagctagcga gaggaagact actgattatc tatgaaagaa  145740
ggcttttaag aatgaaaaaa atcttatctt aaggatagag agccccccgc ctgcgttttc  145800
agatacgagt gagtgagcgc ttttctgct atgaatgaat gacctctcca tttatttca  145860 agcttgctct tcaaaccggc ctatcgctct cctctatgaa aaggttcttc cgtaatcact  145920
ctcaataaga catccattcc cctttcaaat gaaaagagaa ctagacttt ctcttcatca  145980 ttgaaatccg ccattcaatc gcagtgcggt gctctcaaaa ggctcaatcc tctaaggctg  146040
aaacgaatag gtcaggaawt ssmscykksw kccgcccgtt ccgatccttg cctactaaac  146100
agttgcaccc cggatatgta tgttgggaga accccatgat ccttccgtgt ggaagggaag  146160
gaagaaagaa ggcgaacacg aatactaaaa gcggttcatg gggaccccaa aaggggatag  146220
agagcgcgga acgggcttc aagcataaaa caatccctac ctatacattc catggcaaca  146280
gacagaaggc agttttgtcg ttgttcttaa cccaggcaca tttccgttcc caataatctc  146340
catgaaaaga ctaccatgat ttccgaacga accgagggag agtcgaggca tgaaaaactt  146400
atctatgatc tgcttatttc caagtacgta tcatccgctg ccttatccgc cgtctctgcg  146460
gccgccaaaa gcctaccctc tctcggatat tgagtgggtt gaccggggaa gagatccgga  146520
cgaaccttcc aacaagcaga atagaagttg accacaaggc catctctgtg ggaggctgct  146580
acccataagg ccatctcggg catgggaaag aaaggcggcg gacaaccgac ttaactggag  146640
agcctaaacg gcatagagga tgagtccacc ggtcgacaaa cggcttctat ctacaggtgc  146700
tttcattatg gatcggtcga cttgtcacga ttgattgctc acacacaatt aggttaggca  146760
ggcttgggga ggtgatctga atcgctatcg atacgatgcg gggctgattt gctgaccgta  146820
acgaacttga ctctgcccct gaaaaaaaag ggcgggaaga cctttgaccct gggctgggga  146880 gggattgggg tcgcttttct ttaggacttt agtccgtaac aaggctcgaa gacctccggc  146940
tggatttgaa atggatcagg tagggcatcc gtttacgacg tgggtgggat tagcagtttt  147000
ctctattttc ttcaatggta ggaaatacgc atcagcgggg gtatatggga ggaaaccagt  147060
ctgcagtaat tcaaattgct ccttcggatc actaagtaaa atcttgactc acacataccg  147120
cggtgtattg ttgtcaactc acatagtcgc acctaccagc aacaagacga ctactccctg  147180
cacgccacta aacggcgcta tttaacgctt gggttcgccc aatacaagaa ctacagccca  147240
acctagctta aggctaaagc cgtggactac accccgtga gagccctcta ttttactaac  147300 atactcccttt ttgatctccc ccataccttc atatcaaagc tgggaatgat tgactttcgg  147360
```

```
attaaaataa tagcgcataa tggcagtact ccttcccatt tcttcttta tgatcttatc  147420
tacttgaaat gcttacctgt aagtgcggag aaggtaccca ggggaccaaa cgaaagggca  147480
ctgaaaggtc ttcaattaaa gcttcgccag tacttgaaag actcgaaaga cctacttgat  147540
gagtttcctt atgagtgagt tcgtaggtgc ctttaagtcg agtgtagcga agggattctc  147600
ctaagagaag ctttagccct tgaacctgaa acgactttta tgagctgtct cagtagtgac  147660
cgactttatt ttattagctg tatgattagt ggctthgctc dtagtggttb aavagctacg  147720
gtaaaaaaaa tcccctttgaa aataaaccac taatccgcct taggtactct tttaagtccg  147780
tgtaaggcgg agggaatgaa gggacctgca ggaggctgaa aagccgtagt gcgctagcgc  147840
tagcgagtta gcgcaacaac ttagtgtctt gttttcttcg ctgctttttt tgtccgcagg  147900
aaagcggttg ctaaggcttg tagcttgctt ctgtccttag tcaattttgg actgaagctg  147960
ttctgactgc cgtatctttt ttgaaccgaa taccttcctc tgtcatctct ggtctgtctc  148020
ttttgagaga agatttttcta ccccgcctgc ctatgaagaa cttcaagtct atcgggaaag  148080
gatgtggtgg taaccccgca gctttgtcta gaaccgggcg tccagccgtg taggaagact  148140
caccctagcc actatagcga ccccacccc aaccctagct gagaagcacc ctccacccac  148200
ttccatttt ccgtgtgccc aaagcccgcc cgcccggttt ttgagaccct tkctgaktcc  148260
ctcacccaat ctcatgggaa gcaagcccag caggccctgc cttaacctgt cctcagacag  148320
ccagccctca ccaggctgct ggcattgcta aatgctccgc cacgaagcaa gctttcccga  148380
atacgacaga tgcggaagtg gctaaagaag tcggaggaag aaagttgttg gacaactgta  148440
tacacgaggg tacattagta ttctgggaat tggcaacatt gacagaaagg gtaaggggta  148500
ggaagaaact ttttttaggtc ttgctctact aaagtagtcg gcctaacctt cggttcccgt  148560
aaccaagttt ttctttctca ctccttatgt acttttttt acttcatcca tactttttta  148620
ctttttctga agtgtggggc aaacggcgcc ctctacttct acttctaact aaaggcgaac  148680
agccggcatt gcaagcaaat agaaagcccc cgcccgtttg agccggaaag cgtaccggct  148740
gtttgagtcg cgaaagggcc gcttgcttaa tattatttat ataataataa tagatagata  148800
atattatatt atataactat ctataaagat aaataaaaa ctacagaaaa tacttttttw  148860
tnnataaaat tcttcattcc tgggaagagg aagaagcaga tagggcaaag gccttctctt  148920
tccgtccgct cttcccgaag tgagcgaatt gcatgtagag atccgtaggg gcttatagtt  148980
taattggttg aaacgtaccg ctcataacgg tgatattgta ggttcgagcc ctactaagcc  149040
taccaccccc ttctcttcac ctgatacaag gcckgyctct tatacacawc tccgarcmcc  149100
hcaadctagc gacggcatct ggaaccacac tgctgccgct gcccttcggg cacgcctcct  149160
atgcttatca ctcacctacg ctcttgcagc atgccccttc gggcaatacg gtgtaatacg  149220
cgaagcagct gagccatagc tcttcgatcg ctatattctt gcggcgtggt tcatcctctt  149280
vgcghdtada hvcgtattbb ccvvcaggag actgcdgcga gadtcbhbtt vdgtbaghdg  149340
catbbcdgvd gtdtvbggga babagtgaac actcccttgg ttgggggctg tgactcccct  149400
atcctttcaa ttttttgatt cccaggtctt ttttattatc actgttggaa tcttttttaa  149460
gacgacttgg tcagggcggt tcacaatttc tttgctgaag gcgctgttaa gcctaagtt  149520
tgaattcaaa tttcattgcc cttcttccga aagtctaaag tccttcaaat tttcaccaat  149580
tccgacctac ctttatttat gggatatttg aaggagagct ttgtaactgt ttctagaaaa  149640
ttctctctag ctcgaagaat ttgtttgatt ctccctataa aaatagttaa ggaaaaaggg  149700
```

-continued

```
gcgcttttgt taaaggacta actattgtag agaagatctc cttggctcac gaggtggctt    149760
taagtgatag ggattttaac ctaaagacaa cataggaggg aggggtcaaa gaaagtcagg    149820
atatggcaaa agcatctttt ggatcgaatg ggcttttgtg ataaatggcg gaatttgata    149880
catggatgtt tatgtaatga agactttgga gtgcttgtgg atggtgtgcc acatgggtac    149940
tttccagctt ctcgagggct gcgacaaggg ttccaaacct agcctgttga ttttagctga    150000
agaagtgcta agccgggact tggtatcatt gaaaatgata acatcttacc atgcttcgag    150060
atcgtgccca gcactctcct actttctctt tgataacgat gttctaatat tatataatag    150120
ccataaacgg aatcttaaga agcagaaaat cttttctgga agaagtaaga agctgattgt    150180
aatgttgtaa tggccaaaag gtcaatttcg ataagagcca gtgcttcctc tcgaacagag    150240
ctcctcgcag aaattccaga tcattgaaga ggaatcaaaa ggtagttttc ctatcaagta    150300
cctggaagtt ttcttgtccc tcaagagaat aaagagagaa ccttcctcta ctggagaaaa    150360
tgaaaagaga atctcagatt ggaaaagtaa attgttgtcc tccggaggtc gactaaggct    150420
tattaaacat gttatagtct tcctatgcac atgtgcaagt ttttccttaa ttagccggcc    150480
cacacttcgg ctactaataa tgggataaga ccttactact atataggata tgttaccctc    150540
tctccagtga gtgcagtgaa ggactctcgc ctcacccgcc cgtttgactt atggcatcat    150600
cgacttgctt ttcaatcaaa gcgatttcat aaccataaag aaagacctct ccttcgggat    150660
cagtcccgtc cctagatgta gtagtcaatc agcgggacat tcaaagaagc tatgcacctt    150720
cactgaatgt taatgaaaga aagccctttc atcctaatct catctactga aaaggggccg    150780
ggcgtagcac gttcttttgg gacacatagg ctattacaga cgcatcaaaa aagacttttc    150840
gaagcgcgga atccctgaat ggaatcattg cagaagaaag gtataacggt tgggaaccgg    150900
aacaggatta agcttttaag catgcagatg agtgtttgct gtcagcccca atccttcggt    150960
ttccggattg gaataaggag ttccatgttc atactgacgc atcactctat gccattggat    151020
gtatgttggc gcaagaaggg ccgcttgatc actccatcta cttttaaagt atacgacttt    151080
ccgctttgga attatagaac caccgaacct tctttatcat gattcgaccc ataccctcaga   151140
cccaagatcg agcaccagag ctgctcataa caagstacca aaagaagaat gcgagaagtt    151200
catattctcc agattcgact ataaaccagg tagtgaggat gaaaaaaagc ataagctacc    151260
tcgttcgtgc tcccgtcttt ctcgctgcca tcttcggtgg atgcgcccct tcacttaaag    151320
gcggccaaac caacccactg agccaacctt ttagattgaa aaaagttact aagctagtca    151380
cctcacctct ctttcttacc cgcccttatt agtagtaggc aacctttctt tctcgccttt    151440
cttcmagctt tttccagata aagatctaat agagttgcgc tttcttagta cattgccttt    151500
cattaccaat ctgtcgtttt acagcacgaa gttacctgat gttcgctact actaataagg    151560
gcggagagat gttaaccttt cgctattagt aagcactccc ctagttttga cctaatgagc    151620
tttctttacg ttgagttaat taacccggcg ggttcgccta gatgcctagt aaagaacgag    151680
ctggtgggaa agagctggag atcatgaaaa gatttccaca caaggaggca ggcgaccggg    151740
aagctttgct tctcgaatgc cgactacatg ggaacagatg ttatataggt tgattctcat    151800
tcttgctgcc cgctcgattc cgaggaataa agggagggct ttaccacaat ttcccaagta    151860
agagatagaa tctcactaat tggaaggaaa aggagggctt cgatccattg tgattcgctt    151920
tcttggtatg gagagatctc tgccataaag agagagctcc taagcctttat tctgcagatc    151980
aaagagcgag gtaattcccc attcatccga aatagtcttt tagtaaagaa gagaggcatt    152040
ctgggccgac tactacgact acatgcccat ctagtgcagt ggcttggaag caagctacct    152100
```

```
tgaccatctt ccgaagttct aaataattta ctgatcaaag gctgtaaggg cggactgctc  152160
tacattcagc cacaccacag tgaccccgaa gcgatcttct tctagttgcg ggacgaaatc  152220
cgacagccaa ttgctggctc tgaataacca gcccagcaat aagctcaatt cttccataac  152280
ataaggggcg ggcttgcgcg cgagccgaat gacgtaggtg cacaagagta cttcgcgcca  152340
caaccatctc cttttatagg ttctacggac cgatgcctgc tgcttcatct gggagaaaag  152400
aatcatagat atgccggtca ttagaaggaa gaaccgccat aaaagattcc tcgtgtatca  152460
tctgtagcaa aactatgaac gggagctagc aatccggacc gtattgaaaa ggttcctgag  152520
acacagcatg gaaaagtaac aatattaaga acgaggtcc aagaatgaag aaggggttga  152580
attactgaat gaatacgagc tgtggctaat acccgaggca taaagaagca ttttctacgg  152640
gatcccgaaa ccaccagcca ccccgaccta attcatgata agcccaccaa cttcctggca  152700
aaatgcctac ggttaaaacc accgacatgt caagatccaa attcgaattg gttcctggtc  152760
ctggtcagag accactgtgt tcgcgccggc ggtccaacaa agaggcgaag tagtggtatc  152820
tttctttcca ttacgaacga cacgcttcgc ctgctccctc cccgtgtcca ctagcgctcc  152880
tgtccagagc gaagagaagg cgaaaagcgc cgccgaagca gcataagcag gcttctattg  152940
cbacgdaaca ataaagcagg atagcatttt gcgcccacat gtttgaattt gagggtaaag  153000
agctcgcttg ttatacggga tccgacgcat ccaacagagc gaaacagtgt tccattcttt  153060
tcggcggcat ccttccgcat tggcggcgag tggagtgcca caatcccatt catcattttt  153120
gatctacata agccaaagcc catagcactg gcgacgtctc cggcataaat gcahgdaggh  153180
tgtatabctb atvbagbatc ttgtgkaaca ggatttgatt ctgcaakcgg ytcagtamaa  153240
acgaagaaat ttcgaacaaa agggtcggaa ctcgctgata ggaaaggaga gaaacaaag   153300 caatgccaag agctccgtca atccgctgtt catcgataga cgdctctctc tttatcatct  153360
cgtgccagat gcaacatcct ttttccttct cgcgaaccac gggagcgcct agcgcccaga  153420
ggagcaaagc tcattttcct ttcagggtaa agcggcgcat aaaaaagggc tggcccgtca  153480
aaagtccggt tccttcgcga acgaagttca gaatcaacaa gggttcgtag aacgaaggga  153540
gtgtataact ggggcgcagc cccactttt tgttcgtaac gagggagaga tagaatggag  153600
ttcttcacga agttcgaaac aaaggaataa aaaaaagttt ctctatggcc tcctcgtttt  153660
gagacattat ggcttagggg tcgaccccgg taacaaagaa ggaatccata aaaacttagg  153720
atccaacacc atgataaaat actaccctca tgattagacc atgtccctga gatttgataa  153780
aagaaaggtg cattagcggt taatacgttg taattggata agttattagg aatatgacgg  153840
aacgaaagac caaggaaaga aagaagaata caccaaaatg caagtgctgc accaaagact  153900
ggtggttgtt tcttgttgta agtgaatgca acgaaaagac ccggaaataa cgaataatga  153960
aacaattcat atattgacat ttcgtgctca tttccaaatt tatgctttgt tattcccatc  154020
atccggtaac cacaggatga tccacaagaa aggtggcagg attcgaacct atggccggcc  154080
tgcccctgac ctgctgggtt gggtggccgg gttagcaccc ctcgtcgcct ctgtacccga  154140
aacagatgcg ctgcgctacc cagcgcctaa ccttgtctcc cctactcctc ttctggttgt  154200
gccattacca atcgcgggta accccggtcc ggccgccect gacctaagaa gaactattat  154260
ccttatgacc aaacaaggac cagcttactt acttctcgag cgatagttcc acgatcccga  154320
ccagcaactt cttgggagta ggggcatcaa agcttgccca acctagtaaa ggggcttggg  154380
gatagagggt tttctgggga gagaaagttt ccaggttgga tttttgaga tcaaatagta  154440
```

```
ctagttgggt agatagaggt ggtgaaatct aacctttgca tcgatcttct ttagcagggc  154500
gggtcgcttg agtgtcaaaa ccaagcggtg gttgttttcc ttggcttatc gaaccagcgt  154560
atgcccattc ctcctttgat gactcccagt agagaaagcc taaattttcc gatgtggatt  154620
gaaaggaagt tggggatgga catagatcct tccgcctatc cggagtgttg gaaatatagc  154680
aatgttttg  tattttgatt tcccgatcat tggaagcaat cttcactggc acaaggatct  154740
cctcacagca acctccacta cgatagaaac cgacaatgag tttacgaagg cttcgagtag  154800
tgcgggatag gctaatcacc agactgctct ggaataggtt aatcgctgga gacaagaacg  154860
agtgaatcta gtttcgagag catgccttac tctaataggg gcgtagagtt tctaagtgaa  154920
ggcaagcgct actatatatg taatatccta gctgtcagca aggcaggtcc gctataaagc  154980
ctaccggcca gaaagtcctt aagaacgaga agccgactaa aaggcwwtyy ywtarscgrc  155040
ycttgttgcc gagtcgaggg gcttggctgg taccaggctc taaaagagtt ttcttcgagc  155100
gagcggtctt tctatctttt gggttgcatg cccaaggcaa tgcttttgta gattgagatg  155160
gattgatctt cgctatcgtg cctcctcctt gtaccagttg atgctggggc agtgcttaat  155220
taatatgagt tttctcctgc cccagacagc ttcgaggttc ccatcgatyk attmcagagg  155280
tttctaccac tgaacttgct tatgctcccc tttgatcgag tgctatttct ataaataaga  155340
ttgagtagga aaatgttgaa ttggcttcaa tcgagattgc ctcggcttct taggcacatg  155400
aggaaccggc taacatcttt ttcaatcgaa atcccaatca aagacaagtt ctaccaaggc  155460
caggatctga aagagaggat tcactttccg aaattccaag tgacatgatt cctccttcag  155520
aagctaaagt tgaatgatcg aagtctcctt taggttcagt cgaagagayc gaarcgaart  155580
catcaattca accattcgaa tggtctcccc aaagattgac ctcttttcca aataaaccga  155640
acctcgatac cagattcatc aaaaagatat ggccatctct ctaggttgca caacccctt   155700
agatcgttct attcgtgctt gaaaacgacc ccatcggtcc gctccttta  atggacattc  155760
ttagccgtcc tccgaggggtt aacaccccat agatcagatc gtgaactctt tcagacccttt 155820
agtttcactt ggttggggca gagtttcagc ctgccttcca ccgaatataa aaccttagag  155880
ctgcctaacc tgctgacatc ccggcgaaga gagtcattat ttgtgttaca tcttcgaatt  155940
cgagagaagg cttttcctctt atctctcaaa ttataggcat tgaagcgatc gagagaaagt  156000
aagaaaacta ttgcacacgc ccccattcgc ccttactaa tataatgaa ggtaaggcaa    156060
agcaagagtg aaactacgag ctaaaagcag gcgtgcctct cttataagag aatatgatac  156120
catcccccact tttggcgcac ttctttgatg agctaagcct aagcgccata gaagtcaaaa  156180
gctagcctga gacctaaaaa gcaaggtcga aatccatccc tcttttcctg tatttgacta  156240
gtagggctaa tgaacgaccc tttgatctat gtcgttccaa gttcagccag gtctgattag  156300
aagttcaaaa tgagtggagc gaggggcttt agagggaaaa aaggggggcg agctttaatt  156360
gaagtagggg cggagctcct catagagagt tagaaagcgt cagttctcat agcgaggctt  156420
aggccgacgg ggtagggcgc ggccccaatt ctcaacccccg acctagacaa gtggtttaa   156480
cccacatttt gaaaagttct gttaggttct tagtagcaat cggcgacctt ttcctcttt   156540
acttcacata gcttttcgtc tccttgatag ctggaagttc tccaaaagta tgaaagctg   156600
gaggactttg taccatccat tccggtgtgg ttggattctg ttcaacagcc caaggacttg  156660
gagcacatct tttgttcttt ccactgcttg aagtgattgt tacgaccacg aagaaacgac  156720
aaatcccaac tacggatata taagagccaa aactgctaag ggcattccat ccagcgtaag  156780
catctggata atctggaatg cgacgtggca tacccgaaag ccctaagaaa tgcataggaa  156840
```

```
agaaggtcat attaaccccg aaaaagtgat ccaaaatgga tttgacctaa agtttcaggg 156900
tatgtccgac caaagatttt acctacccaa tagwgaaatc ctgcaaataa agcaaaaacg 156960
gctcycatag aaagtacata atggaaatgt gcaaccacat aataagtatc atgtagagca 157020
atgtctagca cagaattagc cagaactatg ccagtgagtc chcctatggt gaacaaaaag 157080
atgaaaccta aagcaaataa catgggdgtt ttgtattgta tcgaaccccc cacatggtag 157140
cgatccaact aaagattttg attccagtgg ggacagctat gatcatggta gctgcggtga 157200
agtaggcacg ggtatcaacg tctaagccca cagtaaacat atgatgagcc caaacaagaa 157260
atccaagaac acctatactg atcatggcat aaaccatgcc tagatacccg aaaccggttt 157320
tcccgaaaag tagaaacgat atgacttatg ataccggatc caggcagaat gggaatatac 157380
acctctggat gaccgaagaa ccaaaagaga tgctggtata atatagggtc ccctccagcg 157440
ggatcagaaa aggttgtatt aaagtttcga tcggttaata acatggtaat tgccctgcca 157500
gtaccggaag tgataataaa agtgggaatg ctgtcactag aacggaccac acaaatagag 157560
gtgatctatg catagtcatt ccaggtccac gcatgttgaa gatagttgtt ataaaattaa 157620
tagaacctaa aatggatgaa acaccagata gatgaagact agaaattgct aaatcaacag 157680
ctcctccaga atggctggta ataccactta agggcggata gaccgtccac ccagtgccgc 157740
tacccacttc tactaaggct gggcttaata ggagcaagag acttggaggc aacaaccaga 157800
atgaaatatt atttaatcgt ggaaatgcca tgtcaggcgc acctatcaga atcggaacag 157860
accaattacc agatccacct atcatcgccg gcataaccat aaaangatca ttaaaaaagc 157920
gtgagccgtt attaaaacat tataaagttg atgattccca ccaagaattt gatcgccggg 157980
tcgtgctaat tccatacgaa tcagtactga gaagcatgtg cccatcactc cagcaatggc 158040
accgaagatg aaataaagag tccctatatc cttgtggtta gtggagaaca gccatcggac 158100
cggatttgtc gtaaaattga gattatttcg tttccttcct tatcagagag ggcccgcggg 158160
gcttatttat tgaaaagggg agtgagggga aggaagaatg gaaagccctc actttattga 158220
tgggacattt tgatcccctt ttcctctcat cctccccggt tctggttcag gaaagggtca 158280
acgcaaggat cttatttcga agcaatctct ggagttttcc cttatccgaa cgggtcttgc 158340
aagaaaatag gatttcatat tgagctccaa atatacgcta ttgggatggg atggctccta 158400
ctagctctcc cccctaaga accgcacgtg cgagttcccc cgcatacggc tcaagtggcg 158460
aaggcccttt ccttcgcgct tggtaagcgc ttcgctgtag ccaagcttac tgctagccta 158520
tcggctagag ccaagcttcg accgcgactg ctcgtcgctt ctggccgcct tattccgtca 158580
cccgagatcc aagtcagcac cggcaaagat ctcttgattc ctcgcggtcg ggccggcttg 158640
gaagcaagct acctcttgcc tatctcacct ccttccttca gctgggtgag ccttcgcttt 158700
ttggatcgtc ttctgcccaa tgcggtaccc cccgtttttt ggttcccatt gggtttacct 158760
tgttcacagg tcgaccccat ggcagcaaga aaaggcgatc ttgtgctata ctccggtgat 158820
ctctttccta ccgagacacg caaactccca tcgtgtccca gatcacattc cgtgaatcga 158880
aaggggaagc ctactcatct atcagctcct ctcgtagatc ggtgtggttt tacgaagcgt 158940
ctaagcacag ttcactcgcg ttgatcaatc aagagggttg ccgccactcc ttaaggttat 159000
ctgttgtatc atacacttct tgcattctgt cccacgcttc atacctcctc tttcttctta 159060
aggtaagata aagggccagg catggtgggg taggagcatc cagtcggcaa tcttttttggc 159120 ttgaccaaga agtcttatgt cctccgagtc gcacggcgtt ttaaccgaaa gaacttcttg 159180
```

```
cgcaaytcat gccrwgcasw aggttktrkd cgaattcttt ctttatbtcg agatadcvdt   159240
gdtctctgga cttttatcaa tatgaggtga tcgtaacaca gtatataaga ctcgtgattc   159300
aggcaatcca atcttccgtg tgtaaggcgg aagcccccaa aaatggtttt caaaaaatgg   159360
gtgatcaaag atcgaattac tatgcctatc ttggtggtcg ttacttttgg tggtctttct   159420
tttggctgac tcctatagac gaagtgcttc gtttcagatc aattcttcgc tgcaatcgct   159480
tcgatccacc cctcggtgaa aaccgtaata cgccctgagg aattcctacc agcagacttc   159540
cctgtactca aagtgaattg tctaagtgct ctcctttgtc tcattgttta tctcgtaatc   159600
attcgattcc gcccctaaag ctagcgccta ctcctcctcc ttctcctcct gaatcctcct   159660
tggtcctttt acataacact ctcggccgcc caagaggact ggctatcttt ctctttatac   159720
gcacaatatt ttgaaaggca agaaaaagat ctaccttggc aacgaagacg tcattgactg   159780
atagtttatc ttccgaaccg gttaaatacc tataacaaaa aaaggccaaa gcccgctgaa   159840
gcactggaaa aatgttgacc acgatttcta acgcttttca aaaccatttg cttgcaacgc   159900
cttgagtgga cagataatta cggccactag atccttcata ctcttactaa agtacactta   159960
agactcaacc aatcttgaaa gtggagtgga caactggcat accttgaatc tagcctgcaa   160020
tcctttcgca cttctcttat caaatttcta gttagagaga gctaaccgct gccaaaatgc   160080
agcagttttt cttatatacg atagcacccc tgccctcctt gttcaagtag ttcaagagtg   160140
aaagggcgta gtgaaagaag gaaagatctc tttcaaagat attctaccca taaggcagt   160200 tctcttatat ggcaatacta gattggcgag acaagagaga aagcttataa agtagtaagg   160260
tgtctatggg gcttgcctta caggtagtga ctataccact tacatatcga acagatctta   160320
ctctcaatgg agtcatttcg atatgaccta ggaacttaca gaataccgaa cttggataat   160380
cggtagaaga atgattggct agatcatttg cttcactgcg gaagaacccc tttctacgct   160440
acgttcccaa taaaaagccg tcatccttct gtcgcctgtt agccacacca gaccaagaaa   160500
aggcaaacta atcaaccaag actcagtcac gacctttgta acctcacggc cactttcttt   160560
cctagagctt gcagccatta tcttcgcttt tcagatatgg tgacattact tgtatdggga   160620
agtgccagat ctttacggat cataagagct tgaggtactt gatgacacag aaggagttga   160680
accttcgcca ggatggcaca cttctattcg gggacgagta tgtgttcctc aggacagtga   160740
cctgtgccat gatatcttgg aggaggcgca tagctcacct tgdgayasac ccagggagca   160800
cgaagatgta caggacgatc cgcccacact attggtggaa aggtatgaag agggatgtcg   160860
ctgagtatgt ggctaaatgc ttagtgtgcc agctggttaa ggctgagcac cagagaccag   160920 caggacccCtt acagccagtt cagataccac agtggaagtg ggacgagata gccatggact   160980
ttgtctctgg attgccgaag actgcgaggc aacatgacgc catttgggtg attattgatc   161040
ggctgaccaa gtcagctcac ttcctgccga tcagtatgac ttactctacg ggcaagctag   161100
cccagatata tattgatgag atagtgcgcc tacacgggat accatcatcc atagtatcag   161160
acagagatcc acggttcact tcagccttgt ggcagagcct acagaaggct ttgggtagca   161220
gagtgagtct tagcacagcc ttccatcctc agaccgatgg ccagtctaag aggaccatcc   161280
agacattgga ggctatgcgg aggtaatccc ttgattttcg aggttgttgg gacagacatc   161340 taccttggt ggagttcgcc tataacaaga gttatcaggc gagtataggc atgccacctt   161400
ttgaggcact ctatgacgc aagtgcagga ctcccctatg ctgggatgaa gtaggggaga   161460
gacagattct tgggccagag attgtacttt ytttwtytta wkcagaagrc ttagtacaag   161520
gttctgtcgt ttaccttgcg cctatctatt cctttaagct tatatcttat accattgcaa   161580
```

```
tcagactcat tggatatctt ccttttctct tctactatcg agagtcgtac gggtgaggag    161640
gtgagctcta agcgtataca catagatagg tctgggtaag cgaccatcag cggtatgggt    161700
agcagctact atcagtacgc cagtctaagg ctgttcgtag aggtaggtcg tagagatcta    161760
tgaagggcta tatttagcat aaatagcatg gttaattata gaatagcgtg atggccgtaa    161820
gaagatcata aataaggtaa atagtctgga gtggatgtct agatcagggt gtcggcatca    161880
cacatatagc atgtgtgccg tgagtgagag ggtggtcgta gatcagccct cagctcttct    161940
ttcgaaattc tcgaacatga tgacttatcg gcttgaggct tcttttcttt tcaagctgag    162000
tagaaatttc ataagagaag aaaagttcac agaaggttct tcaatgtatg cctggttcac    162060
gaggttctac tgcagggccc agtavdmsdw tmgctctaaa gtaaggagac cacttaaaaa    162120
ccctcatcgg ataagaaaag atataccaga tagagcgcaa ccaagtccat ttttgaatga    162180
taagggtaaa tcatcacctt atttgaggaa gtagctatgg aagattgggt ctgtatggct    162240
tcctggggtc gaaagatctt ccttcagcct tgaaagtatg ctgctgcttt agcgcgaatg    162300
aaaccatttc tcaaaatcaa aaggaatcct cctcttgagg ttggtaacct agcccaaaac    162360
catgctcatg ggaaaaaaaa gtatgggaaa atgaaaagag accttgatgt cttcgcccta    162420
agcgcatgcc aggaaactca ttcctctcat gattcccatg acacgaatct tactctaggg    162480
atcgaaataa aagtaaaat actccttact cgtaattaaa cccactaatc atcatatctt    162540
ttttaccttg ttcgatttgc agaatgggga tattcgaatc cggtccttct gacatatctg    162600
catccccatg tatagtaaga gtcttccaa cgaggaactt cactatcgta tagttgactc    162660
gactcgaatg ccctcttagc aatagcatcc gtaaccgcag ctattgagtc tgctgtggga    162720
ataagcgccg cagaataggc agctattgac tccgctctaa gcctaggcac tctgggtga    162780 attaccggtg cgagaagtct gatgtcaatc tatctaatag tataaagatt acaacgacat    162840
agccagagac tgaaacttat tgtttagtat aggctaagcg cttacctaaa catatggtaa    162900
tgcaaccacc ttagtcagtg attactaagc tagcgcctag cgctaaatcg ttgaaagaga    162960
ggtcccccat ccctaagcta acgagaaggg aatctctctc acaagccacg atcagcactt    163020
agcctaaaag cctcttcaac gaataatgaa ttaccgaaag cctcaatctc ttactgctta    163080
cctggtaatg ccactttcg ctccgtatac tctagcaagc tagtactggt cgactaagtg    163140
gtctcatgcc caagtcaaat ccaatgacga gttgagatca tacaagagta ctttaccaat    163200
caagggatag acctatcttg actaagtaag caacctttct cagacctctt ggaatagacc    163260
tttatttacc aagtttttac ccttttgtcc actcactact gatcgcaacg aagattagtc    163320
tcattacggt atcaccagca aaccttcttt ttattaggat cacaagaagg ttacgaaatc    163380
ttcttttctt tttgcattct tacaaatgaa cattcccaat ggaaataatt gagactaacc    163440
atcttatttt taggtaatat tgaattcccg tgcctattgt ttagcctaag aatggaatgg    163500
ggggcaaagc tgtgaataca gttagtgaag ctagaccgcg gaactcaagg gcattctttg    163560
aggtattata aaaacatcgt tccatttgat agtaaattct agcatctttg aagaatcata    163620
ttgagaaaaa gaaagaaggc acgaaaggag ttgagcaaga gctataagaa gaaggtttac    163680
ctcgtaaata tgtaaagtgg aagacaaggc aatctcatag gtgaagcttc gtttttctat    163740
aagcagactt tgagaaagtt gaatacccca aaagtcaaag tcaaccttcc gctatgaaat    163800
gaaggaagaa aacaagggct aacgcgctca tcccttgctt ggttctcccg tgagggaagg    163860
ggaaggtcta gtatacaatt atcttcttcg ggaaggtcta gtatacaatt ttcttcttct    163920
```

```
tgatcgaagc tctatctctc attcagcaag cttccttcaa aaggggagtc cataggcgcg   163980
aatactcgga ttggacttgg aacccccgc ggagttgaag actgacttcg gccaggagat   164040
tgatagagac catcctttg ctttgattga gagagccaga gccagagccc ttcagtggta    164100
gaaggatcta aaattcccaa tgggagagca tgcgcccaga gaagagaagg gcttaagcaa   164160
agaaggttga cttggaagac cgaaaagcac cttttaaaag cacctttttt tgggttctat   164220
cgaagacttt tagtgtggaa agcaagcctt taagccagaa gtgccgctgt gccagtggaa   164280
atctaccagt acccgttgaa gtgaaatccg cttcagcatc atcaagaaga aatggaaaaa   164340
atgggatttg tggactcgcc tcaggatgga gggggaagcta ctgtggaaaa aggcagttgt  164400
tgagcaagtg acattggttg aagttcaata tgaatatgca tcatcaactg gagaagaaag   164460
atgaagattc cgctgaagat gtcgaagatt tagaagaaag atacgatcta atatgattaa   164520
gacgaatatg tcgagttaga gcacggattg aaattgttct cttacagttc ctccaccgaa   164580
ctgtagtaca gaaggaatgg aatagccgtg atgcggtctg tcgccaagcc cgcctctctc   164640
tctcgttgtt gcgcggccat tactctacag aaccagcata gctcgcagac gagcacgcta   164700
atgaggccct gagccgatag atgaagatgg gaaggtcaga cttctactgt ctcgaaggtt   164760
ccgatagaaa gaatgattga ttgcttgaat gccgggccat ctactcgcga aatcaccccg   164820
gtccgaaccc tctcagctcc ttcctaaaga agtgaattaa tgatcgatca acggagggaa   164880
aggaatatca gaattgggac acctggactc ggtctttctg gttccattgg ttggtaggtc   164940
ttaacttctg ggctaggtct cgatacggaa ggaatataga gggcgggcgt cgaaacccca   165000
tgctttgaga gttcctttct gccagcactt tctctacccg ggagtcactt catcagtacc   165060
tggggctact gtcccaggat gccaaaggta tgatccacac attgaaagtg tcaacgttga   165120
ctcacacgcg ccaccctcac cgggtaaatc cggagaaggg gaacttattc taagatagaa   165180
taagaataag cagaattgct taagtaaggt agtggccata aggcttttct tttttcggt    165240 ataccgctct gctcgcagag cgaatgaaga taaatcttac ctaatctcat gaatatcctt   165300
cgccccttat ctcctcatct tcctatttat aagccacagc ttacttcgac gttttcaatt   165360
tcccatagaa tctccggagc tttcctagcc actatagttt tcttttttta tcttctttgt   165420
ctgaaaatag gtttgatttg cttcacctat gagaatttct accaattctt cttttattca   165480
tcaaagctca tcctaatctc cgtcgagatt actgccttag ccctgtccta tcatctgtat   165540
aatggagttc gtcatttatt gacggatttt tcgggatttt tctttcttag aattggaaga   165600
aaaagattga aataactgtt ccaaatttca cctatacctt tctttgagat ttaaacaaaa   165660
aattattctt ttttttatgaa atgtttctta ttcgttgata gatctaaagc ttatgccgta   165720
gaagctgaca tcaggctatt ggccttttat ctgcatcttc cctcgtagag tggcgtcttt   165780
tataagaaaa gactttctca gtggaactaa aaaaaaaaaa aagagtttga gctctttttt   165840
ttgctttact tttagccacg cgcggcggct atgcgcatgt gtcccaaagt gacgtatatt   165900
ttttggtaat gggtatactc gagagaaaag gtttggaatt cgacctcccc ttatacgctc   165960
taaaaagggg tcatggactc ctttttttgta taggatcccc tttctacatt caattattta   166020
ttgagcctgg tgtggaatca ccatcattac acattcattc ttggtctggc tgctggtcta   166080
gcgagccttc ctagccgcct agagtgcagc ctgcctgctg aagaccgtaa cgtaagtaac   166140
tcagtgctcc atacggggga aatgaaagca gaattcgttc ggatcctccc acatgttcaa   166200
tcttttttta gcgtttcccc cagagatctt tatcattaat gcaaccttca ttttgctcat   166260
tcatggagtt gtatttagta cctctaagaa atatgattat ccaccgttag tcagtaatgt   166320
```

```
gggttggctt ggattactta gtgttgcgcg cctaggaggg cagcgcgctt tgggatgcgg    166380
aggagctatt atcgtccagc tccctaacct aaagcggcac cgggtttgga ccgcagggaa    166440
ccgtagcatg gggggacgtc taatccttt gccgccgcaa ggctggctaa tcgtacgcag     166500
caggctcgaa taccctggt tctggaaggc acatgagtcc gaacgctatg ttgaatgtgc     166560
gaccgagact acactacgta ggtacccgtg caggtgaggc gtcggtcggt cctagaaacg    166620
gcggcagcgg cgcgaggagt taacgaccgg acgtgctgca acctagggat caccaggcag    166680
ctctttcgct ctatagggat cggggggca tagcacaatt cttcttggag agggttgtt     166740 tgcccgggtg actgatcctg ccataatgta cttctaccta ttatagcacc ggcaaccgaa    166800
gtcgagcata catacgacga tcttcatgcg tgaatagccg ggaggaaaga aagggcggta    166860
gatgataatg agaaagggcg ccgcgtctgg acgggcggaa tggatgagcg aaaggtgtca    166920
tgccatggag tggggaagag ccctcgtctc atgtaagaca actaaatgca cctcgaggtg    166980
ctgccgagga actgagggac cttctcgagc acaggatagg taattgagag atagagctag    167040
cctattcgtt atgggaaatc aatgctccgg gccaaataga gcttacctac ggcacctggc    167100
tttctccggc gagcttttcta tcgtaaagcc aaagacgccc caagacaagg tacaactgtt    167160
gggaagggga catgatcaat agaacctggc tggatccggg ctgggatagt ggcgcccatt    167220
cttaaccagt tccgagaggg ttcgctcatg ctggagggag catccccact tagtgatcgg    167280
tccgctagtt cacgcaaatc cgaagaagtt atcacggacg agccacatgc agggaaactt    167340
gcacgtgtgg ttctggccgg gctttcctga ggtatctaat aaccttgctt ctgctcgccg    167400
ctggcgcacc tctcctaact attgcccatt tattctggaa taatcttttt aggagggaca    167460 atttacata tttctgccaa atccttctat tattaagtac ggctggtacc atttcgatgt      167520
gtttcaattc tttcgaacaa gagaggtttg atgcttttga atccattgta ttaattccac    167580
ttcctactcg cggtatgctc tttatgatct cggcttatga ttcaattgcc atgtatttag    167640
ctattgagcc tcaaagtta tgttttatg tgatcgcagc atcaaaaaga aagtctgaat        167700
tttctacgga agccggctcg aaatatttga tcttaggtgc atttccctct ggaatattat    167760
tgtttgggta cgaccggaca actaccgata tctattaata tcttttctta gaatgttctt    167820
tagaaatata tatctatcta tctatatcgt aaactatcgg atcgggtatt acttagatgt    167880
gaaacttgca gacctcatag gttgtaagat ttttcttacg gggggaacga aatcaaagaa    167940
tatatagact agtagagacc ctctatgtag tttctatcta gggcgatcga tctacatctt    168000
tccccatagc cctggggctg tgtctcgatc tcctatgtgc taaatataag ggactagttc    168060
ctatagagat tccccttggt ctaattccac gccttatgac gaaagggag tcggcgtggc      168120 gtaaagtgaa gattgggggg agtagaaaaa attcccttat ggggtattcc gaaggtgtaa    168180
cctaggcaac gaaaaagggg cccgatactt caactagagg agcgaccagt tggttcacca    168240
aaccccgacc cagcgtcaca cattctccag gtccgaaggg atccagtgcc caactaccga    168300
ctcctcccgg aattgcgtta tcggagccga gccaggaatg gccgttagtg gacacccacc    168360
acttttcacc ggttagagag gccctctta atacattaag aaaagatgtt cacagggggcc    168420 agaaagactc ggtcatagga atttagaaca cctacgtgct ggtaaacgaa aaccacctcg    168480
accggatcag agtaaacaac aatgtcgaat caggccgccc tttgccttga agaattcac     168540 acgcggccgc cagctttccc aaaataaggg gagatctgct gcttactgct cacggaaaca    168600
tccgacctat actatagtca agtcgttcgc ctatctttct gatctccttt ccttctattc    168660
```

```
atcatctttt ttgctttgac ccagtgaaaa atggggttga tggtgttggc taaaaaaggg 168720
ggagagagga gagccttagg gtacgctcac ttctgcattt ttgtttaggt tctcgagatt 168780
ctcaatcgtt cttttagtg gggaggaata gtacgtgaat ggcggttctc agacgaggga 168840
atcattcctc tataaataaa aaaaagctag aatctttcta ttgatagagc tttcacgtct 168900
gcgcatagaa tccttttttg cccttccatt ctgttcttac ggtagttggg tcggaatccg 168960
tgtgatggtt cgaaagtcgt ttcaaatatt cttcgcatcc ccagagagat agattgttgc 169020
cattgtgcct tggtcgtcaa aagggcacg aacagcctta aagtactgtt ccatgtccca 169080
gaggtcttcg agccttggca tttcgaatcc cgttgaatgg ctgtggttcc gggactcaag 169140
tctggagtcg ccaggtgaga cattcggttc acgaaccgga aacctatctc cacagcaagc 169200
tcctcaattt gacccggtcc gtcacgcttt ggacatcgcc accgggatcg ttgaggcccc 169260
atgaagacgg ctctacttca cagggaagac gcggtactca ttagcgagcg tctggtgacc 169320
aaggattccg gattccctg cctttccgct atagtctaca cttgtccgtc caaatggtcg 169380
accttgccat caagttaagt tgggtcactc gatccttgag tgtttcctta acaacagccg 169440
ccgctgacag cactccactg ctatcgtcat gtacatggta caacaagaag agaattagca 169500
gaaatcgaaa ggttttacc caaaactccg ctctgatacc tcctaaagcg aaataggcac 169560
gcgcacgggt agagagtctg cctgagtcgt gcggccccag gtaacgccta gtttagtgta 169620
gcacctgggt tccgccttct ccttgccgag ttttgcttct gatctctctc tgagtctcta 169680
gttcgttacc ttctactacc gatcttctcc ctctgctgct actggatatc gacctaagag 169740
atactagacc aggtgcgaga ggaagggatg ctgctattga tggaccggtg ctacctctgg 169800
atctaagaat catggaagac gtaattgaaa tatgcacctg gaattgaatc acattggtat 169860
aaagagccgg aaaggaaaaa gaggaggaaa gaagcaaggg actgagcgac gaagcgaggt 169920
ttggaaccct tcaattacaa agtggaagat gcctctcaca atgggtagga ttactgcatt 169980
tcttatattt gactcttcta tttgataata tagggagttg gggcaggttg aaggggaggg 170040
gaagtcaatt taaacatagt gccaccataa ccctaagaaa acgagattgg gtttgtgtgt 170100
gtagactatc cttggaagtg tctattctac caaaccacgg gacgcagccg tagatcgagc 170160
cctggaagtc ctctcctcgc ggctccctgc gttgatattc gaggaagtag ctctcgacac 170220
gagggatata caagaaagac ctgctctaga tccccaagtc tccatggtcg ttcttttaa 170280 catctctttc tattcttcta atgtaatgct atcagtcacc tcgtactacc ccccattgcg 170340
catcctgtgt aacatcaagg aaagggaagg ctcatactac cccggcggga ggtcgtctcc 170400
caacacattc ccctatagt agatctgcca cagattgagg catatctttt ggagatggtc 170460
acgtcagcgg cggcaagtgg atcattcatg cgaagactta actgaaaaag aaagattccc 170520
ttttgttacc gaccttcttc ccttgactgg tgttttaggt cttcttatcc aagaggacac 170580
tttaatcttg ctttagaggc cgaatgctta tcattcttgc cttctaaact tctttatatc 170640
gagggatgag gaaccatatt atcctgcatt ccttaaacct atgtagtgag tcgtgtaggt 170700
ggcgtgttta aattaggacc atacattggg attcttttcc cctcatcgct agccagtcgg 170760
gatgctatct ctcttctcct tcgtcactca accatcaaaa tatggtatat aataatctct 170820
tttttttata tttacttaaa actatactga accacctatc tattcgtttt ttggcgctgt 170880
cccgacactg atgagcatca cttaggcctt cattcatgag actctgctag gatctgcagc 170940
gcttcagtag gccctaggca ctgatgtgag gttaaagttt taaccaatgc ttaatactat 171000
ccataaacat tgtactccca taataataat aaggcaagaa agcggaaaat ttcaaaaaaa 171060
```

```
aagtaaaatg gaaaaagtgc cccctttga ttagccagtt tccaagaggg agaaggtctt   171120
atggcaatct caggcatact caaaatcggt tatttggcct gatcgagcaa cctatgaaca   171180
gttgtcgcct acataaccta cctcccagac caagggaaga aggtatcaga tcactttga   171240 gagccctta gttaaaccag ttcctttact ctttttgaat gaattacagt cagtaaagta    171300
atctggtgga aggggtccat agaataaaaa ttggcttctt tttcttttt ctattttgag   171360 ttttagaata gagaaagagt cgaaactaag ggtacgctct ctagaagatt tgctcggagc  171420 tttttttc acttggtcgc ctggtatctt gaaacctctt tgcttgcggg ggcaggagtg    171480
gaaagagcgc ttcgcgaaag aatcgtgtgg cgcggtgaaa ggtttcccgt tggggtttcc  171540
gaccctccag gtctccacct acttgtggaa tagggggggg ttccttgata ttaaggtgtc   171600
aaggcggtcg aagaaggcca caggtggaag caaccgatgc tttgatcatt caattgactc   171660
cttgctgcca gtccgtgctt gctgtcatgc tggcaaaagc aggggttgcg gtcggttta    171720 cctactattg gatttgaacc aatgactctc gccgtatgaa agcgatactc taaccgctga   171780
gtcaagtagg tcaagctgag tcaagtcacc ctataagaga aagccgcgca accaaagtag   171840
cccttactat acaaggggg cagagcgcta agaaagagaa agccttatca ctatacgaaa   171900
tgaagcagcg gttagcacgc taagctaaga tcaaccaatg ttcgaacgcg gagcctttct  171960
ttctcggtcc tctgtcttaa taagtggatt ccgattcatg cagtcgttct ctgctgcatt   172020
ggtcttttca ctcccccactc tccaccataa caaaatgttt ccactatatc tcaggagtag  172080
tcaaaggaag tacggcgggt ccgagtagga ataaattgac taagaagtag ggcatacaac   172140
aatggatcaa ttcattcaac aagatctgtt cggatcagac caggatgaat gggattggtc   172200
tgacctctcg ctcggatgta agactcccgc cgctgacaga tgtcccatgc cacctttcgt   172260
gaacagctat gcccgagaat gaatgaattg tgatatagcg ccgaataagc cacagctcta   172320
ttcccgactc gaaatccata aaggacttta agggagataa aatagggggc cctataccat   172380
acatcctgct gccttgggac gactgcacgt tacatcatag cagcacgacc aaatggaggt   172440
ggaaagccct tgtataggtt gggcgctagc tagcgccttc cttatactaa tcaaaaatgt   172500
tgggccttcc ccttatttat tagtcttagt aaagttgctc gaggacttct actgggaatg   172560
aaagttcctt attataggat ccctagtaaa gccaatttaa tgatggccgc ttatctgagt   172620
aagaagacga tggctcctat tattggtgag cgatctcctc tacacgttat ctttgggcgt   172680
tttactctct ttcaaagaga tgactattca aacctcagag tattcggatg cacgtgcttt   172740
gttaaaattc catctcctgc acaagacaaa ctgagcccta catctcactc tatgtgtttt   172800
cttgagtgag gttggggtac ccctctctca aaagggctac aagtcttaat gatccttcta   172860
cacgacgatt ccacctttct cgacatgtca ccttttcga acatgtgcct tactacggag   172920
ctcgggcctt tgagattccc tgtgatggtg ggccattatg ttcccttgtc tccccttaga   172980
ggggaggggt ggaactattg aggagtttat gtgagacagc atcagaattc tccgatttaa   173040
tagagtcagc aagatccggg tgaccagagt gatcagcagc ttgatcagct taaggggaag  173100
tttcgcaggt ttgtgaagac agattctcgt cactcagttt tcagagctga gccaactgat   173160
tcagtggtct ccctctctcc ctatacttcg aaccaagact cttcttcaga cttaggttct   173220
ctagcttcta ttctcggggt acgtagatcc accgtcttc gttttcctat tcataggttt   173280
gtatcaacta agtctctgtc tacttcccac gagtcttttt tgcaatttca tccatcttt   173340 ttaacctgat acctttgcag aggccatatc tcaacctgc tggcagctct atgcagaaag   173400
```

```
agatcgtagc actagaatgg tttgctactt gggattgagt ctctcttcct ctagggaaat    173460
ctatagtggg ctactagtgg gtctataaag taaacaaaaa gctgatggag cagttgaggg    173520
gttgaaggct agattggtgg ccaaaggata cacacaagag tattgagtcg aacccctta    173580
gagataggg  aaagatttgc cccagcttgg cgaatcgcat ccccgcgcaa cgaattgcat    173640
tgccaacctc ttgattgtct tcttatcatt ctccgttgca tgttagggat acgtttggtc    173700
ttcaatatat tccctgatgt cagtaaacca tggtttaccg ttgggtgccc tttcaatggc    173760
caaaagatca ctattgaaca tgccgggagt caactcaaaa atttctatta gtttgcaata    173820
caccgggctg cttctttgtt ctatcatgat tgggcggact ttccctcagg aatgtttatc    173880
atggaggcca gtgttgccaa tacatccgcg aacttatttt ttctctgggt agtggagaga    173940
aacttatttt cttgaattgc tcagtgagct tttcaagata agcatggtat gtcaaatttc    174000
atatttattt ggttttcat  ttcttttgag tttggcagat gataagcgtc gaatccctaa    174060
atacttcgat ttcttatatt cccagggtca acgcagtctt taatccatgg atacatgctt    174120
catcttctgt ggtattctta gttccttaaa agtggagctt aatggcaatg ggggtgtgcg    174180
attcatcagg tgcaatcagc aatgcccta  ctccgtaccc attttgatta gtcgtgccat    174240
caaagtcaaa tttccatgcc ctcctcttct gtgacagcta tttcctcgtc tgggaagcaa    174300
tccttaaact catgttcctc cttgataggg tgcaaggtgt tctgctatcg cccttccttt    174360
ttggttacat acgtgatgtc gaattcagac agaagcagta accatcttgc ggtccttccc    174420
gttacgttaa ggcgggtttt tcgaacaaat acttttttg  taggtccatg gaagctatta    174480
aatgtactgg gtaagacagc atgtaatgcc tcaatttccg ccttacccaa accaaagcca    174540
agcaggtttt ctccaaattg gtatacctgg tcttgtagtc agtaattttc ttactaaggt    174600
agtatatggc cctttacttc cgtctgtctt catcgtatta agccaacata gaccccatag    174660
tggtttcagt gactgatagg tatagtaata aaggcttcct ggcgttgtag gcactagaat    174720
ggaggtattc ctgtattttg tcaaaagctt tctggcgggc ttcatcccat tttcctgcta    174780
aattttgatt tcgaaatttg tgtatcggct cgcaagtggt tatacaagag aaagtcaaag    174840
tctgatggga ctattgatcg ctacaaggct cgcgtggtag ccaaaggcta caaccagcaa    174900
tagggtatag actatgatga gacattcagt ccagttatca agatggcatc aagggcgatt    174960
aggtgttact tgcttgataa gggaaagaga agacgtccct caaagcccca ttaacgcaaa    175020
agaagtcgat tcctacgttt ttaaattacc agaagctctt agctactcag ctatactata    175080
ggctctaaag gcattacttg actgaaagag tgcttatatt atggggggctt ccctttccaa    175140
catctgactt atatacaggt caacatcgac ttaaaaagca cgaaaaaaaa aagtagctac    175200
ctcgggagag ggatgagact agtcttttttc caataggcta gctgcctatt gcaggagttc    175260
ctgacctgaa aggacaccag caagctgcta ctgaatgtga acaaagtcaa ggagatggaa    175320
tcaactcaat agaattaggt ttttttatg  actgctgaag cgaccgaacg aaattaagga    175380
ttgattcaat accgaatccc agatctctat agacgactaa tggtaggggc tgcattttc    175440
ggaaagaaag atagtggcaa aaggaagact gttaatcaag aaccgacgtc tcatgccgac    175500
cccgtctgca gttgctacta cactgttaca tccggataaa gtgatccgta ctggtggaat    175560
aattgcaatg cgactatacc gtctgctgat aaagggaaga cagtatacca agcttgtccc    175620
agcagtcagg tttggtcctc cgggcagcaa cccggccggt atacactcca cagagcaaat    175680
tgggctgtga ggtgagtaac tatattcaac aatcatttgc caacatcgtt cctaagccct    175740
actaagtaaa gggggatgtg ttcaatccca agcatcttcg tcaatactcc atctgccccc    175800
```

```
cgccgggggg gttaaggggg aggatgtcaa aaccttaccc ataaaaaaaa gtacatagac  175860
ctgctcacaa agagctacaa gacagccaaa aaaattacag ctaataaaat gaaagtgaac  175920
aaagccaaat caatatgata ttcaataagc ccacttttt gagagaaaaa acctgaattt   175980
gttgaggaag atcagctgta gaggaaaacc tatagtcaaa ctgagaatcg cagccgaagt  176040
ttgctaaaga gtctgccact ttgttgtttt ctctaaatgt atagacgatt ttgaaatggc  176100
cagccgagaa tttggatgaa atgaagctcc accatgagtc taggtatggg taatttagg   176160 ggcttcttta ttttcattga agcaatcaac aatgattttg gagtcaattg cgagtttacg  176220
agcttgatga atgtagagcg catccagaag aatagaatca gtaaacgtcc aagatgatct  176280
gatgtcaaga agctgagaac agtctttcag ccagtccgta atttgttgaa taatagcagc  176340
cggttgagat attgggcttt ctaatttact gctattgcct tccttccaga gttcccaaac  176400
tgaaaaaata gtaagcatag acgtgacgta gccaacttgg gatttcctgc gagatctgtt  176460
aaaccgccgg gactgaatgg aatccgtttg gaaggatctt atattgaaaa ggcgatcaaa  176520
atggttccaa acctccatag caagctcact cttgatgaag aggtgatcaa tactttattt  176580
atcatgctcc gaacagcaca agcatttgct tgctaatctt ataccttcg tttgaattta    176640 ttcccttaac tgattctgaa atccccgcat acaaagtaaa ataagagctt ccacgcaaaa   176700
atgcttcgat atcattgaaa aagcagtttc catgtgcgtc aagcacatct atgattttgg   176760
agaaataact agtaaaggag ttggcctggt caataagagg gagtcatact ttggactgct   176820
tttttcaaaa gaaactatct gaaagcccct atggtttgct gcttccaaac ctggttgtca   176880
ggacttggag tgaaatcagt tctattttca ggcaacccca ccaatactta agggctaaaa   176940
atggtggatt ggaaatggag ctagcactga tttctggttc caccccctggc tctctgatat  177000 tcttctcatt gaaagtaccc ccctcttatt gaccaggtaa acttcatacg aaaagctttt   177060
gaaagctctt gaaaatgtct tgtagtagga ggacccaaag cccttcctg aataggtagg    177120 cacatagtat caaaaaatat ccagtgaagc tttcttttgt cttcatcacc gcctcaccaa   177180
aagttagcta acattttttc ctactggtca agaactccct ttgaaactgg aatccctgca   177240
agaaggtgta taggcatcga gaaaagaaca tgtttgcaaa ataagccgcc ctccactgga   177300
taacaatgct ttcatctcct accactttat tttagactct atccagaaga tgagcaattt   177360
tttttttaag atttaaatag aggtagtcct agataaaaat attaggaatc aaagcaagga   177420
aagttgcatt gatggaacgg gggatcgcac cttcagcgaa gaaataaggt gaccagctgg   177480 aagttttga aatcccaaca agattttcta tataaaaaga atccggaaag ccatcaggct    177540
ttaaaggata ggggagacct tttttgggt tagtgcgcgc cgacatgcta aaaatgacct    177600
tttgaacttc ttccatatta ggagggctcg taagcatctt attatcttcc tctgtgacta   177660
gagaggggat ggtctcaagg atctcatctt caagcaccga accttgagaa gaaagtaatg   177720
tatgaaataa attgagagct tcctgtcata cagagacaag ttctgaattt ggttcaaggt   177780
gcttattctc tatctttctt cgtaaagcag aagttttca aggttactct tggccgaatc    177840
taactccatt ttcttatcag cagaccaact ctgttcaaga gcaaattggc cttcttcgtt   177900
ttcggcattt ctatattctg aaatagttcg ccaattcagt gctttatttg tcgagtcaat   177960
cttcctggag aagacttgaa aaggatttcc cgagcatggt tgagatcaat gtgaaaataa   178020
gaatgccgaa tccacattct ttggaaacga aagacccag gcctgcgagt attagaatct   178080
tctaagaaga ttactagagg agagtgatca gaggatactc taggcaaatg gtcaactctg   178140
```

```
gtggaagcaa aacggctttt atatagaagc gggcagtccc cattcaaaag gattctatct   178200
agtctggccc agatacaatg ttgaccgctt tgattattgc tccaagtcaa tttgctgtca   178260
ttgaaagccc aatcaaataa tccaaacgag aaaatcatat cttcaaagct catcacttca   178320
ataaaggcat tgaagtcagg aggccgaccc ccaagttttt tctaatggat ccgcaattac   178380
attaaagttc ccctactag ccacgccacg ggaagttaat gcaagtcgat aggtccttca    178440
atcatcgagt acactatcga cttcccacac ttatcatgac aacatcaccg atctttggcg   178500
cttatggggg gccctatcat acacatgcac caccagagtc ttcataagaa ctctggggcg   178560
agggccaagg tgaacccgga ttaacgatga gaagcggtca atcagtagc aaaggcacca    178620 ggacggacgg ttggttgaac cgggcgatag cttcgcgatc gatagctcag tgaggtacgc   178680
cacccgccct acttctaatg atagataaa aaggtgggag aggtgctgag ggacggcaaa    178740
ggtacaaaaa caaaaactac atgacatacg tacgttaaat ggtaggccca ttacgaacaa   178800
tcattaaggc ggtctccaat ctcgctcggc tcgggcgat cacttgaaca gggcgggatt    178860
gatcgatcta catcaaaaat tctgccttcc cttcccagga gcgcatctac agaataaaga   178920
gagcacgcac cacactccta ctataccagg gcctttagct ttcactgaga agaagagatt   178980
acttccagct agcttttttc cctaacccta accaatgaat gataggccgg cttaggataa   179040
tcgaaaacga attcactttc gtaatcgga ggcaggtcag gggccggcgg gcacgccccc    179100
agcttcttaa gtttgggaat tgtgcatgac ctatgcaagg agcttccgga atccaatgga   179160
atcttcgtaa agtcgatcat tacgagtgtt acgattcatt cgattggcag gtccaatcgt   179220
tcatagcctc tcgagcacaa cccatattca tgcaaggatt ggtgattgag gatccataca   179280
gagttttatg aaatatctta gagatcaagg aacagatgct ttcttcagga aatatgaata   179340 cttttttggta gggacaagaa attttttggc cttgaatcgg gtcaggaaga acaacttgtt   179400
ccagctccgg ggaaaagatt catcttccaa ttttcccttc cttccaatat tttggatttt   179460
agcttccctc attccttta ttgagcataa tgatgcgaat cgggcttgtt gtatttagta    179520
tacagcgtca agcagttccg ctttccccta ccgatgatgt gccgagaagt gcattgttgg   179580
aactgggttg gaacttaaga ccataagctc tagattcggg ggtttacgct atagccgaac   179640
acaagggaaa gatcatttt ttaccggaaa agatcgtttt atcaggtaat ggatacacta    179700
taagcattcc tttggttatg tataagcttt ccaacaaaga gaaagacttg tatgcatcag   179760
gttcataggg gtaaatacat tcaaaaggga aaaattttag cggctcatat ttcaaataaa   179820
gatcgccgcg tggaaaactc gttttttttgg ggggttgtcc ccactggttt gcgaaagcaa   179880
tgggagactt gctccataga accccccccc agagactttc gtccccagta ttctctatgg   179940
gcaaaggcgc tcaggtgcgc ttaaagtctt attgcctata tcttatctta agacgaggtt   180000 gccacccgc ctgctttagt ctcaaatagg gcgcaaattg aggtgaacag actggaccga    180060
acctccctac gtcaagagct tttggctctt cacaagaaag caccaggtcg taacaccgga   180120
agactgcgcc gttattagtt attattaaaa tgatataatt ttttttgtatg gttagtcacc   180180 agtggcacaa cctacgggct aagtagcgcc tcaatgggag tatttttttc ctccgcgata   180240
gtgtaatacc aagaccagta agagagaatg gacttcatcc attcggacaa aacccatgcc   180300
cccctaacca gtcgtactct gaccaggctt cgaaaaactt cgagatcacc gagtttctcg   180360
ggaatcgagg ggtcaagagc ctaatcaggt ccctcacca taccttgttg ataagaggtt     180420
aagtgtttac cagtggttgc gcttaaccag atccaaaagg ggagaggaca cacaccgttc   180480
ggtgagtgaa agacgaggaa atgccgattc cagtgtctcc taggaggcgc cgtgcgtcga   180540
```

```
gtatacaccc ggtacccagc ttcccgtaaa cgatacgaca atgtaagatc cttatacata   180600
agagccctca ttacaggaac aagggatatg gaactaacta aggatcttaa catgtgacag   180660
gagacaggaa aaaagtcctt agtcactccg cgtacgaaga accgcttagc aaactccaaa   180720
gcaccaactg acgagactaa cgatttctct aacgaaaatg gaacattcag tggcgaaatt   180780
agctcgcgat aacgctcagc cacccgctca tctccgatga cgatatcgtc gccgaggata   180840
gcctagcgtg taaaaggaac tcctggatat acttgggctg ctacgaacca aatcaccaaa   180900
tggtgagtta atgcgaaagc aggccaagct ccgtaaaagc ccaacggggc tcctgttaca   180960
aaacgaactc tacctcgagg aagccgacga cgagaatttc gaatcgtcag aaaagagtag   181020
taggcatact ttcacaatag tcttgtccac aagcaaatca atgttcggca gcggaaaatc   181080
atctttggga acatgcttta ttgagatttc aaaaatagat gcatacgcga acacgtccat   181140
ccctcttggg catggggacg atgttcgaaa tccaatcaga ataatctact gccttaatga   181200
aatcagtata atagtaacaa gacagctgaa gagaggatga cgtagacaag aatcaacctc   181260
ttcccggtga ggttttgatg tatcgcagaa tccgaaaagc agcttctaag tgagatgatc   181320
tcggcttgtc catataaaaa tcggctgatc actccctcct atgttgtaag tgtaagcaat   181380
gtctgggcga taattagtca ggtagaaaag agtcccaaca agtctccttg caagtagatg   181440
ggtcatccaa tagctctcct gcatctaagg ctaattttag atcttattcc ggtttgcatg   181500
cagaaagacc agcttttgac aataaatcca atgaatactt gcactgggtt ccaaaactct   181560
ttgtgacctc atcactttaa tctccagaag agactttgag tctcctaaat ctttcatatc   181620
aaactgggtt cttaatcttc tcttaagctc atttatcgaa gctaagtcat tactagagaa   181680
agcaatgtca tccacataaa gcagaagaag acaatacct gatgtcgacc tccttataaa    181740
cattgaatga tccgatttac ttatttgaaa accggctcct tcctctactc ctatttcggc   181800
tcttatacat gctgctgtca ccttttcaaac caagctcttg gtgcctgctt tagcttgccg   181860
gaggccgtaa cataaatcgc tttcttgagc ttgcatacca agttaggatt cctaggaaa     181920 gagaagcctg gagttggagg aggctgaata gaaacttatt cttgccccct tcccttatgt   181980
tgttgaaagg cattctattc ttcacgtcaa attgaaataa ggccacctt tgattgcagc     182040 caaggcaaga atgccacgaa tggtgtttag caacctgaag caaatggttt ccctatctct   182100
aaaggggttc gactcaatat tcttgaagga atcctttagc tactaatcta gccttgtatc   182160
tatctaccga gccatctgct ttatgcttga tcttgtaaat ccacttgcag ccaatggctt   182220 cttccctgc aggcaatgag actaagtctt attattatta ttttttttcct gggcattgat      182280 ttcttcctgt atagcatctc tccagcaaga atgattggag gcttcagcaa atgattcagg   182340
ttcatgagaa gattgaactg agatgaggta agctcgatct tttggggaaa acgattcata   182400
agccttcaac aggataagaa acttgagagg gtcgacgaag ctgagagcgg gatccagaat   182460
ttgaggaagc gactggaagg gaagcaactg ggctagactg ctgatcttct ggagtagcct   182520
gaccctggga aagagactgt aatcgccgcc gagaataaac atgctgtgcc gggtgacagg   182580
aatcctctga ggtcagctga acaggctgac aatcggcaga aaatgctgag caaagctgct   182640
ggcctgaaga gtgaggctaa tccgtaacat caactgcaga agaatgaggt tcgagttgat   182700
gaacaggaga aggccgcaat acatctccat catcattctc ccccgggggct gattaattag   182760 gttaaggaaa atatgaggcg accctattaa agagagcatt aaggatacat cgactctctt   182820
ggatttcacg tcatagcata tatatacccg gactgagcat atccaagaaa gacacaagtg   182880
```

```
gttgccttgg ggacaatttt tctcttaact gcgcaggaat atgaacaaaa cacgtgcatc   182940
caaacactcg caaatgccta ttatagtact gccccagtaa gaagttcgtg aggtgccgct   183000
gcagcttgga ttatcgtaga ataagaggag ccgtcttagg aaatgactta acttaaaaga   183060
cagatgccgc cgctgcgagg cgagggagca acttgtctgg tcttgcggtg cactcattcc   183120
cgttacgaga atgaaatgag gccccagctt gactcgagac caagactcct tacaactcgc   183180
accaatagcg gcactgagcg gccggagatt gattgaaaag gcaggcccag ccgaccctct   183240 cccccccta ccgcctatct actcgtgttc gtagctcgat cggaggtcaa gactgtggtc    183300
cggcggaaaa acagaagtcg tccgtatcaa gtgatacgtg aattgctcag tagtgcttcg   183360
ccactaccct agctggcgga aatagcttaa tggtagagca tagccttgcc aaggctgagg   183420
ttgagggttc aagtccctcc ttccgctcct ggcttcgtcg tttagtggta acaagtgggg   183480
tgcataagcc actttagaga tagggcgag cagcaagcag ccccttgtat agggttccaa    183540
acctatctga ctaataagta agaggaaagg ggcaagccaa aactgactcc taacaagttg   183600
ctggcttttc atcagccgtt gcgcgctagc gcgctagcct tttcccaacc tagtaaaggg   183660
gctgctagtt gtagcgcgca gtgtactagt gaataggaaa agcgaattga gattactaat   183720
gacggatgga ggttgagggt agaacatgtt cggtgcctcg cccttgtctc cttcgccgta   183780
gactgaaaat gatgggaatc ctatcgataa agaagaggca taagcatcgc ctctcgatcc   183840
aatccatctt ccctggcctc cccagcacac tcttgatacg aaagaaacct cccgcctag    183900 agaagagatc gaaagtctgg gtcccctcga tcaccctccc ttgaacctga actggtcgag   183960
agagatgaac ccgcaccaca ttttctcgaa tcgaaacccc caactagaga tggaattcca   184020
gaacctaaac aactcagttg agagctccgt gactggttca agggaaggtc aaccaatgat   184080
tgataggcca ttccctccct atccgtctct tgatccctca ttccactaat ccgttgttac   184140
tgattcattc aaggcataga ctctccattt cttttgtctta ttagcgcagg tgttcgtcaa   184200
cgatgaaagc cgctgaactt cagactcgag tggagaaaga gggctaggcc cccggagggc   184260
tttcagggac tggggaagac gggtggatta tagaactagg gtaggggcaa atcgaaggtt   184320
ttgcccatcg ggattgggca tggacgagcc tcgactgggc cagcattgat gaaaaaagaa   184380
aaacttcccc catcgcatca ttaaccggtg taggattcaa gatcaggtcc aggattcgag   184440
tcaaatcgac cttccctctc atctcagggt gaggcaagga attgtttcaa atgttcgttg   184500
ttgggacggg ttcaaactgg actgaaggga ggaggataaa aagagtcctc tcttcctggg   184560
gattcatcac tggctagggc tttcgaatca aagcatgggc atccgctatt aagagggagc   184620
agtagatcgt cgattgaaga gccaggtcag tcaacttcta ttgggacttc tattgattat   184680
taattcgact ctagggactc ctagcagcaa actagtataa aaaaaggggc cccatagaga   184740
tgcaggagcc gccagccgga tcgaccaaga aatgataggc cagagagatg ggctcattcg   184800
actaatcagt gatccctggg cctacctaac acagatgtcc ctgaaatagg ggattggttg   184860
atcggaaagc tcaggcagga gtaggacatt ccatacaaat ctttctgatc cgctagctgg   184920
tggtcctctc aaatcccatt ttttcatcga caggtagggt gaattctaag gttccttatt   184980
ccggttgtaa agcggaagaa gagggagaat gggcacagcc ccactagcag cccgcgtttc   185040
cgacccgaaa ggaatggaaa atgaaagaag aatctgtgtg cactatctat ggagtggagt   185100
gactatcctg aatctcctct tccctatctc ccccttttt gccttcggct attaccggct    185160
ggcaaggctt ggcccaacat tggatttgtt tgaaaactac caaggtggca ttcattcaat   185220
caaatctttt atgcctatgc cagcccaaac taattgactt tttttggaaa ggaaggaatg   185280
```

-continued

```
cagggaagaa gtctttcctt tccactggtt cttgaaagct atcaatcccc gcttctccct  185340
ctcgcatcgg ttctgcatca gatgatgagc ccatgcgaaa actttctctt ttattggcgc  185400
ccgataggta ggctattaga ttgagtcgaa agcctaccaa cgcataaaag ttccgattcg  185460
agcgagagcc caaacgggtg aggcgagaag atcttgatcg aaagctccac tgttctgaat  185520
agtgagaaag attttttggaa attcgatcaa atcgatcgag aatctcatca tctgttaggt  185580
gggccaaccg accgaccgag ttgggctggg cgtccatgtc acagaacctt tctctagcca  185640
agaatcccat tattgatcga atcggggcgg atccaattca ttggcaaatg aaaaatctat  185700
cgttttaaca ctcagaaaaa aaacctagaa aagaggaaga gtcactaaga caagagagct  185760
ataggtaagc aagcaagaag gataggtgca aaaaggcgag gcaaggggct ctccatctct  185820
aggaagattg tgtccaggat ctggtaatct aagccttgtt tcttctggtc ggctcgtatt  185880
agcctgtgct ttattacagg tagtcattcc cccgttcctt tagtcttttc aagggtactt  185940
ttttcttaag tcgcggtcat gtcttgcccc cccagtatag tgaccgcttc catgttttcc  186000
ccgaatttca tcagttccag gctcaagtgc ctgttcatcc atcttcattc caaacaaagg  186060
cgaacatctc cattgagtga ctgtaactgc tatggtttac agtcaatagt tcttaaccaa  186120
cccttttcttt tttgaattat taattaatta attcattaca ttattatatt atgtctttct  186180
ttctgaaggg cttgcggttt attacaccaa aggctttcag tgaactattg aagctatcga  186240
gagagtacca aatgctgacg gtgacgaagg ttaccgactt tcggtggacg cggagccaac  186300
aagttcagtc gaacagcgta acgagtctaa ggttacagaa gccttcgcca actttgatag  186360
ttatagcatt gcaagcaaat agagcagaga gcttacccctt tctttctatt agagtcgcga  186420
gcttgttgta gtcggtccta aggggagaac cttgctgctt acttgctata tccccgcgtc  186480
cttgcacggc tcggctcgtt cttcgagccc tgcttctccc ttccccctct ccccgttcct  186540
accgtccaaa acaggtctat ggagtatagc caagtggtaa ggcatcggtt tttggtaccg  186600
gcatgcaaag gttcgaatcc ttttactcca gattatgaac cccgatcgg atctgtcaag  186660
aacgagctga cgactacaag ggaagcagct gactgcagtc cctgagcccg caagccaaaa  186720
gtttgacttg aacctacctt tgctaagaga agagagagaa gggaaagaca gatggcagaa  186780
ataaatcctt ccaaccgcgg aattgaacac aagactgact tcggccaggt tctttatca  186840
atctcctggt ccttgcttaa ctccttgttc cgtaaaccgg tcgctggtag atctgatcgg  186900
atcccggaca cgcgagagcc cagcccggga ggaatgcatg gttccctggc gcttcatggg  186960
acggacgttc gcagtcctcc tccatctaat ctaaccctac ctcgttcgcc caggcctgcc  187020
ggcacaataa gagaatgagg gagctaatct gcttgcttgt gcaggcgagg accgctcggc  187080
tagggcgcgc cagaggagct tcgagtgact ttttctttg ctcttcgaca gccctaacaa  187140
gtcacttgaa gctctgccct ttgctttgcc ccgtgctgtc ttcctccagt tgcccccacc  187200
caatagccaa taggccgaaa aaggttgcag tcaattgccc ttcccgttat catcaaacaa  187260
aagactacca tacacgctgc cggcaagcta ccctcgccta cctcatctat aggcatttct  187320
atccgcccgc gcgcgagatc agatcgacta ctctactacc atcattccga aggttttttt  187380
attcaaaagg acgagaatg aatagcttat tcataatctt ataggcccg caccgcttca  187440
ttcaattgct ctgtcataaa gaaagggaag gaaatctttt tttgatcaat cgcctgaacc  187500
tgcctttctt tctttgccag gaggggtggc ccaatcacta atagatctct caacgggagc  187560
ctcattctgt ctagaggaaa tagcttcggt ggatccggtt gattaagtcg ttgtgtctgt  187620
```

```
cgatacccac ctgctcggag tgcgggtaag ggctcacctg ttgattgtgt cgttgcatgc 187680
tttttggtag agcccccacc tcccacggct acagccagca ccaggagcct agaaaggtat 187740
aggcacccgt tcattcagtc aatgaagctg cagtcggttc tgatgattat gccgtttcaa 187800
gtggatgttc agttggttca gcgatagatg tagtcgatgg ggtagagggt ctgcagatac 187860
tcgtctagct cctcattgcc ccaaccttcc ctgtaggctc cctgctccgc cagcgcgaca 187920
actgtccaaa tcatttgacg cttcttctca ctgagcagcc cctcgacttc acttccaggt 187980
tcggggagct ccggcagggg gacttgagtc tcagcagaac cttccttttt cttctctctc 188040
ctttccctca tctcccgggc tcaaccgaa tttgctccat tttgctcagt tggggagcgg 188100
aggtaccctc gagcggtgta tgggctgtga tatttgtggt agcgggggta gaactcggaa 188160
ggctggccaa ggttgtgtcc ttccgagcgg acgaggtcgg ctcggtgacc gagggcttgc 188220
gtggaggcgg cattgcgacc acgggcttgg acgtcacttc aacatttctc tgcttttttg 188280
aggcccgagt gaaggcatat atgtcgaacg gattcacaat aaacaaaggc gattgaaaaa 188340
cataaaaaaa agaaagggggg cttactcgtg acgatgtcgg gcagggtgtc atagaaagat 188400
gtttggggta gtggctgtaa gttcgaaggc ttttgtgtta ttcgagtgag gatgtgaata 188460
agtagaaaag gaaataatta ggctttgaac ttaccttctc tggatggaag gggtgaccgg 188520
ggtaagtgat gtgcgaaaag cgatatgctt tacacgtccg cttccaggac gtcacgccca 188580
cgcgtctcct gactgtaatg gttgggcttg gctctgctcg ccggttgtgc tgcgtgagcc 188640
ttcagatgcc tccaagcaag cgaaggtttt cggggtaatc gccgcgcgtc cttcccatgc 188700
tccgtgacaa cggcggtacc ccgaaacaaa ggggccagtc ttcgtcgtgc cggggtatcc 188760
cgatccggat gccacgaaaa tttagggaag ccttttctt aaaagacttt ctgcgaccgg 188820
tgagaaagcg gacgacttta gggcttaaag gaacaccttt ctctttcata ttgagtcctc 188880
agaggtgcgg cccacttggt gtcggatcag ctcgacaggt cactcaatag tctttcgcgg 188940
agtatccccc gttttagtga acctgggag ttgtcggcgg ctcgacgatc tttattccaa 189000
aggtttaccg aggtgaagct tttgacaggt attctttat ttgtaggttt ctctacttca 189060
ggctcttccg agggcctttg tttgaggtga ggttctatag tttgatggtt acttatgttc 189120
tcctctcccc ttccccggta gctaggaaag atttctaaat atatttcctt ccttccgttc 189180
aggggcactc taaaggcttt gcaaccttca gagctggttg acagccgtct agtcagtccc 189240
tctcgctctt tgatagacat ctttcggttc tcggtctcat ccgacgaaca acttgaggtc 189300
tttattctgt gtcctatcct tccttgcgga ttccccggttt ctgaaggagt agcggcctgt 189360
gtctccggct ctgggagaac tttacctata gctaacctag agagctttac tttaagatag 189420
ctcgggcagg cactcttctt cggaaagagg agttgcttgc cttaccacac caaccacctt 189480
agcgctggaa gttctagcaa tgggcagcta ggcaaaggaa tattatatag caatttcata 189540
ttcattagat aagagattgt ggatctgttc ttagtgagga caaccggatt gggacgatca 189600
ggtcggttga gggcagcagc acaccaatag gtggattgcc attcttgtac tgtttgggta 189660
aagggcagga gcgctctttc cctctcacca gtacttacta taagggtgg ggcaaccggt 189720
taaaaccaaa tatccaacag ccgctttcct taatggctac ccgctttcga gtgaactgaa 189780
ctcttggact ggctgaaagg gaaagggaa actgtacaag gtcttttca ctcgtttacg 189840
ggaccagtgt caaaggaaag gattgttgca ctctcttgct tgaatgaatc gacatttgtg 189900
gatgcttgtt cattcgggat tcttctatct atatttagaa ctactggatc aactactccg 189960
gcttttagcc tttggaacct gtggaaccct aaagtcactc gcccgttcaa actcttctgt 190020
```

```
ccatcccatc taaaacccett gaatcagtga atccggggac agagacctag cccctgcttt 190080
atttaaacag ctaagataag gtctaagacc gtttcttctt ttccacatcc tccttcctcc 190140
ttctttccgg atacttaagc ttctaatgct acggaacctg ctttcccaat caatcaattc 190200
aaattaatgt gtaggaacct gccctcatcg aactgaatgt ctaccctcc cgcatttgaa 190260
gacagactaa tgtttaagac ctcctgcttt catggagatc ctttcttctc tgaccgccgg 190320
agattaccca tatatggatg aataaccgtg aagttcgaca atcttttgag ggaggggagt 190380
cgactgactg acaaggaact gacagaaggg gaaaagagga gtgaaaccat tcgacggagt 190440
tggaaaggac ttcgctaatc ataataaggt tggtctcacc ttcgtccggg gactcgaacg 190500
aggagatcgc tgatgccgac caccctctgt gtctttgtca gtgaagtaaa tcaccccgag 190560
gctaagcgat ccgcagtgtt caatggttgc ctaagcaccc gactttaata gtaggagaaa 190620
ggaaagcgct cgatccatgg aatccgtcat cggatctccc cattgacaga tagagtagaa 190680
gaatcaatta gcccgggatt taagatttag atcttcaact acttccgaga gggtctcatg 190740
ctacgatacg agtagaatac ataggggtat agttcgggta aagcaaatca gattttgacg 190800
tatccttttt attggaaacc tacaaagtcg caatcctggc agaccttttt gagattcctt 190860
cttgcatccc agtctaactc ccctttctgt ctgtcactgg atctacacta cttgacttgc 190920
gacttgagct agcagactga gctttagctt gagcgagaac gaaggcagac atctcttttt 190980
tggacttttc tgcttgagct ggagctttgg actcgacgag gtattttgtg cttgccctat 191040
tgagagtctc ttccattctc tcttcaccag acagatagac aaataggcaa tccgatagat 191100
agattatggc ttcctcacta tcagcaagct cccacaggcg atgaactgct tccgacttct 191160
tcattcggtt tgtagccata ccgtatagag tgaaaaattc ctttaatgg gagtagctat 191220
attcaagcaa gcattccagc gaaacgatcc tttgacaatg ggctctgccc aacactggga 191280
ctgactttat acagagagag gaaaatcagc aaaaaaagct cttttgaat cgaatattgg 191340
ataggctaag ctaggtgtag cccgctctct ctacggtttt gcttgaactt gtcaagcccg 191400
ggtgcctatg cgattattaa ggcagggtgc tattgtacca gtggtggagt ggcttgaatc 191460
aaatcgtttg tctagagagg gtgtagcgat aaccaaagtg gactctacta gaaagtcaag 191520
atgctgtata ggcaactggc cttagagtag tgtatcgaac taaaggacag gagcgaccca 191580
taatcattga cgaagaggaa ggcttggaaa gggatcaaac atattgagga ggagctttca 191640
caaaggccaa tagccgatag ctgatgtcac tagccttaac ttctttatct acttgaaagc 191700
tgatgggagt acggctttct tcaaggaagt gtcccatatg atattatatt agtaaagagc 191760
ccttgatcct agataagtaa gcagatatgc ctatggctgg aaagatagcg agcgctattc 191820
tcaacttagt ctctcagagg ccagctcgtt gtaaccctaa aacacggcgt tagcggggtt 191880
gggctccccc tgcagaaata caacaaacat gggacagccg ggaacgatga cccttctcaa 191940
gcctgaggcc taagtggac tttctctttc tgcaacttgc cactccgaag tttaggtttt 192000
cgtttcgaac cgatgggatt tttcgaatgg taatgaagct tgccattctg tttatttggc 192060
cgaatccgac tctgggcctg ccctttttgct agcttttttca ttatgctggt tcaactactg 192120
cttatgcttg aaatatctaa acacctgaaa tccactctca atagatgctg ccccttaaac 192180
agtgtgaaag ggtggtaggt agaactaagg gaataatctt cttggttcg gtaatggaat 192240
caatagcttt cccgaacagg gatataggaa gaagccaata gcctacaggc ttgccagcgg 192300
acttgcttga cctattgaaa tgccagtata gacttctggc acatggtcgg ctagctaaag 192360
```

```
gtcagcttcg gttctaggca aagatccgcc agtagcagtt cctatcccag ttcccattca    192420
acattcattc aaagtattct ccccttgcca tgcttcaacc agctgctttg cggactgctc    192480
ttgctcttac tgctactgct cttcctatg cttcctgctt ctgactacta tttaaaatag    192540
tttagaaagc tattcctaca aggaaaggcc tcctttcttt catctaaaag ctggctggtc    192600
tcttttcata ttcaaaaaag gaagccccat tccattctat cataagataa ggggaatga    192660 atctcttcaa agaaagaag gaaactatcc tgacatccta agagctaccc cagtctggag    192720
cacagctaag gctatacttc cgattctgaa ggtaatccca ttttttcttt cttttccgga    192780 acccccgaa aacctaagtg agagcgaaaa ctacatacc taagatccg tcccttactc     192840 ttctttagag gaagcgacct tacctatatt ccaaaaagag gataggagcg aaactgcctc    192900
ttcaagtcca ctccttttcc tatgcttcac acagggctcg aagaatcatc ttatagccta    192960
gaggttaagc ttaaggttaa ggttaaggtt aaggaccttc cagtcttcct cgagttcgtg    193020
ccttctatcc cgccaagcta tagctatagc tagtgtcagt gagttcaacc tcccactcgt    193080
gtggatttgc tttctgttct aatcccctac tagacctcct tgcaaaagaa aagagaaggc    193140
ttacttctta gcttctctaa gattctttat ttacctttga ttcaatcctt tcgcttctct    193200
cacattccca tcccatggta gtcttttgcc ctcttctagt cattctcttt tcctcccctca   193260 gaaggtgaag gagaaggaga agggacctag aaaagcctca aagaggtatg ccgagtcctc    193320
tatcttaaaa cttcctctaa tgtcccatcc cgtcgatgtt gatttcacac aggatgatcg    193380
attggatacc ttgataccgc tctttcgcct tgattgatcc tattactcga cacatctact    193440
cttatgatat gaaattttac cacattgacc gctttctgaa gcgaatcaca tttgcggatg    193500
gaatgtccta aacctccacc tactcctgtg gaaaggcttc cccttcggct tggggataaa    193560
gcaaaaggga gaatttactt tctgcagcta ccagcacacg atcccacttt tggcctgggc    193620
tacaagccaa aagtcaaata ctaaatcagt agaaaaggag agtcagaaga gcgctggaac    193680
agggttgact cctaaaaagc cgcacgagta catgcctacg ccaccgccca actatgtctc    193740 cttccgatc cacatgccgc tacgagaccc ctgtaaacca cccttagcca agaaagacaa    193800
gtccgtcccg tccatagaaa gtccacaccc aaatgtctct atcccctagtc ccacagtact   193860 ctcgactgct gaacaggcat tattatcctg atcttcttg tctgttcttg agtgaggacg    193920
gtcagcttga tgcagacccc gagtctgagt ctagttcgtc aagcacgcg gaggaggtac     193980 ggagagaagg agacgtcgag atggattaag tagggtgac tctgaaccac tcgcgctcga    194040
aggaagaaaa tggagacagg aatcactagc cttagctaga agccccgaaag gcactctagt   194100 cttcgttgac tctgagacct tcgatctagt ggaattagtg gacgactctg aatgcggagt    194160
aagaaagtac gggtttcttt gatcgacaac ttgctagtcg acagaaggat tttcaaactc    194220
gatagcctac tggtttaact agtttctgga actctgatag cactatcctt cgccttccaa    194280
agtctttagt agggcactca agacttcaat cgcgaattct cagttggaat cttctttgga    194340
agagaggtag tataccgggc tagcaggact gaatgcttag taagctaccc ggatagaggg    194400
atgtggtaag gaagcgtagc agttcaattt caaaggttag gtaagtgcta gctcgatcat    194460
cataagatcc accagcaact ctcttatcta cccaattgga aaatctttat gttaagatta    194520
tatagtgaag tagatcgctc gctctttcct tctactttgg acttacattc agcttgcctt    194580
ccgtggagct aacagaccgt gccactatta tacctccctc cccttactcg tccattcact    194640
atgtcagttg ctttagctgc tccttctgta ataggctgct gcttgatcta tatcattaac    194700
tgcagaatcc ccatgagtgt acttacagct agcaaaagac tacttcttgg actgtggccg    194760
```

```
acaccagaga agactatttc gagatttgct aagcgaacga gggactgtct tgactcactg  194820
gatcgcaagc acctattcgt tcagctgaat cgacatagca agcatgggcg agaaacttat  194880
ttctttatta aaccactgga caagaggaca atatgtgtaa agcatatact tggctgtccc  194940
cgcttcttcc cccccttct attagaccgg tacgccaagg aacaagtcca taggtcatgt  195000
caaacttaac acttgatgtc ttcaagtcca tgtgatagga cccaacccgg acatggtcgt  195060
acgtcctcta ccttcggtgc acataggggga aaacgtggaa tactgttata aggacacctt  195120
atcttttcca agaccttacc atctcttttcc ttgtctctct gtgctctctt tgtactttag  195180
ggtataggag agagaaggag tgcatacgag ggggttgaaa gggcaacgaa tgaatatagg  195240
caggctgatg ctgcccaagc agacgcttta tctgatacaa ctcagacctc cgggtttggt  195300
taagtaatct gtctattcat cagtcagttc ggacaagatc tctatctctt gaggacaatc  195360
agatgctttc gaagaatcgg accaagagg atatccattg gaaaatcagg cagatcgcag  195420
gagagctccg ttacacggaa agtccttttt tactgatgga gatcctctag cgggatcaga  195480
ccttccacaa gatagcatcc cgtaacaaga gaccttctct caagaatatt ggttgcggag  195540
aagagagtgt gtcaagccgt aaaggggcag agtaccagcc acgtggcatc ttgacaagga  195600
aatcgaatgc ttaacgcgag caattccaag atcggattct gctacggaat cggataatgt  195660
ttgtgatacc acatccgctg tctcctaatc ttcttctgac agagagtctg ccgttggaaa  195720
atcaactgcc tcggttcggt tatcttatat aagatagcgc attgatgttc gcggatggtg  195780
ttcgtagaca gcaggagttt agtcagagtt atcgcaaata agataagagt ttggtaggta  195840
gaatgcctcc ctcttgagag gatgcatttt tagaacccgc ctcttttact caagtcgaat  195900
tcccctcat ccatgttgta gtatcccttg cccaaagcat caggcaagac agacacgata  195960
gaatatccga tgttgttcgt agggaatccg agagggtcct tctattcttc ccatagaagt  196020
cagacgatcc taagcttacg tacttagttc cggaaaccga tctccagaaa gtcatcgagg  196080
ctagtaaaca agacatccaa gcgtcccaag gcgaatgcaa agaattggcc ctaaggaaag  196140
aatggcatac ctacctcatt tcttcaaagg ggggtacga ggaatggaat gagggacaaa  196200
aaggagtgaa aagctatcag cgcttaccac gattctctca aaaaaggaa ggagatgaat  196260
ctgcctaagt aaggagcccc tccggggctt agtgtgagtc acttcactcg ggaaagaaca  196320
aagaaggggc aatcaattgt ttaagctgtc aagaattct ttaaattagt aatttgactg  196380
cggaaaagcc tactaaggtc cgctcgaggt tatcttcttc ctgattcaat caatagcagc  196440
tccttccttt cttgctaaca gggcaagggc attcgatgca tctgattcaa ttcctgatcc  196500
gccctctctt tcacagccta ggagtacaca tcgatgagct taagtaagcc tttttgacta  196560
aaaaactttg ttgatgcaag gaactctttc tattccacga gcagaacacc agagatgcac  196620
agcacgtggg ccttgtctaa cgaacgacga ctttcgattc ttaatcgaca taggtttctc  196680
tttttgtgta attgaattgg atgggcttgc aacccttagg cctgcctctg tcactgcaag  196740
aagctcgaag ggatgaaatt gctcctttaa tcaacaataa gagggaagcg cttgagcgaa  196800
aggagaaggc agaaaaaaag atgcacaaag gaaaagggc taaaaagaa ggacgaagta  196860
atttcgtata taaagatatg gctttccggg tttagatcga aatggaatcc ccgaaaacca  196920
gggctggagt cttagacttc ttctgcttcg atagagggac tgacagccta agtggaataa  196980
gaatcattcg gccgattgct ctgactctta tccttccttc gctgacagag aagagagaga  197040
gcactcccca agccaaggat gagtgccaaa gagaagatgg gcaagcaatg cccactccca  197100
```

```
tgctttccgt tggtcaacaa ccaaccaaag tgctctatac ttcttcacta ctcgtacagg   197160
cttgacggag ttaagctgta ttgagggaat cgttttgtct caatcaatca atatgtttcc   197220
gaaaattcca cgtatctttt tctttgatga agagagtcta aattccagtg ctacatcctc   197280
tcaaactccg agtcaatcca cgacaactat tagcgatttt agtcttcaat cgtccgatac   197340
tcaaggttct tctaatggta tttttgagga tcatccaggt cttaaccctt ccagtgaacg   197400
tatagtagag cttcaatgtt gtatacgcga aagattcgaa gagttgctgc ctaacaacaa   197460
tgccgaagcc caagcccaag aggctctggt agcggccgaa gttttacatg gcgaaagcaa   197520
cgatatcgcc gagctggaac acctttttgac agatttgaat cttcacggag tactaagtga   197580
agcctttcta gaggcgatgc atctagtgaa ggagctcacc agccccccca acccacctac   197640
cgtccccagc ccacttgaac aatttgaaat aatcccattg attcctatga aaataggaaa   197700
cttatatttc tcattcacaa atccatcttt gtttatgcta ctaactctca gtttggtcct   197760
acttttggtt tattttgtta ctaaaaaggg aggaggaaac tcagtaccaa atgcttggca   197820
atccttggta gagcttattt atgatttcgt gctgaacccg gtaaacgaac aaataggtgg   197880
tctttccgga aatgttaaac aaaagttttc ccctcgcatc tcggtcactt ttactttttc   197940
gttattttgt aatccccagg gtatgatacc ttatagcttc acagttacaa gtcatttttct  198000 cattactttg ggtctctcat tttcgatttt tattggcatt actatagtgg gatttcaaaa   198060
aaatgggctt catttttttaa gcttcttatt acctgcagga gtcccactgc cattagcacc   198120
ctttttagta ctccttgagc taatccctta ttgttttcga gcattaagct caggaatacg   198180
tttatttgct aatatgatgg ccggtcatag ttcagtaaag attttaagtg ggttcgcttg   198240
gactatgcta tgtatgaatg atcttttata tttcataggg gatcttggtc ctttatttat   198300
agttcttgca ttaaccggtc tggaattagg tgtagctata tcacaagctc atgtttctac   198360
gatcttaatc tgtatttact tgaatgatgc tataaatctt catcaaagtg cttatttttt   198420
tataattgaa caaaagcgag tctgaatggg tatacttagt cgtggagcat tccgagtatt   198480
tgctttaggg atcgttcctg cgcatctcct tactttatag cagttattgc tccggttcca   198540
gaaggtatag ctcttggctc agcttttttct tagaaattgg agactgttcc aatttcctac   198600
tgagataggc aagcggaggg agaactagac gtatcttgct aggcaaagac aggttagaat   198660
ggatagctcg cgggtgggat tgacgggata gatcactatt gcagaaggag gtagaaccgg   198720
gggaagaatt atggctataa aggtcctcgc cctcttaggc acatggttct aaagattcaa   198780
tctcaaagcg gtactaaaga ttaggcagaa gcagaactag aactagaatt cttcgccctt   198840
ccccttgtac caagaagcaa gttcagaaca taaggataat gggctcgtct attagaagtt   198900
attagtttac ggagctatct cagatatctc gagtaaggag acggggcggg tttgatagtt   198960
agagttctat ttctaggaag gaagagacta tcgggaagct cactctcggc cgggctcgaa   199020
gcagaaggta gaacgtaata tctcttgttg gttcagctca tcaagctatt acaaagagt    199080 ccagcggaga caaagaaaga agccattttt acggtatttt cgcttccagt ccgtaattag   199140
atcttcaagc ttagtccagt ccggatccat cctaaaccaa agagcggggc taagcgaggg   199200
gcatagcgat acagtgttca tactcgagtt gctcaaatcc agtaggaata tcaggaatag   199260
taggatctag taggagcttg ccttggaatg cagtgaggga gcccggagct attgaattct   199320
ttcataaccc aaggagaaga ataggactct ttaccagtat cataacctct cgatgggaaa   199380
tggaacttag atcacgatgt gaacctactt atgagtggaa tttcgttgac aagcaaattc   199440
cccgggaaaa cgaacttttc tccaattgag atgctttctt catttatgga ttctatgcga   199500
```

```
gattcggtta gtgtgaagtg tgatcctggc tcagaaggaa gagctatatg cttaacacat   199560
agagttcgat gtaggtaagg atgtgctcca aagtttcaa ttccaccttta tcaacctgaa   199620 aagagctaat acgggcttag cctgcctttt atcttatcct tctattctag gcgaggaggt   199680
ttatttttaa atagtaaata gccccataaa aaacaacaaa ctagtcaaag acagcctgc    199740 cttattcttc tcccgttcgg gaccccctat ttctcggaga tagcctggtc tgagctagaa   199800
cagcagattc gtgagcaaga gcgtatttca cagctgattc aacaacagcc attttttctg   199860
gggaactttc atatgagtct gttctttctt ttaatccact ataaaggttc ttaattttct   199920
ctttaatatg aaggagaatt acattcttga aaggatcaag ggctctaccc tctcgcataa   199980
agtcttacgc tcttatcgtc aaccttcgtg gcttttttgct cctttggtct cgctatttca   200040
ttcctggttc tctcttttcaa gcttcttttcc atcctgggga tttcttctca ttccgtccgt   200100
tctgctagct ggtgtcgcct tctctcttac ttatctattc ccatccatct ttacctctcc   200160
tactccacta cttccctcct tcaaagcgtg attaatgcgc cttaaacctc tctcttgaaa   200220
aagagcattt tttagtggag ccttagcacg tgaacccata ggaacagggc ccttcttctt   200280
tgcaaaaaag cttctgaatt atcatcacat cagtaggcgc agaaagcaaa tcttggtatt   200340
gacttattga aaatctcttt gagattgctt agacaaatct ttttgtgtga ggccgctgtt   200400
ccccaccttt cttaccttgt tttttgggct taaaattctg tgactcataa gccctccata   200460
tctaaagata gatggctaaa gggcgggttc cgcagttaac taagaaggcg atcgattggc   200520
ttggagagga aacgaaaccc gggactgaaa acaaaaagga taggaatgaa ttgaataaag   200580
aaagaatata tagaaccttg agcattttct cttctcggca atggttgaga gtaaaaaagg   200640
ggtatccgca tagaaggatt gctggtatac cgggtagatg tttatctttt cgacttcagc   200700
gaaaatgtaa aaagcacaaa tttcgtaaat tttctttctg tcgaaaggga agaggacagg   200760
gtcttactta cttaaaagta aaaaaaaaaa atggaagttt cctgtcttag tttcacttcc   200820
ttgaactggc tactaccgcg caacgtgccc ttgcttggtg ggtcgttaat taatcagttt   200880 taaaagagg gatggatttc gaccttgctt tgagtcgtca ggctagtaaa gcgctacttc    200940
taaaacgatc gttaaggtca ttcactcgat tccctcggtg gctctgctac cgatggatca   201000
agatatgctg cctgcctatc atgccaaagg cgctgctggt ggatatgcca aagatgtcct   201060
ggctctgaac cgggtacttg aaatgctaaa ggtacttctt atggtcctgc ttcaaccacc   201120
cttccttctc tacctttttc ttcaaaaact taagctactt agactgatgc tggcgatctc   201180
gaagggagat atctggacct ggagctactc atcttgatct ttattatatt aggatgcgag   201240
gaaagggaaa gaaggtgata agcaagaaga ggaaagaaga atgttaaaga agtccctata   201300
agtacttcac ttagcctttc tatagtctgt ctttcttccc ctcttccctc aaagcgcgct   201360
ctttcatcca tgcgcatggt tcttactttc atttcccccc tcctcacgta ggagcgcatc   201420
ttgttttcaa agatgagttg tagatgagtc ggttcgatca ccccacatat cgacggtttt   201480
ttaatgcctt atcctaagcc catctagttg atcgagggat agacgagtat aaagaaggga   201540
tggagaatct tttatttgat cttgatttga tgtatatgtt acgatgcctt cgtattcagg   201600
aggattgggg gtacggcaga taagaagagc gacccaaaaa cggaagaag agtatgaggg     201660 gcagcggctc accgataata agaagaactc acattctcgt cctgacagat gaccaacctg   201720
ttaaggcatc tttctcaatg accatcctct cccattccag ttcttttctc tttttttagg   201780
gacaagttca ttttcattcc ctcgatatgg ccaggtgtga agcaacttca cgatccaatg   201840
```

```
aattccctaa aatcggatga cacaaggcga actagaatag gctgatttat ccacaagaat 201900
gtcataaagg ttttctccgg tcttcctcaa aaagacagct ttagagcgca agtcaaactc 201960
atgataggcg agaaatcacg cgcacatggt ttagcggttt gctgtgctct gtgatcttat 202020
tcttctccaa gacccgatgc ttcatctgct tctttagttt agtaggactt ctttcacgct 202080
attgcgtgaa acatttgttt ggtctcccac tgctactgct atctatgcta acttgaaagg 202140
tatggctact ctcttgtttc ctgctgaacc tccttcccaa tacaggcttc gcagccatcc 202200
ctgcttgcat ttttaaaaa agtttggtag gggctgccaa gcttgactaa tagaataggg 202260
gtccccttaa aaggagaatg cctgcccgt gccaccttgg tagcacaaac aaaggtcctg 202320
tgtaccaggg atgtacgaat catagtaata aactttacaa actttattag ttgcaaggcg 202380
actttgctgt aaagtttatt atactcttaa agtatattct aaagtaaaag tcttcttagt 202440
attcaaattt ttgactatga atattcctac ccttgcagtg ctaatatatt cattagtctg 202500
agtcttagtc tactaaaagc ataggaaagg aagagtcaac tcttatgttg caaggttcca 202560
ccccaaccaa gtaataagca ctaaactgaa ctctataagg atagacgggg tgatttctca 202620
ctacaaagaa aaaggctgag gatttgaaat agatagaaag gagtccaatc taagcaagcg 202680
tagtggagga aaaaaatcct aaaagtaagc aagtagttga attagtccct gctagtattg 202740
gttggtctta ctttattata caaaggattg tggcaagcaa cagaaagtca agtgagtgtt 202800
atggtgcagc ggaaggcccc ctcgaatctt ccttgagttg acgtcactgg gacatctacc 202860
gcttggatcc tgccttgtta gtcatccgta gagctaaagg gaattttttg aagccattcc 202920
cattcccaca caccaatacc aaccaggtg gctgttcagt aagtcctacc cctaatagaa 202980
aggataaatt gcttgcgcgc ttcgtcaagt aagagagagg atcttaggcc gaacagatca 203040
ccggctccga aggcctgcaa tcgtgacttt agttccggtg gttcgctttg ctgccgggct 203100
gcaacagcct tttgtgacac ttcgaatgga gtggtccgta cgcccctccc cctcgccaag 203160
cctgaagaaa ggagcaactt agatacctct ttgttaacta gattcctggt ttgctaaaag 203220
ggtccttggg cccaatcaat ctctatactc ttgatgcaat ggactcccca aagccactaa 203280
accgctctct tccacccgat ttgaacagaa cctcgttcta gtgagatttt atccctttt 203340
taaacggaaa ctcagttgcc tatctgatcc ttggtctaat tgggccttc tctatagctc 203400
gaatcgaata gctgggctac cccttccctt ggcttggttg gttatataag agaatcccag 203460
gagaaagcaa gttagacctt acttagggcg aaagattttt tggatggttc attccagtct 203520
gaagtcagtc aagtcatgga attggcagaa gttccccctt aaccaaccct aagagggaat 203580
tcttctattc attaagatga agccattcag tcagctctga atctgaactc aatgattgct 203640
tttcaagaag ggcatgaagc tttggctcag tacagtagca tttgactttg ggaaagagaa 203700
tcgatagaat cgatcgctta ccttgctttg gcatgccaga agcatttcgc tgtggttctc 203760
attgattgag tcgatcccga gacaaagcaa agggagttcc gtgggttcag tttgcttaga 203820
ggcagaaagc ctagaagagg cctagaagtc ataaggaata gcaatgtac cggcaactct 203880
aaggtttggc ttttctttt attgactttt ttgagtcaat gtcgcatttc gcgtgcttgg 203940
ttagatctcc taacctaatg taatgaagga gaaggcagaa aaaaaagatg cctttatccc 204000
tagagatgca ggagcttgcc ttaggacaga aatgatatcc gaatggcgta cggagctgct 204060
taccctaaga cttcaactcc atcttacatc gaagtcagtt cggctggatc gagagaatct 204120
ggataggcat gatcgaaaga gggggcaact ctgtctccgc ctctgctcgt gcactcgtta 204180
aagtcatggc ctagcctagt tggtgaagga gcctacaagt ggtaaccgct ctgtatccgt 204240
```

```
catctctttg aagaagcagt tgggctacaa gcggcgcttt caaaatcccg tgactctcag 204300
tcatctatct tcttttcacc tgaaaatttt ggattggggg aagcagagaa tcaaaaaaaa 204360
aaaaagaaag tcatgcttac tataagaagg aagcgggcgg agacccgtgc gtgcagcagg 204420
tgtagagtca gtcgaactag tcctgcgaat atgcgaaaat gttctttatg aatggagacc 204480
agacacaatt gctttagcgg ggactgaaat cgtgactatg tgttcatgct ttcgaaaaga 204540
aaacaaccat ctacacgggg cgctatttgt ctacttattg cattagtcac gtctattttg 204600
aagtcttatt taactcgttc gatgtgaagc ccttccacac ctgtatgaag catctcctct 204660
cgggattcac cggacttcgt agcttgaaac aacctgtcct tttccctatg ctgaggcagc 204720
accaacaaat caatccatcg aagttcctat tgacatacat aaaaatatag ggatgccctt 204780
gatgattcgg atcatctcaa tcaattgatt gggaagagat tacttatgag caaaagggga 204840
ggacgaagtc gcaggagatt aggtattatt taaactgtca aaataaggga tatcgttgac 204900
tggtacaaga atagaattcc ttgcttacac tttctttcta ctggttggct taccctgtat 204960
ttcaagagta aataccgcag tgaggaatag cggttcctct ctttgtttgg tctaataaaa 205020
agattattca tcaccgcaac cactctcgct tagctaccac ttgtctttgc ttgcttactt 205080
ctaaagcaaa ccagactgaa gacagtagag aaagactttt tattacgtta ccagaatgc 205140 gatgccccaa ggcaagaaag tagcaatcgg ctttcaatcc tatgatttta ctcgaatagc 205200
taatatcaga gtagcagata tggttttagc ggaagctgct ttccccggat gcggaattga 205260
aagaaccatg cctttttttct tataaaagcc tcctcatcaa ctctctatct ttcgaaccca 205320
cctcaccgag cttaacgccc tgtggacttt tttacgaagg cctaacttga caggcccgga 205380
cggccgattc ataagggtct gagccttggt cggctgccct actaggtaag caagcgctc 205440 accgatttct ttacgtcttt tcgatcgtgc tttccgtgaa ttgaaagggg ggaattaatt 205500
atccagcaga gatggcatcc attagcttat tgtcggctct cactctggct catcatccag 205560
aggcgggttg agccccttgc acagcttttt agcagatgat tccaggcaag acaagatcag 205620
ggtcaatgaa gtgtttaagg acaatcaatg gcactgggat tgtctgcaca ctcaacctcc 205680
agactttgtg aagaacatca tctcctctat gcagcttaca ctcagtccag atgaagatga 205740
tttggcaatt ttgtctccaa ctgcatcagg taaattctct cttgcttcag cctggaatat 205800
gcttaaacat aaaaagggg tgtcctttt agattcaaag atatggcata aggatgtgcc 205860
ttttaaaatg gcatttctta cctggagagc agtccatgat aaactcccaa ctgatgggag 205920
agtgtccagg tttggtcatt ctcttttccc taaatgttat tgctgtgttg actctactgt 205980
gaactcaagc ttagaatctg ttgagcatct cttttgctct ggtgtttttg ctcaactggt 206040
ttgggaacat caattgttga atgctacttc ttaattggtg gaaccacaag gtccttaatc 206100
ctgtggcttc atatattact aaggtcatgc ctcctttggt ttgctgggag ctgtggaggt 206160
ccagatgcag caataaatat ggttctgaga accatcact caatagatcc aaggcattga 206220
tcacatactc cttatctcac ctgctgcatt tcagtttgg caaggttaga gtaggtgaga 206280
gctgggagag tatctgtcat ctgtgtgatg cttcaatgac ttagaaatct gtggctttgg 206340
ttaggtggat caagccacca ctgcttttg tcaagcttaa tagtgatggt agctgtagag 206400
atggtatttg tggaggtggt ggtgttgtca gagatagtat gggtgctctt attatggctt 206460
actccattcc cttgggtgct ggaaccagca actgggcaga agcaaaggcc atgcttttg 206520 gccttaaatg gtgcattgaa agaaggtaca ggttggtgat aggggagact gattccttat 206580
```

```
tgctgtcaag ctgcatttca ggagaagtga agtgatcccc acccgggaat cacgaacggg   206640
aatctaaata gaaaagaag gccctggcaa agcctctcct aggcacctaa gggcggataa    206700
tagcagcgga tatatcgctt tctgtttccg ctctatctgc caaggggaaa tcccggtaaa   206760
gggaaccccg accccgagaa gaccgtactc atgtgcaact aattcaatag gaccggttat   206820
gaacccaaga gaagagcgga taggagtact catactcaag gacaggaagc tctcacagcg   206880
tgaaggcaaa gaataactcc tattggaaga agagcgttta cgatcagagc tggaagagtg   206940
ggagggaatg aaatagcaat agccgctact tctgtctgcg gctatcttct cctattgatt   207000
aagcccttca aaggaatttc ttctatttct tctttctaaa ggcaaggcta agccatccgc   207060
ccttcattgc tgggtaaaag gggagacggt tcccaagggg tggctagttc gagtaagaga   207120
gacggataca gataaggtcc ttttttctga gagacccgct cttgactttt atcatcccca   207180
ctagtaagcg cagtggatgc tccttcatac agggacagag aggcgagtga tgggcactac   207240
tcatcataag aaagcagtca tgcagataga aagagtaaaa caatgactct gactaagtaa   207300
agagatgagg tttttttct catctatttt ccataccaca gctctagaca tgcgcccga    207360 ttcaaactat gtttcaatca taccaccctt gtggggtgtt cgcaattcac attaaagacc   207420 cttttccaaag gttgagtacc ttggctcggg taggtggtgc tgggttccgt gtccttggca   207480
ggctcgacca tcggagatcc gttcattacg aacgttttt ctcgatgtgg accaagctcc    207540
gacttccttt ttagctttgg ctcggaagag gccggccttt gagcccgtat ggaaggggga   207600
tcttggtttc tttttttaga aaagaaaccc caagagttac gtcttattcc cgaggagatg   207660
tttgatctcc ctagtctagg gacttcttgt aagggcccct tatttatgga atgggtaatg   207720
tgttaaagga tagcttaggt actgcagtag gtttggaatt agactacctt aatatcagac   207780
atcaaagaca acacagaatc caagtccaag acttgagtga taatgctaga gaacgtatcc   207840
ttcttggcaa ggcaaacaac ctttgccaag gttccgaagg aaagatagat ctgaactaac   207900
acaatcacta taatcatccc tcttgtatgt atataagttt ttcgatgaaa agagggggatt  207960 atcctacgat accctaggag cgtgtcagaa agatgggtac gcgaagtgag taatggtgaa   208020
attctccgcc acaagccctc tgaagcgagg atgcacactg ctttaaatag aaagcgcaat   208080
gcaacatccc cgaacgtcgg gccgtcctca ttaccgtaag agcaaacagg taagctccaa   208140
tacagaactc cttagtaaga ccgtcagcgg ctatcaagat cgctttgtta agcagtgacc   208200
ttaagaaccg agagtcttct aaaactctct gccacaaact aaagaattga attaccttgc   208260
gccggtatca tttcgcttga gccgggaact cctgtttacc ttgcgacagg tattccttct   208320
tatagatacc accgaaaaag cggaagacta agaagacttt tctttgtctc gtccacaccc   208380
aggaaagaaa agatcagatc agcaacggct ttcgagtaga ggatttttt gcttttaatt   208440 attccctcgg agttgagtta gagttagcag atgggatcta attcattaga ggaagggatg   208500
gtgattaact gatagaacct cttctcttct ttcaaatcgc atctctcaag tgagaagaaa   208560
aggcccccca cggagcggtg ggaaagcaag ggcgtagcag gaagaagaag tatgaaagca   208620
gcaaatcttt cctcctcggg ctgggatcac gaacgggaat ctaaatagaa aagaaggccc   208680
aggtcgagag ttcgctccct ctctctcagc taaggaaaga gatagagaat tcatgtacat   208740
cgctatttcc tgcggatcta tcgtatcctt acttctctct gattgtgatt tcccttgtgc   208800
cgtactatac cgctaaggaa aacaaacaag aaccaggcta ggctactcct cttccccttt   208860
ctgaatcaac ttgtccttgc gcttaccact tcttaaaact tgcgagcgag tgtcgatcgc   208920
tcctttgcct gggcaagatc tgacgactcc tgcccaaggc gggttacgaa ttcagattag   208980
```

```
ctactgccaa agaggccagg aacgagcttc cgctttatct aaagaaaaaa cctcttcctt  209040
tctctcttcc tgatcagcgg attcagagtg atcaggtgaa gccccccttc tcgttggatg  209100
accggcccct tcttagactt ggtgaactcc tgtcgcgatg aattaaactc cgttccatgc  209160
cccgctgctt gtcaatcaca tcggaaagtc gttgggtcgg cggagacctc tttcggcaaa  209220
gaattatatc acaaagaaag ccccaactag ggactaccac ttataggagt cttctttgct  209280
agtagaatgc cccccacgag aagaaagaat agtgggatgc tcacgctctc gttggacgtg  209340
acagtcagtt acagtgggta aactaacgaa gggaagaatt ttatttcatc acagaattga  209400
atcgggtctc atcccttcga ttcctcgctg catacttcaa tgagaaagga aaagagcttt  209460
gttgcgtgct tcttcgggtg tggttgcaag atctcgcttt cagttcgaaa atgtgtacgt  209520
agcttccttg tacaatagct ctctctctct gagagagtga tcgggaagca ttctctcttc  209580
ccctccgtat ctgaccctga cccacgctct agccctcttt cgtcgtccaa gtcgcatacc  209640
tcctaaacag tctatttggt ttttaaacgc gatctattta actgattaac tgtgaactag  209700
gtgggacttg attctttttt tgctgaaaag agaaggtacg taggcagctc tcctaaaaaa  209760
gagtgaagtt ccgcccgcgt ttgaaggcta gctcctgctt cggagcttca tccccacatc  209820
tcacatattg gaaaggcaa acaaaaaagg ggaactcagt caatagacaa agaaaaaaac  209880
ggatatgtta cacaaaaaca atccaatctt tgtctttcta aggattgatt tttcttgtcg  209940
tagttcatat tcatattcaa gttggaaaaa ttcttctttt tcttcttatt gtggaaacgg  210000
agggaaggca aagtccgta ggaggacaac tatcaatatt agctgacagg tgacgaggat  210060
catatagttt gagagctgga tcgagtttga aagcgtggtt atggcggaat ggaatgtgcc  210120
ctatcccgcg aaggagagga acgaagtaac tcgacaaaaa gtagaggaac ctgtcatgtg  210180
aggaacttag gtcaaaacta cgctctttca gccggtttag tatagtagta gtttcaaatc  210240
aatgcaagcc aatggaaacc cccccttcac ccccaaaacc tatactcatt cgtcttttac  210300
ttgtgcgttt acaacatcca ttgcttctga ctatgtcgat gaaatgggac cgcgaagaca  210360
acccaccact agagcttgct ttgctctcgc tccgctcgct cccacctgtc ttctttccca  210420
ctatagtgaa agatctttca cttcaccata gcaggaacct cgctaacctt ctcggccagt  210480
tactctaatc taaccacagg gatcccctat gagaactctg tcaagccctc gctaagaggt  210540
agaattggct aaaagcatcg tacttcttcc catagctaag gatgtatcat tatcagaatc  210600
ttggtcttcc gtctacggct tgtagaagta gttttaggat gaggttagac ctcgagcttg  210660
ctgacataac tacttcccta aatctagctc ttgagggaac gagcgaaatg aaatgaagcg  210720
agtgataacc aaaaggaacg agcggaattc tgtagcgata gggacatgta gctaagggag  210780
cgcggggtgc tggttctaat cccttcttcc gactgttata gatgctaaat gctaagaag  210840
aggagttcta aatttatatg gcatcctttg tgacagacga ttcccactct ttcttatact  210900
attatatctg gccatctatc tctacttctc ttatatactc gcctttcggt aactcgttat  210960
actagttaga cttacttcaa acgaacggaa taaatgagtt gaacgaatag ctcttcgagc  211020
tattcgttca actcatttcg tttattccac tcgcttcatc ggatagtgtt ctaattccaa  211080
ggctagtgtg gcctgcctta cctgaatcta tctcttcggg tcgttgcaat ctttctgttg  211140
aaaagtatcc ttcttcgggt attattgata ttggcataga acagagcttc aggtcgaact  211200
agtgggttgg gtggcaagga gactattagg gaaaacatac attcgttgga taggtagctg  211260
gatttaatct aattgctgat tccgacggaa gccataggag ttgtattcga gtaagagcgc  211320
```

-continued
gggaacccga agagaaatac ggatgagtgc aaaaagggca aacgaagggt acgagtgaaa 211380
tgaaattcaa tgcccgtagc gagtcaaaaa gcaggggccg aagacttggt tcttagccgt 211440
gaaaaaatag gcgaataagc atcctttgcg gcgcttgccc ttaggaaagt ctattcagtt 211500
cgattccgcg atgaggccat gcatataaaa acaaagcaag agaagctaca gaaagcgaat 211560
tctttaataa tattttagac cggcgtaaca agaacaagct gaagaataga atttagatct 211620
ttcctccgct tcggattcat tcattagaaa gagttcccta cgccgcctag tcgctatagg 211680
agacacgtgt acaccgccgc gtctgaaatc aaagaacgga ataccttctg cggctatcat 211740
ggctagggta ataattcgta tatggaaacg ccgcttcctc tttatccttt attcgattta 211800
aggatagaag aaggataggg aatacggcct tgaaggcgat gaaaaaagat gataatatag 211860
gaacgcggca aactctttca agaaattagc atcctcagct acagtggtaa aatctctata 211920
ggcaagtagc ccatgatttt ccaattatag ctcgggccga atgccctata gctttggagt 211980
ttccaccctt ctctgaaggt ggtgatttgg ctgtagaagc ctaggctaat gaattgggga 212040
ggtacgcaag cgagggaaaa agctttgatg aagcaaagtg taaagctgag gcatattttt 212100
aaaacttgca attccgactc ttctctcaaa gggtcttggt ctcggtccgg tcttttcttc 212160
cttggtctga cgcttgcgtc ttcctttcag cgaagaacat ccatccttgg ggaggtcacc 212220
tctaaaggcc tataggtccg tctatcgata ggcagtcttt cttttctttc tcttacgggt 212280
cggcaaagtc tgattctatt ggaaaaaagg gccggtctct tcggcgaggg cttgacgcca 212340
tctgaagcgt cagacgatgc ttggcattcc tgaaatctat ctctttgggt gatgatgcta 212400
aaagcacagg tctatacttc ggcacagacc tcttttgaga tttaatgtag gaaagtaaag 212460
tgctagtatt tcttagagct tggctttctc cacaaccagt cttctattgg ggcaccatat 212520
agaggttcta gaggaaagaa gggagctaaa ggagtacgaa gtccgatcag cgtcttcaag 212580
agcatgattc tataggaaag catttaagag ggcaaaaggt ctgatgaagt tgtgcaactg 212640
acctctatcc tttgagaacg atgtcaaggc cttgaaaggc cctttatggc taatgctgca 212700
tccgaagcta ggaaaagggc gcccttgact acgtcttttc tttatttctc attgccatct 212760
tccgcgtctg aaataagaca ataatccttg gaaaggtcac aagtccccaa gggaaggaag 212820
tcgtgggata ttcaagaaaa gcatcctaag cgaattcatt gtctagggaa gtttctcttt 212880
gggggctgcc tatcggtact cccatgaact gaacacatac ctattcgatc taatggtgcg 212940
aggtcaaaag tcgataaagg caggggtagg agaaggagag agaggtgcgc tttacccttt 213000
gagatatcca agaagtttcg actttcaaga gattgaaaga ttttagtctt atttcatagg 213060
ctgcaacaag ggattattaa aagaatgccg tgctttcatc tattagagaa gtatgcccct 213120
agggaaggga gaactgatct tttcaaacga aagccttaga gttggaaggg actatcctaa 213180
acttttatta ataatcttct tttggccctt gattggactt agagttgggg atagaagacc 213240
cgccgcttta ccttgaaatt ggaatcggaa agggcgtaat cgaagaaatt tcaatcacaa 213300
gaaagaaaga ctttcggaac aaaagacaaa gcttcaatta aacactcctt ttagctacag 213360
gaactcctat tacatttgaa ttcaaaatat cttctataag ggtatgactt tttctcaagg 213420
atgggaagcc ctcacttgac ataatatctt agtgggaagg taaaagactt agctgaacgt 213480
tagcgaagcg ctggtacaat gagattcttc atagaaaaga aagaaggaat gcaccgagag 213540
cccttcctct tccacggatt ccattagagc cattttgaat ggtatggcct tagaccaatg 213600
cgctttcagg tcgggtaaat ctagccgtaa cagtcagttc aataggactt agaaaaaaaa 213660
gcgaaaacga aagccttcat tcagctccgg cataagaagg agcgagaagc cactccgact 213720


```
aaaaggaaag gatcacttag ggagcgggta aagcaaagag tggaaagggc aagcttcaca 213780
aatcatgctt tcaaacttgc cgaagttctt ctaaaaaaat aatttatagt aaaccaaggg 213840
aatcgtatca tccatggcga gtgctatcgt atactttcga atgcttgctc agagtcttcg 213900
ttctaggtta gggttacttt cactcgcttt cgagaaccta atctctttca tggtgaaaat 213960
tgcccgagtg catcaaacaa ctcttggagg agaacaaaga catcatgccg gacgagttgc 214020
ccatgcgtct accactgagg cgggagatag accatcaaat tgagttggaa cctggtacga 214080
aaccacccgc ctttgcacca tataggatgg cacccccgga atttgaagag ttgaggaagc 214140
aactcaaaga gttacttgag tccgggcaga ttcgaccatc caaagcacct tttggcgccc 214200
cagtactctt ccaaacaaaa gaagcatgat ggatcattac gactgtgcat cgactatcgc 214260
gcactaaaaa agataactgt gaagaaaaaa tatcctattc ccttgatcgc cgacttgttc 214320
gatagattgg ggaaagccaa gttcttcacg aaggtagatt tgcgcaaagg atattatatt 214380
accaagtgcg catagccgaa ggagatgagc caagaccac gtgcctaaca aggtatggag 214440
cgttcgagtg gctcgtgatg ccgttcgggt taactaacgc accagccacg ttttgcactc 214500
ttatgaataa gattttccag ccatacctg atgagttcgt ggtggtatac ttggatgaca 214560
tagtcatttt tagtaaaacc ctggaggagc acgtggagca tctacgtaaa gtcttccaac 214620
tactaaggga gaatgaactt tacatcaaga aagagaagtg ctcgttcgct aaggaggagg 214680
tacacttctt ggggcatgtc ataagccaaa tcaagatgga cgaggccaag gtgtctgcca 214740
taagggagtg ggaggtgcct acttccgtga ccgagttgcg gtcatttctg gggctcgtga 214800
actactatcg tcgatttaga aagggggtatt ccgccattgc tgcacccta accgacttgt 214860 tgaagaagaa ccgtccttgg gagtggacgg agagcagcca aagagccttt gaagagttga 214920
aggccgcctc tatgtgccaa aatgggggaa cttaaggcgc actcttataa agcagtgtca 214980
tgatacaaag tgggctggtc atccggggca acaacgcacg cgagcactct tggagtcggc 215040
atattattgg ccgcaaatga gagacgagat cgaaggctac gtgcggactt gtcttatttg 215100
ccaacaagac aaagtggaga acaaggagcc cggtggactt ttggaacctc taccagtggc 215160
ggagcgacca tgggatagtg tcacgatgga cttcatcacg gcactaccat tgtccgaagg 215220
gtatggttcc actatggtcg tggttgatag attctcgaag tatgcaacct tcattcccgc 215280
accaccggat tgcaaggccg aagaagcagc tcgtttgttc cttaagaacg tggtaaagta 215340
ttggggacta aaacggacta tcataagtga ccgagacccg cgcttcacgg gtaagttttg 215400
gacggagctg tttcaactct tgggttcgga gttgcacttc tccacgagtt tccacccaca 215460
gacagatggc caaaccgaga gggtaaatgc catacttgag tcttacttga ggcactttgt 215520
gagtgcaaac cagcgggatt gggctaggct tcttgatgtg gcacaattct cctagaactt 215580
gcaaaggagc gaagctacgg ggcgtacacc gttcgagtta gcaacggggc aacaaccaca 215640
tactcccctt tggtgagttc ttacaaagga agaagtcccg gagcatatcg cttggcaaag 215700
acttgggaag aatataccga caccgcccgc tcatacttat agaaggccgc atacaagatg 215760
aggaagttcg cggataagaa gaggcgcccc gtggactaca aggtaggaga ctttgtgatg 215820
gtgaagctta ataggacaca attcaagaca cttcgaaaac atcacaaagg gctcttacgg 215880
aggtacgaag gaccattcga gatcgtggca aaagttggta agatcccctta tcgactcaaa 215940 tagccaccac acttaaaggt ccaccctgtc ttccatgcaa gtcttttcaa accttatcat 216000
gaagacaagg aggatccaag ccgagggttg tcatcgcgcg cacctatggc cgtaaccgca 216060
```

```
tcatatgaca aggacattga agccatcatt gacaagaggg tcgtccgttc aagtggcaag  216120
aagccaagca cggagtactt ggtcgtatgg aaggggttgc cggcgcgaga agctacttgg  216180
gagaaagaaa gagactattg gcaattccga gaccaagtcc aagcatactt ggggagtact  216240
tgcgccgagg acgtcgcaac aataggtggg ggagagtgtc acaacccgct caaaacaccc  216300
caattttccg accaacacaa tgtgccaaag atagccgacg ggagcgcgac ttatgtccgt  216360
ggccgtatgc ccgaccatgc cgaggtgagc acggatggca tggaacatgt tcacaaggat  216420
cttggcatga tggaaggcct aggagtatcg tgggagcacg agggtgcatg tggaagagtg  216480
gccaagacaa tgccaagaac actagaggcc atggaagcac aatgttgcgc tatggaaggt  216540
tctagaatgg cctagcgtgg ccttgccctt gggcaatagg ggctgcccaa tgccccaccg  216600
acttaggggc ctattccacc gactttaagg cttcaagaac tctcctataa aagaaggat   216660 agacaaagaa aagagaaagg gattctatcc tcgtccaacc aagataatat cgattgctcg  216720
cccgacatca gcctcttcac ccaccggggt ggaacgactc ttaacgaggt tgatggactt  216780
gacttttcct ttagcctctc ggcttcgaga agccgtgggc ccagtagtgc tttcttaaag  216840
ccggtaacct gatcgacgta agaaccgatc tcaagctgga tgagaaggca aataaagact  216900
agtgagaata gccgtaattc aactaggcct tgaatcagtg gtttacagag agaattagtc  216960
atctgcttac ggctaatctg ctcttcgaat cttatcttag aataggttgg aacttttaa   217020 acatgagagg cttcttcaga aagtacgcat ttcttgctct aagtccgctg ggttggatcg  217080
aactagttgg tttggcagga agataatggc ataaagaag cattccactt ttggaaagag   217140
aagagtcagt ctgattctag atccctctgt cttgcattgg gttaactgga gcttagataa  217200
agcgataggc agaagagaga gaattagtat gtctttatag actgactttc ctcgcatcaa  217260
agctttccag ttctcttcct ttatgaagaa aggaaaggct tgttatcgac gaagaagatc  217320
tttatactgt tcatcctaag aaaagaagtt ttcttttcac tcggtacaac tattcttatt  217380
ctatgctagc atagcatgct tctacttatg ttgcaaattc cggatcagga agaatccttt  217440
cttattcgtt gatgccagtc taaaaatccg tacttgttga ctaaaaggct ttcggctttc  217500
tttctagctt gaagcttaag ggctaaggga aattcatcct tggatcaatg aaatagttga  217560
attagctaag atgcaagaag gaacctcttc tcttattgaa attactttag ctttaggaag  217620
tgccaaagct ttctccttcg atccgatcct ttctgtgacc catggtctgt aaatgaactt  217680
attctctctt cgtctcttgc ctttgaatcg gatattccga tgaaagcgga ttctctttcc  217740
gtccctcgtc atcgagagga agagtcgcta tctatctatc catataccta tcaacaaatg  217800
tggttccagg gatcggtcga ttgcccctca ccagcagcta gaggaggaga aaggaatgat  217860
gtcccggcct gggcacctat cagccaacta ttccttttag gaatgaaaag aagaaaggat  217920
ggtcgtagat cactgatgtc gaattcagga aaaagatcat atgtgaaaga atcgtcagat  217980
tatgggttcc cggagtagac ggttttgaat ggagaatgaa tgaaatagaa tagtctggga  218040
gaatcgtatg ataggggaag tgcggagcct cccacttgtc tgggttacca ggctggctaa  218100
agtgactatg aatttatatc aatgtcggga tagacagagg tctaggatag tacgctgtcg  218160
gagtgagacc ggggtagagt aaggaagtta gaccgaaatg aacgactcaa ttcctctaga  218220
agaaaggaga gagaaagaag aaccaattca atgaaagaat atcttattta ctagaatcgg  218280
ttgctactag tccgggttac ctcagagata gagccattag gggagaaaaa agaacctagt  218340
tagtgcacga aatgtcctgc taacatagga gcactcctac taagaaatgg aagagcaaat  218400
ttctttcttt ggggtcaaag ggctattcta ttacaaaaaa agttatggac tcggatatga  218460
```

```
tccttctaat gagagttcct tggggatata tgaattagtg gacatatatca agaacgaccc  218520
attttcttac acaagcattt ctgtactcag atcggtaggt atggaggtct ttcctaacct  218580
ctttagttag acaatcagtt atatacggac attcaacaag ataacccga aaggaggcaa  218640
ccccgttcac tccgacaaga aaggtgtcaa gtctgaaagc caagccctcg taccagagcg  218700
ctctcataag tcaaataaag tattcattcc ttcatttatc catatattaa acaccctgtc  218760
tttgaagctt cttgcaaaaa gtcgttcgac gacacaatgc ctcacctgcc ctctgctaca  218820
catctctttc gttcgcccta gacccaccca ccaaagggaa ctctgccctt ttcaaccaag  218880
gaacgagcaa gaacgctttg ctcctggggc tcgtctacac cacatcgact agcgcttagg  218940
cttctcttta tgttccaacg cggcctttga ttgattcgta aacctttccc cgatcgaggg  219000
cttcctatct cctcagacgg tgggaaaagg cgattctctt tagtcaaaga ggccttctcg  219060
tggatttcgc cttttttgat ggctatctcg tgcctctcaa ttcccactgc aagcttggga  219120
agtgccttgc tttctcgatc agccaagccc ttgcttttga atagcaggaa ttcgaaaggg  219180
gaaagaccct gctaatacct tttaggcact agacagaggc tgctaggaag attacataaa  219240
aaagtgccga gttggcagct ctggaagcgc tgatagcttt tcactccctt tccctcatag  219300
ctgaatagta ggtaataaaa cctagtaact gaaataccaa gtaatctcag gcctaaaggg  219360
tactcagtta agggaaatta cataagtagg aatataagcc gaaacatccc cgattgagtt  219420
tcaactattg gtaaggcggt catacttcct tcacctaaac tagaacctaa tttagcggct  219480
cttttccaaaa ggcgtgaatg caaataaaaa acatctcctg gataagcttc acgcccgggc  219540
ggtcttcgta atagaagaga catttggcga taagcttgtg cttgtttgga gggatcatca  219600
taaatgatta aagtgtgtcg ttcacgatac ataaaatatt cagccagagc tgctcctgta  219660
taaggagcaa ggtattgtaa tgtagcaggg gaatctgccg cttcggctac cacaatagtg  219720
tattccatcg ctcccctttc ctgtaaagta gttactacct gggccacaga agatgctttt  219780
tgcccaatag ctacataaac acatattaca ttttgacctt gttgattgag aatcgtatct  219840
gtggctactg ctgttttacc ggtctgtctg tccccaataa ttaattctcg ctgaccacgt  219900
cctataggga tcatcgaatc aatagcaata agcccggttt gaagaggctc atatacgaa  219960
cggcgcgaaa taataccggg ggcggcagat tcaattaatc gaaattcgga agctggaatt  220020
tcacctctac catcaatagg tttagccagc gcatttacaa cacgacccaa ataggcctca  220080
ctcacgggga tctgtgtcgg ggattgaata taggaagacc aatagtggaa ttgaatcgga  220140
ttctcgctca aagcctattc tcgaggcagt ctttttctctt ctagcggaat tcccctttcac  220200
ttccattgag attacgacag attacacact gccactgacc tgagccatgt aaaatattgc  220260
aataaagatt tgcatacgct ccacaattat ggcaacgatg gggatcgcgt tgtatcatct  220320
gaggcccagg tgacatctcc cttccagtgg aaactaatgc accaaagccc aaacttggaa  220380
tatttgcaag ttttttctgt ttcaacacct tgtgagcgga aatagaaca tttgagatt  220440
ccgtagcagg tgtccaatct tcagtagcat cagaactttg gtgatgcagc tcgacagacc  220500
catttgaaaa atggggaggt gatgatgtgg gcagagatga agccgacgaa taggcaagag  220560
gctgagggt ggctggagaa gttctgaatg gcacggcagc aggttggagc ggcgacgaaa  220620
atacaggagg accaggtgga gtgctgagat gaggtgcagg gcttccagtt ctaactccat  220680
tagccggtga tggtaaattg ggggtcttga tggacggaga aggaatctgg ttcggttgta  220740
caattggtgg aggaaatatg ggacctgttg atgacgggaa aggaggagga ctaaatactg  220800
```

```
tttctgggcg aggtgactga gtcccttgct gagagggtgg aatggtgaca gagtacccaa   220860
ctgaggattc aggttgcttc gccatcaaaa tggcatcaaa caccagcttt tcaagaattt   220920
caaaaaaaaa aacgaaaaat aaagccaaga acctagagga ttgaaaattg gaaagaggcg   220980
aagccctcag cagtcacatc caagatctcc tcggagactc agaatcgatc gcacccaagt   221040
cagaattaat cgagatgggc ctttgctcca ggatgattaa tctgatgaca aataatgaaa   221100
gggaaagctt atattttggc atcaaaaaag tgaagatcgc cctgaattgg atcctttgag   221160
ggtctcagag agagggcaag tacaagagga actcaaagta aaaactagac tttgtcttgc   221220
aaactgactt cagccatagt gaataggga agctgctcac tttgatagcc ctacccctagt   221280 gtatgcactc aagcagagta gacggcacgc gtcaccaagc ataccgcccg aggttaaggg   221340
ttcatcagcg aatggagtta ggcccatttc ctagcctagt tttaagcaga acagcaccat   221400
cctagtccag agcagtactt ctcttatggg ctcgaggcaa gacaagcagc ccgcttcgct   221460
tcctcaattg ctcaaggaac aagatgaaat aatgcttttg tggaacgtct tcaggcgagg   221520 cttttgggatt aaaccaatat cttctcttatttt gaagcagtgt gcggtatgcc ttcaattcaa   221580
caagcatacg ctggccagaa tagtactgag atttccgtct ctcttttagct gactcgctcg   221640 ggatatcctc gcatcattcc ggcatttcac cgtaagagga tccttaaagg tgattccaaa   221700
agtgatttgc tagtggtact tgtcgctttt ctccgaaggc tattgaatta gctaaaccac   221760
gtgggtggcg gttgtccatg gatgtcccctt gggcctattc ttcatcggat acgagagcag   221820
gaagagcttc tattccatca acacaagtta ttccagcaac agctcttact ctaacagaac   221880
taggaccgtc aactccaact gtccttatag ataggcgaaa gccacctcct tgacagatta   221940
cggagctacc cagcttctct taatgccaag tagtagaaaa accgctttcc cgagctggct   222000
ttatcgagtt aacgaggtaa caagcggaac cttgcgcaaa gacatacccg gcatactaag   222060
atgaatcatc taagttcccc gccgtcttga ttgatgagct cgaacagccg gttgatggca   222120
atgaatgggt gaagcaggga aggctctgac tttgaagccc gggctcaggc aataaagata   222180
aagaggcgat caagaaagtc acgactgtct gtcccttcct caaagcaagg agcggaaccc   222240
tatgatgact cactttaggt tgaacctgat ctgagatctc tcccgtcttc aaaaaacaag   222300
caatgaagac aactctcacc ttcgattgat agatgaagag ccccgccaaa ccaatgaaag   222360
ttgagaaaga tttggcatct tgaaaggcag ctaagagcgc atctggtctt ccacaacaca   222420
ctggggatat tctcatggac gccagctgga gaggttctta atagtttgtt ccgagatgtc   222480
agtctgcaaa gcatcatctt catctctttc atcgcacgta ggctcaacat ccaagttagc   222540
gtaacgaggc ccaaactatt ctggttggat gaaccaactt gagatgttaa aatattccat   222600
cggcatccct ggtatagtga tagaataata ttaggcacat caagcctaac taggcttgct   222660
tctatcttta tagatcggtg tatgacaaag atatatatgg tctaacagct ccctcaagct   222720
tcgtgtagtt cctcccccttc agcttggacc gaagaggact tagcagaaga taagccttg   222780 gtttggtaaa gacatctgcc aattggtaca tgctggaaac atagcatacc cgaacttcac   222840
cacgcgacac tctcaccggg taaatccgga gaggggaac ttattctaag atagaataag   222900
aataagcaga attgcttaag taaggtagtg gccataaggc ttttcttttt ttcggtatgc   222960
cgctccgcga gcaaggagtg ccacgcacga gcggagcaaa aagaaagcaa ggggaattct   223020
tctctttttt ggggagaaat cctttgattg cgtattgaat atggatccat gtctttcttg   223080
ttccactagc taagaccaaa ttctcacatg tccctttcct tattcaaacc ttcttttttg   223140
atgtcaaaga ccagaagcta cgcgcaaatt ctcattggat ctcggttgtt cttaacagcg   223200
```

```
atggctattc atttaagtct tcgggtagca ccactagatc ttcaacaagg tggaaattct   223260
cgtattccgt atgtacatgt tcctgcggct cggatgagta ttcttgttta tatcgttacg   223320
gctataaaca ctttttttgtt cctattaaca aaacatcccc tttttcttcg ctcttccgga   223380
accggtacag aaataggtgc ttttttctacg ttgtttacct tagttactgg ggggtttcgg   223440
ggaagaccta tgtggggcac cttttgggtg tgggatgctc gtttaacctc tgtattcatc   223500
ttgttcctta tttacctggg tgcactgcgt tttcaaaagc tttctgtcga accggctcct   223560
atttcaatcc gtgctggacc gatcgatata ccaataatca agtcttcagt caactggtgg   223620
aatacattgc atcaacctgg gagcattagc cgatctggta catcaataca tgttcctatg   223680
cccattccaa tcttgtctaa ctttgctaac tcccccttct caacccgtat cttgttcgtt   223740
ctggaaacac gtcttcctat tccatctttt ctcgaatctc cttaacgga agaaatagaa    223800 gctcgagaag gaataccaaa acctatttca ctcgctgagt cttttttgcat ccatggctga  223860 atggttaaag caccttttcct agtaaagggg caaattcgta ggttcgattc ctgctggatg  223920 ttttttatagg atcgggaaag aatatacatg agagtcagtg tgaggagaaa gagctttccc  223980 ttttttttgtt cttctagacc ttgccttttc agctatcact tcttagatgg agctctgacg   224040
ggagacctat gaacgccttg gctctaagcc gtacgaaccc cctttcaatg ccgtattaag   224100
ccaggcggaa actttctttc atgctatagc gtgcttttga gcgcattcat tgctttgagg   224160
gattggttgt gataagcaaa caaggaagcg ttgagttggg cgcgtatggg ttcccggcct   224220
tgattgcttt ttaccttaaa aaaaaagaa atattcgttt ataccattga cattgataat    224280
tatagaaagt tggatagtat gctttgatga atagcaatgg tagttaaaag cattcctttc   224340
ctagggtcaa gataggtctc ttcccctctt cccttattcc tgctcttccc gcttcagttg   224400
atggaaaagc attgaataag gcaaggaagg ggtcgagaca gtgttagcta caatctctgc   224460
ccttagctta gctaaaagga taaagtgaag ctctataact cgaacgcttg gattcgtcta   224520
tcttagagta ggttggcttg ttagatctat atgaactagg agtcatttag ttggcttctc   224580
cgtcgttaga gctttctgtc cgaacttttct tactcttgta agctcgtctt gtcctatcta   224640
tgctcactac ctcgttgtct gacaagcagt ttccctcatc tttctctttc agaagagcct   224700
actttcgccc atggttcgcg tcgctatcgt gcttggtccg ttcgctactc tcttttcagc   224760
cattattgta tgcgtgtagc ctaagtctac ccttcgattg gactttctcc agatcctttg   224820 acaccgctc atcttacttc ccattctggt aggttggtgc gtgatgattc gtggagtaca   224880
aggctctctc tggttgggta cgtaggctgg tcctgcagmt tgtggaggtg accagcgctg  224940
catgcccgaa tggaatattg actatcccgt agaactgacc tagtcgctcg tsaaggagct  225000
ggtcattatg gaatatacta tatgtaggcg caggtcttcc tagagcgaac ctccatgtgt  225060
tttatattaa acatataaaa atcaacagtg gaagaggcac tggttgtgcg agatcattat   225120
gactggagga agcccattcg acaaccataa taggctctat aaccggatca cgcacgctaa   225180
gaacacagcg gattagaggg gacaagaggt tccactcatc aaagtgtgag acgcaaggct  225240
tctgcctgga agtaagctac cctctttgcc actttcaaat caataataac gatgtcatcg  225300
atattccaat ccgatctttt cttcttcac ccaagtaggt aaggtgctct ataggtatcc    225360
ccccgtagcc ctaaaatcga aaaagccca tggttgagtg agcatagagc tctgcccttt   225420
tctttccttt tgaagccgct ttcctccttt ccagctttag tgttttgcta tacattttaa   225480
tgtgttaagc atagtggcat gctctgtagc cggagtaaga aagattcaag gagcgcaggg  225540
```

```
ggatctgctt ttacgagtga tctctctcgc tttcttaagg aatttctaga gtcatatggc   225600
atggctatgg tttccactct tgtgagttcc aattttttct ttggttcgct ttcccttggg   225660
ctcggttgcc cttctttcta tttgctgcag taaatgagac tgggagttgg atttccttta   225720
tgactttcgc tccgctcttc ccacggatat ttcaaagacc ggtaattccc ttgcatcgga   225780
ttcctcgttc tattcctcca aggctcaaag acctcacagc tgattctcaa gaacttgcta   225840
tttcatattc tcttagatag gctatcttcc gattcaatgc catcaaaatg tacttagcat   225900
gcctactttt ccttattagt tcaaatagcc ctagctagat tctcaagctc ggattcaccc   225960
gcaaagcaaa gatcaaaaag ctcttttca agctgcttat tcgaaaacag taagagcttt   226020
tgagtgcaca acttattctt tcactcctgt tctacgatta ccagtggtct cagcgctaac   226080
tggcaaaggc aaacttcttt cagggcatct tagttccttc ccttaggtct aggctaagcc   226140
ttaacaatcc cttcttgaag aaaaacgatt ctgtaacaac tcaacctaag agctgatatg   226200
tctccaaccg cggatacgag acctctaaga acggttattt cagttattcc caaagctaat   226260
tcaattgcaa agagaacagc ggcaacagat atggcaacaa gaggatgata aaccttctcc   226320
ccttaaccgc tggactcgaa ccctaactct acaccgtcgc cttcaactgg cacaaaagga   226380
ataggaaagt catgacctga caaaaatgga aagacttttc ttctttatcg ccagactcga   226440
tcacaagcag gggaggttca attgatctat ctacgtaaag ggagctaatt caatattcct   226500
cggtgagagg aaagaagcct cggacaacat tagcctttct tgtctttctt cactgcaaga   226560
tatccaaata agtttatcgc tcgttcgtgt ggggagccac tcaataacgc ggctagggca   226620
atcttcaacg atcagcccgg tgcttcagga tatggatcac ggatacccgt tcccttcaa   226680 gaagattagg atatgtcgtc taggcctcca ggatgcaagg aggggatag aatggatta   226740 agagttcgag aatgcctctc attacgacta tgatcaagtt tgtacctctt attgtgtcgc   226800
ggaacagcaa gagtcatccg actcttagga acctccatac gaggatgcta aaaaaaagtc   226860
ctattgaggt aagccaatat aaggatccca tacttagcaa ccaagaacaa acagacttcg   226920
gtcaggagtc ggcggatgat gccggatatg cctcgaggac ggcggccaac ctacagtaga   226980
cgaatttaaa gaaagaaaga tgggcgatga gactgaccag cgacctatat tcatcgcgaa   227040
ggctctcccc gatagagtat cagaaagccc taagctaagt agaagaaaga aatgaggtta   227100
gagctgaacc ggaaacatct tacactacac taggtacccc atatagagtg ccaaggagaa   227160
aaggattgag aaaggcagtg atcatcatca attccaaatt tctttcaatg gcccttcttc   227220
ctaaacgaaa ccttgctttt tagaccaaag atgttggata atctgagctg cttatcgagg   227280 gttttttcttt aattcccttt tcgcccctt tttatattat ataggatatt caaaaatgag   227340
ttcaaataag actcataccct atctcctcgc tctctttctt tatctgtctt aaaagtggta   227400
aattttagct atttggggag agtccagtcc cgctggaaga ggtagtagca tccccgtgct   227460
atgaacaaca aatgaatctc aatgaataaa gttgagtacg ttgacaaaaa atccacttta   227520
atagctggac tctacgccaa ccttatctta cgatctgtct ttctcctatc tacgtaatta   227580 catatttgt ttggtccagg agtagttcgt gagacatgga aagccttctt tggcccccata  227640 cgcgtgaatc atagcgatag ggaagctggg tactgcttcg ctttcaatta cgactcgagg   227700
tcgggtgcaa aggccgtggg caagatacat acctcgctag ttgaacgaaa tatagaattt   227760
cttatctaaa taaaaggag ttcaaacttt tgagaggcgg aatcgatcct gcaccttagt   227820
ctacaggtgg gtcaaaatct gaccttgttt tcgccttaaa ccccccgcgct ccatctatca   227880 ttgatgctat caaaaactag atttccaata tccaaaattt ccatagaaag agttttgctt   227940
```

```
cccttgtgtg tgaaaatgaa gaatccatac tagtaagagc tccgtcgtat cctgccaaga   228000
caggactccc ctttactcgt aaatagttca atgcctttt ttaagaagat tctaaaggcg    228060
ccgctatagc ttaatacaaa gaaatccatt cacatagtaa atggaagatg cctctgtaac  228120
tctacaatgc ttgggcttc aaagcttagt gcgaatggtg ggaaaattca tagctttta    228180 aaatcaaacc aagagtactc agtccgccct cggtcaggag aattttgcga aatcaatgct  228240
cggagaaaac taccgaatga aggttcagct taaattgaga gggaaggagg tgctgatcaa  228300
ggctacttgg atcttgagag tagtaaagta ctctgcttac cgctaaaagt acgttagttt  228360
tcggacttaa tctgaatgca cagcgtgctg ttggtgccat tcatgcagct tcttcctctt  228420
attcttcccg aataggacgg aaacgagaaa atgttagacc caggacgagg ctactgccac  228480
tgggaaggtt aaatatatgg atagtcttct tattaatgag gagtgatcga cttggtgatt  228540
ataatagatg ccactactta ttattctttt tgcggacact tgcaaaacct tcgataaaca  228600
gcgcctatgg actttgagac atggagcgca ggaaagaagg acaggagtgg ttccactagc  228660
cgatgcttaa gcgtcagccc ttgcttccac ttcaatgttg ctaaaccgct agccgcttcc  228720
tatgctgcat tgctcacttt gacagagttc cctcgtgctt ttcctcaacg ggaagcacat  228780
cgagatctct gtggttgcac tctttaaaaa attcttttt tgtttagaat gtcccacagt   228840
tactctctct caaatttgtg atttgagttg ctgtaccata cagtctttcc gcttaaagaa  228900
ttctattttc tctagctacg tcacagtgtc ctttcctttc gcgtactcct ctgtctttt    228960 cctatcctct ctcttcaatt accgagaccc gtacatacta agatctaggt agctcatctc   229020
cttctaagaa gtcagatctc cttcctatat tctaaaaaga ataagagccc ttttaaccc   229080 ttcaattgta aagaaaggcc tcatttagga gcgctgtttt catccaacta tcaatctcgt  229140
aagagaataa agcgtggaaa agaaaggttt tgattcgctt tataaagaag aaagcttttt  229200
ccggttctaa caggctaatt aaattagaaa gcgtctgttc acgtcagggt ccgaaggaga  229260
tgtacttgct tttccttttt tgcgtcgaga ttgggttggt gttcagtgta ccgcttgtct  229320
agcctatgct ttgcatgaac atctcaatgt ccaagataaa aagaacgagg ggaagaatcg  229380
acgaggccag tgttctcgaa gagaaaatcg tgatggaaaa agcgtgagga gaattcgaaa  229440
gtcgatatgt tagaaggtgt cacaaatgaa gaatgcgttg gaggttggtt gaagatgatc  229500
ttacgcggcg ttcagaacca gtcttgaagt gaatgaagaa aagaagcgtt gttatgaaaa  229560
agtttccatt tctttcccaa ataataagaa cttttggtgc tgtagtcact tttgcctttg  229620
gacgttttct tttttcggg gcagaaagaa cgatcgcgcc tagctggatc cttctctttc   229680
tcttttgtct tatatttatg attcgggcaa aagaagaac aagaagaaaa aggagtgtgg   229740 ttcattttt cgttgaattc ttcctccttt ttctttttct ttcccttctg cgcctactca   229800
tcatggactg gatttcttcc tttctaggcc tgaccctggg cctgtccact gcttttgttt  229860
cttatgtttc gtctggatcc aatgaaagtg ggaattcggc tcctgaatca gggggtcctc  229920 ccccttaga atccgagtcg agttcggcgt cacttaacac ctttcgaaac cagatcgctg    229980
cggataatga agccgatata tatcggcgca tacaaatttt agaaaaccag gaatactaca  230040
accttcctcc ccagaacagt cctggtgact acgaaaggct ggttcgcgag aacttcgatt  230100
cagccataaa tgtcaatcat tttcggacga ttttgataga ggaatacttt gaccttcgag  230160
tcttagagag gaagggcgtc gtacaagacc aactccaaga tctaatgctt cgggaggaga  230220
atatttcaca gattctagag aaatctcctt attcgaacat taggaaagaa gcctattact  230280
```

-continued

```
atcttgagca caagctcaac cccgttagcg atccacgcca tgcctttcag cgagacattc    230340
ttgacaccag tctcgacttc tttcaacgag atttgaatct gagaggcaaa gattcaacca    230400
tttacaagga atttaagacg tattttatgg acgaatgatt gggaggagta gttctaccta    230460
tagacaagac catcagagag gagacaaccc atttatgatt ccagccgaga agactagtaa    230520
aaggaaggat caagaatgtt atatatttca ggagctagat tagttggcga tgaacaagta    230580
agaattgcct caaccaaaat tgatggaatt ggacctaaaa aagccattca ggttcgttat    230640
cgattaggta tcagtggaaa gataaagata aagaattaa ctaagtatca aatcgaccaa     230700
attgaacaaa tgataggtca agatcatgtt gttcattggg aattgaagag gggagaacga    230760
gcagacatcg aacgattaat ttcgatttct tgttatcgtg gaattcgtca tcaagatgga    230820
tcgcccttac gcggtcaacg aactcatact aatgctagga cttgtcgcaa gctaattcgg    230880
aaatgaaaga agtctaccga aagcccttgg tacttgtctg atcaatcaca ctgatagctt    230940
caatagttca ctgaaatttt gtgtagtttg ctatttcacc ggttactaat ccagtatacg    231000
tatagtaggc ctccttcgcc acgacattag tggcttagcc cttcgcgctt cccttcgccc    231060
gcctatcgta tcggctcggc ttcgtcctcg aagctactgc ttccgcctct ctaggcatga    231120
gagatagctc atgactggta tatggatctc tctatgtagt ggtcggcctt ctagaagctt    231180
cgccagaagc gactagtcgc ttcccgaatg cctctttact ttagtatagt ctaatttctt    231240
tttgcctcct tccttgccgc caacgtacgc tactaggaaa gtaagcaagc tagcttgctt    231300
gcattctcga aacggtagct tccgctacct tcctgcctac tgaaatttat gtgaatgatc    231360
gtgacagctc ttcaaatcct attcagtctg attagatatg tcactgaaac aaagtgattc    231420
cgttctgtct ctgttttctt ttcggattcc gaggatgagc cggccgatcc taacatcatt    231480
tatgaggagc cggacgacga agcctcctcc tcagataaag atgtctccga cgctactctc    231540
ccggcaagaa caactttttc aattgtgatt tttttggcga gttcggtcag gagggacaaa    231600
agagagatgc tttctatcag tcaaaagcgg atatcgcccc ccatgctccc acggtccgct    231660
taccgaggaa tagaagggaa ggacccgggg ccagagcaag ttgggttggg gtatagagcc    231720
gtaagcgcgg tggggggtga cagaggacgt gctcgtacgg ttcatagaag gatatgaaaa    231780
agtacttatt tgttgggaac tttcactcct ctatattcga aatatgcctt tctaggagca    231840
ttacgatctg cagctcaaat ggtcccttat gaagtctcta ttggtcttat tcttattgtg    231900
cgccttgtga gcgcgtttgg atccgcgaag gcaatcgctc ggatgttccc ctaacccaac    231960
ccggaacgg accggaggga accgcagcat ggggaatgtc cgcgtctcgt cgcaaggctc     232020
attttgagtt gtgggtcata aggcgggcag ctttatctga gcaagggccg gggcacaagg    232080
gtcctggtac tatccaggtg cgaagaaccc cggaggtgac tgcaatgagc agaaatctca    232140
ctcacgggcc taaacgacga gcaaacactc gaacgtgaga gcaagggatc acccaacgaa    232200
tggacgagct caaaggggg agggaggcaa gaaccatgct ttcagagacc taacccaacc     232260
cggtccgaat cttatctgaa ctgcgagaat aactgactaa gccgtgccat aagggggtcat   232320
tctccaaacg ggacggggcc aagcctttag gttgtttaag taggttgggt gacagatcgg    232380
ccataggagt actccgggat ataaaccagg gcaacaaaag tggagcatac gacgatgccg    232440
cccgttttca tttcgtggaa gtcccggca gaggaaaggg ctgtaggtga tggcgcgttc      232500
tgcttcttat ctagagaggg gcgtcgaaat cctttctatt ggttcttgcg tggcagctgg    232560
tatagatgat gaaaggcggg ccgcttttc gggaccctatt ctcttaatag gcggcaaagc    232620
gaaataggaa aggggccgag ctgactgatg agtgcctttt tagcctttat tttaaaggct    232680
```

```
ctcatgtgga gctaacatgg ctggctacat acaagtatag ccaaatcaag atgagatggg   232740
acggccgttc agaggccgca gcgggactac cattggaaag cccgccccct tctcccatgc   232800
tgagtcacag gcagcgcctc ggaaagcacg gacgagccac atgcaggaa  acttgcacgt   232860 gtggttctgg ccgggaccc  cggtatactg tactaatatg tgtaggttcc cgtaattcga   232920
gtgagattgt catggcgcaa aagcagatat ggtccggtat tcccttgttc cctgtattgg   232980
ttatgttctt tatatctcgt ctagcagaaa ctaatcgagc tccgtttgat ctcccagaag   233040
cggaagctga atcagttgca ggctataatg tagaatatgc gcgggatgcg atccttaata   233100
gttcactgtt ggcggaagcc aatgtcccgg ggtctcgggg actcattctg actgaaacaa   233160
ggggcgggtc tttaccaact tccaaatatt cgattttagg gaagccaaaa aaggtgagcg   233220
cctagcgcga aaggttgctt tactaagtaa gataaggcaa gaagcaaggg cgcagcagct   233280
gcacgaaagc ccttgcttct tagcgcatcc gttttcttgc tcgttagcgc ttgactaata   233340
agatagaaag agccttcctt gcttgtttag taaagtctcg cttttgata  ggagtaggtg   233400 cttgctaggg cggggcactt ttcattcttc attcgaaact aacaagtgtc gggtcgggga   233460
tttctgcctt gttatcaaaa agggagttgg gtaaagcaaa ctctctcctt ggaggagcac   233520
gggcttagtc aagtagaacc gggttgcgct gcttgatgct ccgatcgaaa acaaatcagt   233580
ggggccatgc cggtacgact gaatatgcgt tagaaaggtc aatccctccc ctacgacacc   233640
aaaaaaaccg ggccgaactt ctaacccgcc cgcttccata gaacaatatc gtggcaacgt   233700
agatctaagt ggtcatattg gatccttggg aaccatcaca agtacggccg gcctatatat   233760
atttgaacga aaatgccgtg tcgtccagcg gagcctagaa gaaggtgact cgcgcagaca   233820
gctgactcct tttcaataga aaagaatagc caaaccaacc cagctggctg gtcaatctca   233880
gagatcttat cggccggcaa accggagacg gacgaccacg gtcccggcct taccagcacc   233940
ggaggtgtac taatcaatga acccacgaaa ccaactttct tttatgacaa aataaaccaa   234000
gcctaagcgg tcacgacatc ttgttgatat tgattgagtt ggagggactt tcgctgactg   234060
aatccatcca taaacctaga ccgcggtaac cttcgtaacc aaagcgtcac gacaacatcc   234120
aaaggtgacc tttggattct taagtagggg ggcaaggagg agcacgtagg aatgccgacc   234180
actacataag ccactagtgg ctgagagaaa gcgagcagca ccttgtatag gttgggcgga   234240
gcttaaagaa gcaagcccct atcagagaaa gccattgcgc gctagcctag ctagctaacg   234300
tttttctttc agctggctgt tatgttagtt gtagcgcgcc ttccctcctt ctctcacttt   234360
ggaaagattt ttcagtattt tcttatgatg acctggtcga gagagtacga tacatcggtg   234420
taaaagattg acttttttct gtgagcttga ccgaagggtg cagtagaacc tgaaggagag   234480
gaataaaaac ctggtctata attttgacaa aaggaggatc actattggga aatatcttcc   234540
tcctcttggt cgtcatcaaa gaagttgacg tccgggctt  cctctttccc tttaaaaccg   234600
gtgaagtcca tcctaaagtt ccaaatctac atccttaacc agaggttcct ggtgagaaca   234660
aattgtaagg cgttgaaaga aactaaagaa agaaatatt  tgaaactcgg gaaggagaa   234720 taagcctctc taagggaaga agacctagcc cagctttctt tccgagccat caataactgc   234780
cggctttcaa cgggtccggc tatcctttca ccggtcggta agtgcatcct attcctatta   234840
agtggggcgg cagttgctaa ataaaaaggt ggcgccattc ccgctaataa agaaaaagca   234900
attcttcatc caatctctgt tccagattct ggtcttacca agtcaccttt ctctaaggct   234960
aaatagctaa atatccccgt actttttttc ctatttttctt tattctttca tgtcgagctt   235020
```

```
tcgaaagcca ctggggaggg agaatgaacg atcgactgct aaagatcttg aataaagcat  235080
tgatagcttt gcagaggaga aaaactttga ttcttcccga aggtcttcct tgcatgctga  235140
agtgaacagg ggcggtacca actacgacta gaaagcggtc actcctgtca atgaatacca  235200
ttcatagttg tctatgttag taacatagcc ataacgactt tgttttactg cttgaggtgg  235260
tgatagcttt tatatattta ctaaattata agcttgcata gtgctcttcc tatttgtttt  235320
ctcggctttc ttctgccgaa ccgaacgaag acagtttctc gtacctctgt acctattgca  235380
ctgatatctt ctctttcact ctctttcttc attcaggaaa ggtgaagatt gaatcgggaa  235440
ccgaaaacga agcaggaaca gacttgtcct ttggtcgaaa agtcttgtac ggttcctcag  235500
tccgggggca ctgcaagaac ccctatgaca cttggagatt gcttgcctat gtcacttgta  235560
cagtcctcta acatggtaag tgtgccatat ccatcttggc ttcaaagtct gattctgaag  235620
agagagacac cgaccctagt cagtctaaat gatgtagaca gaacccgctc cgggcttgat  235680
taccaccgaa aatttcccga gacggtagaa tgtaaactct agggtgaaga agaaagcatt  235740
gcatagaaag cattttttgta taaggttccc acatccaata gataagggat cttgccctat  235800
aacctagtga agagggaaaa taagataaaa atatatgact ttttttaactt ctaaatctat  235860
ttccaaatac cctgaaagca gcaaagaaag cagcaagtga agagataagg cctctcattt  235920
ccattagggc ggatgcattc cattcccatt gtaacggcgg cggagggtgc ctccgggtcg  235980
cagcggttct tccatgtcaa cttaattgaa aagcatccta gagattgatt ggcttttcca  236040
gtactaggct tttgctttct tgtagttctt ctctttacat ctaccttcaa aacaaacaaa  236100
aaggacgacg aaaattactat atctatatat agaaagatgt ggactggaga gtttggattg  236160
agatccatat gcttaacaca tcgtagttgg acagcttatc gaagagagga gaaaaaaact  236220
atgttttgtc ggcatcacac atatagcatg tgtgccgtgc cgtgagtgag aagtcaatca  236280
ctttcagctt ttcttttaaaa attctacaac atgatgaaga actcttttcg gctcgaacct  236340
tcttttttgag ctcggtcaaa atatcaagag gaaagatcgt agcgtagaaa agaaaggaga  236400
aatcgttttg attcgaggcc gatcccttcc ttaaacaagt aagcaagtaa actacccct  236460
ttttttttctt tacggttga gtaaacaaaa gaaaaaaaa gctttttcgt aattttttaac  236520
tctaatgaca aagcgtccgt tcacgtcaag aatagaggcc gttaaggatg tacttgcttt  236580
tcctttttttg cgtcgagatt gggttggtgt tcagtgtacc cctgaagaat ttcaagtaac  236640
tgtctttagt acgaagtgag ttgatcgaga aagcggcagg accgtaaagc aacgccttga  236700
gttggactgt ggtcccgcga agctggtatc ctcagaccgc ctaagagact ttccgactgt  236760
cgaaagaagt gaacataaat tgactagttt atttaattga cttaaagatc tttcttctat  236820
gcctgtgaga ttggcgtaat acctttttcac taaaagtgat ccttattatc attctaatta  236880
tctaatatat attattaatc tcaaataatt aaagttggaa tttgtttaag taattcgatt  236940
aaatctttcc aagctaaatt gagaatgaaa tttcattcaa ttaagaacaa agatcaatat  237000
ggaacgcttt ggcgtcatcg ttccccatta ccattacttt gttaagacga ttcgctttaa  237060
tcattatttt gttcagacga tcgatatgga ataataaata ttatctaata agagtcgctt  237120
tttccctaac ggtcgagtga cttcttacct ctccaaccac tcttagctac gcccctcttc  237180
tcgtaacttc gtacctttct gtgtctaaag acgctcataa gcgattcttt gacttgtgaa  237240
cccatttgcc ttgagtgtat agaatgaata gataagaagg ggtggagcta gttagaccat  237300
taccgatata tgacaactct tacttaaaga agtagtccgt atcgaatcta ttttctatttt  237360
tggaacgaac aacgaccaac taacactttg actttacttt attagattca gaaacattaa  237420
```

```
ttgcaataat atctcgaatg agaagaaaaa aagtatcgcg cgatcgctcg aagaaatcaa 237480
acctttattt cggtctaacc cgattctaag actagtcatt cctatgttct tttcctttta 237540
ggttatttca cgatggtgtt tttcgtagca gtctaagggg ttggtttact tttggacata 237600
cttcatttgc ttttcttatt cggacacatt tggcatggtg ctagaatctt gttcagaggt 237660
gtttttgctg gtagtgaccc agattttcaa gtatataaaa aaacatggat ccaacagatt 237720
tattcattac tactacataa agcactacat tacataaaca accacatatg ccttttacta 237780
gagctttaaa agcattaggc ctactacatt actaaactta ttttcgaaac ataaagatag 237840
gccttaacaa gtagaaagtc actatttta taattttttt tctagtggtt ttccgggaca 237900
ccgaaggtgg caacccgcac aacgagttct tccttctccg tccgcagcgc ttgcagcctc 237960
ctctccaaat cgcttatgtc ctctctggca gcggcaatgc gcgcttcttt tcttgcagga 238020
tcctgtgttc taacacttag caaaagcgcg tttagcgttc tacggcgccc ttgaattgca 238080
ttttgcaggt tactcatttg gacatcaatt tgagaaatcc tgtttatatc agctatatcc 238140
atacgtgcta ttactcaatt tctttgcttt gatatttgat gaagtgaaga agcctctatt 238200
tatagagtgg tagagtaatc tcgccatgca gtacgaattg catggctggc acaatatgag 238260
tactataacc acgctgcctg taacaaactt tgcggaaccc tttcacctaa tcgatcgtgg 238320
tgaggattcg gcggatcatc cacgtcacgc taggatttgg gaaggacatt cacgagattg 238380
aggtgggaat tgcgttgcag agaggaatct cgccatgcgt caccgaattt gatggcaggc 238440
acaattctta ctagttctcc gcacaacttt tctgcagttg aagactatca tgcctattta 238500
gtgaaaaact ggctggctct ggctaccaca aaagatcccc aaatcacact gcctgtatga 238560
acaaacaaac cttgcacaac cagcttacgt agaaaagatt ccatattcta tgccaataga 238620
ctcgtgacat ccatgtactg agtcgtcaaa tgagccacgt taagaaagcc caagcttata 238680
cgcattggcc cacagggtgc cccaataggc cccgaatgaa agaccaagc ctacatgaac 238740
catccaagaa agtcctacaa atgaagactt gtgcgtgcct gtttcgatga aagcaggctt 238800
acatgcttat caaaaatgta atcatttaa gggtttggga tgtatttac gtgaaactga 238860
atctatttcc cacattctca agatcctgat ccagccttct tcgctaacgc tcaacctcgc 238920
atcgcatcct taccttaggc tatcgagctt cgaaaggact atattaatat taatttctaa 238980
tattaatagg taagattgcc tttaagggaa tgtgactctc tttccacggg catttttctga 239040
ctcttgaaag aatgtgattc aaagaattga cggtaaccaa ggtgcctact cttcctaacg 239100
agcctgctta ttaagcatgg tcggtcaatc aggtaatacc ccaaaggctg tctccagaga 239160
tataacattt cttgagatcc aaaactaccc cgagaaatgc tctagatcaa cgaaagggg 239220
gaccagaaaa ggaatcccac atgaggaaat tacttaaaaa aacttattgc taataaagat 239280
gctaattggt atcctggaag ccatcttttac atagaccaag gtacatgttc ctcgacgctt 239340
agggcatcct tattttgctt tgttagagcg cttatttcct agtttagtca gtcagtagac 239400
ctacgtccac cggtgaagct ccactatgga gatcacaaga ttagacaaca aaccttccac 239460
aagtaagaaa accctgatc agacgttggt ggattgtgta atcaagctcc catttcctcc 239520
aaatctcctt ccactctgaa agatccctct tttacacctc cggaagacct acccgatcgc 239580
aaatcaatca acttgactcc acccttgcaa acacagaaga ctaatggagg accgcccatc 239640
ccatcgacta tatctcccca ctcccagagt ctacctccgc tacaaaaccg ccctcttcct 239700
tttcctagcc ttcattgata tcgtatgcgg tttatcggaa tcagaaagat catatattca 239760
```

```
attacttaat ccgtgaacgg aacctttggc ttaccctcat tttccaggga atggaccatc 239820
attcaatgca tattgattta gaatctgtgt tggatcgcga accttctctt ctctcaggtc 239880
cagaggggaa ctcctagtta agtccctcat gatgcctatc ggtaagagga aactcgggat 239940
tcgtgccatg tatgtggcac acaactggtt ttatcgatgt gaatcaacaa atcacaggaa 240000
aatttggtca catagatctt ctttcctaca gtagcagatt cggctagtga tcagtaccct 240060
ctctttattc ccatagaaag actcttatct taaacaaact ctcggattgg ctgagctttc 240120
aaagattgaa gaggacaaga aagggatcga actcatgtaa ctaagaaaag aaatccttag 240180
ctttagtgca gtgacccaat gaaaacgagg agaagaaggc caagggtaag aataacccta 240240
caggctaaga tctctcctgg gctttcctca caataattct gctgttggga taggtgaatc 240300
aatgggctca tttccttttt acgggatgaa gagatgatat agcgtgtgtg ccacaagtgc 240360
gtagtctcat tgaagttcag ttcgataagc aggtcttttt cgtaggctag aaggtaagta 240420
agcagggtta gagaatccga tagcataaga tagactcctc agattatcat tatctaaggt 240480
tgtagccgta aatcatgctc tctactcttg gaaatatgtc tttgcctaag atggtaatag 240540
cgtatgaaat tatataggtc cctttctagt aggagtaact tatctcttcc ttttcttctt 240600
cagaaccgct gacactccgt tcaggcggaa caatcagcga gagaccgtct ttcacctaca 240660
cactgggcag tccattgcta aggactcggt gctcaaccgt gcccatatgc tagttgaaac 240720
caatcttacc ttaccttatt tacgataaac cccgaagaca ctgctcagtc tatgtcctcc 240780
aacgttaggt agtatcttgc gcttaaatgg actggcccct cttttaggga aactatatgc 240840
ttgtcttccc ttagatctga gggcggcaat gttgagaggg cgaaagcaca caagggggg 240900 gcacgtcagc caaagaagg gtatggagtc ggaaatcgaa ccccttgttg ttgacctgtg 240960
acagcctcaa tgctcttatg gcagggcagt agcaagaaca cgatctctcg gaaagaaaa 241020 aaaaagacta aaccctatcc aagatgcccc accaatcaaa taaggcactg cagagccagg 241080
ccccaaagta cgcttttgct cgctccgcaa gtaagtacga accaggcaaa gaagcaatgt 241140
cgaccacccc taaaggtaaa aaaacctgat gcatgggaca agggcggaga gtataaagac 241200
tataaacgca cgcagccctc aggcaaacct ctaaccaggc tgatgaaacc taaccaaaat 241260
gttaaatcaa ttacgtcggt cgttgtgatc cttctttccc ttccagctca tcttgactat 241320
tcctcaaaag aaagaaagga aagaactcga tcacactgca cggaaagaaa ggcttcatta 241380
tatcaaaagg ggcgagcgta tcgattgcag aaaggctggc tgtacccgag agtcgttatt 241440
ctcccttact tcgtccttgc tgctattgta gcagtagtgc cttttggaat tgtatcagaa 241500
cagaagtccc tggcttctta atactactct aagtcatttc gtcccttgaa tgctgatcta 241560
agcgagcgcg aatagggtcc agctagtagg ttgtagttgc atagttccta ggccatccat 241620
cctgccttgt cccttctcgc gtaaaccgct gtattaaagg aggtgagtaa gtaagccagt 241680
tagaaagcat gataaaatag ccccttaaat atccctttct tttatcgagc tagccttta 241740 gtatgattac caggagtgaa agaaagctac gaaaactctg aagttaagga gaagagtgaa 241800
ccccttttac tacccgtaaa aatacgagta cctgttgcaa atgaatcaac cccgcttgtt 241860
ttttctgttg ataggttaga ttctcggttg aacgttagga aaccctacca aaaatggagt 241920
ctttccccta tatcccagtg cctcgactag tgcttttcct aagtggtgga tattttttt 241980 aggcttttag tcatatgtat tccccctcttt gagtgtgcta gtaataagct gggaaagtca 242040
aatccatcaa ggcgaggaaa aactagtttg aaagtagtcc tccttgaagt tccttttaat 242100
tgaatgtggt aaggataaat agaaatgcaa tctctgaatc tcttacatcc cgcctagtac 242160
```

```
cttttttgaat cgaggggcg   aaagcttaat  atcaagtagg  agttctggat  tgaggtccag 242220
ttggttggat  aaaggttgga  gttctaaggg  catcatctcg  aaaaattgcc  tttcctggag 242280
tttcttttta  agtcttttct  ttcttcttct  atatctgctt  tctctccgct  ccgggcaagt 242340
cctaagcttt  gcctttcccc  ccgtctcctt  accgccctac  tcgcaacttg  attttgacca 242400
tatcccgttc  ggggctctct  ggtctaaatg  ctcgaaatga  gcgatattca  ctcggaacct 242460
agagattcaa  acaggcacag  gtcaaccaaa  agcatattgc  cgagctaagg  tggaagataa 242520
aaaagctata  tttaaaataa  taaagagaat  ctcttcaaat  tcatattcaa  aatgggatt  242580
ctcaactata  cttgactgga  aaaaccagcc  aatctactct  cctttttttg  gtctccccc  242640
tgtaaccttta taaatcataa  gagaagaaga  aatcgttgcg  tagaaagtcg  tgcttactat 242700
ctcctccatc  taagttatgt  aagaggaaaa  gagcgaaaag  cttactttta  ggtagtggcc 242760
taagcgctaa  gaagctccaa  tcatgctact  cagactatat  gcttaacaca  tgcaagtcga 242820
accttggttt  tcggagttcg  aaagagaagg  ggaagaagcg  gggtagagga  attggtcgac 242880
tcatcaggct  catgacctga  agactgcagg  ttcgaatcct  gtccccgcct  aatccatctg 242940
aggcccggcc  tcaagatttg  agattccgta  agtaactcag  tgactgcttt  ctaagaaggg 243000
cttggaagaa  gaaaatgaaa  taggaacaac  cgcgctggtc  gtaatagatc  gactttcatg 243060
ctagttcttg  ctccagcatg  aaagttccat  ttcagggaag  gacgacgtac  tatgatactt 243120
tctgttttat  caatctccgc  tgggttgatt  cttcttcgat  atccatagat  tttagatatg 243180
cttacttatg  ttgtaacaaa  cattcaaaat  agcaggttcc  tgatagacgg  caatccacag 243240
ttacattcgg  agttgaagta  catcttagtc  tcgctttgcc  tttatttttt  tgtttattca 243300
ttcgttacaa  tgagaagatg  tcattggtat  tattttaga   agaacacaag  taatattcta 243360
aaaaaaagtg  ctttctgctt  tgcttttcct  tttctattga  taacggcatt  cgccccttca 243420
gtagccttt   gcgcagatcc  tgcgcctgcg  cttccagacc  agacctcaac  gagattccag 243480
taggcctttc  tcctgctgaa  atagcccaat  tgcatcggga  gactgaagag  aatgccgccc 243540
agtgtgggtg  tggcaggctc  ttgcaagaaa  tctgtgtgcg  ggcaaaagaa  gttgcccgtc 243600
aggcaggagt  gcaggacgaa  ctcaagctgg  aaaaactcgt  cgacgccgtc  aagtttcttg 243660
ccgacgtgga  cgagttggac  gaagaggacc  gaatccccac  tctcattgag  ttcagggcca 243720
aaatcgagaa  taaagactcg  acaatttgt   ttcatataga  taaagaaatg  aagaggtggg 243780
gtggccgtgg  tctatgatgc  atttttttc   ttagatagaa  tgaatggaaa  aggggtgctt 243840
gtgttgtggt  tttcgtagtt  gcaagaattt  tcttttcgag  aaaaggtccc  ctccttcaat 243900
atcatgattg  ggtcgaccag  gctagatcat  gagtgaatag  aaaatcgaaa  atgtacatag 243960
ctgttccagc  tgaaatactt  ggaataattc  taccacttct  actaggagta  gccttttag  244020
tgctagctga  acgtaaagta  atggcttttg  tgcaacgtcg  aaagggtcct  gatgtagtgg 244080
gatcgtttgg  attgttacaa  cctctagcag  atggtttgaa  attgattcta  aaagaaccta 244140
tttcaccaag  tagtgctaat  ttctcccttt  ttagaatggc  tccagtggct  acatttatgt 244200
taagtctggt  cgctcgggcc  gttgtaccct  ttgattatgg  tatggtattg  tcagatccga 244260
acatagggct  actttatttg  tttgccatat  cttcgctagg  tgtttatgga  attattatag 244320
caggttggtc  tagtaattag  ggggcggccg  ttcggtcgcc  tatgatacta  ggaccaatag 244380
gttcaaaatg  ggtttgtgcc  gcaggtgttg  aacgatctac  tctacacagg  tgtgggctta 244440
cagggctagg  gctcataaac  cccttctttc  atttatcaat  agggccccgg  tcggtcactt 244500
```

```
ttctggaccg ggatcgataa gtggaagtca taaaaaagag atctttctct tcgcacctca  244560
gatcaagagg aagggttgct tgtcaagctg gcctatatat aatataataa taataaatag  244620
aaagaaattt ctttctattt attattatta tataatagat tatataagaa aaatggaaag  244680
attcgctttc ttttaaccgg ctccttcttc tttgtcaacg ctactaagga cctataggtt  244740
tgcctacttt acttatcaaa gataatgata atggcttatt caaacaaaaa ggaaaaggcc  244800
ctacttagtt tcgcaagcct tgtcattgt cagtcaacta agtagggcct gaggcccct  244860 gcgaatccgt aaatctgagg agcatgccgc aacaaaagga tggtccccta tgcatatgca  244920 tttcatttt tccttaagga aaaaaaagt accccccatc atagtgaacc tctccttgtg  244980
atcgggatga ggtagatgcc tcccagccgg ggggcggatc gaatcggagt ttccttaggt  245040
agccaccgac ctacagttat ccttaaactt ccgtgcttgg tggagaagaa gcaacaaaa  245100 gtacgctcgc ttgctgtctt gttctctgtc gcgaactggg atcgctcgcc agctaggtca  245160
gattggagca agattttatg agaacatatt ccccatattc ggggacaagg ggcggaacga  245220
cctctcgatc tacttactgc agcccaggaa gaaaacgtc gtctaggcgt tccctgttgc  245280
tccgatctac cctacgccta ggacgttgtc tgggccaaga gccatagtta gttgctgttt  245340
ccatttggtt gtttcttcct cgttgttgat accggcaaga cccagccaga tgatgtccgc  245400
tggttggtag tgagaggact cttagtacct gcatacccaa agagggcgc tggttaaaaa  245460 acaatcattt gattttgttt cttgctctcc cttagcagcg ggaaaggagt ctatctatct  245520
gcctagcttt ggtagatttc ccccaacgca atccacagaa attccacgaa tcccttggtg  245580
gataagtccg acgactcagc agcagtgcgg aattgagttt cttgtctggt ggatctgatc  245640
tatagttagg gggcaataca taccaaaagg ttcgaagaag gaaggcgcat aagagtatat  245700
aaccaaccta ccccttctgta taacctattc acattagtga agcggttgga tgcataaggg  245760
aagtgcacgt ttgtgagacc ttagtcggga tgcataggtg agtcaaccta cgagcacgga  245820
agagcgtggt accgctaccc ctctctaagt aaaggtaaga ttcttagccc tgtagatgac  245880
tccatctaaa atacaatagg gacagccgtt tcggctgct cgtttcgtat cttgaagaaa  245940
gagtaggctt aagtaatagg ggtcaggtca ataatagcta tgctattgcc ctagtgattt  246000
aaggcctccg cccgatcccg aatgcacatt ttttcgggtt catcttcaat tgatgttttc  246060
ttaacctttc gaagaccttg cgtaaatttt cgatgtggtc ggttctttct tttgaaagaa  246120
ctaccaaatc gtccacgtaa ggctcgcata tgttatgtag gaggtcaatg agaatttgtg  246180
tcatcgctct ttgatatgtt gcactttctt tttcttttt tggggcatat cgtagtaagg  246240
aaaggaagtg agggcactca ttcgaatcga atagctgaaa ctactataac tcctattttt  246300
ctgctttaag agaagccttc tagctcgttt taaagcgttg aagagagaga taggacattc  246360
taaagatagt tgttgaggaa gcatctgatt tctaactacg agtccgtttt caagctaact  246420
gaatgcctat ctgctgctag ttctgttcca ctatctgctg ttactgctct cgttgccggt  246480
gtgacagtct gagtagacgg tgctctcttt cctgtagttt ttggggttca taaccggtgc  246540
tattgaatct gcagttaagg gaatatcact agttcttgga ataagagctc tgggacttca  246600
tggctttgag ggagggttag cctagcccta agccttttcg gaatagaatg ccccgttaga  246660
atgggcaggg acagtcgatc atcggcttaa tttcctgggt tttgggactc tagtatcaaa  246720
aattcccggt atttcgtcgt gaaagtgtca catttagatt gaacttatta aaggaaagag  246780
ccgaatagac aaagggttta catgaccgct cgctttggac aagatgccat agtctaagaa  246840
gaaggccttt gtttgcaaag atgactttcc cgctttcctt tgtgagggag gtttgtgcac  246900
```

```
atgaattaat agtcaaagta taaggaagat ggcatagagc atagaatgag attgatgctt  246960
cgaatgccct gttttcaggg gttgtgatag aaggagctgt ggcactttcg gaaggggaa   247020 tcagactagg ctgtcactgt tctagaagag gaagcgtagc tggcacgttg aaccatgtct  247080
gtcaacggtg aaagatagcc ctaaagtgag gccccggag atagtatttc tcaactgtcg   247140
atcgacgtga caatcatgcc tgcttgacaa atccttttc attcagtctc ccaataaacg    247200
aaaaaggatt tctggtgaca cgaaagctgt gctcgacgct ctctttccta ttccactgtg  247260
ctaagtggtc tttcccttta ttgctggatg actactatgg aaaaagatga cgactactcc  247320
cagtctctgg tcaatccatg ctgatgcatg aagagctatt cccgccgccc acccgaaaga  247380
gacgaggaag actaaccgcc atcctgctcg aacctttgct gcctgagtta tatagctgac  247440
tgcgagaagg aaggttcaag ctatggctgc cccatgggat gctcatttga aacctttgtc  247500
cggtcaatgc gagaaagaga gaagtgatgt aaacataaga atggaaggtt tgcttgtcag  247560
ctgtcgggcc aatgatgctc ttctagcttt acctacacgg caagggaaag atcaaaggcg  247620
aggtgggaaa tgccccgcac gaactatctg atcaagtttt cttttttccta tcacaggcag 247680 ctggcaaagc cgtgtttgat cgtcgcgtac atgctccgtt acagcttcgt tcatgcgcca  247740
atcaattgac agtgaagcag agaaggaaga gttttgatca ccgtgtgggt agtctctatt  247800
agggtttccg tttcatgtgc actaaaaagg aaggaagact ggtgcgacta tagtaatgcc  247860
aagcatacga gcaaaggact ctacctaccc catactgacg aatgaaagaa gctcatcgcg  247920
gatgatagga caagcgatag cggttccatt cttgctcttc ctattccata ccataaacag  247980
acacctttga ttcatcgaca ttggcgcgtc aggctctacc cccacccccc agccctttat  248040
ggagttagcg gaccaagaga aagaattccc cgatataata aagaaagtaa gaagggttcc   248100
aaaccattga aacagaaagc actaaagact gatatgacgt ggcagagatg atcaccgtca  248160
agcacaagat tcaaagctgg aatcttccta ctcttcttag ttgggacaga gcatcctatc  248220
ttgttgattc tccttttccca ccgcctcgag ctctcgcttt cagggtagat acgcaagaaa  248280
ttcactagga aaattgacat gacacaatcc ctgaagagta tgatgtgccc ggccttgctt  248340
ctcttgatcc ccacccacct cccgtagagg cgggccaata tcaatatcta taccagagat  248400
tgcttttagc tttctctttt cagagacagg agaattcctt ctgtacttac aagaatgcta  248460
cttagggaga agaatctctt gactcaggag cacctgaatc tattctttct gtgtcccaca  248520
tccgcctatg ttaaagcatc cgcccattcc tcagtgaaag gaaatgctac tcagggatca  248580
aaaaagaaag ctggtgcctt gtcagaaaga cttggttcgt agagtagagg cctttcccca  248640
agatattggt tttaagctcc tctccttaca gtcaagtggc tttccgctcc tgcgggttac  248700
tttttgtctt acgacacggc atggtaattg atcgagtgcg cttccttc tcctactccc     248760 acttcgggaa gggaagtgct aaagggcggg catgctcgac tgcctaaaag aaaagaaaga  248820
aagcccggta tggatattca ttccgctaga gcaaaggcat gaagtgaagg aggccgctaa   248880
ggttgagcct tacaaatttt aaagagtcat attcaatcac ccggaaatat ccgcatctgc  248940
gaatagaagc tgtggaggga gatccatgca atggcatttc atcaacagat accacttctt  249000
cttccctgct tgggcatttg gaactcttag cagttgagga cgaacttcag gctttctatg  249060
agtagaaatc ctattagcga accctctttc gtacctccgc cttttccctt c taggtcatgg  249120 tcaccatttt gtgatcaccg ctacagacta cttcaccaag tgggttgaag caataccaat  249180
agccttaaca ttggaaagtc gcttttaagc ccaagtgcaa ccaaactagc aggaaatgaa  249240
```

```
agaagaaatg gatctgtgtc actgtctgta tgcttgtctt cataaaggtt tgagtttgat   249300
tgtttgttgc caaagagaaa agttcattgt ttaggtccta ctctgggtct gtagctgaca   249360
gcggcagtta ttttcttttc gattttgtc gattaataat acccaaaaac ggtagcgagt    249420
agaataaaga agttgcttct agaatgccga ttgctaggta aatcgcccac tatatatagc   249480
acctatcggt gtagaaggtt caagcaaggg atgtggattg agtccaagtt ctggagaaag   249540
aggggccctt ttttttttcat cttttcctaaa tcgatcgatc aaattcttca tatccgaagc  249600
gcaggaagga tctgactaga aagtcgtctt gctgatgcaa tagtcctctg ggtatggcca   249660
cattcgtctc gacaatagga tagggaaaga aaatccatag acgagaccaa cagggaccga   249720
acccttctat cttcttcttt ctcttttgt tcccgcctgc cgaggaccta tctttcaata    249780
acgatgaagg gctactagaa gggaaagggc ttcaggagag atacttagat tggatgggcc   249840
tattcccatt tatgggacag tatcccaagc agtaaggctc tgtagagcta gtctcccttg   249900
agacctgctg ccgcaaaagc tctttctgct gctccttcgc ctgcggatta agctgtagaa   249960
ggcaagcaag caaaccttgg caactggcaa tttcaaggat caggggaggt atgaaatggt   250020
tatctcggct gggaatcaag ccccaacaca aagagctgtg ggccaggttg ctttgcttta   250080
tcggatcaat cagtgtgcag tgggcaagct cttccccaag tcgctgagct gtttaacaga   250140
gggaaggtca aagagctgtg gggctaggag tgttctcaat cttagcattc cgagacaaag   250200
cctgggtcgt cgaactaaag aatctcagca ttggccataa aaacgcgttt gaaggcctgt   250260
ttctgggact gatagggagg ggtctaaaac ttgaatttct gctatatcaa ccttccaaac   250320
caaaagggga ttctgctcct accgctaaag cattgtttcg gcccctgctt ccagaagagt   250380
tggtgcaaaa gtcattgtag tccaaatagc gtatttccgg ttaggggcct aagactcact   250440
aaagcaattg tagctattca ctccttctag ttctagtgaa tttcgctcca aatagcataa   250500
aaagaagctt gagttcaatt aggggggaac cctctgtagt caacctgctc ccaatgaaga   250560
ggtaaggggc gtagcgatga agtcgaacag ggttggtaaa ttcaccgggt gactcgaaag   250620
caggctctta aagaccactc ctagcgcgtc agtcatttcg ctcccaaaga gctccctaaa   250680
aacgttgcca atatcgacag cagctcctgt tcaagtcttt gtttcggttc ccgcaaaaga   250740
aattgttgca gtctcaactg gataaatgaa cagcttcgca tctatttcct attgtaatga   250800
caaaggtttt tctactgatc cagtgtcaga taattgggaa ttcgctttca gctcttaatc   250860
ttcttcggga gacatggaaa aaggcaaggc tcgagagacc tagcgctaaa gcaattgtag   250920
cggcccttgc gtacagaatt gtagcgactc cttctagcat tcatttaaca ccttcgggta   250980
ttctggtatc gaaaactgga gaaaggaagg aagtctttgc ccgagaaagg aaagaggttg   251040
actcactcgc ttggcgaact cataggtcag tagctcccgt taaagctaaa gctattgttg   251100
ggccccctgc gtacaaaaag aaaaaagaca tctttccccc ctcagcactc gaaatctcat   251160
taagagaagt aacgtagaaa agaggacatg aaaaatggct tagattgtaa gagcaggtgt   251220
aagcttatag gcggtagcta agaagttctt tcttgcactt tgcttaacac atgaaattcg   251280
agcagtgatc cactaacaga cacgcgtcaa aaccaaatga ctcagggcat ctccaatcgg   251340
tggcgttggg agctcctggt cgaggtgtgg agttttctgc ttcctgccct gcggaagtct   251400
aaggctgatc cctgctgcta gtgtaattta ttctaaggct cttcgagttt attcactctc   251460
tggtaatccc ttacgagtct caagactctt cggtcaccgg aaagtagttg ttttctatcc   251520
ttctcgatag ggctggcccg ctatagagag gtattgtcgg cttatggggg tataggatat   251580
gacttaagaa tccaccttcc ctttctcttt gtctgagcac aagtgttaag ggtacggtga   251640
```

```
ttacgcagca agatctttcc cccactagat ctctgaggga caactccttc acttggaaag   251700
cggatggaga ggatggcgta gctttcaaac ttagcctagc cgatttgctt tttgggtttg   251760
ttgtcttcct ccctaagact ttcgttcagt gacatcacaa gggttggttt gagcgcttag   251820
ggccattggg aggggctttt ccgatagggc ttccttcgct aggaaatcgg actattctac   251880
cgctactgac tgactggact tacaaaaagg gagttcatta tctaggtgag ctctttgctc   251940
ctggtagacc ggttggtgtt catcagtcag tttgcttctt tttttgactg acgtaattga   252000
tttgcccttc cttccgattc ggatggagat gcggaatctt cttctctgta ttaaccaccc   252060
ttcttcacag aaaagagag ctcagaagac ctcgtctatt acgacggtac ggaaaaatca   252120
atggcaccgg gggaaactca gtccagagaa gaaaatgtca gttaggaaag agtagtcaga   252180
cgcagaccag cgcaggtggg cgccacagct gtcttcctcc atatgatatc acgcaagagg   252240
cgaaagaatc cctttacctt atttacaaaa taagaacccg gtcgatcgga gtaccttcc    252300
tccttttga ggcttttagg cctccggtca gtcaggggtt gacatgagac cggattttt     252360
ggggaatcca ttctttgccc tactgtctgt ggtaagtcag tctgctttgc cttctcgctc   252420
gaattctttt caatgtaatt gaattcaata gtatgacttc tatttcattg ggaacttgat   252480
gagtcgatcc gcctacacgt cttgctttta ctgctatatc gggtcttact ccacgtattg   252540
cttgacgtaa aagagagagt ggatttcttt ctgtcttttg ttgaatcgct cgatagagaa   252600
tttgataagc cagtatccgc ggtaagttcc aatgcttgat agagtaaagt aaagaaaggg   252660
cttttttttaa agagtaagtc agtccccttg aaagatgcat ccaaatctgc actcgggta   252720
cgcataaggc ttcagaacag ggttggaaac gaaattagat gttatagata gttatcggga   252780
aagaaagact tgatgacggc tgcacatact caaagggttc cttagctctt tacagagaat   252840
ctcccagtat gctaaacagt gacatctctc gttatatcga gaatgtgcat cccgttatgg   252900
atgatgcagc ttctcggttt ggcgaagtgt tctgtagcgg agtcgccgcc acacctgccg   252960
gggcgggtaa gctacgactg ttcatcatag gtaactatgt gaagcagagg ctgttgaagc   253020
cttatcacga ctgggcgatg tcagttttgc gtcgcttaga ttgtgatggt acttacaatc   253080
aaacaaaacc ccctagagcg ggttggtccg ctttccaatt tattcttctc ttttctata    253140
tttctaggtc gaaggaatcg gggcagagaa ggtttttatc cctaaaaaaa gccttttcc    253200
gttgctcgac tcgaagcaac cacgagctct aacttaaagt aggtctagaa ccactgagat   253260
taagttgttt tctattttct ctccaggcta tgaaagatct gggatttcgt tccaggaaat   253320
ccgtatattg ttttaacata tctaataggg agaggaggag acagacagta aggtatggcg   253380
agatcacatc tcccgttact atagtagagc ctatacgggg aataagatat agtgatgccg   253440
acaattcaat aactaatcaa gaaagtaact cactgaactg aaccagctcc cactaaacaa   253500
aacaagctta aaatgggggct tattcttgaa caaaccttac tgtagaaaaa aggagatttt   253560
cttctctcggc ttgactaaac tttctttttc ttatactccc ctttgagaag agaaggaata   253620
gaaatagaga aagagatatt cgtgggccgt taaacgacca cctatgaacc tttttaataa   253680
gcttttcctc gcgggaatta catgaataaa gaatcatcct tttcgtatac atttcataga   253740
cctccctatt agcctactaa taagaaagt aaagcactaa tgggtttccg atgaaaagaa   253800
ggaacaagga agttccgagt taagcgatag aaattggtcc acagtgagaa actcaagcga   253860
agcaagagag aagatgcccg gccgagagga agttcaagtc gctgaggtaa tttcagatag   253920
agctacgttc cgggtattcc taccatcttt tcttataggt tactctttga actcttaatt   253980
```

```
aaagcactgg aagagaatcg ctatcgtctt tctaaaggac ggggatttac gtgtattgct  254040
tatgcccgat ttgctgacgc tagcttgact tcactcactt cagagacgga aaaaaagaat  254100
aagaaggggg cgtagcagcc ggaaagaggg agaaatcccc tcttccgctt aaggcaccga  254160
agtcccacag ctaatatcaa tagctgttga ttaaagggaa gttctttcta gagcagtaag  254220
agcctattct gtcttgcttt ctgattcaat tccgctgcta gggcgagcta actccaaaaa  254280
accgtcctca gttcggattg cgggctgcaa ctcgcctgca tgaagccgga atcgctagta  254340
atcgccggtc agccatacgg ctgtgaattc gttccaggat ctctcgctcg ccctcaaaga  254400
ccaactcttc tggaaagagt tctatctccc taggttttaa ttccttccgg agataagcaa  254460
ccatcttccc tttaagatag gggttaagag gatttcccct ccctaaccaa tattctaaag  254520
gtagttgctg tgaaccgtgg ggtttgccag cagccgcttt cagtcgttcc catcgctttg  254580
tttggattga catcaagcga gaccgaacgc gatagcctgc acctgctaag ggttgtaaaa  254640
cagacatctt ttggatgcca tatttacaag ccagctggca caaaccaatg gtcgacctac  254700
aacctgttaa agcacgaaga gatattgggg acaaatcctt ttgcatgtcc ttagtccagt  254760
acctcttcgc gaactcgaga gtaccattct ctgaaataat ggatttttgac agagaaatag  254820
taactccgag tctttccagt aacaggctat actctctggc taccaactca tcggcgataa  254880
gaatatcatc gccaaggaga gcgtagtcat agaaaggggt ggcctctgc gggtaggcct  254940
tcttcgctgc caaccatacc agataatggt gtgacagggc gaaaagcgac caagagccgt  255000
agtaacccaa aggctgtcca gtcaagaaag ccacttcact tatccctta acaaaaggtt  255060
ttgttaaaag gaaagtgtta agaccaagag tactgttgac gattgatgat gccaaagtac  255120
ttccccacat acaagacatg agggagtcta tgacactcaa tggccaacag tccgtagcag  255180
acttcaagtc aaaggaagaa agtttcctca atttcttgac ccgaagccta tgtaaatgta  255240
aggctttctc ttggttgaag gtaccgtcct tccgtattgg tttcctcttg gactccggcg  255300
taatcccgag cctgtaaggt gtcttttaa accggatgtg aagattgttc caatccaccc  255360
ggaagtgact taccacctct actacttta tacgagatgg atcggcgtac tgggactcaa  255420
accagtctgt atcggcccaa gctttagcgg gaccccttgaa cttgactaca ggctcggcct  255480
cccctttagg ttggtaccaa gaggcttcg gtgctaaaaa tagaccttc tctattttgt  255540
cttcaagctt aaacttacct aagacagaag gagaaaccag ctcgtcaggg agtggatgac  255600
caagcacaac agagtcggtg tcggtatagt aacacttctt attacggata atgggtcca  255660
tatgcatcct agcgtaggca gcagccgctg ccgccatctg gaccgcagcg ttcctcaggg  255720
ggcgccattt ttctatggtc gggccagtgt agctagggta ggtagcgagg ttggtgtttt  255780
cttaagctc tacaccgtgc aggaactcct catgggagtg aatcaattct ttccagcgtg  255840
cattatcgca gatctcggca gtcgtgcttt ctgggctaat accgaatctg ccgtagaggg  255900
cattcatcag gatctttaac acataggcta tcgcctcatt accttcttcg cgcgccctca  255960
gcctactctc agagagagag ctaacaaagt ctttaaatgg gcttctttcg cccttctcaa  256020
agaggtagcc ctgggttggg actacagtgt accccagggt tctagcatac tttaactcct  256080
cgctaaagta gaccctata aacctccggg taggaagac ccagaggtcc accccgcgat  256140
cgataaggca gaaagggctt cttgatagtc ttggggcact ccacatatgc ctcgataaag  256200
ccaaagaggc tatctaagtc ctcgccaccc agatcctcac gccagacagg cttcccggcg  256260
ggcatggggc gctccgccat tacaaaggga tagagtgagt tcatcgta gtagtatagg  256320
tccttaccta ttggtatgta ggcatccaca tgaccaccgt agtagccacg ccttataaac  256380
```

```
ctctcttcat tcgtgttggg gatgtggatc cgccctttag cgggatcgtg gaacttcata   256440
cgaaagaggt acattgccaa tgaggaaatg ggaattttgt ttactatgtc aacctcgtat   256500
acctcccaaa atatctcctg cgcccttttgc atcacaccgc caaggagaag dacgtccttc   256560
ttcagatagt ctatcaactc ctctctcata ctgctaagat tctcgagagt cactctctca   256620
tgatcaatag accccttatt cccaagttcg gggcatagac tacgcgaaag tgaatcaagc   256680
gaacccagga gtagagccat agagtctctg aagcggaata agagcctccc ccgctcggaa   256740
tagaggctta gctcgtaaag cctattccct ctcgacagcg gtcttatcct gcccggccac   256800
ttaccggcca ggtgctctag caagagaatt ccatcgaatc tctgaaggtt atgaaagtag   256860
acggttatag acgacctatg cttgatagct atatcattta tcctggatac taaatcgcta   256920
agtaccttag tactcctttc atcaaattct tttaaggtcc tgtactcctc actgaagtag   256980
gtttcaacct tattatattt gaccggctcg ccggggcgaa caatcattag acctgcagca   257040
taagtctttt gaaccccatc ccttattact gtctcgaggt ccgctacaat gaaaggtttc   257100
cgcgccccgg gacgtggttt ggccgctgtc atatagacgg ggggctacg cccatgatgt   257160 ttgatcgccc ttgctggggt ggggccgccc ctaattaatc gggtgccgat acggagggcc   257220
gattgttgta agtcatttct ctcatcaaaa gacggggctg gcccttccgc cctagactcc   257280
cccatataga ctcgtatgtt gagtcgaact agctcggcgt tcttgtactc ttcgcaacga   257340
tctacaatag cttgatatat tttagggtag actacaccca tcgggagtgg cttaccgtca   257400
ttttcggtta atggaatagc ggggcccgcg gtaaatatta gaacatccac agcgggtggt   257460
cgccgcgcct caaagccaat cgtgaacttt ccgacgcccg ctagagcggg gtaagcaaac   257520
cggcataata ggtccacgac cgcgagactg agtagctcag tctcgcccaa aagaggcgag   257580
gggggtgtga aagtcatgga cgcagcgacc aacttagtat ccttactatc cttcttcctt   257640
ttcttattct tattattact tataacgtgc agcacggctt ccccaatcct cccataatac   257700
tcgtccagca ctcggctgcc agttttaat cctccttgat ttttcatggg tgcacgctcc   257760
aatttatcac cccctcatca gaggcccct caagggtagg ggcaagctgg ccccggaaga   257820 cttttccacct taagaaaatgc atttcataat cctagttagg gccgcatacc tcaccagtat   257880
aggcctcata cgccttaacc aggttttgga tccttccaga ccaatctttc atcaatttcc   257940
ggttaaccgt gccaggtata ccctcatgta agcactccgc caggtccgta ctagaaaaga   258000
cccggtcaag gtcaaaagca ccggcgcggc gccatgacgg gccggtgtcc ctactaaaca   258060
ggccggcggg cctaccaagg accggactaa tcacattttc gtatatgaac tggttgatga   258120
ccctaagtgg agggtccaag cgcgaaaagg aaagggtata agaccaggg agcatccagc   258180 tatggtgagc tgtacttaca aagttgtcgt gtacagtgta tataggtgca tcgcgctgcc   258240
gcatttcctt taccacactc atagcaatat aggcgtcctt ctgatggatg aagttggcga   258300
agctagccac ttctgccttc ctacgatctc tcttatcggt aggaacttttg agagtgattt   258360 gccgtctttc aatgcctgtg ccccaaaaga gggctaggtt caagggtagg cacctagtag   258420
ctgcgagcct aagatcaaag gcagttccaa aaaggagttc cctatttcca gcttgataaa   258480
gtaaagtctc agtgccagtt gtaaggttag gaaagcaggg tatgatgaaa tcctcttttc   258540
gaataggaat tgattcgatc ttattattat tatatgaaga tgaaactgaa tatactcttt   258600
ttcaagaagg aatcgccatc accagtggaa gttgaacccg gcgatctctt cctcctgaag   258660
tatggaaaaa ggaagaaaaa gcagtcaacc acagggaagg aaggaggtat agctcaactt   258720
```

-continued

```
tcttgcctct tcctcaatcc agtagcgagg tttcaacgag ttctttgtac gcgtgtaacg 258780
aaaagtatat atacttttc tcccgaattc cctattactc tcggtccttg ttcttggtct 258840
ctgtgaaaga tccagtcgat gggaatgaat ccatgttcaa atcttattac cgggttcgat 258900
tacattgctc gatgtaattg agtcttaaag gggaattgca taaggaatct cttttcttat 258960
gagaactacg aatcatcctc atgaataagc tctactctac cttaaggaga tgtggaggca 259020
ataggtcccg tgcagcttta actaactcga ctcctccata cgcctatcct ttagtttagt 259080
gggccaggtc ctccagcctt ccattagctt tcgatttagt ttgcattcaa agtcttggaa 259140
tgcgagctta tgtgctttca ggtataggca tcctattccc cgttttgact ttcttttgga 259200
atcgtcttct tttaaataag atcttctccc ttgttcttcc ctctgcctat gatcttgacc 259260
tgctaagtga tttccgaaag ctcccactat gactaaaaag ctcccaatag gccacgtagc 259320
agcttaagct tatattataa taaagtaagt aggaaggagc gaaagctact cgaccagacg 259380
ggagaggcga ccaaaggaag ctggttcacc ttctctcctc cgttacaaca taggtcgttc 259440
caatcccgga tgaaaatatt ccaaaacgga agtcaaggag gaaagttcca tcctgtcctt 259500
caaagatcga ctcgaaggta gccatactta tcttacgata taagtggact acccgcgata 259560
tcgaaaacca tgagagataa agcagaaccg gtcagccttt gcatcacgac gtcgaatcat 259620
ctttcgatga aggacggta tgatgcgagg aagccccggc ctggtatttt gaccggctga 259680
agcagcggca gaagctgaac ccgaaccaaa ccctaagcaa agaagggatg tgccttagtt 259740
cagtctcgag gacgggataa tagggggcgta gcaccgaata tgtcggagta gtcccaccca 259800
gtagatggac aagccagtag taccaatcaa ggaagccttt cactgtagag ctttcttttcc 259860 tgatggggac taagaaaagg agacgaatat agctaaacag ctgcagcaga aagaacgaaa 259920
agccaaaagt caaggtgcat agcggtctat tcaagaatag gggagtacag aataaggggg 259980
ttgcaagaca aagagaatc cgctggaact acggacaagg atattttact caattcccct 260040
cttactattt aaaaagcgg aaaaaaatga aattccacca gtgtgtatgt aagacaacct 260100
taattctcta tgttcaacgc tttgggcaag ccagagcaag acttctctgt gggaataccc 260160
ggctatctcc tactttaaat agagaaaatc cctggagtca aagagttatc acccgctgta 260220
tcattgacgc ggacggggct ttctttcctg cggtttccga tattgcaatg gcaagcaaac 260280
agaaggtttc cctctttcgg gtataggctt tcccgattga ttggaaagat tttatactgc 260340
cagagaaaaa aaagctatct aaccctgata tccttggtac tgtccctgct gagaaagatc 260400
ctaatttccc agagagtgct tttccggtgc ggtgtaacca acaactcaag gctatcaagg 260460
gaaggagttg caggaccgga ttctatctc ggatccacag aatgacctgt ttttgtctcg 260520
aaaaccgctc ttagggcagg ttccacgtgg gattggatat cgaaggttcc ttccgagcat 260580
tttggatatg gaatctgtat tgccggaaag gttctccctg tcccgggcaa cctctcttct 260640
tataggattc atagagtgga gtttacctt aaggttggat tctgattgag aagccgcatc 260700
ggatagagaa cacgagatct tgcccccatt gttgaagatt tgctcttctc aggcgtctcc 260760
agggagatga agtatttgtc tttgtcgatt ccactagatc tgagcatgct acgtgtcatc 260820
gggccagtgc gatcacgttc aacggacgca acagcgtaga tattgttgca tgggatgttg 260880
ttgctcttcc ttgaggccat cacagcagtt ggctccagag tctgcagatc tgatttgtga 260940
gagaaagaga tgaagggcag agttggtccc accgggcgtg ccagaaattt gttcgtgaca 261000
aaaatggaat atagaaaata aataactgca atcacaaaac aaatatgaga aaaatcatt 261060 tttttgataa atgtttgagt acaactccaa gtatcccctg attcttgtct ccaagttgtt 261120
```

```
cgccttgatt cgagggctga agcagcgtgt ttctcgaatg aaggatgatg tggacctcct 261180
cgtgatgtat ttgatctccg agaaagtcgg gcagcacttc gggttgatct tgaggaagaa 261240
cttctcttga tcacttcacc cttgctagag aactttgaga agacgatgt  agtcgatgtc 261300
ttgatctcct tgtgaatctt ccaagatgtt atggaatttt caagatgcct ccaaagagaa 261360
tatgtagccc ctttatatag gcatggatta ggcttttagg gtagcctcca agtaatccta 261420
atggacccett gggcttgaaa tatgtgggtg gccatttttg tagaggccca acctagccca 261480
atgtagttgg atttgactta agtcatgcaa ttttgactta aataatgaat ccggctttat 261540
taacccaaaa tgttgacttg ggtcaatatg tcttgaattt agaacttagt ccaaattttg 261600
tatggactta atcccataaa attttgcatg tctacactta ccaaactagg taagctagtc 261660
atatagcttg cttagcacaa agtttagctt gcttgctcct ttaaattact cgtagcgtaa 261720
gcgagcgtag aggaacgaac ggagcatctc tcgtagcacc gtaaggcaac gaagttgctg 261780
cattgcatag aggtcgctaa gattgctggt aagaatcgct attgcaagtc tatcgaagcc 261840
tacgctactt attgattatc aaaaagcgaa ccccccggcc cttcccacct ggggctaccc 261900
ctaccctaag ataagacggt tcccgccctc aggtcaggga atagagctaa ctgcatcgga 261960
aaaaatagca attcctagtc cgaatcctgg acctggttca cgcttgaaag cagcaattct 262020
tcttccaatt tcgtacatca aattgtgtat ataagaaga  gttcgtcctt cttcaaagag 262080
ataaagtcac gcggcccttc aagatagagg cttcagtcat cgttagaatc ccggggcggg 262140
ccaaattaca taagaaagg  agacttattt caaagtggtt caggtagctc agctggactg 262200
aaaatccttg tgtggttcga atccacatcc acttcacagc aaagaaagag aatgcggggt 262260
agaggaattg gtcaactcat caggctcatg acctgaagat ggtgcaccat ctatccatgg 262320
gagtagcgaa agatacctcc ttcagggcaa tgaatgccat ggtttctaat gaactttatc 262380
cagaaggagc tgcagcgatt gagcggccag ctggttaaag aattttttatt ctccgctccg 262440
actctcaaga aaccccatat ctcccttact ggtcgcggtc tcggaagaga cacagcgctg 262500
ccgaccttct gagctacgca aagccttcta atatcagggt ggctgtacac gcaattgaga 262560
gtacttcttg ctacttcatc gtccgtcaaa accatcagct attggccgga gaacctaaca 262620
gaacttttt  ttctttcagg agttggttgg tggcatggtt ttcttattta gtatttgt   262680
ttgtttgctg gcacaggtag tctagtcatt atcagtagca gatgtagaat ctgaaaggtg 262740
ggattaccgg tttcatttaa acctagctta caatcactag tgaaagagtg cccattgacc 262800
caactagcga atctgtttag aaccaggttc agaaagatag ctgaaagtgc tagcataagg 262860
aagagattct atggttttcg gcattcaaag tcaaacgatt cttttcattc aaggaaatcg 262920
tctctattga actatggaaa gcactttcta gtagcgacac ggattcacca tttcgccaat 262980
ggggcaaacg aaggctaacc cgttctggtt gttatgaaat cagtaggttc tttcagtctt 263040
gctttccttc ttacagagat aagagagata agtaagtata agtaatgatc catccaagga 263100
atgagcttcc ccagagtcca atcccgtgga ctaagaacct cgcccggcaa cagcagatgg 263160
ttaacctttc attcgatgct tctgattcaa accaaggtac agagattagg tcgaggtacg 263220
aagtctctgc ggggctaccg cagaggtacg aagtgactcg accaagggga gaggggctac 263280
cgctcgtttc actatgttac ctatgttcag tttcacatag tgaaacgaat cgttacactc 263340
tcatttcgta ccttttccct gcgagcagaa gctctccgct cgtgcttcat tggagcgaga 263400
cagtcgcttc cacacagaat acttggctac ctacctagct cgcatttgtt tatcctctcg 263460
```

```
tgggttgatg acatagcaag gggataagcg gtgtggggcg aagtgagctt ggccgctctg 263520
agtagaagtg ctctctagca gcctagatct agctcagctt gagactttcg tactgaaagg 263580
atgacttcgc tagtcgcgag taagcacccg tacgggaacg gctttcggca gacaagttgc 263640
agcagcaaag agtgcgccct ttcgtttcaa tgtagattct cctctcagag aactagaaga 263700
aggggcctaa gcacggtaca cttgagtgga actcaactcg accaaggta cgaccaacgt 263760
acgaagttgc tagagattcg ttgaacatag ttcaactcat tcgactgaaa ggagagggaa 263820
gaggaattcc cggaaatcct tcttgacgac gcatccagca ggaatcgaac ctacgaattt 263880
gggcgcttta accattcagc catggatgca aagagactca gcgagtgaac taggttttgg 263940
tattccttct cgagcttcta tttcttccgt taaaggagat tcgagaaaag atgaaatagg 264000
aagacgtgtt tccagaacga aaagatacg gggagttagc aaagttagac aagattggaa 264060
tgggcatagg aacatgtatt ggtatatcga tcggtccagc ccaggcttgt gcggttaagg 264120
ttgttgtaca cgatggaagc tgttacgtgt gggattcggt gtcgccatcg gatcggagcc 264180
aaagcatacg ctgctttaaa gcagttactg ttgtggcgtc cccgctcaca actccatccc 264240
ttagtcgcaa taggttctcc agggaatcct cgcccgttaa ggtacgagga ttcgcgagcg 264300
cccaggcacc ccgtcccatc caatcccat ctgggtgaag accgccatg acccgacaga 264360
tatctacctt ggcctcgaag aggtcttcgg cgtcaatccg ggccatttga atggcatggg 264420
cggagggaaa gggggatccc cccaaaagcc tccgctgaat ggattccaca caatcccccc 264480
ctatcaattc attatgggga tagggatagg ggactggggc tgcttgatta gcagctgctt 264540
cctgcataac aggaagagca gcttgttccc ccggaagcgg ctgattgacc gttgaggtac 264600
ttccagaacg ctgggaatcc tccaacatat cggttgtata agtaaacaac tccgtgctgg 264660
tggatccgtg aggaatcatg ctgctcccga tggagagacc cccatcggcg gcactgaata 264720
gtgctcgcac caggcaccca atggcccagg caagtccacc cgtgaggccc aaccctctaa 264780
gagcaaagga gagggcccga cccaaccata aatatgaaat caaggatgca aatgattgac 264840
ccaaggttgt attaaagttt cgatcggtta ataacaagct tgctyrsamm tygctttata 264900
ttgaaagagg tcttcctcct tgagaaggya gcctttctat catttagtgg ataactcctt 264960
gctccattcc gcttaaggtg gcgcgcctta gtcccataag cttatgccta tacctgcttt 265020
cccttgaaat aaacatagta aaccacttta aactcgcagt tagtcttggc ccaactctgc 265080
ccgggggttg gccttttaag gcttatttca cttctttttt tattttctc ttattgctaa 265140
ttggaactcc ggctccggta acctcctgaa ccttatccat tacgtcaacc cttcttcaac 265200
aagggaaga taggagggaa ttcccttttt caaggcccct aacctagtcc tggtttggtt 265260
ctccagtgga aagatttgag ataccttctc ctaccctata aagtaaggga gactgacact 265320
ttatgcttta tagaaagcga aatagtgata aggagttgcg gaaaagtccc gaaaaaagga 265380
agcgactttt cccggaagag caggggacag tctttagccc aggtaaaata aaacctggcc 265440
tcccttcca ccaaattgga ctattctctc atatggagtc taagaaagag atatccttgc 265500
gcaaggcgaa agatcgatgt ccttcagaat tctaaaagat caagattgcg tgcctttaga 265560
tccgtctttc ttgattcata atcaagacag aaaggtcgga tgtacttgtt caggtcaagg 265620
tctacttttg gtcattcttc tctctgaaaa atagaatatt gctcaaagaa ggtgactcat 265680
gtagtccctt ttcgagtatt atcttcgctg tggatgatca gtcggtgtgc gtatgaacga 265740
acggattcca cctctttatg ggctgtatat gccctgcttg tccccatacc cctttcagca 265800
agggttgacg tggtctcaag aatcttcttc cgacctctga ggtggtcgtc aagtcctcta 265860
```

```
gcctaggagt gagtcaataa aaggcaggat tctcgtcttt tttttttttt tctgagagag   265920
atgtcgtcct tcagttcctg atgaattgag tccgccatct atttcatagt aatcacgaac   265980
aagccctatg tgtcacaaag caccacgggt tctttacttt tttggtgggg gtggaggctt   266040
ttgtgcatta tagcacagcc gtgactacct ttaccttgat tgttgctgca tatcgcccgc   266100
ttgttctata gaaactaagt gcctatcaat tggttcaaag cggccggggt ctaactagaa   266160
cttcatttct cgatattgtt ggaattggtc tcgaagaagc gattgcccgc gaagccggta   266220
gccccttaag cttaggggaa tcggccttct ttagtaaaag cttttttcttg cttaatgctt   266280 tcctatctcg actgattccc cgtgatccac ctatgagatc gtttgcaccg gctttggatt   266340
caagaagatc ggccatagaa taaggaatgg gaagaggcga gactctcgat tcgctgctct   266400
acatttcgat aaagtggaat aagaaaggcc gtagtaccct aggcccgaca gaataatgaa   266460
gaaagaggcc gattggagaa gttttgtttg agaggctaag ggactagacc catcaaaagc   266520
agaaagaaaa tgcgtgacta agaaggagta accctagaac aagttgtcaa gacttgaccc   266580
ctgaagaact ggccaaaacg caggacattc cggaagttgg tcggtcaaga cgggcactcc   266640
cttcgctcct ttcgacctga tctcccacaa aaccaataca aagaaggtgg aagtgggtca   266700
ccccatataa gtaatatggg caaagtacgc gagatatgac caatagtttt ttttttcaac   266760
agagtccttc tttcagcaaa atcaaagctc cttagtgcaa tcgatttcag tatgccagtt   266820
taatttgaag agaaagaggg cagaaatcct tacaatctca gaaccaaaag gagagaaggt   266880
ggcgaaggat ccggattcac tttttttatt tgattcatac ccgcgtaaag gcttttcctg   266940
attaaggaag aagcctgaag gaaactctga actaagccca aaggctagat cccatccact   267000
tcgaacttta tgtttcaagc acgttggcat ttgattttca ccataaagag gaacccggt   267060 aaaaaaaaag gcttgcttct ttcttgatgg ttgaacggaa tcaagcccaa gggcaatagc   267120
tgacattgtt gaattagctg acagaagaag cgaaaggtat tctgatttaa gttcatactc   267180 ctaagcccctt attcttgaaa aaataggcat atgggtgatc ttttttataag caaggagcta   267240 tctataggaa gatacttctt tgccaggtca gtctggtcgg aaagaagctt gcttacacct   267300
tgctttatat tgaaagaggt cttcctcctt gagaaggtag cctttctatc atttagtgga   267360
taactccttg ctccattccg cttaaggtgg cgcgccttag tcccataagc ttatgcctat   267420
acctgctttc ccttgaaata aacatagtaa accactttaa actcgcagtt agtcttggcc   267480
caactctgcc cgggggttgg cctttttaagg cttatttcac ttcttttttt atttttctct   267540
tattgctaat tggaactccg gctccggtaa cctcctgaac cttatccatt acgtcaaccc   267600
ttcttcaaca aggggaagat aggagggaat tcccttttttc aaggccccta acctagtcct   267660 ggttggttc tccagtggaa agatttgaga taccttctcc tacccctataa agtaagggag   267720 actgacacta tgctttatag aaagcgaaat agtgataagg agttgcggaa aagtccccga   267780
aaaaaggaag cgacttttcc cggaagagca gaggggacag tctttggccc aggtaaaata   267840
aaacctggcc tccccttcca cccaagtgga ctattctctc cttatggagt ctaagaaaag   267900
agagatatcc ttgcgcaagg cgaaagatcg atgtccttca gaattctaaa aagatcaaga   267960
attgcgtgcc tttagatccc gtcttttcttg attcataatc aagacgaaag gtcggatgta   268020
cttgttcagg tcaggtctac ttttggtcat tcttctctct gaaaaataga atattgctca   268080
aagaaggtga ctcgtagtcc cttttcgagt attatcttcg ctgtggatga tccagtcggt   268140
gtgcgtatga acgaacggat tccacctctt tatgggctat atgccctgct tgtcccccat   268200
```

```
accccctttca gcaagggttg acgtggtctc caagaatctt cttccgacct ctgaggtggt   268260
ccgtcaagtc ctctagccta gggtagtcaa aataaaggca ggattctctc gtcttttatt   268320
tccctttttt ctgagagaga tgtcgtcctt ccagttcctg atgaattgag tccgccatct   268380
atttcatagt aatcacgaaa agcaagccct atgtgtcaca agcaggcacc acgggttctt   268440
tactttttgg tggggtggag ggcttttgtg cattatagca caggccgtga ctacctttt   268500
accttgattt ttgctgcata tcgcccgctt gttctataga aaactaagtg cctatcaatt   268560
agttccaaga aagcggccgg ggtctaacta gaacttcatt ccaatctcga tattgttgga   268620
attggtctcg aagaagcgat tgcccgcgaa agccgtagcc cttttaattgc ttaggggaat   268680
cggccttctt tagtaaaagc ttttttcttgc ttaatgcttt cctatctcga ctgattcccc   268740
gtgatccacc tatgagatcg tttgcaccgg ctttggattc aagaagatcg gccatagaat   268800
aaggaatggg aagagagcga gagactctcg attcgctgct ctacatttcg ataaagtgga   268860
ataagaaagg ccgtagtacc ctaggcccga cagaataatg agaagaaaga ggccgattgg   268920
agaagttttg tttgagaggc taagggacta gacccatcaa aaagcagaaa gaaaatgcgt   268980
gactaagaaa ggtaaaccta gaacaagttg tcaaaagact tgaccctga agaactgacc   269040
caagcaagga cattccggaa gttggtcggt caagacgggc actttccctt cgctcccttc   269100
gacctgatct cccacaaaaa ccaatacaaa gaaggtggaa gtgggtcacc ccatataagt   269160
aatatgggca agtacgcgag atgtaaccaa tagatttcca ttttttcaacg aagtccttct   269220
ttcagcaaaa tcgaagctcc ttagtgcaat cgatttcagt atgccggttt aatttgaaga   269280
gaaagagggc agaaatcctt acaatctcag aaccaaggag agaaggtggc gaaggatccg   269340
gattcacttt ttttttatttg attcatatccc gcgtaaaggc ttttcctgat taaggaagaa   269400
gcctagaagg cagaactctg aactaagccc aaaggctaga tcccatccca cttcgaactt   269460
tatgtttcaa gcacgttggc atttgatttt caccataaag agggaacccc ggtaaaaaaa   269520
aaaggcttgc ttctttcttg atggttgaac ggaatcaagc ccaagggcaa tagctgacat   269580
tgttgaatta gctgacagaa gaagcgaaag gtattctgat ttaagttcac ccaatactct   269640
aagcccttat tcttgaaaaa taggcatatg ggtgataagg aacttgaaac aggcatggac   269700
agaagtatgc ccctcctttt gatggtgaat gtcggaaatc ctcttcccgg atcacctttg   269760
atggacattc aaaaggatct gctaggctgt cttacatgtc ccaaaaagca agcaaaaggg   269820
ctcctttcct tccccatgtg gaagaagtgt acacacaggg ggcctctcga cctcagtatg   269880
aaaagcatga cggaatcgac ggtggtcaat cttccttctt cttttggcatc tcgactgggg   269940
agcatgaaaa caagactgga agagggctca ggtatcaacg tccttagccc gcattgatca   270000
atatcaataa gaatagcagt cgtataggta taggttagcg cttccttgct tgcatccttt   270060
cctctctttc ttaatgaaat agatatagat gtctcgactg ccgaatcctt atcctgcaaa   270120
caactcgatt ctgttgattc actgtccatt tgtccttaaa ccggatgttt ggtcaacgac   270180
tttgacagcc tttccttcac acaaggtttt taatccttct cccccgctta ggacagaaag   270240
gggaagtagc gagattacga ttccttggtg ggaaatcaac gaaggcagtc gctccagcag   270300
ctttagtact tagttaaggc cccagccctt cgcccggttc ttctccggct ccaccagcag   270360
cctttatcag ctgctatggt tcccttcccg caatgcgaat ctctatctct ttgcggctac   270420
agcctattct aataggaccc atattcaatc ttttaagtga cttctgaaga ctagctagct   270480
ctggacctac ctatattagc catgagcgat caccaagcgg agttgaaaga aaagagactt   270540
gacatgccaa aacttcgctc gcgagctcgg aacgaacgga gcggaaggga tcaaaagttc   270600
```

```
cagggagaaa aaaaagacga gcactttggg ccacggagcc aacgtttaag acaaggctaa   270660
aggaggccat acgtgtagta aactcctctc gttgtgaaga gagtgagtct atagagccta   270720
cgagccggcc gatccactgt agtggaatct tgtaggctag cgggcggtcc cgcgcggttt   270780
gcattagagg ggcccgcttt catcatcctt ccccagatct cttctattct gtgatctggg   270840
atgattagat gaggtttcca tgtgtgtgtc ttcgggagca tcttctcctg tgggatcata   270900
gccagttttt cactgcgagt ggttatctaa agtaaaggta aaggagggtg acagatcgat   270960
gagggcgctc ctgcttatcg gttataccct tcgacccctg ttttagcagc tagcgaaaag   271020
gcttcgttct gctgttcccc gtgagtggtc taaatcagct gcggtagtta aggtttggaa   271080
caaatgagcc taagggaacg aagttgtgag cctttagtaa tatatgaata agagatattc   271140
gaaataatca aacctgatgg ttcctgtcct gaaacgaagg atgcgaagaa agtactgccg   271200
cctgtcatca tgctcaatca gtaataagtt ggcttcacct ccggggatca gtccagcctt   271260
gtgaagggag aggactctgt tatcttgctt tcctcattcg catgagagac agacacattg   271320
tgcactcaag atgatgaatg ccacaagaga gatagaagaa agaagatctg tctcgattct   271380
atctctatct ttcgacatct catctctata atagagataa tagtgggtgg agaatccttg   271440
tgtattctac tggtatagaa tctttgtgga aggcgggaaa cttccgtcta gcggtcatgg   271500
gaaagccaaa acttgtatat aataagtcaa tactgggtcg gtcgagactc tttcttagtg   271560
aagtgggaag acagcaccga atcagacggg cacagaagaa gaagtggttt catccgaccg   271620
gcgagataat tcgatttcta gtcagctaac tgagaatcca atagagaaaa ttgcttttct   271680
aatgatttct cgatagaacg atttcttgtg agccacgaaa cagataatcc aagtcgtaag   271740
tacgaaccac tcaatggaga atctcaggcc aataagctac gactacgaaa cgaattggat   271800
cgggttcagc gcttgaaagc tatcgaagaa gagtcaattc aatgctcaag tcaaaggggg   271860
gagtccactt attcaataga agagaagcct atatctgccg accctacttc acttccaact   271920
agtgccttgc ctactgtctt tgaataatgc ttcattccag ggcgtaaaag aaagcttagt   271980
atagcaattg aattgacctt ttgtactgag gacgacctat gagatggttt gaaccggttc   272040
tcaaacctac tactatacga acagtcttct tcggctaagg ctggcaaatc caactatttt   272100
ttgttaaaaa gagatctcgg atcaagggct atcgacccga cagtgctccg ttggtccatt   272160
tagtggatcc tccccccaaa aacaagatca tattgagcag caacttcgag gaagatagca   272220
ttgggacatg ctattaccta tgtatggtga cgggtgtcat gccagagtct gtccgggtgg   272280
gctcaagcta aagcaggaga agagagttag ctttctgctg agtgagcccg aacaggagcg   272340
gacgcacact agatcagagc aagtttagct ggcccaatgg cgcagacacc tactaggatg   272400
aggcatagcg ggaatggaac ccacatctcg ttgagctgct ccagcaagca ccccttccgg   272460
aagctcaatt tgtaggaccg gggagaacac tcgcaggcgt gcaggcgttt tgagagagcg   272520
caaaactcta acttgagtaa gtgccagcca ggcaaaaggg ttagcctgaa gtggtggttt   272580
agccaaaggg agaacgtgca acggttggat tcagcacgct cttagaatag ctgttccaat   272640
ccgaacgcct atcccaacac ggagagctta tccactacat ctacataagg aatagtctag   272700
tccaatattt cttgtcctta aaatagaata tatgcaccgc tgctgatcct ttctaaatcc   272760
agcttcaacc gagcatacgt ctgccgcggg aacaggaaga acggaaattg acttttatgt   272820
tgaagtcttt ccccttggaa ggctgggggg cgccttgcac gtcttggaaa ataatgcttt   272880
tgtatctgaa gttattggcc catggtcctc agtgaggaaa ggacctagaa cagagaagag   272940
```

```
ggccgatagg aagttaaaag caattcttat ttcttctttc tcgaaaacct gatgtgaggg 273000
gggccactgg gatgtccata attgaagcat ttttcttcat cgactgtcgg ttttttacta 273060
ggtggccgat gtctttgatg ctttggtttt cgcaggaaag ggtaaggagc tttagccctt 273120
agcgtgtgag ctttgatgaa gacttgcatc actattcgtt tcctcgtggc tcgattgctc 273180
atttgcttct tcctttgggc atgaagtgtt tggtgaggcc tttcttcgcc tgttgaaaag 273240
ctagcccttg ctcaaagatc tttttatt agcactagag ggagccctcc aatcttaaaa 273300
aaccgatgga atgcgatctc ataggcaatt tgctatgagg gctggacccc ctgcatctgt 273360
agaagaaagg ggaaactcaa tcatgaaact gaatttccaa gcggaaggat gagaaaaaaa 273420
aaatccacta ttgcaaaaaa tctttccttc tttttagta agggtgtcag ccgcaagtat 273480 gaggggggcat tccccatcat agagaaagta ggacaagttg cctaaaaact tcagcttctt 273540
tccaagctaa agatccaccc tgtcttccat gtggggtgtc taaagacata ccatccagac 273600
atggaagacc ctacaagagg cgttcccaag aggccaccgg aaaggatgac gactttcttg 273660
tcgaaggaat atgtgatggc ggaacgcaaa gttaatcgac gtggtgtccc agcttaaaact 273720 tttgacttgg taaagtagaa ggttctaccg aagcagggaa gctctagggt tttgctaacc 273780
agtgtgaagt tgagttctat cttcccctag ttcatgcaag gctaaccttc gggttttgc 273840 tttctggaaa aacctcttac cagatggttg ttcgctacag cctttaagtc tcgcctagcc 273900
tctcccgccg ttctccagga aactagcggc tcgcagctgt tcagccgctt ctctaggaga 273960
taggagatgt gccgctgact gggttcagga cacaaccatc gtccgaaccg tctgctacca 274020
agtccatggg ttggaaccca taagaaactg aaaaagcact tctgccggtc gacgaatgcg 274080
tgctccggtt gtagcagtgt tgaatgaacg gctgatttgg aaccagaccg ggtaacttta 274140
aaggtggtcc cgatgttaga ttctgaagaa ccgacggttc tattggtgac ccattcaaaa 274200
gaagctggcc gctttgactt tgattagcca atcgagtgcg gagggtgctg tgctcctctt 274260
catttgttcc cgttaacgac cacaaagccc ttaactgctc ctgctcgcta cttgcccact 274320 tgccctttt tactactttg actagcgccc ggcaaaggaa tgatttttc ccaaagccga 274380 cttcctttat cgagcggctc tctctgttga cgataaaagc gatggtccgg gctgggctgt 274440
ctgaaataag cggtaatttt ggtcagtcct aatcctaata aataccacgt gaagcgcgtg 274500
atcacccaga ttcctaatgc cttaattatc ttatatatat aataacttat cgacgtcagc 274560
ccccttccta ctccagctaa tggaaaaatg cctttgaatg gtcgtaatcg tcgacaaccc 274620
aaccgacgtc caccataggc tcggcgagct gtcctcctag atttcccgaa ggtaatgcca 274680 gggcctttc agtactgacg actcttgatg ccaagaagga gaccaactag acgagacaga 274740
ccattgttca taggttggtt ataagcccgg agatcgaatc ttattcttcc cctttgagag 274800
ggattctcgt gccaaccata ggaagaagaa ctcggttact catcttggat cggattggat 274860
taatagcttt gtgctgatct acgaacgagc cttctatttg atttatacta tacttcttca 274920
agtctccatc atcccgatct ctcttttccgg gtttgcctgt ccaaagaaaa cagaacctct 274980
tctagttcaa ggtcgaaatc ctcaaaccaa tcaaatatg atttctagtt cactattctt 275040
atgaatagaa gttatgtctc attcatgtga tgagaaagct gagaatgaaa attagcaaat 275100
ttcacatcta cggcagattc tgtgccccaa atcatttaga cttattaaac taagcgggcg 275160
gggaaggtat gacccctccc ccattgaaca aaggggatcc gtagggcggg ctcactcaca 275220
tactggatag gtgactcgga attatagtgc tagttccgtt ccctcgggga agagaaagca 275280
cgaatctatt acaatcttag tagagaacag aggaggaata aaaacgttgg ttcttcgttc 275340
```

```
cgtccttgac ctatgatatg atcaatggct taatccatcc actggaccac ctggaattct    275400
taattaaacc tttacccgaa aaaggaaatt ggatttcctt tttaaatctt cttttcttag    275460
attaagatat catcagaccg gtaagtttaa aaggaatgc attgattttg tgatttcttc     275520
tttccgctct tcgcttagct acaccggctt acagatgccc atgtccttca tggatctagg    275580
agttcatacg aataatggct agcgggattt cgcattcaat cggagttgcc ttagttggtt    275640
tccgaaggga aggcactcaa gactctatat agtggtttat gcccttattt ggcttcaaga    275700
agcattagaa tcccttattt aacttgcggg gcaatcaagg aatagaagct accatcctag    275760
ggggaggatc tattatctct ctacccagct cctcgtctag cagccaagaa caagagagct    275820
acaacactca ggttgttgaa tgatttagga tcagatgaga aaaccaaccc taggagagag    275880
gctcaataag ataagttaat cggagttccc ggaaggaggt cccaccattt acttgactct    275940
tagaaccttt gttggttttg ggcaacgggg atcaacttcc aggacaggaa agggcgatcc    276000
atctatttat ttgactgaac ctagttcacg agaaagagtc ctagggatag accccttttgt   276060 tttgcaccga gaagaaatca atagaatcgt ctaacgaatc gtctgatact agatgaagag    276120
gtaccccgga aagcaggaat agaggaggca caggcctgcc attagaagaa accaaaggca    276180
attagttcat ctttgaatag gtagcccggt taaccagaca agctggaggg acttcctgcc    276240
atacaggaaa ggaaagacct gggacctgta ctccccaact tgggaactca gcttatagcg    276300
aagggaagga gccgctttgt atgcgacact actatggtga agagtgaacc gagactcttt    276360
ttattgagat ttcccccggg tttctgcttc attcaagtct taattcaagt aaggacaagt    276420
ccttatcatc ccgatcggga tagacgggcc tgcctcgctg cgggtcagca cctcgggctc    276480
tctttctgct ttctgtctgt ctacaagcgg aaggcgttaa tgaaaatgtt caagtaaaat    276540
agccatcaaa tgcgaattga tgttgagatg gagtccttac ggaggtactt ctattatcag    276600
atgaggcaga atcagaacct ggagatcaac cccaaggact gactgcggga gcaaggattg    276660
gattggagac tgcatgactt gattcctctg ataagatcca tccatttagc agcaccttag    276720
gatggcatag ccttaaaagt gaagggcgag gttcaaacga ggaaaggctt acggtggata    276780
cctaggcacc cagagacgag gaagggcgta gtaatcgacg aaatgcttcg gggagttgaa    276840
aataagcata gatccggaga ttcccgaata gggcaacctt tcgaactgct gctgaatcca    276900
tgggcaggca agagacaacc tggcgaactg aaacatctta gtagccagag gaaaagaaag    276960
caaaagcgat tcccgtagta gcggcgagcg aaatgggagc agcctaaacc gtgaaaacgg    277020
ggttgtggga gagcaataca agcgtcgtgc tgctaggcga agcagcctga atgctgcacc    277080
ctagatggcg aaagtccagt agccgaaagc atcactagct tacgctctga cccgagtagc    277140
atggggcacg tggaatcccg tgtgaatcag caaggaccac cttgcaaggc taaatactcc    277200
tgggtgaccg atagcgaagt agtaccgtga gggaagggtg aaaagaaccc ccatcgggga    277260
gtgaaataga acatgaaacc gtaagctccc aagcagtggg aggagccagg ctctgaccg    277320 cgtgcctgtt gaagaatgag ccggcgactc ataggcagtg gcttggttaa gggaacccac    277380
cggagccgta gcgaaagcga gtcttcatag ggcaattgtc actgcttatg gacccgaacc    277440
tgggtgatct atccatgacc aggatgaagc ttgggtgaaa ctaagtggag gtccgaaccg    277500
actgatgttg aagaatcagc ggatgagttg tggttagggg tgaaatgcca ctcgaaccca    277560
gagctagctg gttctccccg aaatgcgttg aggcgcagca gttgactgga catctagggg    277620
taaagcactg tttcggtgcg ggccgcgaga gcggtaccaa atcgaggcaa actctgaata    277680
```

```
ctagatatga cctcaaaata acaggggtca aggtcggcta gtgagacgat gggggataag    277740
cttcatcgtc gagagggaaa cagcccggat caccagctaa ggcccctaaa tgaccgctca    277800
gtgataaagg aggtaggggt gcagagacag ccaggaggtt tgcctagaag cagccaccct    277860
tgaaagagtg cgtaatagct cactgatcga gcgctcttgc gccgaagatg aacggggcta    277920
agcgatctgc cgaagctgtg ggatgtcwac tcttttcttt gcagtatttt tattgtgatt    277980
attttgagt attctatttt acgcgtcaca gcaattagga attgagaatc tatatcttta    278040
gatcaaagaa gggtctagct gttggaataa tggtatccat tgctatttga tcccttgttg    278100
ttagtaaaat tggtgaatta agcgaaggta cggaaagaga gggattcgaa ccctcggtaa    278160
acaaaagcct acatagcagt tccaatgcta cgccttcaac cactcggcca tctctcctac    278220
ataatgatta tgaccccaaa accgagtgaa tagcgagtca gtcataatcc atattccatt    278280
attggatagg tacgaccaat ccattttaac tttaactgaa aattttcat caaagtcaaa     278340
gcaaagaacg attttctttt ccttcgaggc tccggtatat atcctccttc cttggattag    278400
tactgggacg catatatcaa aagctcagtg tgaaatttga atgagatata tcttctttt     278460
ttcaaattca aaatttgagt aatagaggtt acacaaaatc ggagccagaa aaggaaaaag    278520
tggaatctgg aaaagtattc tctaagggta atgtaattga gtgaaattca ttttgtatcg    278580
tacaagaaag gaattccatt tgtgtatgtg ctcccgataa aaagaaataa ggtactctat    278640
tccattacat acatggatcg ggttgaaaaa ccagacccag tctctcttgg aatcctgaat    278700
atgccaataa ataattaatt gtactaatcc acatatgtct ctctcccatc aatcggtact    278760
agttgaagta atgaaaaaat cccctatttg tttgatgaga aatgcgaaac gaaaagaaa     278820
aaaaaaaaag atccccgtt gggaatgaaa ttatgctccc tgtccccctt ttcacagaaa     278880
atggagagat gaattgatat atttattgaa tccgtcggga ctgacggggc tcgaacccgc    278940
agcttccgcc ttgacagggc ggtgctctga ccgattgaac tacaatccca ggaaaattag    279000
gtgtacagcc taaaatcaat ttagattcga accatttagt ttcgctgtgt tgtaacagag    279060
acacgaatga tatacttttt tattattatt atctaattat atataattat tagatatata    279120
aaatatagta gactcatagt gggctaattc atgaattgaa tcaaatgggg ccttttaatt    279180
taacaaattt gaacttaatt aaactaaaga gccacgctct ttaaacgccc tataagaaga    279240
agaaagaggc ttaagtcatc gcttccaatc cgataaaggg ctttttatt ttccacgaaa     279300
gtccgtccct taaatttaag cagaggatat aaatatgaat atgaaaaaa aaggtaaccg     279360
cctggagagt cgttttttag ttttaagtg gaatgttcat tatcataata agtagtcgat     279420
taggagaaca gctatctcac tacagagtat actcttcctc atctttcatt attcatattt    279480
tatgtcctgg gacatagata ttctagatac ccccttctat tatgaatcgc caaagtcttc    279540
ctacttctcc attgttacaa tcagatccga aaaatgagaa atcaatcaaa atggacctga    279600
attgaatcat gactatataa gctattctga tattaagaga ttgaatatag atttcattcg    279660
tggaagcgga cttttgattt ccttggacca cgtaagaatt cgtcgtccga ttgaatctgc    279720
tttttcctgg atgctctata ggaatccatc gctattcctt cctccaccg ataaaggttc     279780
atcccgagtc acaagagcaa tctcttttt ttttttgaat tcttttttct tttcgttatg     279840
gtaatgcaat gcaagaggtc ggaaatctgg ttgtttctga tgatgaaaag agcttttatc    279900
ttatgtgaaa tttatgaaaa cccgaaatgt cggtaatgtt agaagacgac ctacggcatc    279960
tgatggtcag atgcctacgg tcggtatatc tttgaaagct cagacggaga gaataaacgg    280020
actcctcgag ggctacttaa gccactttag tgcaaaccag aaggactgga gctgttggat    280080
```

-continued

```
gttgctcagt cctgctataa cttaacaacc aaaaagctct gcgtcgaact tcagcccctt   280140
cgagttggcc acggggtaac agcctctgac gccccacacc attgcgacag gaggggcttt   280200
gcccatcagc ctactttacc aagaggtggc aggagcgcaa cgaccttagc ccaaacctac   280260
ttaaacaacc taaaggcttg gcccggtctg aaagtagacc ttgtagaaaa gcggatagga   280320
aaggtagcct atagactcaa gcgaccagct cggtgaaaac gaaccccgta ttccatgtga   280380
gtcagttgac ttcgattaga ccagaccgcc ccagagagga acgtgcccac gagggcacca   280440
ccagatgttg tagataaacc tactaaagaa gaagttgatt atatcatagc tgaccgcacc   280500
atgggctagc ccatagaccc actgcacgag tggaatacta cttagtcaag tagaaaggcc   280560
aacctgagag cgaggcaagc cgggaacggg ctgagactta cgattcgaag accaagtcag   280620
agactactag acgtctcgca gagcgactct caacgaggac gttgagactg ttcgaaaaaa   280680
aaaagatttt ttggcttaat ccgcctttac taagaaaaaa agagtacact tgtactccgg   280740
ctaataaggg aaaggttttt ttttcaaatc caagtttgac tctgattaga tccttagcgc   280800
aagcgctaag taagcaagct accttatgta aaaaccgagg aaaataaaga aggtcaagta   280860
gaaaggaaca aggtcttacg gcacgatcac tatatctttt cttttctttt ctctctcctc   280920
tatggaaaga ggggatgata cgtggcgtgg tatacctgat cgtttagtca acaagacgta   280980
cgtaagtcga catagctcca tgtatatgtt ctttggagct agaaccaatc aatagaatga   281040
aatgaaataa tggtaagcct agggcgacga acatggctca agagtgtcta tacaaagccc   281100
ctctcttctt cactcaaaga ggcaatgcac cctttgtttg aatggtactt gattcataaa   281160
gaatgattct tttgaagttc tacggacttt ctaaaaaaaa atgccacgcg gagcgtgtca   281220
cgagatatat cgctctcgga cttcttacgg taaggccaat gcaccagcca gccagtgtgg   281280
tggcgaacac gctgtgctct aagctaagct gtttaccttg tagacggagg agatatagaa   281340
agtgtgccgt gcttgattca taagattcta taatcaatag caccagtata ttatttact    281400 tagcctgcct ctcccatgac tttccggacc aaccaacccg gatctgcctt cgcgagtctc   281460
tctgcatttt gggagcagag catgcagcaa aatcgagcaa tggatcttag aagaattcaa   281520 cttttgaagca cgactctttc tatttctgtg ctggcatttg acttgtctcc cttcctcttt  281580
caatcgaaag actcgacgca gatagctccg gtggccccg tttctgcctc tatcaggcgg    281640
cgacagcccc cccctccaca cccacagcat agaggagctg ctccttaatc cgcactacaa   281700
ccaatccaaa ttctctccag agcgatatat gatgctaaac cgagaccgag atatagagag   281760
ggctgtcctt ttgttttgtt gtctcgaaga gagaaaagca ctcatatgaa tggtgctaat   281820
tcccatgttc tttctagtct cgtttggttt cgagagcctc cctctccccg tcccttactc   281880 gtctttgaa agccgtcatc ctggatttga tttccgtatg ccggggaaag taccccaccc   281940
tcacctttct acatttatta ttatatagaa tttcctcggg tctctataaa acagaatgaa   282000
aagcccgggt ggaagcacaa acaaaaggag agagaaaaag tcgaaagaa aggggggaag   282060 aagtctagtg ctagttctta ctaacacttc tttatctaac tttcattttt gagtgctttc   282120
tttgttctct tatttggatt gaaagaaaga aaaaacttcc ctttctttct cttctttatt   282180
tttgttttat cccttcgacg aatttcggct atgaccaatg ccccactagc taaataggcg   282240
taagaaaaag ctacctgaaa aaagagcaag gtgcaccttg aattgaactc gacgaattgc   282300
gttttgccag agagattttt ttagaaagat tctccattgg taattcaaaa atagaaagaa   282360
tataaataaa ggcgcatacg cgggaagggg cccccactac ttcttcattc agggggggagg  282420
```

```
gggggagact agcctcatta cttcccactg ggcgagaggt gcacctaacc cacctaccca   282480
ctcatcaatc acggtgttca gctgacttgc actgatagac ccctattgta ttggaatttg   282540
gcgcccatct ttttactgtt gtcaatgaat ctcttccatg ttcgattcta ctctatgtta   282600
gaacatttct gtgaatgcta ttctgatcta agtggtctta ttctttgtcc cgtgctagga   282660
agcattactc ctcttttcat tccaaattca agaatacgac cgatacgatt aattggtctg   282720
tgcgcctctc ttattacttt tttgtatccc cctgttcttc ggatacaatt cgatccttct   282780
acggccaaat ctcaatttgt ggaaagcctt cgatggcttc cttatgaaaa catcaatttt   282840
tatttgggta tagacggtat ctctttattc ttcgtgatat tgaccacatt tctgatccct   282900
atttgcattt cagtgggttg gtctggtatg agaagttatg ggaaagagta tattacagca   282960
tttctaattc gtgaatttat aatgatcgcc gtgttctgca tgctggatct tctactattc   283020
tatgttcttc ccgaaagtgt gctaatccct atgttgtgcg gagctgagta tcttctattc   283080
gctgggataa agccttttcct ctgcaggggc cttgtgcagt aaaccccta cgggcggtcg   283140
tccgtcgtcc taaagtagtc cccgcgaagc tttcgggaag aggggtagtc ttgtgtgtaa   283200
gcatagcatt tctggtcgaa cccgcccaac ccaactaaga agaaccgaac ctgacagaca   283260
catcttttc cttttgggag ggtactccga gtagtgggta cctcgtagga cctcgaccccg  283320
cctactcggg tcttgtatgg atatgcagga aggggtgctc ctaggtgtgt gtaggggttg   283380
tgtttgttcg cgagaaagga ttcctcgtca agtaagtttg gggggtgtgg acacacttgc   283440
gcgaattcgg gtaacggcta caagggagaa atcgaaagga aactgtaccc gaccagggat   283500
ggacgtaaac tcgtaagcta ccgaaggtag ggataatcgt ccaggtctta ttgtgaaaga   283560
aaaaagccgc cccgccacag cagacgggtt gcttcctctg tcgtcgccgg ggagctcttg   283620
gcgaggagac cttaggataa gttgctaaaa caaaggggat gggaggatcg acccgttcag   283680
ataattccga agaaagactg ttggcagcag gtagagagat ttttttttcc tcttcaaaac   283740
acaaggaaat gcgggcaggg tagagctcgg cagagggttc gagaataggg tagggtcctg   283800
tccttaagat tcagataaga aaagagttcc aaacctttat gcatgcacct ccgtacaagt   283860
gctgcataca agttccggcc aggatgattg agaaagattc aaccaatttg aaccgctcac   283920
atcacaatag tagtagcgta aaggccgtaa gtcgggggc ggccataaca taaggctatt    283980
actttcacac ctctctctct atctatagat agagagagat ccgctgcgtg agcaacccga   284040
ctgtgcctta catgtgctct acaggccgca ctccatcttt cttcccaacg agccttttt    284100
ttgatttgga agacgggcat tgcgttcggt tcgaaaggca tggttttcag tatgtctcca   284160
gatagggccc ccactagtcc ggctagctag tgagcggttc tttcgggcgg gaagcaggcc   284220
gggccctacg ggcgggcatc tcccgcaacg caagcaccat tgttcgacac cacccgagaa   284280
gcaaaagatt ctagagtcca ggctgaaaat acatgcatag atagtggttt aatgccaagg   284340
ccgacgacgg aagctcggga cggagccgta tgaggcggaa gtctcacgta cggttctctg   284400
agaagggagt ggctacctac tggagcttcg accaagcacc accggtcaat ccgctttgg    284460
ggccaccct gactctacca ttattatagg ggtatggggt tcgagacaaa gaaagatcaa    284520
ggcagcatat cagttgttcc tttatacttt acttggatct gttttatgc tattagctat    284580
tctgttgatt cttctccaaa caggaacaac cgatttacaa atctcattaa ccacagaatt   284640
tagtgagcgg cgccaaatct ttctatggat tgcttctttc gcctctttcg ccgtcaaagt   284700
gcctatggta ccagttcata tttggttacc cgaagctcat gtagaggcac ctacggcagg   284760
atccgtcatc ttggcaggaa ttgctttaaa attgggaacc tacgggtttt taagattttc   284820
```

```
aatacccatg tttcccgaag cgacactttg ttccactcct ttcatttata ctttaagcgc   284880
gattgctata atatatactt cctcgaccac tttaaggcag atcgatctta agaagatcat   284940
tgcttactcc tcagtagctc atatgaatct ggtgactatt ggtatgttta gtcgggcggc   285000
ggccgttagg tcacctattt tgagttatgg acacacaagg ccaaaacatg tgtgccggac   285060
gcgcgaccca tcaacctact agcaatgggg gagaaagcat agcatgtcgc aataaaagct   285120
tgattcgagg cgtcagcaaa acactgccgt ctgttccaaa aacaaaagcc cttagcgcc    285180
ccgggacggg agtgggggac ggccctacgc gcaggcaaca gcagcaccgg ctctacgaag   285240
tcagaatcga atctttctgt tggctttccc aattcattcg tgaataataa ttcaaggcg    285300
tgaagcgagt acttctagct gcttcgcctg cttcttatta tggcggctat gttttcgtgg   285360
cgaaaatgaa cgaaaagcga gatgagcgtg ctattttcaa atcgattgat agatagcctg   285420
atctgttctg atagatcgaa agagatagag agggaatctc tcaagaataa ggggaaatct   285480
cctatttcta tctattgatg agacaactat ctattcttga tccatcagaa agaaatcgat   285540
atgtatctga tggagtctac atcgtacgta gagcgcccaa gcttaggccg gctcagttct   285600
cttatccatc ggtccaatgc actgggctca tctcatggaa ggaaaagcca aaatgtagtt   285660
gtcttgttcg ccgcctcgac gcattccctt ctctccccgg tatcgtccca cacagaaaga   285720
aagagcgcag agccccggcc cgacctgtag gtccgctaac gtaaagcgag gagttgagcc   285780
tgaactggcg aaccgaagtc actttcggaa ccatacttcc tacagctaac atgtgtccag   285840
tccagcggga acgcgcagcg caaacgaacc tgagctgcta taccgaatcc cccgctgacc   285900
atcggggacc gagtggtaag gccatgatcc gcaggggaac agatcactca ttcttccatt   285960
ggggacaggt gcacgaacga caactccaaa cgtcacacat ccgccgccta cctaccgttt   286020
aggtggcacc agcgagatcc agctaaggta aggaacttcg tgtcgcggct gctccactcc   286080
gctgcgctgc ggtctcatga actgaacttc gttgccttcc cgcgcgcgaa gcgaatgggc   286140
gctgtgccgt gggtcagttt cggggtgggg agcgaagaga gaccagaaga atgattcatt   286200
tggatcgacg agctttttca gcccaaaaac taagaatcaa tggaatgtcc gtctatccat   286260
gaacatctat tctatctgta tatctagggg atctctctat acatatagat tttttttatg   286320
gaatgatatg atcggctagc cgtagccgca tatcagctac gctcaatgcg ggatttctgt   286380
tggatcagat cttttgggaa gcttttggac ctagcgaaaa gggctctaag ccttcacgca   286440
agcaagcgcg agaggagcgg agcacgaagc taccgcttcc cccgaccgac taaaatacaa   286500
cagtcgcgac ctactttgat tcaaaagaaa ggcgaagggt taggcaacaa gcaaacggct   286560
ttctatcata gttgcaaggg ttccaaacct taactactta agtaccaaag gctgctttcg   286620
gttggtttca taatggggct gttcactaca agctatcagc gctcagcgct gtcttagatt   286680
gaacgttgac ttatcttatt gccgttcaat ctctaaggcg ggtttccgct gagaacggaa   286740
tagtgttcgt gtccaaaggt gaacaaagcc ctagcttcta gagttcgctg cttttcccag   286800
gccggagaag ggcttatact gctcgccttt gtttgatatg ttcattcagt accaatacaa   286860
actaaaacta caccaaagtg gaagggccag tatagaagct agaagtagct agcctatagt   286920
agtcggccta accaaagcct cacgacaaca taaaattagc cttatgaatt gaatcttaag   286980
tagggggctt agcccgcccg cctaccaatc aaagaggctg agagtaagcg taagctcacc   287040
cggaagctcg aagagcttcc cttcattcgc ttcgcgggag ccgcacagca catagctgga   287100
agtcagaggg cccatactac ctgcctaacc cctcgctccg agggaccgta gatcggaaag   287160
```

```
cgccttctaa accaccccat tcatccaaaa gagaagggaa ggggcctatg tatttgcatg   287220
acccctgcag atttaaccct atctataccc ggagccactc ccctagcggt cctgccacca   287280
cgccgcagaa cgggagctcg tgtggaacct tttattctgg cgtaacagcg gtagaacgta   287340
acaaaatatt acggccgcct aacataggggg acggaggtac ggtaaactcg gccaaaatat   287400
gagacccgaa gggcccggcg cgcacaatcc tatcctatcc gaggccgagt ttaccccttg   287460
cacttcggac agccgtccgt agcatcataa ggaggacccc cctttcgagg tacaaaaaga   287520
gtacggtaca taggaggttg gtctttctca acgtggtgta tagcacgaaa aacctttcga   287580
tacaagatag ggccgttcac atgaaagaaa aaaatgaatc ctttcttatc ttctttcccg   287640
agagggaaag agaaagaggg tcttatggag ggaggggaaa ggcttgggcc tacctatccc   287700
gataggaccc cataaaagaa cgggagctgt tgagaggttc catattgccg agacgaagga   287760
cagcacttct gtacgtgatc gtagtatgtc acctcgtctc gtccccgctg catcgaagag   287820
tacctatgca ctatgttccg gttcactgat aaggaagata gcgttggggt gggggtctac   287880
gatgtgatac taaagtatga ccgggggaga tacatgctaa ctatgggtag gaagcaggaa   287940
ccattatgta aaaaatttcg gggggttaca gatctcttat actaccatcg atcgacagag   288000
cggaacgacc agaaaaagaa gttaagttag aaagccgtat gataggtggt aactatcttg   288060
tacggttcgg ggggtaatcg gcgtactccg atcagtgggg gggaatcttt ggctctatcg   288120
aacatacagg gaattggagg tagcattcta ccgatgtcaa gtcatggact ggtttcttca   288180
gccctttttc tatgtgttgg tgttctatat gaccgacata agactcgact tgttagatat   288240
tacgagggtt cagtgagcac catgccgaat ctctctacca ttttcttctc ttccactttg   288300
gccaatatga gttcacctgg tactagcagc tttatcgggg aatttctcat cttagtagga   288360
gctttccaaa gaaatagctt agtagccaca ttagcagcgc ttgggatgat tttaggcgcg   288420
gcctattccc tttggctata taatcgtgcg gtttctggga atttaaaacc cgatttcctc   288480
cataaattct ccgatccaaa tggcagagaa gtttccatat ttataccttt tcttgttgga   288540
ggggcgaccg tacgttaaac taccaaagaa actagggtaa accaatgtga tcatgacatt   288600
gtaggtgctt gcgatgggac ggatgcgact tccctcagtt ggtttgggtg gcatagcccg   288660
ttgcataagt cccccccttt tttttttcc attttttag tctttaggga gccaaagctt   288720
gactttacta aactaataaa taaggctcgc gctaggcgct tacctttttt ggctgagccc   288780
tatcttgctg ggtgagactg atagaaagaa aggacggggg gaaaccatgc atggtacttc   288840
tcgaccctgt ctccgaggga cagttgaact agcgactcat gaatgctgcc gggttggacg   288900
agccaataac tcgaaggcgt tcggtctgtt ttttgagcaa gaatcacagc cttaccttat   288960
cttcaccagg atacggactc caagttctta tggcagagca cgaggagatt tatcatcaat   289020
atgatgattg gaatggaaac cagaagcacg actgggtct tcgtggtcca agataatcaa   289080
accatcaata agagtaacgt aagcatgaga cttttggta gtaccggtga accggatggc   289140
cgcggcgatg gaatctggga cggaggactt gtagtatctc tctagatctg gcaaaagcga   289200 aagacccct aacataattc gaatggaggc tgaccgctga gcccactctg gcctcgcggg   289260 gcgggccct gtggttgcga gctggagctg ccatagctta tggctatagc aatgggaggg   289320
ccccagcaga gagaaaagtc aggataacga gcgctccgcc cgccaagcgg gcggcaggag   289380
cagcgggcaa gtgcttggta agccaacagc ccagtgaacc gggcggggca ctcgaagaaa   289440
ggggggcaca ctgagcaagt acgagaaatt ggccccgctc cgcttcttta aaagcaagga   289500
ccactacggg aggtcaaacc aaggatctat ggaagtgggg gctcgtcccc ggtcaatatt   289560
```

```
ggatcaaaca ataggggggcc gtaacactga cctctttttt tttttttgatt caatacaata    289620
ggggaaaaga tcgtacagtt ccctaccgag acaaactctc aacggatcct ccgcgcgctg    289680
ggaatacctc ttccgtgcgt ctttctcgtg gcgggaacag aacaacaggg aaagacccgg    289740
cccagggcga gctttattta tttaagagag aatggggagt gaatcgaaag gcttccgttt    289800
ccgttctttg ggggctttcg ggcccctctc gatctttttc gtagttgaga aggggaagg     289860
agtctaaatc aatggacatt aatgaaccat cattgatgga cgttgcacat gacacgatca    289920
attcgactca aggtccggcg ctaatagaag ttgcttactt tcctagtagc gaaggaaagg    289980
gcagggcttt tttcgtagta atagtgggcg ggtctcatga gatctatgcc ggccgtcgga    290040
atcaaacgaa ggtcgaagga ccattcgatt cattaagggg catagcggcg ccctcgcctg    290100
gcgccatttc cgggcctagc agcagacggg cgggccgtgc ctgaattcag accgaccag     290160
actcttcttt gtttgagctg ctcccaggca cgcagaccga agatctcact tgtcctggac    290220
aagtacgtag agatcttcgt gggaccgtgg agggagtctc aatcgatctt ttctaggatt    290280
ccttatcacg ccacacatgg agatctttcc attgatagat cagagggtcc ccccttgaac    290340
aaattcttaa aggttaggtt actacctgct tctacgaag aggtttactt tataccgccc      290400
ggaggtcata tagatcggaa tccggagcga taagaacgaa agggttggtg tggccacagc    290460
tacaactact ggcgcttcaa aaggcttaga ttctaagggc gctactgaaa gccttttttt    290520
aggtcctgta atagggaggt gtaagcctcg aaagcctttg gtacttcggt agggcgagca    290580
gcccttaaac caaaaaaaaa gggttggaac ccttccccta ttttttttat gcatttcatt     290640
ctctatttgg cccgcttcaa acaaaatgag aaaaagggt ccggtcaata gcatagctct      290700
ttctttcccc ggtctccttt cgaaggagag gccttcgcat tcctaatccg gtagggtcgg    290760
acggctttct ttgccccagc ttggcgaatc gcatccccgc acaacgacat tctttgtttg    290820
tgcgcccctt accgttctcg ctcagtcttt caacggctgg gaaggcagtc gtagaaagga    290880
agcctatcgc cacgccgacc atcaaatacg agattgggcc ccttctcaaa gatttgatgg    290940
aatggcccac cccacccaag agcgcttatg tcatagggga actcatggct ggaaacaatc    291000
cttatggttt gttttgatat ccggtaggaa taataaaaaa aaagtccagg ttggttggtg    291060
agcctagtga taggagacta tctagcttgg ttcggagagc acttgttggg ttaaatattt     291120
tttggttgct aaatgttacg gcctaaatgc tgaactattg accctacttg ttcggatggg    291180
tgttcacccc aaagtgttcc cggaccgcat gcatacatcc gtaagtaact tagtgcaaca    291240
tggaaaattt cattgagagg aatcagcaaa gaaaagaaaa acgggtcaac aacatcaaca    291300
tgtgtatttg agagattgtc ctcgggctga ggagtgtcca catgagttcg ttgaggtgtt     291360
tacacaggcc tgtggtcctc ttttctattc tgtcgagagt tcggattgct ccacctaagt    291420
agaacgaaaa gaaggaattg gaaaagaaag ggggagcta ttgtgaagcc tagtaaaggc      291480
ggaagcggca aatcgcttat accgagttcc ccaacagcag cttagcttag tagcaacact    291540
cttttctactg gcgtggcgct gctggatgct tctgatcaat agaacacgaa gaggaggaaa    291600
aaaaaagctt atgatgagca tctatttgag tcgatcattt ccaagatcta attccagttt    291660
tttcttatgt agtggaaacg ccttacaatc tgaagttttta cgcttaaggg aagaaatgtt    291720
cttggtggat gcaggacttg gaccccag aatttgtatg caagatgagc ctacaggagt     291780
gccaatcaac cgagccacca ggtttgagaa taaggtggga ttcctggatc tagtggccgg    291840
tgaatcactg atcaaagaga agattttgga gagattcttc atcgatctag tggccggtga    291900
```

-continued

```
atcactgatc aaagagcgag cagccgccag gtttaatgat ttggtgggat ctacagatgt    291960
agtggctggt gaaccgcttc ttcttcttcc acgaagattc agacaaaacc gagcttggat    292020
ggaactgaac aagatttggc gaacgaatac aaaggtcaaa ggctttatta ttgagaaagt    292080
aaaaggaggt tattcagtag ccatcgcagg tttcattact tttcttccat tccgtcgcag    292140
aaggaaaagg atatcgaatg atcgattcac cattgagaac attaacccca aaaagacgaa    292200
tattgtggtg ttctaacagc ggcagatcaa acaagaactg gatgagcgaa atccgctgac    292260
aaaaaaaaag agaacttttt gaattccgat gcctagcgtc ccctgataac ctaggattag    292320
tggtaatagg gctgatgtgg tatctcggaa actgggattt gatggtatct gtagagcgga    292380
tcccatgggc ttctcgggtg gaggttggtt gaagatgatg tgatgcaagt gaacgtctac    292440
gaaaaagctg tcgtaaagtt tcgttcttcg ttccgtcgtc gatcaatcta tcactcaatc    292500
acaggccgct ctgtcattgt ctgatttttg gttgtctgat cacactcgaa attatgtatc    292560
tacttatcgt attttaccc ctgctcggta gttttgtagc aggttgtttc ggacgttttc     292620
taggaaaaga aggaaccgct ataataacca ctacgtgcgt ttcattctct tcgatcttct    292680
ctttgattgc ttttatgaa gtcgcaccgg gagctagtgc ttgctatcta agaattgctc     292740
catggatctc atcggaaatg tttgatgctt cttggggctt cttggcgac cgtgaagtca     292800
ccggatgaat tgccgagtca atagatcaga tccggacgcg gctgttgctc cgcggcgata    292860
cggactcgac ccgctcctac ccactccggg gtaccatagc atgtcgggaa taaggggga    292920
catactggac gtaaccactc ccttggttgg gggctgtgcc gccctgcctt tcgatcgata    292980
cacagttgag gaggccgatc acgaacgcta caggtgtggg agcgatcctg gtcagggaag    293040
gctaagvcgv hdcntcgtat atgggtagca agagggcgct tatgccccga cggtgdgdch    293100
ctcttggatt tbttgvaata tgagahggva tdccadddbb cytctckkgt cgtgvtctgt    293160
atcgwctgwa tmacwcwttt ggtctagtcg gtggaaccgg tgaaccacgc gagctggtta    293220
gatgcgtggg gcagagggct cgtagtaccc cctttgattg atccagcctt tcttcgctt     293280
cggtagtgaa tcacctacta aaggggcagg cctgcacgcc ttatttgaga ctactaaggc    293340
aggcggtgga ctcttttcatt aggtaaggga agaaggggcc taagcacggc agatgccgta   293400
cacttgagtg gcaaaggaaa gcgagacctt accttttttc caggcctgtt cggacatacg   293460
gttcccgcgg aagatcaagt tggtgagccg tgtgatggga aaccttcccg cacgttcgg    293520
agagcactga attagaatga gaggtttacc accacatcat tgcatgcaag gggagctcgc    293580
tcgattcgca gattggtccg actcgtaatt cacttctgac cccgtgttcg atagcccgac    293640
cgtagtgatg ttaattgtgg ttacattcat aagtagcttg gtccatcttt attccatttc    293700
atatatgtct gaggatccgc atagccctcg atttatgtgt tatttatcca ttcctactt    293760
ttttatgcca atgttggtga ctggagataa ctctcttcaa ttattcctgg gatgggaggg    293820
agtaggtctt gcttcatatt tgttaattca tttctggttt acacgacttc aggcagataa    293880
agcagctata aaagctatgc ttgtcaatcg agtaggtgat tttggattag ctcctgggat    293940
tttgggttgt tttactctat ttcaaacagt agactttga gccanttta ctacttyttt     294000
tttycarbrs agtctcyscy wtrwratwwk cymaagtrts rcrtggtmkc cgatatgtaa    294060
ttanacttt tattggtgct gttgggaaat ctgcacagat aggatcgcat acttggtcac    294120
ctgatgctat ggagggtccc actccagtat ccgctttgat tcatgcagct actatggtaa   294180
cagctggcgt tttcatgata gcaaggtgct cccctttatt tgaatacca cctacggctt    294240
tgattgttat tacttttgca ggagctatga cgtcattcct tgcggcaacc actggaatat   294300
```

```
tacagaatga tctaaagagg gtcatagctt attcaacttg cagtcaatta ggctatatga  294360
tctttgcttc gnraatcwgg cgatsntckg ataygktgdb bccchtaatg anthacgcct  294420
tttcaaagca ttactattcc tgagtgcagg ttcggtgatt catgccatgt cggatgagca  294480
agatatgcgg aagatggggg gcttgcctcc tcgttccctt tacctatgcc atgatgctca  294540
tgggcagctt atctctaatt ggatttcctt ttctaactgg attttattcc aaagatgtga  294600
tcttagagct cgcttacact aagtatacca tcagtgggaa ctttgctttc tggttgggaa  294660
gtgtctctgt ccttttcact tcttattact cctttcgttc acttttttcta acatttctag  294720
taccaactaa ttcattcggg cgagacatct tacgatgtca tgatgcgcca ttcctatggc  294780
cattccttta atacttctgg ctctcaggag tctctttgta ggatacttgg ccaaagtgtg  294840
acctgttagc ccataagtaa gtactgtgac gaagcggctg ttgctcaccc gacacgatcg  294900
tacgaggtca caattcaccc gacacgatca tccggggtga acaagaattg gggatcggat  294960
gcgggcgaaa ttcccgccaa tggctgagat gttcagtcga ctccctcccc tttgtgggt  295020
cccgacccta cgagtgagca gaaagggagg aggaaagagg ccctggtgaa ccgtcataat  295080
tagtgaacaa gtgtaagctt cgctgcccga cagtatggag tactgaccac accgagggac  295140
aggccctgaa gcgaaggacg ggaacgagcg gaatcaatgt gttccaattt ctggccttgc  295200
accgaccatc caatggacca tggactaaac ggccactgcc tgaaaggact atgtccaggg  295260
gaccgccgcc ccacaaggta catctcgcgc ctatgggccg ctataactat caagaagaca  295320
ctcgaaactg gaaggataaa caaacccacc cggtggactg ccgagctaca agtcctacga  295380
cacaggagcg ggattctcta aaagccaagg tcgtgggtgg ccaagagggc ccacttggag  295440
acttgggatc tcagcaggaa atgcgaaggt tgcttaaagc cggccggcca aagagaatca  295500
actagtttag ttctgatctg agtaggctca taatagggaa taccctaacc ctgggaaccg  295560
gggcctggcc atccttcgtt tgcggtcgac gttccggctt tgtccgtcga cagctgaatg  295620
tttcgatctg gttcgattca tgatcgcatc tgcaaacctt atcccgtggg ctttagcgga  295680
cgttttcatt cttcacccgg tccttagtag ccttttccaaa gtcaacctaa ccggttacct  295740
ttggaaaggc gctaaataaa ccttcgcctt tacgcctttc tatataattg aagaaaatta  295800
gatagttgta tatagaatta gccagatcgt ctgaagcatg aacagaatcg cctttgttct  295860
gaaggcctag cgagttcctt tttttttcaaa ggcggtcctt ttctttcctc ggaccgatga  295920
ctcgcttgtt cagtactgct aactattata ggaggatgcc gcccctcagg actaccagta  295980
gcttcggttg ttgaatctcg tgcaagttag gttgtggttg tattggctgc aagcggaacg  296040
taggcgcttt aggtgtgtgt tgaccatgca ctctcgcttc gtgtaatgtc gtatgtatga  296100
tagaggtagt gtggtgattg acctcaatgc taatggtgat ccccaaggtt caacgaatga  296160
atgaagctat gatcgtaccc ggatagagat gatggtcttc ctctgatgtc tccaagccgg  296220
ccataataga atagataggc gaagcagtca atagcagtct gttctcgcct atcgatagat  296280
agcaggttgc ttccaagctc aaaccatttg aaagggaatt gctacttttt tcttgttatt  296340
gatagagtgg tattctccgc ccctgtcaaa taaagtagag gggagaactg gaagagaaag  296400
gaaaagagca aaggattgac aagtctaatg gggaagaatg gctgacacgt tgactgcctt  296460
cgatactaga aaaaaaccaa gcggtctaac ctaaccccag ggcggacccc aaccgaaagg  296520
cgctagacga actaagggca agcgagataa agaaagcagc tggccctatg tgtaaaacct  296580
tgccgcggga gagtctttct ccaatgagaa taaagaaagt tttgggcaag acaagaaagg  296640
```

```
aactcgccct ttgacaccaa gggataagag ctgattgctg gcgatgactt ggtaaaggga    296700
atctatgaga gaaggttctc gaaccgggtt acgaccgaat agagcgcgga accaacgagt    296760
tcagtcgaac aaggtaacga gtctaaggga aggatcaagc ttgaaaggaa tggacgggcg    296820
taggcttaat agtgaacgca gacccctgc ttatagatat gagatcaatg acttaaaaaa    296880
aagaaagatg caggaaagga aaatgaaaga agaaatccaa atttgctttg ggagtgtgag    296940
ataggcagac ggggagtacg cagccgaaca accgctgggg tttccagcag tgatagctga    297000
actaatcaga tgggccgccc caaacctgga gctgacattt aaatcggaaa tcaacatcgg    297060
gtcccggcta tccgaaaacg cagactgaag cggaagatca caaaatgcaa cacaacaagg    297120
ggtcgttaga ccgtagcttg cgcgaaggaa gaagctaatc aatcagaatt gagacaggga    297180
ggagaaagag attttcgagc ctgcaagcag caagcaacaa cggcttttca gcccttgcgc    297240
gctagcttgt agtttagggg tatagtaggg tgccccttc tcaaactttt ctataatata    297300
aggtaatttg gaaccctagt tttggagttt tccccaacca acctatacct tactaataaa    297360
aggggcttcc ctttttcagc tgcattgcac tgccgcataa acaatggatc cgctgggctg    297420
gatgagcaac cttctatctg gcctctgtac caatagtcga gtggcttgca actttcaatc    297480
agaaaaggaa gattgagcaa ggcaaaggag aaagaagttg tccctcttc tctggtaacc    297540 cgccgccgca tatgtagaaa agaaggagcg gagaaggaag aacaacctt tgactttggc    297600 acatgaggtg gcgggtttgg ctaggtaaca taatggaaat gtatcggact gcaaatcctg    297660
gaatgacggt tcgaccccgt ccttggcctc gaggagtggt gagcagcacg gaactttaat    297720
caatcaaatg gcatagtatt agggtaggag gctttccttt gttatagaaa tccacagaca    297780
acattctgga acttccaaac caaagaaatg caagatgaga aggagctttt accttacgct    297840
tcaatagaat gaattcggta agggtagaat aggccctatg gtcgatcgaa ggtgctgtgc    297900
cacttgaact caaatctatc tgaccttcaa tccatctttg tccagccagc tcataacaaa    297960
atgttagacc aatctcaggg ctgacacaac cgaattggtt ggggaaaagg aaaccccagc    298020
gaccaagcac tcccgccccc aaaagcggag accgaagaac cgccaggttg tcgaggaccc    298080
gtctgaagag gaggcgggcg cccbctaagd bbavcrcsmt wcccgywwry sgtctkyykc    298140
ttrwacamaw aaccvhvhct ayvmkaaawa gayavcgcty athnnncbcc ttcadhbtvc    298200
aatvadaaag gttggggatg gctggaacca atcagaagtg caaatcgcgc aagcgaagcc    298260
gggaaacgga ccgcagcgca acgactagga ctcgtgtcgg aggagttttg agcgtgagct    298320
aacactcatg cagcggcaag gacccgcaac tctcgaaggg gccaccaacc gcccgaatca    298380
ctgtagcaaa ccctctcttt actcaatgga tagcgcttat tctctttcaa ttaacaaaat    298440
gtgaaatggg rasaaagaaa aaaagaggt ctttatttaa gaggctttgc accggaaata    298500
gghmtaatgc agatccagaa gaatggtctg ggctttagaa aagatgaaga tggaaggggt    298560
aaagagacag tcttttgaac aaccaagctg acataaggat tctagctcgc gcccacttag    298620
agcagatgga gattctcgga cggggaaaag cggcactcga catctattaa acaagaccaa    298680
gaacaaagcc ataccatgcc ctcgggagaa agtagtgatg attgccatga atgctgccct    298740
cgaggacgtg tacaagaagg tctttgccga ttcctatcaa catggtgcat ctcttagtag    298800
aggggcgtga aaagtggaga ctttgaccga atgaataggg atcaattgat agccattttc    298860
ttgaggaaga gaatccagga tgaacgcttt tcattcgct atgcgctgac tggatgcgta    298920
ctcgcgtgat caatcgatgg acggggaatt gcgtgaatga tgagaccggc ctaacctaaa    298980
gtcaaggctc ttccctctct tgatggcgaa tcttgattga ctgacactag aaaccgattc    299040
```

```
ggagaaagaa gaagcatggc atgagatagg cggcggatca atttccgata gcgaattact   299100
tgactcgatg gatggatgga ggagagccct ccaactcaag cacgaaatca atgttgagtc   299160
aacaatcatc gagagggtac caccaagcga gatcgagacc agccccttgt ataggtatag   299220
ggttccaaac ctgcccttct tcaaatatcc cataaatcta aataaagtag ggacttcaaa   299280
gcttgactaa caagcgagaa agttgacttt gagaaagaaa ggggcgccct agctgcaatc   299340
aaaagagcgc taacgagcaa gaaagggccc ttactataga tagggcgtta gcgctttact   299400
aataacatat ataggcttac cttttttcag cttgatcgga atcgattcta tgattgaata   299460
gcagaagtgc tacttagtag tagaaaactcg gagagacaga cagagagggg actctttcat   299520
acctgctaac tcctaggatg agaagtaggt cccttgtttt tggcaggaag agttccagcc   299580
tttgttgccc ctcggtagag tgagtctact tagcgaactg gcaggacgcg gagatctatt   299640
gatcaatatg aatctcgaga gtggatggtt gatcgccgcc tccttgtcct ggaggctctc   299700
cggccgggga ggggcttgct atcgtaacct tttctcccgg tgtatgtgaa aaagagtgac   299760
gaactcattt ttcttcggtc ataggttggt ccaaagaacg agagtcggct tccttaatta   299820
agtccgttgt tcctcagtag ctcagtggta gagcggtcgg ctgttaaccg attggtcgta   299880
ggttcgaatc ctacttgggg agattttttga gttatcgctt ttctgaccta gcgacccctg   299940
tccttctcct tagtttctaa actagcagaa tcgtgggaca tcaaaagcgg taagttgatt   300000
gttggttttt attcctcact ctcgtatagg ttaacttggt tcgttccatt cttagggata   300060
aaaaggatcc actggaaaga ctggagtagt atcttcatta gccggaagga attagtctcc   300120
actagcgtca ttcgaagaac gaacaagaaa agggttacag tttaggtagg atagatggat   300180
gtggcccaat ggctaaagct ctgccagctt cttgtagact gaactctctt taggctccga   300240 gttcttttt gggggggatgg tctaatttac tagtggcaac gaagttcttg gtaattagca   300300
agggggaagg aggatctcca ctcatttcat tcattcagtg cctgcggtga ggcgcgaccc   300360
acaacaaacg aaggggggaaa gcttgctttg cttgctgtag ccctatttta gtagattagg   300420
cttggtaagc gtaagctata tttaagtagg ctcgcagctt cgctcagcag aagagcctga   300480 cttttttatta tattagtaaa gcgctagcgc ccaacctata caagggcttt gaagggatag   300540
gggaagaaaa gaaaacaaag agggtcattt tcttttagga acatggctcg ttcattcact   300600
tgctcatgaa ctcgcagctt cgccagaagc gacgaggggg ggctgggggaa ggccgacgac   300660 tacatgaggg ggaagctttc gtagaagctt taccccttgc tttacagaga tagttatgaa   300720
ctgactaaat gactagattc tcccggaacg ctagctaagc taatcgtctt agttcccttc   300780
aattaaatca ataaggcttt ttgattgatt cagggcgacg cccccccttct tagaattaga   300840 acccattgag gggggcctcg gcccgggaag gggagagtgg ccgagtggtc aaaagcggca   300900
gactgtaaat ctgttgaagt ttttctacgt aggttcgaat cctgcctctc ccacttgttt   300960
gttgtagact tcagagaaga gaaaagaggc attcgtcagc gtaggaaggc caaccgagcg   301020
aagctctttc tttttttttgg ccgtgccgtg aagtgaaatt gtatcgtatg ttagttagag   301080
aggttggcga actactacga tctatagatt tcccatctat atccaatccc aacgagaata   301140
gaagcgagtc gcttccggcc tgtccttgtag tcgtagtctt ttagcttatg tagtcgtcgg   301200
ccttcctaca cgcgtgcgtc cgccagaatg cctccttggt tcgggacgaa gccaagccga   301260
tacatacgat aggcgaagga aagaccccca tttcatagcg cctggggaac gcaagtttga   301320
tcgaggattg gagaggagag gtggaagaaa gggctcggga tggatttagg agtctttgtg   301380
```

```
cgagccgtat gcggtgagag tcgcacgtac ggtaacgagg ggggttcgcg tctatacgtg   301440
tagtgtggtg cttaggccta cccaccctat ttgttccatg atctatgggt ctactggagc   301500
tacccacttc gatcaattag ccaagatttt gaccggatac gaaatcactg gtgctcgatc   301560
tagtggtatt tttatgggga ttctatttat cgctgtagga tccctattca agatcactg    301620 agttcctttt cgggcggctg taggacggac ggccgcctat aggtggtagg gtagggtggg   301680
tggtaccgct cagattgcgg ccaatcttcc taaccgcgcg cgggccgggc ttagagcgcg   301740
tgaaactcat cactacctcg taagggcgtt gagaccatag catgttacac gaaagcgccg   301800
ctttctctgt agtgttgtca cacagctgcc cgcctagaag agcaactcgc tctgtagtgt   301860
tgtcacacaa gataagcacg ccgcccgcct gctggccggg cgaatcgaag ttatcttccg   301920
gtcaactgtc cacccagtca agtgcaaaaa acacagtaga atcacgcaac gcacgctgct   301980
ggtgtgcttc ctgctcgcga ggaaagaaag aagagcgaca gggttcagtt cagatttgac   302040
tgtttgcagc atgggagcag attccccaaa aaatccctgg gaacaatgaa aaaaaaaga    302100 tatctcggta acgaaaacta taggggctg tattggcgag atccaacggt gaacagctgc    302160
ccaaaagaaa gaccgcctgg aagtccgagg acctttagta ctgtactcta cccccgaacc   302220
agcagccttc gcgccaagca agaccgccct tgtccctttc ctttctccat tccgcctcct   302280
tctttgcttt gttccaatag agtctaaggc taagtggttc gtatgcctac tttacctact   302340
tgacgaaagg gaacgaactt tgtttcattt ccgggtttat ggattggatt cagtcagcct   302400
cacgacataa tcagagtgag gctttggtta ccggcaaacg cttctccaaa ggcgaccctc   302460
tcgagtttcc ggctctttcc tagattgaag tagccttcg tcgccctacc aaacgaaaga    302520
agtaactatc aaacagctcg ccctattgaa gtaccaaagg tgcgctcagc ctggtgacta   302580
ggaaatgggt ttgcccttga attgaagtga tgaggtcgga aagagggaag tagggctcct   302640
attgactaaa ggttggttct tcgctttcct ttagaatgaa agttgctatg aagcccctac   302700
tacttacttt gtttgattca aaaggcgaac agccccccca actagttgta tggggtgggg   302760
tgcttgtgaa aagctgcttt ggatatgagt aattcctaaa aaaaggcaaa gtccggtatt   302820
tgacgaagat ctttctatca atagatagga atgagtgttc gatataggg ataggatcca    302880 tctgctcttt atctctccat ttttttttaga gagagcagat ataacgatag aaaaaagaat   302940
cgggagatga taaggatag atagacatct aaagggatgt ctattctatt cctctttttt    303000
tttttagaaa tatatatata tatcgtttat ctatctcttg tctatctatc attgattctc    303060
aagtcaaaag acttcgtttt tgggttcccc gaagccccga atggaatgga tcgtttctgc   303120
caacgaaatg aacgcggagc ccgttccgaa tgcttctacg atccggaagt tctcgcgaag   303180
agaataagat gctgctcccc ttccctcttt cttttcccgc tttgctaatc ttcccctcta   303240
acgcgggccg ggcggcgacg ggcgcgggag gaagaaacct aagagaagac gctcgtctct   303300
taggtccttt ttttcagtgc aacacaggaa agcgccctct ttttgtcatc cctgcagctt   303360
tccagatttt gtattgaacg catggcgtag ctaggaccct tccaattctg tttgagccta   303420
tgttcaagcc aaaaccaccc ccaatttgac taaggctgga agaatgccc accaagttca    303480 gataagggaa tgctttcccc aaccattaaa ggaaaggctc gacgaaggga gggaggtgcg   303540 gcggggaag gaaaacgctt tcggagatca agatttttt tcatcgaaa acgaagaagg      303600 ccgaggatgg cctacggtgc gtcttatctg aagggaacac gctttttga ccgccgtggt    303660 atgattgccg ggccctctcc tcgttccgcc cttcctattg ggatagcagc cttcgggctt   303720
tgcctgccct ttataataaa aaattccggc tcggcccggg aaagcgctgg caacaacaga   303780
```

```
aaggaagggg tccatgtagc tgctgtgtcc gcccccttct tagtcaatgg ggcacagcag 303840
gttcggcatc tactacaaaa gagagaatcc acttcagata accacgtctc tgctaggcag 303900
cgtgtggaat ggccgagagc ggaccttttt ggatatataa tccaagtcga gagtagagtt 303960
agaggaaaag ccgtctgatg gaaaactact ttcacgttcg gttcagagag cactttttc 304020 gttgagaatt cctcgttccc tttcgtgtga attccccagc ggcgaattca aaacttgtgg 304080
ggccctatct attccatctc tcgagccccg aagaaaaccc cctacccttc ggactccata 304140
tatcttttga ctctatatat gtgggcacct gatatctatg agggttcacc caccccggtt 304200
acagcattcc tttctattgc gcctaaaatc tctatttctg ctaatatttc acgtgtttct 304260
atttatggtt cttatggagc tacattgcaa caaatcttct tttctgcag cattgcttct 304320 atgatcttag gagcactggc cgccatggcc caaacgaaag taaaaagact tctagctcat 304380
agttcaattg gacatgtagg ttatattcgt actggtttct catgtggaac catagaagga 304440
attcaatcac tactaattgg tatcttttatt tatgcatcaa tgacgataga tgcattcgcc 304500
atagttttag cattacggca aacccgtgtc aaatatatag cagatttggg cgctctagcc 304560
aaaacgaatc ctattttggc tattaccttc tccattacta tgttctcata cgcaggaata 304620
cccccgttag ccggcttttg tagcaaattc tatttgttct tcgccgcttt gggttgtggg 304680
gcttacttcc tagccccagt gggagtagtg actagcgtta taggttgttg ggcggccgga 304740
aggttgccac gagtaagtaa gtttggggga ccgaaggcag ttctccgtgc accggacacg 304800
tagcttaccg aatcagttgc gacacggatg ggaatgcatg ctacgaaaga tagggtcgag 304860
tctgatacat caaccgtcta ctcaatatcc ttgtacgagt ccacaatgac tacacgagat 304920
gaaccttggt ttggtgaatt gaagttggcc ttaggtgtaa taggactccc agttactgcg 304980
cgcgatcgta tactgaggtg ctccccgccg gttgttggaa cgacgcgagc cgggccgggt 305040
ctcgattcag aaagatgaag ggcccaaaag tctaaatagg gggttacaaa ttccccatct 305100 cattggggc ggaaaacgaa tcgacatctc gatgtgatac agccctttcg attttagttg 305160
ggaaagaacg gcgaagtcca tccgaaccgt ccaatgaaga ataagaggag agcaaagcgc 305220
caatggcgcg cgaagcgcat gcggaacggg cacggagaaa aagaagtgtg gaggagaagc 305280
agccgagctc attcccttcg cttcctgggc ccaaagcagt gcagtctttc ctggccaaat 305340
caaggatttg gggcttcttg ctacgctact aactatata aatccatttt ttttagtaat 305400
atatatgaat agaaagatag atccatccat ctatcctatc cgatttcgat tttgatatct 305460
aaaaaagaat cgatttcatt caacgtttga ttcaaagaac tgcgcttagc ccccccgctc 305520
atgaaacggc tctgctgcaa tggatggcag agggtccgta gtacccgaag cactggagtg 305580
atccagtagc cggaaggggg cctagaagtg cctactacta caccacacta cacttggctc 305640
tacacattta cagagctaac ccctgtccag tgcctggcag agctaagggg gcttcaatcc 305700
ttactcttta tccccatctt cgcccaggct aacgggcct tacttattca gggggagag 305760 tggagcctcg aaaagcactg ttgagaggaa gatccttggc ccctcttcat tctctacagg 305820
gttccaaccc tttcttcaac ataggtgaca acgagccagg cagagatgga agagatcaaa 305880
gacgggaata agaagcaagc tcgccttcct ttttgatcat tttgatagag ggggatgaag 305940
aaagtggaca aaacagactc gcatttctca tcgaacaaat acaggaaagg aatcatattg 306000
aaaacgctcc taacccaacc ccttccttcg tagagcccgt gtattgtaag tgatccgaac 306060
ctgcccggag cgagcctccc atagaggcaa gtgaagttgg tgagccgtat gatgggcaac 306120
```

```
tatctcctgc ggttcggaga ggactcagct gttagttagt accccctggg tttcggggtg 306180
gaccttttca ctctatttta ttatatacgc ttagcgaaaa gaatgttttt tgatacacct 306240
aggacatgga ttctatatga accaatggat cgtgacaagt cgttactact agcaatgact 306300
tcctctttca ttacttcatt cttttccatat ccctctcctt tgttctcagt tactcatcaa 306360
atggcactca gttcatatct ttaagttcga tcattgacaa ggttcaaaga aagggtgggc 306420
cattgataaa gaatcgattc caaaccacaa tgctagcaga tggcgggcct ccgcttttct 306480
tttcattaat gaaacccgcc agttattctt attaggaact caaataaaag gactttcact 306540
tagagtttga ttagcataaa gtgccagccc agctaggctg agttccgttc cattgctttc 306600
ccaataagtg aagtagcgaa acctccctct gaatgaacag aagcggaatg caactcaaaa 306660
aaagttctag gatcacaatg aggtcccacg aaaaaatgag ctgaaacgga gcaaaaggga 306720
aagcccgcgc gcgggaagca agtaccatc gtgcacactc atcaaaccaa tgatcgctgc 306780
caaaaagacg gtgagttcga agccacttcc tatatccgat atccgaggag atggaattgt 306840
gaagaacctg acgaagatga tgatgtccaa aacccggtag aactaaggta gttcagttct 306900
ccgaggttta atctcctacc ttgcttccat tctttaatgg cattctgcag ttcaatgtcg 306960
gcgaagcctt gcattgaata ggttgttata agcctgactt ggctctagaa agcagattca 307020
ttattatagc cttataatct aagaaggtca ggcattgtgc tgtggcataa gctttgtctt 307080
cctctacctt tggattgaga gttcatctgg actgagtaag cactttaaag aaaggaagta 307140
aaagattcaa tcagatcaga agaagactga cttcagcttt gacttcctcc cgagcgagag 307200
cgatcaaagg actggcggag ggaaagcaaa atcagaaaga aaaaggatcg agacaggact 307260
ctcttagcat aggctttcag ccatttcttc ctatagtaag tggaagtcat aaatcctatc 307320
catcttgctc aaacccttg cacgagtcag aaagcagtct acttatggca tcggaaccac 307380
taatgccgca tctctcggtg agaaggaatc aaggaaagaa gagaaacttc ttccttcttt 307440
gatcttctgc cccggaaatt ggaaacgtaa agtaggctg tgggactgat tcttttcctt 307500 cttttcaggca aaataagcgt ctgccagcgg tcagagtgtc aatttgtact catgattgca 307560
catcgcagtc gttgcgtgct tgcttgcgc accggcacag cagaattcga atcgctggc 307620 ttagatgagt ggctcttggc ttactgagaa gggctttctg taactaagaa atgagaattg 307680
ttgatccata tgatctcagg caactttcgt tgatgaaact gacaatttaa cacttagaga 307740
ttgagctact cagtcttgct tccatggata tcttaaacaa gtttgcttac ccatcgttat 307800
ctggcgggaa gtgagccacc tagcctacct tctctctttc tcttaagcaa tttcatgtca 307860
ccttaactct gcccttggga aacttctctc ccttaaggta gcattcatag ttttgagtca 307920
acaagacttt gatttctcc atcgcctctg aagttcaggt caaaatcaga actgaattt 307980 gaaatccagt aggaaaaaga aatgcagact ttttcttgac ttttgaatct attagaaaga 308040
gagtctctga agcctttgct ttcgacccta ctaggatagg acttagaaag cctccttgaa 308100
ctacggttta cagttcacta agatcattct ggccttttct cttctagcct ggttagttac 308160
ttctatttac caagaagtgg aattagatag aggagaccga gcatagaaat agaaaaggat 308220
tggatttgac ttcgaatgga tggttctcgc taatccccat ttctcagatt gtgcttcgtg 308280
gggggagtcg gatattggtc cgtaaaaggg tcaataaccg agctgggttt atgctccgtt 308340
tttccaagaa cggatctagt aaggcgaaag gtattcccca atgcaaagga gtctaatcaa 308400
agcaatcctc gagtaagaaa agagaaggcg ctacttagcg ctattaaata agaatgaag 308460 ctccgtgcga cacccggctc ccaaagaagg aaatgctaac cacagtttca atggtaacgg 308520
```

```
gaatacgcct gacggcgaaa cacagagagt gacgcttcca tcgcttagat ttagggcgat   308580
agggcgcccc acagatacga actagaaagc accattgcat agggaaggct tgctctgaca   308640
atgagtaggc tacactagtc tacgggtacc tagtctttaa agtgggcgag gctaacccta   308700
tactttcttc tcaaaagag gtcgatcttc cgctctagat cttcaaaca attgatttcc    308760
atattggtat ggtaccctt cttcatagaa agggcatttg gcttcctta gtatactcct    308820
aacaacgaaa acaaggaaaa ggtaagtgaa aataggaca gagattctga aagagggcac   308880
taagagaaga agaatgaata actgttaccg aggcccaagg agatgcagcc tagcccttac   308940
ttcaccagat tcaatagcag ctcctattgc gatgtggtaa ggctatggca tcggtttaca   309000
cattcttgac ttgaaaagag ttagaaggat tttcgccata taggaagggt ctgagaacaa   309060
gagccattcg tggtcacatg aaagcggcaa tagagaatcc tcctactgct aggctaaggg   309120
caaagatcac agcagtactt gctaaagtcc cctatcctga acgtgtgcta tgtagaaagt   309180
agttagctag gcatcataat agccatcaac cgtcagcctt cgaaattagc actcgattag   309240
ccggcaaaag cgctcttctt tccatttat gtgatttaa gatggatata gatagaactc     309300
gatcgaacta aatgctattg tggcaaactc gtgggaaaag agatcggggg tatcgatgtg   309360
gatgaaaggc agagatgaga gcgacagaag aggagtggaa caactacctt cccagtctat   309420
cgggaccttt ttggtttatt tttgccctgg gctgaactcc ctgaatcccg ggactcgctc   309480
cttcgctctc cggacttctt ccttcaacaa acaaggtttt ttctgatgag catctttcgg   309540
gactttctct tgttgttttc ggggagctgg ctgggaactc ccactcaaaa tcaaaacaaa   309600
aaaatcctta ctacccctt aatttcaag gagcctccaa cctacgaact ctgaattcgg     309660
ataacataac tatatttagc tgaactccct ttcgctttag agaagacagt tcgagcagaa   309720
tcataagaag aaggtaaggg acaaggtgcc aatctattaa tctcaagcct gcaaaagtca   309780
aagtcactct tcttcagaag aaattttcct tgtagcctta gaggctaaac ttcagtttca   309840
tacgttctat tagtaggtct cttgaaagca gtttcagcat atcgtctaaa tgtatccttt   309900
ttttacctct tccctagtac tgatctcaat cctatgtca tctaatgcgg cttttcact     309960
ggctagcttg ctggatggat tgcacctctg aaaagaacta actataggt ctaatcctga    310020
aaaacttcta cttatacggg gtcgggtttg tgaactactg ctactggtac actaaaacga   310080
aatttaggga ctctcataat ccatcaagtt ctttttagg ccatccgcct atttagccac    310140
attacacgct ctcttacaag cccttacata agacataagg aacaataagt gtcttcttca   310200
tcaaattcaa atcaaagaaa ttgagtacta ctatggatgc tgcaaacagg cttctcttct   310260
agttaagttc ttagaagagc gattggtgta ggctcgggag gcatacgaac atggtgcact   310320
tcgctttggt ttaaaagcgc ttaaactaga tagctgggaa tgcgttaggt tatggtaatt   310380
tatatagaat ataggctgaa aaagtatcta ttaccttgaa ttctcagttt taaaatgtct   310440
taattaataa aataaaaggt aggcccttag acagactgtt agcgcttgtt aggaagggga   310500
agtcttgcat tgcaagcaac ctaattccta tgttatagcc ttcgttccct tctctgtcgg   310560
tgtgctccga cagtgaaccc gagatatctg gttcataagg ttgccaatgg ggctagcggc   310620
gtccccgcct catgaaaggg aagcgatatc attttgtcgc ccgatggaag tcaataagag   310680
agaaagcacg aactaggatc gacctgcatg tgaggcaagt aaaagctgcg agtgaggaaa   310740
gctggttgtc aaagaagtta tggtgtgccc ttcattaaga gtaagagcgc aaacttggca   310800
tttccggtcc ggaaaactct cttattttt agaagtttgc caggaggtga ggtttaaata   310860
```

```
ggcttccaac tgtgttggag tttcagactc actactaacg aatgggcttc gaacagctct   310920 ttttttttcca acaggctgca aatcataagg ataagcctga acctaaagct caaggagcat   310980
agttccaatt caaactacct agagagaaac ctatcatagt cctagctata aggggttttc   311040
agcgaaagcg cgtgttctta gattcgtaag aatatgaatc gtcaaaagga agatgctggt   311100
ctttcattcc tttatcattg aaggccttac ccataggata ggaatcccgg agcccataat   311160
agtcatcgta ggcccagaac tatagttcag aggaaaccgc cggaagactt tgtttaggaa   311220
aagaaagacg aagaacgcca ttcctttgcc ctatgccctt catttacctg ctcaaaggaa   311280
gaaactaaac tataagatca gagaaagcaa gagccttcga tttaactaca tcagtagaac   311340
cggccttaac tttcttttcca tttgaagaat tcctgatgat ggttgataaa ggctttcctt   311400
ccacttaccg tagttctatc aaagtcagcc ttaaattaaa gcttcttgcg aaggccctgc   311460 cttttttaatt tgattttta tttgatcgaa aatctagcta aactaaagag cttcttttaa   311520
agattccccg ctagagcacg gaaacctaga gaatagctag cggattcgcc aacatcgaaa   311580
gcaatcagac ttggtttgga aatctccgcg cttgctatgt tatatcaatc tcaattgccg   311640
attcactgat attggcaact ttcagatcat ctagttatta tccttcaagg catagggccg   311700
tgaggtactt acttttagcg cagccgggat tgattaaggt agttgttcag ccgagggaaa   311760
gaatcattca atgctagtga aagaggaagc tgttcccttc gttgattacc gtggtggctt   311820
ctgtatcatg atacagagaa gacagaagca gcactcttgt cgaccgttca tggctagctt   311880
cgaacaaaag aaaggctagg cgaagaatcc atcccttacc gaaggaagat tgcatcgcta   311940
gttgactcct cctcgtcgac agctagcagt ttccggactc gcttttgttg ccttaaggct   312000
tcctcctaaa ggggaagacc tgctaaggca ctaataagag caacagtagc aacagcgacc   312060
cccctatctc ttaaagcttc tgccttcaga cgggatgatg gctaaacaat catttggtaa   312120
gtagggtggg tggactggtg agccgcttac gctttaagcg aggagacagg agctatcaag   312180
cttaaagtag tccctagacc agacagaggt tctaggggggg gtccggatag aggattcctt   312240
taagcggtct gcccgcagat gtaggatagg aaggcggcct gcctgctaac cgaactgcgt   312300
aactaaagcg actccttctt ggtgtaagat aggtcttggt ccgattcacc tatgtcagtt   312360
cgaacctgac gggtcgttcg tgtggagaat ctctctcctt actcaggatt tctttatctt   312420
cgaggcgagg catattcata tatatgtcga agaaggagga agtgtctcca tattctattt   312480
atgctcatag aacccgaaaa aaaagaatat accgtcgttt aagggccaag gatacgatgt   312540
gagaagcgta ggtcggagta gcaggagtat gcgacaagca gttgcatgtt cgatgtggga   312600
gatcttctgc acttaataca cactctttcg tgccttggtt cgccatcatt tggttaaaca   312660
agaccacatg gggtgattga agttggaaac ccttgtcggt ggaactaacg aagcaaagcg   312720
tgcttggtta tcctagccta ggtggaatgg aattagggac gcttgcttgt gcgcctaaga   312780
ctcctagtta aagagccttt ttctgatgaa cctttaatgg ggatttctag caaattttta   312840
ggctatccct tcgggatct agcatggttc ccctagtccg aaatctagac tctgtcttta   312900
accttcgctc gagcgatgga aagagtcttt acacaggact ggtattctaa gttttcttcg   312960
ttctctgata tcttactata gaaggctcga agagctatgc ttgataagaa gagttagcag   313020
gcgagacatc atctcgtgtt aacaataact cgtaaagact agtttcataa gctagctttg   313080
aataagagaa atcgtagcct agaaagtctt gccaacggaa agaacagcag actcaatagc   313140
cgctctagac gccctaaagg gaagtttggc gctagcttcc taaacaggat tttctatgag   313200
gtagaggccc ggccgcgcaa agcaagagga aataggtata ggctggatca ataaaagaaa   313260
```

```
gataaggaaa gtgtacaaga ttccaatctt rctgtacagc aattggggca ttggtctttg 313320
cagcgttaat gcttttgct ggttggtttc attaccataa agcggcgcca aaattggctt 313380
ggtttcaaga tgtagaatct atgctgaatc accatttggc agggctacta ggacttgggt 313440
ctctctcttg ggcggggcat caagtacatg tatctttacc gattaaccaa tttctaaacg 313500
ctggagtaga tcctaaagag ataccacttc ctcatgaatt tatcttgaat cgagatcttt 313560
tggctcaact ttatccaagt tttgccgagg gagcaacccc attttttcacc ttgaattggt 313620 caaaatatgc ggaatttctt acttttcgtg gagggttaga tccagtaacg gggggtctgt 313680
ggctgactga tattgcccat caccatttag ctattgcaat tcttttcctg atagcgggtc 313740
acatgtatag gaccaactgg ggtattggtc atggactaaa agatatttta gaagctcata 313800
aaggtccatt tacaggtcag ggccataaag gcctatatga gatcctaaca acgtcatggc 313860
atgctcaatt atctcttaac ttagctatgt taggctcttt aaccatccct tactatgaag 313920
ggattaagcc actatcaaag caggaaagag aacaactagg atgaaaggta ttactaatat 313980
tgatatagtg acacaggatg atagaatgta actaggataa gcgtccggtt agaaccatgg 314040
gaagattaga atgacctcac taggaacctc attaaagata gatagctacc ttagagagct 314100
tacacagtca attgatctat cctaggttga ggaatcaggg aagaaggctt tcaagtcaag 314160
aagagattcg ctcctaagga ggaaataagg gactcatatc gaaagggctt acaggactaa 314220
aacctatatc tgagagcttg aaccgacagc agccccatgg gagaaccttt catcttcatc 314280
tctctcactt aaaaaaggct tagcttgggc cttagcctaa aaaagagaat caatggctgc 314340
agatcgtgcc tttcttgcag ctttggctac tgaacttatg aacagaggac agagccttaa 314400
gttaagccgc agagagaact ctttgttccg tctttcgggt tgtagggcgt agggagtagg 314460
cgagtcagtc tatagagcta gttaaagtcg aaaacacgtt cagctccagt gtcttaggga 314520
aatccatctt gtcgctagtt gagttacggg tgccagtatt cttggtctcg tcgtagaaag 314580 tcttttttg ctgtccggta gtcgtagtcc aattcttctt tctcgggctt tttttaagat 314640
ttgaatctga aggttcgtaa accaaagctc tttacgatcc aaaagaatct ttctcttccc 314700
ttatccgcga ttccggttct cgatcgaagg ccgggctttg aatcgtttta ttttagtaca 314760
caacactcgc aacaaaaggc ttatagccga actgaggcag caagcggatt agaaaagata 314820
gagtttcctt gattgggaag gaaggaagga actagtaatc cattcaagag gaccttacct 314880
ttgagttctc gagtgaaagg gtccaagcca taggaaaata tccagtttat ctcgcaacat 314940
atctagttta tcctgaagca gcatttctcg aagtagcatt cccataagta gaggatgaaa 315000
cccttgcttc tttatcccga cgagggttta tgaatcactc aaacgagcct ttctagccgc 315060
atctgaatcg gcatccctat ccatatgttt atgcgcaggg gcatccaaat ccgaatctgt 315120
agaatctatt ggggaatccc catccgcacc cgaattggct aaatctagta tagtgggtct 315180
tgttccgatg cgggaaaaaa tcttttttaaa aggcatctcg gcgaaagagg actgagaacc 315240
ataaggcgag cgccaaaacg ctagcacaaa ctgctcccac agacacgcat gataaggggg 315300
tgtggggaca accaggccac cacttttacc agatatgggt ccggacgacc caagagcccg 315360
ccactagaac ccaacccctta agaggctaag gtccaagggg ctaccgcagg aagtcagctt 315420
cacctgtaac cttaaggaat acagaaagtt acccggaatt cctagcaagg actttgcctg 315480
ctattcattc ctaaatccct ttcaccctta actagctaac tcgatgggac gtcaacagcg 315540
ggaatgccaa atgcaagacc tggacctggt tcacgcagtc aagcagcaaa gacctctttc 315600
```

```
tcttcgggag ctttcgtaac ggctataaag aatgggtctt tccctcgtg  aaaggctatt  315660
gggatcgatc ccttcaaccc tccttggcgt ggaaggtcgc aagagaaaag aaaactattc  315720
ttcttagctg cttttcaac  ctacccgagg taaggaagta aagcaaccaa tagcctttt   315780
acctactatg cctttcaccg ggtgagcaaa aagtagttac ctttagccgg gtcttcctta  315840
ttaattattg ataaggcaca ggggaagcat tatccttata agactgttgc taaacaaaag  315900
caattctttt tcacattcaa ccatgagagg gcaacttgag caatcaaagc taccccctct  315960
tccactgctg actatgaaca gttgacagct aatgatttct actttactaa gccagttcgg  316020
taagttaagg tccatgcttg aaacgataaa aagaggaag  gggaagggt  cgcccaaagc  316080
tgtggagata aggtggaaga taaaaaagct atatttaaaa taataaagag aatctcttca  316140
aattcatatt caaaaatggg attctcaact atacttgact ggaaaaacca gccaatctac  316200
tctcctttt  ttggtctccc ccctgtaact ttataaatca taagagaaga agaaatcgtt  316260
gcgtagaaag tcgtgcttac tatctcctcc atctaagtta tgtaaggaga aaagagcgaa  316320
aagcttactt ttaggtagtg gcctaagcgc taagaagctc caatcatgct actcagacta  316380
tatgcttaac acatgcaagt cgaaccttgg ttttcggagt tcgaaagaga aggggaagaa  316440
gcggggtaga ggaattggtc gactcatcag gctcatgacc tgaagactgc aggttcgaat  316500
cctgtccccg cctaatccat ctgaggcccg gcctcaagat ttgagattcc gtaagtaact  316560
cagtgactgc tttctaagaa gggcttggaa gaagaaaatg aaataggaac aaccgcgctg  316620
gtcgtagagc taatgaagag aaatcttacc taatatgagg atccttttg  ctctttctcg  316680
gctctgtgtt cgtggtaata gtgttactta tctttcgaaa gtcccctacag gtcatagtag  316740
ttcgcgtctc cttgatcttg gttatacttg tgaattagca gctagtaagt ttttgatttt  316800
gcttcttttt tggaagcaaa gaatgttgcg acgatttccc gtcttaaaga aaatatcgcc  316860
caagatgtat atatcgatat gccttttcat ttatctaatt ttccttaaag taggagtatc  316920
gcttggatac ctcttgatgg acgagcttca aagggctgtc gctccatttc ttcatgcatc  316980
gggggggga  atgtctgggt ctgaaggaaa cctggggggt agcagtggag gccccggttg  317040
gccgtccttc ggtgtaggcc tatttgcgga taatagtagt tgttattcaa atgacgaaga  317100
gttcgcccag ccaaaccccc aaaacgcccc taatgcagtg gaggcagtcc ttccagaacc  317160
ggatatggat tctgtgaggg gtgtcatcaa gcagaggtta cttgtgcacc gcttgggtca  317220
gaaaaatttc tcggtttccg agaaagaaat tgaccaaatc gtggagctca agaacgacat  317280
tctaaataga atgggcgaac tggaccccga ccccttctgg actagccatc gaaggaggct  317340
cattcgggac tacatacgac cgcacatggg cggggagtat agaataaagg ttttgactaa  317400
aaatttaaac ttattattgg gggaaagtcc aaccagctcc ttgatttata accaactgat  317460
gaaagagaaa gactggttct ttttagatgc tccatttcaa ggccctagat agagctgaat  317520
catatgtggt tggtctgttc cgatcggtcc ggagggtgga gggtggaggt tggaggttgg  317580
ttgaagatga tgtgatgcaa gtgaacgtct acgaaaaagc tgtcgtaaag tttcgttctt  317640
cgttccgtcg tcgatcttcc tttcctattt cttccggtat gccgctccgc caacaaggag  317700
cgaaagaacc aagttttctg tggtgatgtc agaatttgca cctatttgta tctatttagt  317760
gatcagtccg ctagtttctt tgatcccact cggtcttcct tttctatttt cttccaatag  317820
ttcgacctat ccagaaaaat tgtcggccta cgaatgtggt ttcgatcctt ccggtgatgc  317880
cagaagtcgt tttgatataa gattttatct tgtttccatt ttatttatta ttcctgatcc  317940
ggaagtaacc ttttccttc  cttgggcagt acctcccaac aagattgatc cgtttggatc  318000
```

```
ttggtccatg atggccttttt tattgatttt gacgattgga tctctctatg aatggaaaag 318060
gggtgcttcg gatcgggagt aaccactagt gagagggcaa aaatagggggg gaaggacaaa 318120
ggaaagagcg atgcctacac taaatcaatt gattcgtcat ggtagagaag aaaaacggcg 318180
cacggaccgt actcgagctt tggatcaatg tccccagaag caaggagtat gcccgcgtgt 318240
ttcaacgaga acaccgaaaa aacctaattc agctccacgt aagatagcca aagtacggtt 318300
gagcaatcga catgatatat ttgctcacat tccaggcgaa ggtcataatt tgcaggaaca 318360
ttctatggtc ttaataagag gaggtagagt gaaagattcg ccaggtgtga atcccattg 318420
tattcgagga gtcaaggatt tgctgggaat tccggatcga agaagaggca gatcaaaata 318480
tggtgcggaa aaacccaaat cgatatgaat ggaagatgcc tctggaactt gtttttctcg 318540
gtaaggatag gtacgaagtc actcgactga aaggagaggg aacaaccaca acgttacacc 318600
ccaaaactat acggagccct tccgaatgac ctagaatata gtctactaaa ctagccaaga 318660
aagagtctag tagactatat tcgcccgtgg aggtgagtgg aggaagctgt gaagcttcta 318720
actctaatta ccaactcggg actaaattag taaaaagcgg cattatccct ttactcaatc 318780
cccctcgct taccacctttt cccgatcaat tggttttttaa ttatttaata agaaagatgg 318840
caaatcctac cattgtattt ccttttttca tttggatcct atcaacttttt agagtgtcta 318900
gattaagaca cttctcgtat tcggactatc aagatcgact aaatgagagt gtggctgaca 318960
tggtaaaaga agaaataagc cacacttttc tggacccctt tttctcttta caacgtctta 319020
ctaccacagc tattccactc tggtagatac gaatagtcca aacacgtatc ttcgggcgaa 319080
tagcctttaa ttaagcaagg gcgagaccaa agcacttaac tatagaaatt acttagaata 319140
gtgaaaatcg gcactactca agccttctta tccgcgagtg ctactcgccc aaggaagtct 319200
ctagcggttc aattcaatta ggtgaaaact gtctcggatg ccccttcctc ctcaacccgg 319260
gagaagaccg ggctttagcc gcttgagcgc actcgtctct ctctttaggg gcctttggga 319320
atcttgttca atggggaatt ctgcatccac tttccagccg gttgacgatg tggcatttct 319380
tcctaaacct tcagtcttgt cctaagcgaa aggggaatcg gattcttgca caagccattc 319440
taagaactga ttctagcaag acctattcgt gcacaaggga atctgtccat ttacagcaag 319500
caagccgcaa aaccaaaaga gtaagacatg gtaattgcta cgctactcta gccagtcgaa 319560
tgataaaggg gagtggaaat ggaattgatt taaaaaaaac agctagttcc gcatcaagac 319620
cgctttcacc tgaggaagga gcaaaataag acatactttt attaaccttt ctgtgctatt 319680
attcacttgc ccaagaaagg gctatgcaaa atgaaatggt actggcactt cgtcaaacct 319740
tccatgagca gcagattcaa tagcaattgc agctacttct atcatcctta tttgatttag 319800
ctgcggttac gtcgacgcgc acggcaaaaa cgctttcagt caagtgtcag ttccttgtct 319860
gattcttggc atctagatcg attaccaaca gtggaaagct agtagccttt gacagaagat 319920
cttgatttct ttctcacccc cgtcctatgt tcttgtcgtc tactcaggaa gaacccaacc 319980
aatacagttc gctgggcctt cccaacttga ctagtgagca ctgctcgact ataagagcgt 320040
cgcaatgcta tctatacaaa gcgtcatagc gtagtcgttc ttgttcgttg tcgtagtgag 320100
ctggttgggc tccgttacgc ttgctttcga gccttcttgc tattagaaag gagcgtccta 320160
agacctaaga cgaggataag gaagtttcat atggggccgg ggatatacct acgaatgagt 320220
ggttcagtcc agtcctgaaa taattggact aaccttcaat aatgacttcc gcaacatcga 320280
catgatggtg acacctttta cataaggaat gcaccctaag gtgtcaatct aaggtctcgt 320340
```

```
gttaatcctt ccattaattt cgttatcatt tgaatttctc atacctatct ctttgatcat 320400
gggctatcaa gatacactca tacccaccta agaaaggtgg tattctatct cccaccagac 320460
tgcctatcca gattaccata ctcactaaga gacttgattg cttactctcc ctttcttgct 320520
tgttcttttt ctacatttgc ttcctccgca ctcaatgaac aatcagatgc gggattacct 320580
gttgattgcg gtgtgcttgt cttggttgat ttcgcatatc tctttcttgt ttttgggcaa 320640
gctgctcttg ctcaagtgga atcagttgca gttggcatat ataaagaagt ctaatatcct 320700
gtcttctttt attaaggaat ttctagagag gaatccctg gccttagctc atctagccgt 320760
agctcattgg gcggattgct ttgaatagcc aaagtctttt gaaagagaag aatcaacatt 320820
cttggattag gctggtgcta tctcttattt aagagaaata ataaggagaa aggctgcctt 320880
aggtttagga gtttcgagtt ttctctgctt tcataggcta tcgcttcttg gtgcctagcc 320940
ttctgcttct gatcccggga gaataataag aatggccgtt gttgaatcag ctgtgaaaga 321000
cgctcttgcc tcagtttttg ttggtggaat agaccctacg ggagcccgt gaaggctaat 321060 ttctctgtcc ggctatcccc cctatgtcac caattgttgc aacagggtg acgtcattga 321120 ggccctcaag gacatgctta gcaaaggtat gataaaatgt cgccagttct ataaagtcaa 321180
gggctggaga gtcgaagagc gcactttggg actgaaaaag ttccacccct catcaatgct 321240
tcaaatacgt tgatgagaag ggggtatttg ccgacaagaa gccctttttt aaggagtct 321300 aggcatactt tctgtacgga tgcgcgtctt tacaacgacg gccccagccca gacagtgatg 321360 gatgacaaaa gcccgccagc gaaagccgaa gcacaggttc gtagacctct ccgaatccca 321420
aagtcgaaag ctaagggatt gacggtcaac gctatctcaa agagcatgac cccgttgacg 321480
aaatctctaa actggggctg agggagaatt acttcaactc tcggtaaaga tgccacttcc 321540
tgcattacag caaccttctc aggcagaggt gtttataaaa ctggagcgac attcgtcctc 321600
tcaatggaag gtttttttcct catctttcac agggtagccc ggaagtattc ttctacgttg 321660
gaaagaatcg tcaccgtcac cgatggtgag ataagaaaga gaaagtacag tccgattgca 321720
aagaagcgaa ggacatgggc tatatgacct tgaggagcct gtcgggctga agtgaagaac 321780
ggtcgaggca gaaaagtacc cctcgagccg catctaagtg aagaagaaag ggaagcttgg 321840
ctagccggcc agtacgtcga tctcagaaaa cataggcttg ggctacctgc caactccgct 321900
ccctgcgcca aaaactttgt ctgacgccga aagttctgga gatctttctt tcagatctct 321960
tccaattgtc tataaactct gtctccgtaa acaaagagc aaagagacga gagtaagttc 322020
aagaatagga tgtagagcct gtgccccta cagaggacga ggtcaagtaa atggatctcg 322080
ggactgttga caatcctcgc cctgtattcc taagtgcaag cttctcaaat gaaagagatt 322140
tgacagtaca tggatctact cagagaattc ttttatgttt tcgcttggag ctacgccgaa 322200
ctggactaga ccgaaagata aatgagttag ctcaggctca gggcgtgaaa gaaaatagat 322260
aagaaaggcg attcctgatc tgaagagttt agttgctata gtggaatctg ttgaatttgg 322320
gaaggctcag gtttggtggt atatccttac atatataagt agttttgatc ccggctccgg 322380
tcaaatggat ttaggaaagc ttccacgtga catcctcaag ttagtcttct gcttgaactg 322440
tcttatcgaa agctaaaggt agttaaccta ggggaagaat ccgactaagc tttgccttga 322500
acttggcacc ttaccttcta atcctttgct tgggaattcg attcaataaa gaggaatcac 322560
tgattggaca gtggcactgg aatgatagca agcatccctt cttctctttc ttggtatgag 322620
aagttggtta tgtaggctga caacctttcc taggttgttt cgatcaggcc aaataatcta 322680
ttttgagtat gcctgagatt gccagaagaa cttcccctc ttgaaaactg actaatcaaa 322740
```

```
caaagggggt aacttttttt tatgagggta gggagtttgg gttggtgttc agtgtaccgc 322800
actttgggta caagatcgga aattccattc tcttttttac catccaaaat cgaagaaaag 322860
aaagaagggc gagataaaca aataaagagc taactttctt taaactttct ttattattat 322920
gtaagattag aaagttcaaa atgaatcggc gcaggagctg ctacaattgc ttcagcggga 322980
gctgctgccg gtattggaaa tgttttcagt tccttaattc tgttgcgaga aatcattcat 323040
tggcaaaaca attttttggt tatgctattt tgggatttgc tttaaccgaa gctattgcct 323100
tgttttcctt aatgatggcc ttcttaatcc tccttgtctt ttagaaaaaa aaaaaagaaa 323160
agagtggaag cgggctagtc cccgaaaatg cccggtactt tagcgttggg gacaagtaag 323220
attattatct ggtttatccg ccatcgttat cacaaattga atatcctgtt aatgtgccag 323280
ccctagcccg tcttgctctt ccaattccat ttcgagagtc atcatagctc ttttggactt 323340
atacatgcag cacccttta tctttcggca tagacccttc ttcctccttg cgatgcaaag 323400
gcaatgtcag ggagggcgag aggagagaag gagagcacgt atgggtggta tgaaagccat 323460
aagcggaggc atgggtcttt ctcacgaaga tgcgaagcct agagatgagt ctattcaaaa 323520
ttgactgaaa aatccggggt aggaggcttg atgacaggtg ataaggtgag gaaaagcgaa 323580
gtcaagcctg acctaagaaa agactggttc tcaaccacag cagaatgagg ttttttcctt 323640
taccgatacc tattttttgcg tctttcttcc tcgtctaaga agcagaatca gccttctcct 323700
ccttatagaa tctcattcat ctatggaagg aaggaataat cgttgggtac cctgaacggg 323760
tgagagatcc tggaaaaggg agtcttctgg ttgcgggatc tccggcataa gctttcttcc 323820
cttgtcggcc ctccaatttt catgcccgat agtcaaagta agcacgcac ttcaagtggc 323880
gcgatttatg tcgttgcgca gggatgctct ccccgtagtg ccccttcttc ctccttctct 323940
cttttctctgc ggcctgcgtg ggactgatcc ggactgataa cccgaaccct tcgtagactg 324000
aactctcttc tctttaggct cgcgtaggtt agggaactcg cctccttcac tgcttccact 324060
ccaactcgaa ctaaaaacct cttcctcatc ttgactcatg gcgtcttcat cagtgagtaa 324120
atcctcatca tcatcctccg taagataaaa gaacctaact cctgggcctg tgcagactct 324180
tggtgaggct gttccaagtg tgtaggcccc acatgttgct catctccccc tgttggtggt 324240
cttacagtag caatggacgt agaaggaatt cttttgcatgg cttttaacgt ttgggttcaa 324300
taacattcac cttagtggga cccccccagca ccatctttcc ttagtaaata ctagatggat 324360
tccctattgc tatgctagct tccttgggaa tactaccttg cactggttta ggcggtatcc 324420
gggccctttt agaggcaaca gttgacttct ccttatttat tgtggtccca agaggcgtaa 324480
taacctaaaa gttgtccagt cctaaacaag acaggaaaac ctttaggctt cttcagaaaa 324540
ggaacatcaa acgttactt ggaaaacacg ttatacacgt atgatccaag taaacgtcca 324600
aacatccttt ctagcatacc cgtccgaaga gtcaaaggcc atctatcagt ggccgacttt 324660
aaatcaatca tacgagtatg ctatctcact acccgtcaat ctgagttctc gaaagcgact 324720
gaaccagcca cccagatgag actcccgctg aaaaacattc ttttttccgac aaaacctgcc 324780
actaagcttt gacaagtcgc taacttgctc attttgtaat agggcccagt cacctccctt 324840
cttcccaacc tctggcagtc aaaagggaga cgtgcttcgg tctttccatc gatagaagca 324900
gtaggtatat aacgcatgca gctagtaggt gataggagga tgtaagccct ggtggcagtg 324960
gtactttggc gaatcaggcg tcgcttctat ttcgttttttg attattattt ttgacccctac 325020
aatggcagaa cctagaaagc tgctcttttt tccctgtccc gtgatttgat accgtctagc 325080
```

```
ctctagctag gaagtcttgg attcgtatac catgtaggtg agaaaatcgt ccgtgactag    325140
ctatccttat tctcctccca gggatgttta ggaatatggg tgcgggaggc tgagggacga    325200
ccacgatgag tacgcgtttt tatataggat caaacggttt ttgttcgatc gaaagttagc    325260
ttgactcaag tcgacaagcg agagagaagg ttgggtgagg gtacaaggca tcatgtggga    325320
tctacgatcg actgtgcccg ttgttggctt tgcagatgct ttcaaatact ctagcagtat    325380
attccattca ttgtatatat ccctttttcg tgtcattgac atcagagatt gcattcaatc    325440
gaatggtttg acataagaaa tgttctagtc tatctgtagt agttctcttt gtttatagta    325500
gagtaatgag ggtggcgact cacaagagga gtgtagacca gagcaagagg gagccaagcc    325560
agctactgtg gttgtgccat ttggtgggcc aaagtagtct agtggcggtg aaaagacgat    325620
agtagaccag acgggacac caccagaaca cccgaacaag gatctatttt ctttttaagc    325680
tatagtacat atgcactttta tacgtctgtc ttactaataa tattccttag cgtacatctg    325740
tactataacc ctcccctctg ggaggtgttt tcaaggaagg gcggactccg cagctgcgga    325800
ccgggcacta tcactatact atgcgatgct ttttaccaaa aaaatggaaa ctgtcaagat    325860
tagcgtacta aacgattcga tctatcacct acgtcatttc tactttgaat aaatccatac    325920
ttgttgcact cagtcatcgt tccgtcatcc aacatgcttc tatctaagtg atttcataac    325980
atatggatat gtaaggaata agctaaagaa ggccgcacct ccctattcat tacatcacaa    326040
tatccgcacc atttgcttaa aacacagttt ttgcatttgt gtagcttact cacttgccaa    326100
gaaaaattca tcacatactt cgtggcttta tgcttcgaac tgtgatcaga acgagaggag    326160
tgggcaccga agatgccaaa gaagctagcc actatcattg tatatatttt taaaacaaac    326220
ctgacttctg tggtttgaaa cctgtgccta gcctttctgg cttgccttttt gaatgggcgt    326280 gccaatattc aatatattta ccctttttcct gcttcatcgc tttggcctat tgaatccgca    326340
gctgtctcag taggagtagc acgttttcga ccaggcttgg cttattctat agcatttgtg    326400
ccatctatat ctataagaga ctcctctctg catttacagg taaaaactca catgctttcc    326460
tttcttgctt tcctaagtcc ctttctccat atggattgaa aaagagttat tcggcccgtc    326520
atggaaagaa actacacctg gctcgctaga tcaaggaaag ggctcgcgta gatcaattac    326580
ctgaatcatg cttttcccaa gctgagttct aagacccttt cgtttcggaa gcaaaaccca    326640
aagcaaagaa agcagcaaga gtggagagaa caagctcttc aagctcagct tcggcaacag    326700
caactcgaga aagcaattca gtttgtgagg aaccgtccac ttatttatat acgtcgccct    326760
ttgacgatct gtctgttcag gcaggtgcca cggaagtgag tacggaatca gataatgggg    326820
aacgtaaaag actgagggaa tttagttccg agactcatct aagttcccat cggccgtttg    326880
aagccacggg atggggaaag gagcgtttac actcgacaag aggtctcaga gcaaccccta    326940
tggtatggct aagctccgtt catagcctga aaaacactga cgatctgtcc tcatcgtggt    327000
cttttggtga tagaaccagg atggaaagaa ctgaaaaaca taactcttct tttccgaatt    327060
ttctagcctg gcccatagtc atggtaaact ataaggattc cctagcccgc tttctggatt    327120
ttcggcttta tccgaagact ttggtagatg tgcggggtca gggggcagga tggtcgaaat    327180
ggatttcaag gatcagtaaa attgccaaa aggaggggaa ttttctcgat cctttggtaa    327240
accgaattca gttcggaaag gtgggaaagc agttcttcgg gtgagcagtt tcaaaggatc    327300
aaggaataat aaaaggtacc ctagctggat agctaagaca ctaagaaggc ttaggccgaa    327360
tgcttacctt atgcttacgt accggccgta gagaaggtag gtaggaatag atgggctgac    327420
ggattagggg aatggaccac tggcaagact gaaaactcaa agaagaagca aaaaaaaaaa    327480
```

```
aagaaactaa gaaagagaac ccttttagct acggcaaatg ctgcccaatt cacattcact   327540
cgatctacgt cgagcaaaaa gccttgaaac tgactgacac gctaccgaaa tgccaagcca   327600
aaggatttga attcagttta gcaaggtacc tgatacgatt agaaggatag ctaagagaga   327660
agtcaactaa aggttgcttg cttccttaca ctaagaccac tatcaggctt agagccaagg   327720
ggccactgct tgcacggaca taggggcata cgaacatagg ggtagagtag aggttttttcc  327780 aacgcaggac ggaatggatt agatggacag ctagcactgc ccctcactt cccacttcca    327840 agagaggacc gaatcgagga ctcgaagact tagacggaaa cccctttata tcgctcctgc   327900
aacagaaaga ctcaatcaac agccgtataa tcaagcaaaa aagaaagaga aatattcgag   327960
ggaggaagat gctctcccct acggtcgagt tactttgttc cttcctctcg cttcgctcga   328020
gcatcttcaa acctcactcc ggcgaatggg tacctaggct tctcttgcca atgtatacaa   328080
atagacagac ctgcgaact atctttccaa agcccctgc aagtataatg attagacgaa     328140
gaagaggccg tcagaccaga aagaaagcta ccctttgaag ctagattgag atttaggtaa   328200
tgggctgtca gacagagact gagcgcagac gcacccgagg agtttgattt ctacgcttct   328260
tcttcctttc tgaagggcac tttctttctc ttgaaagatt tgatgcgcca cacgacttac   328320
ccaatagctt ttcgattgtt ggcgccgact tccccttca aagtaagata gtttcgaaca    328380
acatatatga tattgtaact tcactctttt catccaactc gaaatatcgt aagagaagca   328440
cttttacgcc caaaaagccc catgtctttc cggaccaacc accggcgatt tccgacaagt   328500 cttccccgg gggagcagaa aaagaaaaga aaatgaatca aaggaatgga cttgctaatt     328560
taagaataca tcacatctct agggttaacc ctgtctatcg cccttcttgt ggcttttagg   328620
gctggacagg ccagaaatct aaattccatt aatatggaga ataagctcaa tcaattgagt   328680
atagacacgc taaaagaaag aatcgtatcc aaagtagaaa tgcttgtacg ggtttctaaa   328740
gaaactaccc caggtttgga ctttgagctg cctcccatag aacctattgc tcagcagatc   328800 cttttttacag aggaaagtat tccctatctt aattccctat atacgagtct cattgagaac  328860
gggacccaag gggaatactt ggaaaaagta ttcactttgg cttccatgat ccacaagatc   328920
catatagata tggtttagcc agtgaatgtt gtcgacgcta aaaagaacac gttcagatac   328980
accatggaaa tcgaccgctg ctggtaagtc accatctccc gtaggagtag tgtccctata   329040
gactttatat acaatataca gttgatcaac cacttttttct ttaacaacat ctactgcaac  329100
ttttgttaga gcagtttcca tattgatact atttaaagtt gggagaattt gaccagcact   329160
aacggccacc agaatagcta caggcaaagg caaagccatt ttcaatatga aatcagcaac   329220
tagttcaccc attccataca taataccgag tcttagattc cagtttttctt agaccggcaa  329280 ctcctatccc gaatatacaa gacaagtaag cgcccggtcc tcttgcgtcg aagtgaagtg   329340
tagtgtggtg aggttttgcc tcacagaagg cgtgggaaat tggggaaaaa gccgaaactg   329400
attcggccag tacaatactg agtcttattg aggccatgaa gacggacagc acttggttta   329460
gagctgacca acgaaaaaag actccaattc attccgttgg tcaacaacca accagtgatt   329520
tcaatagctg tttattcgtt ccctcaatcc tctgatgtaa acctgagact agtgaaagaa   329580
aataagtgac ttgttctcct ctctttcttc attcaatatc tgtctagcct actaacgacg   329640 cccttttctta tctacgctat ttacccttca ttacttcccc agctttgagt tcagttcctt  329700
tatttgatct tgtctcctag tggtaccatc tctgcttact cttctttctt tccatctact   329760
aagtttgcgg aaaagagaga gcagacggtt ctcggcatca tgatgcaaga atgacatctg   329820
```

-continued

```
agatcgctca ttccattgct ttacagtcat gatgggaatg attctattta ctagaaagag 329880
acaacaccct attcttagca tcgaagaggg aattttgtgt agactgcttt ttgaaagtga 329940
aatagagact ttcactaaag agtgagattg aggagtgaaa gaacccggta ttcacataag 330000
aaagtggcag tagtctaggc ggacaccttt tcttttgcct tacccgcaac gcccccttttc 330060
taagtagcag cttagggttt gacaaacctt aattcaaaag ctggaaactc atatgctagt 330120
acacttgccc tgtatgcccc atctccatga aagtcttagc cagtgcttct ttccgccttc 330180
caacttaata gattctctct atctctattt cactttcagg ggtgagtatt aaaacgccat 330240
aggaaaaaaa aggggttagc tcttagctcg ctggtagtac tgatacaatc aatatgtaca 330300
cacatattag gaaactaaaa agcagaaaga tcctttcaaa aggggggttgg atactaaaac 330360
tcggaacttt ctcccaatct ctcttcaaac ttaccttttc ataaaggtta gaaccttcct 330420
aaaattcagg agagctatgc cgcactctca aatccactca taaaagcata gcgagagata 330480
gcagcttctg attccggaga ttctatctag gttctagtta aactcccaaa ctccctggtt 330540
atagggcctt ataatagtac tggaaagaaa aaggagtatt gtataacgta tcctaataca 330600
ggaaaaaaat atattataag gaaagattct atgttagtac tccaggtact ttcttattcg 330660
agacgagaat aggcccaact cgcctgcatc gacagcaaag gaaactggca gggaaataga 330720
tgccattttt tctcaatggc aactggtact taaactagat atccctcagc cagagactct 330780
gggatgaaat gactcttatg atagtcagat ggcgaagact tagaacgtgg ctaatccgct 330840
ttctcccatt tctctctact ctatctatta aggctatgaa ggaattcgtt catagaatgc 330900
gattgcacta cttttttgaaa acaaccgtac gggatatagt cggccgaggt accaaagcct 330960
tttacggatc cggctctgtc cttaggaagc ttacccaact cattttttaa ctcccaagaa 331020
aggaagacaa ccccagtaaa tcgtgcataa tggaagagga aagacctgtt aacaacagga 331080
taagggaata gcaaaagtta ggaaccaagg gatatgagaa tgtgaaaagc gatacgataa 331140
gacagtcatc tcacacgcta ggcccaaaac ctattccgga tctgattttt tctttcctgg 331200
gtgtggaaaa gacaaagtct tcttagtctt ccgcttttc ggtgatatct ataagaagga 331260
ataccctttct caaggtaaac aggagttccc ggctcaagcg aaatgatacc ggcgcaaggt 331320
cagtcaattc tttctttagg atagattcct agtgctatcg atttagctct tggaagaagg 331380
gaagtttcat tttgaagagt aggcataaga ggtcttggag tcggcattag ccccgttgtt 331440
gtaggagaga tgaaagccat aactctgccc taagcattga gcttacgcga accaagcccc 331500
ccggtctttc atcaggctac ccccactcct tggtcttctt ctttacgctt ttctctgtct 331560
tctatagtaa gttcccccac gggtgcagag atgcgaatcc ctagtttatt aatagaatag 331620
caggtattag gtcctagcgg gcgtaacctc tttgtcctct actgcctttc ccacatttaa 331680
agatgcagga agcgcccaca gagatgttag ctctttcaac tctttatccg gactggaaag 331740
caactctata gaaattggat gcttgtaaag ctgctcattc tgatgaagct gggaactgct 331800
tgctttaaac tcaatcacac agtccggtcg ggctgcccctt tgcccgcatt cctaactccc 331860
ctggtaactc aatagaattc tctcccggaa ggggcttaca ccaaaatagt aactgggaaa 331920
gatcaattat tccttactct tcctacgggt tcaaagaaga tagggacaaa gctccatagc 331980
gggataaagt gttattgtgc ccgtaaggcc tttgtctgca ttgcctccca attgtgtatt 332040
ggaagagatt ctaagggcat agtaagaaat tctataggat aagggcctaa cttccccatg 332100
aatcccaggt catttgaatt tcatatgggt aaagacccag tcctctaact tctaaccaga 332160
taaagagcag ccagcgggaa gaggattagg atcagatgac ctaaaagggc ttttcctcat 332220
```

```
cagtatgttg ttccccgtga atcacaggga agagtcagat cttaggcttt cgggtcctta 332280
gtctctcttt gccgctaaag tctaagaatc cattcaactg caactgcgga ctcaagagaa 332340
gatgccctct aacttacaat caattcctaa ctttcggctt gcacaacaat agacagagga 332400
tgctccgctt tttctcaatc aatgggcaga ggcaggttaa tccccgaggg ttattggatt 332460
gatttctctt cggtagttaa ttgttatagt taaaagggcg attaggagaa ccaaaggttc 332520
tttgaagttc ttagtccccg ctttcctgaa agagttctct ctgctcgggc ttctgtctgg 332580
acttacgtcc ttttcaatca caggaagagc ggtgtaaaac gaaatcataa tattctgcct 332640
tcaatggctt tgcctgcgac gtatcatctt acctcagtct gttacgggcc tacctgtcat 332700
agcctaccag atcatcagct ggaggaggat gggattgaaa gaactaaaga gaactagttt 332760
tcccgggctc ttctaagtat taactgtccg atagcgtagt taagtgactt ctggggtcag 332820
acagatagga atccacacca agcttttcat atgtaatttc gccagtaaat aaagaaagac 332880
ttcttgaact cggtgttccg gtgaagaggc tttccgtctg ttcgctgcta aagtctcatc 332940
agaaagattc gtacttgact tcctcttctt tctaacttac aggcctagca gaaaagtcgg 333000
ttttatagac tgacaaagct gggtaatgca ccctaatatc aatacttcct ggctgatcaa 333060
ttttaggaag ctggggaaag gacagacttg ctttcttcag actgacttca gggtatcaaa 333120
atattatgat tcatactttt gcccacctTt aaagagaagg gatgggattg taccaacaat 333180
agatcgatct aaagaacggg cttttaccaa cctagaaata ctaattcatt ctaattctgg 333240
tcggacgttt aagtcaaagc cgcatctctt ttatcacaaa gttaccattt agcaataaag 333300
gataagctcc gattgaaagg atcttcttct ctttaaggca ttttctcctg ctttgtctat 333360
ttaatttcta ctttgaagtc aagattagcc tactgcagga agggcttcat tcacctcaag 333420
cactaattct tttcgaactc ttattacgga ctctaatgca ataccaagag atagagtaat 333480
tcaatcctcc gctcgtggga actcaatcta aacacactaa ctcctcaagc actaagtcca 333540
tacatcaatc ctcaagagaa tgccttcaa cggcagcatt tactctagct tctacttccg 333600
aagtcagttc cggaaagag gcagaaattg cttatatagt agttcagtgg ggaagacccg 333660
tgagggaata gtaaaagaat tacagggttt cggaattgat taacagggat ggggaactcc 333720
gccttcaaag gtcgtagtgc tttcctaatc aaatgacttg tttacggctc taagatgcca 333780
tgctttaact atttcccgtg taaatatcat gagttcttgc ttgattcatt ctcaggacgt 333840
aatgctactg cttctcaga ctttgcagag aataaagaga cttgcaagga tagattcccc 333900
tacttcagat acttcttagg gctttcaata ctgactacaa ggaagtctgg gaacacagtc 333960
gaaatctatt cccctatcaa gaaaagaaag agtcgaaagc tagagctgac aaaggaaaga 334020
aagcctctaa cttctaactc aacttcctcc gagagggctg cgtcagtctt taagttgct 334080 ttcgtagttg ctaccttctt ttaggcctaa ggaatgaaat cctggaagag tcagagaata 334140
tcgaaatcaa actacgcacc tcgggttaag acttccaaga gcctacaggg gaatctaagg 334200
gaatagctca agagagatcc tgatcttggt ccctagagga agtaaataaa tacatgaatt 334260
aggattttat ttcccgggga acttcttaat ggggagtttg cagatctggg tgtaggggat 334320
tcggaagtaa atactgacta gacttccctc ctggggataa agactgagaa tctgtaagtc 334380
ttgaagctct aactctttat aagactaggc cagcccgtca acctttagag ttgcatttat 334440
gcccttgctt ttggttggaa gttcagaagc tgtcagatcc cctacggctc tgttagcaga 334500
taatggactt gattcaattc aatggcattt catcacaggc attagacttc cagactttcc 334560
```

-continued

```
ttgcttttta gcaatgaact ccgaaacttc agatactgct tacgcctgat caactcataa 334620
ggttgggatt gtattgaaat agtaggcatc tcttccggac aggcgtgtaa caacaaaaga 334680
ttaatcgtaa actgcttttc tttcctacgt aatttcccag tgaagaagcg ggagttgata 334740
tgatcttctt tacctaactg cccgggaaag acagcataat taggaattga atcaatgggc 334800
atagtaattt catcatcggg attatctcaa atagacccaa aggtaagcaa taaagactac 334860
aaagactaca aggaattcaa tccttgcact acgcatctac gggaaattta gaagtcaaga 334920
ttgaaacgaa atcaaggact tcatctacgg attatgcctc tactttttat atgatatttt 334980
tcttgctttt ttcctattct ctttcggatg cagctttgac tctagcagag ctaaagtaac 335040
tgattccact caactacact aattgaggaa gaggatgaaa atctagggga atatcctact 335100
gcaaaagact tagatcaatg aagctcagcc ggccttgttg tatggcgtat tggtcctatt 335160
tgccccttgt attagtataa gtaggccttt ttcctcaatc taacaaggac tcattaggac 335220
cactacacac taaccatagg cctgatcccg tagatgaacc gctaagttaa gtttaggatt 335280
atgagttaga tcttagggtt taagccgccc ataaaggcag agaatcgtct tcgccctgac 335340
ttccgggagg cgaggtagtt taaagcagtg gaaatctcat atgattgggt ttcgactctg 335400
tcccgcagtc ttgactaaaa ttgtttgtcc ctgcagctga aactgctaga tactgacttg 335460
agtttaaaac ctcagatata ggaggaatga caatctaaaa ccatggaagt tcttatgaat 335520
ggtaggctta ttgagttacc ggggaaagac ttagttagga aagcatcata tcttcccctc 335580
tactcactgg aaagtctgac tgatgaaatg caggagtaga atgaagtcaa ggacttttct 335640
ttctttatgg ctttagtcga gccgtaagta gttgaattca gtaatggaga gagtgatagt 335700
tgtctagggt aaagttagtg cgtagttaga caggctttct agatctaagg aaagcaacgt 335760 cttttgctgtt gtgattcctc attgctggag taattcatgc tttctccaga gcgggatcaa 335820
gctttctaat gaaagcctat gttcacacaa tggttaactc attcgatttg gggattgggt 335880
tagtgttcta ggagtgaatt gtagtgcccc tggtggctta ttgcgtagtt aactctttat 335940
atacgacctt actactcctc aattcccatc aagtgttgtc ttatttccca agccactgct 336000
caatcctcct tttctgattg attgaaagta gcaaggaaag acaagcaaaa actttgttgg 336060
ctcaagaagc aactgaggag agacaaagag tagtaaagga aatacaagta gcagtctcag 336120
gtcaaaggaa tcaaggaaga atttcttctg atattgcggt tactcttcca gaatctcatc 336180
ctgagaccta agtatgccat tctcttcgtc aagaaagatc gagcagcata gaagccttga 336240
cttcaagctt aggtcttttt tttgaaaaag ggaactaagg caacttttag gtgcaggaa 336300 agaggttcgc tagccttttc cctagctttt tttgtcaact atctatcttt ccgaactaga 336360
ttagacggac ttacttaaaa tgaaaaaagg gctaaaaaag aaggacgaag taatttcgta 336420
tataaagata tggctttccg ggtttagatc gaaatggaat ccccgaaaac cagggctgga 336480
gtcttagact tcttctgctt cgatagaggg actgacagcc taagtggaat aagaatcatt 336540
cggccgattg ctctgactct tatccttcct tcgctgacag agaagagagc actcccaagc 336600
caaggatgag tgccaaagag aagatgggca agcaatgccc actcccatgc tttccgttgg 336660
tcaacaacca accaaagtgc tctatacttc ttcactactc gtacaggctt gacggagtta 336720
agctgtattg agggaatcgt tttgtctcaa tcaatcaata tgtttccgaa aattccacgt 336780
atcttttctt tgatgaagag agtctaaatt ccagtgctac atcctctcaa actcgagtca 336840
atccacgaca actattagcg atttttagtct tcaatcgtcc gatactcaag gttcttctaa 336900
tggtattttg aggatcatcc aggtcttaac ccttccagtg aacgtatagt agagcttcaa 336960
```

```
tgttgtatac gcgaaagatt cgaagagttg ctgcctaaca acaatgccga agcccaagcc   337020
caagaggctc tggtagcggc cgaagtttta catggcgaaa gcaacgatat cgccgagctg   337080
gaacaccttt gacagatttg aatcttcacg gagtactaag tgaagccttt ctagaggcga   337140
tgcatctagt gaaggagctc accagccccc aacccaccta ccgtcccag cccacttgaa    337200 caatttgaaa taatcccatt gattcctatg aaaataggaa acttatattt ctcattcaca   337260
aatccatctt tgtttatgct actaactctc agtttggtcc tacttttggt ttattttgtt   337320
actaaaaggg aggaggaaac tcagtaccaa atgcttggca atccttggta gagcttattt   337380
atgatttcgt gctgaacccg gtaaacgaac aaataggtgg tctttccgga aatgttaaac   337440
aaaagttttc ccctcgcatc tcggtcactt ttacttttcg ttattttgta atccccaggg   337500
tatgatacct tatagcttca cagttacaag tcattttctc attactttgg gtctctcatt   337560
ttcgattttt attggcatta ctatagtggg atttcaaaaa atgggcttca ttttttaagc   337620
ttcttattac ctgcaggagt cccactgcca ttagcaccct ttttagtact ccttgagcta   337680
atcccttatt gttttcgagc attaagctca ggaatacgtt tatttgctaa tatgatggcc   337740
ggtcatagtt cagtaaagat tttaagtggg ttcgcttgga ctatgctatg tatgaatgat   337800
cttttatatt tcataggga tcttggtcct ttatttatag ttcttgcatt aaccggtctg    337860
gaattaggtg tagctatatc acaagctcat gtttctacga tcttaatctg tatttacttg   337920
aatgatgcta taaatcttca tcaaagtgct tattttttta taattgaaca aaagcgagtc   337980
tgaatgggta tacttagtcg tggagcattc cgagtatttg ctttagggat cgttcctgcg   338040
catctcctta ctttatagca gttattgctc cggttccaga aggtatagct cttggctcag   338100
cttttcttag aaattggaga ctgttccaat ttcctactga gataggcaag cggagggaga   338160
actagacgta tcttgctagg caaagacagg ttagaatgga tagctcgcgg gtgggattga   338220
cgggatagat cactattgca gaaggaggta gaaccgggga agaattatgg ctataaaggt   338280
cctcgccctc ttaggcacat ggttctaaag attcaatctc aaagcggtac taaagattag   338340
gcagaagcag aactagaact agaattcttc gcccctccct tgtaccaaga agcaagttca   338400
gaacataagg ataatgggct cgtctattag aagttattag tttacggagc tatctcagat   338460
atctcgagta aggagacggg gcgggtttga tagttagagt tctatttcta ggaaggaaga   338520
gactatcggg aagctcactc tcggccgggc tcgaagcaga aggtagaacg taatatctct   338580
tgttggttca gctcatcaag ctattacaaa agagtccagc ggagacaaag aaagaagcca   338640
ttttacggta ttttcgcttc cagtccgtaa ttagatcttc aagcttagtc cagtccggat   338700
ccatcctaaa ccaaagagcg gggctaagcg aggggcatag cgatacagtg ttcatactcg   338760
agttgctcaa atccagtagg aatatcagga atagtaggat ctagtaggag cttgccttgg   338820
aatgcagtga gggagcccgg agctattgaa ttctttcata acccaaggag aagaatagga   338880
ctctttacca gtatcataac ctctcgatgg gaaatggaac ttagatcacg atgtgaacct   338940
acttatgagt ggaatttcgt tgacaagcaa attccccgga aaacgaactt ttctccaatt   339000
gagatgcttt cttcatttat ggattctatg cgagattcgg ttagtgtgaa gtgtgatcct   339060
ggctcagaag gaagagctat atgcttaaca catagagttc gatgtaggta aggatgtgct   339120
ccaaagtttt caattccacc ttatcaacct gaaaagagct aatacgggct tagcctgcct   339180
tttatcttat ccttctattc taggcgagga ggttttatttt taaatagtaa atagcccat   339240 aaaaacaaca aactagtcaa aggacagcct gccttattct tctcccgttc gggacccta   339300
```

```
tttctcgga gatagcctgg tctgagctag aacagcagat tcgtgagcaa gagcgtattt 339360
cacagctgat tcaacaacag ccattttttc tggggaactt tcatatgagt ctgttctttc 339420
ttttaatcca ctataaaggt tcttaatttt ctctttaata tgaaggagaa ttacattctt 339480
gaaaggatca agggctctac cctctcgcat aaagtcttac gctcttatcg tcaaccttcg 339540
tggcttttgc tcctttggtc tcgctatttc attcctggtt ctctctttca agcttctttc 339600
catcctgggg atttcttctc attccgtccg ttctgctagc tggtgtcgcc ttctctctta 339660
cttatctatt cccatccatc tttacctctc ctactccact acttccctcc ttcaaagcgt 339720
gattaatgcg ccttaaacct ctctcttgaa aagagcattt tttagtggag ccttagcacg 339780
tgaacccata ggaacagggc ccttcttctt tgcaaaaaag cttctgaatt atcatcacat 339840
cagtaggcgc agaaagcaaa tcttggtatt gacttattga aaatctcttt gagattgctt 339900
agacaaatct tttgtgtgag gccgctgttc cccacctttc ttaccttgtt ttttgggctt 339960
aaaattctgt gactcataag ccctccatat ctaaagatag atggctaaag ggcgggttcc 340020
gcagttaact aagaaggcga tcgattggct tggagaggaa acgaaacccg gactgaaaac 340080
aaaaggatag aatgaattg aataaagaaa gaatatatag aaccttgagc attttctctt 340140
ctcggcaatg gttgagagta aaaaagggta tccgcataga aggattgctg gtataccggg 340200
tagatgttta tcttttcgac ttcagcgaaa atgtaaaagc acaaatttcg taaattttct 340260
ttctgtcgaa agggaagagg acagggtctt acttacttaa aagtaaaaaa aaaatggaa 340320
gtttcctgtc ttagtttcac ttccttgaac tggctactac cgcgcaacgt gcccttgctt 340380
ggtgggtcgt taattaatca gttttaaaag agggatggat ttcgaccttg ctttgagtcg 340440
tcaggctagt aaagcgctac ttctaaaacg atcgttaagg tcattcactc gattccctcg 340500
gtggctctgc taccgatgga tcaagatatg ctgcctgcct atcatgccaa aggcgctgct 340560
ggtggatatg ccaaagatgt cctggctctg aaccgggtac ttgaaatgct aaaggtactt 340620
cttatggtcc tgcttcaacc acccttcctt ctctaccttt tcttcaaaac ttaagctact 340680
tagactgatg ctggcgatct cgaagggaga tatctggacc tggagctact catcttgatc 340740
tttattatat taggatgcga ggaaagggaa agaaggtgat aagcaagaag aggaaagaag 340800
aatgttaaag aagtccctat aagtacttca cttagccttt ctatagtctg tctttcttcc 340860
ctcttccctc aaagcgctct ttcatccatg cgcatggttc ttactttcat ttcccctcct 340920
cacgtaggag cgcatcttgt tttcaaagat gagttgtaga tgagtcggtt cgatcacccc 340980
acatatcgac ggttttttaat gccttatcct aagcccatct agttgatcga gggatagacg 341040
agtataaaga agggatggag aatcttttat ttgatcttga tttgatgtat atgttacgat 341100
gccttcgtat tcaggaggat tggggtacgg cagataagaa gagcgaccca aaacggaaag 341160
aagagtatga ggggcagcgg ctcaccgata ataagaagaa ctcacattct cgtcctgaca 341220
gatgaccaac ctgttaaggc atctttctca atgaccatcc tctcccattc cagttctttc 341280
tcttttttta gggacaagtt cattttcatt ccctcgatat ggccaggtgt gaagcaactt 341340
cacgatccaa tgaattccct aaaatcggat gacacaaggc gaactagaat aggctgattt 341400
atccacaaga atgtcataaa ggttttctcc ggtcttcctc aaaagacagc tttagagcgc 341460
aagtcaaact catgataggc gagaaatcac gcgcacatgg tttagcggtt tgctgtgctc 341520
tgtgatctta ttcttctcaa gacccgatgc ttcatctgct tctttagttt agtaggactt 341580
cttttcacgct attgcgtgaa acatttgttt ggtctcccac tgctactgct atctatgcta 341640
acttgaaagg tatggctact ctcttgtttc ctgctgaacc tccttcccaa tacaggcttc 341700
```

```
gcagccatcc ctgcttgcat tttttaaaaa agtttggtag gggctgccaa gcttgactaa    341760 tagaatagg tcccttaaa aggagaatgc ctgccctgtg ccaccttggt agcacaaaca     341820
aaggtcctgt gtaccaggga tgtacgaatc atagtaataa actttacaaa ctttattagt    341880
tgcaaggcga ctttgctgta aagtttatta tactcttaaa gtatattcta aagtaaaagt    341940
cttcttagta ttcaaatttt tgactatgaa tattcctacc cttgcagtgc taatatattc    342000
attagtctga gtcttagtct actaaaagca taggaaagga agagtcaact cttatgttgc    342060
aaggttccac cccaaccaag taataagcac taaactgaac tctataagga tagacggggt    342120
gatttctcac tacaaagaaa aaggctgagg atttgaaata gatagaaagg agtccaatct    342180
aagcaagcgt agtggaggaa aaaaatccta aaagtaagca agtagttgaa ttagtccctg    342240
ctagtattgg ttggtcttac tttattatac aaagsthhgd ggcaacgcgt htghvgtcad    342300
chgcdtdbgv vgtacdvhvc gaaggcccct cgaatcttcc ttgagttgac gtcactggga    342360
catctaccgc ttggatcctg ccttgttagt catccgtaga gctaaaggga attttttgaa    342420
gccattccca ttcccacaca ccaataccaa ccagggtggc tgttcagtaa gtcctacccc    342480
taatagaaag gataaaattgc ttgcgcgctt cgtcaagtaa gagagggatc ttaggccgaa    342540
cagatcaccg gctccgaagg cctgcaatcg tgactttagt tccggtggtt cgctttgctg    342600
ccggggtgca acagcctttg tgacacttcg aatggagtgg tccgtacgcc cctcccctcg    342660
ccaagcctga agaaggagc aacttagata cctctttgtt aactagattc ctggtttgct    342720
aaaagggtcc ttgggcccaa tcaatctcta tactcttgat gcaatggact ccccaaagcc    342780 actaaccgc tctcttccac ccgatttgaa cagaaccctcg ttctagtgag attttatccc    342840
ttttaaacgg aaactcagtt gcctatctga tccttggtct aattgggcct ttctctatag    342900
ctcgaatcga atagctgggc taccccttcc cttggcttgg ttggttatat aagagaatcc    342960
caggagaaag caagttagac cttacttagg gcgaaagatt ttttggatgg ttcattccag    343020
tctgaagtca gtcaagtcat ggaattggca gaagttcccc ttaaccaacc ctaagaggga    343080
attcttctat tcattaagat gaagccattc agtcagctct gaatctgaac tcaatgattg    343140
cttttcaaga agggcatgaa gctttggctc agtacagtag catttgactt tgggaaagag    343200
aatcgataga atcgatcgct taccttgctt tggcatgcca gaagcatttc gctgtggttc    343260
tcattgattg agtcgatccc gagacaaagc aaagggagtt ccgtgggttc agtttgctta    343320
gaggcagaaa gcctagaaga ggcctagaag tcataaggaa taggcaatgt accggcaact    343380
ctaaggtttg gcttttttctt ttattgactt ttgagtcaat gtcgcatttc gcgtgcttgg    343440
ttagatctcc taacctaatg taatgaagga gaaggcagaa aaaagatgc ctttatccct    343500 agagatgcag gagcttgcct taggacagaa atgatatccg aatggcgtac ggagctgctt    343560
accctaagac ttcaactcca tcttacatcg aagtcagttc ggctggatcg agagaatctg    343620
gataggcatg atcgaaagag gggcaactct gtctccgcct ctgctcgtgc actcgttaaa    343680
gtcatggcct agcctagttg gtgaaggagc ctacaagtgg taaccgctct gtatccgtca    343740 tctcttttgaa gaagcagttg ggctacaagc ggcgctttca aaatcccgtg actctcagtc    343800
atctatcttc ttttcacctg aaaatttttgg attggggaag cagagaatca aaaaaaaaaa    343860
aaagtcatgc ttactataag aaggaagcgg gcggagaccc gtgcgtgcag caggtgtaga    343920
gtcagtcgaa ctagtcctgc gaatatgcga aaatgttctt tatgaatgga gaccagacac    343980 aattgctta gcggggactg aaatcgtgac tatgtgttca tgctttcgaa aagaaaacaa    344040
```

```
ccatctacac ggggcgctat ttgtctactt attgcattag tcacgtctat tttgaagtct 344100
tatttaactc gttcgatgtg aagcccttcc acacctgtat gaagcatctc ctctcgggat 344160
tcaccggact tcgtagcttg aaacaacctg tccttttcct atgctgaggc agcaccaaca 344220
aatcaatcca tcgaagttcc tattgacata cataaaaata tagggatgcc cttgatgatt 344280
cggatcatct caatcaattg attgggaaga gattacttat gagcaaaggg aggacgaagt 344340
cgcaggagat taggtattat ttaaactgtc aaaataaggg atatcgttga ctggtacaag 344400
aatagaattc cttgcttaca cttttctttct actggttggc ttaccctgta tttcaagagt 344460
aaataccgca gtgaggaata gcggttcctc tctttgtttg gtctaataaa aagattattc 344520
atcaccgcaa ccactctcgc ttagctacca cttgtctttg cttgcttact tctaaagcaa 344580
accagactga agacagtaga gaaagacttt tattacgtta tccagaatgc gatgccccaa 344640
ggcaagaaag tagcaatcgg cttcaatcc tatgatttta ctcgaatagc taatatcaga 344700
gtagcagata tggttttagc ggaagctgct ttccccggat gcggaattga aagaaccatg 344760
ccttttttct tataaaagcc tcctcatcaa ctctctatct ttcgaaccca cctcaccgag 344820
cttaacgccc tgtggacttt tttacgaagg cctaacttga caggcccgga cggccgattc 344880
ataagggtct gagccttggt cggctgccct actaggtaag gcaagcgctc accgattcct 344940
ttacgtcttt tcgatcgtgc tttccgtgaa ttgaagggg aattaattat ccagcagaga 345000
tggcatccat tagcttattg tcggctctca ctctggctca tcatccagag gcggggttgag 345060 cccccttgcac agcttttagc agatgattcc aggcaagaca agatcagggt caatgaagtg 345120
tttaaggaca atcaatggca ctgggattgt ctgcacactc aacctccaga ctttgtgaag 345180
aacatcatct cctctatgca gcttacactc agtccagatg aagatgattt ggcaattttg 345240
tctccaactg catcaggtaa attctctctt gcttcagcct ggaatatgct taaacataaa 345300
aaagggtgtc cttttagatt caaagatatg gcataaggat gtgccttta aatggcatt 345360 tcttacctgg agagcagtcc atgataaact cccaactgat gggagagtgt ccaggtttgg 345420
tcattctctt tccctaaatg ttattgctgt gttgactcta ctgtgaactc aagcttagaa 345480
tctgttgagc atctcttttg ctctggtgtt tttgctcaac tggtttggga acatcaattg 345540
ttgaatgcta cttcttaatt ggtggaacca caaggtcctt aatcctgtgg cttcatatat 345600
tactaaggtc atgcctcctt tggtttgctg ggagctgtgg aggtccagat gcagcaataa 345660
atatggttct gagaaaccat cactcaatag atccaaggca ttgatcacat actccttatc 345720
tcacctgctg cattctcagt ttggcaaggt tagagtaggt gagagctggg agagtatctg 345780
tcatctgtgt gatgcttcaa tgacttagaa atctgtggct ttggttaggt ggatcaagcc 345840
accactgctt ttgtcaagct taatagtgat ggtagctgta gagatggtat ttgtggaggt 345900
ggtggtgttg tcagagatag tatgggtgct cttattatgg cttactccat tcccttgggt 345960
gctggaacca gcaactgggc agaagcaaag gccatgcttt tggccttaaa tggtgcattg 346020
aaagaaggta caggttggtg ataggagac tgattcctta ttgctgtcaa gctgcatttc 346080
aggagaagtg aagtgatccc cacccgggaa tcacgaacgg gaatctaaat agaaaagaag 346140
gccctggcaa agcctctcct aggcacctaa gggcggataa tagcagcgga tatatcgctt 346200
tctgtttccg ctctatctgc caagggaaat cccggtaaag ggaacccgga ccccgagaag 346260
accgtactca tgtgcaacta attcaatagg accggttatg aacccaagag aagagcggat 346320
aggagtactc atactcaagg acaggaagct ctcacagcgt gaaggcaaag aataactcct 346380
attggaagaa gagcgtttac gatcagagct ggaagagtgg gagggaatga aatagcaata 346440
```

```
gccgctactt ctgtctgcgg ctatcttctc ctattgatta agcccttcaa aggaatttct 346500
tctatttctt ctttctaaag gcaaggctaa gccatccgcc cttcattgct gggtaaaagg 346560
ggagacggtt cccaaggggt ggctagttcg agtaagagag acggatacag ataaggtcct 346620 tttttctgaga gacccgctct tgacttttat catacccact agtaagcgca gtggatgctc 346680
cttcatacag ggacagagag gcgagtgatg ggcactactc atcataagaa agcagtcatg 346740
cagatagaaa gagtaaaaca atgactctga ctaagtaaag agatgaggtt tttttctcat 346800
ctattttcca taccacagct ctagacatgc gccccgattc aaactatgtt tcaatcatac 346860
cacccttgtg gggtgttcgc aattcacatt aaagacccct tccaaaggtt gagtaccttg 346920
gctcgggtag gtggtgctgg gttccgtgtc cttggcaggc tcgaccatcg gagatccgtt 346980
cattacgaac gttttttctc gatgtggacc aagctccgac ttccttttag ctttggctcg 347040
gaagaggccg gcctttgagc ccgtattgga agggatcttg gtttctttta gaaaagaaac 347100
cccaagagtt acgtcttatt cccgaggaga tgtttgatct cctagtctag ggacttcttg 347160
taagggcccc ttatttatgg aatgggtaat gtgttaaagg atagcttagg tactgcagta 347220
ggtttggaat tagactacct taatatcaga catcaaagac aacacagaat ccaagtccaa 347280
gacttgagtg ataatgctag agaacgtatc cttcttggca aggcaaacaa cctttgccaa 347340
ggttccgaag gaaagataga tctgaactaa cacaatcact ataatcatcc ctcttgtatg 347400
tatataagtt ttcgatgaaa gaggggatta tcctacgata ccctaggagc gtgtcagaaa 347460
gatgggtacg cgaagtgagt aatggtgaaa ttctccgcca caagccctct gaagcgagga 347520
tgcacactgc tttaaataga aagcgcaatg caacatcccc gaacgtcggg ccgtcctcat 347580
taccgtaaga gcaaacaggt aagctccaat acagaactcc ttagtaagac cgtcagcggc 347640
tatcaagatc gctttgttaa gcagtgacct taagaaccga gagtcttcta aaactctctg 347700
ccacaaacta aagaattgaa ttaccttgcg ccggtatcat ttcgcttgag ccgggaactc 347760
ctgtttacct tgcgacaggt attccttctt atagatacca ccgaaaaagc ggaagactaa 347820
gaagactttt ctttgtctcg tccacaccca ggaaagaaaa gatcagatca gcaacggctt 347880
tcgagtagag gattttttgc ttttaattat tccctcggag ttgagttaga gttagcagat 347940
gggatctaat tcattagagg aagggatggt gattaactga tagaacctct tctcttcttt 348000
caaatcgcat ctctcaagtg agaagaaaag gccccacgga gcggtgggaa agcaagggcg 348060
tagcaggaag aagaagtatg aaagcagcaa atctttcctc ctcgggctgg gatcacgaac 348120
gggaatctaa atagaaaaga aggcccaggt cgagvgttcg ctccctctct ctcagctaag 348180
gaaagagata gagaattcat gtacatcgct atttcctgcg gatctatcgt atccttactt 348240
ctctctgatt gtgatttccc ttgtgccgta ctataccgct aaggaaaaca aacaagaacc 348300
aggctaggct actcctcttc ccctttctga atcaacttgt ccttgcgctt accacttctt 348360
aaaacttgcg agcgagtgtc gatcgctcct ttgcctgggc aagatctgac gactcctgcc 348420
caaggcgggt tacgaattca gattagctac tgccaaagag gccaggaacg agcttccgct 348480
ttatctaaag aaaaacctct tcctttctct cttcctgatc agcggattca gagtgatcag 348540
gtgaagcccc ttctcgttgg atgaccggcc cttttcttaga cttggtgaac tcctgtcgcg 348600
atgaattaaa ctccgttcca tgccccgctg cttgtcaatc acatcggaaa gtcgttgggt 348660
cggcggagac ctcttcgcc aaagaattat atcacaaaga aagccccaac tagggactac 348720
cacttatagg agtcttcttt gctagtagaa tgccccacg agaagaaaga atagtgggat 348780
```

```
gctcacgctc tcgttggacg tgacagtcag ttacagtggg taaactaacg aagggaagaa  348840
tttattttca tcacagaatt gaatcgggtc tcatcccttc gattcctcgc tgcatacttc  348900
aatgagaaag gaaaagagct ttgttgcgtg cttcttcggg tgtggttgca agatctcgct  348960
ttcagttcga aaatgtgtac gtagcttcct tgtacaatag ctctctctct gagagagtga  349020
tcgggaagca ttctctcttc ccctccgtat ctgaccctga cccacgctct agccctcttt  349080
cgtcgtccaa gtcgcatacc tcctaaacag tctatttggt tttaaacgcg atctatttaa  349140
ctgattaact gtgaactagg tgggacttga ttcttttgct gaaaagagaa ggtacgtagg  349200
cagctctcct aaaagagtga agttccgccc gcgtttgaag gctagctcct gcttcggagc  349260
ttcatcccca catctcacat attggaaaag gcaaacaaaa aggggaactc agtcaataga  349320
caaagaaaaa acggatatgt tacacaaaac aatccaatct ttgtcttct aaggattgat  349380 ttttcttgtc gtagttcata ttcatattca agttggaaaa attcttcttt tcttcttatt  349440
gtggaaacgg agggaaggca aaggtccgta gaagctagct ctcttatccg cttgcctctt  349500
ttaatgaaga aggggttggtt taattgatag ctttggaata ggtagtccta tggactgctc  349560
ttttcttatg ccccggagtg gcgagaatac gaagctagat cagcaggaat gacagcggtc  349620
tcttccaaaa gtgggtacag gactcggatc ccatttccaa ggtgaattgg aggagaaatg  349680
gatactggta ttatagttgt tgaaagacct attaattaca tgccaaaaga gcaaagttg  349740 aatcatcggc ttggccacct tatccttta tacaaagatt ttccttgttg atataccgtc  349800
cgatgcgctt ggtgtcgact ctgatcttcc ttcacttgac aatggggcga aggaacgacg  349860
tcctgactaa acaaaagttt ctttcttcaa taatggcttg gtcgaaagtc gtaaagaagg  349920
caccggataa gcagctaaca taaacaacta ccgtacagcg catccgtgg gcggccttca  349980 aaggctatca ttcgtaggac gagacgctaa cctacgcccg tacattccaa cctgcctcct  350040
tgggacttag ctctgaagat gaattcccgg ttagccgatt accttgcccg gttaggagaa  350100
cagttagaag taggaaaaga tgccgacacc gaacagttaa agaattctcc gttgcttcaa  350160
gactgccagc ctattcgctt tgagccgaag cagacgctgc ccatggagag ccttttcctt  350220
tgtgaacatt tgtgtgcgtg cccataagac atgacaaaaa atacaaaaat tgggcttcta  350280
gacgccttac aataaagaag ccccggcccc tcggtgtctt acacgtcttc ttcgatcctg  350340
ccgaagctgc tttctttctt caggtagtga agtcactccg gtttgtgtat gacttgacgc  350400
tctaaagtct ctatcttgcc cctagttact taatcgtatt cgacttctat cgcagatctt  350460
ttatttctta cgcatttctt tccattagct ctccaagctt cctatctttc cattcctcta  350520
gctctcattt cgcgcatgcg ctttgcgctc ttggcttaat aacatcaaag aggaatcgaa  350580
cctcttccag ttctgtgaga acaaaaatcc atttgatgtg tagagtagag actgttagat  350640
aatcttctct ctcactagaa agtatatgtg tatatatact ttaacaaagc cgacctggac  350700
gtccacgacc ctgagtacca tgaggaacag ctctaactgg ctatgtatgc tggaggaggt  350760
gcggtaacca tagtaccctg ctgctgcgtg cctgtctgac cagtaccact atctcgaggg  350820
caaaacctcg taatgtgacc aacctctctg caagtgtagc aactttgaga tgtaccccaa  350880
cactcgccac gatgagtgcg gccacaagta gaacatgaac gtgaccctgt ctgagatgat  350940
ccacctctct atctctgagt ctgctgctgg ccctgctggg ctggggtgc ctcggaagta  351000 acctgaagtg ctatctgagt aggtctagac tgaccacgac catgcttgcc cttgctccca  351060
gatggagcac cactctgtcc tcctgtagtc ttgacctctt gctctccctc tcggctatgt  351120
cccgcctctt agatgccttg cacctaaggg tggtatccaa cacgtcggca taagaaccgg  351180
```

```
tccgaacaat cccagcaatt gccatacggt aagccctcct tttcttgaaa aaaaaaatga  351240
agcttagaac tgccagagcc aattattgtg cttttaacc  ctgttttcgt gatactctca  351300
cattaaaccc tactgttcct taaggtaacg gaaagcaaaa ctgaattcct aaggtggaga  351360
gcaaaagcaa taagaaaag  aagttaaaga acatttcaa  tgcgtcgaca taaatatgac  351420
tgattctgtg tcaatacatt gtaaattttc tcaagttgta ctgtgacaaa cagctcaatc  351480
aatagccgac atgtttatcc aaaaaggatt ctgatgaaaa atgttattac ctcatttga   351540 tttctggtct actggaaatt tagttaatag tagagcttca aagtggaatt gatgtgcacc  351600
caattccacg gacattgttg atatagtttg ctactacttg tgtagcttgt tttttagtgc  351660
cgcttactct actctattgg gtaattttag agtgtcttta ttgatgtttc cttgacagga  351720
ttagaataga ttcatactca acatgacaat gatgaaaata tctttatgaa atttctcgaa  351780
atctttgaat gaatcttcat tttggacagt tcttaggcta ccctaacaga cgtgtgggaa  351840
tgaagctact actatctttt ttacacgcat aaatatacat agtaaaaatt catcgcaatt  351900
cattcttgaa cccgttgtgt ttagtctaaa tccgccacta gaagaatccc aacgtatcag  351960
cctctttagt aacttgataa taactataag gtattttgtg tatcataaaa acctatacgt  352020
agctcaagac gaggggtcat cttttggcaac tgaataggg  cagggaggta tctccttgat  352080
taatagttga acatgcttga tgaacttagg gacatgtata tacaataccct cgaggtacaa  352140 gcactaaaat ggcatttttt tgttgtgttg ttctatgata gtggtttcat cttctagatt  352200
aggcactgaa actgatcatt tttttattcc ttcaaatctt ttattcaggg gcctggattt  352260
ttggctgtat tctgtaatgg ttttactacc ttttttttt  caactcttat tcatttttc   352320 agatttaaca ctaacttact gtccacggat tcagatattc aatcccacaa tgattggaaa  352380
tttttgcttt cagtaccccca ctctttttgaa aaataggctt ctgtgcaaaa atgggggtgt 352440
agaatgtgga accaaatccc actagcaaga gcctattcca taataaggtt tctagaggat  352500
tttaagtgct tgttaattgc tttgcctctg tgggcattgg aagagccata ttttacctct  352560
cattttggaa aatgacagct tcagatattt tctcttactc cctcttctat cttatcccctt 352620 atagtcgaaa ttttcttggg gcagtggtac atgcccataa gctacagtac taacagcaaa  352680
aacaatacca atttatttaa gggaagaaca actaaagtat cttgacatgg aaaagaaatc  352740
actttagaaa ccaaacagtc attcaactag atcaaaccct gtaagtagtt aaataggaga  352800
aatagaacaa atcgcttaac acattactct tgttagtgaa tagtgaatct ccatcttttt  352860 ttttttgaatt caaacgttta agtaccttct ccttgctga  gctagacctg atttgaatac  352920 cggtttatg  gcctcttctc ctgggacctg cttcgtcaaa ttcagcaacg ggagcccgag  352980
agggttaagc agcgtcagga gcattggaag tttcattcct gaaatgaaca aatcattaat  353040
gggcactttg aagcaagttg atcctagaag actaacctcg tagctcactt agatcaatca  353100
gttcaagcat tgacaaaccc gccttccttc tgtgttcagg acggagactc tttctgcctt  353160
tgtcgaactg ccttgacgcc ttggcaggct ttgacctgct ttccttcgct taccggagag  353220
cggattcttt attactgact tttcgcggtt gatcgcacct cgcacctaaa ggagccggtc  353280
cttgtgagga ggaggactct tctccttgctg tcaaaagtgc ttactcatgg tctatcgtgc  353340
agttgatgat atcattctgg actagtttcc aggcatacgc caaccataca taccgctttc  353400
tcgttcagga atttcttaag attaaggttc gaaaggacca ggcggcgatg aagtatgagt  353460
ctaaaacact atatgcagag ctgccttagc tcaatagatc aacgaatcag gagatgactt  353520
```

```
cttaaacgtt cgcgaatgga aaagagttgc tttaggcacg gaccacaaac ccacgaacct    353580
aatagttgga tccatgagga gacaggagaa agccattcat tccggtcatt gagcccggat    353640
tgaggattga ttgatctaaa ccaaagactt gattatatag gagaaaggcg ttctcatacc    353700
ctgataccgc tttgtggaaa cctagaacag aagaaagtct ctttaggatg gctctgtcct    353760
agctagaccg agtcacaact acttattata gaagactcag gcacacttcc ctatacttct    353820
cctaagtgac atcaaaatcc tctttcagcc gattcgaaag cagtaataga tgagattgaa    353880
tcagacagaa ggttcacccc tcaccctggg ggattgggga gttgagaggg atttggacgc    353940
ggtagtatcc tactattcgt tggcgctccg taaggcccaa agtcaacgag atcttcttta    354000
tccggtgcgg ggcatgtact atcttctgcc ttctgctagg ggttgaaggt cttctctctc    354060
gtttgatgat ttgagaagcc atcttctctc cctcccaatg cttcattctc tgcttttgt    354120 actcgttcga taacacgaaa cgaagaaaac tcttagcccc aacgaactga ttcatgttct    354180
tgacaggctt cttgactcca ctgctaccca cccggagtcg actattgatc cgtcgcccga    354240
gccccttttc ctttcgtcct tgcctgaggt acgttgttct tatttgtgac acccatatgg    354300
tttgtgtctg acccagcata gtgcttttct ttccattgtt cattcttctt tgaagccgca    354360
aaatgatagt gaggcagcaa ggatccctca gtgtcagcag gccatatctg aggaattgcc    354420
agtcttgcag aagacgtcgt tcattaccat atcagataga gaggggttcc aaacctcttc    354480
ctgacggaaa gaccactatt gaggtgaggg aaattcagac tcactcttgg tatcgatctg    354540
agaatacttt tgccccactg taaaaggtta cttttgtagg gctctgattg aagttgccac    354600
ggaaagaaag tagcctttgt tccagtgaga tgtggggaat cttttctga attgaaaact    354660 acatgagggg atttacatgc caccttcgcc agggcgatca gtttcttcac atctagttag    354720
tcgactcagg aaggcgttgt atggactaaa acaagcaaac tccggctcga aagcaaggga    354780
aggccctatt attggggatc ttccttgacc gggtggaaag gtctcttttt tctatgtgtt    354840
tcgcccattc gagtgttctt tgacgatgac atcataggca ccagaccctc ggtccgtctg    354900
tgctgcttcg aatgatcggg tttcaacggc ttccctagct gtactgatct atctggcagt    354960
tcactacgcg ccgaatgatt ctttgctatt tcctctttct cctccctatt atttgattgg    355020
tgctgcctga aaagagttcc ctgtaagagg gacagtcata acaagattat tatttgcggt    355080
ttcatcagac gggatcaaag atttcgaaat tcgccgatca taggtaagcg gttctacaaa    355140
ggtgaagaga ttcctaaaa ttctcggagg aaattttttg cttagaatgg ggattctgta    355200
gggccttggc ggcccgtaag gggttcatcc ctgtggtata aatatattcc actctttttt    355260
ttttttcttc tgggtcggca acttgaattc cgttcctttg aaggaattgg tcggcttcct    355320
cgctttcgcg agtgtctagc tgttctaact tggtgacctc tactttcgag agattgttag    355380
gctccatggc attcctagac taactatcac ttctgatcgg gattccaagt tcatgagtca    355440 cttttttgtgc acactttgga gaaagcttgg aactcgtctt caatttagct caacttgtca    355500
cccacaaacg gatggccaaa ctgaggttgt taataggatt ttggggattc ttttacggag    355560
ctttgggggt gaaaatattc ggcaatggga cttgctttta gctcaaatag aatttgctta    355620
caatcagtcc actagccaaa ctactggttt tagtccttt taagctgttt atggccaaaa    355680
tcccgagagt cctctggact tagctccact tccagctact cacaactttta gtggagatgc    355740 gggtgaagaa aatgaagaag ttgcatgagc gagaaaattt ctaagcaaaa tgagaagtat    355800
caagctcaag ctaacaagca tcgcaagttt tctgagttca aagaaggtga tctggtctag    355860
gttcatcttc gaaaggagcc tttcccgcga ggacaatttg ctaagctcaa gcctagagct    355920
```

```
gatggaccat tcaaagttct caaacgcatt ggtgaaaatg cctacaagat tgaactacca   355980
gctgagtatg aggtttcaga aactttcaat ctttctgatc tttctcctta ttatggtgaa   356040
gaaagcacta acgactcggg ggcgagtctt cttcaacttg acggggagaa ctagaaataa   356100
aggaagttgt tttggctgta gttttttccag gttgggtaaa tttctttaga aatgtcataa  356160
aagagagggg ctttctttct tcagcatgtg agggaaatgc cccgggtacc gaagttagcg   356220
gatagagagg gcggcgggtg ggcacggtag cagatacgtg aaatgagatc ttcttggaac   356280
aaggtcagag gcgttggacg gaccagtttc ttcagattcc aatgatagat ggatggtcag   356340
gtcggtaaca tatggatgga ggacttctac agggtcttct cgtgcgctcg actagaaagg   356400
tggttttgta ggcgaacgaa ataagttttt ggaggcgagc ggagtgaggc aatgaaattg   356460
tttaggcgaa agaaaggaga gaacgagtgg agtatactcc acgaggtagg tgggcatgga   356520
agcacgagag gtgttggtga gtggggaagg taaggtagtc gacctacggg agtcgcgagc   356580
gttagtgagt tgacaaactc gccatgcatt cattcgtggt tggaacttct ctctgcagag   356640
tagccttgtg catagaggct cgcgcccttg attgattgat tgaccgggcc cctaaagctg   356700
cacagctatg gcctgtaccg ctaactctca tgatgcttct ttctgggaaa ggaagaaaac   356760
taaagcaagc tacctttact ttttgaaaga ggaagacata aaacaaagcc gcttctcctg   356820
attgaatagc tcgtcatgca gcaagactaa agaaggctct gaatggccgc taaattaagt   356880
caaagactaa gtaagctggt acgtcaggtc ttgacctatc attctgttat cgtgctttga   356940
cagctataaa atagcccttt cttaaagatt gtgagagctt ccgttttagt tgttgatttt   357000
gaagcattat aataagaatc atcctttcca caaatagatc ctcaaacata gaatcatggg   357060
cagctagcga taggcaggt ggtcacgtca aagtgtgcca atcatggtga tcaaaccctc    357120
tttttgttag agctcccagc cttgctaagc taagaaagat gcccttcatc ctccttcctt   357180
ccctttaccc ttccctctcg ttccttctct ctttctcgtc tggcttggtc tggtggttcg   357240
cctagttgga ggctttcagc tccatgccgt aggtcagggg tcggtgctaa ttttcctgat   357300
ctttctgatc ttgttgattt ttctttcgat agagtgtgaa tcatacgccg gatctaatta   357360
gatatatatc ataccataat ctagagtctt gtggagtagc ctccgtgcca catatactgg   357420
gcgatttagt tcgttcggga cacgtgggcc aagaagctct aggcaattct cacgatcacg   357480
gtcgatcatg gttcaactcc atgtcgtgaa agtgaaagca atcatttctt tcatcaacat   357540
caacgaatca ctatctctct ttcatcggta gggcgatcag tctttctttt tgtgtctaa    357600 tcggagtcta gtacctctct ggcccttatg ggcctccaca gatgtaacca aaaaagaaa    357660 gtctaaaaag tttttttatcc tcgttggtct ataagcttgt gacttgatcc gctagcgcag   357720
gttcgattcc tgcttgcgag aaacgaaaaa tgaaacgatc tacagggatt tcatgcttct   357780
catccattct ttgagtgagt cgggtcatcg gtaggcttgc ttcaccggta tggctcatcg   357840
gcttattaat gactaagcgg agtcaggagt cgatcgagcc tttattagat atgttctatt   357900
tcattggcag ttccgatccg attaagactg gaaaatccat caataagaga gagaagctac   357960
cagcaagaat catatcaatg ttgggcaaag gaaggtactt tggacaagct tatatctccg   358020
aattcactgc cgattctgat gcccccagtt tcctcggcca ctgggacaag gagatccgat   358080
cttcataatc aatgggacga atgttttgat acctcaaaga gcgaacgaat tcctgccttt   358140
gcaataacag cccatcttgt gccacagaat cggttgtgct ctgcctcttc ccctctatca   358200
gaagattgcc ttgtgtggaa ggttgactct gaacttcagt caatgggagg tatcccctta   358260
```

```
tctaaggttc tttgtatggc actctaaact ctctttctta cgcgagacag aaagtctaac  358320
taccgaagct ctttcaactt gtcctgtctt tggataagta ttgcgcttaa gtcagttaac  358380
aagatgagag tcggaaaatg gaaataagaa ctgtaaagtg attcttgaat ccttctactt  358440
atgtagatgg agtccagtac gctactatat agactgaaaa ttcccaagac aatatcggga  358500
gtacccatct tatcagatat ttaaatatat cgtcaaactc tttcccgctg tacccagccg  358560
attctcaagg acaaaaggta tagcattaca ttttaacaga cagatgaaag ctaggtctct  358620
actccttctt catgaggaag aaaggccttc ttatcatcta gatcgacgta aggtgcgtag  358680
cggtctagag tccaactaag acttccatga aaggtctcat tcatgttgat tgaggagttt  358740
cttactgacc gctaaacctt ctctacttta gaagatagac tggaaagcaa gctcagagaa  358800
tagctaagtg gaagtcagag actcccttt ttaggaactt agactaccta tgtgctggta  358860
aactccacct agactgagat tcatcagttc gatcatttag tttgtgtcct aagtcctata  358920
tccttcagga aaggatcaat tccttctcta acttctactt ggggtcactc ctcggaaaga  358980
ttcttcattc gagttagctt ctttcgctcc ttcacccttg actgcattcc cggaaatgcc  359040
attcccatcc gctaaacctg ctccttctga gaatggtttt accccgctcc tcaatcttat  359100
tcagtttccg atcctgcttc agattctctt tcagttgtgg aaacaaaccc ctattcctat  359160
cggttgagta gcccaagctc cttaagagcg tattgtcccc tctcctgtga agaaagagg   359220 ttgatgcacc cagctacccg aagtagagct ttctttgtcc cacctttcct tactgacttt  359280
cctagtttag atagcgtatt gagaatcatg tcaaaataca ccaagacctg ggcccaggtt  359340
ctctttcttc aagaaagggt tgctttaaac aacccggttc caaacacacc aaacaagcaa  359400
gcgactcccc ttccttagcg tacccgtcca ttaaggcatt cttccttctt gcgtatgtgt  359460
tatagctcat agctctaagc cccaattcct tggctcataa ctggaaaaca taacaacaat  359520
gtctcctagc tgcaaaagaa tggctcccaa ctgaaaatct ctcttgatca ctctctaaca  359580
gaaagccatt ttcccttcg caaaaagtaa acttggactt cttcctaag cggagatttg   359640 gactacatgg acctaagcaa cccgccgaca ggggcagcct ttcactgttg gaaactttga  359700
ttttgattgg taggattctg tctaatcttt cctaatttag aaattgcact caatcaacat  359760
agtttccact cattccttct cgaccgcctc ttttctagtc acttttgatc aaatctttct  359820
tgtgattttc tattatctta tgagaaatgg tttgcttcgt ttgagccgtc gtcgcttaat  359880
gcatgtaggg gggctgggc ttttcccca cgaccccttt taaggagaa ccagaagaac   359940 aacaatgaac tcaaagctaa tgaaggagat ccgcaacttg aacaaggtac acgggatctt  360000
tcctacccct ttctatttcg acttctttga aaggtgaaag agtaagaagc tagaccgact  360060
tgctcttaaa ttaaaagcag caagagcaag taagtaggct tttctccgca agaacaatct  360120
tgactttctt tatactttag aatataaggc cctttaaacg atcgtaaatg gcctgaaatg  360180
taacgaccta tgagagaagg gttttttagaa aagaaagcgt accaatccgg caaacaaagc  360240
aaaaacaacg gctcctacat aaatacaata gaattgaaat gctgtcacta gaacggacca  360300
cacaaataac atctttctag ccgcctaaag gaagtattca aagataagat aacgctatgc  360360
gcacacaagc aaacttcagg tatgcagtta gttctcaagc gattccttcg gatcttaggt  360420
gcgaccttag ggagcttgtt ttggcagcta ctctcttata gttatgtgtc ctggtttccg  360480
agttctagtt caaggcaggg caggacggga ctcacggggg ttgggggag ccttccccca   360540 gggaaaacct aataagactc attcgaatac ttgagttcaa gctcctactt cgaagtaagc  360600
ctatgggttg tttcgaagct tagcagctaa agcgtacttg cgtgttaaag tgggtacgcg  360660
```

```
gatttaggct actaagtgga accagaccat tcaacttgcc atttgcactc tcctagggtg  360720
cgatcgtagg aagctctatt agcgaatgca attccccgcc cgataagact gatcatgccc  360780
tgctgcttgg cttggaatca aactagccta tcatgccctt tcttcattcc tatatggacc  360840
catattccta tgttcttcca atgtttactg tattactggg attcctattt actgaaccat  360900
atcaaagaag ctactttctt tctggctttt atacccaggt ataaagggat agacagtcta  360960
agagagtgcc aagaaagaac acatacctat cacttttgga aggtttggaa ccctcgattc  361020
atccgactca aggagaaaaa gagaacaaga tgggtttggc tcgctgtgcc tccctcttgc  361080
cttaagcgac tcctagtgag cttttgaata atttaatagc tctgcccttc tctcttatac  361140
ctttatcgct tatttccacc ctttgacttt tgagccagcg acacctctcc acgaatcaag  361200
cctataccgt gcaataaaga cttttcctta tctttcttct tcaaattacg agtagagatt  361260
tggggagagt ggataggaca gggtggtgga tgacgtaaag aagggaagg cccatcccgt   361320
gctttcgagc gattcttccc gcaaaaggca gatcttttc tttccgtccc aaatagaaca   361380
atagaatagg gacttagatg tgaccaaggt gcttgcaagc ttagggttag caggttgttg  361440
gctgggagag ctggtaaaag aatgaaacct tcaagagacc gtggttaaca agccagctga  361500
ggaagaacaa tctcccccag caataccgat cctccctagt tcaatcagaa tcgagaactg  361560
cggagaggtt ctaaccggcc tagcctaacc aaccgctaca agcgggcagg aaatagatgt  361620
ggtggagact caagtcaagg cgatggatca ctatcactat agatagatgc tttccctgga  361680
ctgtgttcaa tggcacctga tatgccaaca agggcttact aagagatctt gcatgtttta  361740
tagggtgctt cttatgtctt tccataagca gaagtctgag tagagcagct cttccctat   361800
tcttaatccc acttcttatg tctgtcaaca agagcccagc ccctggttca atcgatagat  361860
aggccgaaaa cttctttctg gacaaatgaa cagaccttc cttacttgac ttgccaacaa   361920
agcggtcaaa ccagtaagca agttcatgcg tcagtaccac gtccaggatc ttaggaaagg  361980
ggaagctcaa atgatatcta atgggatggg catgctcccc actgctctat gatttattat  362040
agtcatactc agtttcgtac ctggtagcta gcctttcgct tcctccttgt actagatttt  362100
gacttgaatt ccccctgaaa gcgagaacgc actatatgcc tttaaaataa aagaaggct   362160
ggaaaaaaga gagagctcct ttcttttcta gctttggcgg gaggaatgaa aatcctatcc  362220
tatacgaagg cctatataca aaaaaagcac tttgcctaga atcccaagtt gcctcccctc  362280
tcctctgagg ccgatcgcat ccacttttgg agccctcgc cagtacggca gcagcccaga   362340
catagaccga attaggggcc taaactcttg agtagattgc ccatggaaag gagcttactc  362400
caagatctga ctccccccgt gtaggagttc gggaaggcca gaagtaaaga aagagcggta  362460
gaagagaata aagtgttgcg cccattcttc tttttcatag ctggagcaaa tggaaggaga  362520
cgtcgtgcaa gccgaagact ttgacaggtg tcggtaggca cgcctctgat aagggctcga  362580
tcctgagaat caatcccaat cgaatctatg aagggagac cctctatcct cttaatctgt   362640
agagtatata tttattttag gataatcagt ccactgcggt gcccaagaca aggcaagatg  362700
aataggaatg ttgaagggac ataaggctca gctaaggtaa ggaaagaccc tgaccatcta  362760
ggtcaccaag tactcttctt ttttaggag ttggagacga tcgaagaggc agcaaaatag   362820
gaactttcga tcagggagag ctcaacaagg tcgagaccaa gatgatggat attccaagga  362880
agatcgaaga agatgaatga aggtttatac ctacccctaa ctggcactat gaatccaatc  362940
ccatctacat agatgttcct agccacgaga tgaggggtt ctctcttact gttaagccgt   363000
```

```
cttcaactct tctttcttta ctcctttccg catcggggct gataattgga tagaatctcc  363060
ttaaataaag aaaggggcg taaaaatagg gttttttggct cgcaataaag ctagggtcct  363120
gatcgagcaa ctagtagtcc tatctatcca cctctccaga cacaatatct tgagtaccta  363180
tgatggtgac cacatctgct ggcatgtgat gtttggacat agaatcgagt ccttgtgaat  363240
gggcaaagcc aggtgctctt attttacgac ggtagggacg attgcttcca ttactgacca  363300
gaaagacacc aaattctcct ttaggtgctt caactgcggt ataggtagaa ggagctggta  363360
cggaaaaacc ttctgtataa ggttcgaaat ggtgaattga ggtagagtag accgatgatc  363420
ctgtagtcat ttggccggct attgaaagaa aaagcttgca tctgcttccc ctattatata  363480
accggtccca tctctctcca aacctaacgt ggtagtttcc catcataggg ctttctatct  363540
atagattaag ccattaccaa ggagctaatt cgttcagaac tcagttgact gcttctatag  363600
agaaggcgga gcgtccttgg ctcagcatta tagcacatag ggcttcggcg ctactacagc  363660
gcttcgctaa ctcgaagcgc ctcgctatga aatctagct tcgctaacgc tcggctaagt  363720
cttgaacctt cgcgctgacc gttcgctttc tcagtagcaa aagcgcttct ctttgcccct  363780
taaccttaag tagaaggaca agaaagatat tattggtttt cttgcccccg cttcctcatc  363840
tgcgctcatc aagccaactt tgctctttgg gaggtgaaac agcggttgaa gcggacattt  363900
cgaaatgaca gcatcgaaga tagatttcta tatatacacg gttagggtta tctcggactg  363960
cgttccggaa aaagcagcct acttgtgggg cactgtgtac ttacagcctc tacgataagc  364020
aagtgaatgt ggccggtgcg tggcgaacgg ttcatcaagc cattttttcgc ctcaactccc  364080
taaataggaa taggggttgt ttacaaaaag gggtaagaat gactgtgata gccctctcga  364140
taccttattg gagctttgta actagtggcc ggtttcccgt cgcgtcagcc ttttcccagt  364200
gcgcggagcc ccaacgagga aggtgttagt gctttatcat tgggtcaata atgctaatcc  364260
ctctttttgt gctactccta gggcgggaag aagataagaa aacgcgaagc gttctcttgc  364320
tttcccaacc tgttctttct aaagactgcc ctctctcggc tggatcttgg tccagcctac  364380
tacgaggatc ccgtatccag caacccaacc tatacaaagg gcatcaaagc cccttgacta  364440
ggttggagct ataaagctta ccttatttat tattattaaa aggggaaagg gccttttcag  364500
ctggtgcgca ggagcgcact tccgttttcc ctttacgagt aggggggtccc gtggttccta  364560
tgccgccgcg tttcccggtc cttttctttt agtgcttcga cccgaagcga tagcttctag  364620
ctagttcagt ggataagatg gctgcgctcc agctcactca agaatgggac ggcagtggtc  364680
cgccggcaag ctcgttctga tcttggacgc agtacattgg aatcctgaag caccaccacg  364740
aacgctaccg cgcgtccgcc tgcggtgcgg taaggcacca ccctcttgtg ccagcagcca  364800
actccggcgt gtcagcttag ttatcctcat caaaccactt acttgatgtc tagcttccca  364860
actggtagac ggttccttt ccccaaatc aatgaagaag ggagacataa gttgattctt  364920
ccgaagaacc ggaagcgaag cgctatgccg gggcggggg acggaaaaag aaacggctcc  364980
gaagaaaaaa attgggttc ccaatgcttc tccacgctca acgagatgcg ccaacctcgg  365040
gatgctttac tcctaacccc acaaggttcc gagacggagc ttaacctgag tctcggttaa  365100
gaacggcgat gatatacgtt tcacacggcg cacgattcca tggatagttt cattcgagat  365160
cgtgatggag gacatagctt acgatcatcg gctttgatca tgccactagg catttgatta  365220
agacattgca caatgatccg aacactttgt cgcatctctt cgatacgaat acagtaacga  365280
tcatagcgat ctcctctggt acctactggt atgtcaggat ccaattggtc atgaacatcg  365340
taaggtgctg ctttttcgcaa atcccagcat accccagaac ctcttaacat tacaccactg  365400
```

```
aatccccaat cctttgcttg ctgtgcagtg acagtaccaa tatccactaa tcgttgtttc 365460
cagatacggt tgccggttga catctcttct aattcgtcga tacgagaagc aaattgttgt 365520
gtgaatgaat caatatctat acataagcca agaggcagat cttgtgccac tccaccaggt 365580
cgtatgaaac tggcatgcat cctggctccc gagactcttt catagaattc caacaatttc 365640
tcccgctcct caaaagccca caggaacgga gttgatgctc ctacatccat agcatgagta 365700
gttaaagcaa gtgaatgatt tgaaattcga gttatttcac ggaataacac tcgtatatat 365760
tgagctcgta atggtacctc gcaattcaaa agtctctcta cggctgaaga atgagcgtgt 365820
tcttgggcca tcatagaaac atagataggg tcgacgacgg aacgaagaac gaaactttac 365880
gacagctttt tcgtagacgt tcacttgcat cacatacaca agtgctctct gaaccgtgca 365940
ataaggtcac ccataacacg ctctcccac ttgagttatc ttagcccag gccatgctat 366000 tcaataatct aggaaaaatg gcagcgtaag gtaacaacga gtatggaaag ctggtcgcct 366060
ttggaagcct tcgccggtaa ccaaagcgta tcgttcccgc aaccactttg gtactttgtt 366120
tctagctttt ttaagttatg caatagaagg gggggcttgc gcttgaattg aagtagcgcc 366180
tttgaaatat gagtagggct cctaagtggc gcgttcgtgg aggcaaaccg aaggaagagc 366240
aaaaggaagg ttgggtgctt gtggggcgag gccatccggc ctcgaatagg aggggcttga 366300
gctctggagc ctccctgctt gcagaaatga atggatcaga aagggcttg gttctctatt 366360 tccgggcggg gggtgaaggc cataagagaa gattgcccta ccggtaagga agaggggaaa 366420 aagtgctgt catctatctc gaccagtttc ccgaggcgtt ggaaatccag accggctcag 366480
agaatcactg tcgctattta gcccttcgtt ccgccaacaa agaagtcatc cttgacgatt 366540
tcccattcct tccccgccga gccgcctctc ttcgccattc gatgcttctg ccttcccttt 366600
ctataacata cccaggcgcc ctcctttcca atcactaaga aaaaaaaat accaataaaa 366660 gccctatcta agtaaagctt cgtctgttat ttttccggcc ccaggggagt ttattcgacc 366720
cattccccag tctcccgcac tgctcaagta agtgtgcgac tccgtatgag gacctccttc 366780
tcttctgccc actctccgtt cacacggttc tcaaagcaga ggaggaaggg tgggcagcag 366840
gtaccacgag ccctctgtcc cacacatcta tccagaagca agtgtagttc accggttcca 366900
ccgaatgctc ctatctctcg gcaaagatcg tgtgagtgtg cagttatgct tcggatgctt 366960
caccatagaa tagatcgatc cagttcccgt tcttttccgg tgcactcgct ttatatctcc 367020
gacacacaag gaaggacgcg gtgggaagga agcagcccta gcctctgtcc ggccgatcat 367080
tccgctggca tctcgcattc acgccccgt ttgactgccg ctcggggatg tagttgtaga 367140
taggttagtc ttagtgggtc gttggctcca cctgttatct ccttctacga catgctgttg 367200
tcgtcgccat attctatatg tcacttagtc atctctgcct cgctgcgggt cagcacctcc 367260
gaaagaaacg gaggacttca ttcagtgacc ccgcgatcgc cctctgaacg atcagaataa 367320
ggtaaagctt gaagataagt tttgtactca attaatttct cagttcctct agtcgggtgg 367380
gcgccggccg gttttcgac cagatccccc taaaaaccgt acgtgcgggt ctccccgcat 367440
gcggctcacg ccattcgagg tggcccagcc cagcattcat tcgcaaatcc tgtagtgaaa 367500
ttgagactgc tcaacctcgg aagctaattc gcgtgtaggc agcgctgtct gtcgtaccgt 367560
tgactctatc tattcatgga attttctttt ttttttttca ttttcgattt tatataggct 367620
cgctccctct ttttccaaga attcatccac ttccctttac tccatagggc cttctctaat 367680
agggaaaagc cttccatttc cgtcaaatga cccggcctcc cctggctctt ccaccgtccg 367740
```

```
ggctcccttt cttccctatg gtatgctcct ccggcgcagg cctaccacgc ttcgcgcctg   367800
cggcgttttc gccagacggt cttttgccagt agtgccatcc tccccgctgg ctgtatgggc   367860
gggttgtccc tcgctgctgc gttcttttaa gctatggatt aaaggaacaa atgtagttga   367920
atggaacagc aggcgggtta cacgttccac tgtgccgaga tgtgaggtgc aggtggtgat   367980
gatcaccccg gggtatgcgc tagcgccctt gacaggcact ccagaacccg ccaacgctcg   368040
tgaaaacccg ggtcggtcgg tcctccattc atccgaccgg aggtatggat aacgaggcca   368100
ccttcacaac cttctccctt ctgtccctat gttggaataa ggtaaggcgg ttcgcttgag   368160
ttgctcaacc gcccttagc ccggtgctca tgacgtgcta cggaacctcc accgtgccgg   368220 gggagggga ccaagcaggg catagctagc ggcataggag ccgactcggc atcagcggct   368280
tcgtgccgca ctggagtaat ccaatatgtg gttccgcacg ttccaccact tctccgttca   368340
tttccaatac tgatcgtgaa acaccatgag cagcaggatg ttgaggtccg aaattcgaag   368400
tgaaattttt gatttgcctg ttcttagtcg tcatgggaaa gaaatacaga aataagaaag   368460
agattattcc cttagagctt gtccaatacc accagtacca gaaatgcatc tccttcgccc   368520
gcgcgagaga cttctatgcc agccgggaat aacggctctg ttatgaaaga aagcggcaga   368580
cagagtaatt tggccggtat tccctaatga gtagctttag gagataaagg tccccctat   368640 attctccacc catctgcgga gggtttccgt atccgtctcc gcggagatct ccagatcata   368700
agacattatc gccttcgcgg cactggacta tatttccgtc atttccggaa agtgcacgga   368760
cagccgccat ttcccccttt cacaatgttc tcgtgaagtt gctcacgaat caaagtgtga   368820
atgtcccttc gaagtctcgc atgctctttt tgatcgggag cggggtgggc tatttatgtc   368880
ggtgctggcg cctgcggcag cgcctctgga gccgcccccc cgttatggag ccagcgggtt   368940
ctgaatgacc tccctctcac ggttaaaaaa gtggttaact atctcgaaaa aatccatatc   369000
gtccatccga aaacgtgtc tcaattacag ccaactcccc ctcccctgtc tctttaccta   369060
tcgaaaaacc agccctactt attttgttct acaaatgcta accaagtgac acactggggc   369120
catgggtcat gaaagaggtt gacccccatc ctccttaact atgtatggct aatgaactcc   369180
tcgctttagt ccgttctttt ccttctttgg gctcgggtcg atagtcgccg tggtagtaat   369240
gccccggagc ccagctaccg acctgaggcg ccgatcggga aagtcataaa gggacgttaa   369300
acgtaattct agaagggcct tcccgcaaaa aaaccgagtc ttggcagttc aagtgaaagt   369360
tttttagact agtcccacta agatggcgag gaaactgact tccgagagag ctgctttcgc   369420
ctcggtaatt acctaacgag agagagccga tgcaaaagtt gtcctttacg cgaggaaacg   369480
ccagacagac tgacctctgc taactacgtt ttctatagac tggaagctag agagatacta   369540
aggtatagtg ctgctaccag agaaggctct ttcatgctag gcgtccagac ctactatacc   369600 ccccggcac atttgctata tctactaacg cttcatccta accaactata cctgatagaa   369660
agccgttcta taaaaattca agacaagaag aaagcaagaa aaggatagcg atcgctttgg   369720
gaacgtcacg gggaggaag atagaaaggt aacctatgac accgggaat taggcttttt   369780 ctcccgcctc agcttcgcgg atggaaggag ggcgagagcg tagcacgcac gctctatgct   369840
tttcgccagc tttccctcta gtaaaagatt agctcgtacc ctctctctgt gtctaggat   369900 tcctggggca tgagttaagg ttaagcatat agttgattgc tctttctttc gattgagcgt   369960
cggtactttt ggagtctctc tctgtaggcg tgcaaaacaa cagagccact gctcttcggg   370020
gtgatgaggt ggacaattcc ttactccagc ttcaaaggag catctttgca tgaatcaata   370080
ctaactcctc agtcagctga ccttcgattt cggagattag agcagaagaa ctccgtaagg   370140
```

```
gcggagaggg gtttcgcctc gaatccaaat gatttctctt cttctcttaa gatatttcta    370200
gttaggactt gatcgaggga tcaattgact ccgaaagata aagtaacaag accataaccc    370260 cgtgccccg ccttaaagga tcccaactca tcaccctcat ctccaactta ttcgtggttt     370320
taaggtgctt ttgactattc taaaaactta tttggagacc aaggcgaggg gtcatcttcg    370380
gcaaccaacc ggggtcatgg agccggcctc cccgccgtcc ccctgcccg caccctccat     370440 aacgaagta cgtagaaacc ttgatctgtt tacttcctcc tttaataaga tcgggatgag     370500
gagtgacctt ttactggacc tcgaggatcg gcttaaactt gaaactgcct cagaagcaaa    370560
gagacgcaaa ataattgaat tcatggagat cttggccttt gatgaagatg aactgatata    370620
ctggcattct cttccaactc cgtatcctaa ctcagggcaa actatctcta gatggcaaag    370680
tgaaaagtcg aattgatctg cacatccctc tattccaata gaaaacgtta gccttcatcc    370740
atgagatcgg ggtatcacta ccagtagggg cccgcttcca taatagactt tgaaacctcg    370800
ccttcccttt cgatgtccga tcccggatac catgacttgc cttcaaacgg gcttcacctt    370860
caaaggagag taatcgatct gcggacagca aggccaatga agatcaaatt gaccggggtc    370920
tgagtcgtgt cttgtccttg agtcctctct atgcctctca tgtccttctt tccttcgctt    370980
gggactcact agcacactcc ttgctgcttt cgtgcttgat ggcttctgat gaaccaatga    371040
tagagatcct ccctaacag ctgctgttca atccgtccct gagagtgaga ggagtcgtag     371100
gaattcacat tgccttttac ggcttggaat tcctattgta tagaataaat gtattgggca    371160
atgtcttttc ttgaattcaa aaattctccg ccttttctca gcttgacacc tactttagaa    371220 ccatccttt ctaagtacga caaagcttcc ttgtaaacta aggctaaggc acgctcgata     371280
gcaagaagct agtgacttct ttcaggtcat taactagaac ttgcacgagg tatcacagtg    371340
gggtctgtct tctgtccggt tcttggggcc ggtcgagcct ctttgaaatt acatccctgc    371400
ctctcgtctt gccccgctcc tttggcagtt aaagtagctc gcttcaagaa gtaagattat    371460
atccctaggg gtatgttacg agcagaagtt ctcttgctag tggaagtaag agtagcaagg    371520
ttaggaccgc atataaatag aatagggggt tcgaaagaaa tttgattccc tagaagtttt    371580
gtccggttgg gaaagccaga actcttgtaa accagcttga taaagggtag tggtagggac    371640
agtctcagta ccactgaaag tgcgatagtg cttcaagcaa gggacttggg caaacaaagt    371700
ccttactcgt attccaccaa caactcgcgt atcgtataga gcttttttcct atcctttccg    371760 catagacttg cttcgcacct gtgtaaaaag ccagtttagt tttactcaag agtaagaatg    371820
ataaagcatt tcgtaagctt gaatccctat aaaaagtccg tcccttaaat ttagcctgaa    371880
aagaaaaaaa gggggctaac ctcccctcca aactattcta ggccagtccc agtgagtgag    371940
tcagtcaatc ctgttcaaaa actagcgccc gctctcgctc caatatacgt gtaggggaa     372000 gcaccaatga aagtgaacct ttattctttc gtttcctttt ctcttcgaac cgattggaag    372060
gaaggcagta gctcctccta catacgagta gggagatcct gaactaaggt atgattccat    372120
tttcctttga cgacaaagaa agttatagta gcttattcca tttggaaggt tttttgttta    372180
agacagcttt tcgtgccctt acttttgagt ctatcagctg caacaagggc tgcgggaacg    372240
agtgctgtgc ttgccccgac cgagaccacc attcattacc gtgaaccggc cttggccttc    372300
acttaaaagt cagatgagtc ctctgatgaa cttgggtcca tactctagtg aaaaaaggaa    372360
attaggcttc tcttccgct tcttaactc tatccttttt cgtacttagc ccttctttgg      372420
catccttccc tatgaatctc tcaatctcgg gagttcctgc cgattggtta gtccctcgcg    372480
```

```
ttttcttctt tcctttcttt ttcactcttg ttaggttagg aaggagcaag ccttttagac 372540
tatggaaggc aagccagctg aagaagtcaa gcctgcagag cagtcacaaa gaagaggttg 372600
tattcactgg aacaagagtc accttcatct tctcgggtca ggccactgcc cttccatagt 372660
gaagactctt tccaggccta acgataagat tccctggtag agctccagat attcgaatat 372720
agaaatatct ttatccggtg gggacaaacc tataagtaga agatcatggt aataggctat 372780
aagatagcta tataatagac tattctaata gttactgact ctaataaaag taattgccgt 372840
tcaaagggca agctcacccc agtcactact ttcttcccct atccctaaac aaatagtcag 372900
aatagtgact agtctcagtc ctacttacat ccattgctct ttcctctcct tgcttagggc 372960
ggcttcgttc cccgctagcc agttcctgta agctgaacta tatcttagtc atactctaag 373020
cccgtggtag ttccattcca tcccgcctag tgcccagtca tgcattttt gtcttaagct 373080
aagcgctttt cattccttct gcaagccatc cagttctaag gtcagccctg ccctttttgt 373140
tgggttagag cgagtatgaa gtcagggagg aagaagaaga gagggaagaa ataatatagt 373200
aatatttacc tttcccagct ctcagaaatg gagaaggaat caaaaatcta gtcaacccct 373260
caaactccgt aggtaattcg agacaattca agaagaataa gataagctaa cacaaagaac 373320
ttgaacattg acaatagaaa gttgaatact accattcttt cgcgttgact cttccgcgga 373380
gtagcctaaa gaatcccctt tcgcttatta ctcctataga gcgagagatt cggcaacatt 373440
cactgagtaa aaacaaacct ccactttctt tcataagaaa acttcttgta aactaagatt 373500
agtcttagat taggtaggaa aggggatcgc atcaccgacc atatctatta ttagtaggaa 373560
ggtaagtaca aaaaactaga tttctctatt tgattgacaa tgtaaatcta ttcggatgat 373620
gtgataattt atgtagccga gtcacgagga cttcttcttc tactcccttc ccggaagata 373680
gagggaactt agcctctgac aaagtagtag ctgacatagg aatagctggc aaaggaagag 373740
cttccgctaa gattctgact tatttggaaa ctagatttgc tgccctgca gactcttctt 373800
ttgaagaatc tgattcgcta acattggttg aattttcggc atggcataga atagaacatg 373860
aatgggtctt ccttgccaac cttcgcttct agaaggaagt aagtagaagc tgaccctcca 373920
acatacattg cagggaagga cccctccagt ggcatacttt atggagaaag gcttccatca 373980
gcaggcaggt atttactttt ctgatacctt cacgtcttgt tgtcaaacca taaactattc 374040
gtattattca ttctctcgcg cttgcacata taattgggct cttaagcaac tggaggtctg 374100
taatgccttt ttacacggaa ctcttgagga ggaggtctat atgtctcaac ctcctggttt 374160
tctggatacc gctcatccag gatatgtctg ccgacttcac aaagctcttt atggactgaa 374220
gcaagctccc agagcttttt tcacttgttt cagcactata ttgtgctcta aagggattcc 374280
gtggcagtgc ctgtgatacc tctttattca ttcgtcacac atctggggat agtatctacc 374340
ttcttttta tgtcgaagat attttatca caggtagtga tcaacaggga atacttgctc 374400
ttctttcgtt cttgcatgct catgaaaata tgaaagactt gggccttctc cactactttc 374460
ttggtatgga agtgtatcgg caggggcgca ctcttatcct tcgtcagcag aaatatgccc 374520
tagatctctt gcctcgtgca gacatgcttg attctcgtcc tttggccact cctcttacta 374580
gtggtaccga gcttcccaag ttggatgtca cttccctctc tgatcccacc aatttcattc 374640
ttctattgag tcggctaact gtaactataa gctacacgcc tcgaactcgt ataaagattc 374700
ttcctctagg gcctccttc acctttttgtt agcgacctt aaacgggttc cagcagtgcc 374760
agttcaagcc ttacctttt cgtttagtct gactattttc cgaattctat atatgaatga 374820
aagctacgtt tcggcaaata ggtctatta tataaactat catcctaagg aagaaactga 374880
```

```
aaaacattag tttcacagcc gaggtcagag cttcaagtca gtaatgtctc tttagcgccc 374940
catacCCtaC tacaattCtt attCaaataa tattactaca atgtcgtgcc gatgtctccc 375000
ttacgaaatt gaagataagt cttttgatta cgggggtgac aaccgaggct tttaagagaa 375060
gttgccatag aggctataaa gagctatctc atatctaata ggaataatca aattgttatg 375120
tctactgtgg gaaatggggt cccaagaccc tctcttcgac gacgtagaca aggggtccca 375180
tcatgggcga tctgagaaga gagatgcaga agaagatgtc ctcctcaacg ggtcaagccc 375240
tcgctcagaa ctaaaggatc cttaacatcg gcactcactg cataagctca tagggcaaga 375300
tgaagatccg gaaaaaggtt aaacagatcg tcaacttcac cttggcatgc ttccatcagc 375360
gctgaaaaga cagcattgaa cgagaagaga actaaggcaa ggctggtgat gtgccactgt 375420
atggagggct cagagagagt agaagcactt tctttcacgc tgagtgtgaa cttccgattt 375480
caggctgctc ttagaccagg aagattgctt atgacatcaa tcagctaggt ccgtcgtatg 375540
tcgaatagtt tgtcaatgca tgcttcCCtt tcttatgcta aagttagtct ttagaaagtt 375600
ttctgatgag caaactcttt ttcttcagat cccttttagt aataaagaaa tgtttgaggc 375660
cttttatctc gtccaaggcc tcaaacctga tatctgagag gagatgtctt tgggagcagc 375720
taaagaaagt gtctaaacgc atccagggac catggttggt caccggggac ttcaattggt 375780
cctttctctc tcctctttca ccagtgagtg gtgagtttcc cttttttttt ctaggtaggt 375840
acctcttgga ttcggacttt gttccaacag ctgccatacg tgagatcctg atcgtcttcc 375900
tcccagtgtt gttgcctgct gggggaagga aggaaagtag ggcttccttc caggaccgga 375960
gaaggtcaaa ctctgggcgg gctgccaggt ttcgcctacg caacggtttc acaagattga 376020 acctttttttg ttcaacccaa gtgttggagt tccagcacc gagggaatgg actttcattc 376080
ccaggaccgc ctcgtctatg tattcggcgc ctcccccgat tgcttgaaga taggcgcgcg 376140
atacgataaa ggcccctggg agaaaccaat gaaaagccag ggtagagcct cggagccgac 376200
ccaagcgaag atcggcactc gattgaggag cagcccgaaa aagggaaagc cgtggagacg 376260
gcagactcgc cagtcaggca cagcgtgagg ctgactacag tagaccggga ggttacaatt 376320
cctgtttcaa tttccgggag tgaatgtagt aagtgcagac ggtggatcag gtgtaaacat 376380
caaccaaagg cgtcttgggg atcggcaata gctaaacatt gtggccatca cagttcaagc 376440
tacgtatggc tggcgtacaa cctacgggct ttttagccaa aataaaaaga acaaaaaagg 376500
atgcctgctt tggtaccttt agtccaatct tagacaaaga gcaatttgga tatgaagcac 376560
tgctgggtag accatggctc caaccaggtg attcatgact gggctaataa aaaaagtctc 376620
aagcagggaa aggcgggatg gaaggcggaa aaggcttggc tttgtttcac agaaaaagga 376680
ctaaggaaat ttcctttccc tagtgttgga gctggctcat tcatgctagt catcttagag 376740
ctatgagtca gaacaatgtt caccaactcc tccatagtaa tcttgttcat atatcgaaaa 376800
agctttagaa tattcgtttt tttatattaa agtgttatat ctcctcccca aggtagcatt 376860
gacgagcggg cgatccctgt cttgtttatc cagctagctt ttttccgtgg tactcaaatt 376920
cgatttgtga gagctctttc ggctcggcta ctctttttt ttaaggtaag gtaggacctt 376980
taaaccgaca aaagtaataa aaaaaaaaat gcctatctat aaagcgctga gttgaagagg 377040
gaacaagtcc cacagagaga tgataagtgg gagaaagagt gaaattacaa tctcttctgg 377100
aatggaagac ctcccatcca ctgactacaa gactgcagcc taacacccaa gttagcctga 377160
cggtcagcta aatgagtccc ttacctcttc acatgatgaa tttgaactca acatatattg 377220
```

```
agaaatgttt tatcaggaga aagcataggc accaaggttc ttgattatta ccattcgccc   377280
atctaatcat tgttaagaga acccctttt gtttgatatg atgacttgaa aagaatcaat    377340
agtttggaca aaactatggc catgcaggag agtttctgct tctgcaaagg ttgcatcttt   377400
aatccctaga ggagatctgt tcaattccac atgacagcac cattgccatc tcttatgacc   377460
cccaccataa tccgaattcc cagagtagcc ttccctactc cttcaaagtt catcttgatg   377520
tgatttgaag aggaaattgc cgcaagattg agatagatat gttgaatt ttttttcttt     377580 taattaagta atgcaataaa acctcgtcat gttcatcctt actaacatcc catacaaaaa   377640
agaaaatctt ttatggtctg gatttttca atcaccttaa cgcttaacga aggaggtgga    377700
cttcaaccaa atcagcccctt cttatgaagt ggctatggaa atttccaaaa gaaagaaaa    377760 agccatggtg ctcatatttg gctgctaagt gcctctccaa tggcaaaaat ggattgacca   377820
acccacctct taaatattct gcatctaaaa aggtattatt tttaatagag agactttcag   377880
gcagaacttg ggctagactt tggttgggca atggtaagct gattcgcttc tgggatgatg   377940
tttggccgcg ccactctcct cagagatgca tgccataatt tatatcaaat cacaaggttc    378000
tcatgacctc aaagtgattg actacattca atataaagga gaaaaaagga tttatccccc    378060
tattcaacta cccatccaag agcatttggc ttcagaaatac tttcttcttt ttctttttct   378120
atggactgcg taaatcttct cttccagccc aaaggaggat aatctctttt ggcagctcaa    378180
tcctcacggt aataattatg ccaattctgc ctaaaaatct cttcaggtga tcaaggggggc   378240 tcccttttc agtagatgag attaggatga aggtattat ctaaacgctt cttttctctg      378300
gcttgctctt tcaaatccaa ttttggcctg cagtaatgta atcgggattt catctcctaa    378360 attcttttt ctatgaaagc aagaggtgga aagttttgtt aaaaattctg ccttattcca     378420
tgagatctag aagcacttct gcaactttct ctcttcccta gcgctagcgc tcttttttt     378480 tttactttt tcaagggca atgaaggcct tccttataag ttctcgctcg atcgaaagga     378540
tataacacat acgaaaccctt agcttcgctg actttatgag gtctaacctt cgccacgaca   378600
ttagtggctt agctcttcgc gcttcccgca ggcttttta tagagagaga gtaaggggggg    378660 ggggcggtac ggaagattgg tccgctccga aaagctgagt ttttcggttc gccccccta    378720 tgtggtcggc cttcttacca gtctgcctcc tttctcttga tggaatatat caatacccga    378780
gctccagctt tgcttgcgtt cttcaccggc gctcgccaga tgtatcactc atcccgctcc   378840
taaggtaagg agtcttcttg tgtgttataa tctttacggg aatgaatcgc atatgttggt    378900
tgagaattgc tcgggaattc attgataatg actttgccag gttctaggga ggctactctt    378960 ctttttgtc gatcgagccg ctttcccctca ttccactcgt ccagccctct tcacgaactt   379020
gtacaatcga tgccacaaag atagccaact ctattatcaa agaataagg aaagggggcga   379080 caattttggca ccagatatcc ggaggtgtgg aaagagcagc tgtgagaagc ggaaaaacca   379140
tcaaaaaacg acgattgttc gtggaggtt ctacagaaag accccttggt tctgcaaac     379200 ggatcacaat tacaggtacc tgggagcata ccgatggaat gaacgaaata cgaacagtta    379260
acataatatg gtcatagatc ttaggttgta acttgatcat gagcgaattt gttgatgttg    379320
cacccatgaa gtatgaaag tgccaaacat tgggaactac ccggggagga gttaggaaca    379380
ggaacaagga gaagcgagaa ccacttaaat ggaggaatcg attgtatttc gtccctttgtt  379440 ccccatagca actgggggatc aaaaagcacc aaatttgatg acttattaag ggaaagacga    379500
agtaagagca tgctattgga gacgttgcaa catatgtagg gaaggcctcc gttgattgtg   379560
tacgaacaaa atacgaatcc aaaggcaggg taagaaaggg tttagctaat ggagatatta   379620
```

```
actcttccgg gaaccagtaa cgcgtaaacc atgtcaaacc aagaccaatc aatatccgaa  379680
cggaacggat tcgaacttct cctagaatag tttccggtgc gaaatgaaat tcataggata  379740
tatatgagta attcaaagga taaatataaa tatttgatag gattcgattc attttagtaa  379800
tgaacaaaac aaataggatt ttttatgtat cacaatttca tcactacatc gaaggctctt  379860
ttgtaaatat attgataaga tagcttggta tccaaactaa aataattatg atccttattg  379920
tgtacataag aaattgggtg ggtatagggc atataacaaa aaggtttcct cggtcataaa  379980
atgaaaaaag aaaagcaga caggaacagt ttgattcttt aaacaagcag gttttggctt  380040
cttttttagc accctaattc tcttgttggc tttgatacca tgaaataaaa tagagaaaaa  380100
gaccttcaag agaataaata aataaaacca ttttcaagag acaaactcca gtgaacccct  380160
ttcctcccat tcattgccct ttgaaagaag taaaaaaaaa aaaagaatc taacgctcta  380220 gtcgaattga agactttcaa cgctcatgct atttgaaaga gctttcaaca tggagtggag  380280
actccataac gtacacaaag agtaagcgat ctatgaatat catcccaatt caggtcttgt  380340
tccgcactta aatggataac tcaaacccctt accttgacca gtttgtagtg gaaaacctca  380400
atgacataat cgtttatagt cactcactgg aggtttggaa ccctgagtac agtgttccgg  380460
gtgtagcagg aaaagaggct gtacgtgaaa cagtactcag acgaaagtgc tatttcttgg  380520
ccattggatc agcaagggtg tgattcagat ggatcaagag aagaccaggt ctgttgtgga  380580
ctgggaagtg ccgaagaagg agagagcagg cagcagtggt gaagctggat gctcgaagtc  380640
attttagata cggcaagaca gctcaggagg agtcgaaagt tgccacaacc taggagggggt  380700 ttctaggaag ccaaaaaagg ggagccttttt tacatacttc ttaaagggggg agagcgccag  380760 gagaatgtcg agacgccatc agtttggagc gcgaggccag cagagcttgc tgcagaggag  380820
ataagaaaag gctcagcaga ggggatctgg taactgttat gaatgtggag gagtggggca  380880
tttttctcgt tactcttcca atgttcagac ggacgaatgc tgctaggggga gtgcagaata  380940 gaccagctga agatggaaga gtgaacgttg tcgagcctag agcccgggaa gctctaaagg  381000
taagttcaag tcggaaacat agcgggggtt ctcaagctta ggagaggaga ctgtttcgct  381060
gtcgttagat tgtgtggcaa cgtgagccaa cgtcagcaga aaggaggaga agacggaagg  381120
ctgtattcaa aatctatgtc ggaattggcc agtgcaaaga taatcattga tgctgggagt  381180
ttggataaga tagcgtccac ggagatggta gatcagttgg ggctgaagcc ctttaagta  381240 agggcctcat ccagagccct atcgaatcag atcaaaaagg gcatgagcgg cgggccctat  381300
gttgagtaag gggggagaag gtgccccttc tgctaagttg gagctaggga agttaaagca  381360
ggacgtctgg tgtgacgtcg tccttatgga cgtattacat atcctactcg gaagaccttg  381420
gtaatacgag tagggttcta cctgcgtaga gagaacaccg gtttactttt aagggggaaag  381480 gcggttattg ccatcagaag actttggttg gctaaggaga aagggtgttt gttggcatac  381540
catttctgga cgtgggaaag agtccataga atgctatgcc ttgatagcaa caaagccaac  381600
tagcagagcc gattcgggga tcggtgggat gccgtagctt taagagatag gggcggaggc  381660
aatcagaaag gctttttagg aacgaggccc cctccctcct atgttgtaaa agggaagtgc  381720
agatctttat ctttctgcaa cactcttccg acttgatgcc gccctgaat ccacaagtac  381780 cggcttgatt accctctaag ataagaggag gatatagaag cagatttagt tgcaggtagg  381840
agcgagtcta ccctgcaaag cggcttctcg cttatcccca ttttcaaatg aggagatccg  381900
acgtcaagtg caggaattgc tgtcaaaggg gcgggagagt ctcagtccgt gttcaacgcc  381960
```

-continued

```
tgcttgacta gctcaaaagg aagcagctgg agtgtgtaga tgggctttga ataagagttg 382020
ggtgatttat ttccaataat gccaacgatg gatgatatta tggattaatt gcctgtcggg 382080
agcgtgttac ttttcaaagc ttaccttatt tagaaaaggg gaaagggctt ttttttatag 382140
agagagagta agggggtttt tctggggctt tgaagaaggg ccacttatat tgcaaaactt 382200
tcagagacgg gatggaaagt cttccgtgag aagagatggt aggcttgata cggatacagc 382260
tgcttatcac ccaccttaga atcaagcagt tcagttcgac tatacccgcc ttaattccct 382320
cattcaggac agatggaagc aggttatgga tctgttcaag ttggtcgatc aatccctccc 382380
ttctttcccc tgcctccgga caccttagaa tagatttgat tggaaggagg gtgaggaacg 382440
aacacagtgg cttgactgct gggatcccaa tcggcctgca tcagcagaaa atggaactat 382500
cgaatcacgg gtgactcgct ttatcgggat gggaagaatt gcttaattgg catttctttc 382560
cttccctaaa tcgatccact agtaggtagc ggtagtagag atccattatg gtgggatgga 382620
ccgttctcga attccggccg gcatttctgt caatcggcgg aagactcacg catactggga 382680
gggtacgact tcaagggatg gactcgatcg aacggccaac cacttgccat ttttgtagga 382740
gatgaaatcc aaaagaccat tattagcgtg tagtagattg gcccgagtgc gtaataggcc 382800
agtcgagaag aaattcaatc aatagattga acggtagata aaggatcaga ggatgagagg 382860
ggtagatcta cccaatatgg accgataacg gatggtcccc gccaactgct tatctctctt 382920
cctcgcattc cattcatgac ctaacgacta tccctgtttc ggggagggaa tcacttgctg 382980
gatcgaaccc aaggataggt ttgatcggcc gggtgttggg tcgaatgaac actcaaccgc 383040
gtcatcacgg cagcgatgga tgtccaacct ttagatctct tctttctcaa taaaggcggg 383100
taaggaaagt ccgaaggcta atccggcaac tgctggctag aaggcgaaaa ccgcttttgc 383160
caatcaaagc cccaaaacta gtaagggcac tcgtgcccca gcaagccacc caacccctac 383220
cgccaaagct tgactttact aaacaagcga gaaaggctct ttctatctta ttagtcaagc 383280
gctaacgagc aagaaaacgg atatgcccta agaagcaagg gctttcgtgc agctgctgcg 383340
cccttgcttc ttgctttaga aagattgctc gttagctagg ccgttttcaa taaggctcgc 383400
gctaggcgct cacctttttt ggctgagccg tatcgtatct tgctggtaat ggattgattc 383460
ttgaatcttg cttggtttag gcaggtaagt gttaagaggc tctttaaggc tttcgttagg 383520
tacacatagg actttcttgc aatacatagt ggttggcttc gaatcacatg aagcccatat 383580
agatgtccac tcctatttcc tctaaagctc tccctgtggg gaacacaatc agtccataca 383640
aggacctact gagtcatcca cccttgcatc tatttgatgc atcatcacat ggccgtcgtc 383700
taactcctcg agaatcatgt cattcgcctg tcacgtgttg ccaccagagt cataaatact 383760
cgaagtaagc cctggctcg cccctatctc taaaggggct tacgaacgag cggagtgctt 383820
acggccgtgg tagctgcgag cctcctgggt cttgctctct cgtctttttt cctccgcctt 383880
cctcttgtaa ttgacccttt cttttctgct acgcctatcc atccgtcaga ttgacatcca 383940
gccgggtgag cgatagcggc tcctgtttac taatagatct gccgccgcta gtataacaaa 384000
aaaaagcaca taaggatcca gaatattcaa atatactgat cactgatcag gatcatataa 384060
agcccggtat taccagaaag gatagtcgtg atgtcccttc atggcggcg ttttcagtat 384120 agagccgaag gcgagggttt ccagcaggcc cccttctctg gctttccctt taagtgacaa 384180 gggggggtgag gtaaggagta gtataagagt ggttcggtca tcgataagcc tctccttatt 384240
cattctatag ggcggggctg cggaccaaca atccagcaaa agggctgaaa agctccttta 384300
ttaaaccttc ccctttttaat aataagaagg taagcatcaa agcccagaaa acccaaccta 384360
```

```
tacaaagagc tcttttcagc ccctactcct aacaagtgaa agttgctggc acccaccata   384420
tcttgcttcg gggccgatct cttgtatcgg agcaaagaaa ttcaatgatt ttctatattc   384480
tatttctttc ttttttttgtt gagttttttc caccacaaac agatttgccg catggattgg  384540
atagagtccc ctgatctcga cattcaagca cgaatcccct gagcgcttcg gcggcggata   384600
gcagcatggg caaagcactc tgctgcggcg agcagccggt tcttattgca ttcaccaaga   384660
tagtcttgct cgctcctgaa ctctgcggcg agttcagcca ccacctccgg gtctgagctc   384720
tgctcgagcg tagtcagcca gcttcgtgac tttgcttagc ttccagcctt gcaaagggat   384780
aacctttcac tatctaggcg ccctcgaagg aggggtccca cggacttctt ccccgaaggt   384840
caagccgtag ttcctgtccc tgggagaagt ggaaggagtt aggaggatgg agcgcccttt   384900
gccctaagaa ataggcggct tcgccttcaa gccgtcaata aaatcgagct aatatgtggt   384960
catgacagta cactgatgca taggtcttct ttactttacg gccttttgat tatgatgcat   385020
catgaacgtg ccaatatgtg atcggggtgc gcggtggtta datataggg cggcttcgcc    385080 ggcttggatt ggaaggaagg gcttcgcttt ccgatcgctt tttgaggccg ctttggatga   385140
gcgtgggcaa gttagggatt cactatcgct ttccgcttgg agcggctcac ccccttgtca   385200
cttaaagggc gaagtcgccg aagcgagtct aaaggccaaa gagtcatctt tgaaggctac   385260
tatgcatcct tattcatagt agagtgtaag gtaggtttgg gtatagcagg acttgaacct   385320
gcgaccatta ggttaaaagc ccaatgctct accaactgag ctatacaccc aaaaaaagat   385380
gtagtagtaa ataaggattg gtacggaaaa gaggccggcc cccccttcttc tcatcatatt    385440 aaaggagcgc ggctctgtat gaggctcgta ctgcagagca ggcggaagaa aacgtaaggt    385500
cgcgcgttag cactcctgca agaaaacgga tgcgctaagg cgcaagggct ttcgcgcagc    385560
tgctacgccc ttgcttcttg ccccttattt caaactcttg atcgatatga gaaagatgcg    385620
ctcaagcacc caacctatac aaggggcttg ggctcgaaag ccggccttac tcaacaagca    385680
cctttcttag taaggttgct tctttccact cattgaagat tctatctaca aagaaggtc     385740 aacgggggat actcaaattg ctctcactga caccagagaa ggtgaggtcg tctttctttc    385800
cagccgccat acggttcgcc ttaaagcctt aaggagaagg ggaggagcag ttatctatgt    385860
aattacggtc tttgttggcc gttgttccgg tcgagcactc tcttttcttt gtccaattcc    385920
gtcttaccaa acaagactga cttcttacca acccgcgaag ggttgtgagg ctggaccagg    385980
tacgaagaat gaatctatat ctgtgcacgg aagttgctgg ccggcggccg ctcaactgtt    386040
cgagcgcaat gcagtggtgt tggttccgat tcgacaaagg tggaatgcct ggtcgaaggt    386100
ccagtacagt aggtagcagg cgtgttcgtt ttggctcccg agcgagaacg ataaataggc    386160
gatgcaccat ccttgctgct acgtacgttt tccttgactt gacagattca ttcaattgaa    386220
cccacactca aaggaggacc acaagctcgg ggctcgacga aacagaaagt ttcagcatgt    386280
tgaaacctct tggggttagc agtgaaagaa agagcccggc attcatttct tcatgaatat    386340
tcatagctga gtctactaaa agagggacca gcctcgtcgt ggtgattaga ggacacctct    386400
gatcgttcac ctctaatgtg acacgttccc tcccagttat atgatcaacg ggatcagtcg    386460
gctagagagc ggggctattc ttcttccggg gagacaaagt cgtcccttct actgaccgaa    386520
ccctcagttc gggggccttc gtcaacatgt tacgaagctc cagtcttcgg tgggtcacca    386580
ttacttgact tcgaaaggcg aacatctggg caagggaaag cgcagtgcgc ctggtgcaaa    386640
tggctttctt ttttcatgat ataccaatca gaatggaggg tcctacctac gtacatgatt    386700
```

```
gatagaatca ctacgtaggg ggggcggtca acttgatgcg ggagaggcat gagtgcagtt   386760
cgatcttgtg gtgtattcgt ttgtagtgag tagggcctct ttctcgttga tcagtccgcc   386820
tccgctctat tgaaaagtcg gaattcctac ggcggttttg tcaacgaacg cgtctcgggc   386880
cggattgact aacctaaccc acccttaagg aggcttttcc atagttgggt gtccgcttta   386940
gtgtgattta cgaaggctag gctaggtttg gtaatatcca aaacaaatga aaagagatcg   387000
gggtcgatag gtggcagctg gcaaggaact tgatccccccc caaaaaaagg gggaagccgc   387060
ggtcgaactc gaattctgga aataagtcgg ggcccttttta ccaagtctac cagatagaag   387120
atgatagagg gccaactatc gttgccttgc acaagacggt gcccttttcac ttcgagttcc   387180
ttccttcgta gtcaaatctg atgatacgct ttggcgatgt tacctaccaa ataaaaggcc   387240
tgctaggtga tcgaaatcgc tcaggtcagt gaggactcac tcactcacct actccttatc   387300
tatttaatac tttcttctat ctacttaatt taaaaggcga cccgccgcgc cgggctataa   387360
gataagatac agttcttgta ctacttgatt gactggtaag aaagagcttc cgtaagaact   387420
ggaagactct tgtatgtacg gtaaccctct cttccgctac tggtggactg ttgcacagaa   387480
agggcgacag aagcaacctt tcttagcgcg cttttcaagc gcttagcttc tgctagtggc   387540
ggggcggcaa ggccattaag ttcagttgga agcctaagcc aagaaggtac gaacgaagtg   387600
acgggcccct ttagaagata gggggcggct ttcttgtggt agtaattgcg aacatctctc   387660
ctcttctctt agcgtgcaca gtttgcttac atgccgcctt aggcacatct ctctttctta   387720
gtttcacgct ggactaatga taatgaatga aagtcagtct tttagtaaac gtatataagc   387780
agctgtttag tgtataagca attctttagt ggtcgcaccg aaagtacggt ggaggttggt   387840
tgaagatgat cttacgcggc gttcagaacc agtcttgaag tgaatgaatt agaaagaacg   387900
aagaagtaag gaaatgagac gactctttct tgaactatat cataaacaga tcttcccctc   387960
cacaccaatc acgagttttt ctctattcct ctcgtatatc gtcgtaacgc ccttaatgct   388020
aggttttgaa aaagacttttt tatgtcattc ccatttaggt ccgattcgga tccctccgtt   388080
gtttccttttt ccttccgcac ctttttcctcg aaatgagaaa aagatggta cacttgaatt   388140
gtattattta agtgcttatt gcttgccaaa aatcctactt ctacaattgg taggccaccg   388200
ggttattcaa ataagtcgtg ttttccgtgg ctttcccatg ttacaacttc cgtaccaatt   388260
cggtcgatcc ggaatggatc ggttaaacat tccattaggg agcctggtct tgactcttct   388320
gtgtggtatt cattctcgtt cggctcttgg aatcacatcc agcagtggtt ggaacagctc   388380
gcaaaatcca accacttcac ctacttcatt gcccccaacc gtttctcgta cctctattga   388440
aacagaatgg tttcatgttc tttcatcgat tggttattcc tctccgttcg tatctctttt   388500
tccaatttcg gtctcgatta gttcacaaga ttgaatggcc aattctcctc cgaaccctcg   388560
attcgattgt tttccaagaa tgttgagccg ggtatgtaag ccatgtatct gggaggaact   388620
taataaaaag aagggctttc ggttttttgc accccgtttt ggtcttgcag ctattttttaa   388680
aatatacata aaagtctctt tttttttatta aaatgattat atatatgtcc aatctctagt   388740
ggtggtggaa ccaaccaaga tgtatgtcgt ccgacccgac ctcagactcc ttcttcccga   388800
cctatttgac tctctggccg tagttattta ggtggtattc cgagatcgaa ttcctcccag   388860
gaacacacga aacaaagata tgaactgggt aaatagaaat ggaaaagaga tctttctatt   388920
tcatccaaat tagaagcttt ttctacatct atatgatcta ctaaagtaga tcggtattga   388980
ccatataata aaagcagatc ttggtccatg gagtcccaag aaggtaagaa ctccaacctg   389040
tccgatgctt cttcggccaa atacgatata caagtgggac ctgcactatg agcaagctgt   389100
```

```
gcgaaaaacc gcttcttttt tccggttccg aaagaacttg ggcgaaatag ggttctaccg 389160
ggaaaccatg aattttttgag ttttcgccat tggttactgg ttgagccact ggaatggaat 389220
gagataagaa tctctggaga tctttcctct ccacttactc gtaacaggct tttcttctgt 389280
agaagacttt ttccgaatgg cataattgtc cgacactacg ttcctcgatc ttcaaagaaa 389340
actgactcct cctactccac cttctccttt aggataggat cctccttggt ccttctttca 389400
ctaatggtct caccattttc tagtagtagt tcgcgcgagg gactatcctt tctatcgctt 389460
gcccttgcct ttcactctca tttggtctct ttcttataga aaataaagcg aagcaaagcg 389520
catggcaaag aagcagccag ctgactgccc ccttccactc ggccttttctt cgctgtgtga 389580 ataaggtctt agtctgtatg ggcattctgg gcaggtcgca ataagtcgct agtcgaaggt 389640
ttagaccaat cgcaattcat caccatcttg cccgcttcca attgatgact ggctattata 389700
taagtgttga cctaagcccc tgcgcagggg ctcggctccc gaaccgtacg tgagctgtct 389760
cgtacggctc ttcctaagaa cttgaagccc cctctctcta aatagaaaaa aatgaattta 389820
caaaacaaaa aagactttt caaaaagcct tcgccctcct attcaagggg gctattagag 389880
aagcagcttc gttccttgac ttcttttctc agtcaagctt ccttgttcct tagtgtagtc 389940
tcggtccata gtttaagact ccgttcctta tagcctagtc tatatccaca gctgacgtga 390000
ctccgtaccg acgcctttcc cttttgtatag tatacggcta agtgacttcg taaccttaac 390060 gtacttttttt tcttactgta gcataggcct tcgtcgggct ttcgtcccttt cgcctataga 390120 cggcggcttg gcttctagca ctaaataata ggcattaggc attctgagct gaaaggaggc 390180
aagcaaatga agggaggcat tacgggccga ctacaagaaa agcaaagctt cgtagactcg 390240
gtcaagtcgc ttatagaatg ccgacgacga ttttccactt aataagtgaa ggggagaggg 390300
aagcgaggct tagcgagctt tataaggccg accactacat aagccgctgg cggagaaagc 390360
tcgaagagct tcccttcatt cattactaag ccaaggtccc aggtctccga gtcagcccgc 390420 gcttttttcga agaatcctgc acccatgggc atacggcctg gcaggccttc cctttccgcc 390480
ggagcttcat gggcgttgcc ccgttcccca atcagatgtt tggatgtgag ctatactccg 390540
cgaggagcca aacgggcgta tggccttgcc ttgccatttg acctcttttc ccgtgtgact 390600
aggaatgctc agtgacaacc tctcaattgt caccgcctgg cctctcttgc taccacggta 390660
gcacctagtg tggtcagcac caatcgtgtt cgggcaacga agcttacact cattcacatt 390720
ggttcatcct gctatgccct gggccttttg ctcttctaac gtaaaaggtg gccggccatt 390780
cgtcaaggcc caggaatccg ctggacatct cagcggcggg atttgatacc cgcatccgat 390840
cgaagttgca ttttagtgct cccctaacat aaagggagc ttttcaaag tgggtcgctt 390900 cgcgcaagac attgcttagg accaacgggt cacacgacag gtgcacgatc tactttgcac 390960
gttccatcct tcagcccttc gcctatcggc ttggcaggca agctaccttg atccgtcttc 391020
ggcttcgatt cgttacgctc agaagctcca acaagcccta aagtctcttg ccgcctaaaa 391080
ctctgccaag agagcgctgc tttacgtttg atcctatgta cccatagaat gctatgcgtt 391140
ctccactttc ggatctcgca aagagataac gtgttttttc ctctgactttt ctctctcatt 391200 cgcggagcga agaaagcggg ctttgcccca gctaccgcta tccttgggaa accaaaagag 391260
ctaccgaagg aaagggatgc agtctctccc ttggcctttg gagaggagag ggcagagaag 391320
aaaacgtcct tcgcgcaagt tttttttgctt cctgcgtcct tactagtaaa aaagggggctc 391380 ttcgagcaag aaggcatttt ggtaggaagg ccgaccacta cataagtcgc catccgtcca 391440
```

```
ggagagaagc aagctacctt tctttgatcc cccttttcgg gcagggaaga gaacgaaaat   391500
ggaccgcaga tggtagtcgt ggttgattcg aggatcttac gcggcggagc gaactcttct   391560
atcgtgttgc attttctctg gcggaccccc ccccggtcc atcgtactgg agcgattcga    391620
gaagaacgat taggctcata ttctatcctt tctacaatgc ctatagacga agtgcttcgt   391680
ttcagatcaa ttcttcgctg caatcgcttc gatccacccc ctcggtgaaa aaccgtaata   391740
cgccctgagg aattcctacc agcagacttc cctgtactca aagtgaattg tctaagtgct   391800
ctcctttgtc tcattgttta tctcgtaatc attcgattcc gccctaaag ctagcgccta    391860 ctcctcctcc ttctcctcct gaatcctcct tggtcctttt tacataacac tctcggccgc   391920
ccaagaggac tggctatctt tctctttata cgcacaatat cttgaaaggc aaagaaaaag   391980
atctaccttg gcaacgaaga cgtcattgac tgatatattc attgcatgga atgccacact   392040
caattgtcag cgactgggga cccggtcttc attagcaatt tatggcatga gctctttcgt   392100
ttacaaggga cacaatttaa catgagtact gctttacact cttttcccgg gtggggcttc   392160
ttatacctaa acgcagcagg ccccgcgagt agtcgaacaa atgagaggtt gtcgacgaag   392220
gggtcaaagg ttgcgcttgc gagaatccga aggttgcgca agacccttc aacctcgccc    392280 gcgtcttagc ttgcttgtac tatcgctcgc ctgcctgacc tgctttctgg ctagcttctt   392340
tatggcaagc gctaccgtaa cctagctagc gctacatctt gctaacgtcg tctgaattgc   392400
cttgcaagcg ctacatctat atggcaagcg ctacccgtcg cttgcactac attgtctgac   392460
gataaccttg cctgaccgct tccgctctga ctgagctgac cgccgcacct gacttctata   392520
tcccattatc catagatctc cttccttatc gttgccggtc taagcagaag gttgctaagt   392580
cagatgtctg gtgaacacat tcgtaatgag tatgggtcta gtaggtgtac tagtaaggaa   392640
gcgaggtact gagtttagcg tcgacaaggc aagtagtgga tctttattct cgaatgatat   392700
gggagacagt caaagcatca gtctcagcat caacagaaga aaaggactga ccgaccgccg   392760
ttcaagagag atcccgaagg ctcgaacttt tgctagctt tgaaacatgg gccgaaggaa    392820
agaggaagac caaacaaagt cgcggtcaaa gcaaagaaaa agatgccaaa aaagattcac   392880
tttagcttct agctcgctta gtgtaggttg cttgcaagac tttcgatagc tggctcggcc   392940
gaacggaatc accgatctag atagaagggt cgttcactcc ctattctttg agaggttgct   393000
tgcgacggta gcattagcta ggcaatcaag gcaggtcgaa cagagtcagt cctagggtga   393060
agatcatcgg atggaaaaat ggattgagct ggctaatcac ttgatgaccc ggtggagaat   393120
gggaacagag agtcgctccc ataaacgaat gaatgggact cctggtcctg atcgaaccag   393180
agattccgac aacccgggga atcggcagaa agagatggtt cggatactgg aatctgccca   393240
aaagtcctga cttttcgag gcagggcttc gacccgtatc tggccaactc ctcgaactgc    393300
tgggtgcggc atattcatgg actggcaaag cgaactctca atttgatcag gagagcctag   393360
agagctctct atctttcccc aaattccgac tagcgcggtt cttttctcg accaatttga    393420 attccatttc atttttatt ttaagttaag tagagtagta agtagctagg cggatttcag     393480
cgcatgctgc attgagaatc tccaaagaaa ttagaagggc ctatgagagc gtattattct   393540
tcccatttgt gaccgacggt tgcttgcaag aggtggcgat cggcagtgtt ccaaagcgcc   393600
ataacgacgt gcgttagagc gttatgccaa acgatcccca gcaccagtag ttatggggat   393660
cgccttcggc ttgctatact cttttcccta cgcatgctgg ttaccataaa gacaccgagg   393720
gatatcgcat gcgctagttt cggggatgtt gtttacacta ctattggtaa caactcaaag   393780
tgccggaacg actctagtgg tgcaagcgaa ggtttcagtc ttgtcgagcg aagcaaccac   393840
```

```
tagtcgccct tagtgctcca aaacacccctt tcgcttgcgt gagcaacggc ccctagcgcc 393900
cagagcaagc gcctttagtg ttcccgaccg cctgcctttc ggccttagcg ttccaaacaa 393960
ccagtagtgt gaccgatctg tgttcaaaac aaccgatgac gctagcgacg actcgtgggg 394020 cccctaacg ccgaacaaaa aggactagtg ctataacgac gagtggtgtg gtcctaacaa 394080
ccgactacgg taacgacaac tcgtagtggt cctaactact agcaacaacc actacggcaa 394140
gcgccacaac gacgataggt gaggctagac cgtaatatag gcttgcgaag caagcactcg 394200 ttgtcctta gttgtccgtc actcgtagtc tctgcgtcag aggtggttgt tcggaagggt 394260
ttgacaaggc aacagacagc caggcagtta ctacgcaaca cacattgggg tggtgcaaca 394320
atggaacgac tagtagtcta cgactagtgg tgttacggaa caactacccg acgagtggta 394380
ataacgacaa ctacagtagg tttgacagta gcgttaggac gactggttct cgtagttgta 394440
ttgccctaag gcaacgactc aaacaacaac gagtgctccc aagacgatga gacgcatgcg 394500
ctataccgtc gagtattgct tgcgaagcaa ccgcaactcg ttgtaggtcc tctccaacca 394560
ttacagtcga gtagctttca ctccttcgct tgaaatgtgc ggttggttta cctaacgcat 394620
ggcttcccca acgccaatag tcgcatgagt tctcctaggc cataacccat gcgttgaaag 394680
aaagcgcatg atgcgttccg gagttgccgt agttccgtta ccgccttgtc gtcttgggtt 394740
gggaaggata cgacaggctc aattcaagga cactcaattt caagctcaat ttcaggcttt 394800
cgaagctctg acgctttctg tcgcatttgt tctctctttt gtttacctt cattttcact 394860 ttctttaacc gtacttaggt agctcttcgt tcggtagagg cgtagagtcc tagaacgcta 394920
tctacttggt cgcgactggc tctgctacgc taggttctcc ctatggcgct acgcatcgtt 394980
cccttcggtc gagcgaatcc cgttgttccg gtccgagaat ccctatgtct gaggtcgagc 395040
agctaggctc tcgttggtcg aggttagatc ctcgtatgtc gccactctcg tcactgggcg 395100
ttgtcactga tgtcttgtta tctcaggaca ctctgccagg ttgttccttg ttgaccggcc 395160
ttgtgattct cgttatagaa tgtagtgccc aacagtttaa aggaacgggt gaagtctcgg 395220
gatccgctct agtcgagttg ttagatgtct ctctccggag tcgctcctct atctttcgtg 395280
aaagcatacg agtcgttatg ttaagcatct aatcctagtc tttatgttat ctgtgttaga 395340
ggagttagat gtccctcatg ttgaacagtc tgacatcaag ttgttaggac cttagtcgct 395400
atgcgaacac ttaacacaag actgaaagcg ttagtggttt atgaatcagt catcaaggat 395460
cttagccaaa cggtgaccgg ctacgtaagc actttgggcg caggtttctc gatcggactt 395520
gacgaattgt cataaagaca tcactctgct atatatataa gaaaattgga ttctaaaaaa 395580
agattcaatt aattagaagc attcgcagtt ttcagttcgt ttgtcatcat ctaaaagaaa 395640
agagaaaacg aaagtcattt tgaaagacaa aactgctaag ctataagtag aagttgttga 395700
agtagaaaat gcttgctgct cgcttagcgc acggatcata ggctatctca tcactcacta 395760
aggctagcga aaagtgatcg aataaagcat ttgttcgtac agctctcgaa cctcacgctc 395820
tatcacgcac ggaaaagaag ctgactcaaa gaaactagct ctcgcttaat ccgcatatct 395880
ggaactcctt gatttgaact actccgaatc cggcgatgaa ctcacatttc ccccctgggg 395940
ggactcttgc ttctgtcttc ctctttctgg catctggtgg aaatgttatc tcgatcgatc 396000
agtttcttct actctatgcc tactaaaagc ttaaccatgc cctaccacca agaacagatt 396060
ctcgccatct atttatagga aaacttcgc aatatgccag agctatcatt acctttagtt 396120
gattatgtcc agactgggaa caagaggcct ggtttttttc ctgtgtctga ttccagagta 396180
```

```
tcagcaccag ttgttcttgt aatagacgag tgtttagatg aacctcatct ccagcatcta    396240
caaagctcct tgcatgcatt tgtagattca ttaccccaa caacaagact cgggattgtc    396300
acgtatggca gcacagtgtc agtttatgat ttctcagaag agtctatggc atcagcagat    396360
gtatttccag gtaaaaaatc accaaatttg gagtcattga aggcattgat ttatgggacc    396420
gggatatact tgtctcctat gcacgcatca cttcctgtcg cacactcaat attctcatca    396480
ttgaggccat atagactgaa tatcccggaa gcttctagag accgttgcct gggtacagca    396540
gttgaagttg ctttggcaat tattcaaggt ccatcggcag aaatgtcaca gggtgttgtt    396600
aaaaggcccg gtggaaatag cagaattctt gtttgtgctg gtggacccaa tacttgtggc    396660
cctggttcgg ttcctcattc tttcactcat ccaaactatg cccatatgga gaaaactgca    396720
ttgaagtgga tggaaaacct aggtcgtgag gcttttagga agaagaagac tttgatttac    396780
atattttgtg caggcacatg tcctgtaaga gtgcctgtcc tgcaacctct tgccaaagcc    396840
tccgggggtg tacttatact ccacgatgac tttggagagg cttttggtgt gaacttgcag    396900
agagcatctg ggagggctgc aggttcacat ggtttattgg aggtccgctg ttctgaggat    396960 attttgtta gtcaagttat aggccctggt gaagaggcac atgtggacag caatgaaact    397020
tttcaaaatg acgagactct tgtcatacaa atgttaagca tcgaagaaac acagagcttt    397080
gcattatcca tggaaaccaa gagagacatt aagcgcgatt tgtgtatt ccagtttgca    397140 tttcaattt ctgatgtcta ccaatcggat atcaccagag tcattactgt tagattgcct    397200
actgtagaca gtgtttcatc ataccttgag agtgttcaag atgaagtggc tgctgttctt    397260
atcttattgc caagaggaca ggagagccaa gaatgccaat gatgcacttg atatgcgagt    397320
cacggtcgat gaaagaatca agatattgc aagcaaattt ggttctcaaa tgcccaaatc    397380
aaaactctat cggttcccta gggagctctc attgttacca gaactcttat tccatcttag    397440 aaggggggcca cttttaggaa gcattcttgg tcatgaagac gagagatctg tgctgcggaa    397500
cttgtttctg aatgcagcat ttgatttgtc ccttcgaatg gtggcatctc gctgtctgaa    397560
aaaaaaaaag ttcctattgt aagaacataa aagaagcatt ccacagtcgt aggttcttct    397620 cttttctctgg cataaacaat aaaaagcttc aactaatccg atctttcaac cgcacttcat    397680
ggcaaagcgg tcttctttca agaatctcc gtccctagtc catacccacg tctggggaac    397740
ttcttcactt catgttcaca tctttgtctc cctctttcaa gtgagttcag ttagcccta    397800 gggtcagaag agagctcatc tttacttcct ttcctataga aagctactga ttctcttata    397860
gccttcgttc attttgttta agaaggctgc gacatataca gcatcttcc ttatacttt    397920 tcttgcctgg atgaaaatac aatagatgaa tagtcattcc ctcacaaatt ctttatttga    397980
atatctttgc tttgttcgtt ctacagatat agattcaact tcctttcttg gcaccatccc    398040
tattctgatg gctcagtaca agaccgacgg aagagaaggg gtgaaaaggc tagcgaggca    398100
gaattctttt tctcttcat agcgccgcac aatggagaca ttgtagtgct agaccagatt    398160
taccagcgga cagttgaaaa acgatacgac ccaggacctc cctccactcg tgggacgggg    398220
ttcttctttc tatcaaaata aatcgaattc gaaagcgcac caccttctt tactttacaa    398280 ccagcctccg acccaaggtg ctttttagaaa aggtcagcgg ggcaatcaaa aaagacttgc    398340
ttttgacgcc ccgctgtgcc gaccagcagc gggatgctac ttacgagctg gtcagggaca    398400
ggttccggtc actctttcga tgccatgcca ttgtggtggc acgggaacca ctgaatgggg    398460
gctgttttca tctcatcgct ggcgtgtgga agactagtgc atccaagcac agcgcagcca    398520
agagggtcca agattgcttc gtcgaatggg acggacatcg atcttcgctt ctacaaggcc    398580
```

```
tggtcgactc tttgtaggag ccttttttta tcaaggggtg acctggcttc ctttccttta 398640
cctttaaaca gttagagcct cttctcttat cagtcctttc agtcagttcc ttttcggtta 398700
gctacttagg atgaatcaca cagaggcgat ctctaacata agaatacaat attttcaaga 398760
gacagaaggc ttaagagaga tggggaactt ctctcctata aatcttcttt gcacgagctt 398820
ctgtaagccc cgaaacagac tccaattaca tgtgttaagc atcgtgccat ttcaaaaaaa 398880
atcaaataat agagaaaaaa cggctagaaa gaaggtcaag tgaggaagcc ataatcttca 398940
taagcagacg tgtgagtcta gctttcaatt agcgaagaag gaaggaggca aagcaaggct 399000
ttcttctttc tttcagagtg agaaacgaat cgaagcgggg aggcttgaaa ggtccttcga 399060
ggctcgtcaa tggcttggct tcaggtcgcg aatggaagcg cggattagcg ggtgtccgct 399120
tgactcagtc atagtctcgc ctggtacgca ctcgaagcct atgttcacta gaaaaatgga 399180
aaaaaaaaaa aagtgtgaag atccgcccat gattcatgga accattcctt cgcgtgccgt 399240
agcttaggat tcgtgctatt gctattgttt aggggcgtca agaccgggtt ccgacttttt 399300 cttttttgaga aagaagaggt tactggacaa gcgaaagaga tgccgaaaga gcagatgctt 399360
ttatttgaaa caaaagcatt agccgagaca tacctcccgc taaagaacac tattgacaat 399420
ggggtccggg aggccctcaa aaaaagcgat agagcaagaa agaaagaaag gatcaaaaca 399480
tcacgcacgg gccgcacgca aaagaagaga gaggatagcc agaattgtat tgaggccgca 399540
gcagcaagaa aacaagaaga gcacgtcttc ccaaacaaag cagccttcag caggagctgc 399600
actacaatgc ctcagctctg ggaacaggaa ggaactgagc gccccggcga ataaagaaaa 399660
cctagaacaa aaatggaagc ctaagccttc acatccgaaa ctgaaaaatc atcagttgga 399720
gaatcgtttt tacagggtag gcatggtgaa ggcagaatgg aaatagaaaa caactaaatg 399780
acttagtctt ggcttcttct tcctttatgg agagaggccc ctttagcttc aggggggaaat 399840 tcctatgtct ttcttttcatc ctctctgtct atggcctatg ccaattggtc ttattcggat 399900
gagttgcatt tcgttttcct tttgttagtt tctcagtcag ggccaaatcc ttctccctaa 399960
aaattccaga ttttctttcc tcggcgagtg aagtttctgc ccttgttgag tgagtaaggc 400020
ccgatcgagc ttatgtgctt gccaggtctt tcaccatctg cttttcctcg agaatgtgag 400080
actgctcacc ctcagtaatc gtattgtccg ctcttttcat tgattgtaca gcttctctcta 400140 aacaaggaat ttctagggag tcctcccagt cggctaaagg cgcaatggct tttggttttg 400200
aatccggcta aggttgaatt tgcttttgct ttagttgttg tcgtagagcg accttctgtt 400260
ctttcagttt tgtaagcctt ccacctctct cttagctttg catcttttcc attcggtcca 400320
agaactaaga gcggtcgaag tcctgtctca gggaatgggc ttgaaggcta gtggtcatat 400380
tagtcgtcta aggggaaatg cctttttccgg gcctatcccc attcgcctat cgctttcttg 400440
agttgatgtt taacttgcac ctagggggatt aaatcttcct tgaggtttta gtgggagttc 400500 cttttttgatg cccattcgcg agtggctaaa gggaaatttg cttgttccga tagttagtct 400560
aaccccttct ccgcagcatt ccattcgaag tcgtcgaaaa agtctaagac ggagaaagtg 400620
gtgatgctct ttgattgcat ccgcttgctt gatctttgat cgtctagctg tcccctaagc 400680
ccctctcttt agcctatgtt gtctcagtct tggatagagt ccattaccta tctttctttg 400740
tttgaatgag actatctgat gtccttttcat ctcaaactga atgtaataag agtgaaaaat 400800
taggaaattt cgtacgaaaa ggaggctatg tagtatggcc cctatccctt ctttttacgc 400860
cagttgctct gctccttatc cctttggggc tagacctcag ttcagatcat ccttggatgc 400920
```

```
tagcgatcct ttcaccgaag aactcttcaa agaggacact ggctttctat ctttgaaggg    400980
tttacccaca gaccagaggg ttaaggctct caccttcttt tcaaatcaaa gaaagaagag    401040
cccttcgatt cgggcccttt cccacctcct tagtatgaat ttgatttatc cttttctttt    401100
gttgcgtact taacctgaac cctgtctatg agtatagcaa tcctttgaat cttttcctaat   401160 ccgctttctc ttttttcttat gccttgggag cccagtcttt aggagaagca gctgctcact   401220
cgtgacaatg gatgcctgct tatgtcaaac tatcctcaat ctctttcccc taaagctagg    401280
atttttttct tagcttccgc tatttcaaga gtttgctgag cttcttgtgg atcaatgtca    401340
ctacccttct ccgcatcatt tactaaaaca gtgatctcat tattgcctat tctagcaaaa    401400
ccacccatca gagccatcgt taaccattgg tcgttaaggc gtattctcaa aatccctata    401460
tctacagctg tggcaatagg ggcgtgactt ggtaatatgc caatttgacc actatttgta    401520
gataaaatga tttcttccac ttctgaatcc caaacaattc gattagggt cagtacacta     401580 agatttaagg tcatttcttc gcattgctct ccatttctaa gttcatagcc ttcgcggtag    401640
cttcatcgat attacctacc aaataaaagg cctgttcagg aagaccatct aattctccgg    401700
aaaggatcaa ttgaaatcct cgaattgttt ctgctagacc aacatatttc cctggcgaac    401760
cggtaaacac ttctgctacg aaaaagggtt gtgataagaa acgctcaatt tttcgcgctc    401820
ttgctacgac taaacgatct tcttcggata attcgtccaa cccaaggata gctataatgt    401880
cctgaagttc tttgtaacgt tgtaaagttt gcttaactct ttgggcagtt tcgtaatgtt    401940
cctcaccaac gatccgaggt tgcagcatgg ttgacgttga atctaaagga tctactgctg    402000
gataaatacc tttggcggcc aatcctcttg atagtacggt agtagcatct aaatgtgcaa    402060
atgtcgtagc aggagcaggg tcggttgata acccacagcg gaaggcattc tacccaataa    402120
ggccgatact tcggatcctg cttggacgaa acggaagata ttgtcaataa atagaagtac    402180
gtcttgttca ttaacatctc ggaaatattc cgccatagtt agggcagtca aaccaactct    402240
catacgagct cccggcggtt cattcatctg accgtaaact agggccactt tagattctgc    402300
aatattttct tcattaatca ccccagattc tttcatttcc atgtaaagat catttccttc    402360
ccgagtacgt tcacccactc cgccaaatac ggatacaccc ccgtgagctt tagcaatatt    402420
gttaatcaat tccataatga gtactgtttt acccactcca gctcccccga atagtccgat    402480
ttttcctcca cgacgataag gggctaaaag atctactact ttaattcctg tttcaaaaat    402540
cgctaatttt gtatccaact gtataaaggc gggcgcagat ctatgaatag gagacgttgt    402600
actagtatct acaggcccta aattatcaac aggctctccg agcacgttaa aaatccgtcc    402660
cagagtcgct ccaccgaccg gaacacttat agcagctcct gtgtcaatca cttccattcc    402720
tctcgttaga ccgtctgtag cactcatagc tacagcccta actcgattat ttcctaataa    402780
ttgctgtacc tcacaactca cattaattgg ttgaccaaca ctatctcgac cttgaactac    402840
cagagcgtta taaatattcg gcatcttgcc cgggggaaag gctacatcta gtaccggacc    402900
gctsgtaacc tcgctcctga ctattcatat tcacggctta ttcataataa aggctgtaac    402960
ctcctaatca aggagtggaa ttctctgctc ccctcggaaa accccattgc tttgaccatc    403020
ctcaatgacc tgaggatgct tctagccttc aaagaagagc aattgaccac tactactata    403080
atggagaaag gacaatctgc cttctaaccc gaggtccagg tattccggcc ccagagagag    403140
agcgtgccaa agcccgatga atagacaggg gatggacagt cctcccgttc agggaagagg    403200
aaggggggga agtccttggc attcctgcct ttctgtcaaa aagacaataa acatagaaga    403260
gaaaaagact ggcgtcctcc cggaggtcta gccggtgaag gccaacttaa gtactgacct    403320
```

-continued

```
ggcttactta acttaatagg cttgcagagg aaaggcctag cccttggagc cgtaccacca 403380
agaagaagat cagggaatc tctaccatca ggcttcgaat ctgaggttga ggtctagcct 403440
ctcttttcag tggaagttga gctcgtcgga tctgctgccc gtgacgtgag tgatcgttga 403500
ccctgcccct tcttattgct atttgtgaca tcgagtgctt aagtgagatc agcggtctgg 403560
caggtccttg gacgctggcc cttatagtct agtctactcg gacctctact agggctagag 403620
ctagccggaa aagaaaaga cttagccaaa agaagtaca taataagaaa atgctccacg 403680
ctctaccttc cgtcctcctt aaactaggct ttcttgcaca gtagcctacc tttggtctca 403740
ggttcgctac ttgctagcct agagctgacc ctggctgtga tcaagaagtc tgcagctaat 403800
tctagtttcg gggtcgccaa agcattgaga gatggaagga atgctctgtc taaccgcaat 403860
gcttgtctgg cctctccagc caaattgaga aattctgaga gaaattcatc cttccttcta 403920
tctttttttt ctgaaaggcg ggtcttccta gtgggctcgt cgccactagg cagtcatctt 403980
tgatcctgat cggccgacct ttccgatccc gaaacaaaga gagttcggct ctcttttttc 404040
gctcattcag atgaataaat tccgtgaaga cgacgagaga tgccgcctgc tctttccgtt 404100
ccttctcttt cggagtggag cactcctctt tgttctgttc ctttctaata aaagcttggt 404160
acgtgttctg agcgagcctt cacgtgacgt gaacggtacc tatgaagtgg aatccgtttg 404220
tcttggcttc caactcataa gggagttgcg ttctgaggga ctcaaaatat ccacagctat 404280
tgtcaagctt gggcatacta aagaatgacc caattgagac cgtggccaca ccttgataaa 404340
acagtgatga tgtggtcaac cctggatacg tggctcttcg atgggggaag gaccacgcta 404400
gtcgtctgag tgtgtggtgt gtagtgggtg cgtcttagtg tcttcttact acgaaaaga 404460 aatgagaaaa tagatgattc tcgttctcga aactccactc ttttttctctt tcaaaccagg 404520 aggattggca tttggccaag atgtgatcta tctctttcct tggccttctt tctatttaga 404580
tccccgttcg tgatcccagc cctggaatca cttcactctt tattcaagag aataataaag 404640
taaagaagag gttcaagaca gaactgtgag cagggatatt tagctattta gccttagaga 404700
aaggctgact tgagagcccct agtcccttac ttttagagaa gaaggacaac tccgttcgtg 404760
attcccgggt ggggatcact tcactcctgc gcctgtagag tctttaagca tctttccttg 404820
aaaatcgact aagcgggaag cctacttgtg aagtgggcta ttgcagagtg aaggaaggtg 404880
ggttccagag aggattgcgc ctaccaaagc tttgactctg agagtgagag ttgttctgtt 404940
tgagttctga actagaggag agatttcgat tatcttcgat tctagggtct tgtgcttacc 405000
taagtgttga agcgtggaag cggaagatca ccctaggtga cttagtttaa gagcttcggt 405060
atatagaaag caaaagcata tttttttta gaaatttctt tcactttccc ccctccaaaa 405120
gagttctttc ttcctccatt agcatagttc caaacctcta ttgcttggat gaagagcttg 405180
atgccaaagc aatagtgcaa taggagacga tggccagtat gaagagattc aaaaggatg 405240 cttcccgaga aagcttttg cttctttac tcaactcgtc gcggcgagct aggagcatct 405300
agaatagcat aatggctatc ttttatttat aggcttcaaa caaagagtcc aaagattgaa 405360
agggcaccaa aggtgaaata gccgggataa gggctttggc tttctctcta atatgccaga 405420
tgccggtgaa aggaagggaa tgaaagatgg catgaacaca aaaaactgcc atttcccct 405480 agttggagtc ttagcataaa atagaaaagg aatggctgcc ttaactttac taaaagtaaa 405540
gttaagaggc agattccgga ctggagcatt aaaaggaaga cttgaagccg ctttagaata 405600
aagaaatttt ttctatgggg aaagcatcga atcctctctt ttcacgaatc cgcagcaaaa 405660
```

```
agacgcagat attttcatga agaataagct cttagatgta gcattaccgg acgtgaatct    405720
aaaggttaga actaataatc tagctctttg caataagggc ttttttcagg acaaatgcca    405780
aacgcaaaga aagcagaaga tgcggcttag ccagctcgct ctagtcccct acaataagga    405840
tgagaaaagg ccaaggagtg aataggaggg aataggggca atataggggc atcagtctta    405900
gctcttactg ttcgagaatc aactgtacat gaatgcccat ttataggctc ttccttaggc    405960
catcaaggag gaagcgaggg tgggacaagt gaatccgatg tgagggaagg attgcagcta    406020
gagtcgaaac tagggcttat gcaattgaat cagaaaaggc tgcacatgta atataagaat    406080
gggaggagac agccaaagct gggattgatt gatctattcc aaaaccacta ggaagggacc    406140
tattcctaag ccattttcag tagacagaca gggaaaagga ctaaaagat tcttcgcaag     406200
atgagagcaa gcattagatg aagccgactt tgtccatctc gcatatcaac atcctctatc    406260
gatagcctaa tatagcccca cacagagaac gaagatggtc ggtaggtcct tcctctattt    406320
caagagttct agtacttgca ttgcggtccg tccattagtt cgatgattct tcttcgcctt    406380
taagttaagg ctttttcaat caatctcata ggttcctata gctcgtccta taagaaagtg    406440
ttggattcaa agctggtgtt aaagagtaca aattgactta ttatactcct gagtaccaaa    406500
ccaaggatac tgatatattg gcagcattcc gagtaactcc tcaacctgga gttccacctg    406560
aagaagcagg ggccgcagta gctgccgaat cttctactgg tacatggaca actgtatgga    406620
ccgatggact taccagcctt gatcgttaca aagggcgatg ctaccgcatc gagcgtgtta    406680
ttggagaaaa agatcaatat attgcttatg tagcttaccc tttagacctt tttgaagaag    406740
gttctgttac caacatgttt acttccattg taggtaacgt atttgggttc aaagcccttc    406800
gcgctctacg tctggaagat ctgcgaatcc ctgttgctta tgttaaaact ttccaagggc    406860
cgcctcatgg tatccaagtt gaaagagata aattgaacaa gtatggtcgt cccctactgg    406920
gatgtactat taaacctaaa ttgggggttat ctgctaaaaa ctacggtaga gctgtttatg    406980
aatgtcttcg cggtggactt gattttacca aagatgatga gaacgtgaac tcacaaccat    407040
ttatgcgttg gagagaccgt ttcttgtttt gtgccgaagc aatttataaa tcacaggctg    407100
aaacaggtga aatcaaaggg cattacttga atgctactgc aggtacatgc gaagaaatga    407160
tgaaagkaat gttgtgttgt aatggcttgt gctaaaggaa ctgagagatg ccatgccacg    407220
atctttagta ttcctgctat cccaaagggc gggaaggaag agagcattac gaattgccct    407280
atttgagata gtctctataa ttaccaagac ccgtacatac taagatcgtt ctagcgaagt    407340
acgagtttac gaggcaattt ccttccgagc tcacattcgt tctagactct atttagatta    407400
ttatatctca taagagaaga aagatcgtag gaaaggtgaa gattcgagaa aacgtccgtt    407460
cacgtcaggc aatgtttcgt ttcgagattg gcttcagcct tctgcttaac acatgcaagt    407520
ctactagttg atcgaccgat tcccccgagc ttaggggtca attacggggg aatcggaaac    407580
tattgtatct tttctaaagt ggcattctcc cttttgagga ccggctttcc tattgatttg    407640
acttttgcgg gattatgaat atatcaatcg actcttgcat tcctcccttg ctttccaccg    407700
gccttggcct gaaaatgaag agtcttctct gctgacctat agagaggtag gaaagatttt    407760
ccctacactg gcttcctccc ctagctactg aggaagaggg atctcgaatc aatcaattcc    407820
tgggttgttg tattaaagaa agcttttagt gcgcgttgca tgctttgtaa tagtacgaac    407880
tcattatgct cgtcaactag gtcaagcagg tgaaccccct tacgctgtct gtgacttttt    407940
ttgccttcaa aaaccgatgc ttaaaacata gaattctatc ttctcagtcg tcgatcgatc    408000
attctctgcg gccaactaaa aaggatggaa aatataggca aattctgaaa tggaccgaga    408060
```

```
tggcctatac accaattgac tgagaaagga agattgttgc aagcccttaa aagtactcta    408120
aagcaagcct tgttccaggc agaggcccac ggaacggtaa tgaaattccc tgcctgcttc    408180
acttctttct ttattccaaa aaaaggtcca atcagaactt ttgctaaagc tgtcgatcag    408240
gtcggtcagg caacgataag ccaataggcg atcctaagag ccagatttct ttcttcgagc    408300
taaagaaggt tcacctaaga aaagacaatg tctgagattt ccgtcaattg acttttggtt    408360
ggctaatagc tcgtcaattt ctagattttc catggtaccc gctcattgat ggaattgatg    408420
cgtggaatgc taaacccaag agagtgatac cagcgagtcg ggcaagagag ctaggaatag    408480
ttagttagcc attcaagtgt gctattccta tggggaagga taactccttt ctctgacgag    408540
aagaaggttt gctttcgaat aaataagccg ataggcgaaa gaatagcacg agcgctagag    408600
cggtagggac ggggactaac ccaccatctt tagattttgg cattctttct tgtgacctaa    408660
caatttagat agtgtggaag agcaggacta tggtcaagtg atccctcgca taagagcgtg    408720
ttaccagggt cccccagttg gagaagaaaa ggcttgcatt cacccattcg attcgactcg    408780
aagcagacag ttcaattgaa gcgcgaactt cattttcacc gcctaaaggc cgaaaaatag    408840
gactttgtta ccggaaaggc gggaacaggc gcctaagaaa gagagccatc tttgttgaca    408900
gtagcatata cctcaatctg acctaccagc cttcgtattt aaacggatgc gtaaagaaag    408960
aaaaaagaca gacgacgctt gtagtaagcc gaaggagcta gcccaaccaa agtctgcctt    409020
tattcgctag gctcagtctc atatgtaacg ataccggct gacaatccat tctctctcat    409080
gggatataaa gaatatgtga attagaagca tccgaggcaa aaagaggtca atcccctag    409140 ttgggctttc ttcgagcaag ctcttagcga cgaagggact cgttttctat taattgttgg    409200
tgtgatcgta tcagctgtga ttgagtatgt cagtgtgaaa gaaacccctg cagatctgat    409260
cgtatcgggt gctttagtat gagtacgagt aggaactcct gcagttgccg ttgctagtgt    409320
tttcgtaacc ggtcttcttc ttagagtaag cgctgaaatt gaatctactc ttggcctatc    409380
agctcttgtg cactcattgg cagttctcga agaagcagct cttgaggaag catccaattc    409440
ccagtctcta tccaatccat gcggcaaatc tatttgtggt ggaaaaaagt caacaataaa    409500
atataggaac ttattctatt ttgagaataa caataaaaag aattgcttaa gtaaggtagt    409560
cgtttctttt tttcggtata ccccgctctg cgagtagagc gaatgaagat aaatcttacc    409620
taatctcatg aatatcctc actcaatttc tcgtctttgt ctgcatgtgt caaaaaacct    409680
acttgttcca accaatctat ttttttagaaa gaatatcgtc cgttgtttct ccccctgtct    409740
cctccttctt gtctttctaa ctatcatctt tctagttctt ggcaaaagtg acctctttca    409800
cttttacctt tcgaaggcat tcatagccgc ggtaagccgc accctctcgt ctttattaat    409860
caagatgggc ttctcgggcg tgctagcctt ggccgttgca tggtctctga aatttttttt    409920
cattgcagac tcatgtaaca tgatggctcc ttcgggggcc tctggctcag gatcagggga    409980
gagcgctgga ggaagggct tcaggtggac tgatttattt ggaagcagtt cccctgctaa    410040
ttccgaagcg agtctggacc aaccggcccc ggactctccc aaccctggtg aacccgcagc    410100
gcctattgct gaggtttatc atccgttaca ggaggacgaa cagaggcgtc gggagctcag    410160
tgatcgtctt gcactgaata caattaagga gcccttgagc gaagagattt ttgaggcaat    410220
tatagaaact caattccaaa cggaattgaa aattgagaaa gctcttcgct cggacatggt    410280
tcaggagggt tccatttag agaagaggca caaaattaga ggggcgctct tctattctaa    410340
aggaaggcca ttatcattgg cgacctattt ggaccacctt aaccaaatgg agaaccaggg    410400
```

```
gacccaccgt agcccgcctt ataaaaacct tatgaaagcc attttttgata agatggaatt    410460
tgacctggat tttaaaggaa tcaaaaaaag gagatactgg tagagctcat ctttgtcagc    410520
ggcattctcc ctttactttc taataattag atagattatt atggaacttt ctccccgagc    410580
tgcggaacta acgagtctat tagaaagtcg aattagcaac ttttacacga attttcaagt    410640
ggatgagatc ggtcgagtgg tctcagttgg agatgggatt gcacgtgttt atggattgaa    410700
cgagattcaa gctggggaaa tggttgaatt tgccagcggt gtgaaaggaa tagccttgaa    410760
tcttgagaat gagaatgtag ggattgttgt ctttggtagc gatactgcta ttaaagaagg    410820
agatcttgtc aagcgcactg gatctattgt ggatgttcct gcgggaaagg ctatgctagg    410880
gcgtgtggtc gacggcttgg gactacctat tgatggaaag ggggctctaa gcgatcacga    410940
gcgaagacgt gtcgaagtga aagcccctgg gattatagaa cgtaaatctg tgcacgagcc    411000
tatgcaaaca gggttaaaag cggtagatag cctggttcct ataggtcgtg gtcaacgaga    411060
acttataatc ggggaccgac aaactggaaa aacagctatt gctatcgata ccatattaaa    411120
ccaaaagcaa ctgaactcaa gggccacctc tgagagtgag acattgtatt gtgtctatgt    411180
agcgattgga cagaaacgct caactgtggc acaattagtt caaattcttt cagaagcgaa    411240
tgctttggaa tattctattc ttgtagcagc caccgcttcg gatcctgctc ctctacaatt    411300
tttggcccca tattctgggt gtgccatggg ggaatatttc cgtgataatg gaatgcacgc    411360
attaataatc tatgatgatc ttagtaaaca ggcggtagca tatcgacaaa tgtcattatt    411420
gttacgccga ccaccaggtc gtgaggcttt cccagggggat gttttctatt tacattcccg    411480
tctcttagaa agagcggcta aacgatcgga ccagacaggc gcaggtagct tgaccgcctt    411540
acccgtcatt gaaacacaag ctggagacgt atcggcctat attcccacca atgtgatccc    411600
cattactgat ggacaaatct gtttggaaac agagctcttt tatcgcggaa ttagacctgc    411660
tattaacgtc ggcttatctg tcagtcgcgt cgggtctgcc gctcagttga aaactatgaa    411720
acaagtctgc ggtagttcaa aactggaatt ggcacaatat cgcgaagtgg ccgcccttgc    411780
tcaatttggc tcagaccttg atgctgcgac tcaggcatta ctcaatagag gtgcaaggct    411840
gacagaagta ccgaaacaac cacaatatgc accactgcca attgaaaaac aaattctagt    411900
catttatgca gctgtcaatg gattctgtga tcgaatgcca ctagacagaa tttctcaata    411960
tgagagagcc attccaaata gtgtcaaacc agaattacta caatccttt tagaaaaagg    412020
tggcttaact aacgaaagaa agatggaacc agatacattc ttaaaagaaa gtgctttagc    412080
ttttatttaa tacaatacaa gaaaaagcaa aaatagctaa aaacagcctg cctccttat    412140
catatatatg agatgggcgg gccttttaaa gcaaagatg atccgatcca ctatcggttg    412200
taatcttctt gacatagaaa gtccttttt tccaattgat cgtttatgaa atggaagagt    412260
agctcatgtt agactgatgt gatgagcgag gcccctagcg atgggggaa aggggagtgg    412320
gtaagcgggc tcctttcact tgactgctta gttaggagtg atctttccca tgctttccgt    412380
tggtcaacaa ccaaccaaag tgctctatac ttcttcacta ctcgtacagg cttgacgggg    412440
ttaagctgta ttgagggaat cgttttgtct caatcaatca agaatgcctc aactggataa    412500
attcacttat ttcacacaat tcttctggtc atgcctttc ctctttactt tctattttgc    412560
gtgttccatt tttaatattc aatataggct ttactttctc tatgtgatag atcctagatt    412620
tcagcggatc attttctact tgaaattttt tttcttttc tttttagtgg tgcgcgctgg    412680
cttttctcctt tgggaaaaca tccatctcct tcttttccca cgtacctgtt ttggtattct    412740
tccctctgaa ctaagccttc ttcatttctg cttaaaccaa ccgcatcaag accctgagtg    412800
```

```
ggtggaatat gtacatcaag tgctaagaac cacccccagg atgtcggcca catatgaggt   412860
catggtccga aacgtcctaa acacagagat gtgtttttcg acgcgagaac agatttactc   412920
tatatacaaa cttatttct atggtcgaga ggacccttcc ctctttcttg atcctctcga    412980
cctggaaggc atccttcaag tccatctaga aagatggaa tttgatcaag ccgctctgaa    413040
cgaagtatta cgaagtctat gtaccgagag ggatgattcc cccttttatc aagaggtaaa   413100
gacgactcaa gctcattatt ttcgggactt tataaactta aagaagaaag ccgaattgga   413160 gatggggggaa aagctcaatt tgcatagaga gtgggaatct ctctcgagga agacagactt  413220
cttagagaag gagaactcct ctctcagaga aaaactttg cttctcgaga gggggccagt    413280
cggaaaaaaa gaataataaa gtaatataaa gcaataaagt agagaaagaa agtcccggtt   413340
tttttgttgt atagagagaa ttctccaatt tcccttcgt tattactttt ttttatgtca    413400
aagaccagaa gctggaaaca tagtttttt cattcttttc ttatgaggtc gtgtacaaca    413460
accttaaccg cacaagcctg ggctgggcct acctccatcc ctagaggagc cgtatgaggc   413520
ggaagctcca cgtacggttt tgaagccgag cctttccagc aatggggcct agggaccgat   413580
atgatgattg gtttaggtag ggcggccggc ctactacggg cacctgtagg gattagtgtg   413640
tgagaccgcg atccacaaac tgacgcatgg gactcacccc tttacttggg aatagagagg   413700
ggaaacatag catgtcacaa gagcgaggcg aggtttggaa ccctactgcg agagggacgc   413760
ctcgcgagcc gggcttttag agatgaggcc ttttggcgaa gccaagtcaa tttcgggcca   413820
ccaaaccctg caactgatga aaggcccta tggagtaaag ggaagcgtgt acgttgtcac    413880
actccctgcc ttccaaaggt gcctagagga cgggccagac gcagcagagc gacgaccggg   413940
gagcgggttc cccactggaa gggggacagg agacggccat ctcaaggcac atcacgacct   414000
acaggcaaca ccggcgagac ctgggaaggc aacccgattg ggtgtcagag gatccatagt   414060
acctgcagcc tcccggactt catattcatc atttttgaaa gcgaggggaa gggatctctt   414120
ttctgcaacg gaaaaaaacg gagcagattt gactcggcac aacctaacga tacatccaat   414180
accaatgatc tgtgcctaga atgcgttgct agatctctgc tctagaaagc tatacaggca   414240
acaacgaagg cgctttgacc ccgggcttcc ctttcattac ttctttcacg acgagagaac   414300
cgcgtccgca tcagtcgaag tggtggaagg ccccctgagt caaagggaga gcttctgcac   414360
ttctctccaa gagatacgat tcggtatctg aataggctga aggagagtga agaggcggct   414420
actttcccag cccacgggaa agcctcttct ttctggtatt cttctttgg ctttggagat   414480 cgagagcggg gtccggaaga gcatgatgtc ttcgtctgga acttcctgcc catcaagctc   414540
ttcggggcga ccgcctatcg atttgaattt gcctcctcag ccggaggcgg aaccggctcc   414600
ccctgaacca tcctcggaag agtaagaaag gagaaggaaa cggagtttc tcgcctccaa    414660 agagtataaa gaagcggagt gtcaccccaa aaactagacg cacgcatcaa ggcgttctgc   414720
caacgagcga aggcgatcgc tcaagaaagg ggattcagcc ccggcaaatg cgatgcagtg   414780
aaagacgctg cggactatgt ggccggtgac gtaaagata tgccggcagc tagccaactc    414840
cgctttctaa cgaggttaag gcatgaccta gaaaacggaa acagcgagac ctggggtctc   414900
atcgaacgag aagttcgaag atggagacca ggttcggcac gaaatcataa aggtttgagg   414960
acccgttggt caaaggaaag ggaaggtcct gcttccggga cggagccgta tgacgcgaga   415020
gtgtcacgta cggttccttt gagaagggtg tgataccacc acctatcagg cccgacgagc   415080
ggtccacgga gctgcatccc tactcacctg gtctatgcac atcgctctct ccaggaggtt   415140
```

```
ggccgcctat cctagatctt cccatttcca agaagatccc gggctcgatc tggtttagta    415200
tcaaggtgat tctttttctg ttcctatata tatgggtccg tgcagcattt ccacgatatc    415260
gttatgatca attaatggga cttggccgga aagtgttctt gcctctatca ttagctcggg    415320
tagtccccgt ttctggtgtt ttagtcacct ttcaatggct cccttaatta tgtgcgagga    415380
attgccctat tgagtaatgg gaagcgggct agtccccgaa aatgcccgc ccgtaagttc     415440 gtttgtcgtt ggggaaaaaa aaagatcttt ttcaataaat aagcccctct ctgataagga    415500
aagaaacaaa aaacctaata tcatgaatat ccttcgcccc ctatctcctc ctgcattgcg    415560
ccacttcatt ctttctgtga ttcttcttgc aaggcttatc ttgtgtactt ggctcttctg    415620
tcatttgatc ggctttgacc cctaccttat tattgagaaa gtcaaaggtt cttttttcct    415680
ccttgggtta cgtgcaattt ttaggctctt tggtttgcgg attccttctg tacttcttct    415740
ttcgatcgtc cctttggtac tagattgctg cttgcacatg caggatcccg caggaggtca    415800
acctgcagcg gagcaaccct ccaacctgcc ttcgggcgaa tccagcgaag ctagcgtgaa    415860
tcagcagcct gtgattcccg aactgcagcc tccccttctc gatgacaaca cccgtcgagc    415920
ggagctcgct agccgattga ggactcattt ttgggggta gcttatacca accgaatttt     415980
agactctttt gttcatactc aagtgcaaat tgaaaaagat ctcgaagccg cacttgtgga    416040
cgacggctat tctcgtgatt ctcttcttgc gagagagat cagatcaggg gattcatttt     416100
ctacccgaat ggacaggcgc ttagtgaaga cacttacgct ttgcatctga agcaaattct    416160
caattcgggt acacgccaaa gcattccata ccatcggatt gaaagagcca tcaatgacta    416220
gaatctcctt ttagattcga aattcttcgt tttttctcc caatttccca ctctttctgt     416280
gaggcaaaac ctcaccacac tacactacac ttcgacacaa gagaagagga ccgggcgctt    416340
tgtatcttcg ggataggagt tggcggtctt ctttaagaga acttcaatct aatactcatt    416400
atggatcaac tcatgtttcc actctatttt cattacgaag atgtatcacg tcaggatccg    416460
ttgctcaaac cgaatcacgc caacgttatg gaagttcctg gatcgtgtaa aataatagta    416520
gtaccgaaga cagcaccttc tatcaaaaat ggaaaattgg ctatggagat tccgtgcggt    416580
cagaaattaa tacagacaca aagggcttca acaggaaagt cgtttcgatc caatccattc    416640
ttggggtcaa ataaagacaa aaaaggatat gtcagtgacc tagcacgaca aagcactctc    416700
cgagggcatg gaatgtctaa ttttttggtc agaatatcca cagtaatgtc tctgttagat    416760
tctccggtcg aaataaggga aaggtcaatt caattctcga tggaaacgga attttgcgaa    416820
ttctcccccg aactgaaaga tcatttcgag atcttcgaac atattcgagg gttcaatgtt    416880
actattgtaa cttcggccaa cacacaagat gagactttac caccgtggag cggcttttg     416940 caaaaagatg aggggaaac tcagtaagat gtcggagaag agaagcgaaa tataggagat     417000
cacaaacgta gattgctcgc ggctaaatat gaattgagac gaaagcttta taagcccctt    417060
tgtaaagatc ccgatcttcc tagtgatatg cgggacaaac atcgttataa gttgtccaag    417120
ttgccaagaa atagttcctt tgcacgagta agaaaccgat gtatttacac gggtcgccct    417180
cgttccgtat atgagttcta aaaaatttct cgtatccttt ttcgtggatt agcatctcga    417240
ggtcctttga tgggcataaa gaaatcgtct tggtagcaac caccaaacca atagaacaag    417300
gggtagctcc gcagcaggtc tacaagcaag gtaagtaggt ccattaccag ccggctccgg    417360
accgaaaaga cctaacggac taatccctta tctcggatcg tagatgctaa cggggcggga    417420
atcgaagtgg gggacccctc taccgcctgt gtctatctcc tgtcaagtat gctcccaga    417480 catagactac gtacagggta gtactcttgg aaagatagaa tatcaccgcg tgaacataac    417540
```

```
attacattaa gttacgaatg taactcccga aggatcgacc acttttctaa atatagtaag    417600
gcggagaact gttgttcagt ggagcgccgg agtgcggagg ttgttcccat cattgaagtc    417660
agggtgtggg actgagcctt ccgaatgaga aagaagaaaa gtgcttagtt tcgttggaaa    417720
aaccaacgca aatatcatat tgactttctc tcgccctact tctaaagata gatagaaaag    417780
gttggaaaga atgactttct gaaattctct cctttctaaa gctgcgcaag gycgtggggc    417840
cccagaacaa aagcccaccc ctcttttccc ctttaatgaa ggaccctcgw rkwctattca    417900
tttgtgggtc tggatbcgvd gtctbtddtt ttttttttth btnnaggtga tttcgaaaat    417960
caaccaacgg aaaaatccgt agcccaggtg actcacagcc tccctctcgc ccaaataaat    418020
gaaatgggat gaatcaaatc aataagcttt ttgattgatt cagggcgcag cgaagccaaa    418080
ttcaatcaag gcaaggggc ttacttttcc tgaggctgat tcatcctatt caaatttagc    418140
tatgctaatg aagaggaaa agttttcaga tgagatggac ccccaagaga tgagcgagaa    418200
cccccaattg cttaggggtc gcactctgtc ccgcttggtg gacgaaatct tctctccttt    418260
tagaattctt tctcccacac acctttttg ccctctttca cttcaccgag gaggaaagaa    418320
taatcttcca agcggacaga gacctaaatt tccattagat tcattcctaa gcttgctttg    418380
ttgcagcaag atgatcagtc cgagagtgct ggagagaaga gaaagcggta aaaacctctc    418440
ttattcggtc accgagaagt cggacgactc ttcagtaacc cagggtgatc cgacccttc    418500
gacgctttt tcgctgtata ccccctccat ccttcggagg tggaagaaag ggtactctaa    418560
ttttaataat agtagggccc cagaacgcta aaaggtgggg gaacaagagt tgtcacgata    418620
gaaaagataa aaaaataaat gactataagg aaccaacgac tctctcttct taaacaacct    418680
atatcctcca cacttaatca gcatttgata gattatccaa ccccgagcaa tcttagttat    418740
tggtggggtt tcggttcgtt agctggtatt tgtttagtca ttcagatagt gactggcgtt    418800
tttttagcta tgcattacac acctcatgtg gatctagctt tcaacagcgt agaacacatt    418860
atgagagatg ttgaaggggg ctggttgctc cgttatatgc atgctaatgg ggcaagtatg    418920
tttttcattg tggttcacct tcatattttt cgtggtctat atcatgccag ttatagcagt    418980
cctagggaat ttgttcggtg tctcggagtt gtaatcttcc tattaatgat tgtgacagct    419040
tttataggat atgtactacc ttggggtcag atgagctttt ggggagctac agtaattaca    419100
agcttagcta gcgccatacc tgtagtagga gataccatag tgacttggct ttggggtggg    419160
ttctccgtgg acaatgccac cttaaatcgt tttttagtc ttcatcattt actcccctt    419220
attttagtag gcgccagtct tcttcatctg gccgcattgc atcaatatgg atccaataat    419280
ccattgggtg tacattcaga gatggataaa atagcttctt acccttattt ttatgtaaag    419340
gatctagtag gttgggtagc ttttgctatc ttttttttcca tttggatttt ttatgctcct    419400
aatgttttgg ggcatcccga caattatata cctgctaatc cgatgtccac cccgcctcat    419460
attgtgccag aatggtattt cctaccgatc catgccattc ttcgtagtat acctgacaaa    419520
gcgggaggtg tagccgcaat agcaccagtt tttatatgtc tgttggcttt accctttttt    419580
aaaagtatgt atgtacgtag ttcaagtttt cgcccgattc accaaggaat attttggttg    419640
cttttggcgg attgcttact actaggttgg atcggatgtc aacctgtgga ggcaccttt    419700
gttactattg gacaaatttc tcctttagtt ttcttcttgt tctttgccat aacgcccatt    419760
ctgggacgag ttggaagagg aattcctaat tcttacacgg atgagactga tcacacctga    419820
ttagtgagaa attctgacac caatcattta cgagtgagta ttacaccaag aatttacaag    419880
```

```
cggatcgagg aatgaaggga gaggaattag aatagaaaga aagagaggga tttcgaatta   419940
gagtaagggc acgctaagac attccttttc gtgctttcga tctgcttact ttgaataaag   420000
agaaaaaaaa gaatagaata gataggcgga aaggctttac acaagaccac agagcgagag   420060
agagagcctt cgcttacctg cttaaccgta ccctcctatc gtacctatat agcctttcct   420120
tcagttatat ccagtttcag ttctgcttcc aactaccgat gggagaaggc ttggacgtat   420180
agcaagatta aataagaggt attgcatacg ggaatgataa aaaaaaaggt tggaaacaga   420240
gctggagatg agcgctagcc aatggttaag acttcagaaa gcaccttagc aattaccagt   420300 aatgcccta tcgacctcag tcttgttttt tgctagcttg agttcataac tttactattt   420360
ttcattaaac gtagaatatc ccgacttcgc tagccagaac gaaatggaca taggagcgat   420420
cgattacgag agctcgaccg atcagaccgg gaagaagaga aagaaaggtc aatctccgaa   420480
aggccttcgc agagctgagc tttagggggg aatactttt gtggtcttgc acatggaaaa   420540
gtcaagtatt ctacgcaggc ttgatttacc ggaattttg cttcaaagaa tgctttcaag   420600
ctaggaattt aagcacggat agcttttattt gacaattagc tggaagtcgg gtatgccata   420660
aactaaggcg ctgggtagat cgtagattgc cgggtatgaa ttcgattcta agtcggagaa   420720
tgcccatgaa tagggtctta ttacagaatc cgcagttttg aaagtagccc tagacagatc   420780
attgctaaga ggagagcagg gaatttcttg ctaatctggt gctatcatcg tattctaatg   420840
attattccga cgtcagagca gacgggacta ccaatcccag agtgaattaa ccttgtctgc   420900
actaccacct tagtttacta gaccttgggg aattggctag ttaccttcac tccgcgtggc   420960
agcctaccta cgttttgtct ttttcctacg agaccttaga gtttcccagc ctttctccgc   421020
ctacatgccc cccgaaatca gattgggttt ttcttgagg aaggtccatc tgcttttgtt   421080
ttcgaataag actaaggcgt gagcgagggt ctctttgtgg tggtcttca ccatcttcct   421140 tttgattggc ctatatcttg gaataaggtc tttagctatt cccacagtac cttagtcccg   421200
taccggctgt cggtctatct catattcgca gaagaaggaa cttgcttaat gccatgccgg   421260
aagtgtaatt aagtaggcgg ctggtcgtag aatagtcttt tcagtaagtg ctgttgcagt   421320
tgtagaacca ttggccattg attcttcctc gcaaaccttt catccccgct gtctagctct   421380
ctcgtagtcc aaagcgaatt caatcgtatc cgcctttgag gaaaagaccg aatcagtctt   421440
tgagccatcc taataaatcc tcgtaggtaa tgctcttggt ctgccttcaa tcagtttatc   421500
agcctaaggc ttcgctctat tacctgtgtt gtaagctttc cagtctttga agtaaggttc   421560
aatgctagga aaaatgcttt tgcttcgcgg gtctatcgcc ccaataggtt ttgttaggaa   421620 atttttata tgagtatgcc cctatcccgt aagccttcca tcgttgcaag ccccttccat   421680
tcggcccaag ctttctttcg attacgtctg cttccgattc tgttattccg ttagcctgag   421740
ttagtcgttt agtcaaagcc gtacgtatgc cccttttcgaa tcgttctatc attcgaagta   421800
ggagctgggg ttgcgggcag agaactattg gtatagcgag ttcatgtgct tgcagttggg   421860
ttactaccat cccctaacc attagtatca cactctgtga agtgtctctc tggtattggg   421920
ataacttcaa gccccttagc tcgcttgtat cggggggagc ttacttcact tgtttctttt   421980
tagtcacttg ccaggaggga aagcagcaga taaagagcac catcacctta cttaacaaag   422040
ggcttatgcg aaagagagca ccgcttcccc gataagataa tccgctttcc taaaatccct   422100
actttattgc tctagctctt gactcatatg gcactgaaat tggataggtt cacgcttagg   422160
cctggttatg gaaactcttt aagcatagga aattttcct tttccataag aaactccaac   422220
ttaaacagga actggcctgg aactatatgt aagggcactc tcatccactg gctgcaagga   422280
```

```
aacaactgga ttggcctttc taactctctt taaaagagac tgctttcaaa ttcacttgcc   422340
ctagaacctg cttttattg agattgatct agaatccgct attcctagtt tttttattat   422400
tcctagccag agaaataaaa caaatctcga gatccagaaa cctatctata cgcctagcct   422460
taagcaaaag aaatctcctt agccctacca tagaaactat tacctcgact tggattgaaa   422520
ggaagaactt aggactttgg gacttcccct aggactccaa cccctagcat tccaattgaa   422580
actcaaggag atggaactaa acaggcttag gccctttttcc tctttcaagg agactagagg   422640
gaatgcaact actgagacag caactcaaac aaaatcccga gagaaaataa aagattagtg   422700
aggtaaggtc tatagactgt aaggcagaag gcttgaaagg aagagcactc ctacttactt   422760
ttcttttggg agaaatccta gacaccttag acaccggatc ctcgtagga ctcttatttg    422820 ataggcatta ggggatttga ggttttgggg tttcacttgc agacccagcc ctgctgcttc   422880
cataagtctc ctatcctaag tttctttctc tgcatgaatc aagttcttcg acaggaccat   422940
cccgaccgag ggctaatcat agatctacta tggtcttttt ttttttttta ttcttttatc   423000
ttatttccgg ttaaaagcct tttctggaag cattatgttg agtcactcca agagtagaat   423060
cagcagctca cctcacgttt taggaaccaa atgaggaatc acacgtagac ggacctgagc   423120
attctcctgc tctacggagc cctctggagc tagagttggg gctgcttgac gctcttctcc   423180
tttcgagtga attgaattac ttcggctcgg atgcctttga tcaaatggaa ggatggatgc   423240
ctgcctttag cgacttcgtt cggtcattcc ttctttactt gttcgctatg gcttgagagt   423300
taatcgcacg agagagtaag taagagattg aaaggaggat cattggacct cgctctcggg   423360
cccagaggca gagcaaagaa agccttagat cttttgcttgt ttcgtggtat ggaccaaagc   423420
aaaggttctg ctgctatcga cacctaccca attaaccaaa agtataatcg atcgagaccg   423480
aagcttatgc aattgtggaa ttccgttcaa atagaaagct ttttggccag ttcaaggtca   423540
gtcgtgagct gtaggaaaag atagtagcga accagaagaa attcccgtag ttgcataagg   423600
gggacgttga aaacattcca gcagatagta tgtaatactc ttctcaaaac gagcactata   423660
ctctttctta gtttagggca gaaacatact caaggaatgc aaagctaacc ctaaaaatgg   423720
aatattacct cagctcaaag gttgtttact cagatatttc ttatcaaagc gagggattcg   423780
tttcaggcga aatcaaatca gaagctattt ccgctctacc attaattgtt gctatttccg   423840
cacccctgtc cggtggtttg agaaagaaag tcgagacatt cagaaagaga gttatggcat   423900
ttctaggatt ctaatatggt cctattgatt caatctttat gcttggcccg gaactcttgt   423960
ttcgagtgaa agggagagca gtggcccgca ccgcattcac cggtaaattt ccctctacgg   424020
ggcggggtgt ggaaagcact ataagttagt tgacttctcg accaaaggta gtctagctca   424080
acctccaagt aggaatagat tctatgagtc gtgatccagt taagataggg ggcatttcta   424140
gcattgaaaa tccctattct tattgaatag ttcaaataac tagttgaaca tacctattct   424200
tttcaagaat agcctcccct tatcgaaaag aagggtccga agaagacaga actggccatc   424260
cttctcatcc ccctaaggaa gtagagcgcg gtgaaagaat tccgtcgttc agtcgaaggg   424320
gacaggttag cagcttcagg ataacccgag cagtgaaaga gaagtagggt tcagkytgwt   424380
agatttttat ttattattta tcgtgaatgg gggaatcatt acacatagta tatcaaaccg   424440 gcgtatttt ttgttttacg ccccgtaact cttcctcagc caggcttggg cagaatagca    424500
gagcaagtat tagtagcata acaaaaaggc cttcctcatc aaagatgcag tgctagtaca   424560
tctgagactt cttaattggc tagttgtaaa tagccccagg gctatggaac aaaggattat   424620
```

```
ctcggaccta gaccgaggca ttgatggtga ttttctaatc tcgcagaaca gaatgtgata   424680
cgatgagata gaatgcaata gaaacaaaga ctgggaacgg gttacctact cttaacgggc   424740
aaagcgagcc cctttatttt attctgaatt ctttaattca gaatcaatca aatctcccca   424800
agtaggattc gaacctacga ccaatcggtt aacagccgac cgctctacca ctgagctact   424860
gaggaacaac aggagattcg atctcataga gttcaattcc cgttcccaac ccatgaccaa   424920
tatgagctcg aagcttcctt cgtaactccc ggaacttctt cgtagtggct cccttacatg   424980
cctcatttca gagcatcymg gacaasgagg cggcgatsaa ccatccrctc tcgagattca   425040
tattgatcaa tagatctccg cgtcctgcca gttcgctaag tagactcact ctaccgaggg   425100
gcaacaaagg ctgaactct tcctgccaaa aacaagggac ctacttctca tcctaggagt   425160
tagcaggtat gaaagagtcc cctctctgtc tgtctctccg agtttctact actaagtagc   425220
acttctgcta ttcaatcata gaatcgattc cgatcaagct gaaaaagta agccctatat   425280 atgttattag taaagcgcta acgccctatc tatagtaagg ggcccttttct tgctcgttag   425340 cgctcttttt tgattgcagc tagggcgccc cttttctttc tcaaagtcaa cttttctcgct   425400 tgttagtcaa gcttttgaagt ccctacttta tttagattta tgggatattt gaagaagggc   425460
aggtttggaa ccctataccct atacaagggg ctggtctcga tctcgcttgg tggtacccct   425520
ctcgatgatt gttgactcaa cattgatttc gtgcttgagt tggagggctc tccctccatc   425580
catccatcga gtcaagtaat tcgctatcgg aaattgatcc gccgcctatc tcatgccatg   425640
cttcttcttt ctccgaatcg gtttctagtg tcagtcaatc aagattcgcc atcaagagag   425700
ggaagagcct tgactttagg ttaggccggt ctcatcattc acgcaattcc cccgtccatc   425760
gattgatcac gcgagtacgc atccagtcag cgcatagcga atgaaaaaag cgttcatcct   425820
ggattctctt cctcaagaaa aatggctatc aattgatccc tattcattcg gtcaaagtct   425880
ccacttttca cgcccctcta ctaagagatg caccatgttg ataggaatcg gcaaagacct   425940
tcttgtacac gtcctcgagg gcagcattca tggcaatcat cactactttc tcccgagggc   426000
atggtatggc tttgttcttg gtcttgttta atagatgtcg agtgccgctt ttccccgtcc   426060
gagaatctcc atctgctcta agtgggcgcg agctagaatc cttatgtcag cttggttgtt   426120
caaaagactg tctctttacc ccttccatct tcatctttc taaagcccag accattcttc   426180
tggatctgca ttagtcctat ttcaggtgca aagcctcttc aataaagacc tctttttttt   426240
ctttctcccc catttctcat tttgttgatt gaaagagaat aagcgctatc cattgagtaa   426300
agagagggtt tgctacagtg attcgggcgg ttggtggccc cttcgagagt tgcgggtcct   426360
tgccgctgca tgagtgttag ctcacgctca aaactcctcc gacacgagtc ctagtcgttg   426420
cgctgcggtc cgtttcccgg cttcgcttgc gcgatttgca cttctgattg gttccagcca   426480
tccccaacct taatgaatgg actatgaagg ggttagtcaa gcggtcgggg ttttcggtcg   426540
gttcccgttc gccttccccc ccctcatag tccattagtg ggtagggtgg tcaacttaga   426600
gggcgcccgc ctcctcttca gacgtgtcct cgacaacctg gcggttcttc ggtctccgct   426660
tttgggggcg ggagtgcttg gtcgctgggg tttccttttc cccaaccaat tcggttgtgt   426720
cagccctgag attggtctaa cattttgtta tgagctggct ggacaaagat ggattgaagg   426780
tcagatagat ttgagttcaa gtggcacagc accttcgatc gaccataggg cctattctac   426840
ccttaccgaa ttcattctat tgaagcgtaa ggtaaaaagc tccttctcat cttgcatttc   426900
tttggtttgg aagttccaga atgttgtctg tggatttcta taacaaagga aagcctccta   426960
ccctaatact atgccatttg attgattaaa gttccgtgct gctcaccact cctcgaggcc   427020
```

```
aaggacgggg tcgaaccgtc attccaggat ttgcagtccg atacatttcc attatgttac 427080
ctagccaaac ccgccacctc atgtgccaaa gtcaaagggt tgttcttcct tctccgctcc 427140
ttctttttct acatatgcgg cggcgggtta ccagagaaga ggggacaact tctttctcct 427200
ttgccttgct caatcttcct tttctgattg aaagttgcaa gccactcgac tattggtaca 427260
gaggccagat agaaggttgc tcatccagcc cagcggatcc attgtttatg cggcagtgca 427320
atgcagctga aaaagggaag ccccttttta ttagtaaggt ataggttggt tggggaaaac 427380
tccaaaacta gggttccaaa ttaccttata ttatagaaaa gtttgagaaa ggggcacccc 427440
tactatacce ctaaactaca agctagcgcg caagggctga aaagccgttg ttgcttgctg 427500
cttgcaggct cgaaaatctc tctttctcct ccctgtctca attctgattg attagcttct 427560
tccttcgcgc aagctacggt ctaacgaccc ccttgttgtg ttgcattttg tgatcttccg 427620
cttcagtctg cgttttcgg atagccggga cccgatgttg atttccgatt taaatgtcag 427680
ctccaggttt ggggcggccc atctgattag ttcagctatc actgctggaa accccagcgg 427740
ttgttcggct gcgtactccc cgtctgccta tctcacactc ccaaagcaaa tttggatttc 427800
ttctttcatt ttccttttcct gcatctttct ttttttaag tcattgatct catatctata 427860
agcagggggg tctgcgttca ctattaagcc tacgcccgtc cattccttc aagcttgatc 427920
cttcccttag actcgttacc ttgttcgact gaactcgttg gttccgcgct ctattcggtc 427980
gtaacccggt tcgagaacct tctctcatag attcccttta ccaagtcatc gccagcaatc 428040
agctcttatc ccttggtgtc aaagggcgag ttccttcctt gtcttgccca aaaactttct 428100
ttattctcat tggagaaaga ctctcccgcg gcaaggtttt acacataggg ccagctgctt 428160
tctttatctc gcttgccctt agtccgtcta gcgccttcg gttggggtcc gccctggggg 428220
ttaggttaga ccgcttgggt ttttttctag tatcgaaggc agtcaacgtg tcagccattc 428280
ttcccccatt agacttgtca atcctttgct cttttttcctt ttctcttcca gttctccccc 428340
tctactttat ttgacagggg cggagaatac cactctatca ataacaagaa aaaagtagca 428400
attccctttc aaatggtttg agcttggaag caacctgcta tctatcgata ggcgagaaca 428460
gactgctatt gactgcttcg cctatctatt ctattatggc cggcttggag acatcagagg 428520
aagaccatca tctctatccg ggtacgatca tagcttcatt cattcgttga accttgggga 428580
tcaccattag cattgaggtc aatcaccaca ctacctctat catacatacg acattacacg 428640
aagcgagagt gcatggtcaa cacacaccta aagcgcctac gttccgcttg cagccaatac 428700
aaccacaacc taacttgcac gagattcaac aaccgaagct actggtagtc ccgagggggc 428760
ggcatcctcc tataatagtt agcagtactg aacaagcgag tcatcggtcc gaggaaagaa 428820
aaggaccgcc tttgaaaaaa aaaggaact cgctaggcct tcagaacaaa ggcgattctg 428880
ttcatgcttc agacgatctg gctaattcta tatacaacta tctaatttc ttcaattata 428940
tagaaaggcg taaggcgaa ggcctattta gcgccttcc aaaggtaacc ggttaggttg 429000
actttggaaa ggctactaag gaccgggtga agaatgaaaa acgtccgcta aagcccacgg 429060
gataaggttt gcagatgcga tcatgaatcg aaccagatcg aaacattcag ctgtcgacgg 429120
acaaagccgg aacgtcgacc gcaaacgaag gatggccagg ccccggttcc cagggttagg 429180
gtattcccta ttatgagcct actcagatca gaactaaact agttgattct ctttggccgg 429240
ccggctttaa gcaaccttcg catttcctgc tgagatccca agtctccaag tgggccctct 429300
tggccacccca cgaccttggc ttttagaga atcccgctcc tgtgtcgtag gacttgtagc 429360
```

```
tcggcagtcc accgggtggg tttgtttatc cttccagttt cgagtgtctt cttggatagt    429420
tatagcggcc cataggcgcg agatgtacct tgtgggggggg ggcggcggtc ccctggacat   429480
agtcctttca ggcagtggcc gtttagtcca tggtccattg gatggtcggt gcaaggccag    429540
aaattggaac acattgattc cgctcgttcc cgtccttcgc ttcagggcct gtccctcggt    429600
gtggtcagta ctccatactg tcgggcagcg aagcttacac ttgttcacta attatgacgg    429660
ttcaccaggg cctctttcct cctccttttt ctgctcactc gtaggggtcg ggaccccac     429720
aaaggggggag ggagtcgact gaacatctca gccattggcg ggaatttcgc ccgcatccga   429780
tccccaattc ttgttcaccc cggatgatcg tgtcgggtga attgtgacct cgtacgatcg    429840
tgtcgggtga gcaacagccg cttcgtcaca gtacttactt atgggctaac aggtcacact    429900
ttggccaagt atcctacaaa gagactcccg agagccagaa gtattaaagg aatggccata    429960
ggaatgggcg catcatgaca tcgtaagatg tctcgcccga atgaattagt tggtactaga    430020
aatgttagaa aaagtgaacg aaaggagtaa taagaagtga aaaggacaga gacacttccc    430080
aaccagaaag caaagttccc actgatggta tacttagtgt aagcgagctc taagatcaca    430140
tctttggaat aaaatccagt tagaaaagga aatccaatta gagataagct gcccatgagc    430200
atcatggcat aggtaaaagg gaacgaggag gcaagccccc ccatcttccg catatcttgc    430260
tcatccgaca tggcatgaat caccgaacct gcactcagga atagtaatgc tttgaaaaag    430320
gcgtgattca ttaagtgaaa gacgctaacc gaatagttag agatgccgca agcaaagatc    430380
atatagccta attgactgca agttgaataa gctatgaccc tctttagatc attctgtaat    430440
attccagtgg ttgccgcaag gaatgacgtc atagctcctg caaaagtaat aacaatcaaa    430500
gccgtaggtg ggtattcaaa taaaggggag caccttgcta tcatgaaaac gccagctgtt    430560
accatagtag ctgcatgaat caaagcggat actggagtgg gaccctccat agcatcaggt    430620
gaccaagtat gcgatcctat ctgtgcagat ttcccaacag caccaataaa aagtaaaata    430680
caaataagag ttatggcatt caatctcata ttgcaagaaa tccaagaatt tctggggca    430740
ctagcacgag caaaaatggt tgaaaagtct actgtttgaa atagagtaaa acaacccaaa    430800
atcccaggag ctaatccaaa atcacctact cgattgacaa gctagctttt tatagctgct    430860
ttatctgcct gaagtcgtgt aaaccagaaa tgaattaaca aatatgaagc aagacctact    430920
ccctcccatc ccaggaataa ttgaagagag ttatctccag tcaccaacat ggcataaaa    430980
aaagtaggaa tggataaata acacataaat cgagggctat gcggatcctc agacatatat    431040
gaaatggaat aaagatggac caagctactt atgaatgtaa ccacaattaa catcactacg    431100
gtcgggctat cgaacacggg gtcagaagtg aattacgagt cggaccaatc tgcgaatcga    431160
gcgagctccc cttgcatgca atgatgtggt ggtaaacctc tcattctaat tcagtgctct    431220
ccgaaccgtg cgggaaggtt tcccatcaca cggctcacca acttgatctt ccgcgggaac    431280
cgtatgtccg aacaggcctg gaaaaaaagg taaggtctcg ctttcctttg ccactcaagt    431340
gtacggcatc tgccgtgctt aggccccttc ttcccttacc taatgaaaga gtccaccgcc    431400
tgccttagta gtctcaaata aggcgtgcag gcctgccccct ttagtaggtg attcactacc    431460
gaagcgaaga aaaggctgga tcaatcaaag ggggtactac gagccctctg ccccacgcat    431520
ctaaccagct cgcgtggttc accggttcca ccgactagac caaaagagtg attcagtcga    431580
tacagaggtg cgcttgaagt ggggggtgtg ctgtccctat tgggctgggc ccttccccat    431640
aaggccccac cgtcggggca taagcgccct cttgctaccc atatgcgagg cgccgtctta    431700
gccttccctg accaggatcg ctcccacacc tgtagcgttc gtgatcggcc tcctcaactg    431760
```

```
tgtatcgatc gaaaggcagg gcggcacagc ccccaaccaa gggagtggtt acgtccagta 431820 tgtccccct tattcccgac atgctatggt accccggagt gggtaggagc gggtcgagtc 431880
cgtatcgccg cggagcaaca gccgcgtccg gatctgatct attgactcgg caattcatcc 431940
ggtgacttca cggtcgccaa agaagcccca agaagcatca acatttccg atgagatcca 432000 tggagcaatt cttagatagc aagcactagc tcccggtgcg acttcataaa agcaatcaa 432060 agagaagatc gaagagaatg aaacgcacgt agtggttatt atagcggttc cttctttcc 432120 tagaaaacgt ccgaaacaac ctgctacaaa actaccgagc aggggtaaaa atacgataag 432180
tagatacata atttcgagtg tgatcagaca accaaaaatc agacaatgac agagcggcct 432240
ttatacaagc tgtatattgg tttggtatat tatcctatgg ctcgctagct tgacggtcat 432300
aaaatgcgag tcttcttcag aggggaaaa ggcaagtcaa ggtcatattg ggaccgtgct 432360
tttagaatgc acgcatataa tttgctacgg tgggccccac agttctctat ttgattcagg 432420
tggttcaagt acgtacccaa tgtaagaggt tttccttgag gatagaagag gatacctcta 432480
atctggtgcc ttttcgcgac aagttgatcg tcggacacca agtcagaacg aagtgctctt 432540
tctatatgaa gttctgcttt cgcttgggcc tcaattattt gatcaaaaat actatcgggc 432600
aagggacgcc ctatagtatt tatgctcaga cgatctgtca gctccagacg cctctcccct 432660
tcttcctgta atgggtggta aacctcagcc tcgggcaaaa taggcgccgc gggttcgcta 432720
ggtgtttcgc cggtttcagt ggaactgcta ccgaataaat cgctccacct taattcacct 432780
gagccagagg aagccatcat gttacacatg ttacaatccc caatgaagaa tttttgggac 432840
aatgtaatgg ccaaggctag tccgcctgag aagcccatct tgatcaataa agacgagatg 432900
gtgcgccttc ccacggctat gaacccttc caaaagaaaa agtgaaaaac ttccccttcc 432960
ataaagatta gagctataat tagcacaatg gctattatta gcacaatacg gtaaaaaaaa 433020 accgcttta aacctgtttg catcggctcg tgcacagatt tacgttctat aatcccaggg 433080
gctttcactt cgacacgtct tcgctcgtaa tcgcttagag cccctcttcc atcaataggt 433140
actcccaacg cgtcgaccac acgtcctagc atagcctttc ccgcaggaac atccacaata 433200
gatccagtgc gcttgacaag atctccttcc ttaatagcag tatcactacc aaagacaaca 433260
atccctacat tctcattctc aagattcaag gctattcctt tcacaccgct ggcaaattca 433320
accatttccc caacttgaat ctcgttcaat ccataaacac gtgcaatccc atctccaact 433380
gagaccactc gaccgatctc atccacttga aaattcgtgt aaaagttgct aattcgactt 433440
tctaatagac tcgttagttc cgcagctcgg ggagaaagtt ccataataat ctatctaatt 433500
attagaaagt aaagggagaa tgccgctgac gaaaagattt ctcttagaga gtaggtactg 433560
tctatgccat tggtaagtag atctaaatag atcttttgta gtccgagaaa ttttctgtc 433620 caagactcgt ctccattttg cttcaaatcc ggagtttcgt ttcactggtt gtgttaaaat 433680
aatctttcaa tcctattagt aaactattag cgtaccaaag ctcaagcgag cggccacttc 433740
ttcctctatt cgatttttct tcttcccagg cccgggtagc tttggctctt gttgaagcat 433800
tgccggaagc ttcactctgt gtaaagtaag gacttagctt ttacggggaa atccccgaat 433860 ggggaccta ggagctttgt tcagcactga cctttctag accgatccct gcgtagaagt 433920
gaagtttcaa agcgctaata atcccatctt ttcacgaata aactgattct ctgcttgctt 433980
ttggggaagc cctgcttgg cccttttactg gcagtccttt gtaatgcccg aacccggct 434040 actaccgatt ctaaattcta cgggtaaccc ttcccatgac tacttcttgt cgtaagacag 434100
```

```
ttcgcttacc cgattggctg gggcttagac aagacttaaa aacaatcact aaaggcctgg   434160
tgaagctcca cctttccat ccgctgtctc tcttctcgct accatgttga aaagaaaat    434220 tcgtatttga gagaatcgta aacagaggat ttcggtggca ccatctatcc atgaggaaaa   434280
cctttaacag tagactagtt ccatagtatg gtcagtcact catgaattcc ttctcgaatc   434340
actactggaa tatagcaaca aagcttgaag caagtggaaa tgcgtcaagg gcatttcttt   434400
ctcactggaa gcctacttga gtagtgcgtt ggatctacac ttggacagct tcatcgagac   434460
ttcacatacg tagcatacgt agattgccat gtttatatcc gaacgaaaac accttactga   434520 tgttttgtt tccagactta aatctttaac tataagaagg gaatcgattc aagccagatt    434580
acttgaccgg tcttaagctt aagctaacta agtatatgta tgtgaggacg gccatccggt   434640
tagctgcctc tgctgttctt ccagtccttc tatttacttt tttgcctttt ataatctata   434700
tcgtatatcg gccttataaa cttctaaagc ggtaaagatc taaaaagata taaatagaac   434760
ctcgtttgga gagtaattgc ttgttaatgc agtaagcagt tcgttcgact cgctcaaaga   434820
ttcgtctcac taataaggaa tagtcacttc gtacctcttc gaggaacgaa gtcccgcgac   434880
caaatgagtt gaactatgtt caacgaattc ccgtagggag agggaatgtg gtaccgaacg   434940
gttattgtgt gtcaccaagt acttccactt gtcactgagt aaggtaaagc cacgagggta   435000
ggtgggaatc tttcctcaag gcgcaaccaa cccagtaaga agcagctccg gggaacctct   435060
agctagttat gaaactacgt ttcataatta caatgaatca acaccaaccc agaatgtgga   435120
caacgtcttt tccgaccgga gaatacgtta ttaggtaact agagtcaagt gaggaatgag   435180
aggtactcgc tcttatccaa agacgatcta gctgcttatc cgggccttca agcaagttca   435240
aaaactctca ctatgtgaaa tcaacgaatc gttacactct agccacttcg tacctagtcg   435300
ctagagattc ctctcccgtt ggtcgagaga cttcgtacct ctcccgttgg tcgaattcgt   435360
tgttcgttga actatgtgaa acgaacttcg tacgttggtc gtacctcttt cgatagatag   435420
tcagagttct tatttctttg acctttgaca cttgctggat tccttctggt tgtcacatct   435480
tgtcaccctg tctgctttgg ctatctgttc gtaatgcttc cttcttttct tcgatccttc   435540
ttaacttgaa tcatgaattg gattcgaacc aatatctctc caggatctcg gcatccctcc   435600
cacctttcgg cgagatattt gccgtgagca atgcgacatt cccaagacct aacgagagat   435660
ctctctctcc ctctcttttt gggcagagat tactgctttt agtttccatt gccctaagcc   435720
tgtcgctcgg cccgggcgcc catgaggtgt ggttcgggtt cctcctcagg cgaacatgaa   435780 aaaaaaaag gggtttagtc aagggccaaa atttggtttt atgccatgtt gtctttacac   435840
agctctgaaa taccccccac ctaatatata tataatatat atatatagaa acaaccaacc   435900
aaagagtacc agacagataa cgtcttgcaa atgcaagtag catgtaaaac aatcaaagat   435960
aagatcgaag agaatgaaac gcacgtagtg gtcattatga atgaatctcc cagaaaacga   436020
ttgactatat atactggtga taggaaacaa gtcaaattca tgacgaaggc tatcatatag   436080
agtcgaacaa atttggggca aagccacatc ggggctatgg gagtcgaacc caattcaatt   436140
cttccgcgac cctttctctt ttctacgaaa atttctgttt cgctgctttt ctaaactaga   436200
cagagtgcgg taaatcaat ctcgactgtt cactacgtac gatatttctt gaaatttgc     436260 atgaagatgt gatcaaagct acatgttccg cttttcctca atgaaattac agagagagtg   436320
gaattggaat ttagcactgt gcggagctct cgctccttct ttgcttttct gatctcattc   436380
tggacatata gaggagatag gaaccttacc ttatctatga aattatgaaa taatgatctc   436440
acactcttca agacagattc gtgaaaggta tatctacgcc atggaagttt catggctgaa   436500
```

```
tgatttgtct gctaccaact ccttcctcta tgtctatgct atgggcagga tctctctctc   436560
tacatgtgaa atcttgtata ataatttctc acataccaga ttcccgagga agaaagcaag   436620
caagcctata aagatacgag gtttcaccag attacaggta tggatccggt atgaaataga   436680
tccctccttt tttttatccc ttaggagcta actaagaggg caggcggaca cttctcttcg   436740
ttagacaagg aaatgctttc aaaataaaag cattatgtga ttggttgtcc ttcttcactt   436800
caattcttca agaaggacct cgccaactta tgttgttcac ccaccccctt cggataggcg   436860
cttccgttct ttttcatat ccgcgagaat gggaggtaag taagaagtaa ggtggagact   436920
tacatatatt atattatgca acttatgcaa ctcagtgacc tatcctgttc ttgggatgag   436980
gcttgacttc tcagatgctg cttctccttt cttgtcttgt ggcagggaa agacggaaaa   437040 aaaccttctt cgcgaacctc tcttcgatgc cgtcttcttt gcgcccctct cccgttggtc   437100
gaatgagttt cactatgtga aacgttggtc gagtgacttc gtacctccta ttagggacat   437160
ctttgtgaat ttaactcacg agatggcctc atttatgttt catttaaaca aaaccctgat   437220
ccctctattc tatgggccga gtggatcata tatccattcg atcccaggaa tacggctata   437280
gctaattggt gccttgattg gtttgagcga cggaaaccta tcaaggtatc ccattagtta   437340
caggtaggtt agcgcagaca ctctcagggg ctgggaactt tgctatatgt aactatatca   437400
agcaaagact tcttgctccc gtcaatgaat gtattatcta caatagagat ggatagtacg   437460
tatgaccaag agcggcccat tcttaggtta gctcgtaagg gttaaagggt tataataata   437520
cttattgtta tgttgttatg acctgaaaag tgcgaccgac agatggttat ctatcatttt   437580
gattcgggac aacatatggt caactatccg ttgactaaga agattcatga gatttcattc   437640
ttggcaggtc aacctttagg ttacctcggc tcctggtcat ttctcaccac tttgtcatgt   437700
gattggcagc acaaatgacg tatccagaac ggtcaaggac tatgccatat taggtgatga   437760
tgttcttatc actgatgatg gggaattata ggatgagctt ggtgtgtcta tctctgatag   437820
gaaatctatt attatatcaa atggcgtacg gagctgctta ccctctttgg atcgacagcg   437880
ggggggaaac tggctctggc tttgttgtaa tgagcatttt ttctacaatt gcctctacgg   437940
atacaacttt cgccatctag ggtgggctgc ttcgcctagc agcacgtttt cacggttttc   438000
gctcgccgct actatttttcc tctagatctt cctgcccatg gattcagcag ttgccctatt   438060
cgggaatctc cggatctatg cttcagatac ccgttttggt ctcctttgga ggtctgacga   438120
cttggtcgcg ttgaagggta tagatttcaa agtgcttttct cgatgtgaat catagctaga   438180
aattacatta tttctcattc actcggactc ttagatcaaa cggaacgatt cgttgaacat   438240
agttcaactc atttcgtacc ttctttttt ctgattttt agcaaaaacc tgttgataaa   438300
cggttgataa acggttgata aacgaccggt cgactcacgg agttggcact ccaggagatc   438360
gaggagtccc ctttgactga ttcgtgattc cgtacaacgg gacggcgggt ccaactgacc   438420
atcttctcca ctacaggaat atcatggatc agaagactat ctgatgtgcc gtgtctccca   438480
gccagcctac gcgggatccc agcgaaatct tcctagctgt aaccggagga tcttgactac   438540
ctcttcaacc tgaagaagag gattccacta agcgattctg agcttcagcc cttcgggttg   438600
acaactgcaa cgagcagcca gcagtggtag cctacaagaa agggctaccc gtagagtcca   438660
agctctacca gtctctggtc gattcttgac cagagaccct ttaaggccct ccccaacagc   438720
tgtcccttct taagcaatga atatgcatct ttgactaaac ggttaataga aatattctta   438780
atgaaccttt agtgggatgg ggcaaagccc tgggataacc ctatccatga gctgcaagat   438840
```

```
caattgtcca gtacgggtta ctccagccgg ttattcatat tattcatact agtaatggaa    438900
ctctagtgcc ctatatactt tgacacatac atctctgtct gaacgagcaa tttcgatgct    438960
tcttctggcc caacctttag gtttaggtac gaagtcacta atatagtaat atagctagta    439020
tagctagcta tattaggaag agatcccatt cgtaggaatc tccactccat tcaccgaagc    439080
agaagcgcct gatcccacag gatctggggt aatttgtcag cttgccttta catggaaaaa    439140
ccccattcct tagctgagag tgatgcagct ggcgcagaag acgtcgttca ttaccttatc    439200
agatagagct gacggaaaga ccactttggt atcgattctg agaagacgcc ccactggcca    439260
gttgccacgg aaaactacat gaggttcgcc gagggcgaga ggaggcaaat cactgagatt    439320
tccgagacaa agtcttcttc ggatgatttc actgtcttct cgaattgtat ttgctgttgg    439380
ctcttgccta ttatatcagt catgccattc tggtcttcct ttcctgcctt tagttctcta    439440
tcgaaatcac aagcagaggg gaactcggac tatgacactt tgtttggacc ggggaattgc    439500
accgacaagt cacctgctct gcttagtttt cataatatct ggaagtagga aagacattcc    439560
cttgtcgttt actgcgcgaa ctcatacgca tactttgatg ctaactcgaa tgatggatgt    439620
ctcgggataa ttccttttc aaggacctcc tgcaggactg gatcctcatt ctggacaaaa     439680
agcaatctca aaataggaaa tctactctta gagtaactag gatctcgcct tgaccactaa    439740
ctagacttgc ctattcttcg ctaaccacct actgtctagt gtacgcttag ttaacgaata    439800
aatccttttg caataacagg gaatagcaat ctaaatattg cctcccctt taacatcttt      439860
caattcccga ctccatcagt attcactgga atgcggctat gaagtgtgac ctgacgggcg    439920
aacatgatct ttacaatctt tacataacca agagtttggt cggttctccg atccaccttg    439980
aatgagctaa acaaagactg ggaacgggtt acctactctt aacgggcaaa gcgagcccct    440040
ttattttatt ctgaattctt taattcagaa tcaatcaaat ctccccaagt aggattcgaa    440100
cctacgacca atcggttaac agccgaccgc tctaccactg agctactgag gaacaacagg    440160
agattcgatc tcatagagtt caattcccgt tcccaaccca tgaccaatat gagctcgaag    440220
cttccttcgt aactcccgga acttcttcgt agtggctccc ttacatgcct catttcagag    440280
ggaacctcaa agtggctcta tttcattata ttccatccat atcccaattc cattcattta    440340
atatcccttt ggtgtcattg acataacaga tgtcgtttct agtctatctc tttctatttc    440400
gtttctatat atggaaagtt caaaaatcat catataataa tccagaaatt gcaatagaaa    440460
agaaataagg gaggtttgtg atgatttttc aatctttct actaggtaat ctagtatcct     440520
tatgcatgaa gataatcaat tcggtcgttg tggtcggact ctattatgga tttctgacca    440580
cattctccat agggccctct tatctcttcc ttctccgagc tctggttatg gaagaaggaa    440640
ccgagaagaa ggtatcagca acaactggtt ttattacggg acagctcatg atgttcatat    440700
cgatctatta tgcgcctctg catctagcat tgggtagacc tcatacaata actgtcctag    440760
ctctaccata tcttttgttt catttcttct ggaacaatca caaacacttt tttgattatg    440820
gatctactac cagaaattca atgcgtaatc tcagcattca atgtgtattc ctgaataatc    440880
tcattttca attattcaac catttcattt taccaagttc aatgttagcc agattagtca     440940
acatttatct ctttcgatgc aacaacaaga tcttatttgt aacaagtggt tttgttggtt    441000
ggttaattgg tcacatttta ttcatgaaat ggcttggatt ggtattagtc tggatacggc    441060
aaaatcattc tattagatcg aataagtaca ttcgatctaa taagtacctt gtgttagaat    441120
tgagaaattc tatggctcgg atctttagta ttctcttatt tattacctgt gtctactatt    441180
taggcagaat accctcaccc attcttacta agaaactgaa agaagcctca aaaacagaag    441240
```

```
aaagggtgga aagtgaggaa gaaagagats acggtctggg gctggagttc taaggttgaa 441300
ttctgggcat gtggataatc cgaatcttaa acaactgacc tggaaggctt tactaccact 441360
ggggaactaa tccctgaaaa gagctcttgc gaactctgac ttagaaagca ttgtactact 441420
cagctgttag agtccattag agtgtttgaa atccctgaat ccttactctg tacagagcag 441480
taggcttgag ttagaagtcc gtatcccgtt ggagtgtgga gtcttttacc aggccgtttt 441540
ctagccttta cagctggtgt aagagtagtg gcattctcac cagcctgaat agcaagattt 441600
cctccagtag agggctatag ataagattat aaggtagggt tatacggtag aatcattaaa 441660
atgtgaattc cttgtgagga tctaaggtag taatagaata tcatagcgct agagctgggt 441720
caagagtaag gggcaagtgc ctatagaaag ccaatttctt ttattagaac cctgggaaaa 441780
ttcatatttt gcatttctac ttcctccatc agacaaggga gctgatgggt tttaaatcag 441840
agcagaagta cctctttcag ccagtttttct tacaccccgg ccagccttttt tttcatctct 441900 ctcttttgta agacgccctg cctgaaaata ataccttatc ctggcctgtt ggagtggtag 441960
ttcacagttt tccaagcgca tctagctcca ttctttcttg ttggaaggct acctcgggat 442020
atggcaatga agcctatctg tggctatagt ttcctgagtg aggggattgg agagtacgac 442080
atatcctttg aggcagctta ttttcagata tttaatttcc taaaagataa gcctatctag 442140
ttgaagtgta agtcccccccc ttttttttcca gttggagttt cttccccgg tataactatg 442200 accggctata aagcagttga ttagggcaga ggttttctag taggcgctat ctggctgaaa 442260
ttctaagtca aaagagatcc tggtgtgcag tccatcatct tgttagagg gctcccagcg 442320 gatttgttag ctgctacaaa tagggaagaa atcacgaaat ggaataggat cgagagtttt 442380
cgttctcttt agccacagtc ttagtcttag acttttgagt tcttctcctc gcgatccagt 442440
gccgttgcag caaatgataa acccagtgaa agaaagtttg ccattcctgc gcgtgtaatt 442500
ccttcttcct actaggattt tcagtcctaa gctaagcaca tgcagtctaa gtttcggagg 442560
aatctacttg aagtgcttcc ccatcttgct tgactcaagt ttgaacttttc ttactttact 442620 tatggataaa atagaatcta tcttacccta cttcatatga atagaggaga gggatgaaga 442680
tgaagacgag atttcttttta cgatatgtct ctgggttgcc ctacatagag ggattctaat 442740
gggatttcta aagcgagaaa cctatccaat tgctgcagtt tcttattctg tagttgcctg 442800
ccgctgtata acgagttgtt tccgatgggt aagccgtgga aagaagactc tggctaaggc 442860
atttgactac tccttccgaa cagctataga acagcttatt caatagcagc agattcgaga 442920
gaatttccta ttatgaaag gtagtcttca gactcccaga tattggaatg ccctaggatt 442980
ggattcatat ggaagtcaag ctcgacaaca agaagagaaa gtcactgaac acaaactatc 443040
tttctcatgt cttgcaatag acgattcaaa atgaaacaaa cgatagaaca cttatatacc 443100
gaactttcca tcaacttctt atttcttcaa ctactatatt acatactata ctatatgtat 443160
atatgtttga gatttgctcc gagatgatag attgtatgaa aacaaaagag aaagggcatc 443220 acccccagctc cggttccggc aacgctaggc gattcatctc tctcaattcc tgaaccaaag 443280
ctaattcaac taccttcccc ctcctgttta gacatctagc agccagaaaa tttgataact 443340
aagaaataag ggatccttttt gcaaaaatag caattggatt gagatggatg gttgtgctttt 443400 cagtcttttc catgccgaat agacaactgc ctcttatgag tgattgctct acagccaagg 443460
cagactgagg aatcccctaa aaagagatct ccatagtaaa tagaatcgta catccaagaa 443520
gcaagactga cagagcgagc tgtaaatgcc ataccattga ttcttgcttt tttacttatt 443580
```

```
agcattaagt ggactaaggg caccaatcaa tttgaaccca acgctcggga atccattctt   443640
ctatagcagc ttgccggaat gccttcaagc ctttgaaact acccgggaat ttaaaaacct   443700
tccttccttc aagtcttcta tgagggatcg atcttgggta aatacactag gggatggtcc   443760
cataccaaag agaacctcga gcggacggct tttccgcagt caaatgactt attgcttgac   443820
agcttcaaca atagattgcc ttttcttttt tctttagtga ctcagtccct ccgcagcccc   443880
ttacttagtc taattttttg atagaatcgt ggtaatggct gaagatcgag ttcacgcttt   443940
tgggcttgtg taaggatttc cctatcagtt agccggagaa ggtaatcaag gagttccgtc   444000
ttctacgatg tatgctcttt aactggttca tactggaaga atggatggcg caggagtctc   444060
tcttctgaga cttggactga tgaactctgt aacctatatt ctccaacctt cctcgatacc   444120
ctagaggtcg actcttgcca caggaatgt catcgctttt cggctgttct acgatattcc   444180
ttggaggatg aaacttttct gttgacctaa cttttccagtg agcggaccta ctcgaaggaa   444240
ggaaaaaaaa gggggttggg ggtgcttcta tataatctct aatccgagtc ttaccccta t  444300
atatgtgaa attctgctac aaatggattg gatgcacgga actcacctaa aaaccccaac    444360
ctgcgtgcag tcgaactgct ttattcaact tggcaaagac aaagcatgac ctctggaacc   444420
aaatcgttct tgtctctgga ttgcctcaac tcgaagcatg aggcctggac ccatcggtgg   444480
ataagatcac ctcttcatga caaaggtgt acacgttagg cctcactcaa ggtaatgggc    444540
caaacctaac gagtccaaac aaattggatc ttttgtatg acaaaccac agattgggct     444600
taattcaaag cccacaacca atggaagagc ctacaacttg accatgcact tacacatacc   444660
aacactaggt tctattcgaa ggtctcgacc accgatgggt cttgttctaa gcccaatcct   444720
ctcgtcttag gataggatat ccataaaccg gaacttctc cttttttagtt gacaacctat   444780
gttgggctga ctaagcccac tatcctaata gggtcccagg gttaaggctc cacctcatct   444840
tgggttaagg gcttagttga acccaatttc ttcttttcct atgattgttc cgtgatgggt   444900
tttctccttc taggattagc tttctatccc cgtgttgtgc taagctcatt tctcttatta   444960
ggtatgacct tttgtactct gtggatgttc agattgcata ccttgcaagt cattcattat   445020
ccacacatgt catacatctt tcatatagga tgattttaga aagcacctaa gtgttggaca   445080
tttgtcaccc ctacactcag ctgaggccac aggtctagtc gacgtggcca ttcatattct   445140
acagtaaact actagtcaca ccaccatctt tctttcagct ctctctcttc tgtcatgtgc   445200
ttaaagaatt taaagtcaaa aagacgtgat caactttctc gatctggttc agactcatca   445260
ctctaactaa tgtctcgtcc aggtcggggg gtgaattggg ccctctgaat gaatggtgaa   445320
ccagtcctac gagtgggtgg atccgccgca attattgtta tatatatata taagtcctga   445380
cccggaaagg taccgccacc ttgttcaggc tttccaaaga aagcccatca agtgaatgaa   445440
gtctaattcc cattccgggc cggcccaggc ctgctcgcta tccgagtgta gtcagcaaaa   445500
gctagtttag aactaccatc cggccttaaa aaaaaaccac tcgacatgtg ctcttattct   445560
tctgtcaaaa gtagggaaca gcaagtgtct gatcagatca atcaagcgat aggggcagag   445620
actttacttc gctaggacgg agctgctgtc gattgaggat tggccgaggg gcccttttc    445680
ttttctaagg gaatagattg tagctgggta caaataggcc gggacgagta ggcagggtac   445740
gacgaagccc gcggggtgac acatggttgt actggtcagc tttgggctgg agattgacga   445800
ttgactgagc gtgctttggc agctcgtggt ggagtactct ctgacggatt cgctctatta   445860
ttgcctccta ttcttgaggg agtgatcggg attaagccgc gtggcgaaaa agcactattc   445920
gctcttgggg gtgggccttt cgtactcaaa tccgtacggg gaaaggacaa ttattcagcg   445980
```

```
cactaaaatc tagtgaatgg ggttccatat tcatgaaaag ccaggtttga aatgatccat  446040
gttacggaac caagacaacc tatcttacta ataataagaa agggttaagg gcctccaacg  446100
cctataaata gaagcttctt tcagtctcta tttggcaaag ggagacggag aggaacttag  446160
aagtcggcaa aaaaaagctt tgagtgtagc catggattct tttataagac ttcaagaaat  446220
ttcgcaagaa atctctcaag tggaagagga gaagctccaa tcggagcaaa ccctggctgc  446280
cttttgggag cacctgcctc ccatcgatcc tgcacttgtg gctgcagcca tgcagcggat  446340
ccgggaccgc attagcgtcc tggaagacag gaaacgggcc ctcctccaaa aacaggaaga  446400
cctaattgtg ggtgctgtca cccgtggtcg ccagggagac tagaatagaa gagtccgtcg  446460 actctttta gttttagaag gtttaaataa gtgtctgtag acgcaaagta gtgtgtttct  446520 tcttttctt tgtttggtgg agatctactc ctatcctaag tagattgctt ttttggggtg  446580
tgtttgcatg tatcactagt agtcttcaat gcttccgttg ttaactttgt aatgttgtct  446640
ttagttgtgt ggctggtcta tgtgtgtgta agcttcctat ttgatgtatt cccatgtaac  446700
ggctattaat gaataaaaag tgctggtctg ctttgttaaa tattccttat gtatacgtaa  446760
ttaataatcc cagagggaat ccggatcttg agtgaacctc aaagccatgc cagcctggag  446820
ttaattcttt ctatggacag cctttttttt aagacctaat ctaggcatta gccatttaaa  446880
aagatggatt taggtttcgg aggtagatcg aaaacctcag cgaaggtcac cgaacacgaa  446940
caagatacga aagatgttag acagcggacc acttaaacta cttagttaga gattctttgc  447000
tattgcttat gcctcagcag agaagtaaag ttctgctctc ctctctttct cttgcgtatc  447060
tagttctata gcttaaccct gacttttacg atgtaagggc ggaacgtaat agtaataaag  447120
gaaaagcaag gtgtggcggt aagtcaaaac ttttggtct ccatgttccg gtcccggaag  447180
aagcttattt ttatcgctat aaggcataag tagtgaaaga agtagaccta taagagaaa   447240 aggaagcgct atccctccta cttatgattc aacatttagc tcgatctatt ctagatgtct  447300
tttttacatc aatggcatca gctggagctt gcaccgaatt gcttacccgc ggaactcatt  447360
taacccgacc ctgcataagt accaatgccc cttcccttt cacctctagg aaaaacttct   447420
gggatgagcc cttctactcg tcatttttat attgagggga aaattctcga tcccagacca  447480
ggctccgatc aaggcttata aaagcatcaa cctcatccta aaaggactcc tttagctttg  447540
gggttgattt acgtggctca agactttgag tcaagaggtc aggtgttcag aaaggtggtg  447600
atgcggcatt ggcattttca gcaaattcat cagatagctt gccttctttt cgtttacgtg  447660
gctacatact tgtagcgatc aaagggcata tttattcttt tttattattt atataaggaa  447720
aaggtaattg tatgggcctt tgcttcgaga acaatcgtat tagcgccttc gcagcctgcc  447780
tttccattct tcgagtgcag ttccttcttg agccttttct ttttgactcc taccgaagca  447840
agcctctcaa gtgctgacct ttcttcccac ccggaaatcg tagtaagccg ggagaaagac  447900
attcatatat tccccaggca cgggataaag agagagccga gagccgggaa cgcaacaaaa  447960
agaatttccc tctccctgta ggtcgagcct ccttttcagt cgccctctca cgggaatctt  448020
cttctttata atacgtacga gactaccaaa gaaaatgaaa cttctttccc cggagcagca  448080
actgaaagag aaaataccgc tttcttcatc tgcaccggaa aagagctaag cccggaagtc  448140
acggagctct cttctctttc aatggcagca gctagtttaa gttcaatgtc agccggattt  448200
ctaagcacta gtctttcctt ctcacctgct aactcataga aagaaataga gtcaacccat  448260
gcgcctttcg cggggtgagc aaaaagcctt tccctggatc ctggtatgaa ctcaaaaaaa  448320
```

```
gcatttaccc gtcgcctgct tcatctgcag agcttcctct tgttcacagc aaagagagcg 448380
gattcgttca agcaagctaa tcacattacc ctttctaggg tagggtagg ctacgatgtc 448440 attactctcg ctccctcact ccttaaaggg atcaaacgac tttgagcttt ggcattaagt 448500
acgcgtggga aggaattcca ttcaactagt tcaatgaccc tagagggaat gaacgcatta 448560
agcttgaaag cattaaattt agttgctagc tggactgact gtcttctctc tctttcggtt 448620
tctagtcttt gcttcagaaa gtcatttaga aagacccgct tttaacagag aggatttcct 448680
tacattacat acgatatttg agtggggatt cactaagcgt aagttcttaa cccggtatga 448740
tgcgacgatg acttcttgct ttgtttccgt ctctcctgcc tttgttagtc tttaatcgtc 448800
tctaaagcga gtgaagtcac ctgagggtta gaatccgatg tgatcttaga gctattgacc 448860
ctacccaact aactctctct aagtaagagc tcgccctgac ttattagtct tatcgaagtc 448920
gatagggaaa agagaaaagg tcagtgcttc tcctgtgagc gactccgaag tgggctcctt 448980
tcacttgact atttctcttt tttaggaggg agagactgaa tccacctaaa agctaaggga 449040
agcccggaag tattcgaagg ctgataaaaa gagacgtgta ctacgagacc accaagactg 449100
ataggcattc cgaccaaaag gggcaagttt cttataggat ccaccctccc aacaaaaaaa 449160
gaattccttg ctgtggaaaa gctgttcaag ttgaaaagca taaaggttga aggaaatgca 449220
ccttctccga ttagaagggt acgggactcc ttttcctacg caatttccta cgatagggta 449280
gggatgaatt gaatgagaga ctacgaaagt gaggcaaacc cacataagga aagaaatcaa 449340
tctaatcact ccatttcaag ccttagagaa tccgactaaa aagcctaaat tagcgaattc 449400
acctccctct gagtccgatt agaaaaacag ggatgaaagg cctagttttc ggtgagctag 449460
tgggattcaa gtatgaattt gaattttcct cgatccggac ttattaccgt gatcaattca 449520
ctaccagtgc ccatgtggcc gaggttgtcc cgaagcggat caccccgatg cctgtaatga 449580
aaggacagac tttcatcagc tgcaaactgg aagcggtttt tcgttagtgc gttaaggttg 449640
caagaaccta ctcctaacta aacaaagact catccgagga gccaccatcg gtactagtcc 449700
aggaggtcaa tactagcgag agtcccacag ctacgctagt tatttaggta taacgtgttt 449760
cggtcagctt taaaggccaa actaacccag tcgcttttttt gcagccctgt ggagtcaagg 449820
cgaatcgaat ggtcaggaag gaagcaagca attcggacag aattaagagg gcttgaaaga 449880
ataagatacg tagagcgtga accaaggttc ataggcggat caaagtcgaa aggcaaagct 449940
gttggttaga cgtagacgaa gccaaagtat agttagacga agccgtagga actcttgcaa 450000
cgcaatccca gctacaggaa gctaactccc taagacgaat gagtcacttt ctgatcctta 450060
ctccccgaag gaactcttag cctcatagct acatgagcta cattaggttc cgtagggtta 450120
gcaatacaag aatctcgatt ggaaaatacc tgaggtagga ttactcaacg atccttgtta 450180
ccttaactcc cttctcccgg gatgaagcct tagaaggaaa agtatagggg accccaaaaa 450240
ctctttagct ttagatgtta tatgaacccc taacaaggaa ccgtaggcat agagctatcg 450300
ggtcataact cttctcactc tggccttagg gttcttcttt caacaatcta aaatcctttc 450360
ttcatttgca aacacttatg tgataatatt cctaacaaag attccgtttg acttgaccgt 450420
aggacatcgc gttcctcaat gcaatggaaa actaggagcg cggaagcgat gaaagcatgc 450480
ccactttcgc cggctaacac aatggatcaa tacagggaa actggccgag aagcctaagc 450540
tagctatcag ctgccctagc gaacgaagtc tagtcttctt atcgagatga gcatgagtgg 450600
tcaagccctg caatgagatc atgcgcccta acctaagcct gggctactgt tgtgtgttcc 450660
gatccttcta gtgagagctt gtgaccatcg cagtgaccgc agtatgctta atcgactgtc 450720
```

```
tctctacctt cttgatcgtt gcatcacaag ttcgcacgac aagccgcatt gtgcactcaa    450780
gatgatgaat gcctttgaaa gatagaggat ttgaacctgt aatgtgtacc taagggctag    450840
atacacagat gccttcctat cttccttctt tactggacca atcgaagact gaaaagacaa    450900
agagatttcg cttagccaat gcttactgat agactagatg gagagcctgg tgcaaggtgg    450960
gaagactgag tgagaactag ccctttgagg agctctctaa gctgtctaac tctctattac    451020
cataggcaga gggaaaccag gttcaatagc cggatagagt aagaaaacaa gaaatttgac    451080
gatcaactat gtaaaccccc cgaaggggga aggtaagccc gccgctgatc ccgctttacc    451140
ttcgcctacc gtgaaaagag agtcccctat cacgataggc cctcccagct cccgaacgtg    451200
tctttctatc aatcgagaga ggtacataaa agaagagcaa ctaaactgtg aaactaaaag    451260
catgggaaaa agaaagcggt gaaaagcata catctactaa ggaccctcat actagaagac    451320
atagtttata ctatcgagaa aattacagag atcttctaca agccaactcg aaccccccct    451380
taaaagaaca tcgtaataga tatcttggag gtgtcctgga atttgaaaag cctcgtctcc    451440
cataacagcc tgaacaagat ctgctatgtt ccactccgga ggtaattccc tacctctgag    451500
tcgaagcaac tccgcgctat tttggcagat tctatcaaat acctgttcta actcaggtgg    451560
agcgctttgc gcgtccgacc tagttgagga aagagtggaa gtgctactag cagaagggaa    451620
cgaagaagtg gaactttgca aaagtgaag atcactaggg gtaggatctc catagagtat    451680
tacagcatta tttcgaagaa tcatttggtt tggttcattc tttcactgct ctgctccccc    451740 aaaaaagaa gagagactga atttcttcca ccttccctgt acgagtagtg aagaagtata    451800
gagcacttta gttggttgtt gaccaacgga aagcatggga gaaaaaaga tgcacaaagg    451860 aaaggagtc tcattaacag ctgaatgtgc caaactagta gcccgaaata gagatctgat    451920
ttaaaggacc aggtacagcg agttcgatcc attaggttct ttttttttt cagaaaagaa    451980 acgagagaca agaaaacatc tttgattacg attaaaagga acaatctcaa atagaccaag    452040
atccaatttc gggtcatttc ttggtgaaca tgatctgcca taatctcttc gatcccttca    452100
tttatgtgcc agaatagaga gagatttggt aggaaagtgg aagagacctt tttgtatatg    452160
ataatcaaag ggagtgggaa agctgcagta attctttgga aaagcccggt tctctttgtc    452220
ttcgaacttt cattcctcaa tccactgatt ccttccttca tatacctccc caccaataga    452280
tagagacaaa tgggaataac cgaaccacgt ctacaaaatg ccagtaccat gcagctgctt    452340
caaagccaac gtgatgctcc ttggtcagat gaccaagata ttggcgaatg ccacatatga    452400
tcaagaaaat agtacctata atcacatgaa accatgaaa gccagttgct aagaaaaagg    452460
tagaaccata aatactatcc gaaatagtga agggtgcttg ataatattcc attccttgaa    452520
agcctgtgaa tactagagcc agtgaaacg tagctactaa agcgtaaact gctcgttttt    452580
ccttccccgc gagtatagca tgatgagccc aagttacggc agctccggat gaaagggaa    452640 taagggtatt aagaaaaggg atttcccaag gatctaaaac tgcaatccct ttcggggcc    452700 aaatacctcc gatctctacc gtaggcgcca aggaagaatg agaagaagcc cgaaaaagag    452760
caaaaaagaa cataacctcc gatacgataa acagaataaa accatatcga ggtcctaatt    452820
gtacgacttt ggtatgatgt ccttcgaacg tggattcacg tagaacatcg cgccaccata    452880
cgaacatggt atataggata aatatgaggc ccaaactgag aagtgttgca ccccccttgaa    452940 atgagtgcat gtacatcaca cctcctacgg ttgttgccaa agctccgagt gaacccgaaa    453000
taggccatgg acttggatct accaaatgat aagaatgcct ctgagattca atcataaacc    453060
```

```
actttgcctc ggttctatgt aaaccccccc ttcaccccca cccctaaag tagtaaagta  453120
aagaagggct ctttggggtc ttatttctt tctatctgac aggacaaaca aagaaatagg  453180
aagggagggt tctttcattc cattgataga agtctaacta gaaaagact ctctctatta  453240
ctttgagaag agaatcgttg gtttgaccga cgaactacgt gggaaaatag accttctttc  453300
tttgatttga agcaagattt ttggcaagta acaattccat tcagttcgct ttcggaaaac  453360
ttgctggtcg cggattagtt cgttctgcgc cgccagcggc ctcaactcaa aggcgcaggt  453420
tgaactctct ggttgaggct gcattcattt attcatattc aacttgacac gtgggaaggg  453480
cttactctac tagtggctcg gcttggtctc gctcccttcc cgcactattc ctccccacta  453540
aaaagagcga ttgagaatct cgagaacctt tccgaacgtc tgtcttcgcg gggcgattgg  453600
aaaagaaagg agtcttcaat tcttttactg ccttccattc cactattttg atcgaattaa  453660
ttgctcttcc gaacgaccaa gtcataatga gattaaaaac cgatgcttcc ttggccgtgt  453720
ggaacatgga ttagcattat gtcattccta caagtgatga cccacccagg attgctatgt  453780
acggacttag agatcaaata taatatgttt ctttccattc ctcgtgagcc acttattct  453840
ccgaaacaag agattaaagt catcttcctc ctttttccca agaagtcgac ggccttacac  453900
cattgggata cttcgaataa acttgagtac atataggaaa caccggtgct aaaacctttt  453960
ctcaagatat cttccaaact gttggggtcg ttgctccgga tcttgttctc ccggtgtgaa  454020
accagttggt tccgtagttt tagaattctg ctgatcccaa gtactccatc tccatcattg  454080
catataggaa tatagaaagt aaagaggaaa aggcatgacc agaagaattg tgtgaaataa  454140
gtgaatttat ccagttgagg cattcttgat tgattgagac aaaacgattc cctcaataca  454200
gcttaacccc gtcaagcctg tacgagtagt gaagaagtat agagcacttt ggttggttgt  454260
tgaccaacgg aaagcatggg aaagatcact cctaactaag cagtcaagtg aaaggagccc  454320
gcttacccac tcccctttcc ccccatcgct aggggcctcg ctcatcacat cagtctaaca  454380
tgagctactc ttccatttca taaacgatca attggaaaaa aaggactttc cttttccttt  454440
ctggtggaaa aacgaaagaa aaggtgttcc ccttattgt aatgctccag ttgaagtgct  454500
tccactcttg aaagcagagc tttagaaaag ccaactgtcg cattattcaa gtgaagggt  454560
tcaatatagg tcgaaaacat ttcatcggac agcgtttttt ttcgacctat attgaatagg  454620
tatcgcaatt gttcgttaat atgtcttaac agacagtccg gcgctagttg attctcggga  454680
agagaaagcg ccgtttccca ttccggcttg gcttggaaaa ggaggtagag gcttccgagc  454740
ttgatgggca ggaagttcca gacgaagaca tcatgctctt ccggacccg ctctcgatct  454800
ccaaagccaa agaaagaata ccaagaagaa tgagacttgc gccccctcc catccaaaag  454860
ccctactaca aaataaggcg agggatcgcc tccccacaga gaacccaacc ctttcaagta  454920
gggcctgaaa gaaatcaatt gaagccattt tcaaacaaag aagataaaat aagaaaacta  454980
tagtggctag gaacagtaac ggaatacggc gttttttcat aatcgaaccg agatgcatca  455040
tattaggtaa gatgtatctt cattcgctct gcgagcagag cggtataccg aaaaaaagaa  455100
aagccttatg gccactacct tacttaagca attctgctta ttcttattct atcttagaat  455160
aagaataagt tccccctctc cggatcccga taagaatgga agatggtgca agatcgaatc  455220
ctgttacctt acttcgaatg gaatcttagc ccgcctcact tgctttcttt actgcataaa  455280
taagggcata agcgaagtca agggatttcc gtctaactag tgtctgagag taagcaagct  455340
accttcattc aacagatttg tggttgagtc aataacatgc tctgctctgg gtcgggaatc  455400
tttgctcttc tcttttgcat ttccgctgcc tgcctaaagg cttattgcta gctcttaggt  455460
```

```
tctctgtcag tagagtgatt gccaaaacct aggtatgttt tcggagaata ataagaagag 455520
acggttgtag cttttagaga ctatcctctg cagctgtagc tacgtggaag ccagctgctt 455580
aaagacaagc cccctaacca ttctgctatt cctgccctaa agcaagggaa tccgctctga 455640
cccaccaccc tggtaggaat tgccagattt acagttatg aatccttgta atacaagttc 455700
tttcctctaa cgatggctac gaactacgcg aactgaactg tcaaggcttt caaaccaaga 455760
ctgagaaagc tcaatcaaaa aagagtattt tagtggaatg gcttaacgaa gttactcccc 455820
atacgagacc ggaaaggaag ctagcgaacc tagggtcaac accaaggtag gggcgaaagg 455880
gaaaagaacg atgtttgatg tgaacggaag caagcatttc gctaagaaag caaaacagga 455940
agcggcgata gcaaacatta ccctgactca gaacaatatg ctcttgggag acatgaagca 456000
caatcaacct ctctacctta agacttctaa catggtcgat tctagataga gcacggtaac 456060
ccacaacccc ctactctaca aaacaaagag tggaaaatct cttcataggg tactgtagct 456120
gtacagccat agtaccatag ggatggtgag agttcataag agcccgaatt tagataggtg 456180
aaagatcctt actcaaatta cgaaccctga acctctttgc gaattcacag ctgaaccttg 456240
atgggaaatc atagatttct gataggaaag aaaaagccca attacccaca attttttcat 456300
atacacgagc gtcctcctac attgtcccct agtacagcat acttaataaa gcggtttcca 456360
gggtcaacct gtttaactgc atgccagacc actaagtgat gagaccatgc aaacaaggc 456420 aacgaggagc gctagccgga actggacaat gggtgggtgt ccaacaaaca ttccttagct 456480
aagaaggatt cattcaccgc agcttctctt actagcagat gaaactagca acatcacatc 456540
atatagaata ccgattgaca ggcattccag tctatcttat agtttatgtt gatgatctca 456600
ttgtttccgc gagcgcatcc ttcatttcca agctttattt ctatcgtaat ttttccatgc 456660
ctattcattc ttttttgggg tgtataatat aaagccacgg agcgattcag gcatctatct 456720
tattgtattg acgcaattgg aagatcagga tttctcccta ccgctcaagc gggatcagat 456780
cgggctttag cgagaacagc tgtaattgaa tcgggaacgg aaagacttca cttcaactca 456840
ataaatgacg tctacttcgt aagtgctaag gcaaaatata tcaccgaaag gaaaggtgat 456900
aggggagcct agccatttca ctctacctga gtaataaagt ggaaaccccc ctcacgatcg 456960
attaaaagga aagtcgccca gagatatttg ttcaaatcca attcgtgaag acagagtaaa 457020
ttcaacaaat ctaagaaagc aagtcctagg cctcactatc tatcaatcaa gaaggtaaag 457080
gagagaaggt ttgattgaaa gtagtacgtc tgcagggatc tgtcgttaac gatttgaccg 457140
ggacacatcc aattgaaagt ctaatcccaa cctctttgga aggagctcca aaaaagactt 457200
gacttcagag cggggaatct tcctacaagt gagcaccaag tcaaatgtat gaaaaaggg 457260 ctatacctct gcctagacaa agaggacttt aagacagcct cgtaggagac attggatgta 457320
accagccttc aaaggcggag gagtcaaaag cgactttcga ttcaaattag agaaatgctg 457380
agctttatcc gcttcaattc attaaggtat tattttttcc ttctaaatag tcagagtggg 457440
aactcaaaag caagaactct taaccatcat tccttaactc taaagggcgt gaatgtgtgg 457500
atcaaggaag aagggtggga tagcgcccga ttgattgagc gtcttacagc ccgtcatgca 457560
agctagcaaa gccagcgcag aagcagccct ttccatcgtc tttcgctgac cctggttcta 457620
tcaaaccagc ttcttcaatc ctggtgtgaa cttcttcctg ccttcttacc caagagctct 457680
gattccgctt aaataaaagc agcccttctt ccttactctt tcgagtaagc attttgaaac 457740
ttccttaaac atctgcttca aagagctaag ccccggtctc actgaactgg gtcaagaac 457800
```

```
taccttcctg gagctaccto cttacttaga tcgttcgttc cccaattcaa actcggatca    457860
gttggcaagt ggattccatg cctgggtacg aaactcgaaa ttcgatcttg aaagagtgaa    457920
atctagcctt ttgtctttat cctttatagg tctgggctaa ttcttgaaag cagcaactcc    457980
tacacctacc gaaactttaa cagaacaact acggattctc accctcgagt caggagctcg    458040 cttctcaatct ctaagagccg attcgatggc atctttttt atgatctttc tagttagcac    458100
gtagtgggaa tagtccctca tcgacacggg aagagagctt caagcaaaaa gggcttgtgc    458160
aagcaagtga cactttactt caagcgaata gtgctgcctc actttcttta gctaggctga    458220
gaagccgatt cccgacatag actatttcct tctcatcgaa agatgcctaa gaccttttca    458280
ccaaaacaaa acctctaccc cctactctag tcagctttct atctctttct ccaaccttcg    458340
atgatcctcc tgcaggcaaa tcatcgaagt caagaagaag tgatgggcct gatcttccga    458400
tatcgatatc tgatccctaa gctgagctcc aaagtctaga tttcttccta aagctaaagt    458460
aagggcaagg ccccggtcgg ttctcccttt cttcttttcc tggttctctg ttctctagtc    458520
gtataatcat accattctgc catactattt tcagaattca ttccacgtgg aaaatcgtct    458580
agctagggaa ctcttcatca gacgatttct catatgatta ttttcgtgaa ttcgacgtag    458640
aagaagttcg ccttgcctcc cttattaag tactgggcta agggcggacc ccccttcta    458700 tctgggtcct agtctcgtcc cttgttagtg caataaagag aagtgtatta aattccaatt    458760
cttttccgcc cttcctaacc ttgctcgatc caatagcccg atcctagccc actcaccttt    458820
ctccaagatt gaagttagaa ctaggagtcc taaaatctta atgaaaagga gcttggcatc    458880
catgtgttcg agaggtagaa aacgaccct gtggcgggt ttaccaggta ggtataattc    458940
aatgggaccc tatcccgtcc tgtggtcctg aacaaaggtt ccatcctaaa aagaaaagag    459000
agccttcacg gaaaaactgt tggaacgaga tctctcatac aaaaagacct gaactaacta    459060
ctcgctcaat gcgcattgaa attctaatga atgcccttat ttagcatctt tgagttgagc    459120
ttagccctct tcctatccta aatccctaga atcataagga acgattgatg gttgatctgg    459180
caattctttt tagtaattag ttagtctatc aagcagaaaa ctatgactga ggaagtctca    459240
gggagggcac ccccttttaa ggtaattata tgccatttgt ggccccccac gttagaactc    459300 tcttaaccg gaatctttat ggctaaacct tttttttaa ccgatttaat cgtaagttgc    459360
atcctcaact tctggacggg ttcgagagtt tggttcgact gagactgatg tctcatcggg    459420
ttcagaaggg gatgggaatg cagattttga tgcctcgtat cgtatgacaa agaagagagt    459480
ttttacaaag ccctagagct agagcttgtt gagaaagtag ctttgaagat gggcttccta    459540
tgggaaatag ggaagtttaa agcgataaca aaggccttag ggaataggat ctctttctgc    459600
gtctactgat gcttttgaaa aaagcctttg gtttggcttg tttaattgat tcgtacgtaa    459660
tccgagagct tcatacgtgg gattttttg gcaaaggaaa gtcaagagaa aaggtggtag    459720
ctattctagc aagtcttctg tggaggagta gcactaggct agtaacttat tacactagtc    459780
tcgattcctc aaggttgtac gagctgtaat agtagttgaa aaacctcccg tcccgagttg    459840
gcttaagcca tgccttact aaagaattct cgccatctct gataaaatct ggtgtggagc    459900
ccaggctagc caacaatgag aaatgccttc ctctttttg ttgatttagg tgacgtagtc    459960
ttatccgatg aatggcagtg agaaggcgga aaaggtcgta aagggctaag ctaagggagg    460020
ttggcattcc gaagtcaagt gggctttct cacaccgcat ggggtggttt cctacgcata    460080
tgcaacaagc tcttatttgg atctccctaa tctagagggt tctcacgcca aggttccttt    460140
gtttcgggca agtccaatta caaacaaaag agaaggtcgg tcccgtccca cgggttaggt    460200
```

```
gcttagctga aggtggaagt ccaaagctta ataaggtgga aggcgaagcc gaggcaagag   460260
caagggttga aagacaagag agaagaattc aatctcccct atttgttcca ttctcaatgg   460320
ttggccagga tgctttggtt tatcggatcg atcgcagtgg tcaagtgcgc tggacgacac   460380
ggcattctcg tttaaatagt accatcgact ggagaccgga ttgctaccag agagaggaat   460440
gactataggc acggaactta cttttgaccc tttctttgcc ccttggttcg ctagctgact   460500
tgccagcgct tggattctcg aactctaaga gcggatttca ggaatttgtt cacatccgat   460560
tcgatggcat ctgtctgctt ccacccttt gcaagcgtgc tactgactcg atggacaaac    460620
tcaaggaact gctttgcctc taggttgact tggatcacat catcctgaac ttttgatcgt   460680
atgtcgtcca gctttgttgg tgctgtgggt gtcagtcttc taatgtcagc tctctggtag   460740
gccaatcgat ctctgcttga ttggccgtaa ctgcatgatc gatctgacga agattcccat   460800
gtagatctat gaaactacag ccgaaccaaa tgggaatcct aggtataggc aaaggtggga   460860
gggatgagag agcaagctgg cgtgggggca agggcaataa catccgagca aggcaagccc   460920
tagaaatcgg cagggtatga tgaaaagctc tcaccaggat tgtgtttcca gatcgattga   460980
tcaacatttc cctcttttgtg atagctgaga agcgttctaa atacttttcg acaaggagag   461040
agttccaaca aagacgcgat cttctgcaac ggaagctaac gtggatgttc caccggcacc   461100
ggggttcgaa ggtcacgatc atcggagcaa tcaacggagt gtttccttca gtcagtaagg   461160
ggagaaatcc cttattctaa ggaaatgttt ttggtaagaa agcctgtcct agaaggaagc   461220
ctgcccgcaa gaactctggt taagtgccct ccaccgcaac cgacataaca taaagaaaga   461280
aggaaccggt ccccatggtc gccttcgttc gtaaggtaaa aacgaataga cattcttgtc   461340
ttggcccagg tgacgcacat gaccggtcaa gaaagttctt attttggat ttcgcttcg     461400 ctacggctac agtcaagtgg ctccccttt acaagactcc ctcccaccag aagaaagatt     461460
gatcgctttc ggtaacccag ggctccattg cgtgtgctcg aggtagaagt tttttttttt   461520
tttagatgtg aatgggaaaa aattctgacc accggtagcg aatgcttttg aaaagatttg   461580
aaggtagaag gctgtttcag tctagctccg gaagcattgt ctgaagtaat aagaagaagg   461640
aagtgaccac tctgaagttc ttttttctttg attccaatga ccgatatcgt acaagacgga   461700
agtcatgagc gatagcgaag ataggtatag gtcttagatt agagtgccag tgcccctcgg   461760
gaaaaaggaa acctagctat tctttttgtt cttaagaaag gttgcggtaa gggtgggcgt   461820
caatcggcca ttcctccatc ataacctttg gaactctacg cccgcgcttg gttctcatgc   461880
actaggtgca cccgagtcga ctatagcact aaccaacttg ccattgatta caacatcgac   461940
ctttgaatcg tatcatccat ggtgagtggt atcatatata agtataagag caaccttag     462000 gaaggatctt tctctctaac tagaaatttt agaagaaagc gtagaaaatc aaggtttga    462060 ttcaacaacg gataacccg aaaggcaaaa aaactcgaac tgaatcaaag tacaaggctg     462120
acgtacttat ataagtgatg aatatgtagt taatcagata tttccatttg gagactgatt   462180
catgtattct atctttatct accgctacgc cctggaaaag cagtgaaact tctaaagctt   462240
attagcacag aaaaaaggat ttgaataccc tagtttataa gggaatcacc aatccctcta   462300
tataagctat cgttcgaaac tacattcatc agttgtccaa ggaggcaaac atggaatgga   462360
gatagaaaga ttcagtcggt ctatccctgt ggatcggtat atgcacctat agttgagttg   462420
agttggttga ttcaatccac aacaccgcca accagagggg aatcaaactc gcttagcaaa   462480
gtgcaaaaag aaaaggaatc gaaagtatga atatcataaa gcagcagctg ctcccctagc   462540
```

```
cttctaaaga gctagtcccg aagtagcaac agagctcttc ttccctatta gtctatgaac 462600
tatggatgct actaactagc aatgtatata ggtaagctac taaccttatg gatgatatct 462660
actctttgct gtataagtct ttctcattcc tcttctctta ataagcctag cagctttctt 462720
ttcttcactg ggaaatatcc ataggaataa gaatctctat atatcaaaga tcttaaaatc 462780
cctctacaac gggaaagcga cggaaaagcc gtttcaccac cgaagcgaac taccttaggc 462840
caatgggaaa tgccagagta gagcgcaaaa gaaagggatt ttcaatccac ttcaggtggg 462900
actaagaaaa gaaaatctga acctgggaag cagatttaca ggttgtactt ttcccgttag 462960
tccataagga tcggacaccc atattccagg accatacaag cctgttacat gaaatgcacc 463020
aaaaccaaag caagccaagt agccttccat taatagcctc tctttcaggc tcttctgtgg 463080
gaatactttc aatcgttggc attccctag gcggagacag ttttcgcaat agctagattc 463140
tcaagctctg attcacttgc acccttcttc ttgaaatggc attagctgct ctttctattc 463200
catcaaagat ccaagcagga gattctgtaa gaaaagatc gcttaggccg acataacata 463260
tgtcacttcc acttccttta ggagatgttt ttcagggacc aaagagaagg cgatttggtc 463320
aaattgatcc ttttcattt ccatgccatg acatgagaca gatctctcgc aactagttcc 463380
tttgctgatg aaatgcctta gtcagtagcc tgccttacga ctgaaaatgg ttcacgttca 463440
cagccctata gcgctagtct tgctaaagga atggtgaaga aaatccccct atagctagtg 463500
agcatcttta cttttagtag gtaaagagcc tcaatgaaag gggaattgcc gccctcaagg 463560
gagaactaag atagtggttg attgtctacg gtctcgttac aggatgaagc tacagataga 463620
acagatagag tagaagagtc ggtggggctt acctttcttg ttgaactaga gtagagggtg 463680
agcagagaaa tcccttgaag aaagagctta ttccacctcc tggatcggta agggcttcgg 463740
ttccatcaat tcgatgttgc tcgataagca ggattacgat tctagtttag ttcatcagat 463800
ctacgctctc aggcacaccc accaacgtaa gacaggatca aagtccaata gaatagctcg 463860
ggcatgaata aagataggaa tcgacgagac cttttcctac ttaaaacaat tcgaaatctc 463920 gaaccctgg tatttcattg aggagacaag acaaataggg acctaaaaac gccctgagtg 463980
ggacgccccc ttcgggctga gatgcttttcc ggacatgcta ttcttttttat ataagacttc 464040 gctacacggc ttagccgacc tttccgagag aacttcaaga catactttga gtattctata 464100
aatatcctaa gtcgagttat aggccaaatg ccctaccaga tcagtctcga agaaatagca 464160
aaaggatggc tacgggatcc cactctacct ttccaggatg aacttcccct cctgcttctg 464220
tagcactgga agtgacccgt gtttggatct aggattcaat tcatccagct ttcatttaaa 464280
gtaaactctt taagataagg ctttttccct cgcctaagtt atgaatctat tgcaattgaa 464340
aactccctcg cgactgattt gccatttgga tcgatttgag atatagagag ttgtgtcttt 464400
ctaacgctaa cgatgctaag cttaagctct ttcctttagc ttaaacagga atagctcttc 464460
cagcttgttc gttgcactca ccctcaccct gaccttctcc cagaaacaaa ggaaaaaacc 464520
taacattcgc tccttcaccc gcgagggatt ctcttcatcg ctactaacta gaaaaagttc 464580
ctgggctaag aagagctccg ttaaaggata tctatagctg cggagaggga agcgcttaga 464640
agctatgctc ttcttcagct ttctaagctt ctactttcgt gagctcttat tgctcttta 464700 gtcgagaatg ctaccattca tccctaaaag aggaagatag tgaatcagtg cttactttag 464760
aggaagagta gtttagctag acagattata tagagaaagg gaaggggctt gcttactcgg 464820
aagagaaagg actgaaggtg aatgtattca tggatatgat tcgattctct gatcggagaa 464880
tgtaaggtat gaactcctaa gaggaggaga gggaagatct acattttaa aagaaagatg 464940
```

```
tatatcagac attatgctgt gcttactaag gtctttagtc tttactttag atagaggttc  465000
atctgtcctt tctttcctct agcaaagcct acttcctgat taaggatttg aagcttcatg  465060
gccttctttt cttcctcaga aacacagaaa gaaagattta aaaaagcaac aaaatctgta  465120
tttaacacaa aacggaaact aaggagagag ctggtcttac tgttagacac agtaaacata  465180
ggagacacct tatacacgtt aggaatttag gaagagtagt accgatagcc ttagtatgag  465240
ttgaaccttt cttattctta gtcctcttat acaagctagc tctcttatcc gcttgcctct  465300
tttaatgaag aagggttggt ttaattgata gctttggaat aggtagtcct atggactgct  465360
cttttcttat gccccggagt ggcgagaata cgaagctaga tcagcaggaa tgacagcggt  465420
ctcttccaaa agtgggtaca ggactcggat cccatttcca aggtgaattg gaggagaaat  465480
ggatactggt attatagttg ttgaaagacc tattaattac atgccaaaag agcaaaagtt  465540
gaatcatcgg cttggccacc ttatccttt atacaaaaat tttcyttgat gatataccgy  465600
ycraggsgaw ttstcwcgac ntcctctgcy agamaaagaa aahagaaacc cvscagbtsc  465660
cwcctcwsat camwgaaraa accaaawcac yacamwavac haaccgcaaa ahgctcccac  465720
tcbtstdtgt yctmgratsc tgcttgtatt caancttatr tttnygkaan cctctnchdc  465780 tyswtmwac                                                          465789
```